(12) United States Patent
Li et al.

(10) Patent No.: US 11,827,628 B2
(45) Date of Patent: *Nov. 28, 2023

(54) COMPOSITIONS AND METHODS FOR INHIBITION OF THE JAK PATHWAY

(71) Applicant: Rigel Pharmaceuticals, Inc., South San Francisco, CA (US)

(72) Inventors: Hui Li, Santa Clara, CA (US); Sambaiah Thota, Union City, CA (US); David Carroll, San Francisco, CA (US); Ankush Argade, Foster City, CA (US); Kin Tso, San Francisco, CA (US); Arvinder Sran, Fremont, CA (US); Jeffrey Clough, Watsonville, CA (US); Holger Keim, Newbury Park, CA (US); Somasekhar Bhamidipati, Foster City, CA (US); Vanessa Taylor, San Francisco, CA (US); Robin Cooper, St. George Island, FL (US); Rajinder Singh, Belmont, CA (US); Brian Wong, Los Altos, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 39 days.

This patent is subject to a terminal disclaimer.

(21) Appl. No.: 17/517,428

(22) Filed: Nov. 2, 2021

(65) Prior Publication Data

US 2022/0098181 A1    Mar. 31, 2022

Related U.S. Application Data

(60) Continuation of application No. 16/551,393, filed on Aug. 26, 2019, now Pat. No. 11,198,689, which is a
(Continued)

(51) Int. Cl.
| | | |
|---|---|---|
| C07D 413/12 | (2006.01) | |
| C07D 403/04 | (2006.01) | |
| C07D 239/42 | (2006.01) | |
| C07D 401/12 | (2006.01) | |
| C07D 403/12 | (2006.01) | |
| C07D 413/14 | (2006.01) | |
| C07D 239/48 | (2006.01) | |
| A61K 31/343 | (2006.01) | |
| A61K 31/436 | (2006.01) | |
| A61K 31/505 | (2006.01) | |
| A61K 31/506 | (2006.01) | |
| A61K 31/5377 | (2006.01) | |
| A61K 31/538 | (2006.01) | |
| A61K 31/5383 | (2006.01) | |
| A61K 31/541 | (2006.01) | |
| A61K 31/695 | (2006.01) | |
| A61K 38/13 | (2006.01) | |
| A61K 39/395 | (2006.01) | |
| C07D 498/04 | (2006.01) | |
| C07F 7/10 | (2006.01) | |
| A61K 45/06 | (2006.01) | |
| C07D 401/14 | (2006.01) | |
| C07D 417/12 | (2006.01) | |

(Continued)

(52) U.S. Cl.
CPC .......... *C07D 413/12* (2013.01); *A61K 31/343* (2013.01); *A61K 31/436* (2013.01); *A61K 31/505* (2013.01); *A61K 31/506* (2013.01); *A61K 31/538* (2013.01); *A61K 31/5377* (2013.01); *A61K 31/5383* (2013.01); *A61K 31/541* (2013.01); *A61K 31/695* (2013.01); *A61K 38/13* (2013.01); *A61K 39/3955* (2013.01); *A61K 45/06* (2013.01); *C07D 239/42* (2013.01); *C07D 239/48* (2013.01); *C07D 401/12* (2013.01); *C07D 401/14* (2013.01); *C07D 403/04* (2013.01); *C07D 403/12* (2013.01); *C07D 413/14* (2013.01); *C07D 417/12* (2013.01); *C07D 498/04* (2013.01); *C07F 7/0812* (2013.01); *C07F 7/10* (2013.01); *C07D 285/22* (2013.01)

(58) Field of Classification Search
CPC .. C07D 403/04; C07D 513/04; A61K 31/506; A61K 31/5415
See application file for complete search history.

(56) References Cited

U.S. PATENT DOCUMENTS

| | | | |
|---|---|---|---|
| 4,166,452 A | 9/1979 | Constantine | |
| 4,256,108 A | 3/1981 | Theeuwes | |

(Continued)

FOREIGN PATENT DOCUMENTS

| | | | |
|---|---|---|---|
| CA | 2463989 | 4/2004 | |
| CA | 2542492 | 4/2005 | |

(Continued)

OTHER PUBLICATIONS

"Acute Leukemia," *Merck Manual for Health Care Professionals* (Online Edition), 6 pages (pp. 1-6), 2013.

Anderson et al., "Imidazol[1,2a]pyridines: A potent and selective class of cyclin-dependent kinase inhibitors identified through structure-based hybridization," *Bioorganic & Medicinal Chemistry Letters* 13(18):3021-3026, 2003.

Bamborough et al., "N-4-Pyrimidinyl-1H-indazol-4-amine inhibitors of Lck: Indazoles as phenol isosteres with improved pharmakinetics," *Bioorganic & Medicinal Chemistry Letters* 17(15):4363-4368, 2007.

(Continued)

*Primary Examiner* — Deepak R Rao
(74) *Attorney, Agent, or Firm* — Travis Young; Bozicevic, Field & Francis LLP

(57) ABSTRACT

The invention encompasses compounds having formula I-V and the compositions and methods using these compounds in the treatment of conditions in which modulation of the JAK pathway or inhibition of JAK kinases, particularly JAK3, may be therapeutically useful.

19 Claims, No Drawings

Related U.S. Application Data continuation of application No. 15/637,833, filed on Jun. 29, 2017, now Pat. No. 10,421,752, which is a continuation of application No. 14/974,143, filed on Dec. 18, 2015, now Pat. No. 9,732,073, which is a continuation of application No. 14/315,073, filed on Jun. 25, 2014, now Pat. No. 9,248,190, which is a continuation of application No. 13/750,632, filed on Jan. 25, 2013, now Pat. No. 8,815,848, which is a division of application No. 12/193,627, filed on Aug. 18, 2008, now Pat. No. 8,399,472, which is a continuation of application No. 11/450,901, filed on Jun. 8, 2006, now Pat. No. 7,491,732.

(60) Provisional application No. 60/776,636, filed on Feb. 24, 2006, provisional application No. 60/706,638, filed on Aug. 8, 2005, provisional application No. 60/689,032, filed on Jun. 8, 2005.

(51) Int. Cl.
*C07F 7/08* (2006.01)
*C07D 285/22* (2006.01)

(56) References Cited

U.S. PATENT DOCUMENTS

| | | | |
|---|---|---|---|
| 4,265,874 A | 5/1981 | Bonsen et al. |
| 5,700,904 A | 12/1997 | Baker et al. |
| 5,728,536 A | 3/1998 | Ihle et al. |
| 5,958,935 A | 9/1999 | Davis et al. |
| 6,080,747 A | 6/2000 | Uckun et al. |
| 6,080,748 A | 6/2000 | Uckun et al. |
| 6,133,305 A | 10/2000 | Tang et al. |
| 6,177,433 B1 | 1/2001 | Uckun et al. |
| 6,210,654 B1 | 4/2001 | Ihle et al. |
| 6,313,130 B1 | 11/2001 | Uckun et al. |
| 6,316,635 B1 | 11/2001 | Tang et al. |
| 6,342,503 B1 | 1/2002 | Aldrich et al. |
| 6,433,018 B1 | 8/2002 | Siddiqui et al. |
| 6,486,185 B1 | 11/2002 | McMahon et al. |
| 6,506,763 B2 | 1/2003 | Tang et al. |
| 6,528,509 B1 | 3/2003 | Hale et al. |
| 6,579,983 B1 | 6/2003 | Batchelor |
| 6,593,326 B1 | 7/2003 | Bradbury et al. |
| 6,593,357 B1 | 7/2003 | Green et al. |
| 6,608,048 B2 | 8/2003 | Tsou et al. |
| 6,610,688 B2 | 8/2003 | Liang et al. |
| 6,635,651 B2 | 10/2003 | Uckun |
| 6,677,368 B2 | 1/2004 | Cui et al. |
| 6,683,082 B2 | 1/2004 | Tang et al. |
| 6,696,448 B2 | 2/2004 | Tang et al. |
| 6,699,865 B2 | 3/2004 | Hale et al. |
| 6,710,052 B2 | 3/2004 | Pease et al. |
| 6,777,417 B2 | 8/2004 | Liang et al. |
| 6,784,195 B2 | 8/2004 | Hale et al. |
| 6,815,439 B2 | 11/2004 | Harris et al. |
| 6,825,190 B2 | 11/2004 | Moon et al. |
| 6,908,920 B2 | 6/2005 | Thomas et al. |
| 6,939,874 B2 | 9/2005 | Harmange et al. |
| 6,949,580 B2 | 9/2005 | Hale et al. |
| 6,969,760 B2 | 11/2005 | Ihle et al. |
| 6,998,391 B2 | 2/2006 | Lyons et al. |
| 7,056,944 B2 | 6/2006 | Hale et al. |
| 7,060,827 B2 | 6/2006 | Singh et al. |
| 7,074,793 B2 | 7/2006 | Hudkins et al. |
| 7,105,529 B2 | 9/2006 | Davis et al. |
| 7,115,617 B2 | 10/2006 | Buchanan et al. |
| 7,122,542 B2 | 10/2006 | Singh et al. |
| 7,122,552 B2 | 10/2006 | Ledford |
| 7,153,964 B2 | 12/2006 | Pease et al. |
| 7,166,599 B2 | 1/2007 | Bornemann et al. |
| 7,173,028 B2 | 2/2007 | Dahmann et al. |
| 7,235,561 B2 | 6/2007 | Brumby et al. |
| 7,279,469 B2 | 10/2007 | Pierce et al. |
| 7,288,547 B2 | 10/2007 | Lucking et al. |
| 7,312,227 B2 | 12/2007 | Ledeboer et al. |
| 7,329,671 B2 | 2/2008 | Singh et al. |
| 7,329,672 B2 | 2/2008 | Singh et al. |
| 7,332,484 B2 | 2/2008 | Singh et al. |
| 7,452,879 B2 | 11/2008 | Singh et al. |
| 7,485,724 B2 | 2/2009 | Singh et al. |
| 7,491,732 B2 | 2/2009 | Li et al. |
| 7,550,460 B2 | 3/2009 | Singh et al. |
| 7,563,892 B1 | 7/2009 | Singh et al. |
| 7,582,648 B2 | 9/2009 | Singh et al. |
| 7,642,351 B2 | 1/2010 | Singh et al. |
| 7,655,797 B2 | 2/2010 | Singh et al. |
| 7,803,939 B2 | 9/2010 | Singh et al. |
| 7,812,029 B1 | 10/2010 | Argade et al. |
| 7,834,024 B2 | 11/2010 | Li et al. |
| 7,851,480 B2 | 12/2010 | Cooper et al. |
| 7,915,273 B2 | 3/2011 | Argade et al. |
| 7,962,290 B1 | 6/2011 | Qu |
| 7,979,448 B2 | 8/2011 | Singh et al. |
| 8,163,902 B2 | 4/2012 | Bhamidipati et al. |
| 8,334,296 B2 | 12/2012 | Singh et al. |
| 8,399,472 B2 | 3/2013 | Li et al. |
| 8,415,365 B2 | 4/2013 | Li et al. |
| 8,735,400 B2 | 5/2014 | Chen et al. |
| 8,815,848 B2 | 8/2014 | Li et al. |
| 9,248,190 B2 | 2/2016 | Li et al. |
| 9,593,082 B2 | 3/2017 | Argade et al. |
| 9,732,073 B2 | 8/2017 | Li et al. |
| 10,421,752 B2 | 9/2019 | Li et al. |
| 11,198,689 B2 * | 12/2021 | Li ................. C07D 239/42 |
| 2001/0007033 A1 | 7/2001 | Tang et al. |
| 2002/0115173 A1 | 8/2002 | Ben-Sasson |
| 2002/0137141 A1 | 9/2002 | Ben-Sasson |
| 2003/0134838 A1 | 7/2003 | Bornemann et al. |
| 2003/0149064 A1 | 8/2003 | Pease |
| 2003/0236244 A1 | 12/2003 | Ledford |
| 2004/0029902 A1 | 2/2004 | Singh et al. |
| 2004/0102455 A1 | 5/2004 | Burns et al. |
| 2004/0142404 A1 | 7/2004 | Wilks et al. |
| 2004/0147507 A1 | 7/2004 | Ledeboer et al. |
| 2004/0214817 A1 | 10/2004 | Pierce et al. |
| 2005/0113398 A1 | 5/2005 | Argade et al. |
| 2005/0173743 A1 | 8/2005 | Leucking et al. |
| 2005/0192301 A1 | 9/2005 | Li et al. |
| 2005/0209224 A1 | 9/2005 | Singh et al. |
| 2005/0209230 A1 | 9/2005 | Singh et al. |
| 2005/0234049 A1 | 10/2005 | Singh et al. |
| 2005/0272753 A1 | 12/2005 | Nagashima et al. |
| 2006/0025410 A1 | 2/2006 | Singh et al. |
| 2006/0035891 A1 | 2/2006 | Li et al. |
| 2006/0035916 A1 | 2/2006 | Singh et al. |
| 2006/0058292 A1 | 3/2006 | Singh et al. |
| 2006/0058525 A1 | 3/2006 | Singh et al. |
| 2006/0111378 A1 | 5/2006 | Cleve et al. |
| 2006/0135543 A1 | 6/2006 | Singh et al. |
| 2006/0167249 A1 | 7/2006 | Argade et al. |
| 2006/0167254 A1 | 7/2006 | Cooper et al. |
| 2006/0211657 A1 | 9/2006 | Singh et al. |
| 2006/0234983 A1 | 10/2006 | Singh et al. |
| 2006/0270694 A1 | 11/2006 | Wong |
| 2007/0004626 A1 | 1/2007 | Masuda et al. |
| 2007/0060603 A1 | 3/2007 | Singh et al. |
| 2007/0117775 A1 | 5/2007 | Payan |
| 2007/0129360 A1 | 6/2007 | Bhamidipati et al. |
| 2007/0129362 A1 | 6/2007 | Bhamidipati et al. |
| 2007/0167439 A1 | 7/2007 | Singh et al. |
| 2007/0197782 A1 | 8/2007 | Clough et al. |
| 2007/0203161 A1 | 8/2007 | Argade et al. |
| 2007/0203162 A1 | 8/2007 | Li et al. |
| 2007/0225321 A1 | 9/2007 | Singh et al. |
| 2007/0225495 A1 | 9/2007 | Singh et al. |
| 2007/0293520 A1 | 12/2007 | Singh et al. |
| 2007/0293521 A1 | 12/2007 | Singh et al. |
| 2007/0293522 A1 | 12/2007 | Singh et al. |
| 2007/0293523 A1 | 12/2007 | Singh et al. |
| 2007/0293524 A1 | 12/2007 | Singh et al. |
| 2007/0299095 A1 | 12/2007 | Singh et al. |

(56) References Cited

U.S. PATENT DOCUMENTS

| | | |
|---|---|---|
| 2008/0039622 A1 | 2/2008 | Singh et al. |
| 2008/0194603 A1 | 2/2008 | Li et al. |
| 2008/0221089 A1 | 9/2008 | Argade et al. |
| 2008/0260754 A1 | 10/2008 | Li et al. |
| 2008/0279867 A1 | 11/2008 | Atuegbu et al. |
| 2008/0306099 A1 | 12/2008 | Li et al. |
| 2008/0312438 A1 | 12/2008 | Singh et al. |
| 2009/0124580 A1 | 5/2009 | Singh et al. |
| 2009/0156622 A1 | 6/2009 | Singh et al. |
| 2010/0130486 A1 | 5/2010 | Singh et al. |
| 2010/0152218 A1 | 6/2010 | Argade et al. |
| 2013/0142807 A1 | 6/2013 | Li et al. |

FOREIGN PATENT DOCUMENTS

| | | |
|---|---|---|
| CN | 87210811 | 4/1988 |
| WO | WO 95/03701 | 2/1995 |
| WO | WO 99/15500 | 4/1999 |
| WO | WO 99/41253 | 8/1999 |
| WO | WO 00/00202 | 1/2000 |
| WO | WO 00/10981 | 3/2000 |
| WO | WO 00/12485 | 3/2000 |
| WO | WO 00/27825 | 5/2000 |
| WO | WO 00/39101 | 7/2000 |
| WO | WO 00/47583 | 8/2000 |
| WO | WO 00/51587 | 9/2000 |
| WO | WO 00/55159 | 9/2000 |
| WO | WO 00/78731 | 12/2000 |
| WO | WO 01/42246 | 6/2001 |
| WO | WO 01/45641 | 6/2001 |
| WO | WO 01/47897 | 7/2001 |
| WO | WO 01/52892 | 7/2001 |
| WO | WO 01/54564 | 8/2001 |
| WO | WO 01/56993 | 8/2001 |
| WO | WO 01/57022 | 8/2001 |
| WO | WO 01/60816 | 8/2001 |
| WO | WO 01/64654 | 9/2001 |
| WO | WO 01/64655 | 9/2001 |
| WO | WO 01/64656 | 9/2001 |
| WO | WO 01/72758 | 10/2001 |
| WO | WO 01/85699 | 11/2001 |
| WO | WO 01/85700 | 11/2001 |
| WO | WO 02/00661 | 1/2002 |
| WO | WO 02/04429 | 1/2002 |
| WO | WO 02/43735 | 6/2002 |
| WO | WO 02/48336 | 6/2002 |
| WO | WO 02/50066 | 6/2002 |
| WO | WO 02/059110 | 8/2002 |
| WO | WO 02/059112 | 8/2002 |
| WO | WO 02/060492 | 8/2002 |
| WO | WO 02/060927 | 8/2002 |
| WO | WO 02/062789 | 8/2002 |
| WO | WO 02/066461 | 8/2002 |
| WO | WO 02/066480 | 8/2002 |
| WO | WO 02/066481 | 8/2002 |
| WO | WO 02/096888 | 12/2002 |
| WO | WO 02/096909 | 12/2002 |
| WO | WO 02/102313 | 12/2002 |
| WO | WO 02/102800 | 12/2002 |
| WO | WO 03/000186 | 1/2003 |
| WO | WO 03/002542 | 1/2003 |
| WO | WO 03/016306 | 2/2003 |
| WO | WO 03/018021 | 3/2003 |
| WO | WO 03/018022 | 3/2003 |
| WO | WO 03/020698 | 3/2003 |
| WO | WO 03/026664 | 4/2003 |
| WO | WO 03/030909 | 4/2003 |
| WO | WO 03/032994 | 4/2003 |
| WO | WO 03/032997 | 4/2003 |
| WO | WO 03/048133 | 6/2003 |
| WO | WO 03/048162 | 6/2003 |
| WO | WO 03/063794 | 8/2003 |
| WO | WO 03/066601 | 8/2003 |
| WO | WO 03/074515 | 9/2003 |
| WO | WO 03/076437 | 9/2003 |
| WO | WO 03/078404 | 9/2003 |
| WO | WO 03/094920 | 11/2003 |
| WO | WO 03/101989 | 12/2003 |
| WO | WO 03/106416 | 12/2003 |
| WO | WO 2004/014382 | 2/2004 |
| WO | WO 2004/016597 | 2/2004 |
| WO | WO 2004/026406 | 4/2004 |
| WO | WO 2004/041789 | 5/2004 |
| WO | WO 2004/041810 | 5/2004 |
| WO | WO 2004/041814 | 5/2004 |
| WO | WO 2004/043467 | 5/2004 |
| WO | WO 2004/043953 | 5/2004 |
| WO | WO 2004/046112 | 6/2004 |
| WO | WO 2004/046118 | 6/2004 |
| WO | WO 2004/046120 | 6/2004 |
| WO | WO 2004/047843 | 6/2004 |
| WO | WO 2004/058749 | 7/2004 |
| WO | WO 2004/058753 | 7/2004 |
| WO | WO 2004/069812 | 8/2004 |
| WO | WO 2004/074244 | 9/2004 |
| WO | WO 2004/080980 | 9/2004 |
| WO | WO 2004/742621 | 9/2004 |
| WO | WO 2004/085388 | 10/2004 |
| WO | WO 2004/092154 | 10/2004 |
| WO | WO 2004/099159 | 11/2004 |
| WO | WO 2004/101549 | 11/2004 |
| WO | WO 2004/101564 | 11/2004 |
| WO | WO 2004/007621 | 1/2005 |
| WO | WO 2005/007646 | 1/2005 |
| WO | WO 2005/009957 | 2/2005 |
| WO | WO 2005/009980 | 2/2005 |
| WO | WO 2005/012262 | 2/2005 |
| WO | WO 2005/012294 | 2/2005 |
| WO | WO 2005/012304 | 2/2005 |
| WO | WO 2005/012307 | 2/2005 |
| WO | WO 2005/013996 | 2/2005 |
| WO | WO 2005/016344 | 2/2005 |
| WO | WO 2005/016893 | 2/2005 |
| WO | WO 2005/016894 | 2/2005 |
| WO | WO 2005/026130 | 3/2005 |
| WO | WO 2005/026158 | 3/2005 |
| WO | WO 2005/028467 | 3/2005 |
| WO | WO 2005/028475 | 3/2005 |
| WO | WO 2005/028479 | 3/2005 |
| WO | WO 2005/033107 | 4/2005 |
| WO | WO 2005/037800 | 4/2005 |
| WO | WO 2005/051366 | 6/2005 |
| WO | WO 2005/061458 | 7/2005 |
| WO | WO 2005/066156 | 7/2005 |
| WO | WO 2005/075468 | 8/2005 |
| WO | WO 2005/080393 | 9/2005 |
| WO | WO 2005/107760 | 11/2005 |
| WO | WO 2005/118544 | 12/2005 |
| WO | WO 2006/034872 | 4/2006 |
| WO | WO 2006/035068 | 4/2006 |
| WO | WO 2006/074057 | 7/2006 |
| WO | WO 2006/078846 | 7/2006 |
| WO | WO 2006/129100 | * 12/2006 |
| WO | WO 2006/133426 | 12/2006 |
| WO | WO 2007/006926 | 1/2007 |
| WO | WO 2007/053452 | 5/2007 |
| WO | WO 2007/085540 | 8/2007 |
| WO | WO 2007/098507 | 8/2007 |
| WO | WO 2007/107318 | 9/2007 |
| WO | WO 2009/003136 | 12/2008 |
| WO | WO 2009/007839 | 1/2009 |

OTHER PUBLICATIONS

Banker et al., *Prodrugs, Modern Pharmaceuticals*, 3$^{rd}$ ed., Revised and Expanded, pp. 451 and 596, 1996
Bean-Knudsen et al., "Porcine mast cell leukemia with systemic mastocytosis," *Vet. Pathol.* 26(1):90-92, 1989.
Blair et al., "Lack of expression of Thy-1 (CD90) on acute myeloid leukemia cells with long-term proliferative ability in vitro and in vivo," *Blood* 89(9):3104-3112, 1997.
Boloor et al., CAPLUS Abstract, 137:140534, 2002.

(56) References Cited

OTHER PUBLICATIONS

Borie et al., "JAK3 inhibition, a viable new modality of immunosuppression of solid organ transplants," *Trends in Molecular Medicine* 10(11):532-541, 2004.
Bundgaard, "Design of prodrugs: Bioreversible derivatives for various functional groups and chemical entities," *Design of Prodrugs*, Elsevier Science Publishers B.V., Introduction, p. 1, 1985.
Bundgaard et al., "A novel solution-stable, water-soluble prodrug type for drugs containing a hydroxyl or an NH-acidic group," *J. Med. Chem.* 32(12):2503-2507, 1989.
Carreras et al., "Activated T cells in an animal model of allergic conjunctivitis," *Br. J. Ophthalmol* 77(8):509-514, 1993.
Casanova et al., PubMed Abstract, *Rev. Neurol.* 28(9):909-915, May 1999.
Catlett-Falcone et al., "Constitutive activation of Stat3 signaling confers resistance to apoptosis in human U266 myeloma cells," *Immunity* 10(1):105-115, 1999.
Cetkovic-Cvrlje et al., "Therapeutic potential of Janus kinase 3 (JAK3) inhibitors," *Current Pharmaceutical Design* 10(15) 1767-1784, 2004.
Chan et al., "Expression of interleukin-4 in the epidermis of transgenic mice results in a pruritic inflammatory skin disease: an experimental animal model to study atopic dermatitis," *J. Invest. Dermatol.* 117(4):977-983, 2001.
Chang et al., "JAK3 Inhibition Significantly Attenuates Psoriasiform Skin Inflammation in CD18 Mutant PL/J Mice, " *The Journal of Immunology* 183:2183-2192, 2009.
Changleian, "Prevention of organ allograft rejection by a specific Janus kinase 3 inhibitor," *Science* 302(5646):875-878, 2003.
Claman et al., "Immunoglobulin dysregulation in murine graft-vs-host disease: a hyper-IgE syndrome," *Clin. Immunol. Immunopathol.* 56(1):46-53, 1990.
Damasio, "Alzheimer's Disease and Related Dementias," *Cecil Textbook of Medicine*, 20$^{th}$ ed., 2:1992-1996, 1996.
Demoulin et al., "A single tyrosine of the interleukin-9 (IL-9) receptor is required for STAT activation, antiapoptotic activity, and growth regulation by IL-9," *Mol. Cell. Biol.* 16(9):4710-4716, 1996.
Deuse et al., "Novel Immunosuppression: R348, a JAK3- and Syk-Inhibitor Attenuates Acute Cardiac Allograft Rejection, " *Transplantation* 86(6):885-892, Mar. 27, 2008.
El-Kerdawy et al., "2,4-Bis (Substituted)-5-Nitropyrimidines of Expected Diuretic action," *Egypt. J. Chem.* 29(2):247-251, 1986.
Ettmayer et al., "Lessons learned from marketed and investigational prodrugs," *J. Med. Chem.* 47(10):2393-2404, 2004.
Foster, "The pathophysiology of ocular allergy: current thinking," *Allergy* 50(21Suppl):6-9, 1995.
Frank, "STAT signaling in the pathogenesis and treatment of cancer," *Mol. Med.* 5(7):432-456, 1999.
Garcia-Bustos et al., "PIK1, an essential phosphatidylinositol 4-kinase associated with the yeast nucleus," *EMBO J.* 13(10):2352-2361, 1994.
Getts et al., "Current landscape for T-cell targeting in autoimmunity and transplantation," *Immunotherapy* 3(7):853-870, 2011.
Ghosh, "2,4-Bis(arylamino)pryimidines as Antimicrobial Agents," *Journal of Medicinal Chemistry* 9:423-424, 1966.
Gura et al., "Systems for identifying new drugs are often faulty," *Science* 278:1041-1042, 1997.
Hakim et al, "A nine-amino acid peptide from IL-1beta augments antitumor immune responses induced by protein and DNA vaccines," *J. Immunol.* 157(12):5503-5511, 1996.
Hanks et al., "Protein kinases 6. The eukaryolic protein kinase superfamily: kinase (catalytic) domain structure and classification," *FASEB J.* 9(8):576-596, 1995.
Harkiolaki et al., "T Cell-Mediated Autoimmune Disease Due to Low-Affinity Crossreactivity to Common Microbial Peptides," *Immunity* 30:348-357, 2009.
Hiles et al., "Phosphatidylinositol 3-kinase: structure and expression of the 110 kd catalytic subunit," *Cell* 70(3):419-429, 1992.

Hough et al., "A model for spontaneous B-lineage lymphomas in IgHmu-HOX11 transgenic mice," *Proc. Nat. Acad. Sci. USA* 95(23):13853-13858, 1998.
Johnson et al., "Relationships between drug activity in NCI preclinical in vitro and in vivo models and early clinical trials," *British Journal of Cancer* 84(10): 1424-1431, 2001.
Jurlander et al., "Characterizations of interleukin-10 receptor expression on B-cell chronic lymphocytic leukemia cells," *Blood* 89(11):4146-4152, 1997.
Kaneko et al., "Rescue by cytokines of apoptotic cell death induced by IL-2 deprivation of human antigen-specific T cell clones," *Clin. Exp. Immun.* 109(1):185-193, 1997.
Kawaguchi et al., "Nasal mast cells in experimentally induced allergic rhinitis in guinea-pigs," *Clin. Exp. Allergy* 24(3):238-244, 1994.
Kirken, "Targeting Jak3 for immune suppression and allograft acceptance," *Transpl. Proc.* 33(7-8):3268-3270, 2001.
Knighton et al., "Crystal structure of the catalytic subunit of cyclic adenosine monophosphate-dependent protein kinase," *Science* 253(5018):407-414, 1991.
Kudlacz et al., "The novel Jak-3 inhibitor CP-690550 is a potent immunosuppressive agent in various murine models," *Am. J. Transplant* 4(1):51-57, 2004.
Kunert et al., "Alternation of goblet cell numbers and mucin gene expression in a mouse model of allergic conjunctivitis," *Invest. Ophthalmol. Vis. Sci.* 42(11):2483-2489, 2001.
Kuno et al., "Constructive kinase activation of the TEL-Syk fusion gene in myelodysplastic syndrome with t(9,12)(q22;p12)," *Blood* 97(4):1050-1055, 2001.
Kunz et al., "Target of rapamycin in yeast, TOR2 is an essential phosphatidylinositol kinase homolog required for G1 progression," *Cell* 73(3):585-596, 1993.
Layzer, "Degenerative diseases of the Nervous System," *Cecil Textbook of Medicine* 20$^{th}$ ed., 2:2050-2057, 1996.
Leonard et al., "Cytokine receptor signaling pathways," *J. Allergy Clin. Immunol.* 105(5):877-888, 2000.
Levine et al., "Myeloproliferative Disorders," *Blood* 112(6):2190-2198, 2008.
Luo et al., "Inhibitors of JAKs/STATs and the kinases: a possible new cluster of drugs," *Drug Discovery Today* 9(6):268-275, Mar. 2004.
Malaviya et al., "Genetic and biochemical evidence for a critical role of Janus kinase (Jak)-3 in mast cell mediated type I hypersensitivity reactions," *Biochem. Biophys. Res. Commun.* 257(3):807-813, 1999.
Malavinya et al., "Targeting Janus kinase 3 in mast cells prevents immediate hypersensitivity reactions and anaphylaxis," *J. Biol. Chem.* 274(38):27028-27038, 1999.
Mocsai et al.,"Syk is required for integrin signaling in neutrophils," *Immunity* 16(4):547-558, 2002.
Muller-Ladner et al., "Activation of the IL-4 STAT pathway in rheumatoid synovium," *J. Immunol.* 167(7):3894-3901, 2000.
Nakamura et al., "An epidermal growth factor receptor/Jak2 tyrosine kinase domain chimera induces tyrosine phosphorylation of Stat5 and transduces a growth signal in hematopoietic cells," *J. Biol. Chem.* 271(32):19483-19488, 1996.
Nelson et al., "Constitutive activation of a slowly migrating isoform of Stat3 in mycosis fungoides: tyrphostin AG490 inhibits Stat3 activation and growth of mycosis fungoides tumor cell lines," *Proc. Natl. Acad. Sci. USA* 94(13):6764-6769, 1997.
O'Keefe et al.,"Systemic mastocytosis in 16 dogs," *J. Vet. Intern. Med.* 1(2):75-80, 1987.
O'Shea et al., "A new modality for immunosuppression: targeting the JAK/STAT pathway," *Nature Reviews Drug Discovery* 3(7):555-564, 2004.
Passegue et al., "Normal and leukemic hematopoiesis: are leukemias a stem cell disorder or a reacquisition of stem cell characteristics?" *Proc. Natl. Acad. Sci. USA* 100(Suppl 1):11842-11849, 2003.
Pearce et al., "Failure modes in anticancer drug discovery and development," *Cancer Drug Design and Discovery*, edited by Stephen Neidle, Chapter 18, pp. 424-435, 2008.
Rajinder et al., CAPLUS Abstract, 124:219300, 2005.

(56) References Cited

OTHER PUBLICATIONS

Saiga et al., "Clinical and cytologic aspects of ocular late-phase reaction in the guinea pig," *Ophthalmic Res.* 24(1):45-50, 1992.
Sammond et al., "Discovery of a novel and potent series of dianilinopyrimidineurea and urea isostere inhibitors of VEGFR2 tyrosine kinase," *Bioorganic & Medicinal Chemistry Letters* 15(15):3519-3623, 2005.
Seidel et al., "Pharmaceutical intervention in the JAK/STAT signaling pathway," *Oncogene* 19(21):2645-2656, 2000.
Silverman, "Prodrugs and drug delivery systems," *The Organic Chemistry of Drug Design and Drug Action*, Academic Press, Inc., pp. 352-400, 1992.
Simone, "Oncology: Introduction," *Cecil Textbook of Medicine*, 20th ed., 1:1004-1010, 1996.
Singh et al., CAPLUS Abstract, 140:199334, 2004.
Sudbeck et al., "Structure-based design of specific inhibitors of Janus kinase 3 as apoptosis-inducing antileukemic agents," *Clin. Cancer Res.* 5(6):1569-1582, 1999.
Sugimoto et al., "A new model of allergic rhinitis in rats by topical sensitization and evaluation of H91)-receptor antagonists," *Immunopharmacology* 48(1):1-7, 2000.
Suto et al., "NC/Nga mice: a mouse model for atopic dermatitis," *Int. Arch. Allergy Immunol* 120(Suppl 1):70-75, 1999.
Suzuki et al., "Role of common cytokine receptor gamma chain (gamma(c))- and Jak3-dependent signaling in the proliferation and survival of murine mast cells," *Blood* 96(6):2171-2180, 2000.
Szelenyi et al., "Animal models of allergic rhinitis," *Arzneimittelforschung* 50(11):1037-1042, 2000.
The Non-Hodgkin's Lymphoma Pathologic Classification Project, "National Cancer Institute sponsored study of classifications of non-Hodgkin's lymphomas: summary and description of a working formulation for clinical usage," *Cancer* 49(10):2112-2135, 1982.
Traxler, "Protein Tyrosine Kinase inhibitors in cancer treatment," *Exp. Opin. Ther. Patents* 7(6):571-588, 1997.
Trieu et al., "A specific inhibitor of janus kinase-3 increases survival in a transgenic mouse model of amyotrophic lateral sclerosis," *Biochem Biophys. Res. Commun.* 267(1):22-25, 2000.
Tumas et al., "Anti-IgE efficacy in murine asthma models is dependent on the method of allergen sensitization," *J. Allergy Clin. Immunol.* 107(6):1025-1033, 2001.
Turhan et al., "Highly purified primitive hematopoietic stem cells are PML:RARA negative and generate nonclonal progenitors in acute promyelocytic leukemia," *Blood* 85(8):2154-2161, 1995.
Turner et al., "Tyrosine kinase SYK: essential functions for immunoreceptor signaling," *Immunology Today* 21:148-154, 2000.
Ulrich, "Crystallization," *Kirk-Othmaer Encyclopedia of Chemical Technology*, John Wiley & Sons, Inc., Chapter 4: Crystal Characteristics, 2002.
Velotta et al., "A Novel JAK3 Inhibitor, R348, Attenuates Chronic Airway Allograft Rejection," *Transplantation* 87(5):653-659, Mar. 15, 2009.
Versotovsek, "Therapeutic potential of JAK2 inhibitors," *Hematology*, American Society of Hematology Education Program Book, pp. 636-642, 2009.
Vippagunta et al.,"Crystalline Solids," *Advanced Drug Delivery Reviews* 48:3-26, 2001.
West, "Solid State Chemistry and its Applications," Wiley, New York, Ny, pp. 358, 365, 1988.
Wolff, "Some Consideration for Prodrug Design," *Burger's Medicinal Chemistry and Drug Discovery*, 5th ed., vol. 1, Principles and Practices, pp. 975-977, 1995.
Yu, "Constitutive activation of the Janus kinase-STAT pathway in T lymphoma overexpressing the Lck protein tyrosine kinase," *J. Immunol* 159(11):5206-5210, 1997.

\* cited by examiner

COMPOSITIONS AND METHODS FOR INHIBITION OF THE JAK PATHWAY

I. CROSS REFERENCE TO RELATED APPLICATIONS

This is a continuation of U.S. patent application Ser. No. 16/551,393, filed on Aug. 26, 2019, which is a continuation of U.S. patent application Ser. No. 15/637,833, filed on Jun. 29, 2017, issued as 10,421,752, which is a continuation of U.S. patent application Ser. No. 14/974,143, filed on Dec. 18, 2015, issued as U.S. Pat. No. 9,732,073, which is a continuation of U.S. patent application Ser. No. 14/315,073, filed on Jun. 25, 2014, issued as U.S. Pat. No. 9,248,190, which is a continuation of Ser. No. 13/750,632, filed on Jan. 25, 2013, issued as U.S. Pat. No. 8,815,848, which is a divisional of U.S. patent application Ser. No. 12/193,627, filed on Aug. 18, 2008, issued as U.S. Pat. No. 8,399,472, which is a continuation of U.S. patent application Ser. No. 11/450,901, filed on Jun. 8, 2006, issued as U.S. Pat. No. 7,491,732, which claims the benefit of U.S. provisional application No. 60/689,032, filed on Jun. 8, 2005, U.S. provisional application No. 60/706,638, filed on Aug. 8, 2005, and U.S. Provisional application No. 60/776,636, filed on Feb. 24, 2006.

II. INTRODUCTION

A. Field

The present disclosure relates to compounds, prodrugs, and methods of using these compounds and prodrugs thereof in the treatment of conditions in which modulation of the JAK pathway or inhibition of JAK kinases, particularly JAK3, may be therapeutically useful.

B. Background

Protein kinases constitute a large family of structurally related enzymes that are responsible for the control of a variety of signal transduction processes within cells (see e.g., Hardie and Hanks, *The Protein Kinase Facts Book, I and II*, Academic Press, San Diego, CA, 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these families (see, e.g., Hanks & Hunter, (1995), *FASEB J.* 9:576-596; Knighton et al., (1991), *Science* 253:407-414; Hiles et al., (1992), *Cell* 70:419-429; Kunz et al., (1993), *Cell* 73:585-596; Garcia-Bustos et al., (1994), *EMBO J.* 13:2352-2361).

JAK kinases (JAnus Kinases) are a family of cytoplasmic protein tyrosine kinases including JAK1, JAK2, JAK3 and TYK2. Each of the JAK kinases is selective for the receptors of certain cytokines, though multiple JAK kinases may be affected by particular cytokine or signaling pathways. Studies suggest that JAK3 associates with the common gamma (γc) chain of the various cytokine receptors. JAK3 in particular selectively binds to receptors and is part of the cytokine signaling pathway for IL-2, IL-4, IL-7, IL-9, IL-15 and IL-21. JAK1 interacts with, among others, the receptors for cytokines IL-2, IL-4, IL-7, IL-9 and IL-21, while JAK2 interacts with, among others, the receptors for IL-9 and TNF-α. Upon binding of certain cytokines to their receptors (e.g., IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

Phosphorylated JAK kinases bind various STAT (Signal Transducer and Activator of Transcription) proteins. STAT proteins, which are DNA binding proteins activated by phosphorylation of tyrosine residues, function both as signaling molecules and transcription factors and ultimately bind to specific DNA sequences present in the promoters of cytokine-responsive genes (Leonard et al., (2000), *J. Allergy Clin. Immunol.* 105:877-888). JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas. For a review of the pharmaceutical intervention of the JAK/STAT pathway see Frank, (1999), *Mol. Med.* 5:432:456 and Seidel et al., (2000), *Oncogene* 19:2645-2656.

JAK3 in particular has been implicated in a variety of biological processes. For example, the proliferation and survival of murine mast cells induced by IL-4 and IL-9 have been shown to be dependent on JAK3- and gamma chain-signaling (Suzuki et al., (2000), *Blood* 96:2172-2180). JAK3 also plays a crucial role in IgE receptor-mediated mast cell degranulation responses (Malaviya et al., (1999), *Biochem. Biophys. Res. Commun.* 257:807-813), and inhibition of JAK3 kinase has been shown to prevent type I hypersensitivity reactions, including anaphylaxis (Malaviya et al., (1999), *J. Biol. Chem.* 274:27028-27038). JAK3 inhibition has also been shown to result in immune suppression for allograft rejection (Kirken, (2001), *Transpl. Proc.* 33:3268-3270). JAK3 kinases have also been implicated in the mechanism involved in early and late stages of rheumatoid arthritis (Muller-Ladner et al., (2000), *J. Immunal.* 164:3894-3901); familial amyotrophic lateral sclerosis (Trieu et al., (2000), *Biochem Biophys. Res. Commun.* 267:22-25); leukemia (Sudbeck et al., (1999), *Clin. Cancer Res.* 5:1569-1582); mycosis fungoides, a form of T-cell lymphoma (Nielsen et al., (1997), *Prac. Natl. Acad. Sci. USA* 94:6764-6769); and abnormal cell growth (Yu et al., (1997), *J. Immunol.* 159:5206-5210; Catlett-Falcone et al., (1999), *Immunity* 10:105-115).

The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., (1996), *Mol. Cell. Biol.* 16:4710-6; Jurlander et al., (1997), *Blood.* 89:4146-52; Kaneko et al., (1997), *Clin. Exp. Immun.* 109:185-193; and Nakamura et al., (1996), *J. Biol. Chem.* 271:19483-8). They are also known to be important to lymphocyte differentiation, function and survival. JAK-3 in particular plays an essential role in the function of lymphocytes, macrophages, and mast cells. Given the importance of this JAK kinase, compounds which modulate the JAK pathway, including those selective for JAK3, can be useful for treating diseases or conditions where the function of lymphocytes, macrophages, or mast cells is involved (Kudlacz et al., (2004) *Am. J. Transplant* 4:51-57; Changelian (2003) *Science* 302:875-878). Conditions in which targeting of the JAK pathway or modulation of the JAK kinases, particularly JAK3, may be therapeutically useful include, leukemia, lymphoma, transplant rejection (e.g. pancreas islet transplant rejection, bone marrow transplant applications (e.g. graft-versus-host disease), autoimmune diseases (e.g. diabetes), and inflammation (e.g. asthma, allergic reactions). Conditions which may benefit from inhibition of JAK3 are discussed in greater detail below.

In view of the numerous conditions that may benefit by treatment involving modulation of the JAK pathway, it is immediately apparent that new compounds that modulate JAK pathways and methods of using these compounds should provide substantial therapeutic benefit to a wide variety of patients. Provided herein are novel 2,4-substituted pyrimidinediamine compounds for use in the treatment of conditions in which targeting of the JAK pathway or inhibition of JAK kinases, particularly JAK3, may be therapeutically useful.

Patents and patent applications related to modulation of the JAK pathway include: U.S. Pat. Nos. 5,728,536; 6,080,747; 6,080,748; 6,133,305; 6,177,433; 6,210,654; 6,313,130; 6,316,635; 6,433,018; 6,486,185; 6,506,763; 6,528,509; 6,593,357; 6,608,048; 6,610,688; 6,635,651; 6,677,368; 6,683,082; 6,696,448; 6,699,865; 6,777,417; 6,784,195; 6,825,190; U.S. Pat. App. Pub. No. 2001/0007033 A1; 2002/0026053 A1; 2002/0115173 A1; 2002/0137141 A1; 2002/0151574 A1; 2003/0040536 A1; 2003/0065180 A1; 2003/0069430 A1; 2003/0225151 A1; 2003/0236244 A1; 2004/0009996 A1; 2004/0072836 A1; 2004/0082631 A1; 2004/0102455 A1; 2004/0102506 A1; 2004/0127453 A1; 2004/0142404 A1; 2004/0147507 A1; 2004/0186157 A1; 2004/0205835 A1; and 2004/0214817 A1; and International patent applications WO 95/03701A1; WO 99/15500A1; WO 00/00202A1; WO 00/10981A1; WO 00/47583A1; WO 00/51587A2; WO 00/55159A2; WO 01/42246A2; WO 01/45641A2; WO 01/52892A2; WO 01/56993A2; WO 01/57022A2; WO 01/72758 A1; WO 02/00661A1; WO 02/43735A1; WO 02/48336A2; WO 02/060492A1; WO 02/060927A1; WO 02/096909A1; WO 02/102800A1; WO 03/020698A2; WO 03/048162A1; WO 03/101989A1; WO 04/016597A2; WO 04/041789A1; WO 04/041810A1; WO 04/041814A1; WO 04/046112A2; WO 04/046120A2; WO 04/047843A1; WO 04/058749A1; WO 04/058753A1; WO 04/085388A2; WO 04/092154A1; WO 05/009957A1; WO 05/016344A1; WO 05/028475A2; and WO 05/033107A1.

Patents and patent applications describing substituted pyrimidinediamine compounds include: U.S. Pat. App. Pub. No. 2004/0029902 A1; 2005/0234049 A1, and published International applications WO 03/063794, WO 04/014382, and WO 05/016893, the disclosures of which are incorporated herein by reference. Substituted pyrimidinediamine compounds are also described in international patent application publication numbers: WO 02/059110, WO 03/074515, WO 03/106416, WO 03/066601, WO 03/063794, WO 04/046118, WO 05/016894, WO 05/0122294, WO 05/066156, WO 03/002542, WO 03/030909, WO 00/039101, WO 05/037800 and U.S. Pat. Pub. No. 2003/0149064.

All of the above publications are herein incorporated by reference in their entirety to the same extent as if each individual publication was specifically and individually indicated to be incorporated by reference in its entirety.

III. SUMMARY OF THE INVENTION

This invention is directed to compounds, prodrugs, and methods of using these compounds and prodrugs thereof in the treatment of conditions in which modulation of the JAK pathway or inhibition of JAK kinases, particularly JAK3, may be therapeutically useful.

One embodiment of the invention provides compounds or solvates, prodrugs or pharmaceutically acceptable salts of compounds of formula I:

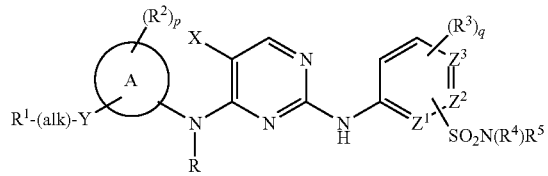

I wherein:
X is selected from the group consisting of alkyl, substituted alkyl, alkoxy, substituted alkoxy, amino, substituted amino, carboxyl, carboxyl ester, cyano, halo, nitro, alkenyl, substituted alkenyl, alkynyl and substituted alkynyl;
R is selected from the group consisting of hydrogen, alkyl, substituted alkyl, alkenyl, substituted alkenyl, alkynyl, substituted alkynyl, cycloalkyl and substituted cycloalkyl;
ring A is selected from the group consisting of aryl, heteroaryl, cycloalkyl, cycloalkenyl and heterocyclic, wherein ring A is not indolyl or benzimidazolyl;
Y is selected from the group consisting of a bond, $-NR^7-$, $-C(O)NR^7-$, $-NR^7C(O)-$, $-NR^7C(O)O-$, $-OC(O)NR^7-$, $-NR^7C(O)NR^7-$, oxygen and sulfur, where $R^7$ is independently hydrogen, alkyl or substituted alkyl;
alk is a bond or a straight or branched chain alkylene group, wherein when alk and Y each are a bond then $R^1$ is attached to ring A by a single covalent bond;
$R^1$ is selected from the group consisting of cyano, acylamino, aminoacyl, aryl, substituted aryl, carboxyl, carboxyl ester, carboxyl ester oxy, heteroaryl, substituted heteroaryl, heterocyclic, substituted heterocyclic, acyl, aminoacyloxy, and aminocarbonylamino; or
$R^1$-alk-Y— is $R^{10}$—C(O)—S-alk-C(O)—, wherein alk is as defined herein and $R^{10}$ is alkyl or substituted alkyl; or
$R^1$-alk-Y— is $R^{11}R^{12}NS(O)_2-$, wherein $R^{11}$ and $R^{12}$ independently are alkyl or substituted alkyl;
p is 0, 1, 2 or 3 when ring A is a single ring or p is 0, 1, 2, 3, 4, or 5 when ring A comprises multiple rings;
each $R^2$ independently is selected from the group consisting of alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro, and halo, or two of $R^2$ on the same carno form an oxo (═O);
$Z^1$, $Z^2$, and $Z^3$ each independently is carbon or nitrogen, wherein if $Z^1$ is nitrogen then $Z^2$ and $Z^3$ are carbon, if $Z^2$ is nitrogen then $Z^1$ and $Z^3$ are carbon, and if $Z^3$ is nitrogen then $Z^1$ and $Z^2$ are carbon, wherein if $Z^1$, $Z^2$, or $Z^3$ is nitrogen then $SO_2R^4R^5$ is not attached to the nitrogen;

q is 0, 1, 2 or 3;

each $R^3$ independently is selected from the group consisting of hydrogen, alkyl, substituted alkyl, alkoxy, substituted alkoxy, cycloalkyl or substituted cycloalkyl, halo, heterocyclic and substituted heterocyclic;

$R^4$ and $R^5$ independently are selected from the group consisting of hydrogen, alkyl, substituted alkyl, acyl and $M^+$, wherein $M^+$ is a metal counterion selected from the group consisting of $K^+$, $Na^+$, $Li^++$ or $^+N(R^6)_4$, wherein $R^6$ is hydrogen or alkyl, and the nitrogen of $SO_2NR^4R^5$ is $N^-$; or $R^4$ or $R^5$ is a divalent counterion selected from the group consisting of $Ca^+$, $Mg^{2+}$, and $Ba^{2+}$, and the nitrogen of $SO_2NR^4R^5$ is $N^-$; or $R^4$ and $R^5$ together with the nitrogen atom bound thereto, form a heterocyclic or substituted heterocyclic group; or when q is 1, 2 or 3, $R^5$ can be joined with one $R^3$ group bound alpha thereto, to form a fused ring as illustrated in formula II:

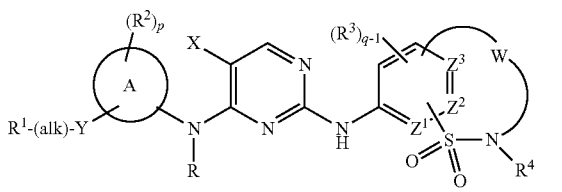

II wherein W is selected from the group consisting of $C_1$-$C_3$ alkylene, substituted $C_1$-$C_3$ alkylene, $C_2$-$C_3$ alkenylene and substituted $C_2$-$C_3$ alkenylene wherein one or more of the carbon atoms have been replaced with a moiety selected from oxygen, sulfur, S(O), S(O)$_2$, C(O), or $NR^8$ where $R^8$ is selected from the group consisting of hydrogen and alkyl or is a bond participating in a —N=C< site of unsaturation;

provided that:

when alk is a bond and Y is a bond, then $R^1$ is not cyano, carboxyl, carboxyl ester, or aminoacarbonylamino;

when alk is —CH$_2$—, Y is oxygen and $R^1$ is phenyl, ring A is not cycloalkyl;

when alk is a bond, Y is a bond, ring A is phenyl, then $R^1$ is not heterocyclic, substituted heterocyclic or aminoacyloxy;

when Y or $R^1$-alk-Y— provide for direct linkage of either —NR$^7$C(O)O— or —NR$^7$C(O)NR$^7$— to ring A, then $R^7$ is hydrogen; and when Y is —C(O)NR$^7$—, —NR$^7$C(O)—, —OC(O)NR$^7$—, —NR$^7$C(O)O— or —NR$^7$C(O)NR$^7$— and alk is a bond, then $R^1$ is not acyl, acylamino, aminoacyl or aminocarbonylamino.

Another embodiment of the invention provides compounds, or solvates, prodrugs of pharmaceutical acceptable salts of compounds of formula III:

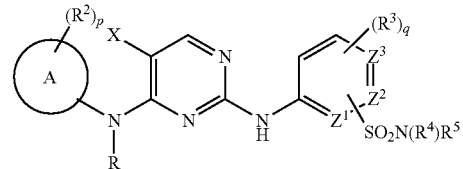

III where:

X is selected from the group consisting of alkyl, substituted alkyl, alkoxy, substituted alkoxy, amino, substituted amino, carboxyl, carboxyl ester, cyano, halo, nitro, alkenyl, substituted alkenyl, alkynyl and substituted alkynyl;

R is selected from the group consisting of hydrogen, alkyl, substituted alkyl, alkenyl, substituted alkenyl, alkynyl, substituted alkynyl, cycloalkyl and substituted cycloalkyl;

ring A is selected from the group consisting of aryl, heteroaryl, cycloalkyl, cycloalkenyl and heterocyclic, wherein ring A is not indolyl or benzimidazolyl;

p is 0, 1, 2 or 3;

each $R^2$ independently is selected from the group consisting of alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, sulfonyl, oxo, nitro and halo;

$Z^1$, $Z^2$, and $Z^3$ each independently is carbon or nitrogen, wherein if $Z^1$ is nitrogen then $Z^2$ and $Z^3$ are carbon, if $Z^2$ is nitrogen then $Z^1$ and $Z^3$ are carbon, and if $Z^3$ is nitrogen then $Z^1$ and $Z^2$ are carbon, wherein if $Z^1$, $Z^2$, or $Z^3$ is nitrogen then $SO_2R^4R^5$ is not attached to the nitrogen;

q is 0, 1, 2 or 3;

each $R^3$ independently is selected from the group consisting of hydrogen, alkyl, substituted alkyl, alkoxy, substituted alkoxy, cycloalkyl or substituted cycloalkyl, halo, heterocyclic and substituted heterocyclic;

$R^4$ and $R^5$ independently are selected from the group consisting of hydrogen, alkyl, substituted alkyl, acyl and $M^+$, wherein $M^+$ is a metal counterion selected from the group consisting of $K^+$, $Na^+$, $Li^+$ or $^+N(R^6)_4$, wherein $R^6$ is hydrogen or alkyl, and the nitrogen of $SO^2NR^4R^5$ is $N^-$; or $R^4$ or $R^5$ is a divalent counterion selected from the group consisting of $Ca^{2+}$, $Mg^{2+}$, and $Ba^{2+}$, and the nitrogen of $SO_2NR^4R^5$ is $N^-$; or $R^4$ and $R^5$ together with the nitrogen atom bound thereto, form a heterocyclic or substituted heterocyclic group; or when q is 1, 2 or 3, $R^5$ can be joined with one $R^3$ group bound alpha thereto, to form a fused ring as illustrated in formula IV:

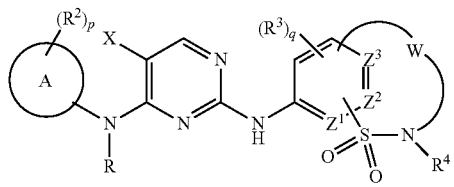

wherein W is selected from the group consisting of $C_1$-$C_3$ alkylene, substituted $C_1$-$C_3$ alkylene, $C_2$-$C_3$ alkenylene and substituted $C_2$-$C_3$ alkenylene wherein one or more of the carbon atoms have been replaced with a moiety selected from oxygen, sulfur, S(O), S(O)$_2$, C(O), or NR$^8$ where R$^8$ is selected from the group consisting of hydrogen and alkyl or is a bond participating in a —N=C< site of unsaturation;

provided that:
if p=0, then X is not bromo;
if ring A is cycloalkyl, then X is not bromo;
if p=2 and each of R$^2$ is methoxy, halo, trihalomethyl or trihalomethoxy, then R$^4$ and R$^5$ are not one hydrogen and one methyl;
if p=2 and R$^2$ is fluoro and methyl, then R is not substituted alkenyl; and
if ring A is phenyl, p=1 and R$^2$ is chloro, then R$^4$ and R$^5$ are not one hydrogen and one methyl.

Yet another embodiment of the invention provides a compound selected from the group consisting of:

| cmpd | name |
|---|---|
| I-1 | N2-(4-Aminosulphonylphenyl)-N4-(3-cyanomethoxy-4,5-dimethoxyphenyl)-5-fluoro- 2,4-pyrimidinediamine; |
| I-2 | N2-(3-Aminosulphonyl-4-methylphenyl)-N4-(3-cyanomethoxy-4,5-dimethoxyphenyl)-5-fluoro- 2,4-pyrimidinediamine; |
| I-3 | N2-(4-Aminosulfonyl)phenyl-N4-(3-cyanomethoxy)phenyl-5-fluoro-2,4-pyrimidinediamine; |
| I-4 | N2-(3-Aminosulfonyl)phenyl-N4-(3-cyanomethoxy)phenyl-5-fluoro-2,4-pyrimidinediamine; |
| I-5 | N4-(3-Cyanomethoxy)phenyl-5-fluoro-N2-[3-(4-methylpiperazin-1-yl)sulfonyl]phenyl-2,4-pyrimidinediamine; |
| I-6 | N4-(3-Cyanomethoxy)phenyl-5-fluoro-N2-[4-(4-methylpiperazin-1-yl)sulfonyl]phenyl-2,4-pyrimidinediamine; |
| I-7 | N2-(4-Aminosulfonyl-3-methoxy)phenyl-N4-(3-cyanomethoxy)phenyl-5-fluoro-2,4-pyrimidinediamine; |
| I-8 | N2-(3-Aminosulfonyl-4-iso-propylphenyl)-N4-(4-cyanomethyleneoxyphenyl)-5-fluoro-2,4-pyrimidinediamine; |
| I-9 | N2-[3-Aminosulfonyl-4-(4-methylpiperazin-1-yl)phenyl]-5-fluoro-N4-(4-cyanomethyleneoxyphenyl)-2,4-pyrimidinediamine; |
| I-10 | N2-[3-Aminosulfonyl-4-(4-methylpiperazine-1-yl)phenyl]-5-fluoro-N4-(4-cyanomethyleneoxy-3-fluorophenyl)-2,4-pyrimidinediamine; |
| I-11 | N2-(3-Aminosulfonyl-4-methylphenyl)-5-fluoro-N4-(4-cyanomethyleneoxy-3-fluorophenyl)-2,4-pyrimidinediamine; |
| I-12 | N2-(3-Aminosulfonylphenyl)-5-fluoro-N4-(4-cyanomethyleneoxy-3-fluorophenyl)-2,4-pyrimidinediamine; |
| I-13 | N2-(3-Aminosulfonylphenyl)-5-bromo-N4-(4-cyanomethyleneoxyphenyl)-2,4-pyrimidinediamine; |
| I-14 | N2-(3-Aminosulfonyl-4-methylphenyl)-5-bromo-N4-(4-cyanomethyleneoxyphenyl)-2,4-pyrimidinediamine; |
| I-15 | N2-(3-Aminosulfonylphenyl)-N4-(4-cyanomethyleneoxyphenyl)-5-trimethylsilylacetylene-2,4-pyrimidinediamine; |
| I-16 | N2-(4-Aminosulfonyl)phenyl-N4-(4-cyanomethoxy)phenyl-5-fluoro-2,4-pyrimidinediamine; |
| I-17 | N2-(3-Aminosulfonyl)phenyl-N4-(4-cyanomethoxy)phenyl-5-fluoro-2,4-pyrimidinediamine; |
| I-18 | N4-(4-Cyanomethoxy)phenyl-5-fluoro-N2-[4-(4-methylpiperazin-1-yl)sulfonyl]phenyl-2,4-pyrimidinediamine; |
| I-19 | N4-(4-Cyanomethoxy)phenyl-5-fluoro-N2-[3-(4-methylpiperazin-1-yl)sulfonyl]phenyl-2,4-pyrimidinediamine; |
| I-20 | N2-(3-Aminosulfonyl-4-methyl)phenyl-N4-(4-cyanomethoxy)phenyl-5-fluoro-2,4-pyrimidinediamine; |
| I-21 | N2-(3-Aminosulfonyl-4-chlorophenyl)-N4-(4-cyanomethoxy)phenyl-5-fluoro-2,4-pyrimidinediamine; |
| I-22 | N2-(4-Aminosulfonyl)phenyl-N4-(4-cyanomethoxy-3-methyl)phenyl-5-fluoro-2,4-pyrimidinediamine; |
| I-23 | N2-(3-Aminosulfonyl)phenyl-N4-(4-cyanomethoxy-3-methyl)phenyl-5-fluoro-2,4-pyrimidinediamine; |
| I-24 | N2-(3-Aminosulfonyl-4-methyl)phenyl-N4-(4-cyanomethoxy-3-methyl)phenyl-5-fluoro-2,4-pyrimidinediamine; |
| I-25 | N2-(4-Aminosulfonyl)phenyl-N4-(4-cyanomethoxy-3,5-dimethyl)phenyl-5-fluoro-2,4-pyrimidinediamine; |
| I-26 | N2-(3-Aminosulfonyl)phenyl-N4-(4-cyanomethoxy-3,5-dimethyl)phenyl-5-fluoro-2,4-pyrimidinediamine; |
| I-27 | N2-(3-Aminosulfonyl-4-methyl)phenyl-N4-(4-cyanomethoxy-3,5-dimethyl)phenyl-5-fluoro-2,4-pyrimidinediamine; |
| I-28 | N2-(4-Aminosulfonyl-3-methoxyphenyl)-N4-(4-cyanomethoxy)phenyl-5-fluoro-2,4-pyrimidinediamine; |
| I-29 | N2-(4-Aminosulfonyl-3-methoxy)phenyl-N4-(4-cyanomethoxy-3-methyl)phenyl-5-fluoro-2,4-pyrimidinediamine; |
| I-30 | N4-(4-Cyanomethyleneoxy)phenyl-5-fluoro-N2-(4-methyl-3-propionylaminosulfonyl)phenyl-2,4-pyrimidinediamine (68); |
| I-31 | N4-(4-Cyanomethyleneoxy)phenyl-5-fluoro-N2-(4-methyl-3-propionylaminosulfonyl)phenyl-2,4-pyrimidinediamine sodium salt (69); |
| I-32 | N2-(4-Aminosulfonyl-3-methoxy)phenyl-N4-(4-cyanomethoxy-3,5-dimethyl)phenyl-5-fluoro-2,4-pyrimidinediamine; |
| I-33 | N2-(3-Aminosulfonyl-4-fluoro)phenyl-N4-(4-cyanomethoxy)phenyl-5-fluoro-2,4-pyrimidinediamine; |
| I-34 | N2-(3-Aminosulfonyl-4-fluoro)phenyl-N4-(4-cyanomethoxy-3-methyl)phenyl-5-fluoro-2,4-pyrimidinediamine; |
| I-35 | N2-(3-Aminosulfonyl-4-fluoro)phenyl-N4-(4-cyanomethoxy-3,5-dimethyl)phenyl-5-fluoro-2,4-pyrimidinediamine; |
| I-36 | N2-(3-Acetylaminosulfonyl-4-methyl)phenyl-N4-(4-cyanomethyleneoxy)phenyl-5-fluoro-2,4-pyrimidinediamine; |
| I-37 | N4-(4-Cyanomethyleneoxy)phenyl-5-fluoro-N2-(3-isobutyrylaminosulfonyl-4-methyl)phenyl-2,4-pyrimidinediamine; |
| I-38 | N2-(3-Acetylaminosulfonyl-4-methyl)phenyl-N4-(4-cyanomethyleneoxy)phenyl-5-fluoro-2,4-pyrimidinediamine sodium salt; |
| I-39 | N4-(4-Cyanomethyleneoxy)phenyl-5-fluoro-N2-(3-isobutyrylaminosulfonyl-4-methyl)phenyl-2,4-pyrimidinediamine sodium Salt; |
| I-40 | N4-(4-Cyanomethoxy-3,5-dimethylphenyl)-5-fluoro-N2-[4-(4-methylpiperazin-1-yl)sulfonylphenyl]-2,4-pyrimidinediamine; |
| I-41 | N2-(4-Aminosulfonylphenyl)-N4-(3-chloro-4-cyanomethoxyphenyl)-5-fluoro-2,4-pyrimidinediamine; |
| I-42 | N2-(3-Aminosulfonylphenyl)-N4-(3-chloro-4-cyanomethoxyphenyl)-5-fluoro-2,4-pyrimidinediamine; |
| I-43 | N2-(3-Aminosulfonyl-4-methylphenyl)-N4-(3-chloro-4-cyanomethoxypheny)-5-fluoro-2,4-pyrimidinediamine; |
| I-44 | N2-(4-Aminosulfonylphenyl)-N4-(4-cyanomethoxy-3-fluorophenyl)-5-fluoro-2,4-pyrimidinediamine; |
| I-45 | N2-(4-Aminosulfonylphenyl)-N4-(4-cyanomethoxy-3-methoxyphenyl)-5-fluoro-2,4-pyrimidinediamine; |
| I-46 | N2-(3-Aminosulfonylphenyl)-N4-(4-cyanomethoxy-3-methoxyphenyl)-5-fluoro-2,4-pyrimidinediamine; |
| I-47 | N2-(3-Aminosulfonyl-4-methylphenyl)-N4-(4-cyanomethoxy-3-methoxyphenyl)-5-fluoro-2,4-pyrimidinediamine; |
| I-48 | N4-(4-Cyanomethoxy-3-fluorophenyl)-5-fluoro-N2-(4-methyl-3-propionylaminosulfonylphenyl)-2,4-pyrimidinediamine; |
| I-49 | N4-(4-Cyanomethoxy-3-fluorophenyl)-5-fluoro-N2-(4-methyl-3-propionylaminosulfonylphenyl)-2,4-pyrimidinediamine Sodium Salt; |
| I-50 | N2-(3-Aminosulfonylphenyl)-N4-(4-cyanomethoxy-3-hydroxymethylphenyl)-5-fluoro-2,4-pyrimidinediamine; |
| I-51 | N2-(3-Aminosulfonyl-4-methylphenyl)-N4-(4-cyanomethoxy-3-hydroxymethylphenyl)-5-fluoro-2,4-pyrimidinediamine; |
| I-52 | N2-(4-Aminosulfonylphenyl)-N4-[4-cyanomethoxy-3-(1-cyanomethylpyrazol-3-yl)phenyl]-5-fluoro-2,4-pyrimidinediamine; |
| I-53 | N2-(3-Aminosulfonylphenyl)-N4-[4-cyanomethoxy-3-(1-cyanomethylpyrazol-3-yl)phenyl]-5-fluoro-2,4-pyrimidinediamine; |
| I-54 | N2-(3-Aminosulfonyl-4-methylphenyl]-N4-[4-cyanomethoxy-3-(1-cyanomethylpyrazol-3-yl)phenyl]-5-fluoro-2,4-pyrimidinediamine; |

-continued

| cmpd | name |
|---|---|
| I-55 | N2-(3-Aminosulfonylpyrid-4-yl)-N4-(4-cyanomethoxyphenyl)-5-fluoro-2,4-pyrimidinediamine; |
| I-56 | N2-(3-Aminosulfonyl-4-methoxyphenyl)-N4-(4-cyanomethoxyphenyl)-5-fluoro-2,4-pyrimidinediamine; |
| I-57 | N2-(4-Aminosulfonylphenyl)-N4-(4-cyanomethoxyphenyl-5)-methyl-2,4-pyrimidinediamine; |
| I-58 | N2-(3-Aminosulfonylphenyl)-N4-(4-cyanomethoxyphenyl)-5-methyl-2,4-pyrimidinediamine; |
| I-59 | N2-(3-Aminosulfonyl-4-methylphenyl)-N4-(4-cyanomethoxyphenyl)-5-methyl-2,4-pyrimidinediamine; |
| I-60 | Racemic N2-(4-Aminosulfonyl)phenyl-N4-[4-(1-cyano)ethoxy-3-methyl]phenyl-5-fluoro-2,4-pyrimidinediamine; |
| I-61 | Racemic N2-(3-Aminosulfonyl)phenyl-N4-[4-(1-cyano)ethoxy-3-methyl]phenyl-5-fluoro-2,4-pyrimidinediamine; |
| I-62 | Racemic N2-(3-Aminosulfonyl-4-methyl)phenyl-N4-[4-(1-cyano)ethoxy-3-methyl]phenyl-5-fluoro-2,4-pyrimidinediamine; |
| I-63 | Racemic N2-(4-Aminosulfonyl)phenyl-N4-[4-(1-cyano)ethoxy-3,5-dimethyl]phenyl-5-fluoro-2,4-pyrimidinediamine; |
| I-64 | Racemic N2-(4-Aminosulfonyl-3-methoxy)phenyl-N4-[4-(1-cyano)ethoxy-3-methyl]phenyl-5-fluoro-2,4-pyrimidinediamine; |
| I-65 | Racemic N2-(3-Aminosulfonyl)phenyl-N4-[4-(1-cyano)ethoxy]phenyl-5-fluoro-2,4-pyrimidinediamine; |
| I-66 | Racemic N2-(4-Aminosulfonyl)phenyl-N4-[4-(1-cyano)ethoxy]phenyl-5-fluoro-2,4-pyrimidinediamine; |
| I-67 | Racemic N2-(3-Aminosulfonyl-4-methyl)phenyl-N4-[4-(1-cyano)ethoxy]phenyl-5-fluoro-2,4-pyrimidinediamine; |
| I-68 | Racemic N2-(3-Aminosulfonyl-4-fluoro)phenyl-N4-[4-(1-cyano)ethoxy]phenyl-5-fluoro-2,4-pyrimidinediamine; |
| I-69 | Racemic N2-(3-Aminosulfonyl-4-fluoro)phenyl-N4-[4-(1-cyano)ethoxy-3-methyl]phenyl-5-fluoro-2,4-pyrimidinediamine; |
| I-70 | Racemic N2-(4-Aminosulfonyl-3-methoxy)phenyl-N4-[4-(1-cyano)ethoxy]phenyl-5-fluoro-2,4-pyrimidinediamine; |
| I-71 | Racemic N2-(3-Aminosulfonyl)phenyl-N4-[4-(1-cyano)ethoxy-3,5-dimethyl]phenyl-5-fluoro-2,4-pyrimidinediamine; |
| I-72 | Racemic N2-(3-Aminosulfonyl-4-methyl)phenyl-N4-[4-(1-cyano)ethoxy-3,5-dimethyl]phenyl-5-fluoro-2,4-pyrimidinediamine; |
| I-73 | N2-(3-Aminosulfonyl-4-methyl)phenyl-N4-[4-(1-cyano-1-methyl)ethoxy]phenyl-5-fluoro-2,4-pyrimidinediamine; |
| I-74 | N2-(3-Aminosulfonyl-4-fluoro)phenyl-N4-[4-(1-cyano-1-methyl)ethoxy]phenyl-5-fluoro-2,4-pyrimidinediamine; |
| I-75 | N2-(4-Aminosulfonyl)phenyl-N4-[4-(1-cyano-1-methyl)ethoxy]phenyl-5-fluoro-2,4-pyrimidinediamine; |
| I-76 | N2-(3-Aminosulfonyl)phenyl-N4-[4-(1-cyano-1-methyl)ethoxy]phenyl-5-fluoro-2,4-pyrimidinediamine; |
| I-77 | N2-(4-Aminosulfonyl-3-methoxy)phenyl-N4-[4-(1-cyano-1-methyl)ethoxy]phenyl-5-fluoro-2,4-pyrimidinediamine; |
| I-78 | N2-(3-Aminosulfonylphenyl)-N4-[4-(N-cyanoacetyl)aminophneyl]-5-fluoro-2,4-pyrimidinediamine. |
| I-79 | N2-(3-Aminosulfonyl-4-methylphenyl)-N4-[4-(N-cyanoacetyl)aminophneyl]-5-fluoro-2,4-pyrimidinediamine; |
| I-80 | N2-(3-Aminosulfonylphenyl)-5-fluoroN4-[3-methyl-4-(N-cyanoacetyl)aminophneyl]-2,4-pyrimidinediamine; |
| I-81 | N2-(3-Aminosulfonyl-4-methylphenyl)-5-fluoroN4-[3-methyl4-(N-cyanoacetyl)aminophneyl]-2,4-pyrimidinediamine; |
| I-82 | N2-(3-Aminosulfonylphenyl)-N4-[3-chloro-4-(N-cyanoacetyl)aminophneyl]-5-fluoro-2,4-pyrimidinediamine; |
| I-83 | N2-(3-Aminosulfonyl-4-methylphenyl)-N4-[3-chloro-4-(N-cyanoacetyl)aminophneyl]-5-fluoro-2,4-pyrimidinediamine; |
| I-84 | N2-(3-Aminosulfonylphenyl)-5-fluoroN4-[3-methoxy-4-(N-cyanoacetyl)aminophneyl]-2,4-pyrimidinediamine; |
| I-85 | N2-(3-Aminosulfonyl-4-methylphenyl)-5-fluoroN4-[3-methoxy-4-(N-cyanoacetyl)aminophneyl]-2,4-pyrimidinediamine; |
| I-86 | N2-(3-Aminosulfonylphenyl)-N4-[4-(N-cyanoacetyl-N-methyl)aminophneyl]-5-fluoro-2,4-pyrimidinediamine; |
| I-87 | N2-(3-Aminosulfonyl-4-methylphenyl)-N4-[4-(N-cyanoacetyl-N-methyl)aminophneyl]-5-fluoro-2,4-pyrimidinediamine; |
| I-88 | N4-(3-Aminocarbonylmethoxy)phenyl-N2-(3-aminosulfonyl)phenyl-5-fluoro-2,4-pyrimidinediamine; |
| I-89 | N4-(3-Aminocarbonylmethoxy)phenyl-5-fluoro-N2-[3-(4-methylpiperazin-1-yl)sulfonyl]phenyl-2,4-pyrimidinediamine; |
| I-90 | N4-(3-Aminocarbonylmethoxy)phenyl-N2-(3-aminosulfonyl-4-methyl)phenyl-5-fluoro-2,4-pyrimidinediamine; |
| I-91 | N4-(3-Aminocarbonylmethoxy)phenyl-N2-(4-aminosulfonyl)phenyl-5-fluoro-2,4-pyrimidinediamine; |
| I-92 | N4-(4-Aminocarbonylmethoxy-3-methyl)phenyl-N2-(3-aminosulfonyl)phenyl-5-fluoro-2,4-pyrimidinediamine; |
| I-93 | N4-(4-Aminocarbonylmethoxy-3,5-dimethyl)phenyl-N2-(3-aminosulfonyl)phenyl-5-fluoro-2,4-pyrimidinediamine; |
| I-94 | N4-(4-Aminocarbonylmethoxy)phenyl-N2-(3-aminosulfonyl-4-methyl)phenyl-5-fluoro-2,4-pyrimidinediamine; |
| I-95 | N4-(4-Aminocarbonylmethoxy-3-methyl)phenyl-N2-(3-aminosulfonyl-4-methyl)phenyl-5-fluoro-2,4-pyrimidinediamine; |
| I-96 | N4-(4-Aminocarbonylmethoxy-3,5-dimethyl)phenyl-N2-(3-aminosulfonyl-4-methyl)phenyl-5-fluoro-2,4-pyrimidinediamine; |
| I-97 | N4-(4-Aminocarbonylmethoxy-3-chlorophenyl)-N2-(4-aminosulfonylphenyl)-5-fluoro-2,4-pyrimidinediamine; |
| I-98 | N4-(4-Aminocarbonylmethoxy-3-chlorophenyl)-N2-(3-aminosulfonylphenyl)-5-fluoro-2,4-pyrimidinediamine; |
| I-99 | N4-(4-Aminocarbonylmethoxy-3-chlorophenyl)-N2-(3-aminosulfonyl-4-methylphenyl)-5-fluoro-2,4-pyrimidinediamine; |
| I-100 | N4-(4-Aminocarbonylmethoxy-3-fluorophenyl)-N2-(4-aminosulfonylphenyl)-5-fluoro-2,4-pyrimidinediamine; |
| I-101 | N4-(4-Aminocarbonylmethoxy-3-fluorophenyl)-N2-(3-aminosulfonylphenyl)-5-fluoro-2,4-pyrimidinediamine; |
| I-102 | N4-(4-Aminocarbonylmethoxy-3-fluorophenyl)-N2-(3-aminosulfonyl-4-methylphenyl)-5-fluoro-2,4-pyrimidinediamine; |
| I-103 | N4-(4-Aminocarbonylmethoxy-3-methoxyphenyl)-N2-(4-aminosulfonylphenyl)-5-fluoro-2,4-pyrimidinediamine; |
| I-104 | N4-(4-Aminocarbonylmethoxy-3-methoxyphenyl)-N2-(3-aminosulfonylphenyl)-5-fluoro-2,4-pyrimidinediamine; |
| I-105 | N4-(4-Aminocarbonylmethoxy-3-methoxyphenyl)-N2-(3-aminosulfonyl-4-methylphenyl)-5-fluoro-2,4-pyrimidinediamine; |
| I-106 | N4-(4-Aminocarbonylmethoxy-3-hydroxymethylphenyl)-N2-(3-aminosulfonyl-4-methylphenyl)-5-fluoro-2,4-pyrimidinediamine; |
| I-107 | N4-(4-Aminocarbonylmethoxy-3-hydroxymethylphenyl]-N2-(3-aminosulfonylphenyl)-5-fluoro-2,4-pyrimidinediamine; |
| I-108 | N4-(4-Aminocarbonylmethoxyphenyl)-N2-(4-aminosulfonylphenyl)-5-methyl-2,4-pyrimidinediamine; |
| I-109 | N4-(4-Aminocarbonylmethoxyphenyl)-N2-(3-aminosulfonylphenyl)-5-methyl-2,4-pyrimidinediamine; |
| I-110 | N4-(4-Aminocarbonylmethoxyphenyl)-N2-(3-aminosulfonyl-4-methylphenyl)-5-methyl-2,4-pyrimidinediamine; |
| I-111 | N4-(4-Aminocarbonylmethoxy)phenyl-N2-(3-aminosulfonyl)phenyl-5-fluoro-2,4-pyrimidinediamine; |
| I-112 | N4-(4-Aminocarbonylmethoxy)phenyl-5-fluoro-N2-[3-(4-methylpiperazin-1-yl)sulfonyl]phenyl-2,4-pyrimidinediamine; |
| I-113 | N4-(4-Aminocarbonylmethoxy-3-methyl)phenyl-N2-(4-aminosulfonyl)phenyl-5-fluoro-2,4-pyrimidinediamine; |
| I-114 | N4-(4-Aminocarbonylmethoxy-3,5-dimethyl)phenyl-N2-(4-aminosulfonyl)phenyl-5-fluoro-2,4-pyrimidinediamine; |
| I-115 | N4-(4-Aminocarbonylmethoxy)phenyl-N2-(4-aminosulfonyl)phenyl-5-fluoro-2,4-pyrimidinediamine; |
| I-116 | Racemic N4-[4-(1-Aminocarbonyl)ethoxy]phenyl-N2-(4-aminosulfonyl)phenyl-5-fluoro-2,4-pyrimidinediamine; |
| I-117 | Racemic N4-[4-(1-Aminocarbonyl)ethoxy]phenyl-N2-(3-aminosulfonyl)phenyl-5-fluoro-2,4-pyrimidinediamine; |
| I-118 | N4-[4-(1-Aminocarbonyl)ethoxy]phenyl-N2-(3-aminosulfonyl-4-methyl)phenyl-5-fluoro-2,4-pyrimidinediamine; |
| I-119 | Racemic N4-[4-(1-Aminocarbonyl)ethoxy-3-methyl]phenyl-N2-(4-aminosulfonyl)phenyl-5-fluoro-2,4-pyrimidinediamine; |
| I-120 | Racemic N4-[4-(1-Aminocarbonyl)ethoxy-3-methyl]phenyl-N2-(3-aminosulfonyl)phenyl-5-fluoro-2,4-pyrimidinediamine; |
| I-121 | Racemic N4-[4-(1-Aminocarbonyl)ethoxy-3-methyl]phenyl-N2-(3-aminosulfonyl-4-methyl)phenyl-5-fluoro-2,4-pyrimidinediamine; |
| I-122 | Racemic N4-[4-(1-Aminocarbonyl)ethoxy-3,5-dimethyl]phenyl-N2-(4-aminosulfonyl)phenyl-5-fluoro-2,4-pyrimidinediamine; |
| I-123 | Racemic N4-[4-(1-Aminocarbonyl)ethoxy-3,5-dimethyl]phenyl-N2-(3-aminosulfonyl)phenyl-5-fluoro-2,4-pyrimidinediamine; |
| I-124 | Racemic N4-[4-(1-Aminocarbonyl)ethoxy-3,5-dimethyl]phenyl-N2-(3-aminosulfonyl-4-methyl)phenyl-5-fluoro-2,4-pyrimidinediamine; |
| I-125 | N4-[4-(1-Aminocarbonyl-1-methyl)ethoxy]phenyl-N2-(4-aminosulfonyl)phenyl-5-fluoro-2,4-pyrimidinediamine; |
| I-126 | N4-[4-(1-Aminocarbonyl-1-methyl)ethoxy]phenyl-N2-(3-aminosulfonyl)phenyl-5-fluoro-2,4-pyrimidinediamine; |
| I-127 | N4-[4-(1-Aminocarbonyl-1-methyl)ethoxy]phenyl-N2-(3-aminosulfonyl-4-methyl)phenyl-5-fluoro-2,4-pyrimidinediamine; |
| I-128 | N2-(4-Aminosulfonylphenyl)-N4-(4-dimethylaminocarbonylmethoxyphenyl)-5-fluoro-2,4-pyrimidinediamine; |
| I-129 | N2-(3-Aminosulfonylphenyl)-N4-(4-dimethylaminocarbonylmethoxyphenyl)-5-fluoro-2,4-pyrimidinediamine; |

-continued

| cmpd | name |
|---|---|
| I-130 | N2-(3-Aminosulfonyl-4-methylphenyl)-N4-(4-dimethylaminocarbonylmethoxyphenyl)-5-fluoro-2,4-pyrimidinediamine; |
| I-131 | N2-(4-Aminosulfonylphenyl)-N4-(3-chloro-4-dimethylaminocarbonylmethoxyphenyl)-5-fluoro-2,4-pyrimidinediamine; |
| I-132 | N2-(3-Aminosulfonylphenyl)-N4-(3-chloro-4-dimethylaminocarbonylmethoxyphenyl)-5-fluoro-2,4-pyrimidinediamine; |
| I-133 | N2-(3-Aminosulfonyl-4-methylphenyl)-N4-(3-chloro-4-dimethylaminocarbonylmethoxyphenyl)-5-fluoro-2,4-pyrimidinediamine; |
| I-134 | N2-(4-Aminosulfonylphenyl)-N4-(3-chloro-4-dimethylaminocarbonylmethoxyphenyl)-5-methyl-2,4-pyrimidinediamine; |
| I-135 | N2-(3-Aminosulfonylphenyl)-N4-(3-chloro-4-dimethylaminocarbonylmethoxyphenyl)-5-methyl-2,4-pyrimidinediamine; |
| I-136 | N2-(3-Aminosulfonyl-4-methylphenyl)-N4-(3-chloro-4-dimethylaminocarbonylmethoxyphenyl)-5-methyl-2,4-pyrimidinediamine; |
| I-137 | N2-(4-Aminosulfonylphenyl)-N4-(4-dimethylaminocarbonylmethoxy-3-fluorophenyl)-5-methyl-2,4-pyrimidinediamine; |
| I-138 | N2-(3-Aminosulfonylphenyl)-N4-(4-dimethylaminocarbonylmethoxy-3-fluorophenyl)-5-methyl-2,4-pyrimidinediamine; |
| I-139 | N2-(3-Aminosulfonyl-4-methylphenyl)-N4-(4-dimethylaminocarbonylmethoxy-3-fluorophenyl)-5-methyl-2,4-pyrimidinediamine; |
| I-140 | N2-(3-Aminosulfonyl-4-chlorophenyl)-N4-(3-chloro-4-dimethylaminocarbonylmethoxyphenyl)-5-fluoro-2,4-pyrimidinediamine; |
| I-141 | N2-(3-Aminosulfonyl-4-chlorophenyl)-N4-(3-chloro-4-dimethylaminocarbonylmethoxyphenyl)-5-methyl-2,4-pyrimidinediamine; |
| I-142 | N2-(3-Aminosulfonyl-4-chlorophenyl)-N4-(4-dimethylaminocarbonylmethoxy-3-fluorophenyl)-5-methyl-2,4-pyrimidinediamine; |
| I-143 | N2-(4-Aminosulfonylphenyl)-5-fluoro-N4-(4-methylaminocarbonylmethoxyphenyl)-2,4-pyrimidinediamine; |
| I-144 | N2-(3-Aminosulfonylphenyl)-5-fluoro-N4-(4-methylaminocarbonylmethoxyphenyl)-2,4-pyrimidinediamine; |
| I-145 | N2-(3-Aminosulfonyl-4-methylphenyl)-5-fluoro-N4-(4-methylaminocarbonylmethoxyphenyl)-2,4-pyrimidinediamine; |
| I-146 | N2-(4-Aminosulfonylphenyl)-N4-(3-chloro-4-methylaminocarbonylmethoxyphenyl)-5-fluoro-2,4-pyrimidinediamine; |
| I-147 | N2-(3-Aminosulfonylphenyl)-N4-(3-chloro-4-methylaminocarbonylmethoxyphenyl)-5-fluoro-2,4-pyrimidinediamine; |
| I-148 | N2-(3-Aminosulfonyl-4-methylphenyl)-N4-(3-chloro-4-methylaminocarbonylmethoxyphenyl)-5-fluoro-2,4-pyrimidinediamine; |
| I-149 | N2-(4-Aminosulfonylphenyl)-N4-(3-chloro-4-methylaminocarbonylmethoxyphenyl)-5-methyl-2,4-pyrimidinediamine; |
| I-150 | N2-(3-Aminosulfonylphenyl)-N4-(3-chloro-4-methylaminocarbonylmethoxyphenyl)-5-methyl-2,4-pyrimidinediamine; |
| I-151 | N2-(3-Aminosulfonyl-4-methylphenyl)-N4-(3-chloro-4-methylaminocarbonylmethoxyphenyl)-5-methyl-2,4-pyrimidinediamine; |
| I-152 | N2-(3-Aminosulfonyl-4-chlorophenyl)-N4-(3-chloro-4-methylaminocarbonylmethoxyphenyl)-5-fluoro-2,4-pyrimidinediamine; |
| I-153 | N2-(3-Aminosulfonyl-4-chlorophenyl)-N4-(3-chloro-4-methylaminocarbonylmethoxyphenyl)-5-methyl-2,4-pyrimidinediamine; |
| I-154 | N2-(4-Aminosulfonylphenyl)-N4-(3-fluoro-4-methylaminocarbonylmethoxyphenyl)-5-methyl-2,4-pyrimidinediamine; |
| I-155 | N2-(3-Aminosulfonylphenyl)-N4-(3-fluoro-4-methylaminocarbonylmethoxyphenyl)-5-methyl-2,4-pyrimidinediamine; |
| I-156 | N2-(3-Aminosulfonyl-4-methylphenyl)-N4-(3-fluoro-4-methylaminocarbonylmethoxyphenyl)-5-methyl-2,4-pyrimidinediamine; |
| I-157 | N4-(4-Allylaminocarbonylmethoxyphenyl)-N2-(4-aminosulfonylphenyl)-5-fluoro-2,4-pyrimidinediamine; |
| I-158 | N4-(4-Allylaminocarbonylmethoxyphenyl)-N2-(3-aminosulfonylphenyl)-5-fluoro-2,4-pyrimidinediamine; |
| I-159 | N4-(4-Allylaminocarbonylmethoxyphenyl)-N2-(3-aminosulfonyl-4-methylphenyl)-5-fluoro-2,4-pyrimidinediamine; |
| I-160 | N2-(3-Aminosulfonyl-4-methylphenyl)-5-fluoro-N4-[4-(2-pyridinyl)methyleneoxyphenyl]-2,4-pyrimidinediamine; |
| I-161 | 5-Fluoro-N2-[3-(N-methylaminosulfony)-4-methylphenyl]-5-fluoro-N4-[4-(2-pyridinyl)methyleneoxyphenyl]-2,4-pyrimidinediamine; |
| I-162 | N2-(3-Aminosulfonylphenyl)-5-fluoro-N4-[4-(2-pyridinyl)methyleneoxyphenyl]-2,4-pyrimidinediamine; |
| I-163 | N2-(4-Aminosulfonylphenyl)-5-fluoro-N4-[4-(2-pyridinyl)methyleneoxyphenyl]-2,4-pyrimidinediamine; |
| I-164 | N2-(3-Aminosulfonylpyrid-4-yl)-5-fluoro-N4-[4-(2-pyridinyl)methyleneoxyphenyl]-2,4-pyrimidinediamine; |
| I-165 | N2-[4-(2-N,N-Diethylaminoethyl)aminosulfonylphenyl]-5-fluoro-N4-[4-(2-pyridinyl)methyleneoxyphenyl]-2,4-pyrimidinediamine; |
| I-166 | N2-[3-(2-N,N-Diethylaminoethyl)aminosulfonylphenyl]-5-fluoro-N4-[4-(2-pyridinyl)methyleneoxyphenyl]-2,4-pyrimidinediamine; |
| I-167 | N2-(3-Aminosulfonylphenyl)-5-fluoro-N4-[(4-((pyridin-2-yl)methoxy)-3-methylphenyl)]-2,4-pyrimidinediamine; |
| I-168 | N2-(3-Amino-4-methylsulfonylphenyl)-5-fluoro-N4-[(4-((pyridin-2-yl)methoxy)-3-methylphenyl)]-2,4-pyrimidinediamine; |
| I-169 | N2-(3-Aminosulfonylphenyl)-5-fluoro-N4-[4-(2-pyridinyl)-3-fluoromethyleneoxyphenyl]-2,4-pyrimidinediamine; |
| I-170 | 5-Fluoro-N2-[3-N-(methyl)aminosulfonyl-4-methylphenyl]-N4-[4-(2-pyridinyl)-3-methylmethyleneoxyphenyl]-2,4-pyrimidinediamine; |
| I-171 | N2-(3-Aminosulfonylphenyl)-5-fluoro-N4-[4-(2-pyridinyl)-3-chloromethyleneoxyphenyl]-2,4-pyrimidinediamine; |
| I-172 | N2-(3-Aminosulfonyl-4-methylphenyl)-5-fluoro-N4-[4-(2-pyridinyl)-3-fluoromethyleneoxyphenyl]-2,4-pyrimidinediamine; |
| I-173 | 5-Fluoro-N2-[3-N-(methyl)aminosulfonyl-4-methylphenyl]-N4-[4-(2-pyridinyl)-3-fluoromethyleneoxyphenyl]-2,4-pyrimidinediamine; |
| I-174 | N2-(3-Aminosulfonyl-4-methylphenyl)-5-fluoro-N4-[4-(2-pyridinyl)-3-chloromethyleneoxyphenyl]-2,4-pyrimidinediamine; |
| I-175 | N2-(3-Aminosulfonylphenyl)-5-fluoro-N4-[4-(2-pyridinyl)-3-chloromethyleneoxyphenyl]-2,4-pyrimidinediamine; |
| I-176 | N2-(4-Aminosulfonylphenyl)-5-fluoro-N4-[4-(2-pyridinyl)-3-methylmethyleneoxyphenyl]-2,4-pyrimidinediamine; |
| I-177 | N2-(4-Aminosulfonylphenyl)-5-fluoro-N4-[4-(2-pyridinyl)-3-fluoromethyleneoxyphenyl]-2,4-pyrimidinediamine; |
| I-178 | N2-(3-Aminosulfonyl-4-methylphenyl)- 5-fluoro-N4-[4-(3-pyridylmethoxy)phenyl]-2,4-pyrimidinediamine; |
| I-179 | N2-(3-Aminosulfonylphenyl)-5-methyl-N4-[4-(2-pyridinyl)methyleneoxyphenyl]-2,4-pyrimidinediamine; |
| I-180 | 5-Methyl-N2-[3-(N-methylaminosulfony)-4-methylphenyl]-N4-[4-(2-pyridinyl)methyleneoxyphenyl]-2,4-pyrimidinediamine; |
| I-181 | N2-(4-Aminosulfonylphenyl)-5-methyl-N4-[4-(2-pyridinyl)methyleneoxyphenyl]-2,4-pyrimidinediamine; |
| I-182 | N2-(3-Aminosulfonylphenyl)-5-fluoro-N4-[3-(3-pyridinyl)methyleneoxyphenyl]-2,4-pyrimidinediamine; |
| I-183 | N2-(3-Aminosulfonyl-4-methylphenyl)-5-fluoro-N4-[3-(3-pyridinyl)methyleneoxyphenyl]-2,4-pyrimidinediamine; |
| I-184 | 5-Fluoro-N2-[3-(N-methylaminosulfony)-4-methylphenyl]-5-fluoro-N4-[3-(3-pyridinyl)methyleneoxyphenyl]-2,4-pyrimidinediamine; |
| I-185 | N2-(4-Aminosulfonylphenyl)-5-fluoro-N4-[3-(3-pyridinyl)methyleneoxyphenyl]-2,4-pyrimidinediamine; |
| I-186 | N2-[4-(2-N,N-Diethylaminoethyl)aminosulfonylphenyl]-5-fluoro-N4-[3-(3-pyridinyl)methyleneoxyphenyl]-2,4-pyrimidinediamine; |
| I-187 | N2-[3-(2-N,N-Diethylaminoethyl)aminosulfonylphenyl]-5-fluoro-N4-[3-(3-pyridinyl)methyleneoxyphenyl]-2,4-pyrimidinediamine; |
| I-188 | N2-(3-Aminosulfonylphenyl)-5-fluoro-N4-[4-(3-pyridinyl)methyleneoxyphenyl]-2,4-pyrimidinediamine; |
| I-189 | N2-(3-Aminosulfonyl-4-methylphenyl)-5-fluoro-N4-[4-(3-pyridinyl)methyleneoxyphenyl]-2,4-pyrimidinediamine; |
| I-190 | 5-Fluoro-N2-[3-(N-methylaminosulfony)-4-methylphenyl]-5-fluoro-N4-[4-(3-pyridinyl)methyleneoxyphenyl]-2,4-pyrimidinediamine; |
| I-191 | N2-[4-(2-N,N-Diethylaminoethyl)aminosulfonylphenyl]-5-fluoro-N4-[4-(3-pyridinyl)methyleneoxyphenyl]-2,4-pyrimidinediamine; |
| I-192 | N2-(3-Aminosulfonylphenyl)-5-fluoro-N4-[4-(3-pyridinyl)-methylenethiophenyl]-2,4-pyrimidinediamine; |

-continued

| cmpd | name |
|---|---|
| I-193 | N2-(3-Aminosulfonylphenyl)-5-fluoro-N4-[4-(4-pyridinyl)methyleneoxyphenyl]-2,4-pyrimidinediamine; |
| I-194 | N2-(3-Aminosulfonyl-4-methylphenyl)-5-fluoro-N4-[4-(4-pyridinyl)methyleneoxyphenyl]-2,4-pyrimidinediamine; |
| I-195 | 5-Fluoro-N2-[3-(N-methylaminosulfony)-4-methylphenyl]-5-fluoro-N4-[4-(4-pyridinyl)methyleneoxyphenyl]-2,4-pyrimidinediamine; |
| I-196 | N2-(3-Aminosulfonylphenyl)-5-fluoro-N4-4-[(2-pyridinyl)methyleneoxyphenyl]-2,4-pyrimidinediamine Hydrochloride Salt; |
| I-197 | N2-(3-Aminosulfonyl-4-methylphenyl)-5-fluoro-N4-[4-(3-methyl-(1H)-pyrazol-5-yl)methyleneoxyphenyl]-2,4-pyrimidinediamine; |
| I-198 | N2-(3-Aminosulfonyl-4-methylphenyl)-N4-[4-(1,3-dimethyl-(1H)-pyrazol-5-yl)methyleneoxyphenyl]-5-fluoro-2,4-pyrimidinediamine; |
| I-199 | N2-(3-Aminosulfonyl-4-methylphenyl)-N4-[4-(1-benzyl-3-methyl-(1H)-pyrazol-5-yl)methyleneoxyphenyl]-5-fluoro-2,4-pyrimidinediamine; |
| I-200 | N2-(3-Aminosulfonyl-4-fluorophenyl)-5-fluoro-N4-[4-(2,4-dihydro-3-oxo-1,2,4-triazol-5-yl)methyleneoxyphenyl]-2,4-pyrimidinediamine (76); |
| I-201 | N2-(3-Aminosulfonylphenyl)-5-fluoro-N4-[4-(2,4-dihydro-3-oxo-1,2,4-triazol-5-yl)methyleneoxyphenyl]-2,4-pyrimidinediamine; |
| I-202 | N2-(3-Aminosulfonyl-4-methylphenyl)-5-fluoro-N4-[4-(2,4-dihydro-3-oxo-1,2,4-triazol-5-yl)methyleneoxyphenyl]-2,4-pyrimidinediamine; |
| I-203 | N2-(3-Aminosulfonylphenyl)-5-fluoro-N4-[4-methyl-3-(2-morpholinoethyloxy)phenyl]-2,4-pyrimidinediamine; |
| I-204 | N2-(3-Aminosulfonyl-4-methylphenyl)-5-fluoro-N4-[4-methyl-3-(2-morpholinoethyloxy)phenyl]2,4-pyrimidinediamine; |
| I-205 | N2-(4-Aminosulfonylphenyl)-5-fluoro-N4-[4-(2-morpholinoethyloxy)phenyl]-2,4-pyrimidinediamine; |
| I-206 | N2-(3-Aminosulfonylphenyl)-5-fluoro-N4-[4-(2-morpholinoethyloxy)phenyl-2,4-pyrimidinediamine; |
| I-207 | 5-Fluoro-N2-(3-morpholinosulfonylphenyl)-N4-[4-(2-morpholinoethyloxy)phenyl]-2,4-pyrimidinediamine; |
| I-208 | N2-(3-Aminosulfonylphenyl)-5-fluoro-N4-[4-methyl-3-(2-morpholinocarbonylmethyleneoxy)phenyl]-2,4-pyrimidinediamine; |
| I-209 | N2-(4-Aminosulfonylphenyl)-5-fluoro-N4-[4-methyl-3-(2-morpholinocarbonylmethyleneoxy)phenyl]-2,4-pyrimidinediamine; |
| I-210 | N2-(4-Aminosulfonylphenyl)-5-fluoro-N4-[4-(2-morpholin-4-yl-2-oxo-ethoxy)phenyl]-2,4-pyrimidinediamine; |
| I-211 | N2-(3-Aminosulfonylphenyl)-5-fluoro-N4-[4-(2-morpholin-4-yl-2-oxo-ethoxy)phenyl]-2,4-pyrimidinediamine; |
| I-212 | N2-(3-Aminosulfonyl-4-methylphenyl)-5-fluoro-N4-[4-(2-morpholin-4-yl-2-oxo-ethoxy)phenyl]-2,4-pyrimidinediamine; |
| I-213 | 5-Fluoro-N4-(4-methoxycarbonylmethoxyphenyl)-N2-(4-methyl-3-propionylaminosulfonylphenyl)-2,4-pyrimidinediamine; |
| I-214 | N2-(3-Aminosulfonyl-4-methylphenyl)-N4-[3-(5-methylisoxazol-3-yl)methyleneoxyphenyl]-2,4-pyrimidinediamine; |
| I-215 | 5-Fluoro-N2-[3-(N-methoxycarbonylmethylene)aminosulfonylphenyl]-N4-[4-(5-methylisoxazol-3-yl)methyleneoxyphenyl]-2,4-pyrimidinediamine; |
| I-216 | N2- (3-Aminosulfonyl-5-chloro-4-methylphenyl)-5-fluoro- N4-[3-methyl-4-(5-methylisoxazol-3-yl)methyleneoxyphenyl]-2,4-pyrimidinediamine; |
| I-217 | N2-(3-Aminosulfonyl-4-fluoro-5-methylphenyl)-5-fluoro-N4-[4-(5-methylisoxazol-3-yl)methyleneoxyphenyl]-2,4-pyrimidinediamine; |
| I-218 | N2-(3-Aminosulfonyl-4-chloro-5-methylphenyl)-5-fluoro-N4-[4-(5-methylisoxazol-3-yl)methyleneoxyphenyl]-2,4-pyrimidinediamine; |
| I-219 | N2-(3-Aminosulfonyl-4-methylphenyl)-5-fluoro-N4-[4-(5-methylisoxazol-3-yl)methyleneoxyphenyl]-2,4-pyrimidinediamine; |
| I-220 | N2-(3-Aminosulfonyl-4-chlorophenyl)-5-fluoro-N4-[4-(5-methylisoxazol-3-yl)methyleneoxyphenyl]-2,4-pyrimidinediamine; |
| I-221 | N2-(3-Aminosulfonyl-4-methylphenyl)-N4-[3-chloro-4-(5-methylisoxazol-3-yl)methyleneoxyphenyl]-5-fluoro-2,4-pyrimidinediamine; |
| I-222 | N2-(3-Aminosulfonyl-4-methylphenyl)-5-fluoro-N4-[3-fluoro-4-(5-methylisoxazol-3-yl)methyleneoxyphenyl]-2,4-pyrimidinediamine; |
| I-223 | N2-(3-Aminosulfonyl-5-chloro-4-methylphenyl)-5-fluoro-N4-[3-fluoro-4-(5-methylisoxazol-3-yl)methyleneoxyphenyl]-2,4-pyrimidinediamine; |
| I-224 | N2-(3-Aminosulfonyl-4-fluoro-5-methylphenyl)-5-fluoro-N4-[3-fluoro-4-(5-methylisoxazol-3-yl)methyleneoxyphenyl]-2,4-pyrimidinediamine; |
| I-225 | N2-(3-Aminosulfonyl-4-methylphenyl)-5-fluoro-N4-methyl-N4-[4-(5-methylisoxazol-3-yl)methyleneoxyphenyl]-2,4-pyrimidinediamine; |
| I-226 | N2-(3-Aminosulfonyl-4-methylphenyl)-5-fluoro-N4-[3-fluoro-4-(5-methylisoxazol-3-yl)methyleneoxyphenyl]-N4-methyl-2,4-pyrimidinediamine; |
| I-227 | N2-(3-Aminosulfonyl-4-methylphenyl)-5-fluoro-N4-methoxycarbonylmethyl-N4-[4-(5-methylisoxazol-3-yl)methyleneoxyphenyl]-2,4-pyrimidinediamine; |
| I-228 | 5-Fluoro-N4-[4-(5-methylisoxazol-3-yl)methyleneoxyphenyl]-N2-(4-methyl-3-propionylaminosulfonylphenyl)-2,4-pyrimidinediamine; |
| I-229 | 5-Fluoro-N4-[4-(5-methylisoxazol-3-yl)methyleneoxyphenyl]-N2-(4-methyl-3-(2-methylpropionyl)aminosulfonylphenyl)-2,4-pyrimidinediamine; |
| I-230 | N2-(3-Aminosulfonylphenyl)-5-fluoro-N4-[4-(5-methylisoxazol-3-yl)methyleneoxyphenyl]-2,4-pyrimidinediamine (59, X = H); |
| I-231 | N2-(4-Aminosulfonylphenyl)-5-fluoro-N4-[4-(3-methyl-1,2,4-oxadiazol-5-yl)methyleneoxyphenyl]-2,4-pyrimidinediamine; |
| I-232 | N2-(3-Acetamidosulfonylphenyl)-5-fluoro-N4-[4-(5-methylisoxazol-3-yl)methyleneoxyphenyl]-2,4-pyrimidinediamine; |
| I-233 | N2-(3-Aminosulfonyl-4-fluorophenyl)-5-fluoro-N4-[4-(5-methylisoxazol-3-yl)methyleneoxyphenyl]-2,4-pyrimidinediamine; |
| I-234 | N2-(3-Aminosulfonyl-4-methylphenyl)-5-fluoro-N4-[3-methyl-4-(5-methylisoxazol-3-yl)methyleneoxyphenyl]-2,4-pyrimidinediamine; |
| I-235 | 5-Fluoro-N2-[3-(N-methyl)aminosulfonyl-4-methylphenyl]-N4-[4-(5-methylisoxazol-3-yl)methyleneoxyphenyl]-2,4-pyrimidinediamine; |
| I-236 | 5-Fluoro-N4-[4-(5-methylisoxazol-3-yl)methyleneoxyphenyl]-N2-(3-N-propanamido)sulfonylphenyl)]-2,4-pyrimidinediamine; |
| I-237 | N2-(3-Aminosulfonyl-4-fluorophenyl)-5-fluoro-N4-[3methyl-4-(5-methylisoxazol-3-yl)methyleneoxyphenyl]-2,4-pyrimidinediamine; |
| I-238 | N2-(3-Aminosulfonylphenyl)-5-fluoro-N4-[3-methyl-4-(5-methylisoxazol-3-yl)methyleneoxyphenyl]-2,4-pyrimidinediamine; |
| I-239 | 5-Fluoro-N2-[3-N-(methyl)aminosulfonyl-4-methylphenyl]-N4-[3-methyl-4-(5-methylisoxazol-3-yl)methyleneoxyphenyl]-2,4-pyrimidinediamine; |
| I-240 | N2-(4-Aminosulfonylphenyl)-5-fluoro-N4-[3methyl-4-(5-methylisoxazol-3-yl)methyleneoxyphenyl]-2,4-pyrimidinediamine; |
| I-241 | N2-[3-(2-N,N-Diethylaminoethyl)aminosulfonylphenyl)-5-fluoro-N4-[4-(5-methylisoxazol-3-yl)methyleneoxyphenyl]-2,4-pyrimidinediamine; |
| I-242 | 5-Fluoro-N4-[4-(5-methylisoxazol-3-yl)methyleneoxyphenyl]-N2-(3-N-propanamido)sulfonylphenyl)]-2,4-pyrimidinediamine sodium salt; |
| I-243 | N2-(3-Acetamidosulfonylphenyl)-5-fluoro-N4-[4-(5-methylisoxazol-3-yl)methyleneoxyphenyl]-2,4-pyrimidinediamine sodium salt; |

-continued

| cmpd | name |
|---|---|
| I-244 | N2-[3-(2-N,N-Diethylaminoethyl)aminosulfonylphenyl]-5-fluoro-N4-[3-methyl-4-(5-methylisoxazol-3-yl)methyleneoxyphenyl]-2,4-pyrimidinediamine; |
| I-245 | N2-[4-(2-N,N-Diethylaminoethyl)aminosulfonylphenyl]-5-fluoro-N4-[3-methyl-4-(5-methylisoxazol-3-yl)methyleneoxyphenyl]-2,4-pyrimidinediamine; |
| I-246 | N2-[4-(2-N,N-Diethylaminoethyl)aminosulfonylphenyl]-5-fluoro-N4-[4-(5-methylisoxazol-3-yl)methyleneoxyphenyl]-2,4-pyrimidinediamine; |
| I-247 | N2-{3-[(N-5-Methyl-1,3-dioxolene-2-one-4-yl)methylene]aminosulfonylphenyl}-5-fluoro-N4-[4-(5-methylisoxazol-3-yl)methyleneoxyphenyl]-2,4-pyrimidinediamine; |
| I-248 | N2-{3-[N-N-Di-[(5-Methyl-1,3-dioxolene-2-one-4-yl)methylene]]aminosulfonylphenyl}-5-fluoro-N4-[4-(5-methylisoxazol-3-yl)methyleneoxyphenyl]-2,4-pyrimidinediamine; |
| I-249 | N2-{3-[N-N-Di-[(5-t-Butyl-1,3-dioxolene-2-one-4-yl)methylene]]aminosulfonylphenyl}-5-fluoro-N4-[4-(5-methylisoxazol-3-yl)methyleneoxyphenyl]-2,4-pyrimidinediamine; |
| I-250 | N2-{3-[(N-5-t-Butyl-1,3-dioxolene-2-one-4-yl)methylene]aminosulfonylphenyl}-5-fluoro-N4-[4-(5-methylisoxazol-3-yl)methyleneoxyphenyl]-2,4-pyrimidinediamine; |
| I-251 | N2-[3-Aminosulfonyl-4-(4-methylpiperazin-1-yl)phenyl]-5-fluoro-N4-[2-fluoro-4-(5-methylisoxazol-3-yl)methyleneoxyphenyl]-2,4-pyrimidinediamine; |
| I-252 | N2-(3-Aminosulfonylphenyl)-5-fluoro-N4-[3-(3-methyl-1,2,4-oxadiazol-5-yl)methyleneoxyphenyl]-2,4-pyrimidinediamine (60); |
| I-253 | N2-(4-Aminosulfonylphenyl)-5-fluoro-N4-[3-(3-methyl-1,2,4-oxadiazol-5-yl)methyleneoxyphenyl]-2,4-pyrimidinediamine; |
| I-254 | N2-(3-Aminosulfonyl-4-methylphenyl)-5-fluoro-N4-[3-(3-methyl-1,2,4-oxadiazol-5-yl)methyleneoxyphenyl]-2,4-pyrimidinediamine; |
| I-255 | 5-Fluoro-N2-[3-(N-methylaminosulfony)-4-methylphenyl]-N4-[3-(3-methyl-1,2,4-oxadiazol-5-yl)methyleneoxyphenyl]-2,4-pyrimidinediamine; |
| I-256 | N2-[4-(2-N,N-Diethylaminoethyl)aminosulfonylphenyl]-5-fluoro-N4-[3-(3-methyl-1,2,4-oxadiazol-5-yl)methyleneoxyphenyl]-2,4-pyrimidinediamine; |
| I-257 | N2-{3-[(N-5-Methyl-1,3-dioxolene-2-one-4-yl)methylene]aminosulfonylphenyl}-5-fluoro-N4-[4-(3-methyl-1,2,4-oxadiazol-5-yl)methyleneoxyphenyl]-2,4-pyrimidinediamine; |
| I-258 | N2-(3-Aminosulfonylphenyl)-5-fluoro-N4-[4-(3-methyl-1,2,4-oxadiazol-5-yl)methyleneoxyphenyl]-2,4-pyrimidinediamine; |
| I-259 | N2-(3-Aminosulfonyl-4-methylphenyl)-5-fluoro-N4-[4-(3-methyl-1,2,4-oxadiazol-5-yl)methyleneoxyphenyl]-2,4-pyrimidinediamine; |
| I-260 | 5-Fluoro-N2-[3-N-(methyl)aminosulfonyl-4-methylphenyl]-N4-[4-(3-methyl-1,2,4-oxadiazol-5-yl)methyleneoxyphenyl]-2,4-pyrimidinediamine; |
| I-261 | N2-[3-(2-N,N-Diethylaminoethyl)aminosulfonylphenyl]-5-fluoro-N4-[3-(3-methyl-1,2,4-oxadiazol-5-yl)methyleneoxyphenyl]-2,4-pyrimidinediamine; |
| I-262 | 5-Fluoro-N4-[4-(3-methyl-1,2,4-oxadiazol-3-yl)methyleneoxyphenyl]-N2-[(3-N-propanamido)sulfonylphenyl)]-2,4-pyrimidinediamine; |
| I-263 | N2-[4-(2-N,N-Diethylaminoethyl)aminosulfonylphenyl]-5-fluoro-N4-[4-(3-methyl-1,2,4-oxadiazol-5-yl)methyleneoxyphenyl]-2,4-pyrimidinediamine; |
| I-264 | 5-Fluoro-N4-[4-(3-methyl-1,2,4-oxadiazol-3-yl)methyleneoxyphenyl]-N2-[(3-N-propanamido)sulfonylphenyl)]-2,4-pyrimidinediamine; |
| I-265 | N2-(3-Aminosulfonyl-4-chloro-5-methylphenyl)-5-fluoro-N4-[4-(3-methyl-1,2,4-oxadiazol-5-yl)methyleneoxyphenyl]-2,4-pyrimidinediamine; |
| I-266 | N2-(3-Aminosulfonyl-4-fluorophenyl)-5-fluoro-N4-[4-(3-methyl-1,2,4-oxadiazol-5-yl)methyleneoxyphenyl]-2,4-pyrimidinediamine; |
| I-267 | N2-(3-Aminosulfonyl-4-fluorophenyl)-5-fluoro-N4-[4-(3-methyl-1,2,4-oxadiazol-5-yl)ethylenephenyl]-2,4-pyrimidinediamine; |
| I-268 | N2-(4-Aminosulfonylphenyl)-5-fluoro-N4-(4-[3-methyl-1,2,4-oxadiazol-5-yl]methyleneoxyphenyl)-2,4-pyrimidinediamine; |
| I-269 | 5-fluoro-N2-(4-N-methylaminosulfonyl)-3-methoxyphenyl-N4-(4-trifluoromethoxy-3-chlorophenyl)-2,4-pyrimidinediamine; |
| I-270 | 5-fluoro-N4-(3-hydroxyphenyl)- N2-(4-N-methylaminosulfonyl)-3-methoxyphenyl]-2,4-pyrimidinediamine; |
| I-271 | N2-(5-N,N-Diethylaminosulfonyl-2-methoxyphenyl)-5-fluoro-N4-(4-[3-methyl-1,2,4-oxadiazol-5-yl]methyleneoxyphenyl)-2,4-pyrimidinediamine; |
| I-272 | 5-Fluoro-N4-(4-[3-methyl-1,2,4-oxadiazol-5-yl]methyleneoxyphenyl)-N2-(5-piperidinesulfonylphenyl)-2,4-pyrimidinediamine; |
| I-273 | 5-Fluoro-N4-[4-(3-methyl-1,2,4-oxadiazol-3-yl)methyleneoxyphenyl]-N2-[(3-N-propanamido)sulfonylphenyl)]-2,4-pyrimidinediamine Sodium Salt; |
| I-274 | 5-Fluoro-N4-[4-[(5-methyl-1,2,4-oxadiazol-3-yl)methoxy]phenyl-N2-[3-(4-methylpiperazin-1-yl)sulfonyl]phenyl-2,4-pyrimidinediamine; |
| I-275 | N2-(4-Aminosulfonyl)phenyl-5-fluoro-N4-[4-(5-methyl-1,2,4-oxadiazol-3-yl)methoxy]phenyl-2,4-pyrimidinediamine; |
| I-276 | N2-(3-Aminosulfonyl)phenyl-5-fluoro-N4-[4-(5-methyl-1,2,4-oxadiazol-3-yl)methoxy]phenyl-2,4-pyrimidinediamine; |
| I-277 | N2-(3-aminosulfonylphenyl)-5-fluoro-N4-[4-(5-methyl-1,3,4-oxadiazol-2-yl)methyleneoxyphenyl]-2,4-pyrimidinediamine (71); |
| I-278 | N2-(3-Aminosulfonyl-4-fluorophenyl)-5-fluoro-N4-[4-(5-methyl-1,3,4-oxadiazol-2-yl)methyleneoxyphenyl]-2,4-pyrimidinediamine; |
| I-279 | N2-(3-Aminosulfonyl-4-methylphenyl)-5-fluoro-N4-[4-(5-methyl-1,3,4-oxadiazol-2-yl)methoxyphenyl]-2,4-pyrimidinediamine; |
| I-280 | N2-(3-Aminosulfonyl-4-methylphenyl)-5-fluoro-N4-[4-(2-methylthiazol-4-yl)methyleneoxyphenyl]-2,4-pyrimidinediamine; |
| I-281 | N2-(3-Aminosulfonylphenyl)-5-fluoro-N4-[4-(2-methylthiazol-4-yl)methyleneoxyphenyl]-2,4-pyrimidinediamine; |
| I-282 | 5-Fluoro-N2-[3-(N-methylaminosulfony)-4-methylphenyl]-N4-[4-(2-methylthiazol-4-yl)methyleneoxyphenyl]-2,4-pyrimidinediamine; |
| I-283 | N2-[3-(2-N,N-Diethylaminoethyl)aminosulfonylphenyl]-5-fluoro-N4-[4-(2-methylthizol-4-yl)methyleneoxyphenyl]-2,4-pyrimidinediamine; |
| I-284 | N2-[4-(2-N,N-Diethylaminoethyl)aminosulfonylphenyl]-5-fluoro-N4-[4-(2-methylthizol-4-yl)methyleneoxyphenyl]-2,4-pyrimidinediamine; |
| I-285 | N2-(4-Aminosulfonylphenyl)-5-fluoro-N4-[4-(2-methylthiazol-4-yl)methyleneoxyphenyl]-2,4-pyrimidinediamine; |
| II-1 | Racemic N2-(3-aminosulfonyl-4-methylphenyl)-5-fluoro-N4-{3-[(1-methylpiperidin-3-yl)oxy]phenyl}-2,4-pyrimidinediamine; |
| II-2 | N2-(3-Aminosulfonyl-4-methylphenyl)-5-fluoro-N4-{3-[(1-methylpiperidin-4-yl)oxy]phenyl}-2,4-pyrimidinediamine; |
| II-3 | Racemic N2-(3-aminosulfonyl-4-methylphenyl)-N4-{3-chloro-4-[(1-methylpiperidin-3-yl)oxy]phenyl}-5-fluoro-2,4-pyrimidinediamine; |
| II-4 | Racemic N2-(3-aminosulfonyl-4-methylphenyl)-5-fluoro-N4-{4-[(1-methylpiperidin-3-yl)oxy]phenyl}-2,4-pyrimidinediamine; |
| II-5 | N2-(3-Aminosulfonyl-4-methylphenyl)-5-fluoro-N4-{3-methyl-4-[(1-methylpiperidin-4-yl)oxy]phenyl}-2,4-pyrimidinediamine; |
| II-6 | N2-(3-Aminosulfonyl-4-methylphenyl)-5-fluoro-N4-{4-[(1-methylpiperidin-4-yl)oxy]-3-trifluoromethylphenyl}-2,4-pyrimidinediamine; |

-continued

| cmpd | name |
|---|---|
| II-7 | N2-(3-Aminosulfonyl-4-methylphenyl)-5-fluoro-N4-{4-[(1-methylpiperidin-4-yl)oxy]phenyl}-2,4-pyrimidinediamine; |
| II-8 | N2-(3-Aminosulfonyl-4-methylphenyl)-5-fluoro-N4-{3-chloro-4-[(1-methylpiperidin-4-yl)oxy]phenyl}-2,4-pyrimidinediamine; |
| II-9 | N2-(3-Aminosulfonylphenyl)-5-fluoro-N4-(N-methylpyrrolidin-3-yloxyphenyl)-2,4-pyrimidinediamine; |
| II-10 | N2-(3-Aminosulfonyl-4-methylphenyl)-5-fluoro-N4-(N-methylpyrrolidin-3-yloxyphenyl)-2,4-pyrimidinediamine; |
| II-11 | N2-(3-Aminosulfonylphenyl)-5-fluoro-N4-[4-(3-pyridyloxy)phenyl]-2,4-pyrimidinediamine; |
| II-12 | N2-(3-Aminosulfonyl-4-methylphenyl)-5-fluoro-N4-[4-(3-pyridyloxy)phenyl]-2,4-pyrimidinediamine; |
| II-13 | 5-Fluoro-N2-[3-N-(methylaminosulfonyl)-4-methylphenyl]-N4-[4-(3-pyridyloxy)phenyl]-2,4-pyrimidinediamine; |
| II-14 | N2-(4-Aminosulfonylphenyl)-5-fluoro-N4-[4-(3-pyridyloxy)phenyl]-2,4-pyrimidinediamine; |
| II-15 | N2-[3,5-bis(Aminosulfonyl)phenyl]-5-fluoro-N4-[4-(3-pyridyloxy)phenyl]-2,4-pyrimidinediamine; |
| II-16 | N2-(3-Aminosulfonyl-4-methylphenyl)-5-fluoro-N4-[4-(4-pyridyloxy)phenyl]-2,4-pyrimidinediamine; |
| II-17 | N2-(3-Aminosulfonylphenyl)-5-fluoro-N4-[4-(4-pyridyloxy)phenyl]-2,4-pyrimidinediamine; |
| II-18 | 5-Fluoro-N2-[3-(N-methylaminosulfony)-4-methylphenyl]-5-fluoro-N4-[4-(4-pyridyloxy)phenyl]-2,4-pyrimidinediamine; |
| II-19 | N2-(3-Aminocarbonyl-5-methylphenyl)-5-fluoro-N2-[4-(1-methylpyrazol-3-yl)amidophenyl]-2,4-pyrimidinediamine; |
| II-20 | N2-(3-Aminocarbonyl-5-methylphenyl)-5-fluoro-N2-[4-(1-ethylpyrazol-5-yl)amidophenyl]-2,4-pyrimidinediamine; |
| II-21 | N2-(3-Aminocarbonyl-5-methylphenyl)-5-fluoro-N2-[4-(1-methylpyrazol-5-yl)amidophenyl]-2,4-pyrimidinediamine; |
| II-22 | N2-(3-Aminocarbonyl-5-methylphenyl)-5-fluoro-N2-[4-(1H-pyrazol-5-yl)amidophenyl]-2,4-pyrimidinediamine; |
| III-1 | 5-Fluoro-N2-[3-(N-methylaminosulfony)-4-methylphenyl]-5-fluoro-N4-(4-cyanomethylphenyl)-2,4-pyrimidinediamine; |
| III-2 | N2-[4-(2-N,N-Diethylaminoethyl)aminosulfonylphenyl]-5-fluoro-N4-(4-cyanomethylphenyl)-2,4-pyrimidinediamine; |
| III-3 | N2-(4-Aminosulfonyl)phenyl-N4-(4-cyanomethyl)phenyl-5-fluoro-2,4-pyrimidinediamine; |
| III-4 | N2-(3-Aminosulfonyl)phenyl-N4-(4-cyanomethyl)phenyl-5-fluoro-2,4-pyrimidinediamine; |
| III-5 | N4-(4-Cyanomethyl)phenyl-5-fluoro-N2-[3-(4-methylpiperazin-1-yl)sulfonyl]phenyl-2,4-pyrimidinediamine; |
| III-6 | N4-(4-Cyanomethyl)phenyl-5-fluoro-N2-[4-(4-methylpiperazin-1-yl)sulfonyl]phenyl-2,4-pyrimidinediamine; |
| III-7 | N2-(3-Aminosulfonyl-4-methyl)phenyl-N4-(4-cyanomethyl)phenyl-5-fluoro-2,4-pyrimidinediamine; |
| III-8 | N2-(3-Aminosulfonyl-4-chloro)phenyl-N4-(4-cyanomethyl)phenyl-5-fluoro-2,4-pyrimidinediamine; |
| III-9 | N2-(4-Aminosulfonyl-3-methoxy)phenyl-N4-(4-cyanomethyl)phenyl-5-fluoro-2,4-pyrimidinediamine; |
| III-10 | N2-(3-Aminosulfonyl-4-fluoro)phenyl-N4-(4-cyanomethyl)phenyl-5-fluoro-2,4-pyrimidinediamine; |
| III-11 | N2-(3-Aminosulfonyl-4-methylphenyl)-N4-(4-cyanoethylenephenyl)-5-methyl-2,4-pyrimidinediamine; |
| III-12 | N2-(3-Aminosulfonyl-4-chlorophenyl)-N4-[4-(2-cyanoethyl)phenyl]-5-methyl-2,4-pyrimidinediamine; |
| III-13 | N2-(3-Aminosulfonyl-4-chlorophenyl)-N4-[4-(2-cyanoethyl)phenyl]-5-fluoro-2,4-pyrimidinediamine; |
| III-14 | N2-(3-aminosulfonylphenyl)-N4-[4-(cyanoethylene)phenyl]-5-fluoro-2,4-pyrimidinediamine; |
| III-15 | N2-(3-Aminosulfonyl-4-methylphenyl)-N4-[4-(cyanoethylene)phenyl]-5-fluoro-2,4-pyrimidinediamine; |
| III-16 | N2-(3-Aminosulfonyl-4-fluorophenyl)-N4-[4-(cyanoethylene)phenyl]-5-fluoro-2,4-pyrimidinediamine; |
| III-17 | N2-(3-Aminosulfonyl-4-methylphenyl)-5-fluoro-N4-[4-(2-cyanoethyl)-3-fluorophenyl]-2,4-pyrimidinediamine; |
| III-18 | N2-(3-Aminosulfonylphenyl)-N4-[4-(2-cyanoethyl)-3-fluorophenyl]-5-fluoro-2,4-pyrimidinediamine; |
| III-19 | N2-(3-Aminosulfonyl-4-methylphenyl)-N4-[4-(2-cyanoethyl)-3-methylphenyl]-5-fluoro-2,4-pyrimidinediamine; |
| III-20 | N2-(3-Aminosulfonylphenyl)-N4-[4-(2-cyanoethyl)-3-methylphenyl]-5-fluoro-2,4-pyrimidinediamine; |
| III-21 | N2-(3-Aminosulfonyl-4-methylphenyl)-N4-[3-chloro-4-(2-cyanoethyl)phenyl]-5-fluoro-2,4-pyrimidinediamine; |
| III-22 | N2-(3-Aminosulfonylphenyl)-N4-[3-chloro-4-(2-cyanoethyl)phenyl]-5-fluoro-2,4-pyrimidinediamine; |
| III-23 | N2-(3-Aminosulfonyl-4-methylphenyl)-N4-(4-cyanoethylene-2-methylphenyl)-5-fluoro-2,4-pyrimidinediamine |
| III-24 | N2-(3-Aminosulfonylphenyl)-N4-(4-cyanoethylene-2-methylphenyl)-5-fluoro-2,4-pyrimidinediamine |
| III-25 | N2-(3-Aminosulfonyl-4-methylphenyl)-N4-(4-cyanoethylene-3-methoxyphenyl)-5-fluoro-2,4-pyrimidinediamine |
| III-26 | N2-(3-Aminosulfonylphenyl)-N4-(4-cyanoethylene-2-methylphenyl)-5-fluoro-2,4-pyrimidinediamine |
| III-27 | N2-(4-Aminosulfonylphenyl)-N4-(4-cyanoethylenephenyl)-5-methyl-2,4-pyrimidinediamine and its prodrug |
| III-28 | N4-(3-Chloro-4-cyanoethylene-phenyl)-5-fluoro-N2-(4-methyl-3-propionylaminosulfonylphenyl)-2,4-pyrimidinediamine |
| III-29 | N4-(3-Chloro-4-cyanoethylene-phenyl)-5-fluoro-N2-(4-methyl-3-propionylaminosulfonylphenyl)-2,4-pyrimidinediamine Sodium salt |
| III-30 | N4-(4-Cyanoethylene-3-trifluoromethylphenyl)-5-fluoro-N2-(4-methyl-3-aminosulfonylphenyl)-2,4-pyrimidinediamine |
| III-31 | N4-(4-Cyanoethylene-3-trifluoromethylphenyl)-5-fluoro-N2-(3-aminosulfonylphenyl)-2,4-pyrimidinediamine |
| III-32 | N4-(4-Aminocarbonylaminomethylphenyl)-N2-(4-aminosulfonylphenyl)-5-fluoro-2,4-pyrimidinediamine; |
| III-33 | N4-(4-Aminocarbonylaminomethylphenyl)-N2-(3-aminosulfonylphenyl)-5-fluoro-2,4-pyrimidinediamine; |
| III-34 | N4-(4-Aminocarbonylaminomethylphenyl)-N2-(3-aminosulfonyl-4-methylphenyl)-5-fluoro-2,4-pyrimidinediamine; |
| III-35 | N2-(4-aminosulfonyl)phenyl-N4-(4-ethylcarbonylaminomethyl)phenyl-5-fluoro-2,4-pyrimidinediamine; |
| III-36 | N2-(3-aminosulfonyl)phenyl-N4-(4-ethylcarbonylaminomethyl)phenyl-5-fluoro-2,4-pyrimidinediamine; |
| III-37 | N2-(3-aminosulfonyl-4-methyl)phenyl-N4-(4-ethylcarbonylaminomethyl)phenyl-5-fluoro-2,4-pyrimidinediamine; |
| III-38 | N2-(4-aminosulfonyl)phenyl-N4-(3-cyclopropylcarbonylaminomethyl)phenyl-5-fluoro-2,4-pyrimidinediamine; |
| III-39 | N2-(3-aminosulfonyl)phenyl-N4-(3-cyclopropylcarbonylaminomethyl)phenyl-5-fluoro-2,4-pyrimidinediamine; |
| III-40 | N2-(3-aminosulfonyl-4-methyl)phenyl-N4-(3-cyclopropylcarbonylaminomethyl)phenyl-5-fluoro-2,4-pyrimidinediamine; |
| III-41 | N2-(4-aminosulfonyl)phenyl-N4-(4-cyclopropylcarbonylaminomethyl)phenyl-5-fluoro-2,4-pyrimidinediamine; |
| III-42 | N2-(3-aminosulfonyl)phenyl-N4-(4-cyclopropylcarbonylaminomethyl)phenyl-5-fluoro-2,4-pyrimidinediamine; |
| III-43 | N2-(3-aminosulfonyl-4-methyl)phenyl-N4-(4-cyclopropylcarbonylaminomethyl)phenyl-5-fluoro-2,4-pyrimidinediamine; |
| III-44 | N4-(4-Acrylamidomethylphenyl)-N2-(4-aminosulfonylphenyl)-5-fluoro-2,4-pyrimidinediamine; |
| III-45 | N4-(4-Acrylamidomethylphenyl)-N2-(3-aminosulfonylphenyl)-5-fluoro-2,4-pyrimidinediamine; |
| III-46 | N4-(4-Acrylamidomethylphenyl)-N2-(3-aminosulfonyl-4-methylphenyl)-5-fluoro-2,4-pyrimidinediamine; |
| III-47 | N4-[4-(2-Aminocarboxyethylene)phenyl]-5-fluoro-N2-(4-methyl-3-aminosulfonylphenyl)- 2,4-pyrimidinediamine; |
| III-48 | N4-[4-(2-Aminocarboxyethylene)phenyl]-N2-(3-aminosulfonylphenyl)-5-fluoro-2,4-pyrimidinediamine |
| III-49 | N4-[4-(2-Aminocarboxyethylene)phenyl]-N2-(4-aminosulfonylphenyl)-5-fluoro-2,4-pyrimidinediamine |
| III-50 | N2-(3-Aminosulfonylphenyl)-5-fluoro-N-4[4(1-methylpyrazolyl-3-aminocarbonylmethylene)phenyl]-2,4-pyrimidinediamine; |
| III-51 | N2-(3-Aminosulfonylphenyl)-N4-[(1-ethylpyrazolyl-5-aminocarbonylmethylene)phenyl]-5-fluoro-2,4-pyrimidinediamine; |
| III-52 | N2-(3-Aminosulfonyl-4-methylphenyl)-5-N4-[(1-ethylpyrazolyl-5-aminocarbonylmethylene)phenyl]-5-fluoro-2,4-pyrimidinediamine; |
| III-53 | N4-{4-[2-(Aminocarbonyloxy)ethyl]phenyl}-N2-(3-aminosulfonyl-4-methylphenyl)-5-fluoro-2,4-pyrimidinediamine |
| III-54 | N4-{4-[2-(Aminocarbonyloxy)ethyl]phenyl}-N2-(3-aminosulfonylphenyl)-5-fluoro-2,4-pyrimidinediamine |
| III-55 | N4-{4-[2-(Aminocarbonyloxy)ethyl]phenyl}-N2-(3-aminosulfonyl-4-chlorophenyl)-5-fluoro-2,4-pyrimidinediamine |
| III-56 | N2-(3-Aminosulfonyl-4-methylphenyl)-N4-{4-[2-(dimethylaminocarbonyloxy)ethyl]phenyl}-5-fluoro-2,4-pyrimidinediamine; |
| III-57 | N2-(3-Aminosulfonylphenyl)-N4-{4-[2-(dimethylaminocarbonyloxy)ethyl]phenyl}-5-fluoro-2,4-pyrimidinediamine; |
| III-58 | N2-(3-Aminosulfonyl-4-chlorophenyl)-N4-{4-[2-(dimethylaminocarbonyloxy)ethyl]phenyl}-5-fluoro-2,4-pyrimidinediamine; |
| III-59 | N2-(3-Aminosulfonyl-4-methylphenyl)-5-fluoro-N4-{4-[2-(methylaminocarbonyloxy)ethyl]phenyl}-2,4-pyrimidinediamine; |

-continued

| cmpd | name |
|---|---|
| III-60 | N2-(3-Aminosulfonylphenyl)-5-fluoro-N4-{4-[2-(methylaminocarbonyloxy)ethyl]phenyl}-2,4-pyrimidinediamine; |
| III-61 | N2-(3-Aminosulfonyl-4-chlorophenyl)-5-fluoro-N4-{4-[2-(methylaminocarbonyloxy)ethyl]phenyl}-2,4-pyrimidinediamine; |
| III-62 | N2-(3-Aminosulfonylphenyl)-N4-(4-benzylphenyl)-5-fluoro-2,4-pyrimidinediamine; |
| III-63 | N2-(3-Aminosulfonyl-4-methylphenyl)-N4-(4-benzylphenyl)-5-fluoro-2,4-pyrimidinediamine; |
| III-64 | N2-(3-Aminosulfonyl-4-chlorophenyl)-N4-(4-benzylphenyl)-5-fluoro-2,4-pyrimidinediamine; |
| III-65 | N2-(3-Aminosulfonyl-4-methoxy-5-methylphenyl)-N4-(4-benzylphenyl)-5-fluoro-2,4-pyrimidinediamine; |
| III-66 | N2-(3-Aminosulfonyl-4-methoxyphenyl)-5-fluoro-N4-[4-(4-pyridinylmethyl)phenyl]-2,4-pyrimidinediamine; |
| III-67 | N2-[4-(2-N,N-Diethylaminoethyl)aminosulfonylphenyl]-5-fluoro-N4-[4-(4-pyridinylmethyl)phenyl]-2,4-pyrimidinediamine; |
| III-68 | 5-Fluoro-N4-[4-(4-pyridinylmethyl)phenyl]-N2-[(3-N-propanamido)sulfonylphenyl)]-2,4-pyrimidinediamine; |
| III-69 | 5-Fluoro-N4-[4-(4-pyridinylmethyl)phenyl]-N2-[(3-N-propanamido)sulfonylphenyl)]-2,4-pyrimidinediamine sodium salt; |
| III-70 | N2-(3-Aminosulfonylphenyl)-5-fluoro-N4-[4-(4-pyridinylmethyl)phenyl]-2,4-pyrimidinediamine; |
| III-71 | N2-(4-Aminosulfonylphenyl)-5-fluoro-N4-[4-(4-pyridinylmethyl)phenyl]-2,4-pyrimidinediamine; |
| III-72 | N2-[4-(2-N,N-Diethylaminoethyl)aminosulfonylphenyl]-5-fluoro-N4-[4-(4-pyridinylmethyl)phenyl]-2,4-pyrimidinediamine; |
| III-73 | N2-(3-Aminosulfonylphenyl)-5-fluoro-N4-[4-(4-pyridylmethyl)phenyl]-2,4-pyrimidinediamine Hydrochloride Salt; |
| III-74 | N2-(3-Aminosulfonyl-4-methylphenyl)-5-fluoro-N4-[4-(4-pyridinylmethyl)phenyl]-2,4-pyrimidinediamine; |
| III-75 | 5-Fluoro-N2-[3-(N-methylaminosulfony)-4-methylphenyl]-5-fluoro-N4-[4-(4-pyridinylmethyl)phenyl]-2,4-pyrimidinediamine; |
| III-76 | N2-(3-Aminosulfonylphenyl)-5-fluoro-N4-[4-(4-pyridinyl)phenethyl]-2,4-pyrimidinediamine; |
| III-77 | N2-(3-Aminosulfonyl-4-methylphenyl)-5-fluoro-N4-[4-(4-pyridinyl)phenethyl]-2,4-pyrimidinediamine; |
| III-78 | 5-Fluoro-N2-[3-N-(methyl)aminosulfonyl-4-methylphenyl]-N4-[4-(4-pyridinyl)phenethyl]-2,4-pyrimidinediamine; |
| III-79 | N2-(4-Aminosulfonylphenyl)-5-fluoro-N4-[4-(4-pyridinyl)phenethyl]-2,4-pyrimidinediamine; |
| III-80 | Preparation of N2-(3-Aminosulfonylphenyl)-5-fluoro-N4-[4-(1-oxido-4-pyridylmethyl)phenyl]-2,4-pyrimidinediamine; |
| III-81 | N2-(3-Aminosulfonylphenyl)-5-fluoro-N4-[4-(1-imidazolylmethyl)phenyl]-2,4-pyrimidinediamine; |
| III-82 | N2-(3-Aminosulfonyl-4-methylphenyl)-5-fluoro-N4-[4-(1-imidazolylmethyl)phenyl]-2,4-pyrimidinediamine; |
| III-83 | 5-Fluoro-N2-[3-(N-methylaminosulfony)-4-methylphenyl]-5-fluoro-N4-[4-(1-imidazolylmethyl)phenyl]-2,4-pyrimidinediamine; |
| III-84 | N2-[4-(2-N,N-Diethylaminoethyl)aminosulfonylphenyl]-5-fluoro-N4-[4-(1-imidazolylmethyl)phenyl]-2,4-pyrimidinediamine; |
| III-85 | 5-Fluoro-N2-[3-(N-methylaminosulfony)-4-methylphenyl]-N4-[4-(1-imidazolylmethyl)phenyl]-2,4-pyrimidinediamine hydrochloride |
| III-86 | 5-Fluoro-N2-[3-(N-methylaminosulfony)-4-methylphenyl]-N4-[4-(1-imidazolylmethyl)phenyl]-2,4-pyrimidinediamine dihydrochloride |
| III-87 | N2-(3-Aminosulfonylphenyl)-5-fluoro-N4-[4-(1-imidazolyl)phenethyl]-2,4-pyrimidinediamine; |
| III-88 | N2-(3-Aminosulfonyl-4-methylphenyl)-5-fluoro-N4-[4-(1-imidazolyl)phenethyl]-2,4-pyrimidinediamine; |
| III-89 | 5-Fluoro-N2-[3-(N-methylaminosulfony)-4-methylphenyl]-N4-[4-(1-imidazolyl)phenethyl]-2,4-pyrimidinediamine; |
| III-90 | N2-(4-Aminosulfonylphenyl)-5-fluoro-N4-[4-(1-imidazolyl)phenethyl]-2,4-pyrimidinediamine; |
| III-91 | N2-(3-Aminosulfonyl-4-methylphenyl)-5-fluoro-N4-[4-(2-methyl-1-imidazolylmethyl)phenyl]-2,4-pyrimidinediamine; |
| III-92 | N2-(4-Aminosulfonylphenyl)-5-fluoro-N4-[4-(2-methyl-1-imidazolylmethyl)phenyl]-2,4-pyrimidinediamine; |
| III-93 | 5-Fluoro-N2-[3-(N-methylaminosulfony)-4-methylphenyl]-N4-[4-(2-methyl-1-imidazolylmethyl)phenyl]-2,4-pyrimidinediamine; |
| III-94 | N2-(3-Aminosulfonylphenyl)-5-fluoro-N4-[4-(2-methyl-1-imidazolylmethyl)phenyl]-2,4-pyrimidinediamine; |
| III-95 | N2-(3-Aminosulfonyl-4-methylphenyl)-5-fluoro-N4-{4-[1-(1,2,3-triazolyl)methyl]phenyl}-2,4-pyrimidinediamine; |
| III-96 | N2-4-Aminosulfonylphenyl)-5-fluoro-N4-{4-[1-(1,2,3-triazolyl)methyl]phenyl}-2,4-pyrimidinediamine; |
| III-97 | N2-(3-Aminosulfonylphenyl)-5-fluoro-N4-{4-[1-(1,2,3-triazolyl)methyl]phenyl}-2,4-pyrimidinediamine; |
| III-98 | 5-Fluoro-N2-[3-(N-methylaminosulfony)-4-methylphenyl]-N4-{4-[1-(1,2,3-thazolyl)methyl]phenyl}-2,4-pyrimidinediamine; |
| III-99 | N2-(4-Aminosulfonylphenyl)-5-fluoro-N4-{4-[1-(1,2,4-thazolyl)methyl]phenyl}-2,4-pyrimidinediamine; |
| III-100 | N2-(3-Aminosulfonylphenyl)-5-fluoro-N4-{4-[1-(1,2,4-thazolyl)methyl]phenyl}-2,4-pyrimidinediamine; |
| III-101 | N2-(3-Aminosulfonyl-4-methylphenyl)-5-fluoro-N4-{4-[1-(1,2,4-thazolyl)methyl]phenyl}-2,4-pyrimidinediamine; |
| III-102 | 5-Fluoro-N2-[3-(N-methylaminosulfony)-4-methylphenyl]-N4-{4-[1-(1,2,4-thazolyl)methyl]phenyl}-2,4-pyrimidinediamine; |
| III-103 | N2-(3-Aminosulfonylphenyl)-5-fluoro-N4-(4-N-morpholinomethylenephenyl)-2,4-pyrimidinediamine; |
| III-104 | N2-(3-Aminosulfonyl-4-methylphenyl)-5-fluoro-N4-(4-N-morpholinomethylenephenyl)-2,4-pyrimidinediamine; |
| III-105 | N2-(3-Aminosulfonyl-4-methyleneoxyphenyl)-5-fluoro-N4-(4-N-morpholinomethylenephenyl)-2,4-pyrimidinediamine; |
| III-106 | N2-(3-Aminosulfonylphenyl)-5-fluoro-N4-[4-(3-methyl-1,2,4-oxadiazol-5-yl)ethylenephenyl]-2,4-pyrimidinediamine; |
| III-107 | N2-(3-Aminosulfonylphenyl)-5-fluoro-N4-(4-thiomorpholinomethylenephenyl)-2,4-pyrimidinediamine; |
| III-108 | N2-(3-Aminosulfonyl-4-methylphenyl)-5-fluoro-N4-(4-thiomorpholinomethylenephenyl)-2,4-pyrimidinediamine; |
| III-109 | N2-(3-Aminosulfonyl-4-methyoxyphenyl)-5-fluoro-N4-(4-thiomorpholinomethylenephenyl)-2,4-pyrimidinediamine; |
| III-110 | N2-(3-Aminosulfonylphenyl)-5-fluoro-N4-{4-[(1,1-dioxothiomorpholin-4-yl-)methyl]phenyl}-2,4-pyrimidinediamine; |
| III-111 | N2-(3-Aminosulfonyl-4-methylphenyl)-5-fluoro-N4-{4-[(1,1-dioxothiomorpholin-4-yl-)methyl]phenyl}-2,4-pyrimidinediamine; |
| III-112 | N2-(3-Aminosulfonyl-4-methyloxyphenyl)-5-fluoro-N4-{4-[(1,1-dioxothiomorpholin-4-yl-)methyl]phenyl}-2,4-pyrimidinediamine; |
| III-113 | N4-(3-aminocarbonylaminomethyl)phenyl-N2-(4-aminosulfonyl)phenyl-5-fluoro-2,4-pyrimidinediamine; |
| III-114 | N4-(3-aminocarbonylaminomethyl)phenyl-N2-(3-aminosulfonyl)phenyl-5-fluoro-2,4-pyrimidinediamine; |
| III-115 | N4-(3-aminocarbonylaminomethyl)phenyl-N2-(3-aminosulfonyl-4-methyl)phenyl-5-fluoro-2,4-pyrimidinediamine; |
| III-116 | N2-(4-aminosulfonyl)phenyl-N4-(3-ethylaminocarbonylaminomethyl)phenyl-5-fluoro-2,4-pyrimidinediamine; |
| III- | N2-(3-aminosulfonyl)phenyl-N4-(3-ethylaminocarbonylaminomethyl)phenyl-5-fluoro-2,4-pyrimidinediamine; |

-continued

| cmpd | name |
|---|---|
| III-117 | N2-(3-aminosulfonyl-4-methyl)phenyl-N4-(3-ethylaminocarbonylaminomethyl)phenyl-5-fluoro-2,4-pyrimidinediamine; |
| III-118 | N2-(4-Aminosulfonylphenyl)-N4-(4-ethylaminocarbonylaminomethylphenyl)-5-fluoro-2,4-pyrimidinediamine; |
| III-119 | N2-(3-Aminosulfonylphenyl]-N4-(4-ethylaminocarbonylaminomethylphenyl)-5-fluoro-2,4-pyrimidinediamine; |
| III-120 | N2-(3-Aminosulfonyl-4-methylphenyl)-N4-(4-ethylaminocarbonylaminomethylphenyl)-5-fluoro-2,4-pyrimidinedia; |
| III-121 | N2-(4-aminosulfonyl)phenyl-N4-[4-(2-ethylaminocarbonylamino)ethyl]phenyl-5-fluoro-2,4-pyrimidinediamine; |
| III-122 | N2-(3-aminosulfonyl)phenyl-N4-[4-(2-ethylaminocarbonylamino)ethyl]phenyl-5-fluoro-2,4-pyrimidinediamine; |
| III-123 | N2-(3-aminosulfonyl-4-methyl)phenyl-N4-[4-(2-ethylaminocarbonylamino)ethyl]phenyl-5-fluoro-2,4-pyrimidinediamine; |
| III-124 | N2-(4-aminosulfonyl)phenyl-N4-[4-(N-carbamoyl-N-propyl)aminomethyl]phenyl-5-fluoro-2,4-pyrimidinediamine; |
| III-125 | N2-(3-aminosulfonyl)phenyl-N4-[4-(N-carbamoyl-N-propyl)aminomethyl]phenyl-5-fluoro-2,4-pyrimidinediamine; |
| III-126 | N2-(3-aminosulfonyl-4-methyl)phenyl-N4-[4-(N-carbamoyl-N-propyl)aminomethyl]phenyl-5-fluoro-2,4-pyrimidinediamine; |
| III-127 | N2-(3-Aminosulfonylphenyl)-5-fluoro-N4-[4-(4-pyridylmethyl)phenyl]-2,4-pyrimidinediamine p-Toluenesulfonic Acid Salt; |
| III-128 | N2-(3-Aminosulfonylphenyl)-5-fluoro-N4-[4-(4-pyridylmethyl)phenyl]-2,4-pyrimidinediamine Methanesulfonic Acid Salt; |
| IV-1 | N2-(3-Aminosulfonylphenyl)-5-fluoro-N4-[3-(1,3-oxazol-5-yl)phenyl]-2,4-pyrimidinediamine; |
| IV-2 | N2-(3-Aminosulfonyl-4-methylphenyl)-5-fluoro-N4-[3-(1,3-oxazol-5-yl)phenyl]-2,4-pyrimidinediamine; |
| IV-3 | N2-(4-Aminosulfonylphenyl)-5-fluoro-N4-[3-(1,3-oxazol-5-yl)phenyl]-2,4-pyrimidinediamine; |
| IV-4 | 5-Fluoro-N2-[3-(N-methylaminosulfony)-4-methylphenyl]-N4-[3-(1,3-oxazol-5-yl)phenyl]-2,4-pyrimidinediamine; |
| IV-5 | N2-(3-Aminosulfonylphenyl)-5-fluoro-N4-[4-(1,3-oxazol-5-yl)phenyl]-2,4-pyrimidinediamine; |
| IV-6 | N2-(3-Aminosulfonyl-4-methylphenyl)-5-fluoro-N4-[4-(1,3-oxazol-5-yl)phenyl]-2,4-pyrimidinediamine; |
| IV-7 | 5-Fluoro-N2-[3-(N-methylaminosulfony)-4-methylphenyl]-N4-[4-(1,3-oxazol-5-yl)phenyl]-2,4-pyrimidinediamine; |
| IV-8 | N2-(4-Aminosulfonylphenyl)-5-fluoro-N4-[4-(1,3-oxazol-5-yl)phenyl]-2,4-pyrimidinediamine; |
| IV-9 | N2-(3-Aminosulfonylphenyl)-5-fluoro-N4-[3-(N,N-dimethylaminosulfonyl)phenyl]-2,4-pyrimidinediamine; |
| IV-10 | N2-(3-Aminosulfonyl-4-methylphenyl)-5-fluoro-N4-[3-(N,N-dimethylaminosulfonyl)phenyl]-2,4-pyrimidinediamine; |
| IV-11 | N2-(3-Aminosulfonylhenyl)-5-fluoro-N4-[3-(N-methylaminosulfonyl)phenyl]-2,4-pyrimidinediamine; |
| IV-12 | N2-(3-Aminosulfonyl-4-methylphenyl)-5-fluoro-N4-[3-(N-methylaminosulfonyl)phenyl]-2,4-pyrimidinediamine; |
| V-1 | N2-(3-Aminosulfonyl-4-methylphenyl)-5-fluoro-N4-[2-(5-methylisoxazol-3-yl)methyleneoxypyridin-5-yl]-2,4-pyrimidinediamine; |
| V-2 | N2-(3-Aminosulphonyl-4-methylphenyl)-5-fluoro-N4-[3-oxo-4-(2-pyridylmethy)-benz[1,4]oxazin-6-yl]-2,4-pyrimidinediamine; |
| V-3 | N2-(3-Aminosulphonyl-4-methylphenyl)-5-fluoro-N4-[3-oxo-4-(2-pyridylmethy)-benz[1,4]oxazin-6-yl]-2,4-pyrimidinediamine; |
| V-4 | Racemic N2-(4-Aminosulphonylphenyl)-5-fluoro-N4-[2-methyl-3-oxo-4-(4-methoxybenzyl)-benz[1,4]oxazin-6-yl]-2,4-pyrimidinediamine; |
| V-5 | Racemic N2-(3-Aminosulphonylphenyl)-5-fluoro-N4-[2-methyl-3-oxo-4-(4-methoxybenzyl)-benz[1,4]oxazin-6-yl]-2,4-pyrimidinediamine; |
| V-6 | N2-(4-Aminosulphonylphenyl)-5-fluoro-N4-(3-oxo-4-cyanomethyl-benz[1,4]oxazin-6-yl)-2,4-pyrimidinediamine; |
| V-7 | N2-(3-Aminosulphonylphenyl)-5-fluoro-N4-(3-oxo-4-cyanomethyl-benz[1,4]oxazin-6-yl)-2,4-pyrimidinediamine; |
| V-8 | N2-(3-Aminosulphonyl-4-methylphenyl)-5-fluoro-N4-[3-oxo-4-cyanomethyl-benz[1,4]oxazin-6-yl]-2,4-pyrimidinediamine; |
| V-9 | (R/S)-N2-(3-Aminosulphonyl-4-methylphenyl)-5-fluoro-N4-[2-methyl-3-oxo-4-(4-methoxybenzyl)-benzo[1,4]thiazin-6-yl]-2,4-pyrimidinediamine; |
| V-10 | (R/S)-N2-(4-Aminosulphonylphenyl)-5-fluoro-N4-[2-methyl-3-oxo-4-(4-methoxybenzyl)-benzo[1,4]thiazin-6-yl]-2,4-pyrimidinediamine; |
| V-11 | N2-(4-Aminosulphonylphenyl)-5-fluoro-N4-(3-oxo-4-cyanomethyl-benzo[1,4]thiazin-6-yl)-2,4-pyrimidinediamine; |
| V-12 | N2-(3-Aminosulphonylphenyl)-5-fluoro-N4-(3-oxo-4-cyanomethyl-benzo[1,4]thiazin-6-yl)-2,4-pyrimidinediamine; |
| V-13 | N2-(3-Aminosulphonyl4-methylphenyl)-5-fluoro-N4-(3-oxo-4-cyanomethyl-benzo[1,4]thiazin-6-yl)-2,4-pyrimidinediamine; |
| V-14 | N2-(3-Aminosulfonyl-4-methylphenyl)-N4-[2,2-dimethyl-3-oxo-4-cyanomethyl-5-pyrid[1,4]oxazin-7-yl]-5-fluoro-2,4-pyrimidinediamine; |
| V-15 | N2-(3-Aminosulfonyl-4-chlorophenyl)-N4-[2,2-dimethyl-3-oxo-4-cyanomethyl-5-pyrid[1,4]oxazin-7-yl]-5-fluoro-2,4-pyrimidinediamine; |
| V-16 | N2-(3-Aminosulfonyl-4-methylphenyl)-N4-(2-cyanoethylene-benzothiophen-5-yl)-5-fluoro-2,4-pyrimidinediamine |
| V-17 | N-2-(3-aminosulfonylphenyl)-N4-[2,2-dimethyl-3-oxo-4H-pyrid[1,4]oxazin-7-yl]-5-fluoro-2,4-pyrimidinediamine; |
| V-18 | N-2-(3-aminosulfonyl-4-methylphenyl)-N4-[2,2-dimethyl-3-oxo-4H-pyrid[1,4]oxazin-7-yl]-5-fluoro-2,4-pyrimidinediamine; |
| V-19 | (4R)-N2-(3-aminosulfonyl-4-methylphenyl)-N4-(1-cyanomethylenecarbonyl-4-methylpiperidin-3-yl)-5-fluoro-2,4-pyrimidinediamine) or (4S)-N2-(3-aminosulfonyl-4-methylphenyl)-N4-(1-cyanomethylenecarbonyl-4-methylpiperidin-3-yl)-5-fluoro-2,4-pyrimidinediamine) |
| VIII-1 | 5-Fluoro-N4-[4-(5-methylisoxazol-3-yl)methyleneoxyphenyl]-N2-(sacchrin-6-yl)-2,4-pyrimidinediamine; and |
| VIII-2 | N4-(3-Chloro-4-cyanomethyleneoxyphenyl)-5-fluoro-N2-(5-methyl-2H-1,1-dioxide-1,2,4-benzothiadiazin-7-yl)-2,4-pyrimidinediamine. |

Another embodiment of the invention provides compounds selected from the group consisting of:

| cmpd | name |
| --- | --- |
| VI-1 | 5-Fluoro-N4-(3-hydroxyphenyl)-N2-[4-(N-methyl)aminosulfonyl-3-methoxyphenyl]-2,4-pyrimidinediamine; |
| VI-2 | N2-(3-Aminosulfonyl-4-chlorophenyl)-N4-(3-chloro-4-methoxyphenyl)-5-fluoro-2,4-pyrimidinediamine; |
| VI-3 | N2-(3-Aminosulfonyl-4-chlorophenyl)-N4-(3,4-dichlorophenyl)-5-fluoro-2,4-pyrimidinediamine; |
| VI-4 | N2-(3-Aminosulfonyl-4-methylphenyl)-N4-(3-chloro-4-methoxyphenyl)-5-fluoro-2,4-pyrimidinediamine; |
| VI-5 | N2-(3-Aminosulfonyl-4-methylphenyl)-N4-(4-chloro-3-methoxyphenyl)-5-fluoro-2,4-pyrimidinediamine; |
| VI-6 | N2-(3-Aminosulfonyl-4-methylphenyl)-N4-(3,4-dichlorophenyl)-5-fluoro-2,4-pyrimidinediamine; |
| VI-7 | N4-(3-Chloro-4-methoxyphenyl)-5-fluoro-N2-[3-(N-methoxycarbonylmethylene)aminosulfonylphenyl]-2,4-pyrimidinediamine; |
| VI-8 | N4-(3,4-Dichlorophenyl)-5-fluoro-N2-[3-(N-methoxycarbonylmethylene)aminosulfonylphenyl]-2,4-pyrimidinediamine; |
| VI-9 | N4-(3-Chloro-4-methoxyphenyl)-5-fluoro-N2-[3-(4-methylpipendin-1-yl)aminosulfonylphenyl]-2,4-pyrimidinediamine; |
| VI-10 | N4-(3,4-Dichlorophenyl)-5-fluoro-N2-[3-(4-methylpipendin-1-yl)aminosulfonylphenyl]-2,4-pyrimidinediamine; |
| VI-11 | N2-(3-Aminosulfonyl-4-chlorophenyl)-N4-(4-chloro-3-methoxyphenyl)-5-fluoro-2,4-pyrimidinediamine; |
| VI-12 | N2-[3-(N-Acetyl)aminosulfonyl-4-chlorophenyl]-N4-(3-chloro-4-methoxyphenyl)-5-fluoro-2,4-pyrimidinediamine; |
| VI-13 | N2-(3-Aminosulfonyl-5-chloro-4-methylphenyl)-N4-(3-chloro-4-methoxyphenyl)-5-fluoro-2,4-pyrimidinediamine; |
| VI-14 | N2-(3-Aminosulfonyl-5-chloro-4-methylphenyl)-N4-(3-chloro-4-trifluoromethoxyphenyl)-5-fluoro-2,4-pyrimidinediamine; |
| VI-15 | N2-(3-Aminosulfonyl-4-fluoro-5-methylphenyl)-N4-(3-chloro-4-methoxyphenyl)-5-fluoro-2,4-pyrimidinediamine; |
| VI-16 | N2-(3-Aminosulfonyl-4-fluoro-5-methylphenyl)-N4-(3-chloro-4-trifluoromethoxyphenyl)-5-fluoro-2,4-pyrimidinediamine; |
| VI-17 | N2-(3-Aminosulfonyl-4-chloro-5-methylphenyl)-N4-(3-chloro-4-methoxyphenyl)-5-fluoro-2,4-pyrimidinediamine; |
| VI-18 | N2-(3-Aminosulfonyl-4-chloro-5-methylphenyl)-N4-(3-chloro-4-trifluoromethoxyphenyl)-5-fluoro-2,4-pyrimidinediamine; |
| VI-19 | N2-(3-Aminosulfonyl-4-methylphenyl)-N4-(3-chloro-4-methoxyphenyl)-5-fluoro-N4-methyl-2,4-pyrimidinediamine; |
| VI-20 | N2-(3-Aminosulfonyl-4-fluoro-5-methylphenyl)-N4-(3-chloro-4-methoxyphenyl)-5-fluoro-N4-methyl-2,4-pyrimidinediamine; |
| VI-21 | N2-(3-Aminosulfonyl-4-chloro-5-methylphenyl)-N4-(3-chloro-4-methoxyphenyl)-5-fluoro-N4-methyl-2,4-pyrimidinediamine; |
| VI-22 | N2-(3-Aminosulfonyl-4-methylphenyl)-N4-(3-chloro-4-methoxyphenyl)-5-fluoro-N4-propyl-2,4-pyrimidinediamine; |
| VI-23 | N2-(3-Aminosulfonyl-4-fluoro-5-methylphenyl)-N4-(3-chloro-4-methoxyphenyl)-5-fluoro-N4-propyl-2,4-pyrimidinediamine; |
| VI-24 | N2-(3-Aminosulfonylphenyl)-5-carboethoxy-N4-(N-carboethoxymethylene-N-3-chloro-4-methoxyphenyl)-2,4-pyrimidinediamine; |
| VI-25 | N2-(3-Aminosulfonyl-4-methylphenyl)-5-carboethoxy-N4-(N-carboethoxymethylene-N-3-chloro-4-methoxyphenyl)-2,4-pyrimidinediamine; |
| VI-26 | N2-(3-aminosulfonylphenyl)-5-bromo-N4-(3-chloro-4-methoxyphenyl)-2,4-pyrimidinediamine; |
| VI-27 | 2-(3-aminosulfonyl-4-methylphenyl)-5-bromo-N4-(3-chloro-4-methoxyphenyl)-2,4-pyrimidinediamine; |
| VI-28 | N2-(3-Aminosulfonylphenyl)-N4-(3-chloro-4-methoxyphenyl)-5-trimethylsilylacetylene-2,4-pyrimidinediamine; |
| VI-29 | N2-(3-Aminosulfonyl-4-methoxyphenyl)-N4-(3-chloro-4-methoxyphenyl)-5-fluoro-2,4-pyrimidinediamine; |
| VI-30 | N2-(3-Aminosulfonyl-4-methoxy-5-methylphenyl)-N4-(3-chloro-4-methoxyphenyl)-5-fluoro-2,4-pyrimidinediamine: |
| VI-31 | N2-(3-Aminosulfonylpyrid-4-yl)-N4-(3-chloro-4-methoxyphenyl)-5-fluoro-2,4-pyrimidinediamine. |
| VI-32 | N2-(3-aminosulfonyl-4-methylphenyl)-5-fluoro-N4-(4-trofluoromethoxyphenyl)-2,4-pyrimidinediamine; |
| VI-33 | N2-(3-aminosulfonylphenyl)-5-fluoro-N4-(4-trofluoromethoxyphenyl)-2,4-pyrimidinediamine; |
| VI-34 | N2-(3-Aminosulfonyl-4-methoxy-5-methylphenyl)-5-fluoro-N4-(4-trifluoromethylphenyl)-2,4-pyrimidinediamine; |
| VI-35 | N2-(3-Aminosulfonylphenyl)-N4-(4-tert-butylphenyl)-5-fluoro-2,4-pyrimidinediamine; |
| VI-36 | N2-(3-Aminosulfonyl-4-methylphenyl)-N4-(4-tert-butylphenyl)-5-fluoro-2,4-pyrimidinediamine; |
| VI-37 | N2-(3-Aminosulfonyl-4-methoxy-5-methylphenyl)-N4-(4-tert-butylphenyl)-5-fluoro-2,4-pyrimidinediamine; |
| VI-38 | N2-(3-Aminosulfonylphenyl)-N4-(4-chloro-3-trifluoromethylphenyl)-5-fluoro-2,4-pyrimidinediamine; |
| VI-39 | N2-(3-Aminosulfonyl-4-methyl-phenyl)-N4-(4-chloro-3-trifluoromethylphenyl)-5-fluoro-2,4-pyrimidinediamine; |
| VI-40 | N2-(3-Aminosulfonyl-4-methoxy-5-methylphenyl)-N4-(4-chloro-3-trifluoromethyl-phenyl)-5-fluoro-2,4-pyrimidinediamine; |
| VI-41 | N2-(3-Aminosulfonyl-4-chlorophenyl)-5-fluoro-N4-(4-trifluorophenyl)-2,4-pyrimidinediamine; |
| VI-42 | N2-(3-Aminosulfonyl-4-chlorophenyl)-5-fluoro-N4-(4-trifluoromethoxyphenyl)-2,4-pyrimidinediamine; |
| VI-43 | N2-(3-Aminosulfonyl-4-chlorophenyl)-N4-(4-tert-butylphenyl)-5-fluoro-2,4-pyrimidinediamine; |
| VI-44 | N2-(3-Aminosulfonyl-4-chlorophenyl)-N4-(3-chloro-4-trifluoromethyl-phenyl)-5-fluoro-2,4-pyrimidinediamine; |
| VI-45 | N2-(3-Aminosulfonyl-4-iso-propylphenyl)-N4-(3-chloro-4-methoxy-phenyl)-5-fluoro-2,4-pyrimidinediamine; |
| VI-46 | N2-(3-Aminosulfonyl-4-methylphenyl)-5-fluoro-N4-(4-trifluoromethylmethyleneoxyphenyl)-2,4-pyrimidinediamine; |
| VI-47 | N2-(3-Aminosulfonylphenyl)-5-fluoro-N4-(4-trifluoromethylmethyleneoxyphenyl)-2,4-pyrimidinediamine; |
| VI-48 | N2-(3-Aminosulfonyl-4-chlorophenyl)-5-fluoro-N4-(4-trifluoromethylmethyleneoxyphenyl)-2,4-pyrimidinediamine; |
| VI-49 | N2-(3-Aminosulfonyl-4-methylphenyl)-5-fluoro-N4-[3-(methylaminocarbonyloxymethyl)phenyl]-2,4-pyrimidinediamine; |
| VI-50 | N2-(3-Aminosulfonyl-4-methylphenyl)-5-fluoro-N4-(4-trifluoromethylphenyl)-2,4-pyrimidinediamine; |
| VI-51 | N2-(3-Aminosulfonylphenyl)-5-fluoro-N4-(4-trifluoromethylphenyl)-2,4-pyrimidinediamine; |
| VI-52 | N2-(3-Aminosulfonyl-4-methylphenyl)-5-fluoro-N4-(4-hydroxymethylphenyl)-2,4-pyrimidinediamine; |
| VI-53 | N2-(3-Aminosulfonyl-4-methylphenyl)-5-fluoro-N4-[4-(prop-2-ynyloxy)phenyl]-2,4-pyrimidinediamine; |
| VI-54 | N2-(3-Aminosulfonyl-4-methylphenyl)-5-fluoro-N4-(4-vinylphenyl)-2,4-pyrimidinediamine; |
| VI-55 | N2-(3-Aminosulfonyl-4-chlorophenyl)-5-fluoro-N4-[4-(prop-2-ynyloxy)phenyl]-2,4-pyrimidinediamine; |
| VI-56 | 5-Fluoro-N2-(4-methyl-3-propionylaminosulfonylphenyl)-N4-[4-(prop-2-ynyloxy)phenyl]-2,4-pyrimidinediamine; |
| VI-57 | N2-(3-Aminosulfonyl-4-methylphenyl)-5-fluoro-N4-[3-(prop-2-ynyloxy)phenyl]-2,4-pyrimidinediamine; |
| VI-58 | N2-(3-Aminosulfonyl-4-methylphenyl)-5-fluoro-N4-[3-methyl-4-(prop-2-ynyloxy)phenyl]-2,4-pyrimidinediamine; |
| VI-59 | N2-(3-Aminosulfonyl-4-methylphenyl)-5-fluoro-N4-[3-chloro-4-(prop-2-ynyloxy)phenyl]-5-fluoro-2,4-pyrimidinediamine; |
| VI-60 | N2-(3-Aminosulfonyl-4-methylphenyl)-5-fluoro-N4-[3-fluoro-4-(prop-2-ynyloxy)phenyl]-2,4-pyrimidinediamine; |
| VI-61 | N2-(3-Aminosulfonyl-4-methylphenyl)-N4-[4-(but-2-ynyloxy)phenyl]-5-fluoro-2,4-pyrimidinediamine; |
| VI-62 | N2-[3-propionylaminosulfonyl-4-methylphenyl]-5-fluoro-N4-[4-(prop-2-ynyloxy)phenyl]-2,4-pyrimidinediamine; |
| VI-63 | N2-[3-Aminosulfonyl-4-(2-propyl)phenyl]-5-fluoro-N4-[4-(prop-2-ynyloxy)phenyl]-2,4-pyrimidinediamine; |
| VI-64 | N4-{4-[2-(Dimethylaminocarbonyloxy)ethyl]phenyl}-5-fluoro-N2-(3-propionylaminosulfonylphenyl)-2,4-pyrimidinediamine; |
| VI-65 | N2-(3-Aminosulfonyl-4-methylphenyl)-5-fluoro-N4-[4-(prop-2-ynylamino)phenyl]-2,4-pyrimidinediamine; |
| VI-66 | N4-{4-[2-(Dimethylaminocarbonyloxy)ethyl]phenyl}-5-fluoro-N2-(3-propionylaminosulfonylphenyl)-2,4-pyrimidinediamine sodium salt |
| VI-67 | N2-(3-Aminosulfonyl-4-methylphenyl)-N4-{4-[bis(prop-2-ynyl)amino]phenyl}-5-fluoro-2,4-pyrimidinediamine; |
| VI-68 | 5-Fluoro-N2-(4-methyl-3-methylaminosulfonylphenyl)-N4-[4-(prop-2-ynyloxy)phenyl]-2,4-pyrimidinediamine; |
| VI-69 | 5-Fluoro-N2-{[4-methyl-3-((1-methylpiperidin-4-yl)aminosulfonyl)]phenyl} N4-[4-(prop-2-ynyloxy)phenyl]-2,4-pyrimidinediamine; |
| VI-70 | N2-[3-Aminosulfonyl-4-(1-methylpiperazin-4-yl)phenyl]-5-fluoro-N4-[4-(prop-2-ynyloxy)phenyl]-2,4-pyrimidinediamine; |
| VI-71 | N4-{4-[2-(Aminocarbonylamino)ethyl]phenyl}-N2-(3-aminosulfonyl-4-methylphenyl)-5-fluoro-2,4-pyrimidinediamine; |
| VI-72 | N4-{4-[2-(Aminocarbonylamino)ethyl]phenyl}-N2-(3-aminosulfonylphenyl)-5-fluoro-2,4-pyrimidinediamine; |
| VI-73 | N2-(3-Aminosulfonyl-4-methylphenyl)-5-fluoro-N4-{4-[(prop-2-ynyloxy)carbonylaminomethyl]phenyl}-2,4-pyrimidinediamine; |
| VI-74 | N2-(3-Aminosulfonylphenyl)-5-fluoro-N4-{4-[(prop-2-ynyloxy)carbonylaminomethyl]phenyl}-2,4-pyrimidinediamine; |

-continued

| cmpd | name |
| --- | --- |
| VI-75 | N2-(3-Aminosulfonylphenyl)-5-fluoro-N4-[4-(prop-2-ynylaminosulfonyl)phenyl]-2,4-pyrimidinediamine; |
| VI-76 | N2-(3-Aminosulfonyl-4-methylphenyl)-5-fluoro-N4-[4-(prop-2-ynylaminosulfonyl)phenyl]-2,4-pyrimidinediamine; |
| VI-77 | N2-(4-Aminosulfonylphenyl)-5-fluoro-N4-[4-(prop-2-ynylaminosulfonyl)phenyl]-2,4-pyrimidinediamine; |
| VI-78 | 5-Fluoro-N2-[3-(prop-2-ynylaminosulfonyl)phenyl]-N4-[4-(prop-2-ynyloxy)phenyl]-2,4-pyrimidinediamine; |
| VI-79 | N2-(3-Aminosulfonyl-4-methylphenyl)-5-fluoro-N4-[3-(prop-2-ynylaminosulfonyl)phenyl]-2,4-pyrimidinediamine; |
| VI-80 | N2-(4-Aminosulfonylphenyl)-5-fluoro-N4-[3-(prop-2-ynylaminosulfonyl)phenyl]-2,4-pyrimidinediamine; |
| VI-81 | N2-(3-Aminosulfonylphenyl)-5-fluoro-N4-[3-(prop-2-ynylaminosulfonyl)phenyl]-2,4-pyrimidinediamine; |
| VI-82 | N2-(4-Aminosulfonylphenyl)-5-fluoro-N4-[4-(3-fluoropropyl)phenyl]-2,4-pyrimidinediamine; |
| VI-83 | N2-(3-Aminosulfonylphenyl)-5-fluoro-N4-[4-(3-fluoropropyl)phenyl]-2,4-pyrimidinediamine; |
| VI-84 | N2-(3-Aminosulfonyl-4-methylphenyl)-5-fluoro-N4-[4-(3-fluoropropyl)phenyl]-2,4-pyrimidinediamine; |
| VI-85 | N2-(4-Aminosulfonylphenyl)-5-fluoro-N4-[4-(3-hydroxypropyl)phenyl]-2,4-pyrimidinediamine; |
| VI-86 | N2-(3-Aminosulfonylphenyl)-5-fluoro-N4-[4-(3-hydroxypropyl)phenyl]-2,4-pyrimidinediamine; |
| VI-87 | N2-(3-Aminosulfonyl-4-methylphenyl)-5-fluoro-N4-[4-(3-hydroxypropyl)phenyl]-2,4-pyrimidinediamine; |
| VI-88 | N2-(4-Aminosulfonylphenyl)-5-fluoro-N4-[4-(4-hydroxybutyl)phenyl]-2,4-pyrimidinediamine; |
| VI-89 | N2-(3-Aminosulfonylphenyl)-5-fluoro-N4-[4-(4-hydroxybutyl)phenyl]-2,4-pyrimidinediamine; |
| VI-90 | N2-(3-Aminosulfonyl-4-methylphenyl)-5-fluoro-N4-[4-(4-hydroxybutyl)phenyl]-2,4-pyrimidinediamine; |
| VI-91 | N2-(4-Aminosulfonylphenyl)-5-fluoro-N4-[4-(4-fluorobutyl)phenyl]-2,4-pyrimidinediamine; |
| VI-92 | N2-(3-Aminosulfonylphenyl)-5-fluoro-N4-[4-(4-fluorobutyl)phenyl]-2,4-pyrimidinediamine; |
| VI-93 | N2-(3-Aminosulfonyl-4-methylphenyl)-5-fluoro-N4-[4-(4-fluorobutyl)phenyl]-2,4-pyrimidinediamine; |
| VI-94 | N2-(4-aminosulfonyl)phenyl-5-fluoro-N4-(4-thiomethylcarbonyl)phenyl-2,4-pyrimidinediamine; |
| VI-95 | N2-(3-aminosulfonyl-4-methyl)phenyl-5-fluoro-N4-(4-thiomethylcarbonyl)phenyl-2,4-pyrimidinediamine; |
| VI-96 | N2-(3-Butylaminosulfonylphenyl)-N4-(3-cyano-4-methylphenyl)-5-fluoro-2,4-pyrimidinediamine; |
| VI-97 | N2-(3-Butylaminosulfonylphenyl)-N4-(3-chloro-4-fluorophenyl)5-fluoro-2,4-pyrimidinediamine; |
| VI-98 | N2-(3-Aminosulfonylphenyl)-N4-(3-cyano-4-fluorophenyl)-5-fluoro-2,4-pyrimidinediamine; |
| VI-99 | N2-(3-Aminosulfonylphenyl)-N4-(3-cyano-4-methylphenyl)-5-fluoro-2,4-pyrimidinediamine; |
| VI-100 | N2-(3-Aminosulfonyl-4-fluorophenyl)-5-fluoro-N4-(4-hydroxyphenyl)-2,4-pyrimidinediamine; |
| VI-101 | N2-(3-Aminosulfonylphenyl)-5-fluoro-N4-(4-hydroxyphenyl)-2,4-pyrimidinediamine; |
| VI-102 | N2-(3-Aminosulfonyl-4-methylphenyl)-5-fluoro-N4-[4-hydroxyphenyl]-2,4-pyrimidinediamine; |
| VI-103 | N4-[4(2-Cyanoethyl)-3-methylphenyl]-5-fluoro-N2-(4-methyl-3-propionylaminosulfonylphenyl)-2,4-pyrimidinediamine; |
| VI-104 | N4-[4(2-Cyanoethyl)-3-methylphenyl]-5-fluoro-N2-(4-methyl-3-propionylaminosulfonylphenyl)-2,4-pyrimidinediamine Sodium Salt; |
| VI-105 | N4-(3,4-dichlorophenyl)-N4-methyl-5-fluoro-N2-[3-(N,N-diethyl)aminosulfonyl-4-methoxyphenyl]-2,4-pyrimidinediamine; |
| VI-106 | N2-(4-Aminosulfonylphenyl)-5-fluoro-N4-(4-methoxy-3-chlorophenyl)-2,4-pyrimidinediamine; |
| VI-107 | N2-(3-Aminosulfonylphenyl)-5-fluoro-N4-(4-methoxy-3-chlorophenyl)-2,4-pyrimidinediamine; |
| VI-108 | N4-(3-chloro-4-methoxyphenyl)-N2-(3-N,N-diethylaminosulfonyl-4-methoxyphenyl)-5-fluoro-2,4-pyrimidinediamine; |
| VI-109 | N2-(4-Aminosulfonylphenyl)-N4-(3,4-dichlorophenyl)-5-fluoro-2,4-pyrimidinediamine; |
| VI-110 | N2-(3-Aminosulfonylphenyl)-N4-(3,4-dichlorophenyl)-5-fluoro-2,4-pyrimidinediamine; |
| VI-111 | N2-(3-Aminosulfonyl-4-chlorophenyl)-5-fluoro-N4-[4-(2-methoxyethyleneoxy)phenyl]-2,4-pyrimdinediamine; |
| VI-112 | N2-(3-Aminosulfonyl-4-methylphenyl)-5-fluoro-N4-[4-(2-methoxyethyleneoxy)phenyl]-2,4-pyrimdinediamine; |
| VI-113 | N2,N4-Bis-(3-aminosulfonylphenyl)-5-fluoro-2,4-pyrimidinediamine; |
| VI-114 | N2,N4-Bis-(3-aminosulfonyl-4-methylphenyl)-5-fluoro-2,4-pyrimidinediamine; |
| VI-115 | N2,N4-Bis-(3-aminosulfonyl-4-chlorophenyl)-5-fluoro-2,4-pyrimidinediamine; |
| VI-116 | N2-[3-Aminosulfonyl-4-(4-methylpiperazine-1-yl)phenyl]-N4-(3-chloro-4-methoxyphenyl)-5-fluoro-2,4-pyrimidinediamine; |
| VII-1 | N2-(3-Aminosulfonyl-4-methylphenyl)-N4-[(2S,4R)-1-(2-cyanoacetyl)-2-methoxycarbonylpyrrolidin-4-yl]-5-fluoro-2,4-pyrimidinediamine; |
| VII-2 | N2-(3-Aminosulfonyl-4-methylphenyl)-N4-[(2S,4S)-1-(2-cyanoacetyl)-2-methoxycarbonylpyrrolidin-4-yl]-5-fluoro-2,4-pyrimidinediamine; |
| VII-3 | Racemic N2-(3-aminosulfonyl-4-methylphenyl)-N4-(1-benzyl-4-methylpiperidin-3-yl)-5-fluoro-2,4-pyrimidinediamine; |
| VII-4 | Racemic N2-(3-aminosulfonyl-4-methylphenyl)-5-fluoro-N4-(4-methylpiperidin-3-yl)-2,4-pyrimidinediamine; |
| VII-5 | Racemic N2-(3-aminosulfonyl-4-methylphenyl)-N4-(1-cyanomethylenecarbonyl-4-methylpiperidin-3-yl)-5-fluoro-2,4-pyrimidinediamine; |
| VII-6 | N2-(3-Aminosulfonylphenyl)-5-fluoro-N4-(2-methoxypyrid-5-yl)-2,4-pyrimidinediamine; |
| VII-7 | N2-(3-Aminosulfonylphenyl)-N4-(2-amino-3-methoxypyrid-6-yl)-5-fluoro-2,4-pyrimidinediamine; |
| VII-8 | N2-(3-Aminosulfonyl-4-chlorophenyl)-N4-(2-amino-3-methoxypyrid-6-yl)-5-fluoro-2,4-pyrimidinediamine; |
| VII-9 | N2-(3-Aminosulfonyl-4-methylphenyl)-N4-[2-amino-3-methoxypyrid-6-yl]-5-fluoro-2,4-pyrimidinediamine (66); |
| VII-10 | N4-(2-Amino-3-methoxypyrid-6-yl)-N2-[3-(ethoxycarbonylmethylene)aminosulfonylphenyl]-5-fluoro-2,4-pyrimidinediamine; |
| VII-11 | N2-(3-Aminosulphonylphenyl)-5-fluoro-N4-(2,2,4-trimethyl-1,1,3-trioxo-benzo[1,4]thiazin-6-yl)-2,4-pyrimidinediamine; |
| VII-12 | N2-(4-Aminosulphonylphenyl)-5-fluoro-N4-(2,2,4-trimethyl-1,1,3-trioxo-benzo[1,4]thiazin-6-yl)-2,4-pyrimidinediamine; |
| VII-13 | N2-(4-aminosulfonyl)phenyl-N4-[(N-ethylsulfonyl)-1,2,3,4-tetrahydroisoquinolin-6-yl]-5-fluoro-2,4-pyrimidinediamine |
| VII-14 | N2-(3-aminosulfonyl)phenyl-N4-[(N-ethylsulfonyl)-1,2,3,4-tetrahydroisoquinolin-6-yl]-5-fluoro-2,4-pyrimidinediamine |
| VII-15 | N2-(3-aminosulfonyl-4-methyl)phenyl-N4-[(N-ethylsulfonyl)-1,2,3,4-tetrahydroisoquinolin-6-yl]-5-fluoro-2,4-pyrimidinediamine |
| VII-16 | N2-(3-Aminosulfonyl-4-methylphenyl)-5-fluoro-N4-(1,2,3,4-tetrahydroisoquin-7-yl)-2,4-pyrimidinediamine; |
| VII-17 | N2-(3-Aminosulfonyl-4-methylphenyl)-5-fluoro-N4-[2-(methylaminocarbonyl)-1,2,3,4-tetrahydroisoquin-7-yl]-2,4-pyrimidinediamine; |
| VII-18 | N2-(3-Aminosulfonyl-4-methylphenyl)-5-fluoro-N4-[2-(dimethylaminocarbonyl)-1,2,3,4-tetrahydroisoquin-7-yl]-2,4-pyrimidinediamine; |
| VII-19 | N2-(3-Aminosulfonyl-4-methylphenyl)-5-fluoro-N4-[1-(methylaminocarbonyl)-1,2,3,4-tetrahydroquin-6-yl]-2,4-pyrimidinediamine; |
| VII-20 | N2-(3-Aminosulfonylphenyl)-5-fluoro-N4-[1-(methylaminocarbonyl)-1,2,3,4-tetrahydroquin-6-yl]-2,4-pyrimidinediamine; |
| VII-21 | N2-(3-Aminosulfonyl-4-methylphenyl)-N4-[3,4-dihydro-(1H)-quinolin-2-one-6-yl]-5-fluoro-2,4-pyrimidinediamine |
| VII-22 | N2-(3-Aminosulfonylphenyl)-5-fluoro-N4-[1-(3-methoxypropyl)indazolin-5-yl]-2,4-pyrimidinediamine; |
| VII-23 | N2-(3-Aminosulfonylphenyl)-5-fluoro-N4-[1-(2-methoxyethyl)indazolin-5-yl]-2,4-pyrimidinediamine; |
| VII-24 | N4-(3,4-Ethylenedioxyphenyl)-5-fluoro-N2-[4-(pyrrolidin-1-ylsulfonyl)phenyl]-2,4-pyrimidinediamine; |
| VII-25 | N4-(3,4-Ethyenedioxyphenyl)-5-fluoro-N2-[4-(N-methyl)aminosulfonyl-3-methoxyphenyl]-2,4-pyrimidinediamine; |
| VII-26 | Racemic N2-(3-Aminosulfonyl-4-methylphenyl)-N4-[2-(N,N-dimethylaminocarbonyl)-2,3-dihydrobenzofuran-5-yl]-5-fluoro-2,4-pyrimidinediamine; |

| cmpd | name |
|---|---|
| VII-27 | Racemic N2-(3-Aminosulfonyl-4-chlorophenyl)-N4-[2-(N,N-dimethylaminocarbonyl)-2,3-dihydrobenzofuran-5-yl]-5-fluoro-2,4-pyrimidinediamine; |
| VII-28 | N2-(3-Aminosulfonylphenyl)-N4-(chroman-4-amine-6-yl)-5-fluoro-2,4-pyrimidinediamine; |
| VII-29 | N2-(4-Aminosulfonylphenyl)-N4-(chroman-4-amine-6-yl)-5-fluoro-2,4-pyrimidinediamine; |
| VII-30 | N2-(3-Aminosulphonyl-4-methylphenyl)-5-methyl-N4-(3-oxo-benz[1,4]oxazin-6-yl)-2,4-pyrimidinediamine; |
| VII-31 | N2-(4-Aminosulphonylphenyl)-5-methyl-N4-(3-oxo-benz[1,4]oxazin-6-yl)-2,4-pyrimidinediamine; |
| VII-32 | N2-(3-Aminosulphonylphenyl)-5-methyl-N4-(3-oxo-benz[1,4]oxazin-6-yl)-2,4-pyrimidinediamine; |
| VII-33 | N2-(3-Aminosulphonyl-4-methylphenyl)-5-methyl-N4-(4-methyl-3-oxo-benzo[1,4]thiazin-6-yl)-2,4-pyrimidinediamine; |
| VII-34 | N2-(4-Aminosulphonylphenyl)-5-methyl-N4-(4-methyl-3-oxo-benzo[1,4]thiazin-6-yl)-2,4-pyrimidinediamine; |
| VII-35 | N2-(3-Aminosulphonylphenyl)-5-methyl-N4-(4-methyl-3-oxo-benzo[1,4]thiazin-6-yl)-2,4-pyrimidinediamine; |
| VII-36 | N2-(3-Aminosulphonylphenyl)-5-fluoro-N4-(3-oxo-4-cyanomethyl-benzo[1,4]thiazin-6-yl)-2,4-pyrimidinediamine; |
| VII-37 | N4-(2,2-Dimethyl-3-oxo-4H-benz[1,4]oxazin-6-yl)-5-fluoro-N2-[4-(N-methyl)aminosulfonyl-3-methoxyphenyl]-2,4-pyrimidinediamine; |
| VII-38 | N2-(3-Aminosulfonyl-4-methoxy-5-methylphenyl)-N4-(2,2-difluoro-4H-benz[1,4]oxazin-3-on-6-yl)-5-fluoro-2,4-pyrimidinediamine; |
| VII-39 | 5-Amino-N2-(3-amionsulfonylphenyl)-N4-(2,2-dimethyl-3-oxo-4H-benz[1,4]oxazin-6-yl)-2,4-pyrimidinediamine; |
| VII-40 | N2-(4-Aminosulfonylphenyl)-5-fluoro-N4-(4-methyl-3-oxo-benz[1,4]oxazin-6-yl)-2,4-pyrimidinediamine; |
| VII-41 | N2-(3-Aminosulfonylphenyl)-5-fluoro-N4-(4-methyl-3-oxo-benz[1,4]oxazin-6-yl)-2,4-pyrimidinediamine; |
| VII-42 | N2-(3-Aminosulfonylphenyl)-N4-[2,2,4-trimethyl-3-oxo-pyrid[1,4]oxazin-7-yl]-5-fluoro-2,4-pyrimidinediamine; |
| VII-43 | N2-(4-Aminosulfonylphenyl)-N4-[2,2,4-trimethyl-3-oxo-pyrid[1,4]oxazin-5-yl]-5-fluoro-2,4-pyrimidinediamine; |
| VII-44 | N2-(3-Aminosulphonyl-4-methyl-phenyl)-5-fluoro-N4-(3-oxo-4H-benzo[1,4]thiazin-6-yl)-2,4-pyrimidinediamine; |
| VII-45 | N2-(3-Aminosulphonyl-4-methyl-phenyl)-5-fluoro-N4-(3-oxo-4H-benzo[1,4]thiazin-6-yl)-2,4-pyrimidinediamine; |
| VII-46 | N2-(4-Aminosulphonylphenyl)-5-fluoro-N4-(2,2,4-trimethyl-1,1,3-trioxo-benzo[1,4]thiazin-6-yl)-2,4-pyrimidinediamine; |
| VII-47 | N2-(4-Aminosulphonylphenyl)-N4-cyanomethyl-5-fluoro-N4-[3-oxo-4-methyl-benzo[1,4]thiazin-6-yl]-2,4-pyrimidinediamine; |
| VII-48 | N2-(4-Aminosulfonylphenyl)-5-fluoro-N4-(4-methyl-3-oxo-benz[1,4]thiazin-6-yl)-2,4-pyrimidinediamine; |
| VII-49 | N2-(3-Aminosulfonylphenyl)-5-fluoro-N4-(4-methyl-3-oxo-benz[1,4]thiazin-6-yl)-2,4-pyrimidinediamine; |
| VII-50 | 5-Fluoro-N4-(4-methyl-3-oxo-benz[1,4]thiazin-6-yl)-N2-(3-pipendinosulfonylphenyl)-2,4-pyrimidinediamine; |
| VII-51 | N2-(3-Aminosulfonylphenyl)-N4-[2,2-dimethyl-3-oxo-4H-5-pyrid[1,4]oxazin-7-yl]-5-fluoro-2,4-pyrimidinediamine; |
| VII-52 | N2-(4-Aminosulfonylphenyl)-N4-[2,2-dimethyl-3-oxo-4H-5-pyrid[1,4]oxazin-7-yl]-5-fluoro-2,4-pyrimidinediamine; |
| VII-53 | N2-(3-Aminosulfonyl-4-methylphenyl)-N4-(2-cyanobenzofuran-5-yl)-5-fluoro-2,4-pyrimidinediamine; |
| VII-54 | N2-(3-Aminosulfonylphenyl)-N4-(2-aminocarbonylbenzofurane-5-yl)-5-fluoro-2,4-pyrimidinediamine; |
| VII-55 | N2-(3-Aminosulphonylphenyl)-5-fluoro-N4-[4-(3-pyridinylmethyl)benzo[1,4]oxazin-7-yl]-2,4-pyrimidinediamine; |
| VII-56 | N2-(3-Aminosulphonylphenyl)-5-fluoro-N4-[4-(3-pyridinylmethyl)benzo[1,4]oxazin-7-yl]-2,4-pyrimidinediamine; |
| VII-57 | N2-(3-Aminosulfonyl-4-methylphenyl)-N4-(benzothiophen-5-yl)-5-fluoro-2,4-pyrimidinediamine; |
| VII-58 | N2-(3-Aminosulfonylphenyl)-N4-(benzothiophen-5-yl)-5-fluoro-2,4-pyrimidinediamine; |
| VII-59 | N2-(4-Aminosulfonylphenyl)-N4-(4-N-tert-butoxycarbonylamino-3,4-dihydro-2H-1-benzopyran-6-yl)-5-fluoro-2,4-pyrimidinediamine; |
| VII-60 | N2-(3-Aminosulfonylphenyl)-5-fluoro-N4-[4-(1-methylsulfonyl)indolin-5-yl]-2,4-pyrimidinediamine; |
| VII-61 | N2-(3-Aminosulfonyl-4-methylphenyl)-5-fluoro-N4-[4-(1-methylsulfonyl)indolin-5-yl]-2,4-pyrimidinediamine; |
| VII-62 | 5-Fluoro-N2-[3-(N-methylaminosulfony)-4-methylphenyl]-N4-[4-(1-methylsulfonyl)indolin-5-yl]-2,4-pyrimidinediamine; |
| VII-63 | N2-(4-Aminosulfonylphenyl)-5-fluoro-N4-+4-(1-methylsulfonyl)indolin-5-yl]-2,4-pyrimidinediamine; |
| VII-64 | N2-(3-Aminosulfonyl-4-methylphenyl)-5-fluoro-N4-(quinolin-2-yl)-2,4-pyrimidinediamine; |
| VII-65 | N2-(3-Aminosulfonyl-4-methylphenyl)-5-fluoro-N4-(quinolin-3-yl)-2,4-pyrimidinediamine; |
| VII-66 | N2-(3-Aminosulfonylphenyl)-5-fluoro-N4-(quinolin-3-yl)-2,4-pyrimidinediamine; |
| VII-67 | N2-(3-Aminosulfonyl-4-methylphenyl)-5-fluoro-N4-(quinolin-5-yl)-2,4-pyrimidinediamine; |
| VII-68 | N2-(3-Aminosulfonylphenyl)-5-fluoro-N4-(quinolin-5-yl)-2,4-pyrimidinediamine; |
| VII-69 | N2-(3-Aminosulfonyl-4-methylphenyl)-5-fluoro-N4-(quinolin-6-yl)-2,4-pyrimidinediamine; |
| VII-70 | N2-(3-Aminosulfonylphenyl)-5-fluoro-N4-(quinolin-6-yl)-2,4-pyrimidinediamine; |
| VII-71 | N2-(3-Aminosulfonyl-4-methylphenyl)-5-fluoro-N4-(2-methylquinolin-6-yl)-2,4-pyrimidinediamine; |
| VII-72 | N2-(3-Aminosulfonylphenyl)-5-fluoro-N4-(2-methylquinolin-6-yl)-2,4-pyrimidinediamine; |
| VII-73 | N2-(3-Aminosulfonyl-4-methylphenyl)-5-fluoro-N4-(2-hydroxy-4-methylquinolin-6-yl)-2,4-pyrimidinediamine |
| VII-74 | N2-(3-Aminosulfonylphenyl)-5-fluoro-N4-(2-hydroxy-4-methylquinolin-6-yl)-2,4-pyrimidinediamine |
| VII-75 | N2-(3-Aminosulfonyl-4-methylphenyl)-N4-(2-N,N'-dimethylamine-quinolin-6-yl)-5-fluoro-2,4-pyrimidinediamine |
| VII-76 | N2-(3-Aminosulfonylphenyl)-N4-(2-N,N'-dimethylamine-quinolin-6-yl)-5-fluoro-2,4-pyrimidinediamine |
| VII-77 | N2-(3-Aminosulfonyl-4-methylphenyl)-5-fluoro-N4-(quinolin-8-yl)-2,4-pyrimidinediamine; |
| VII-78 | N2-(3-Aminosulfonylphenyl)-5-fluoro-N4-(quinolin-8-yl)-2,4-pyrimidinediamine; |
| VII-79 | N2-(3-Aminosulfonyl-4-fluorophenyl)-5-fluoro-N4-(quinolin-8-yl)-2,4-pyrimidinediamine; |
| VII-80 | N2-(3-Aminosulfonyl-4-methylphenyl)-5-fluoro-N4-(2-methylquinolin-8-yl)-2,4-pyrimidinediamine; |
| VII-81 | N2-(3-Aminosulfonylphenyl)-5-fluoro-N4-(2-methylquinolin-8-yl)-2,4-pyrimidinediamine; |
| VII-82 | (1R,2R,3S,4S)N4-(3-Aminocarbonylbicyclo[2.2.1]hept-5-en-2-yl)-N2-(3-aminosulfonyl-4-methylphenyl)-5-fluoro-2,4-pyrimidinediamine; |
| VII-83 | (1R,2R,3S,4S)N2-(3-Aminosulfonyl-4-methoxy-5-methylphenyl)-N4-(3-aminocarbonylbicyclo[2.2.1]hept-5-ene-2-yl)-5-fluoro-2,4-pyrimidinediamine; and |
| VIII-3 | N4-(3-Chloro-4-methoxyphenyl)-5-fluoro-N2-(5-methyl-2H-1,1-dioxo-1,2,4-benzothiadiazin-7-yl)-2,4-pyrimidinediamine. |

Yet another aspect of the invention provides compounds selected from the group consisting of:

| cmpd | name |
|---|---|
| IX-1 | N2-(3-Aminosulfonyl-4-methylphenyl)-5-fluoro-N4-[1-(propyn-3-yl)indol-5-yl]-2,4-pyrimidinediamine; |
| IX-2 | N2-(3-Aminosulfonylphenyl)-5-fluoro-N4-[1-(propyn-3-yl)indol-5-yl]-2,4-pyrimidinediamine; |
| IX-3 | N2-(3-Aminosulfonyl-4-methylphenyl)-5-fluoro-N4-[1-(propyn-3-yl)indol-6-yl]-2,4-pyrimidinediamine; |
| IX-4 | N2-(3-Aminosulfonylphenyl)-5-fluoro-N4-[1-(propyn-3-yl)indol-6-yl]-2,4-pyrimidinediamine; |

| cmpd | name |
|---|---|
| IX-5 | N2-(3-Aminosulfonylphenyl)-N4-(1-cyanomethyleneindol-5-yl)-5-fluoro-2,4-pyrimidinediamine; |
| IX-6 | N2-(4-Aminosulfonylphenyl)-N4-(1-cyanomethyleneindol-5-yl)-5-fluoro-2,4-pyrimidinediamine; |
| IX-7 | N2-(3-Aminosulfonyl-4-chlorophenyl)-N4-(1-cyanomethyleneindol-5-yl)-5-fluoro-2,4-pyrimidinediamine; |
| IX-8 | N2-(3-Aminosulfonyl-4-methylphenyl)-N4-(1-cyanomethyleneindol-5-yl)-5-fluoro-2,4-pyrimidinediamine; |
| IX-9 | N4-[3-(Aminocarbonyl)-1H-indol-6-yl]-N2-(3-aminosulfonyl-4-methylphenyl)-5-fluoro-2,4-pyrimidinediamine; |
| IX-10 | N4-[3-(Aminocarbonyl)-1H-indol-6-yl]-N2-(3-aminosulfonyl-4-chlorophenyl)-5-fluoro-2,4-pyrimidinediamine; |
| IX-11 | N2-(3-Aminosulfonyl-4-methylphenyl)-N4-(3-cyanomethyl-1H-indol-6-yl)-5-fluoro-2,4-pyrimidinediamine; |
| IX-12 | N2-(3-Aminosulfonylphenyl)-N4-(3-cyanomethyl-1H-indol-6-yl)-5-fluoro-2,4-pyrimidinediamine; |
| IX-13 | N2-(3-Aminosulfonylphenyl)-N4-(3-cyanomethyl-1H-indol-5-yl)-5-fluoro-2,4-pyrimidinediamine; |
| IX-14 | N2-(3-Aminosulfonyl-4-methylphenyl)-N4-(3-cyanomethyl-1H-indol-5-yl)-5-fluoro-2,4-pyrimidinediamine; |
| IX-15 | N2-(3-Aminosulfonylphenyl)-N4-(3-cyanomethyl-1H-indol-7-yl)-5-fluoro-2,4-pyrimidinediamine; |
| IX-16 | N2-(3-Aminosulfonyl-4-methylphenyl)-N4-(3-cyanomethyl-1H-indol-7-yl)-5-fluoro-2,4-pyrimidinediamine; |
| IX-17 | N2-[3-Aminosulfonyl-4-(4-methylpiperazine-1-yl)phenyl]-N4-(3-cyanomethylene-1H-indol-6-yl)-5-fluoro-2,4-pyrimidinediamine; |
| IX-18 | N2-[3-Aminosulfonyl-4-(4-methylpiperazine-1-yl)phenyl]-N4-(3-cyanomethylene-1H-indol-7-yl)-5-fluoro-2,4-pyrimidinediamine; |
| IX-19 | N4-(3-cyanomethylene-1H-indol-5yl)-5-fluoro-N2-[3-(1-methyl-4-aminopiperadine)sulfonyl-4-methylphenyl]-2,4-pyrimidinediamine; |
| IX-20 | N2-(3-Aminosulfonyl-4-methylphenyh-N4-(3-cyanomethyl-1-methyl-indol-5-yl)-5-fluoro-2,4-pyrimidinediamine; |
| IX-21 | N2-(3-Aminosulfonyl-4-chlorophenyh-N4-(2-cyanobenzofuran-5-yl)-5-fluoro-2,4-pyrimidinediamine; |
| IX-22 | N2-(3-Aminosulfonyl-4-iso-propylphenyl)-N4-(2-cyanobenzofuran-5-yl)-5-fluoro-2,4-pyrimidinediamine; |
| IX-23 | N4-[4-(1-Acetyl-4-piperizinyl)carbonylphenyl]-N2-(3-Aminosulfonylphenyl)-5-fluoro-2,4-pyrimidinediamine; |
| IX-24 | N4-[4-(1-Acetyl-4-piperizinyl)carbonylphenyl]-N2-(3-Aminosulfonyl-4-methylphenyl)-5-fluoro-2,4-pyrimidinediamine; |
| IX-25 | N4-[4-(1-Acetyl-4-piperizinyl)carbonylphenyl]-5-fluoro-N2-[3-(N-methylaminosulfony)-4-methylphenyl]-2,4-pyrimidinediamine; |
| IX-26 | N4-[4-(1-Acetyl-4-piperizinyl)carbonylphenyl]-N2-(4-aminosulfonylphenyl)-5-fluoro-2,4-pyrimidinediamine; |
| IX-27 | N2-(3-Aminosulfonyl-4-methylphenyl)-5-fluoro-N4-[4-(4-methylpiperazin-1-ylcarbonyl)phenyl]-2,4-pyrimidinediamine; |
| IX-28 | N2-(3-Aminosulfonylphenyl)-5-fluoro-N4-[4-(4-methylpiperazin-1-ylcarbonyl)phenyl]-2,4-pyrimidinediamine; |
| IX-29 | N2-(3-Aminosulfonylphenyl)-5-fluoro-N4-[4-(1-methanesulfonyl-4-piperizinyl)carbonylphenyl]-2,4-pyrimidinediamine; |
| IX-30 | N2-(3-Aminosulfonyl-4-methylphenyl)-5-fluoro-N4-[4-(1-methanesulfonyl-4-piperizinyl)carbonylphenyl]-2,4-pyrimidinediamine; |
| IX-31 | 5-Fluoro-N2-[3-(N-methylaminosulfony)-4-methylphenyl]-5-fluoro-N4-[4-(1-methanesulfonyl-4-piperizinyl)carbonylphenyl]-2,4-pyrimidinediamine; |
| IX-32 | N2-(4-Aminosulfonylphenyl)-5-fluoro-N4-[4-(1-methanesulfonyl-4-piperazinyl)carbonylphenyl]-2,4-pyrimidinediamine; |
| IX-33 | 5-Fluoro-N2-[3-(N-methylaminosulfony)-4-methylphenyl]-5-fluoro-N4-[4-(4-thiomorpholino)carbonylphenyl]-2,4-pyrimidinediamine; |
| IX-34 | N2-(3-Aminosulfonylphenyl)-5-fluoro-N4-[4-(4-thiomorpholinyl)carbonylphenyl]-2,4-pyrimidinediamine; |
| IX-35 | N2-(3-Aminosulfonyl-4-methylphenyl)-5-fluoro-N4-[4-(4-thiomorpholinyl)carbonylphenyl]-2,4-pyrimidinediamine; |
| IX-36 | N2-(4-Aminosulfonylphenyl)-5-fluoro-N4-[4-(4-thiomorpholinyl)carbonylphenyl]-2,4-pyrimidinediamine; |
| IX-37 | N2-(3-Aminosulfonylphenyl)-N4-[4-(1,1-dioxo-4-thiomorpholinyl)carbonylphenyl]-5-fluoro-2,4-pyrimidinediamine; |
| IX-38 | N2-(3-Aminosulfonyl-4-methylphenyl)-N4-[4-(1,1-dioxo-4-thiomorpholinyl)carbonylphenyl]-5-fluoro-2,4-pyrimidinediamine; |
| IX-39 | N4-[4-(1,1-dioxo-4-thiomorpholinyl)carbonylphenyl]-5-Fluoro-N2-[3-(N-methylaminosulfony)-4-methylphenyl]-2,4-pyrimidinediamine; |
| IX-40 | N2-(4-Aminosulfonylphenyl)-N4-[4-(1,1-dioxo-4-thiomorpholinyl)carbonylphenyl]-5-fluoro-2,4-pyrimidinediamine; |
| IX-41 | N4-(4-Acetylthiomethylcarbonylphenyl)-N2-(4-aminosulfonylphenyl)-5-fluoro-2,4-pyrimidinediamine; |
| IX-42 | N4-(4-Acetylthiomethylcarbonylphenyl)-N2-(3-aminosulfonylphenyl)-5-fluoro-2,4-pyrimidinediamine; |
| IX-43 | N4-(4-Acetylthiomethylcarbonylphenyl)-N2-(3-aminosulfonyl-4-methylphenyl)-5-fluoro-2,4-pyrimidinediamine; |
| IX-44 | N2-(4-Aminosulfonylphenyl)-N4-[3,5-dimethyl-4-(4-methylpiperazin-1-yl]phenyl)-5-fluoro-2,4-pyrimidinediamine; |
| IX-45 | N2-(3-Aminosulfonyl-4-methylphenyl)-N4-[(4R)-1-(2-cyanoacetyl)-pyrrolidin-4-yl)-5-fluoro-2,4-pyrimidinediamine |
| IX-46 | N2-(3-Aminosulfonyl-4-methylphenyl)-5-fluoro-N4-(5-methoxycarbonyl-thiophene-2-yl)-2,4-pyrimidinediamine |
| IX-47 | N2-(3-Aminosulfonylphenyl)-5-fluoro-N4-(5-methoxycarbonyl-thiophene-2-yl)-2,4-pyrimidinediamine |
| IX-48 | N2-(3-Aminosulfonyl-4-fluorophenyl)-5-fluoro-N4-(5-methoxycarbonyl-thiophene-2-yl)-2,4-pyrimidinediamine |
| IX-49 | N2-(4-Aminosulfonylphenyl)-5-fluoro-N4-(5-methoxycarbonyl-thiophene-2-yl)-2,4-pyrimidinediamine |
| IX-50 | N4-(3,4-Dimethoxyphenyl)-5-fluoro-N2-[4-(N-methyl)aminosulfonyl-3-methoxyphenyl]-2,4-pyrimidinediamine |
| IX-51 | N4-(3,5-Dimethoxyphenyl)-5-fluoro-N2-[4-(N-methyl)aminosulfonyl-3-methoxyphenyl]-2,4-pyrimidinediamine |
| IX-52 | N4-(4-Chloro-3-trifluoromethylphenyl)-5-fluoro-N2-[4-(N-methyl)aminosulfonyl-3-methoxyphenyl]-2,4-pyrimidinediamine |
| IX-53 | N4-(3-Chloro-4-trifluoromethoxyphenyl)-5-fluoro-N2-[4-(N-methyl)aminosulfonyl-3-methoxyphenyl]-2,4-pyrimidinediamine |
| IX-54 | 5-Fluoro-N2-[3-N-(methyl)aminosulfonyl-4-methylphenyl]-N4-[4-(2-pyridinyl)-3-chloromethyleneoxyphenyl]-2,4-pyrimidinediamine; |
| X-1 | 6-carbonylmethoxy-N4-(3,4-dichlorophenyl)-N2-(3-N,N-diethylaminosulfonyl-6-methoxyphenyl)-2,4-pyrimidinediamine; |
| X-2 | 6-carbonylmethoxy-(3-N,N-diethylaminosulfonyl-6-methoxyphenyl)-N4-[3-oxo-benz[1,4]oxazin-6-yl]-2,4-pyrimidinediamine; and |
| X-3 | N2-(3-Aminosulfonylphenyl)-5-fluoro-N4-(2-methylindol-6-ylmethylene)-2,4-pyrimidinediamine. |

In another embodiment, this invention provides a method of inhibiting an activity of a JAK kinase, comprising contacting in vitro a JAK3 kinase with an amount of a compound effective to inhibit an activity of the JAK kinase wherein the compound is selected from the compounds of this invention, as described herein, and the compounds of Table XI (CAS Reg. No. 845817-97-2, CAS Reg. No. 841290-42-4, and CAS Reg. No. 841290-41-3).

In another embodiment, this invention provides a method of treating a T-cell mediated autoimmune disease, comprising administering to a patient suffering from such an autoimmune disease an amount of a compound effective to treat the autoimmune disease wherein the compound is selected from the compounds of this invention, as described herein, and the compounds of Table XI (CAS Reg. No. 845817-97-2, CAS Reg. No. 841290-42-4, and CAS Reg. No. 841290-41-3).

In yet another embodiment, this invention provides a method of treating a T-cell mediated autoimmune disease, comprising administering to a patient suffering from such an autoimmune disease an amount of a compound effective to treat the autoimmune disease wherein the compound is selected from the compounds of this invention, as described herein, and the compounds of Table XI (CAS Reg. No.

845817-97-2, CAS Reg. No. 841290-42-4, and CAS Reg. No. 841290-41-3) and the compound is administered in combination with, or adjunctively to, a compound that inhibits Syk kinase with an $IC_{50}$ in the range of 10 µM or less.

In another embodiment, this invention provides a method of treating or preventing allograft transplant rejection in a transplant recipient, comprising administering to the transplant recipient an amount of a compound effective to treat or prevent the rejection wherein the compound is selected from the compounds of this invention, as described herein, and the compounds of Table XI (CAS Reg. No. 845817-97-2, CAS Reg. No. 841290-42-4, and CAS Reg. No. 841290-41-3). The rejection can be acute rejection or chronic rejection. The rejection can also be mediated by HVGR or GVHR. In certain embodiments, the allograft transplant is selected from a kidney, a hear, a liver and a lung. The compound, optionally, can be administered in combination with, or adjunctively to, an immunosuppressant. In certain preferred embodiments, the immunosuppressant is selected from cyclosporine, tacrolimus, sirolimus, an inhibitor of IMPDH, mycophenolate, mycophanolate mofetil, an anti-T-Cell antibody and OKT3.

In another embodiment, this invention provides a method of treating or preventing a Type IV hypersensitivity reaction, comprising administering to a subject an amount of a compound of effective to treat or prevent the hypersensitivity reaction wherein the compound is selected from the compounds of this invention, as described herein, and the compounds of Table XI (CAS Reg. No. 845817-97-2, CAS Reg. No. 841290-42-4, and CAS Reg. No. 841290-41-3). In a preferred embodiment, the compound is administered prior to exposure to an allergen.

In another embodiment, this invention provides a method of inhibiting a signal transduction cascade in which JAK3 kinase plays a role, comprising contacting a cell expressing a receptor involved in such a signaling cascade with a compound wherein the compound is selected from the compounds of this invention, as described herein, and the compounds of Table XI (CAS Reg. No. 845817-97-2, CAS Reg. No. 841290-42-4, and CAS Reg. No. 841290-41-3).

In another embodiment, this invention provides a method of treating or preventing a JAK kinase-mediated disease, comprising administering to a subject an amount of compound effective to treat or prevent the JAK kinase-mediated disease wherein the compound is selected from the compounds of this invention, as described herein, and the compounds of Table XI (CAS Reg. No. 845817-97-2, CAS Reg. No. 841290-42-4, and CAS Reg. No. 841290-41-3). In a preferred embodiment, the JAK-mediate disease is selected from the group consisting of HVGR, GVHR, acute allograft rejection, and chronic allograft rejection.

In another embodiment, this invention provides a pharmaceutical formulation comprising a compound selected from the compounds of this invention, as described herein, and the compounds of Table XI (CAS Reg. No. 845817-97-2, CAS Reg. No. 841290-42-4, and CAS Reg. No. 841290-41-3) or a prodrug thereof, and at least one pharmaceutically acceptable excipient, diluent, preservative, or stabilizer, or mixtures thereof.

In another embodiment, this invention provides a kit comprising a compound selected from the compounds of this invention, as described herein, and the compounds of Table XI (CAS Reg. No. 845817-97-2, CAS Reg. No. 841290-42-4, and CAS Reg. No. 841290-41-3) or a prodrug thereof, packaging and instructions for use. In a preferred embodiment, the kit includes a pharmaceutical formulation comprising a compound selected from the compounds of this invention, as described herein, and the compounds of Table XI (CAS Reg. No. 845817-97-2, CAS Reg. No. 841290-42-4, and CAS Reg. No. 841290-41-3) or a prodrug thereof, and at least one pharmaceutically acceptable excipient, diluent, preservative, or stabilizer, or mixtures thereof, packaging, and instructions for use.

IV. DETAILED DESCRIPTION

A. Overview

The invention encompasses compounds having formulae I-V and the compositions and methods using these compounds in the treatment of conditions in which modulation of the JAK pathway or inhibition of JAK kinases, particularly JAK3, may be therapeutically useful.

B. Definitions

As used herein, the following definitions shall apply unless otherwise indicated.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—).

"Substituted alkyl" refers to an alkyl group having from 1 to 5 hydrogens replaced with substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, alkynyl, substituted alkynyl, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, sulfonyl, sulfonyloxy, thioacyl, thiol, alkylthio, substituted alkylthio, silyl and trialkylsilyl wherein said substituents are defined herein. In some embodiments, the alkyl has 1 to 3 of the aforementioned groups. In other embodiments, the alkyl has 1 to 2 of the aforementioned groups.

"Alkylene" refers to divalent saturated aliphatic hydrocarbyl groups preferably having from 1 to 5 and more preferably 1 to 3 carbon atoms that are either straight-chained or branched. This term is exemplified by groups such as methylene (—$CH_2$—), ethylene (—$CH_2CH_2$—), n-propylene (—$CH_2CH_2CH_2$—), iso-propylene (—$CH_2CH$($CH_3$)—) or (—$CH(CH_3)CH_2$—) and the like.

"Substituted alkylene" refers to an alkylene group having from 1 to 3 hydrogens replaced with substituents selected from the group consisting of alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, substituted heterocyclic wherein said substituents are defined herein. In some embodiments, the alkylene has 1 to 2 of the aforementioned groups.

"Alkoxy" refers to the groups —O-alkyl, —O-alkenyl, and —O-alkynyl, wherein alkyl, alkenyl and alkynyl are as defined herein.

"Substituted alkoxy" refers to the groups —O-(substituted alkyl), —O-(substituted alkenyl), and —O-(substituted alkynyl), wherein substituted alkyl, substituted alkenyl, and substituted alkynyl are as defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)-cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Acyl includes the "acetyl" group $CH_3C(O)$—.

"Acylamino" refers to the groups —$NR^{20}$C(O)alkyl, —$NR^{20}$C(O)substituted alkyl, —$NR^{20}$C(O)cycloalkyl, —$NR^{20}$C(O)substituted cycloalkyl, —$NR^{20}$C(O)cycloalkenyl, —$NR^{20}$C(O)substituted cycloalkenyl, —$NR^{20}$C(O)alkenyl, —$NR^{20}$C(O)substituted alkenyl, —$NR^{20}$C(O)alkynyl, —$NR^{20}$C(O)substituted alkynyl, —$NR^{20}$C(O)aryl, —$NR^{20}$C(O)substituted aryl, —$NR^{20}$C(O)heteroaryl, —$NR^{20}$C(O)substituted heteroaryl, —$NR^{20}$C(O)heterocyclic, and —$NR^{20}$C(O)substituted heterocyclic wherein $R^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —$NH_2$.

"Substituted amino" refers to the group —$NR^{21}R^{22}$ where $R^{21}$ and $R^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$— substituted alkenyl, —$SO_2$-cycloalkyl, —$SO_2$-substituted cycloalkyl, —$SO_2$-cycloalkenyl, —$SO_2$— substituted cylcoalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein $R^{21}$ and $R^{22}$ are optionally joined, together with the nitrogen bound thereto to form a heterocyclic or substituted heterocyclic group, provided that $R^{21}$ and $R^{22}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When $R^{21}$ is hydrogen and $R^{22}$ is alkyl, the substituted amino group is sometimes referred to herein as "alkylamino" When $R^{21}$ and $R^{22}$ are alkyl, the substituted amino group is sometimes referred to herein as "dialkylamino." When referring to a monosubstituted amino, it is meant that either $R^{21}$ or $R^{22}$ is hydrogen but not both. When referring to a disubstituted amino, it is meant that neither $R^{21}$ or $R^{22}$ is hydrogen.

"Aminoacyl" refers to the group —C(O)$NR^{21}R^{22}$ where $R^{21}$ and $R^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonyl" refers to the group —C(S)$NR^{21}R^{22}$ where $R^{21}$ and $R^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonylamino" refers to the group —$NR^{20}$C(O)$NR^{21}R^{22}$ where $R^{20}$ is hydrogen or alkyl and $R^{21}$ and $R^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonylamino" refers to the group —$NR^{20}$C(S)$NR^{21}R^{22}$ where $R^{20}$ is hydrogen or alkyl and $R^{21}$ and $R^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminoacyloxy" refers to the group $-O-C(O)NR^{21}R^{22}$ where $R^{21}$ and $R^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyl" refers to the group $-SO_2NR^{21}R^{22}$ where $R^{21}$ and $R^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyloxy" refers to the group $-O-SO_2NR^{21}R^{22}$ where $R^{21}$ and $R^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonylamino" refers to the group $-NR^{20}-SO_2NR^{21}R^{22}$ where $R^{20}$ is hydrogen or alkyl and $R^{21}$ and $R^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkyenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkyenyl, aryl, substituted aryl, heteroaryl, substituted heteroaryl, heterocyclic and substituted heterocyclic are as defined herein.

"Sulfonylamino" refers to the group $-NR^{21}SO_2R^{22}$ where $R^{21}$ and $R^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Amidino" refers to the group $-C(=NR^{20})R^{21}R^{22}$ where $R^{20}$, $R^{21}$ and $R^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 1,2,3,4-tetrahydronaphthalene, and the like) provided that the point of attachment is at an aromatic carbon atom. Some representative examples include 1H-indenyl, 2,3-dihydro-1H-indenyl (indanyl), 1,2-dihydronaphthalenyl (tetralenyl), 1,4-dihydronaphthalenyl (tetralenyl), 1,2,3,4-tetrahydronaphthalenyl (tetralinyl), 9,10-dihydrophenanthrenyl, 9H-fluorenyl, 4a,10-dihydroanthracenyl, 4a,9,9a,10-tetrahydroanthracenyl, phenanthrenyl, anthracenyl, phenalenyl, etc. Preferred aryl groups include phenyl and naphthyl.

"Substituted aryl" refers to aryl groups having 1 to 5 hydrogens replaced with substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO₃H, sulfonyl, sulfonyloxy, thioacyl, thiol, alkylthio, and substituted alkylthio, wherein said substituents are defined herein. In some embodiments, the aryl has 1 to 3 of the aforementioned groups. In other embodiments, the aryl has 1 to 2 of the aforementioned groups. In some embodiments, aryl group having multiple condensed rings (e.g., naphthyl or anthryl) which condensed rings may or may not be aromatic (e.g., 1,2,3,4-tetrahydronaphthalene, and the like), the non-aromatic condensed ring may be optionally substituted with oxo in addition to the above defined substituents.

"Aryloxy" refers to the group —O-aryl, where aryl is as defined herein, that includes, by way of example, phenoxy, naphthoxy, and the like.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Alkenyl" refers to monovalent unsaturated hydrocarbyl groups having from 2 to 6 carbon atoms and preferably 2 to 4 carbon atoms and having at least 1 and preferably from 1 to 2 sites of unsaturation. Such groups are exemplified by vinyl, allyl, but-3-en-1-yl, and the like.

"Substituted alkenyl" refers to alkenyl groups having from 1 to 3 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO₃H, sulfonyl, sulfonyloxy, thioacyl, thiol, alkylthio, and substituted alkylthio, wherein said substituents are defined herein and with the proviso that any hydroxy substitution is not attached to a vinyl (unsaturated) carbon atom. In some embodiments, the alkenyl has 1 to 2 of the aforementioned groups.

"Alkenylene" refers to divalent unsaturated hydrocarbyl groups having from 2 to 10 carbon atoms and preferably 2 to 6 carbon atoms and having at least 1 and preferably from 1-2 sites of vinyl (double bond) unsaturation. The term "alkenylene" encompasses any and all combinations of cis and trans isomers arising from the presence of unsaturation.

"Substituted alkenylene" refers to divalent alkenylene group having from 1 to 3 substituents selected from the group consisting of alkyl, substituted alkyl, alkoxy, substituted alkoxy, acyl, acylamino, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic provided that any hydroxyl substitution is not on a vinyl carbon atom. In some embodiments, the alkenylene has 1 to 2 of the aforementioned groups.

"Alkynyl" refers to monovalent unsaturated hydrocarbyl groups having from 2 to 6 carbon atoms and preferably 2 to 3 carbon atoms and having at least 1 and preferably from 1 to 2 sites of triple bond unsaturation.

"Substituted alkynyl" refers to alkynyl groups having from 1 to 3 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO₃H, sulfonyl, sulfonyloxy, thioacyl, thiol, alkylthio, and substituted alkylthio, wherein said substituents are defined herein and with the proviso that any hydroxy substitution is not attached to an acetylenic carbon atom. In some embodiments, the alkynyl has 1 to 2 of the aforementioned groups.

"Carboxyl" or "carboxy" refers to —COOH or salts thereof.

"Carboxyl ester" or "carboxy ester" refers to the groups —C(O)O-alkyl, —C(O)O— substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —NR—C(O)O-alkyl, substituted —NR—C(O)O-alkyl, —NR—C(O)O-alkenyl, —NR—C(O)O-substituted alkenyl, —NR—C(O)O-alkynyl, —NR—C(O)O-substituted alkynyl, —NR—C(O)O-aryl, —NR—C(O)O-substituted aryl, —NR—C(O)O-cycloalkyl, —NR—C(O)O-substituted cycloalkyl, —NR—C(O)O-cycloalkenyl, —NR—C(O)O-substituted cycloalkenyl, —NR—C(O)O-heteroaryl, —NR—C(O)O-substituted heteroaryl, —NR—C(O)O-heterocyclic, and —NR—C(O)O-substituted heterocyclic wherein R is alkyl or hydrogen and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, substituted —O—C(O)O-alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Carbonate ester" refers to the groups —OC(O)O-alkyl, —OC(O)O— substituted alkyl, —OC(O)O-alkenyl, —OC(O)O-substituted alkenyl, —OC(O)O-alkynyl, —OC(O)O-substituted alkynyl, —OC(O)O-aryl, —OC(O)O-substituted aryl, —OC(O)O-cycloalkyl, —OC(O)O-substituted cycloalkyl, —OC(O)O-cycloalkenyl, —OC(O)O-substituted cycloalkenyl, —OC(O)O-heteroaryl, —OC(O)O-substituted heteroaryl, —OC(O)O-heterocyclic, and —OC(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like.

"Cycloalkenyl" refers to non-aromatic cyclic alkyl groups of from 3 to 10 carbon atoms having single or multiple cyclic rings and having at least one >C=C<ring unsaturation and preferably from 1 to 2 sites of >C=C<ring unsaturation.

"Substituted cycloalkyl" and "substituted cycloalkenyl" refers to a cycloalkyl or cycloalkenyl group having from 1 to 5 substituents selected from the group consisting of oxo, thioxo, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, sulfonyl, sulfonyloxy, thioacyl, thiol, alkylthio, and substituted alkylthio, wherein said substituents are defined herein. In some embodiments, the cycloalkyl or cycloalkenyl has 1 to 3 of the aforementioned groups.

"Cycloalkoxy" refers to —O-cycloalkyl.

"Substituted cycloalkoxy" refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)NH$_2$.

"Substituted guanidino" refers to —NRC(=NR)N(R)$_2$ where each R is independently selected from the group consisting of hydrogen, alkyl, substituted alkyl, aryl, substituted aryl, heteroaryl, substituted heteroaryl, heterocyclic, and substituted heterocyclic and two R groups attached to a common guanidino nitrogen atom are optionally joined together with the nitrogen bound thereto to form a heterocyclic or substituted heterocyclic group, provided that at least one R is not hydrogen, and wherein said substituents are as defined herein.

"Halo" or "halogen" refers to fluoro, chloro, bromo and iodo and preferably is fluoro or chloro.

"Hydroxy" or "hydroxyl" refers to the group —OH.

"Heteroaryl" refers to an aromatic group of from 5 to 15 ring atoms including 1 to 4 heteroatoms selected from the group consisting of oxygen, nitrogen and sulfur. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. In preferred embodiments, the heteroaryl group is a 5-14 membered heteroaryl, with 5-10 membered heteroaryl being particularly preferred. Preferred heteroaryls include pyridinyl, pyrimidinyl, pyrazinyl, pyridizinyl, triazine, pyrrolyl, indolyl, thiophenyl, and furanyl.

"Substituted heteroaryl" refers to heteroaryl groups that are substituted with from 1 to 5 substituents selected from the group consisting of the same group of substituents defined for substituted aryl. In some embodiments, the heteroaryl has 1 to 3 of the aforementioned groups. In other embodiments, the heteroaryl has 1 to 2 of the aforementioned groups. In some embodiments, heteroaryl group having multiple condensed rings which condensed rings may or may not be aromatic, the non-aromatic condensed ring may be optionally substituted with oxo in addition to the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or unsaturated group having a single ring or multiple condensed rings, including fused bridged and spiro ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5 of the same substituents as defined for substituted cycloalkyl. In some embodiments, the heterocyclyl has 1 to 3 of the aforementioned groups.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, acridine, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Typical heteroaryl groups include, but are not limited to, groups derived from acridine, azetidine, benzimidazole, benzisoxazole, benzo[b]thiophene, benzodiaxole, benzodioxan, benzofuran, benzopyrone, benzothiadiazole, benzothiazole, benzotriazole, benzoxazine, benzoxazole, benzoxazoline, carbazole, carboline, β-carboline, chromane, chromene, cinnoline, dihydroindole, 1,1-dioxothiomorpholinyl, furan, imidazole, imidazolidine, imidazoline, indazole, indole, indoline, indolizine, isobenzofuran, isochromene, isoindole, isoindoline, isoquinoline, isothiazole, isoxazole, morpholinyl, naphthylpyridine, naphthyridine, oxadiazole, oxazole, perimidine, phenanthridine, phenanthroline, phenazine, phenothiazine, phenoxazine, phthalazine, phthalimide, piperazine, piperidine, pteridine, pteridine, purine, pyran, pyrazine, pyrazole, pyridazine, pyridine, pyrimidine, pyrrole, pyrrolidone, pyrrolizine, quinazoline, quinoline, quinolizine, quinoxaline, 4,5,6,7-tetrahydrobenzo[b]thiophene, tetrahydrofuranyl, 1,2,3,4-tetrahydroisoquinoline, tetrazole, thiadiazole, thiazole, thiazolidine, thiomorpholinyl (also referred to as thiamorpholinyl), thiophene, triazole, xanthene, and the like, as well as the various hydro isomers thereof.

"Nitro" refers to the group —NO$_2$.

"Oxo" refers to the atom (=O).

"Spirocycloalkyl" refers to cyclic groups from 3 to 10 carbon atoms having a cycloalkyl ring with a spiro union (the union formed by an alkylene or substituted alkylene bridge wherein both ends are bonded to a single atom in a chain or part of another ring system) as exemplified by the following structure:

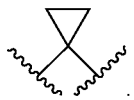 [SMILES: *C1(*)CC1]

"Sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$— substituted cylcoalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Sulfonyl includes groups such as methyl-SO$_2$—, phenyl-SO$_2$—, and 4-methylphenyl-SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cycloalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thiol" refers to the group —SH.

"Thioxo" refers to the atom (=S).

"Alkylthio" refers to the group —S-alkyl wherein alkyl is as defined herein.

"Silyl" refers to the group —SiH$_3$. "Trialkylsilyl" refers to the group —SiR$_3$, wherein each R is independently alkyl or substituted alkyl.

"Substituted alkylthio" refers to the group —S-(substituted alkyl) wherein substituted alkyl is as defined herein.

"Stereoisomer" or "stereoisomers" refer to compounds that differ in the chirality of one or more stereocenters. Stereoisomers include enantiomers and diastereomers.

"Tautomer" refer to alternate forms of a molecule that differ in the position of a proton, such as enol-keto and imine-enamine tautomers, or the tautomeric forms of heteroaryl groups containing a ring atom attached to both a ring —NH— moiety and a ring=N— moeity such as pyrazoles, imidazoles, benzimidazoles, triazoles, and tetrazoles.

"Patient" refers to humans and non-human animals.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

"Prodrug" refers to a derivative of an active 2,4-pyrimidinediamine compound (drug) that may require a transformation under the conditions of use, such as within the body, to release the active 2,4-pyrimidinediamine drug. Prodrugs are frequently, but not necessarily, pharmacologically inactive until converted into the active drug. Prodrugs are typically obtained by masking one or more functional groups in an active 2,4-pyrimidinediamine drug believed to be in part required for activity with a progroup (defined below) to form a promoiety which undergoes a transformation, such as cleavage, under the specified conditions of use to release the functional group, and hence the active 2,4-pyrimidinediamine drug. The cleavage of the promoiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

"Progroup" refers to a type of protecting group that, when used to mask a functional group within an active 2,4-pyrimidinediamine drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH$_3$ comprises the progroup —C(O)CH$_3$. Even more specifically, one or more sulfonamide groups of a 2,4-pyrimidinediamine compound of the invention protected by an acyl group to for —SO$_2$N(H)C(O)CH$_3$ and the like.

"Pharmaceutically effective amount" or "therapeutically effective amount" refers to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or to decrease the growth rate of the tumor.

"Solvate" refers to a compound formed by combination of solvent molecules with molecules or ions of the solute. The solvent can be either an organic or an inorganic compound. Some examples of solvents include but are not limited to, methanol, N,N-dimethylformamide, tetrahydrofuran, dimethylsulfoxide, water, etc.

Unless indicated otherwise, the nomenclature of substituents that are not explicitly defined herein are arrived at by naming the terminal portion of the functionality followed by the adjacent functionality toward the point of attachment. For example, the substituent "arylalkyloxycabonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are easily recognized by a person having ordinary skill in the art.

C. Compounds of the Invention

This invention provides novel 2,4-substituted pyrimidinediamine compounds, prodrugs of the compounds, methods of making the compounds and methods of using these compounds in the treatment of conditions in which targeting of the JAK pathway or inhibition of JAK kinases, particularly JAK3, may be therapeutically useful. These conditions include, but are not limited to, debilitating and fatal diseases and disorders that affect both children and adults, for example, oncological diseases, such as leukemia, including e.g., childhood leukemia, lymphoma, autoimmune conditions, such as transplant rejection, and the other conditions described herein. Given the severity of and suffering caused by these conditions, it is vital that new treatments are developed to treat these conditions.

In one embodiment, the present invention provides a compound of formula I, prodrugs, solvates, or pharmaceutically acceptable salts thereof:

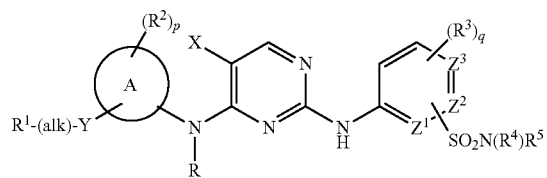

I wherein

X is selected from the group consisting of alkyl, substituted alkyl, alkoxy, substituted alkoxy, amino, substituted amino, carboxyl, carboxyl ester, cyano, halo, nitro, alkenyl, substituted alkenyl, alkynyl and substituted alkynyl;

R is selected from the group consisting of hydrogen, alkyl, substituted alkyl, alkenyl, substituted alkenyl, alkynyl, substituted alkynyl, cycloalkyl and substituted cycloalkyl;

ring A is selected from the group consisting of aryl, heteroaryl, cycloalkyl, cycloalkenyl and heterocyclic, wherein ring A is not indolyl or benzimidazolyl;

Y is selected from the group consisting of a bond, —NR$^7$—, —C(O)NR$^7$—, —NR$^7$C(O)—, —NR$^7$C(O)O—, —OC(O)NR$^7$—, —NR$^7$C(O)NR$^7$—, oxygen and sulfur, where R$^7$ is independently hydrogen, alkyl or substituted alkyl;

alk is a bond or a straight or branched chain alkylene group, wherein when alk and Y each are a bond then R$^1$ is attached to ring A by a single covalent bond;

R$^1$ is selected from the group consisting of cyano, acylamino, aminoacyl, aryl, substituted aryl, carboxyl, carboxyl ester, carboxyl ester oxy, heteroaryl, substituted heteroaryl, heterocyclic, substituted heterocyclic, acyl, aminoacyloxy, and aminocarbonylamino; or R$^1$-alk-Y— is R$^{10}$—C(O)—S-alk-C(O)—, wherein alk is as defined herein and R$^{10}$ is alkyl or substituted alkyl; or R$^1$-alk-Y— is R$^{11}$R$^{12}$NS(O)$_2$—, wherein R$^{11}$ and R$^{12}$ independently are alkyl or substituted alkyl;

p is 0, 1, 2 or 3 when ring A is a single ring or p is 0, 1, 2, 3, 4, or 5 when ring A comprises multiple rings;

each R$^2$ independently is selected from the group consisting of alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro, and halo, or two of $R^2$ on the same carbon form an oxo (=O);

$Z^1$, $Z^2$, and $Z^3$ each independently is carbon or nitrogen, wherein if $Z^1$ is nitrogen then $Z^2$ and $Z^3$ are carbon, if $Z^2$ is nitrogen then $Z^1$ and $Z^3$ are carbon, and if $Z^3$ is nitrogen then $Z^1$ and $Z^2$ are carbon, wherein if $Z^1$, $Z^2$, or $Z^3$ is nitrogen then $SO_2R^4R^5$ is not attached to the nitrogen;

q is 0, 1, 2 or 3;

each $R^3$ independently is selected from the group consisting of hydrogen, alkyl, substituted alkyl, alkoxy, substituted alkoxy, cycloalkyl or substituted cycloalkyl, halo, heterocyclic and substituted heterocyclic;

$R^4$ and $R^5$ independently are selected from the group consisting of hydrogen, alkyl, substituted alkyl, acyl and $M^+$, wherein $M^+$ is a metal counterion selected from the group consisting of $K^+$, $Na^+$, $Li^+$ or $^+N(R^6)_4$, wherein $R^6$ is hydrogen or alkyl, and the nitrogen of $SO^2NR^4R^5$ is $N^-$; or $R^4$ or $R^5$ is a divalent counterion selected from the group consisting of $Ca^{2+}$, $Mg^{2+}$, and $Ba^{2+}$, and the nitrogen of $SO_2NR^4R^5$ is $N^-$; or $R^4$ and $R^5$ together with the nitrogen atom bound thereto, form a heterocyclic or substituted heterocyclic group; or when q is 1, 2 or 3, $R^5$ can be joined with one $R^3$ group bound alpha thereto, to form a fused ring as illustrated in formula II:

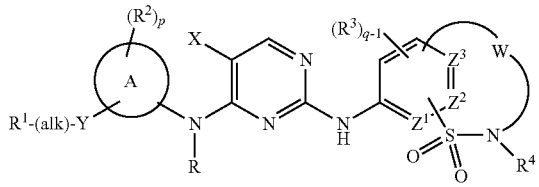

II wherein W is selected from the group consisting of $C_1$-$C_3$ alkylene, substituted $C_1$-$C_3$ alkylene, $C_2$-$C_3$ alkenylene and substituted $C_2$-$C_3$ alkenylene wherein one or more of the carbon atoms have been replaced with a moiety selected from oxygen, sulfur, S(O), S(O)$_2$, C(O), or $NR^8$ where $R^8$ is selected from the group consisting of hydrogen and alkyl or is a bond participating in a —N=C<site of unsaturation;

provided that:
when alk is a bond and Y is a bond, then $R^1$ is not cyano, carboxyl, carboxyl ester, or aminocarbonylamino;
when alk is —CH$_2$—, Y is oxygen and $R^1$ is phenyl, ring A is not cycloalkyl;
when alk is a bond, Y is a bond, ring A is phenyl, then $R^1$ is not heterocyclic, substituted heterocyclic or aminoacyloxy;
when Y or $R^1$-alk-Y— provide for direct linkage of either —NR$^7$C(O)O— or —NR$^7$C(O)NR$^7$— to ring A, then $R^7$ is hydrogen; and when Y is —C(O)NR$^7$—, —NR$^7$C(O)—, —OC(O)NR$^7$—, —NR$^7$C(O)O— or —NR$^7$C(O)NR$^7$— and alk is a bond, then $R^1$ is not acyl, acylamino, aminoacyl or aminocarbonylamino.

When $R^4$ or $R^5$ is a divalent counterion selected from the group consisting of $Ca^{2+}$, $Mg^{2+}$, and $Ba^{2+}$, the nitrogen of sulfonamide would carry a negative charge, but the counterion would be associated with two parent molecular ions, or alternatively, there might be another group on the ring that can provide another anion. For example, a chloride or similar anions can be used to satisfy the charge of the divalent metal (such as Mg$^{++}$Cl$^-$ etc.).

Certain embodiments of the invention provide compounds having the structure of formula IA, prodrugs, solvates, or pharmaceutically acceptable salts thereof:

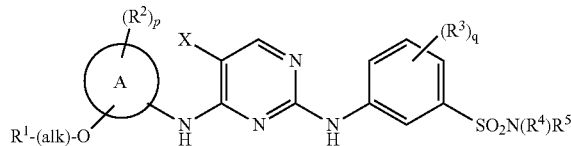

IA wherein:
X is selected from the group consisting of alkyl, substituted alkyl, alkoxy, substituted alkoxy, amino, substituted amino, carboxyl, carboxyl ester, cyano, halo, nitro, alkenyl, substituted alkenyl, alkynyl and substituted alkynyl;

R is selected from the group consisting of hydrogen, alkyl, substituted alkyl, alkenyl, substituted alkenyl, alkynyl, substituted alkynyl, cycloalkyl and substituted cycloalkyl;

ring A is selected from the group consisting of aryl, heteroaryl, cycloalkyl, cycloalkenyl and heterocyclic, wherein ring A is not indolyl or benzimidazolyl;

alk is a bond or a straight or branched chain alkylene group;

$R^1$ is selected from the group consisting of cyano, acylamino, aminoacyl, aryl, substituted aryl, carboxyl, carboxyl ester, carboxyl ester oxy, heteroaryl, substituted heteroaryl, heterocyclic, substituted heterocyclic, acyl, aminoacyloxy, and aminocarbonylamino;

p is 0, 1, 2 or 3 when ring A is a single ring or p is 0, 1, 2, 3, 4, or 5 when ring A comprises multiple rings;

each $R^2$ independently is selected from the group consisting of alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro and halo;

q is 0, 1, 2 or 3;

each $R^3$ independently is selected from the group consisting of hydrogen, alkyl, substituted alkyl, alkoxy, substituted alkoxy, cycloalkyl or substituted cycloalkyl, halo, heterocyclic and substituted heterocyclic; $R^4$ and $R^5$ independently are selected from the group consisting of hydrogen, alkyl, substituted alkyl, acyl and $M^+$, wherein $M^+$ is a metal counterion selected from the group consisting of K$^+$, Na$^+$, Li$^+$ or $^+$N(R$^6$)$_4$, wherein R$^6$ is hydrogen or alkyl, and the nitrogen of SO$^2$NR$^4$R$^5$ is N$^-$; or R$^4$ or R$^5$ is a divalent counterion selected from the group consisting of Ca$^{2+}$, Mg$^2$+, and Ba$^{2+}$, and the nitrogen of SO$_2$NR$^4$R$^5$ is N$^-$; or R$^4$ and R$^5$ together with the nitrogen atom bound thereto, form a heterocyclic or substituted heterocyclic group; or when q is 1, 2 or 3, R$^5$ can be joined with one R$^3$ group bound alpha thereto, to form a fused ring as illustrated in formula IIA:

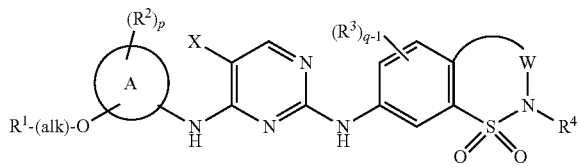

IIA wherein W is selected from the group consisting of C$_1$-C$_3$ alkylene, substituted C$_1$-C$_3$ alkylene, C$_2$-C$_3$ alkenylene and substituted C$_2$-C$_3$ alkenylene wherein one or more of the carbon atoms have been replaced with a moiety selected from oxygen, sulfur, S(O), S(O)$_2$, C(O), or NR$^8$ where R$^8$ is selected from the group consisting of hydrogen and alkyl or is a bond participating in a —N═C<site of unsaturation.

Preferably ring A is phenyl.

Other embodiments include compounds having the structure of formula IB, and prodrugs, solvates, or pharmaceutically acceptable salts thereof:

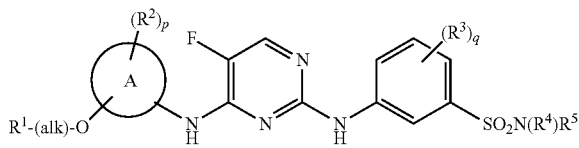

IB wherein:
ring A is selected from the group consisting of aryl, heteroaryl, cycloalkyl, cycloalkenyl and heterocyclic, wherein ring A is not indolyl or benzimidazolyl;
alk is a bond or a straight or branched chain alkylene group;
R$^1$ is selected from the group consisting of cyano, acylamino, aminoacyl, aryl, substituted aryl, carboxyl, carboxyl ester, carboxyl ester oxy, heteroaryl, substituted heteroaryl, heterocyclic, substituted heterocyclic, acyl, aminoacyloxy, and aminocarbonylamino;
p is 0, 1, 2 or 3 when ring A is a single ring or p is 0, 1, 2, 3, 4, or 5 when ring A comprises multiple rings;
each R$^2$ independently is selected from the group consisting of alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro and halo;
q is 0, 1, 2 or 3;
each R$^3$ independently is selected from the group consisting of hydrogen, alkyl, substituted alkyl, alkoxy, substituted alkoxy, cycloalkyl or substituted cycloalkyl, halo, heterocyclic and substituted heterocyclic;
R$^4$ and R$^5$ independently are selected from the group consisting of hydrogen, alkyl, substituted alkyl, acyl and M$^+$, wherein M$^+$ is a metal counterion selected from the group consisting of K$^+$, Na$^+$, Li$^+$ or $^+$N(R$^6$)$_4$, wherein R$^6$ is hydrogen or alkyl, and the nitrogen of SO$^2$NR$^4$R$^5$ is N$^-$; or
R$^4$ and R$^5$ together with the nitrogen atom bound thereto, form a heterocyclic or substituted heterocyclic group.

Yet other embodiments provide compounds having the structure of formula IC, prodrugs, solvates, or pharmaceutically acceptable salts thereof:

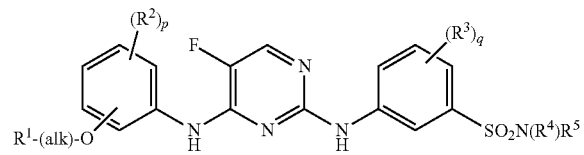

IC wherein:
alk is a bond or a straight or branched chain alkylene group;
R$^1$ is selected from the group consisting of cyano, acylamino, aminoacyl, aryl, substituted aryl, carboxyl, carboxyl ester, carboxyl ester oxy, heteroaryl, substituted heteroaryl, heterocyclic, substituted heterocyclic, acyl, aminoacyloxy, and aminocarbonylamino;
p is 0, 1, 2 or 3 when ring A is a single ring or p is 0, 1, 2, 3, 4, or 5 when ring A comprises multiple rings;
each R$^2$ independently is selected from the group consisting of alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro and halo;
q is 0, 1, 2 or 3;
each R$^3$ independently is selected from the group consisting of hydrogen, alkyl, substituted alkyl, alkoxy, substituted alkoxy, cycloalkyl or substituted cycloalkyl, halo, heterocyclic and substituted heterocyclic;
R$^4$ and R$^5$ independently are selected from the group consisting of hydrogen, alkyl, substituted alkyl, acyl and M$^+$, wherein M$^+$ is a metal counterion selected from the group consisting of K$^+$, Na$^+$, Li$^+$ or $^+$N(R$^6$)$_4$, wherein R$^6$ is hydrogen or alkyl, and the nitrogen of SO$^2$NR$^4$R$^5$ is N$^-$; or
R$^4$ and R$^5$ together with the nitrogen atom bound thereto, form a heterocyclic or substituted heterocyclic group.

Other embodiments include compounds having the structure of formula ID, prodrugs, solvates, or pharmaceutically acceptable salts thereof:

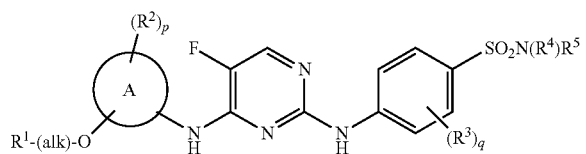

ID wherein:
- ring A is selected from the group consisting of aryl, heteroaryl, cycloalkyl, cycloalkenyl and heterocyclic, wherein ring A is not indolyl or benzimidazolyl;
- alk is a bond or a straight or branched chain alkylene group;
- $R^1$ is selected from the group consisting of cyano, acylamino, aminoacyl, aryl, substituted aryl, carboxyl, carboxyl ester, carboxyl ester oxy, heteroaryl, substituted heteroaryl, heterocyclic, substituted heterocyclic, acyl, aminoacyloxy, and aminocarbonylamino;
- p is 0, 1, 2 or 3 when ring A is a single ring or p is 0, 1, 2, 3, 4, or 5 when ring A comprises multiple rings;
- each $R^2$ independently is selected from the group consisting of alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro, and halo, or two of $R^2$ on the same carno form an oxo (=O);
- q is 0, 1, 2 or 3;
- each $R^3$ independently is selected from the group consisting of hydrogen, alkyl, substituted alkyl, alkoxy, substituted alkoxy, cycloalkyl or substituted cycloalkyl, halo, heterocyclic and substituted heterocyclic;
- $R^4$ and $R^5$ independently are selected from the group consisting of hydrogen, alkyl, substituted alkyl, acyl and $M^+$, wherein $M^+$ is a metal counterion selected from the group consisting of $K^+$, $Na^+$, $Li^+$ or $^+N(R^6)_4$, wherein $R^6$ is hydrogen or alkyl, and the nitrogen of $SO^2NR^4R^5$ is $N^-$; or
- $R^4$ or $R^5$ is a divalent counterion selected from the group consisting of $Ca^{2+}$, $Mg^{2+}$, and $Ba^{2+}$, and the nitrogen of $SO_2NR^4R^5$ is $N^-$; or
- $R^4$ and $R^5$ together with the nitrogen atom bound thereto, form a heterocyclic or substituted heterocyclic group.

Yet other preferred embodiments of the invention provide compounds having the structure of formula IE, prodrugs, solvates, or pharmaceutically acceptable salts thereof:

IE

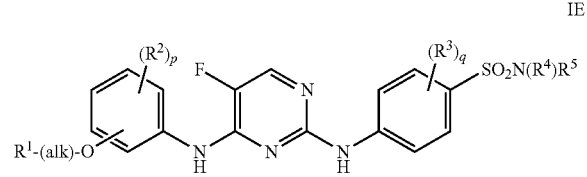

wherein:
- alk is a bond or a straight or branched chain alkylene group;
- $R^1$ is selected from the group consisting of cyano, acylamino, aminoacyl, aryl, substituted aryl, carboxyl, carboxyl ester, carboxyl ester oxy, heteroaryl, substituted heteroaryl, heterocyclic, substituted heterocyclic, acyl, aminoacyloxy, and aminocarbonylamino;
- p is 0, 1, 2 or 3;
- each $R^2$ independently is selected from the group consisting of alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro, and halo, or two of $R^2$ on the same carno form an oxo (=O);
- q is 0, 1, 2 or 3;
- each $R^3$ independently is selected from the group consisting of hydrogen, alkyl, substituted alkyl, alkoxy, substituted alkoxy, cycloalkyl or substituted cycloalkyl, halo, heterocyclic and substituted heterocyclic;
- $R^4$ and $R^5$ independently are selected from the group consisting of hydrogen, alkyl, substituted alkyl, acyl and $M^+$, wherein $M^+$ is a metal counterion selected from the group consisting of $K^+$, $Na^+$, $Li^+$ or $^+N(R^6)_4$, wherein $R^6$ is hydrogen or alkyl, and the nitrogen of $SO^2NR^4R^5$ is $N^-$; or
- $R^4$ or $R^5$ is a divalent counterion selected from the group consisting of $Ca^{2+}$, $Mg^{2+}$, and $Ba^{2+}$, and the nitrogen of $SO_2NR^4R^5$ is $N^-$; or
- $R^4$ and $R^5$ together with the nitrogen atom bound thereto, form a heterocyclic or substituted heterocyclic group.

Yet other preferred embodiments of the invention provide compounds having the structure of formula III, prodrugs, solvates, or pharmaceutically acceptable salts thereof:

III

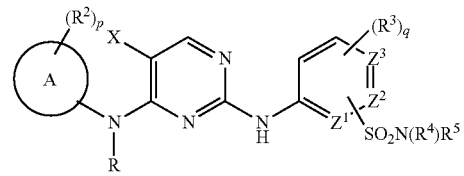

wherein:
- X is selected from the group consisting of alkyl, substituted alkyl, alkoxy, substituted alkoxy, amino, substituted amino, carboxyl, carboxyl ester, cyano, halo, nitro, alkenyl, substituted alkenyl, alkynyl and substituted alkynyl;
- R is selected from the group consisting of hydrogen, alkyl, substituted alkyl, alkenyl, substituted alkenyl, alkynyl, substituted alkynyl, cycloalkyl and substituted cycloalkyl;
- ring A is selected from the group consisting of aryl, heteroaryl, cycloalkyl, cycloalkenyl and heterocyclic, wherein ring A is not indolyl or benzimidazolyl;
- p is 0, 1, 2 or 3;
- each $R^2$ independently is selected from the group consisting of alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, sulfonyl, oxo, nitro and halo;

$Z^1$, $Z^2$, and $Z^3$ each independently is carbon or nitrogen, wherein if $Z^1$ is nitrogen then $Z^2$ and $Z^3$ are carbon, if $Z^2$ is nitrogen then $Z^1$ and $Z^3$ are carbon, and if $Z^3$ is nitrogen then $Z^1$ and $Z^2$ are carbon, wherein if $Z^1$, $Z^2$, or $Z^3$ is nitrogen then $SO_2R^4R^5$ is not attached to the nitrogen;

q is 0, 1, 2 or 3;

each $R^3$ independently is selected from the group consisting of hydrogen, alkyl, substituted alkyl, alkoxy, substituted alkoxy, cycloalkyl or substituted cycloalkyl, halo, heterocyclic and substituted heterocyclic;

$R^4$ and $R^5$ independently are selected from the group consisting of hydrogen, alkyl, substituted alkyl, acyl and $M^+$, wherein $M^+$ is a metal counterion selected from the group consisting of $K^+$, $Na^+$, $Li^+$ or $^+N(R^6)_4$, wherein $R^6$ is hydrogen or alkyl, and the nitrogen of $SO^2NR^4R^5$ is $N^-$; or $R^4$ or $R^5$ is a divalent counterion selected from the group consisting of $Ca^{2+}$, $Mg^{2+}$, and $Ba^{2+}$, and the nitrogen of $SO_2NR^4R^5$ is $N^-$; or $R^4$ and $R^5$ together with the nitrogen atom bound thereto, form a heterocyclic or substituted heterocyclic group; or when q is 1, 2 or 3, $R^5$ can be joined with one $R^3$ group bound alpha thereto, to form a fused ring as illustrated in formula IV:

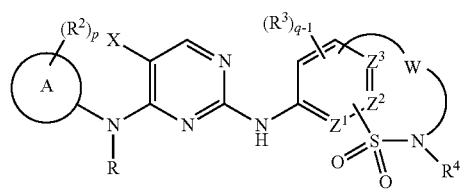

IV wherein W is selected from the group consisting of $C_1$-$C_3$ alkylene, substituted $C_1$-$C_3$ alkylene, $C_2$-$C_3$ alkenylene and substituted $C_2$-$C_3$ alkenylene wherein one or more of the carbon atoms have been replaced with a moiety selected from oxygen, sulfur, S(O), S(O)$_2$, C(O), or $NR^8$ where $R^8$ is selected from the group consisting of hydrogen and alkyl or is a bond participating in a —N=C<site of unsaturation;

provided that:
if p=0, then X is not bromo;
if ring A is cycloalkyl, then X is not bromo;
if p=2 and each of $R^2$ is methoxy, halo, trihalomethyl or trihalomethoxy, then $R^4$ and $R^5$ are not one hydrogen and one methyl;
if p=2 and $R^2$ is fluoro and methyl, then R is not substituted alkenyl; and
if ring A is phenyl, p=1 and $R^2$ is chloro, then $R^4$ and $R^5$ are not one hydrogen and one methyl.

Yet other preferred embodiments of the invention provide compounds having the structure of formula IIIA, prodrugs, solvates, or pharmaceutically acceptable salts thereof:

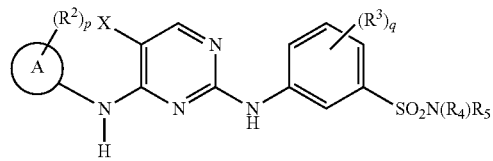

IIIA wherein:
X is selected from the group consisting of alkyl, substituted alkyl, alkoxy, substituted alkoxy, amino, substituted amino, carboxyl, carboxyl ester, cyano, halo, nitro, alkenyl, substituted alkenyl, alkynyl and substituted alkynyl;

ring A is selected from the group consisting of aryl, heteroaryl, cycloalkyl, cycloalkenyl and heterocyclic, wherein ring A is not indolyl or benzimidazolyl;

p is 0, 1, 2 or 3;

each $R^2$ independently is selected from the group consisting of alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro and halo;

q is 0, 1, 2 or 3;

each $R^3$ independently is selected from the group consisting of hydrogen, alkyl, substituted alkyl, alkoxy, substituted alkoxy, cycloalkyl or substituted cycloalkyl, halo, heterocyclic and substituted heterocyclic;

$R^4$ and $R^5$ independently are selected from the group consisting of hydrogen, alkyl, substituted alkyl, acyl and $M^+$, wherein $M^+$ is a metal counterion selected from the group consisting of $K^+$, $Na^+$, $Li^+$ or $^+N(R^6)_4$, wherein $R^6$ is hydrogen or alkyl, and the nitrogen of $SO^2NR^4R^5$ is $N^-$; or $R^4$ or $R^5$ is a divalent counterion selected from the group consisting of $Ca^{2+}$, $Mg^{2+}$, and $Ba^{2+}$, and the nitrogen of $SO_2NR^4R^5$ is $N^-$; or $R^4$ and $R^5$ together with the nitrogen atom bound thereto, form a heterocyclic or substituted heterocyclic group each $R^2$ independently is selected from the group consisting of alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro and halo.

Yet other preferred embodiments of the invention provide compounds having the structutre of formula IIIA, prodrugs, solvates, or pharmaceutically acceptable salts thereof wherein:

ring A is selected from the group consisting of aryl, heteroaryl, cycloalkyl, cycloalkenyl and heterocyclic, wherein ring A is not indolyl or benzimidazolyl;

p is 0, 1, 2 or 3;

each $R^2$ independently is selected from the group consisting of alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro and halo;

q is 0, 1, 2 or 3;

each $R^3$ independently is selected from the group consisting of hydrogen, alkyl, substituted alkyl, alkoxy, substituted alkoxy, cycloalkyl or substituted cycloalkyl, halo, heterocyclic and substituted heterocyclic;

X is fluoro or methyl; and $R^4$ and $R^5$ independently are selected from the group consisting of hydrogen, alkyl, substituted alkyl and acyl; or $R^4$ and $R^5$ together with the nitrogen atom bound thereto, form a heterocyclic or substituted heterocyclic group.

Yet other preferred embodiments of the invention provide compounds having the structutre of formula IIIA, prodrugs, solvates, or pharmaceutically acceptable salts thereof wherein:

ring A is phenyl;

p is 0, 1, 2 or 3;

each $R^2$ independently is selected from the group consisting of alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro and halo;

q is 0, 1, 2 or 3;

each $R^3$ independently is selected from the group consisting of hydrogen, alkyl, substituted alkyl, alkoxy, substituted alkoxy, cycloalkyl or substituted cycloalkyl, halo, heterocyclic and substituted heterocyclic;

X is fluoro or methyl; and $R^4$ and $R^5$ independently are selected from the group consisting of hydrogen, alkyl, substituted alkyl and acyl; or $R^4$ and $R^5$ together with the nitrogen atom bound thereto, form a heterocyclic or substituted heterocyclic group.

Yet other preferred embodiments of the invention provide compounds having the structutre of formula IVA, prodrugs, solvates, or pharmaceutically acceptable salts thereof:

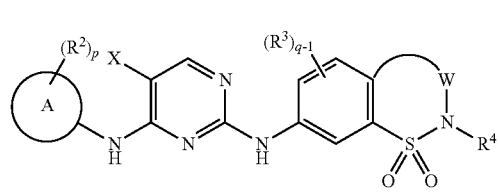

IVA wherein:

X is selected from the group consisting of alkyl, substituted alkyl, alkoxy, substituted alkoxy, amino, substituted amino, carboxyl, carboxyl ester, cyano, halo, nitro, alkenyl, substituted alkenyl, alkynyl and substituted alkynyl;

ring A is selected from the group consisting of aryl, heteroaryl, cycloalkyl, cycloalkenyl and heterocyclic, wherein ring A is not indolyl or benzimidazolyl;

p is 0, 1, 2 or 3;

each $R^2$ independently is selected from the group consisting of alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, sulfonyl, oxo, nitro and halo;

each $R^3$ independently is selected from the group consisting of hydrogen, alkyl, substituted alkyl, alkoxy, substituted alkoxy, cycloalkyl or substituted cycloalkyl, halo, heterocyclic and substituted heterocyclic;

$R^4$ is independently selected from the group consisting of hydrogen, alkyl, substituted alkyl, acyl and M$^+$, wherein M$^+$ is a metal counterion selected from the group consisting of K$^+$, Na$^+$, Li$^+$ or $^+$N(R$^6$)$_4$, wherein R$^6$ is hydrogen or alkyl, and the nitrogen of SO$^2$NR$^4$ is N$^-$; or $R^4$ is a divalent counterion selected from the group consisting of Ca$^{2+}$, Mg$^2$+, and Ba$^{2+}$, and the nitrogen of SO$_2$NR$^4$ is N$^-$;

q–1 is 0, 1 or 2; and

W is selected from the group consisting of $C_1$-$C_3$ alkylene, substituted $C_1$-$C_3$ alkylene, $C_2$-$C_3$ alkenylene and substituted $C_2$-$C_3$ alkenylene wherein one or more of the carbon atoms have been replaced with a moiety selected from oxygen, sulfur, S(O), S(O)$_2$, C(O), or NR$^8$ where R$^8$ is selected from the group consisting of hydrogen and alkyl or is a bond participating in a —N═C<site of unsaturation;

provided that:

if p=0, then X is not bromo;

if ring A is cycloalkyl, then X is not bromo;

if p=2 and each of R$^2$ is methoxy, halo, trihalomethyl or trihalomethoxy, then R$^4$ and R$^5$ are not one hydrogen and one methyl;

if p=2 and R$^2$ is fluoro and methyl, then R is not substituted alkenyl; and if ring A is phenyl, p=1 and R$^2$ is chloro, then R$^4$ and R$^5$ are not one hydrogen and one methyl.

Yet other preferred embodiments of the invention provide compounds having the structutre of formula IVA, prodrugs, solvates, or pharmaceutically acceptable salts thereof wherein:

X is selected from the group consisting of alkyl, substituted alkyl, alkoxy, substituted alkoxy, amino, substituted amino, carboxyl, carboxyl ester, cyano, halo, nitro, alkenyl, substituted alkenyl, alkynyl and substituted alkynyl;

ring A is phenyl;

p is 0, 1, 2 or 3;

each $R^2$ independently is selected from the group consisting of alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, sulfonyl, oxo, nitro and halo;

each R³ independently is selected from the group consisting of hydrogen, alkyl, substituted alkyl, alkoxy, substituted alkoxy, cycloalkyl or substituted cycloalkyl, halo, heterocyclic and substituted heterocyclic;

R⁴ is independently selected from the group consisting of hydrogen, alkyl, substituted alkyl, acyl and M⁺, wherein M⁺ is a metal counterion selected from the group consisting of K⁺, Na⁺, Li⁺ or ⁺N(R⁶)₄, wherein R⁶ is hydrogen or alkyl, and the nitrogen of SO²NR⁴ is N⁻; or R⁴ is a divalent counterion selected from the group consisting of Ca²⁺, Mg²+, and Ba²⁺, and the nitrogen of SO₂NR⁴ is N⁻;

q–1 is 0, 1 or 2; and

W is selected from the group consisting of C₁-C₃ alkylene, substituted C₁-C₃ alkylene, C₂-C₃ alkenylene and substituted C₂-C₃ alkenylene wherein one or more of the carbon atoms have been replaced with a moiety selected from oxygen, sulfur, S(O), S(O)₂, C(O), or NR⁸ where R⁸ is selected from the group consisting of hydrogen and alkyl or is a bond participating in a —N=C<site of unsaturation;

provided that:
if p=0, then X is not bromo;
if ring A is cycloalkyl, then X is not bromo;
if p=2 and each of R² is methoxy, halo, trihalomethyl or trihalomethoxy, then R⁴ and R⁵ are not one hydrogen and one methyl;
if p=2 and R² is fluoro and methyl, then R is not substituted alkenyl; and
if ring A is phenyl, p=1 and R² is chloro, then R⁴ and R⁵ are not one hydrogen and one methyl.

Yet other preferred embodiments of the invention provide compounds having the structutre of formula IIIB, prodrugs, solvates, or pharmaceutically acceptable salts thereof:

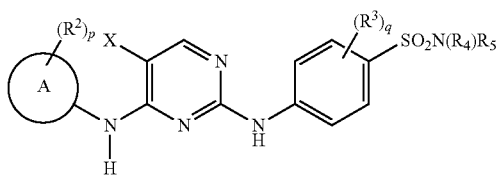

wherein:
X is selected from the group consisting of alkyl, substituted alkyl, alkoxy, substituted alkoxy, amino, substituted amino, carboxyl, carboxyl ester, cyano, halo, nitro, alkenyl, substituted alkenyl, alkynyl and substituted alkynyl;
ring A is selected from the group consisting of aryl, heteroaryl, cycloalkyl, cycloalkenyl and heterocyclic, wherein ring A is not indolyl or benzimidazolyl;
p is 0, 1, 2 or 3;
each R² independently is selected from the group consisting of alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro and halo;
q is 0, 1, 2 or 3;
each R³ independently is selected from the group consisting of hydrogen, alkyl, substituted alkyl, alkoxy, substituted alkoxy, cycloalkyl or substituted cycloalkyl, halo, heterocyclic and substituted heterocyclic;
R⁴ and R⁵ independently are selected from the group consisting of hydrogen, alkyl, substituted alkyl, acyl and M⁺, wherein M⁺ is a metal counterion selected from the group consisting of K⁺, Na⁺, Li⁺ or ⁺N(R⁶)₄, wherein R⁶ is hydrogen or alkyl, and the nitrogen of SO²NR⁴R⁵ is N⁻; or
R⁴ or R⁵ is a divalent counterion selected from the group consisting of Ca²⁺, Mg²+, and Ba²⁺, and the nitrogen of SO₂NR⁴R⁵ is N⁻; or
R⁴ and R⁵ together with the nitrogen atom bound thereto, form a heterocyclic or substituted heterocyclic group.

Yet other preferred embodiments of the invention provide compounds having the structutre of formula IIIB, prodrugs, solvates, or pharmaceutically acceptable salts thereof wherein:
X is fluoro or methyl;
ring A is selected from the group consisting of aryl, heteroaryl, cycloalkyl, cycloalkenyl and heterocyclic, wherein ring A is not indolyl or benzimidazolyl;
p is 0, 1, 2 or 3;
each R² independently is selected from the group consisting of alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro and halo;
q is 0, 1, 2 or 3;
each R³ independently is selected from the group consisting of hydrogen, alkyl, substituted alkyl, alkoxy, substituted alkoxy, cycloalkyl or substituted cycloalkyl, halo, heterocyclic and substituted heterocyclic;
R⁴ and R⁵ independently are selected from the group consisting of hydrogen, alkyl, substituted alkyl and acyl; or
R⁴ and R⁵ together with the nitrogen atom bound thereto, form a heterocyclic or substituted heterocyclic group.

Yet other preferred embodiments of the invention provide compounds having the structutre of formula IIIB, prodrugs, solvates, or pharmaceutically acceptable salts thereof wherein:
X is fluoro or methyl;
ring A is phenyl;
p is 0, 1, 2 or 3;
each R² independently is selected from the group consisting of alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester, nitro and halo;
q is 0, 1, 2 or 3;
each R³ independently is selected from the group consisting of hydrogen, alkyl, substituted alkyl, alkoxy, substituted alkoxy, cycloalkyl or substituted cycloalkyl, halo, heterocyclic and substituted heterocyclic;

$R^4$ and $R^5$ independently are selected from the group consisting of hydrogen, alkyl, substituted alkyl and acyl; or $R^4$ and $R^5$ together with the nitrogen atom bound thereto, form a heterocyclic or substituted heterocyclic group.

Yet other preferred embodiments of the invention provide compounds having the structutre of formula V, prodrugs, solvates, or pharmaceutically acceptable salts thereof wherein:

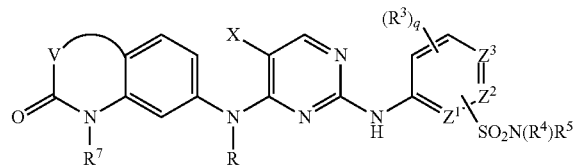

V wherein:
X is selected from the group consisting of alkyl, substituted alkyl, alkoxy, substituted alkoxy, amino, substituted amino, carboxyl, carboxyl ester, cyano, halo, nitro, alkenyl, substituted alkenyl, alkynyl and substituted alkynyl;

R is selected from the group consisting of hydrogen, alkyl, substituted alkyl, alkenyl, substituted alkenyl, alkynyl, substituted alkynyl, cycloalkyl and substituted cycloalkyl;

$Z^1$, $Z^2$, and $Z^3$ each independently is carbon or nitrogen, wherein if $Z^1$ is nitrogen then $Z^2$ and $Z^3$ are carbon, if $Z^2$ is nitrogen then $Z^1$ and $Z^3$ are carbon, and if $Z^3$ is nitrogen then $Z^1$ and $Z^2$ are carbon, wherein if $Z^1$, $Z^2$, or $Z^3$ is nitrogen then $SO_2R^4R^5$ is not attached to the nitrogen;

q is 0, 1, 2 or 3;

each $R^3$ independently is selected from the group consisting of hydrogen, alkyl, substituted alkyl, alkoxy, substituted alkoxy, cycloalkyl or substituted cycloalkyl, halo, heterocyclic and substituted heterocyclic;

$R^4$ and $R^5$ independently are selected from the group consisting of hydrogen, alkyl, substituted alkyl, acyl and $M^+$, wherein $M^+$ is a metal counterion selected from the group consisting of $K^+$, $Na^+$, $Li^+$ or $^+N(R^6)_4$, wherein $R^6$ is hydrogen or alkyl, and the nitrogen of $SO^2NR^4R^5$ is $N^-$; or $R^4$ or $R^5$ is a divalent counterion selected from the group consisting of $Ca^{2+}$, $Mg^{2+}$, and $Ba^{2+}$, and the nitrogen of $SO_2NR^4R^5$ is $N^-$; or $R^4$ and $R^5$ together with the nitrogen atom bound thereto, form a heterocyclic or substituted heterocyclic group; or $R^4$ and $R^5$ independently are selected from the group consisting of hydrogen, alkyl, substituted alkyl and acyl; or $R^4$ and $R^5$ together with the nitrogen atom bound thereto, form a heterocyclic or substituted heterocyclic group;

$R^7$ is selected from the group consisting of hydrogen, alkyl or substituted alkyl; and V is selected from the group consisting of $C_1$-$C_3$ alkylene, substituted $C_1$-$C_3$ alkylene, $C_2$-$C_3$ alkenylene and substituted $C_2$-$C_3$ alkenylene wherein one or more of the carbon atoms have been replaced with a heteroatom selected from oxygen, sulfur, S(O), S(O)$_2$, or $NR^8$ where $R^8$ is selected from the group consisting of hydrogen and alkyl or is a bond participating in a —N=C<site of unsaturation.

Yet other preferred embodiments of the invention provide compounds having the structutre of formula VA, prodrugs, solvates, or pharmaceutically acceptable salts thereof wherein:

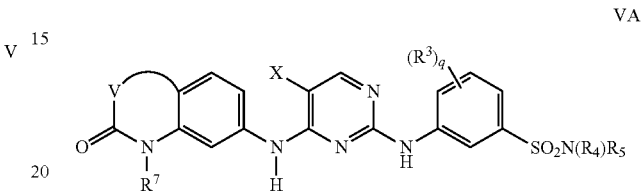

VA wherein:
X is fluoro or methyl;

q is 0, 1, 2 or 3;

each $R^3$ independently is selected from the group consisting of hydrogen, alkyl, substituted alkyl, alkoxy, substituted alkoxy, cycloalkyl or substituted cycloalkyl, halo, heterocyclic and substituted heterocyclic;

$R^4$ and $R^5$ independently are selected from the group consisting of hydrogen, alkyl, substituted alkyl, acyl and $M^+$, wherein $M^+$ is a metal counterion selected from the group consisting of $K^+$, $Na^+$, $Li^+$ or $^+N(R^6)_4$, wherein $R^6$ is hydrogen or alkyl, and the nitrogen of $SO^2NR^4R^5$ is $N^-$; or $R^4$ or $R^5$ is a divalent counterion selected from the group consisting of $Ca^{2+}$, $Mg^{2+}$, and $Ba^{2+}$, and the nitrogen of $SO_2NR^4R^5$ is $N^-$; or $R^4$ and $R^5$ together with the nitrogen atom bound thereto, form a heterocyclic or substituted heterocyclic group; or $R^4$ and $R^5$ independently are selected from the group consisting of hydrogen, alkyl, substituted alkyl and acyl; or $R^4$ and $R^5$ together with the nitrogen atom bound thereto, form a heterocyclic or substituted heterocyclic group;

$R^7$ is selected from the group consisting of hydrogen, alkyl or substituted alkyl; and V is selected from the group consisting of $C_1$-$C_3$ alkylene, substituted $C_1$-$C_3$ alkylene, $C_2$-$C_3$ alkenylene and substituted $C_2$-$C_3$ alkenylene wherein one or more of the carbon atoms have been replaced with a heteroatom selected from oxygen, sulfur, S(O), S(O)$_2$, or $NR^8$ where $R^8$ is selected from the group consisting of hydrogen and alkyl or is a bond participating in a —N=C<site of unsaturation.

Yet other preferred embodiments of the invention provide compounds having the structutre of formula VB, prodrugs, solvates, or pharmaceutically acceptable salts thereof wherein:

VB

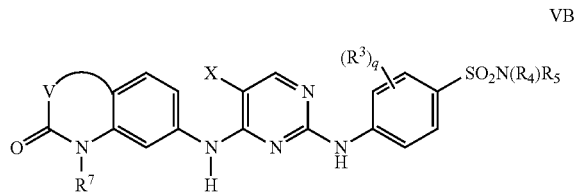

wherein:
X is fluoro or methyl;
q is 0, 1, 2 or 3;
each $R^3$ independently is selected from the group consisting of hydrogen, alkyl, substituted alkyl, alkoxy, substituted alkoxy, cycloalkyl or substituted cycloalkyl, halo, heterocyclic and substituted heterocyclic;
$R^4$ and $R^5$ independently are selected from the group consisting of hydrogen, alkyl, substituted alkyl, acyl and $M^+$, wherein $M^+$ is a metal counterion selected from the group consisting of $K^+$, $Na^+$, $Li^+$ or $^+N(R^6)_4$, wherein $R^6$ is hydrogen or alkyl, and the nitrogen of $SO^2NR^4R^5$ is $N^-$; or
$R^4$ or $R^5$ is a divalent counterion selected from the group consisting of $Ca^{2+}$, $Mg^2+$, and $Ba^{2+}$, and the nitrogen of $SO_2NR^4R^5$ is $N^-$; or
$R^4$ and $R^5$ together with the nitrogen atom bound thereto, form a heterocyclic or substituted heterocyclic group; or
$R^4$ and $R^5$ independently are selected from the group consisting of hydrogen, alkyl, substituted alkyl and acyl; or
$R^4$ and $R^5$ together with the nitrogen atom bound thereto, form a heterocyclic or substituted heterocyclic group;
$R^7$ is selected from the group consisting of hydrogen, alkyl or substituted alkyl; and
V is selected from the group consisting of $C_1$-$C_3$ alkylene, substituted $C_1$-$C_3$ alkylene, $C_2$-$C_3$ alkenylene and substituted $C_2$-$C_3$ alkenylene wherein one or more of the carbon atoms have been replaced with a heteroatom selected from oxygen, sulfur, S(O), S(O)$_2$, or $NR^8$ where $R^8$ is selected from the group consisting of hydrogen and alkyl or is a bond participating in a —N═C<site of unsaturation.

Those of skill in the art will appreciate that the 2,4-substituted pyrimidinediamine compounds described herein may include functional groups that can be masked with progroups to create prodrugs. Such prodrugs are usually, but need not be, pharmacologically inactive until converted into their active drug form. Indeed, many of the 2,4-substituted pyrimidinediamine compounds described in this invention include promoieties that are hydrolyzable or otherwise cleavable under conditions of use. For example, ester groups commonly undergo acid-catalyzed hydrolysis to yield the parent carboxylic acid when exposed to the acidic conditions of the stomach, or base-catalyzed hydrolysis when exposed to the basic conditions of the intestine or blood. Thus, when administered to a subject orally, 2,4-substituted pyrimidinediamine compounds that include ester moieties may be considered prodrugs of their corresponding carboxylic acid, regardless of whether the ester form is pharmacologically active.

The mechanism by which the progroup(s) metabolizes is not critical, and can be caused by, for example, hydrolysis under the acidic conditions of the stomach, as described above, and/or by enzymes present in the digestive tract and/or tissues or organs of the body. Indeed, the progroup(s) can be selected to metabolize at a particular site within the body. For example, many esters are cleaved under the acidic conditions found in the stomach. Prodrugs designed to cleave chemically in the stomach to the active 2,4-substituted pyrimidinediamine, can employ progroups including such esters. Alternatively, the progroups may be designed to metabolize in the presence of enzymes such as esterases, amidases, lipolases, phosphatases including ATPases and kinase etc. Progroups including linkages capable of metabolizing in vivo are well-known, and include, by way of example and not limitation, ethers, thioethers, silylethers, silylthioethers, esters, thioesters, carbonates, thiocarbonates, carbamates, thiocarbamates, ureas, thioureas, carboxamides, etc. In some instances, a "precursor" group that is oxidized by oxidative enzymes such as, for example, cytochrome P450 of the liver, to a metabolizable group, can be selected.

In the prodrugs, any available functional moiety may be masked with a progroup to yield a prodrug. Functional groups within the 2,4-substituted pyrimidinediamine compounds that may be masked with progroups for inclusion in a promoiety include, but are not limited to, amines (primary and secondary), hydroxyls, sulfanyls (thiols), carboxyls, etc. A wide variety of progroups, as well as the resultant promoieties, suitable for masking functional groups in active 2,4-pyrimidinediamine compounds to yield prodrugs are well-known in the art. For example, a hydroxyl functional group may be masked as a sulfonate, ester or carbonate promoiety, which may be hydrolyzed in vivo to provide the hydroxyl group. An amino functional group may be masked as an amide, carbamate, imine, urea, phosphenyl, phosphoryl or sulfenyl promoiety, which may be hydrolyzed in vivo to provide the amino group. A carboxyl group may be masked as an ester (including silyl esters and thioesters), amide or hydrazide promoiety, which may be hydrolyzed in vivo to provide the carboxyl group. Other specific examples of suitable progroups and their respective promoieties will be apparent to those of skill in the art. All of these progroups, alone or in combinations, may be included in the prodrugs.

In some embodiments of the 2,4-substituted pyrimidinediamine compounds and methods of using the compounds, the progroup(s) can be attached to any available primary or secondary amine, including, for example, the N2 nitrogen atom of the 2,4-pyrimidinediamine moiety, the N4 nitrogen atom of the 2,4-pyrimidinediamine moiety, and/or a primary or secondary nitrogen atom included in a substituent on the 2,4-pyrimidinediamine compound.

In particular embodiments of the 2,4-substituted pyrimidinediamine compounds and methods of using the compounds, the prodrugs described herein are 2,4-substituted pyrimidinediamine compounds that are substituted at the N4 nitrogen of the 2,4-pyrimidinediamine moiety with a substituted or unsubstituted nitrogen-containing bicyclic ring that includes at least one progroup at one or more of: the nitrogen atom(s) of the bicyclic ring, the N2 nitrogen of the 2,4-pyrimidinediamine moiety and/or the N4 nitrogen of the 2,4-pyrimidinediamine moiety.

As noted above, the identity of the progroup is not critical, provided that it can be metabolized under the desired conditions of use, for example under the acidic conditions found in the stomach and/or by enzymes found in vivo, to yield a the biologically active group, e.g., the 2,4-substituted pyrimidinediamines as described herein. Thus, skilled artisans will appreciate that the progroup can comprise virtually any known or later-discovered hydroxyl, amine or thiol protecting group. Non-limiting examples of suitable protecting groups can be found, for example, in *Protective Groups* in *Organic Synthesis*, Greene & Wuts, 2nd Ed., John Wiley & Sons, New York, 1991 (especially pages 10-142 (alcohols, 277-308 (thiols) and 309-405 (amines) the disclosure of which is incorporated herein by reference).

Additionally, the identity of the progroup(s) can also be selected so as to impart the prodrug with desirable characteristics. For example, lipophilic groups can be used to decrease water solubility and hydrophilic groups can be used to increase water solubility. In this way, prodrugs specifically tailored for selected modes of administration can be obtained. The progroup can also be designed to impart the prodrug with other properties, such as, for example, improved passive intestinal absorption, improved transport-mediated intestinal absorption, protection against fast metabolism (slow-release prodrugs), tissue-selective delivery, passive enrichment in target tissues, targeting-specific transporters, etc. Groups capable of imparting prodrugs with these characteristics are well-known, and are described, for example, in Ettmayer et al., 2004, J. Med. Chem. 47(10): 2393-2404, the disclosure of which is incorporated by reference. All of the various groups described in these references can be utilized in the prodrugs described herein.

As noted above, progroup(s) may also be selected to increase the water solubility of the prodrug as compared to the active drug. Thus the progroup(s) may include or may be a group(s) suitable for imparting drug molecules with improved water solubility. Such groups are well-known, and include, by way of example and not limitation, hydrophilic groups such as alkyl, aryl, arylalkyl, or cycloheteroalkyl groups substituted with one or more of an amine, alcohol, a carboxylic acid, a phosphorous acid, a sulfoxide, a sugar, an amino acid, a thiol, a polyol, an ether, a thioether and a quaternary amine salt.

The suitability of any particular progroup for a desired mode of administration can be confirmed in biochemical assays. For example, if a prodrug is to be administered by injection into a particular tissue or organ, and the identities of the various enzyme(s) expressed in the tissue or organ are known, the particular prodrug can be tested for metabolism in biochemical assays with the isolated enzyme(s). Alternatively, the particular prodrug can be tested for metabolism to the active 2,4-substituted pyrimidinediamine compound with tissue and/or organ extracts. Using tissue and/or organ extracts can be of particular convenience when the identity (ies) of the enzymes expressed in the target tissues or organs are unknown, or in instances when the isolated enzymes are not conveniently available. Skilled artisans will be able to readily select progroups having metabolic properties (such as kinetics) suitable for particular applications using such in vitro tests. Of course, specific prodrugs could also be tested for suitable metabolism in in vitro animal models.

Numerous references teach the use and synthesis of prodrugs, including, for example, Ettmayer et al., ibid and Bungaard et al., (1989) *J. Med. Chem.* 32(12): 2503-2507. Additionally, the preparation and use of prodrugs of 2,4-pyrimidinediamines is specifically taught in U.S. Provisional Patent Application 60/654,620, filed Feb. 18, 2005, entitled "Pyrimidinediamine Prodrugs and their Uses," the disclosure of which is hereby incorporated by reference in its entirety.

One of ordinary skill in the art will appreciate that many of the compounds and prodrugs thereof, as well as the various compound species specifically described and/or illustrated herein, may exhibit the phenomena of tautomerism, conformational isomerism, geometric isomerism and/or optical isomerism. For example, the compounds and prodrugs of the invention may include one or more chiral centers and/or double bonds and as a consequence may exist as stereoisomers, such as double-bond isomers (i.e., geometric isomers), enantiomers and diasteromers and mixtures thereof, such as racemic mixtures. As another example, the compounds and prodrugs of the invention may exist in several tautomeric forms, including the enol form, the keto form and mixtures thereof. As the various compound names, formulae and compound drawings within the specification and claims can represent only one of the possible tautomeric, conformational isomeric, optical isomeric or geometric isomeric forms, it should be understood that the invention encompasses any tautomeric, conformational isomeric, optical isomeric and/or geometric isomeric forms of the compounds or prodrugs having one or more of the utilities described herein, as well as mixtures of these various different isomeric forms. Atropisomers are stereoisomers resulting from hindered rotation about single bonds where the barrier to rotation is high enough to allow for the isolation of the conformers (Eliel, E. L.; Wilen, S. H. *Stereochemistry of Organic Compounds*; Wiley & Sons: New York, 1994; Chapter 14). Atropisomerism is significant because it introduces an element of chirality in the absence of stereogenic atoms. The invention is meant to encompass atropisomers, for example in cases of limited rotation around bonds between the 2,4-pyrimidinediamine core structure and groups attached thereto or for example around bonds between the A ring or the ring bearing $Z^{1-3}$ and respective groups attached thereto. It is intended that the compounds encompassed herein are, with the exception of forms of isomerism, chemically stable and able to be isolated.

Depending upon the nature of the various substituents, the 2,4-pyrimidinediamine compounds and prodrugs of the invention may be in the form of salts. Such salts include salts suitable for pharmaceutical uses ("pharmaceutically-acceptable salts"), salts suitable for veterinary uses, etc. Such salts may be derived from acids or bases, as is well-known in the art.

In one embodiment, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydroiodic acid, etc.), sulfuric acid, nitric acid, phosphoric acid, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion or an aluminum ion) or coordinates with an organic base (e.g., ethanolamine, diethanolamine, triethanolamine, N-methylglucamine, morpholine, piperidine, dimethylamine, diethylamine, triethylamine, ammonia, etc.).

The 2,4-pyrimidinediamine compounds and prodrugs thereof, as well as the salts thereof, may also be in the form of hydrates, solvates and N-oxides, as are well-known in the art.

In another embodiment, this invention provides a compound, or stereoisomer, tautomer, prodrug, solvate, or pharmaceutically acceptable salt thereof, selected from Tables I-XI.

TABLE I

| # | R¹— | -alk-Y— | (R²)$_p$ | R | X | Z | (R³)$_q$ | SO$_2$NR⁴R⁵ |
|---|---|---|---|---|---|---|---|---|
| I-1 | 3-NC— | —CH$_2$—O— | 4,5-di-OMe | H | F | C | — | 4-SO$_2$NH$_2$ |
| I-2 | 3-NC— | —CH$_2$—O— | 4,5-di-OMe | H | F | C | 4-Me | 3-SO$_2$NH$_2$ |
| I-3 | 3-NC— | —CH$_2$—O— | — | H | F | C | — | 4-SO$_2$NH$_2$ |
| I-4 | 3-NC— | —CH$_2$—O— | — | H | F | C | — | 3-SO$_2$NH$_2$ |
| I-5 | 3-NC— | —CH$_2$—O— | — | H | F | C | — | 3-SO$_2$(4-Me-piperazin-1-yl) |
| I-6 | 3-NC— | —CH$_2$—O— | — | H | F | C | — | 4-SO$_2$(4-Me-piperazin-1-yl) |
| I-7 | 3-NC— | —CH$_2$—O— | — | H | F | C | 3-MeO | 4-SO$_2$NH$_2$ |
| I-8 | 4-NC— | —CH$_2$—O— | — | H | F | C | 4-iPr | 3-SO$_2$NH$_2$ |
| I-9 | 4-NC— | —CH$_2$—O— | — | H | F | C | 4-(4-Me-piperazin-1-yl) | 3-SO$_2$NH$_2$ |
| I-10 | 4-NC— | —CH$_2$—O— | 3-F | H | F | C | — | 3-SO$_2$NH$_2$ |
| I-11 | 4-NC— | —CH$_2$—O— | 3-F | H | F | C | 4-(4-Me-piperazin-1-yl) | 3-SO$_2$NH$_2$ |
| I-12 | 4-NC— | —CH$_2$—O— | 3-F | H | F | C | 4-Me | 3-SO$_2$NH$_2$ |
| I-13 | 4-NC— | —CH$_2$—O— | — | H | Br | C | — | 3-SO$_2$NH$_2$ |
| I-14 | 4-NC— | —CH$_2$—O— | — | H | Br | C | 4-Me | 3-SO$_2$NH$_2$ |
| I-15 | 4-NC— | —CH$_2$—O— | — | H | Me$_3$SiC≡C— | C | 4-Me | 3-SO$_2$NH$_2$ |
| I-16 | 4-NC— | —CH$_2$—O— | — | H | F | C | — | 3-SO$_2$NH$_2$ |
| I-17 | 4-NC— | —CH$_2$—O— | — | H | F | C | — | 4-SO$_2$NH$_2$ |
| I-18 | 4-NC— | —CH$_2$—O— | — | H | F | C | — | 3-SO$_2$NH$_2$ |
| I-19 | 4-NC— | —CH$_2$—O— | — | H | F | C | 4-(4-Me-piperazin-1-yl) | 4-SO$_2$(4-Me-piperazin-1-yl)
3-SO$_2$(4-Me-piperazin-1-yl) |
| I-20 | 4-NC— | —CH$_2$—O— | — | H | F | C | 4-Me | 3-SO$_2$NH$_2$ |
| I-21 | 4-NC— | —CH$_2$—O— | 3-Me | H | F | C | 4-Cl | 3-SO$_2$NH$_2$ |
| I-22 | 4-NC— | —CH$_2$—O— | 3-Me | H | F | C | — | 4-SO$_2$NH$_2$ |
| I-23 | 4-NC— | —CH$_2$—O— | 3-Me | H | F | C | — | 3-SO$_2$NH$_2$ |
| I-24 | 4-NC— | —CH$_2$—O— | 3-Me | H | F | C | 4-Me | 3-SO$_2$NH$_2$ |
| I-25 | 4-NC— | —CH$_2$—O— | 3,5-di-Me | H | F | C | — | 4-SO$_2$NH$_2$ |
| I-26 | 4-NC— | —CH$_2$—O— | 3,5-di-Me | H | F | C | — | 4-SO$_2$NH$_2$ |
| I-27 | 4-NC— | —CH$_2$—O— | 3,5-di-Me | H | F | C | 4-Me | 3-SO$_2$NH$_2$ |
| I-28 | 4-NC— | —CH$_2$—O— | — | H | F | C | 3-Ome | 3-SO$_2$NH$_2$ |
| I-29 | 4-NC— | —CH$_2$—O— | — | H | F | C | 3-MeO | 4-SO$_2$NH$_2$ |
| I-30 | 4-NC— | —CH$_2$—O— | — | H | F | C | 4-Me | 3-SO$_2$NHC(O)Et |
| I-31 | 4-NC— | —CH$_2$—O— | — | H | F | C | 4-Me | 3-SO$_2$NHC(O)Et |
| I-32 | 4-NC— | —CH$_2$—O— | 3,5-di-Me | H | F | C | 3-MeO | 4-SO$_2$NH$_2$ |

TABLE I-continued

| # | R¹— | —alk-Y— | (R²)ₚ | R | X | Z | (R³)q | SO₂NR⁴R⁵ |
|---|---|---|---|---|---|---|---|---|
| I-33 | 4-NC— | —CH₂—O— | — | H | F | C | 4-F | 3-SO₂NH₂ |
| I-34 | 4-NC— | —CH₂—O— | 3,5-di-Me | H | F | C | 4-F | 3-SO₂NH₂ |
| I-35 | 4-NC— | —CH₂—O— | — | H | F | C | 4-F | 3-SO₂NH₂ |
| I-36 | 4-NC— | —CH₂—O— | — | H | F | C | 4-Me | 3-SO₂NHC(O)Me |
| I-37 | 4-NC— | —CH₂—O— | — | H | F | C | 4-Me | 3-SO₂NHC(O)i-Pr |
| I-38 | 4-NC— | —CH₂—O— | — | H | F | C | 4-Me | 3-(N(Na)C(O)Me) |
| I-39 | 4-NC— | —CH₂—O— | — | H | F | C | 4-Me | 3-(N(Na)C(O)i-Pr) |
| I-40 | 4-NC— | —CH₂—O— | 3,5-di-Me | H | F | C | — | 4-SO₂(4-Me-piperazin-1-yl) |
| I-41 | 4-NC— | —CH₂—O— | 3-Cl | H | F | C | — | 4-SO₂NH₂ |
| I-42 | 4-NC— | —CH₂—O— | 3-Cl | H | F | C | — | 4-SO₂NH₂ |
| I-43 | 4-NC— | —CH₂—O— | 3-Cl | H | F | C | 4-Me | 3-SO₂NH₂ |
| I-44 | 4-NC— | —CH₂—O— | 3-F | H | F | C | — | 4-SO₂NH₂ |
| I-45 | 4-NC— | —CH₂—O— | 3-Ome | H | F | C | — | 4-SO₂NH₂ |
| I-46 | 4-NC— | —CH₂—O— | 3-Ome | H | F | C | — | 3-SO₂NH₂ |
| I-47 | 4-NC— | —CH₂—O— | 3-Ome | H | F | C | 4-Me | 3-SO₂NH₂ |
| I-48 | 4-NC— | —CH₂—O— | 3-F | H | F | C | 4-Me | 3-SO₂NHC(O)Et |
| I-49 | 4-NC— | —CH₂—O— | 3-F | H | F | C | 4-Me | 3-SO₂N(Na)C(O)Et |
| I-50 | 4-NC— | —CH₂—O— | 3-CH₂OH | H | F | C | — | 3-SO₂NH₂ |
| I-51 | 4-NC— | —CH₂—O— | 3-CH₂OH | H | F | C | 4-Me | 3-SO₂NH₂ |
| I-52 | 4-NC— | —CH₂—O— | 3-(1-cyanomethyl-(1H)-pyrazol-3-yl)- | H | F | C | 4-Me | 4-SO₂NH₂ |
| I-53 | 4-NC— | —CH₂—O— | 3-(1-cyanomethyl-(1H)-pyrazol-3-yl)- | H | F | C | — | 3-SO₂NH₂ |
| I-54 | 4-NC— | —CH₂—O— | 3-(1-cyanomethyl-(1H)-pyrazol-3-yl)- | H | F | C | 4-Me | 3-SO₂NH₂ |
| I-55 | 4-NC— | —CH₂—O— | — | H | F | N | — | 2-SO₂NH₂ |
| I-56 | 4-NC— | —CH₂—O— | — | H | F | C | 4-Ome | 3-SO₂NH₂ |
| I-57 | 4-NC— | —CH₂—O— | — | H | Me | C | — | 4-SO₂NH₂ |
| I-58 | 4-NC— | —CH₂—O— | — | H | Me | C | — | 3-SO₂NH₂ |
| I-59 | 4-NC— | —CH₂—O— | — | H | Me | C | 4-Me | 3-SO₂NH₂ |
| I-60 | 4-NC— | —CH(Me)O— | 3-Me | H | F | C | — | 4-SO₂NH₂ |
| I-61 | 4-NC— | —CH(Me)O— | 3-Me | H | F | C | — | 3-SO₂NH₂ |
| I-62 | 4-NC— | —CH(Me)O— | 3-Me | H | F | C | 4-Me | 3-SO₂NH₂ |
| I-63 | 4-NC— | —CH(Me)O— | 3,5-di-Me | H | F | C | — | 4-SO₂NH₂ |
| I-64 | 4-NC— | —CH(Me)O— | 3-Me | H | F | C | — | 4-SO₂NH₂ |
| I-65 | 4-NC— | —CH(Me)O— | — | H | F | C | 3-MeO | 4-SO₂NH₂ |
| I-66 | 4-NC— | —CH(Me)O— | — | H | F | C | — | 4-SO₂NH₂ |
| I-67 | 4-NC— | —CH(Me)O— | — | H | F | C | 4-Me | 3-SO₂NH₂ |

TABLE I-continued

| # | R¹ | -alk-Y- | (R²)$_p$ | R | X | Z | (R³)$_q$ | SO$_2$NR⁴R⁵ |
|---|---|---|---|---|---|---|---|---|
| I-68 | 4-NC— | —CH(Me)O— | — | H | F | C | 4-F | 3-SO$_2$NH$_2$ |
| I-69 | 4-NC— | —CH(Me)O— | 3-Me | H | F | C | 4-F | 3-SO$_2$NH$_2$ |
| I-70 | 4-NC— | —CH(Me)O— | — | H | F | C | — | 4-SO$_2$NH$_2$ |
| I-71 | 4-NC— | —CH(Me)O— | 3,5-di-Me | H | F | C | 3-Ome | 3-SO$_2$NH$_2$ |
| I-72 | 4-NC— | —CH(Me)O— | 3,5-di-Me | H | F | C | — | 3-SO$_2$NH$_2$ |
| I-73 | 4-NC— | —C(Me)$_2$O— | — | H | F | C | 4-Me | 3-SO$_2$NH$_2$ |
| I-74 | 4-NC— | —C(Me)$_2$O— | — | H | F | C | 4-Me | 3-SO$_2$NH$_2$ |
| I-75 | 4-NC— | —C(Me)$_2$O— | — | H | F | C | 4-F | 4-SO$_2$NH$_2$ |
| I-76 | 4-NC— | —C(Me)$_2$O— | — | H | F | C | — | 3-SO$_2$NH$_2$ |
| I-77 | 4-NC— | —C(Me)$_2$O— | — | H | F | C | 3-MeO | 4-SO$_2$NH$_2$ |
| I-78 | 4-NC— | —CH$_2$C(O)NH— | — | H | F | C | — | 3-SO$_2$NH$_2$ |
| I-79 | 4-NC— | —CH$_2$C(O)NH— | — | H | F | C | 4-Me | 3-SO$_2$NH$_2$ |
| I-80 | 4-NC— | —CH$_2$C(O)NH— | 3-Me | H | F | C | — | 3-SO$_2$NH$_2$ |
| I-81 | 4-NC— | —CH$_2$C(O)NH— | 3-Me | H | F | C | 4-Me | 3-SO$_2$NH$_2$ |
| I-82 | 4-NC— | —CH$_2$C(O)NH— | 3-Cl | H | F | C | — | 3-SO$_2$NH$_2$ |
| I-83 | 4-NC— | —CH$_2$C(O)NH— | 3-Cl | H | F | C | 4-Me | 3-SO$_2$NH$_2$ |
| I-84 | 4-NC— | —CH$_2$C(O)NH— | 3-MeO | H | F | C | — | 3-SO$_2$NH$_2$ |
| I-85 | 4-NC— | —CH$_2$C(O)NH— | 3-MeO | H | F | C | 4-Me | 3-SO$_2$NH$_2$ |
| I-86 | 4-NC— | —CH$_2$C(O)N(CH$_3$)— | — | H | F | C | — | 3-SO$_2$NH$_2$ |
| I-87 | 4-NC— | —CH$_2$C(O)N(CH$_3$)— | — | H | F | C | 4-Me | 3-SO$_2$(4-Me-piperazin-1-yl) |
| I-88 | 3-NH$_2$C(O)— | —CH$_2$—O— | — | H | F | C | — | 4-SO$_2$NH$_2$ |
| I-89 | 3-NH$_2$C(O)— | —CH$_2$—O— | — | H | F | C | — | 3-SO$_2$NH$_2$ |
| I-90 | 3-NH$_2$C(O)— | —CH$_2$—O— | — | H | F | C | 4-Me | 3-SO$_2$NH$_2$ |
| I-91 | 3-NH$_2$C(O)— | —CH$_2$—O— | 3-Me | H | F | C | — | 4-SO$_2$NH$_2$ |
| I-92 | 4-NH$_2$C(O)— | —CH$_2$—O— | 3-Me | H | F | C | — | 3-SO$_2$NH$_2$ |
| I-93 | 4-NH$_2$C(O)— | —CH$_2$—O— | 3,5-di-Me | H | F | C | 4-Me | 3-SO$_2$NH$_2$ |
| I-94 | 4-NH$_2$C(O)— | —CH$_2$—O— | 3-Me | H | F | C | 4-Me | 3-SO$_2$NH$_2$ |
| I-95 | 4-NH$_2$C(O)— | —CH$_2$—O— | 3,5-di-Me | H | F | C | 4-Me | 4-SO$_2$NH$_2$ |
| I-96 | 4-NH$_2$C(O)— | —CH$_2$—O— | 3-Cl | H | F | C | — | 3-SO$_2$NH$_2$ |
| I-97 | 4-NH$_2$C(O)— | —CH$_2$—O— | 3-Cl | H | F | C | — | 4-SO$_2$NH$_2$ |
| I-98 | 4-NH$_2$C(O)— | —CH$_2$—O— | 3-Cl | H | F | C | 4-Me | 3-SO$_2$NH$_2$ |
| I-99 | 4-NH$_2$C(O)— | —CH$_2$—O— | 3-F | H | F | C | — | 3-SO$_2$NH$_2$ |
| I-100 | 4-NH$_2$C(O)— | —CH$_2$—O— | 3-F | H | F | C | — | 4-SO$_2$NH$_2$ |
| I-101 | 4-NH$_2$C(O)— | —CH$_2$—O— | 3-F | H | F | C | 4-Me | 4-SO$_2$NH$_2$ |
| I-102 | 4-NH$_2$C(O)— | —CH$_2$—O— | 3-Ome | H | F | C | — | 3-SO$_2$NH$_2$ |
| I-103 | 4-NH$_2$C(O)— | —CH$_2$—O— | 3-Ome | H | F | C | 4-Me | 4-SO$_2$NH$_2$ |
| I-104 | 4-NH$_2$C(O)— | —CH$_2$—O— | 3-Ome | H | F | C | — | 3-SO$_2$NH$_2$ |
| I-105 | 4-NH$_2$C(O)— | —CH$_2$—O— | 3-CH$_2$OH | H | F | C | 4-Me | 3-SO$_2$NH$_2$ |
| I-106 | 4-NH$_2$C(O)— | —CH$_2$—O— | 3-CH$_2$OH | H | F | C | 4-Me | 3-SO$_2$NH$_2$ |
| I-107 | 4-NH$_2$C(O)— | —CH$_2$—O— | — | H | F | C | — | 3-SO$_2$NH$_2$ |
| I-108 | 4-NH$_2$C(O)— | —CH$_2$—O— | — | H | Me | C | — | 4-SO$_2$NH$_2$ |

TABLE I-continued

| # | R¹ | -alk-Y- | (R²)ₚ | R | X | Z | (R³)q | SO₂NR⁴R⁵ |
|---|---|---|---|---|---|---|---|---|
| I-109 | 4-NH₂C(O)— | —CH₂—O— | — | H | Me | C | — | 3-SO₂NH₂ |
| I-110 | 4-NH₂C(O)— | —CH₂—O— | — | H | Me | C | 4-Me | 3-SO₂NH₂ |
| I-111 | 4-NH₂C(O)— | —CH₂—O— | — | H | F | C | — | 3-SO₂NH₂ |
| I-112 | 4-NH₂C(O)— | —CH₂—O— | — | H | F | C | — | 3-SO₂(4-Me-piperazin-1-yl) |
| I-113 | 4-NH₂C(O)— | —CH₂—O— | 3-Me | H | F | C | — | 4-SO₂NH₂ |
| I-114 | 4-NH₂C(O)— | —CH₂—O— | 3,5-di-Me | H | F | C | — | 4-SO₂NH₂ |
| I-115 | 4-NH₂C(O)— | —CH₂—O— | — | H | F | C | — | 4-SO₂NH₂ |
| I-116 | 4-NH₂C(O)— | —CH(Me)O— | — | H | F | C | — | 4-SO₂NH₂ |
| I-117 | 4-NH₂C(O)— | —CH(Me)O— | — | H | F | C | — | 4-SO₂NH₂ |
| I-118 | 4-NH₂C(O)— | —CH(Me)O— | — | H | F | C | 4-Me | 3-SO₂NH₂ |
| I-119 | 4-NH₂C(O)— | —CH(Me)O— | 3-Me | H | F | C | — | 4-SO₂NH₂ |
| I-120 | 4-NH₂C(O)— | —CH(Me)O— | 3-Me | H | F | C | — | 3-SO₂NH₂ |
| I-121 | 4-NH₂C(O)— | —CH(Me)O— | 3-Me | H | F | C | 4-Me | 4-SO₂NH₂ |
| I-122 | 4-NH₂C(O)— | —CH(Me)O— | 3,5-di-Me | H | F | C | — | 3-SO₂NH₂ |
| I-123 | 4-NH₂C(O)— | —CH(Me)O— | 3,5-di-Me | H | F | C | 4-Me | 4-SO₂NH₂ |
| I-124 | 4-NH₂C(O)— | —CH(Me)O— | 3,5-di-Me | H | F | C | — | 3-SO₂NH₂ |
| I-125 | 4-NH₂C(O)— | —C(Me)₂O— | — | H | F | C | 4-Me | 4-SO₂NH₂ |
| I-126 | 4-NH₂C(O)— | —C(Me)₂O— | — | H | F | C | — | 3-SO₂NH₂ |
| I-127 | 4-NH₂C(O)— | —C(Me)₂O— | — | H | F | C | 4-Me | 4-SO₂NH₂ |
| I-128 | 4-Me₂NC(O)— | —CH₂—O— | — | H | F | C | — | 3-SO₂NH₂ |
| I-129 | 4-Me₂NC(O)— | —CH₂—O— | — | H | F | C | 4-Me | 4-SO₂NH₂ |
| I-130 | 4-Me₂NC(O)— | —CH₂—O— | — | H | F | C | — | 3-SO₂NH₂ |
| I-131 | 4-Me₂NC(O)— | —CH₂—O— | — | H | F | C | 4-Me | 4-SO₂NH₂ |
| I-132 | 4-Me₂NC(O)— | —CH₂—O— | 3-Cl | H | F | C | — | 3-SO₂NH₂ |
| I-133 | 4-Me₂NC(O)— | —CH₂—O— | 3-Cl | H | Me | C | 4-Me | 4-SO₂NH₂ |
| I-134 | 4-Me₂NC(O)— | —CH₂—O— | 3-Cl | H | Me | C | — | 3-SO₂NH₂ |
| I-135 | 4-Me₂NC(O)— | —CH₂—O— | 3-Cl | H | Me | C | 4-Me | 4-SO₂NH₂ |
| I-136 | 4-Me₂NC(O)— | —CH₂—O— | 3-Cl | H | Me | C | — | 3-SO₂NH₂ |
| I-137 | 4-Me₂NC(O)— | —CH₂—O— | 3-F | H | Me | C | — | 3-SO₂NH₂ |
| I-138 | 4-Me₂NC(O)— | —CH₂—O— | 3-F | H | F | C | 4-Me | 3-SO₂NH₂ |
| I-139 | 4-Me₂NC(O)— | —CH₂—O— | 3-Cl | H | F | C | 4-Cl | 3-SO₂NH₂ |
| I-140 | 4-Me₂NC(O)— | —CH₂—O— | — | H | F | C | 4-Cl | 4-SO₂NH₂ |
| I-141 | 4-Me₂NC(O)— | —CH₂—O— | 3-F | H | Me | C | — | 3-SO₂NH₂ |
| I-142 | 4-Me₂NC(O)— | —CH₂—O— | — | H | F | C | 4-Me | 4-SO₂NH₂ |
| I-143 | 4-MeNHC(O)— | —CH₂—O— | — | H | F | C | — | 3-SO₂NH₂ |
| I-144 | 4-MeNHC(O)— | —CH₂—O— | — | H | F | C | — | 4-SO₂NH₂ |
| I-145 | 4-MeNHC(O)— | —CH₂—O— | 3-Cl | H | F | C | — | 3-SO₂NH₂ |
| I-146 | 4-MeNHC(O)— | —CH₂—O— | 3-Cl | H | F | C | — | 4-SO₂NH₂ |
| I-147 | 4-MeNHC(O)— | —CH₂—O— | — | H | F | C | — | 3-SO₂NH₂ |
| I-148 | 4-MeNHC(O)— | —CH₂—O— | 3-Cl | H | F | C | 4-Me | 3-SO₂NH₂ |
| I-149 | 4-MeNHC(O)— | —CH₂—O— | — | H | Me | C | — | 4-SO₂NH₂ |

TABLE I-continued

| # | R¹ | -alk-Y- | (R²)$_p$ | R | X | Z | (R³)$_q$ | SO$_2$NR⁴R⁵ |
|---|---|---|---|---|---|---|---|---|
| I-150 | 4-MeNHC(O)— | —CH$_2$—O— | 3-Cl | H | Me | C | — | 3-SO$_2$NH$_2$ |
| I-151 | 4-MeNHC(O)— | —CH$_2$—O— | 3-Cl | H | Me | C | 4-Me | 3-SO$_2$NH$_2$ |
| I-152 | 4-MeNHC(O)— | —CH$_2$—O— | 3-Cl | H | F | C | 4-Cl | 3-SO$_2$NH$_2$ |
| I-153 | 4-MeNHC(O)— | —CH$_2$—O— | 3-Cl | H | Me | C | 4-Cl | 3-SO$_2$NH$_2$ |
| I-154 | 4-MeNHC(O)— | —CH$_2$—O— | 3-F | H | Me | C | — | 4-SO$_2$NH$_2$ |
| I-155 | 4-MeNHC(O)— | —CH$_2$—O— | 3-F | H | Me | C | — | 3-SO$_2$NH$_2$ |
| I-156 | 4-MeNHC(O)— | —CH$_2$—O— | 3-F | H | Me | C | 4-Me | 3-SO$_2$NH$_2$ |
| I-157 | 4-CH$_2$=CHCH$_2$NHC(O)— | —CH$_2$—O— | — | H | F | C | — | 4-SO$_2$NH$_2$ |
| I-158 | 4-CH$_2$=CHCH$_2$NHC(O)— | —CH$_2$—O— | — | H | F | C | — | 3-SO$_2$NH$_2$ |
| I-159 | 4-CH$_2$=CHCH$_2$NHC(O)— | —CH$_2$—O— | — | H | F | C | 4-Me | 3-SO$_2$NH$_2$ |
| I-160 | 4-pyridin-2-yl- | —CH$_2$—O— | — | H | F | C | 4-Me | 3-SO$_2$NH$_2$ |
| I-161 | 4-pyridin-2-yl- | —CH$_2$—O— | — | H | F | C | — | 3-SO$_2$NHMe |
| I-162 | 4-pyridin-2-yl- | —CH$_2$—O— | — | H | F | C | — | 3-SO$_2$NH$_2$ |
| I-163 | 4-pyridin-2-yl- | —CH$_2$—O— | — | H | F | C | — | 4-SO$_2$NH$_2$ |
| I-164 | 4-pyridin-2-yl- | —CH$_2$—O— | — | H | F | N | — | 2-SO$_2$NH$_2$ |
| I-165 | 4-pyridin-2-yl- | —CH$_2$—O— | — | H | F | C | — | 4-SO$_2$NHCH$_2$CH$_2$NEt$_2$ |
| I-166 | 4-pyridin-2-yl- | —CH$_2$—O— | — | H | F | C | — | 3-SO$_2$NHCH$_2$CH$_2$NEt$_2$ |
| I-167 | 4-pyridin-2-yl- | —CH$_2$—O— | 3-Me | H | F | C | — | 3-SO$_2$NH$_2$ |
| I-168 | 4-pyridin-2-yl- | —CH$_2$—O— | 3-Me | H | F | C | 4-Me | 3-SO$_2$NH$_2$ |
| I-169 | 4-pyridin-2-yl- | —CH$_2$—O— | 3-F | H | F | C | — | 3-SO$_2$NHMe |
| I-170 | 4-pyridin-2-yl- | —CH$_2$—O— | 3-Me | H | F | C | 4-Me | 3-SO$_2$NH$_2$ |
| I-171 | 4-pyridin-2-yl- | —CH$_2$—O— | 3-Cl | H | F | C | 4-Me | 3-SO$_2$NH$_2$ |
| I-172 | 4-pyridin-2-yl- | —CH$_2$—O— | 3-F | H | F | C | 4-Me | 3-SO$_2$NHMe |
| I-173 | 4-pyridin-2-yl- | —CH$_2$—O— | 3-Cl | H | F | C | 4-Me | 4-SO$_2$NH$_2$ |
| I-174 | 4-pyridin-2-yl- | —CH$_2$—O— | 3-Cl | H | F | C | 4-Me | 4-SO$_2$NH$_2$ |
| I-175 | 4-pyridin-2-yl- | —CH$_2$—O— | 3-Cl | H | F | C | — | 4-SO$_2$NH$_2$ |
| I-176 | 4-pyridin-2-yl- | —CH$_2$—O— | 3-Me | H | F | C | — | 3-SO$_2$NH$_2$ |
| I-177 | 4-pyridin-2-yl- | —CH$_2$—O— | 3-F | H | F | C | — | 3-SO$_2$NH$_2$ |
| I-178 | 4-pyridin-2-yl- | —CH$_2$—O— | — | H | Me | C | 4-Me | 3-SO$_2$NHMe |
| I-179 | 4-pyridin-2-yl- | —CH$_2$—O— | — | H | Me | C | — | 4-SO$_2$NH$_2$ |
| I-180 | 4-pyridin-2-yl- | —CH$_2$—O— | — | H | Me | C | 4-Me | 3-SO$_2$NH$_2$ |
| I-181 | 4-pyridin-2-yl- | —CH$_2$—O— | — | H | F | C | — | 3-SO$_2$NH$_2$ |
| I-182 | 3-pyridin-3-yl- | —CH$_2$—O— | — | H | F | C | — | 3-SO$_2$NH$_2$ |
| I-183 | 3-pyridin-3-yl- | —CH$_2$—O— | — | H | F | C | 4-Me | 3-SO$_2$NHMe |
| I-184 | 3-pyridin-3-yl- | —CH$_2$—O— | — | H | F | C | 4-Me | 3-SO$_2$NH$_2$ |
| I-185 | 3-pyridin-3-yl- | —CH$_2$—O— | — | H | F | C | — | 4-SO$_2$NH$_2$ |
| I-186 | 3-pyridin-3-yl- | —CH$_2$—O— | — | H | F | C | — | 4-SO$_2$NHCH$_2$CH$_2$NEt$_2$ |
| I-187 | 3-pyridin-3-yl- | —CH$_2$—O— | — | H | F | C | — | 3-SO$_2$NHCH$_2$CH$_2$NEt$_2$ |

TABLE I-continued

| # | R¹ | -alk-Y— | (R²)ₚ | R | X | Z | (R³)q | SO₂NR⁴R⁵ |
|---|---|---|---|---|---|---|---|---|
| I-188 | 4-pyridin-3-yl- | —CH₂—O— | — | H | F | C | — | 3-SO₂NH₂ |
| I-189 | 4-pyridin-3-yl- | —CH₂—O— | — | H | F | C | 4-Me | 3-SO₂NH₂ |
| I-190 | 4-pyridin-3-yl- | —CH₂—O— | — | H | F | C | 4-Me | 3-SO₂NHMe |
| I-191 | 4-pyridin-3-yl- | —CH₂—O— | — | H | F | C | — | 4-SO₂NHCH₂CH₂NEt₂ |
| I-192 | 4-pyridin-3-yl- | —CH₂—O— | — | H | F | C | — | 3-SO₂NH₂ |
| I-193 | 4-pyridin-4-yl- | —CH₂—O— | — | H | F | C | — | 3-SO₂NH₂ |
| I-194 | 4-pyridin-4-yl- | —CH₂—O— | 4-Me | H | F | C | — | 3-SO₂NH₂ |
| I-195 | 4-pyridin-4-yl- | —CH₂—O— | — | H | F | C | 4-Me | 3-SO₂NH₂ |
| I-196 | 4-pyridin-4-yl- | —CH₂—O— | — | H | F | C | — | 3-SO₂NHMe |
| I-197 | 4-(3-methyl-(1H)pyrazol-5-yl)- | —CH₂—O— | — | H | F | C | 4-Me | 3-SO₂NH₂ |
| I-198 | 4-(1,3-dimethyl-(1H)pyrazol-5-yl)- | —CH₂—O— | — | H | F | C | 4-Me | 3-SO₂NH₂ |
| I-199 | 4-(1-benzyl-3-methyl-(1H)-pyrazol-5-yl)- | —CH₂—O— | — | H | F | C | 4-Me | 3-SO₂NH₂ |
| I-200 | 4-(2,4-dihydro-3-oxo-1,2,4-triazol-5-yl)- | —CH₂—O— | — | H | F | C | 4-F | 3-SO₂NH₂ |
| I-201 | 4-(2,4-dihydro-3-oxo-1,2,4-triazol-5-yl)- | —CH₂—O— | — | H | F | C | — | 4-SO₂NH₂ |
| I-202 | 4-(2,4-dihydro-3-oxo-1,2,4-triazol-5-yl)- | —CH₂—O— | — | H | F | C | 4-Me | 3-SO₂NH₂ |
| I-203 | 3-morpholin-1-yl- | —CH₂CH₂—O— | 4-Me | H | F | C | — | 3-SO₂NH₂ |
| I-204 | 3-morpholin-1-yl- | —CH₂CH₂—O— | 4-Me | H | F | C | 4-Me | 4-SO₂NH₂ |
| I-205 | 4-morpholin-1-yl- | —CH₂CH₂—O— | 4-Me | H | F | C | — | 4-SO₂NH₂ |
| I-206 | 4-morpholin-1-yl- | —CH₂CH₂—O— | 4-Me | H | F | C | — | 3-SO₂NH₂ |
| I-207 | 4-morpholin-1-yl- | —CH₂—O— | — | H | F | C | — | 3-SO₂-(morpholin-1-yl) |
| I-208 | 3-morpholin-1-yl-C(O)— | —CH₂—O— | — | H | F | C | — | 3-SO₂NH₂ |
| I-209 | 3-morpholin-1-yl-C(O)— | —CH₂—O— | — | H | F | C | — | 4-SO₂NH₂ |
| I-210 | 4-morpholin-1-yl-C(O)— | —CH₂—O— | — | H | F | C | — | 4-SO₂NH₂ |
| I-211 | 4-morpholin-1-yl-C(O)— | —CH₂—O— | — | H | F | C | 4-Me | 3-SO₂NH₂ |
| I-212 | 4-morpholin-1-yl-C(O)— | —CH₂—O— | — | H | F | C | 4-Me | 3-SO₂NH₂ |
| I-213 | 4-CH₃OC(O)— | —CH₂—O— | — | H | F | C | — | 3-SO₂NHC(O)Et |
| I-214 | 3-(5-methylisoxazol-3-yl)- | —CH₂—O— | — | H | F | C | — | 3-SO₂NHCH₂C(O)OMe |
| I-215 | 4-(5-methylisoxazol-3-yl)- | —CH₂—O— | — | H | F | C | — | 3-SO₂NH₂ |
| I-216 | 4-(5-methylisoxazol-3-yl)- | —CH₂—O— | — | H | F | C | 5-Cl-4-Me | 3-SO₂NH₂ |
| I-217 | 4-(5-methylisoxazol-3-yl)- | —CH₂—O— | — | H | F | C | 4-F-5-Me | 3-SO₂NH₂ |
| I-218 | 4-(5-methylisoxazol-3-yl)- | —CH₂—O— | — | H | F | C | 4-Cl-5-Me | 3-SO₂NH₂ |
| I-219 | 4-(5-methylisoxazol-3-yl)- | —CH₂—O— | — | H | F | C | 4-Me | 3-SO₂NH₂ |
| I-220 | 4-(5-methylisoxazol-3-yl)- | —CH₂—O— | — | H | F | C | 4-Cl | 3-SO₂NH₂ |

TABLE I-continued

| # | R¹ | -alk-Y- | $(R^2)_p$ | R | X | Z | $(R^3)_q$ | $SO_2NR^4R^5$ |
|---|---|---|---|---|---|---|---|---|
| I-221 | 4-(5-methylisoxazol-3-yl)- | —CH$_2$—O— | 3-Cl | H | F | C | 4-Me | 3-SO$_2$NH$_2$ |
| I-222 | 4-(5-methylisoxazol-3-yl)- | —CH$_2$—O— | 3-F | H | F | C | 4-Me | 3-SO$_2$NH$_2$ |
| I-223 | 4-(5-methylisoxazol-3-yl)- | —CH$_2$—O— | 3-F | H | F | C | 5-Cl-4-Me | 3-SO$_2$NH$_2$ |
| I-224 | 4-(5-methylisoxazol-3-yl)- | —CH$_2$—O— | 3-F | H | F | C | 4-F-5-Me | 3-SO$_2$NH$_2$ |
| I-225 | 4-(5-methylisoxazol-3-yl)- | —CH$_2$—O— | — | Me | F | C | 4-Me | 3-SO$_2$NH$_2$ |
| I-226 | 4-(5-methylisoxazol-3-yl)- | —CH$_2$—O— | 3-F | Me | F | C | 4-Me | 3-SO$_2$NH$_2$ |
| I-227 | 4-(5-methylisoxazol-3-yl)- | —CH$_2$—O— | — | CH$_2$CO$_2$Me | F | C | 4-Me | 3-SO$_2$NH$_2$ |
| I-228 | 4-(5-methylisoxazol-3-yl)- | —CH$_2$—O— | — | H | F | C | 4-Me | 3-SO$_2$NHC(O)Et |
| I-229 | 4-(5-methylisoxazol-3-yl)- | —CH$_2$—O— | — | H | F | C | — | 3-SO$_2$NHC(O)i-Pr |
| I-230 | 4-(5-methylisoxazol-3-yl)- | —CH$_2$—O— | — | H | F | C | — | 3-SO$_2$NH$_2$ |
| I-231 | 4-(5-methylisoxazol-3-yl)- | —CH$_2$—O— | — | H | F | C | — | 3-SO$_2$NHC(O)Me |
| I-232 | 4-(5-methylisoxazol-3-yl)- | —CH$_2$—O— | — | H | F | C | 4-F | 3-SO$_2$NH$_2$ |
| I-233 | 4-(5-methylisoxazol-3-yl)- | —CH$_2$—O— | 3-Me | H | F | C | 4-Me | 3-SO$_2$NH$_2$ |
| I-234 | 4-(5-methylisoxazol-3-yl)- | —CH$_2$—O— | — | H | F | C | 4-Me | 3-SO$_2$NHMe |
| I-235 | 4-(5-methylisoxazol-3-yl)- | —CH$_2$—O— | — | H | F | C | — | 3-SO$_2$NHC(O)Et |
| I-236 | 4-(5-methylisoxazol-3-yl)- | —CH$_2$—O— | — | H | F | C | 4-F | 3-SO$_2$NH$_2$ |
| I-237 | 4-(5-methylisoxazol-3-yl)- | —CH$_2$—O— | 3-Me | H | F | C | 4-Me | 3-SO$_2$NH$_2$ |
| I-238 | 4-(5-methylisoxazol-3-yl)- | —CH$_2$—O— | 3-Me | H | F | C | — | 3-SO$_2$NHMe |
| I-239 | 4-(5-methylisoxazol-3-yl)- | —CH$_2$—O— | 3-Me | H | F | C | 4-Me | 3-SO$_2$NH$_2$ |
| I-240 | 4-(5-methylisoxazol-3-yl)- | —CH$_2$—O— | 3-Me | H | F | C | — | 4-SO$_2$NH$_2$ |
| I-241 | 4-(5-methylisoxazol-3-yl)- | —CH$_2$—O— | — | H | F | C | — | 3-SO$_2$NHCH$_2$CH$_2$NEt$_2$ |
| I-242 | 4-(5-methylisoxazol-3-yl)- | —CH$_2$—O— | — | H | F | C | — | 3-SO$_2$NHC(O)Et |
| I-243 | 4-(5-methylisoxazol-3-yl)- | —CH$_2$—O— | — | H | F | C | — | 3-SO$_2$NHC(O)Me |
| I-244 | 4-(5-methylisoxazol-3-yl)- | —CH$_2$—O— | 3-Me | H | F | C | — | 4-SO$_2$NHCH$_2$CH$_2$NEt$_2$ |
| I-245 | 4-(5-methylisoxazol-3-yl)- | —CH$_2$—O— | 3-Me | H | F | C | — | 4-SO$_2$NHCH$_2$CH$_2$NEt$_2$ |
| I-246 | 4-(5-methylisoxazol-3-yl)- | —CH$_2$—O— | — | H | F | C | — | 4-SO$_2$NHCH$_2$CH$_2$NEt$_2$ |
| I-247 | 4-(5-methylisoxazol-3-yl)- | —CH$_2$—O— | — | H | F | | — | 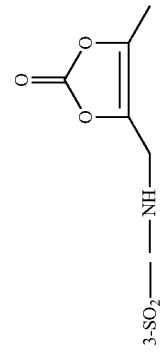 |

TABLE I-continued

| # | R¹ | -alk-Y- | $(R^2)_p$ | R | X | Z | $(R^3)_q$ | $SO_2NR^4R^5$ |
|---|---|---|---|---|---|---|---|---|
| I-248 | 4-(5-methylisoxazol-3-yl)- | —CH₂—O— | — | H | F | C | — | 3-SO₂-N(dioxol-methylene)₂ (cyclic carbonate ring) |
| I-249 | 4-(5-methylisoxazol-3-yl)- | —CH₂—O— | — | H | F | C | — | 3-SO₂-N-(4-tert-butyl-dioxol-2-one-methylene) |
| I-250 | 4-(5-methylisoxazol-3-yl)- | —CH₂—O— | — | H | F | C | — | 3-SO₂-NH-(4-tert-butyl-dioxol-2-one-methylene) |
| I-251 | 4-(5-methylisoxazol-3-yl)- | —CH₂—O— | 3-F | H | F | C | 4-(4-Me-piperazin-1-yl) | 3-SO₂NH₂ |
| I-252 | 3-(3-methyl-1,2,4-oxadiazol-5-yl)- | —CH₂—O— | — | H | F | C | — | 3-SO₂NH₂ |
| I-253 | 3-(3-methyl-1,2,4-oxadiazol-5-yl)- | —CH₂—O— | — | H | F | C | — | 4-SO₂NH₂ |
| I-254 | 3-(3-methyl-1,2,4-oxadiazol-5-yl)- | —CH₂—O— | — | H | F | C | 4-Me | 3-SO₂NH₂ |
| I-255 | 3-(3-methyl-1,2,4-oxadiazol-5-yl)- | —CH₂—O— | — | H | F | C | 4-Me | 3-SO₂NHMe |
| I-256 | 3-(3-methyl-1,2,4-oxadiazol-5-yl)- | —CH₂—O— | — | H | F | C | — | 4-SO₂NHCH₂CH₂NEt₂ |

TABLE I-continued

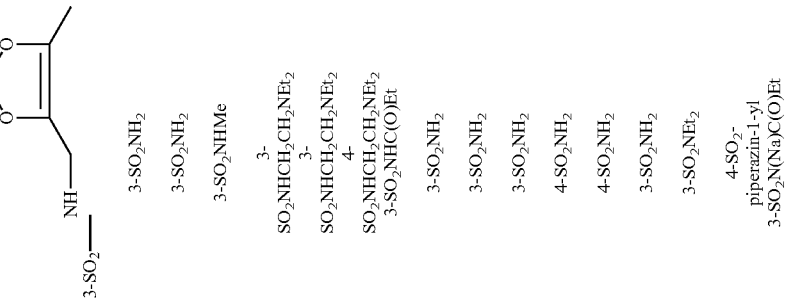

| # | R¹ | -alk-Y— | (R²)$_p$ | R | X | Z | (R³)$_q$ | SO$_2$NR⁴R⁵ |
|---|---|---|---|---|---|---|---|---|
| I-257 | 3-(3-methyl-1,2,4-oxadiazol-5-yl)- | —CH$_2$—O— | — | H | F | C | — |  |
| I-258 | 4-((3-methyl-1,2,4-oxadiazol-5-yl)- | —CH$_2$—O— | — | H | F | C | — | 3-SO$_2$NH$_2$ |
| I-259 | 4-((3-methyl-1,2,4-oxadiazol-5-yl)- | —CH$_2$—O— | — | H | F | C | 4-Me | 3-SO$_2$NH$_2$ |
| I-260 | 4-((3-methyl-1,2,4-oxadiazol-5-yl)- | —CH$_2$—O— | — | H | F | C | 4-Me | 3-SO$_2$NHMe |
| I-261 | 4-((3-methyl-1,2,4-oxadiazol-5-yl)- | —CH$_2$—O— | — | H | F | C | — | 3-SO$_2$NHCH$_2$CH$_2$NEt$_2$ |
| I-262 | 4-((3-methyl-1,2,4-oxadiazol-5-yl)- | —CH$_2$—O— | — | H | F | C | — | 3-SO$_2$NHCH$_2$CH$_2$NEt$_2$ |
| I-263 | 4-((3-methyl-1,2,4-oxadiazol-5-yl)- | —CH$_2$—O— | — | H | F | C | — | 4-SO$_2$NHCH$_2$CH$_2$NEt$_2$ |
| I-264 | 4-((3-methyl-1,2,4-oxadiazol-5-yl)- | —CH$_2$—O— | — | H | F | C | — | 3-SO$_2$NHC(O)Et |
| I-265 | 4-((3-methyl-1,2,4-oxadiazol-5-yl)- | —CH$_2$—O— | — | H | F | C | 4-Cl-3-Me | 3-SO$_2$NH$_2$ |
| I-266 | 4-((3-methyl-1,2,4-oxadiazol-5-yl)- | —CH$_2$—O— | — | H | F | C | 4-F | 3-SO$_2$NH$_2$ |
| I-267 | 4-((3-methyl-1,2,4-oxadiazol-5-yl)- | —CH$_2$—O— | — | H | F | C | 4-F | 3-SO$_2$NH$_2$ |
| I-268 | 4-((3-methyl-1,2,4-oxadiazol-5-yl)- | —CH$_2$—O— | — | H | F | C | — | 4-SO$_2$NH$_2$ |
| I-269 | 4-((3-methyl-1,2,4-oxadiazol-5-yl)- | —CH$_2$—O— | — | Me | F | C | — | 4-SO$_2$NH$_2$ |
| I-270 | 4-((3-methyl-1,2,4-oxadiazol-5-yl)- | —CH$_2$—O— | — | Me | F | C | — | 3-SO$_2$NH$_2$ |
| I-271 | 4-((3-methyl-1,2,4-oxadiazol-5-yl)- | —CH$_2$—O— | 6-Ome | H | F | C | — | 3-SO$_2$NH$_2$ |
| I-272 | 4-((3-methyl-1,2,4-oxadiazol-5-yl)- | —CH$_2$—O— | — | H | F | C | — | 3-SO$_2$NEt$_2$ |
| I-273 | 4-((3-methyl-1,2,4-oxadiazol-5-yl)- | —CH$_2$—O— | — | H | F | C | — | 4-SO$_2$-piperazin-1-yl 3-SO$_2$N(Na)C(O)Et |

TABLE I-continued

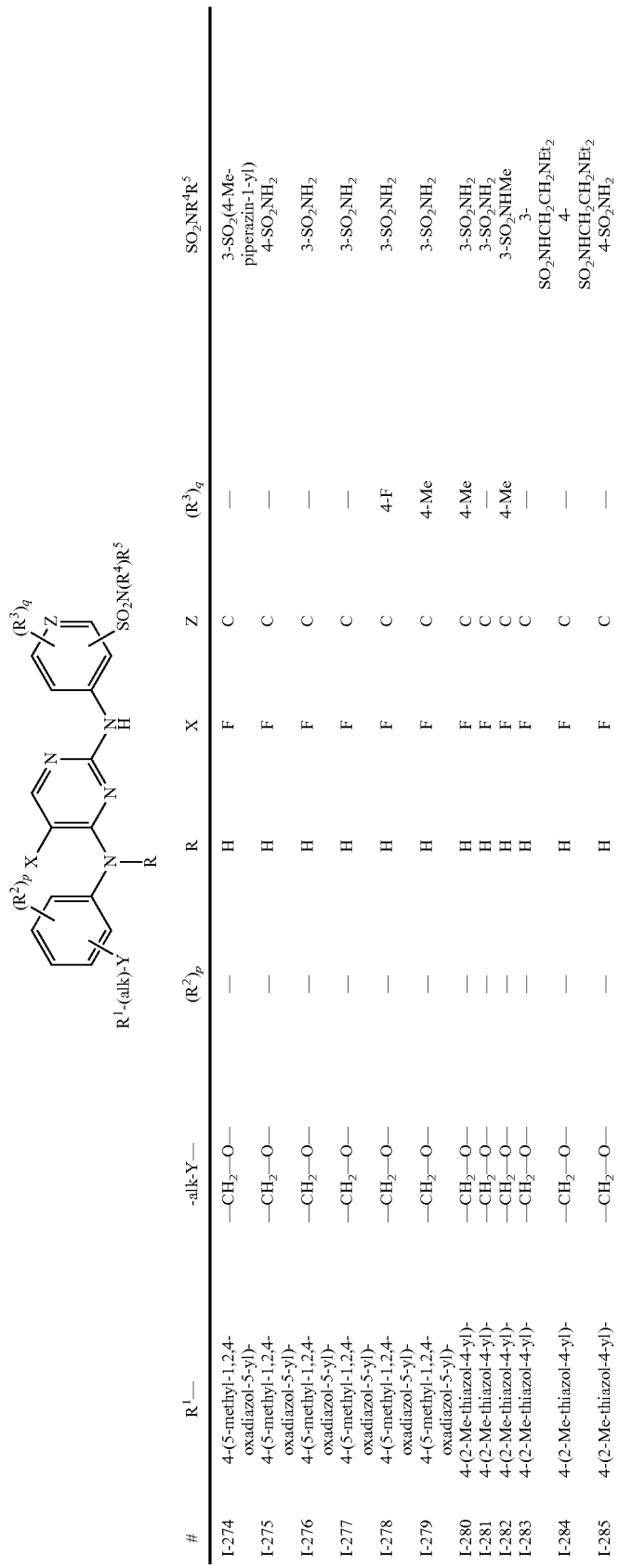

| # | R¹ | -alk-Y- | (R²)ₚ | R | X | Z | (R³)q | SO₂NR⁴R⁵ |
|---|---|---|---|---|---|---|---|---|
| I-274 | 4-(5-methyl-1,2,4-oxadiazol-5-yl)- | —CH₂—O— | — | H | F | C | — | 3-SO₂(4-Me-piperazin-1-yl) |
| I-275 | 4-(5-methyl-1,2,4-oxadiazol-5-yl)- | —CH₂—O— | — | H | F | C | — | 4-SO₂NH₂ |
| I-276 | 4-(5-methyl-1,2,4-oxadiazol-5-yl)- | —CH₂—O— | — | H | F | C | — | 3-SO₂NH₂ |
| I-277 | 4-(5-methyl-1,2,4-oxadiazol-5-yl)- | —CH₂—O— | — | H | F | C | — | 3-SO₂NH₂ |
| I-278 | 4-(5-methyl-1,2,4-oxadiazol-5-yl)- | —CH₂—O— | — | H | F | C | 4-F | 3-SO₂NH₂ |
| I-279 | 4-(5-methyl-1,2,4-oxadiazol-5-yl)- | —CH₂—O— | — | H | F | C | 4-Me | 3-SO₂NH₂ |
| I-280 | 4-(2-Me-thiazol-4-yl)- | —CH₂—O— | — | H | F | C | 4-Me | 3-SO₂NH₂ |
| I-281 | 4-(2-Me-thiazol-4-yl)- | —CH₂—O— | — | H | F | C | — | 3-SO₂NH₂ |
| I-282 | 4-(2-Me-thiazol-4-yl)- | —CH₂—O— | — | H | F | C | 4-Me | 3-SO₂NHMe |
| I-283 | 4-(2-Me-thiazol-4-yl)- | —CH₂—O— | — | H | F | C | — | 3-SO₂NHCH₂CH₂NEt₂ |
| I-284 | 4-(2-Me-thiazol-4-yl)- | —CH₂—O— | — | H | F | C | — | 4-SO₂NHCH₂CH₂NEt₂ |
| I-285 | 4-(2-Me-thiazol-4-yl)- | —CH₂—O— | — | H | F | C | — | 4-SO₂NH₂ |

TABLE II

| # | R¹— | —Y— | (R²)$_p$ | R | X | Z | (R³)$_q$ | SO$_2$NR⁴R⁵ |
|---|---|---|---|---|---|---|---|---|
| II-1 | 3-(N—Me-piperidin-3-yl)- | —O— | — | H | F | C | 4-Me | 3-SO$_2$NH$_2$ |
| II-2 | 3-(N—Me-piperidin-4-yl)- | —O— | — | H | F | C | 4-Me | 3-SO$_2$NH$_2$ |
| II-3 | 4-(N—Me-piperidin-3-yl)- | —O— | 3-Cl | H | F | C | 4-Me | 3-SO$_2$NH$_2$ |
| II-4 | 4-(N—Me-piperidin-3-yl)- | —O— | — | H | F | C | 4-Me | 3-SO$_2$NH$_2$ |
| II-5 | 4-(N—Me-piperidin-4-yl)- | —O— | 3-Me | H | F | C | 4-Me | 3-SO$_2$NH$_2$ |
| II-6 | 4-(N—Me-piperidin-4-yl)- | —O— | 3-CF$_3$ | H | F | C | 4-Me | 3-SO$_2$NH$_2$ |
| II-7 | 4-(N—Me-piperidin-4-yl)- | —O— | — | H | F | C | 4-Me | 3-SO$_2$NH$_2$ |
| II-8 | 4-(N—Me-piperidin-4-yl)- | —O— | 3-Cl | H | F | C | 4-Me | 3-SO$_2$NH$_2$ |
| II-9 | 4-(N—Me-pyrrolidin-3-yl)- | —O— | — | H | F | C | — | 3-SO$_2$NH$_2$ |
| II-10 | 4-(N—Me-pyrrolidin-3-yl)- | —O— | — | H | F | C | 4-Me | 3-SO$_2$NH$_2$ |
| II-11 | 4-(pyridin-3-yl)- | —O— | — | H | F | C | — | 3-SO$_2$NH$_2$ |
| II-12 | 4-(pyridin-3-yl)- | —O— | — | H | F | C | 4-Me | 3-SO$_2$NH$_2$ |
| II-13 | 4-(pyridin-3-yl)- | —O— | — | H | F | C | 4-Me | 3-SO$_2$MHMe |
| II-14 | 4-(pyridin-3-yl)- | —O— | — | H | F | C | — | 4-SO$_2$NHMe |
| II-15 | 4-(pyridin-3-yl)- | —O— | — | H | F | C | 3-SO$_2$NH$_2$ | 4-SO$_2$NH$_2$ |
| II-16 | 4-(pyriclin-4-yl)- | —O— | — | H | F | C | 4-Me | 3-SO$_2$NH$_2$ |
| II-17 | 4-(pyriclin-4-yl)- | —O— | — | H | F | C | — | 3-SO$_2$NH$_2$ |
| II-18 | 4-(pyriclin-4-yl)- | —O— | — | H | F | C | 4-Me | 3-SO$_2$NHMe |
| II-19 | 4-(1-methyl-(1H)-pyrazol-3-yl)- | —NHC(O)— | — | H | F | C | 4-Me | 3-SO$_2$NH$_2$ |
| II-20 | 4-(2-ethyl-(2H)-pyrazol-3-yl)- | —NHC(O)— | — | H | F | C | 4-Me | 3-SO$_2$NH$_2$ |
| II-21 | 4-(2-methyl-(2H)-pyrazol-3-yl)- | —NHC(O)— | — | H | F | C | 4-Me | 3-SO$_2$NH$_2$ |
| II-22 | 4-(pyrazol-(2H)-3-yl)- | —NHC(O)— | — | H | F | C | 4-Me | 3-SO$_2$NH$_2$ |

TABLE III

| # | R$_1$— | —alk— | (R²)$_p$ | R | X | Z | (R³)$_q$ | SO$_2$NR⁴R⁵ |
|---|---|---|---|---|---|---|---|---|
| III-1 | 4-NC— | —CH$_2$— | — | H | F | C | 4-Me | 3-SO$_2$NHMe |
| III-2 | 4-NC— | —CH$_2$— | — | H | F | C | 4-Me | 4-SO$_2$NHCH$_2$CH$_2$NEt$_2$ |
| III-3 | 4-NC— | —CH$_2$— | — | H | F | C | — | 4-SO$_2$NH$_2$ |
| III-4 | 4-NC— | —CH$_2$— | — | H | F | C | — | 3-SO$_2$NH$_2$ |
| III-5 | 4-NC— | —CH$_2$— | — | H | F | C | — | 3-SO$_2$(4-Me-piperazin-1-yl) |
| III-6 | 4-NC— | —CH$_2$— | — | H | F | C | — | 4-SO$_2$(4-Me-piperazin-1-yl) |
| III-7 | 4-NC— | —CH$_2$— | — | H | F | C | 4-Me | 3-SO$_2$NH$_2$ |
| III-8 | 4-NC— | —CH$_2$— | — | H | F | C | 4-Cl | 3-SO$_2$NH$_2$ |
| III-9 | 4-NC— | —CH$_2$— | — | H | F | C | 3-OMe | 4-SO$_2$NH$_2$ |
| III-10 | 4-NC— | —CH$_2$— | — | H | F | C | 4-F | 3-SO$_2$NH$_2$ |
| III-11 | 4-NC— | —CH$_2$CH$_2$— | — | H | Me | C | 4-Me | 3-SO$_2$NH$_2$ |
| III-12 | 4-NC— | —CH$_2$CH$_2$— | — | H | Me | C | 4-Cl | 3-SO$_2$NH$_2$ |
| III-13 | 4-NC— | —CH$_2$CH$_2$— | — | H | F | C | 4-Cl | 3-SO$_2$NH$_2$ |
| III-14 | 4-NC— | —CH$_2$CH$_2$— | — | H | F | C | — | 3-SO$_2$NH$_2$ |
| III-15 | 4-NC— | —CH$_2$CH$_2$— | — | H | F | C | 4-Me | 3-SO$_2$NH$_2$ |
| III-16 | 4-NC— | —CH$_2$CH$_2$— | — | H | F | C | 4-F | 3-SO$_2$NH$_2$ |
| III-17 | 4-NC— | —CH$_2$CH$_2$— | 3-F | H | F | C | 4-Me | 3-SO$_2$NH$_2$ |
| III-18 | 4-NC— | —CH$_2$CH$_2$— | 3-F | H | F | C | — | 3-SO$_2$NH$_2$ |
| III-19 | 4-NC— | —CH$_2$CH$_2$— | 3-Me | H | F | C | 4-Me | 3-SO$_2$NH$_2$ |
| III-20 | 4-NC— | —CH$_2$CH$_2$— | 3-Me | H | F | C | — | 3-SO$_2$NH$_2$ |
| III-21 | 4-NC— | —CH$_2$CH$_2$— | 3-Cl | H | F | C | 4-Me | 3-SO$_2$NH$_2$ |
| III-22 | 4-NC— | —CH$_2$CH$_2$— | 3-Cl | H | F | C | — | 3-SO$_2$NH$_2$ |
| III-23 | 3-NC— | —CH$_2$CH$_2$— | 6-Me | H | F | C | 4-Me | 3-SO$_2$NH$_2$ |
| III-24 | 3-NC— | —CH$_2$CH$_2$— | 6-Me | H | F | C | — | 3-SO$_2$NH$_2$ |
| III-25 | 4-NC— | —CH$_2$CH$_2$— | 3-MeO | H | F | C | 4-Me | 3-SO$_2$NH$_2$ |
| III-26 | 4-NC— | —CH$_2$CH$_2$— | 3-MeO | H | F | C | — | 3-SO$_2$NH$_2$ |
| III-27 | 4-NC— | —CH$_2$CH$_2$— | — | H | Me | C | — | 4-SO$_2$NH$_2$ |
| III-28 | 4-NC— | —CH$_2$CH$_2$— | 3-Cl | H | F | C | 4-Me | 3-SO$_2$NHC(O)Et |
| III-29 | 4-NC— | —CH$_2$CH$_2$— | 3-Cl | H | F | C | 4-Me | 3-SO$_2$NHC(O)Et |
| III-30 | 4-NC— | —CH$_2$CH$_2$— | 4-CF$_3$ | H | F | C | 4-Me | 3-SO$_2$NH$_2$ |
| III-31 | 4-NC— | —CH$_2$CH$_2$— | 4-CF$_3$ | H | F | C | — | 3-SO$_2$NH$_2$ |

TABLE III-continued structure:

Ar-X-pyrimidine with R¹—(alk)— on one aniline (with $(R^2)_p$ and NR), and —NH—Ar—$SO_2N(R^4)R^5$ with $(R^3)_q$ on the other.

| # | R₁— | —alk— | (R²)ₚ | R | X | Z | (R³)_q | SO₂NR⁴R⁵ |
|---|---|---|---|---|---|---|---|---|
| III-32 | 4-NH₂C(O)NH— | —CH₂— | — | H | F | C | — | 4-SO₂NH₂ |
| III-33 | 4-NH₂C(O)NH— | —CH₂— | — | H | F | C | — | 3-SO₂NH₂ |
| III-34 | 4-NH₂C(O)NH— | —CH₂— | — | H | F | C | 4-Me | 3-SO₂NH₂ |
| III-35 | 4-CH₃CH₂C(O)NH— | —CH₂— | — | H | F | C | — | 4-SO₂NH₂ |
| III-36 | 4-CH₃CH₂C(O)NH— | —CH₂— | — | H | F | C | — | 3-SO₂NH₂ |
| III-37 | 4-CH₃CH₂C(O)NH— | —CH₂— | — | H | F | C | 4-Me | 3-SO₂NH₂ |
| III-38 | 3-cyclopropyl-C(O)NH— | —CH₂— | — | H | F | C | — | 4-SO₂NH₂ |
| III-39 | 3-cyclopropyl-C(O)NH— | —CH₂— | — | H | F | C | — | 3-SO₂NH₂ |
| III-40 | 3-cyclopropyl-C(O)NH— | —CH₂— | — | H | F | C | 4-Me | 3-SO₂NH₂ |
| III-41 | 4-cyclopropyl-C(O)NH— | —CH₂— | — | H | F | C | — | 4-SO₂NH₂ |
| III-42 | 4-cyclopropyl-C(O)NH— | —CH₂— | — | H | F | C | — | 3-SO₂NH₂ |
| III-43 | 4-cyclopropyl-C(O)NH— | —CH₂— | — | H | F | C | 4-Me | 3-SO₂NH₂ |
| III-44 | 4-CH₂=CHC(O)NH— | —CH₂— | — | H | F | C | — | 4-SO₂NH₂ |
| III-45 | 4-CH₂=CHC(O)NH— | —CH₂— | — | H | F | C | — | 3-SO₂NH₂ |
| III-46 | 4-CH₂=CHC(O)NH— | —CH₂— | — | H | F | C | 4-Me | 3-SO₂NH₂ |
| III-47 | 4-H₂NC(O)— | —CH₂CH₂— | — | H | F | C | 4-Me | 3-SO₂NH₂ |
| III-48 | 4-H₂NC(O)— | —CH₂CH₂— | — | H | F | C | — | 3-SO₂NH₂ |
| III-49 | 4-H₂NC(O)— | —CH₂CH₂— | — | H | F | C | — | 4-SO₂NH₂ |
| III-50 | 4-(1-methyl-(2H)-pyrazol-3yl)—NHC(O)— | —CH₂— | — | H | F | C | — | 3-SO₂NH₂ |
| III-51 | 4-(2-ethyl-(2H)-pyrazol-3)—NHC(O)— | —CH₂— | — | H | F | C | — | 3-SO₂NH₂ |
| III-52 | 4-(2-ethyl-(2H)-pyrazol-3)—NHC(O)— | —CH₂— | — | H | F | C | 4-Me | 3-SO₂NH₂ |
| III-53 | 4-NH₂C(O)O— | —CH₂CH₂— | — | H | F | C | 4-Me | 3-SO₂NH₂ |
| III-54 | 4-NH₂C(O)O— | —CH₂CH₂— | — | H | F | C | — | 3-SO₂NH₂ |
| III-55 | 4-NH₂C(O)O— | —CH₂CH₂— | — | H | F | C | 4-Cl | 3-SO₂NH₂ |
| III-56 | 4-Me₂NC(O)O— | —CH₂CH₂— | — | H | F | C | 4-Me | 3-SO₂NH₂ |
| III-57 | 4-Me₂NC(O)O— | —CH₂CH₂— | — | H | F | C | — | 3-SO₂NH₂ |
| III-58 | 4-Me₂NC(O)O— | —CH₂CH₂— | — | H | F | C | 4-Cl | 3-SO₂NH₂ |
| III-59 | 4-Me₂NC(O)O— | —CH₂CH₂— | — | H | F | C | 4-Me | 3-SO₂NH₂ |
| III-60 | 4-Me₂NC(O)O— | —CH₂CH₂— | — | H | F | C | — | 3-SO₂NH₂ |
| III-61 | 4-Me₂NC(O)O— | —CH₂CH₂— | — | H | F | C | 4-Cl | 3-SO₂NH₂ |
| III-62 | phenyl | —CH₂— | — | H | F | C | — | 3-SO₂NH₂ |
| III-63 | phenyl | —CH₂— | — | H | F | C | 4-Me | 3-SO₂NH₂ |
| III-64 | phenyl | —CH₂— | — | H | F | C | 4-Cl | 3-SO₂NH₂ |
| III-65 | phenyl | —CH₂— | — | H | F | C | 4-MeO, 5-Me | 3-SO₂NH₂ |
| III-66 | 4-pyridin-4-yl- | —CH₂— | — | H | F | C | 4-Ome | 3-SO₂NH₂ |
| III-67 | 4-pyridin-4-yl- | —CH₂— | — | H | F | C | — | 3-SO₂NHCH₂CH₂NEt₂ |
| III-68 | 4-pyridin-4-yl- | —CH₂— | — | H | F | C | — | 3-SO₂NHC(O)Et |
| III-69 | 4-pyridin-4-yl- | —CH₂— | — | H | F | C | — | 3-SO₂N(Na)C(O)Et |
| III-70 | 4-pyridin-4-yl- | —CH₂— | — | H | F | C | — | 3-SO₂NH₂ |
| III-71 | 4-pyridin-4-yl- | —CH₂— | — | H | F | C | — | 4-SO₂NH₂ |
| III-72 | 4-pyridin-4-yl- | —CH₂— | — | H | F | C | — | 4-SO₂NHCH₂CH₂NEt₂ |
| III-73 | 4-pyridin-4-yl- | —CH₂— | — | H | F | C | — | 3-SO₂NH₂ |
| III-74 | 4-pyridin-4-yl- | —CH₂— | — | H | F | C | 4-Me | 3-SO₂NH₂ |
| III-75 | 4-pyridin-4-yl- | —CH₂— | — | H | F | C | 4-Me | 3-SO₂MHMe |
| III-76 | 4-pyridin-4-yl- | —CH₂CH₂— | — | H | F | C | — | 3-SO₂NH₂ |
| III-77 | 4-pyridin-4-yl- | —CH₂CH₂— | — | H | F | C | 4-Me | 3-SO₂NH₂ |
| III-78 | 4-pyridin-4-yl- | —CH₂CH₂— | — | H | F | C | 4-Me | 3-SO₂MHMe |
| III-79 | 4-pyridin-4-yl- | —CH₂CH₂— | — | H | F | C | — | 4-SO₂NH₂ |
| III-80 | 4-(N-hydroxy-pyridin-4-yl)- | —CH₂— | — | H | F | C | — | 3-SO₂NHC(O)Et |
| III-81 | 4-imidazol-1-yl- | —CH₂— | — | H | F | C | — | 3-SO₂NH₂ |
| III-82 | 4-imidazol-1-yl- | —CH₂— | — | H | F | C | 4-Me | 3-SO₂NH₂ |
| III-83 | 4-imidazol-1-yl- | —CH₂— | — | H | F | C | 4-Me | 3-SO₂MHMe |
| III-84 | 4-imidazol-1-yl- | —CH₂— | — | H | F | C | — | 4-SO₂NHCH₂CH₂N(Et)₂ |
| III-85 | 4-imidazol-1-yl- | —CH₂— | — | H | F | C | 4-Me | 3-SO₂MHMe |
| III-86 | 4-imidazol-1-yl- | —CH₂— | — | H | F | C | 4-Me | 3-SO₂MHMe |
| III-87 | 4-imidazol-1-yl- | —CH₂CH₂— | — | H | F | C | — | 3-SO₂NH₂ |
| III-88 | 4-imidazol-1-yl- | —CH₂CH₂— | — | H | F | C | 4-Me | 3-SO₂NH₂ |
| III-89 | 4-imidazol-1-yl- | —CH₂CH₂— | — | H | F | C | 4-Me | 3-SO₂MHMe |
| III-90 | 4-imidazol-1-yl- | —CH₂CH₂— | — | H | F | C | — | 4-SO₂NH₂ |
| III-91 | 4-(2-methyl-imidazol-1-yl)- | —CH₂— | — | H | F | C | 4-Me | 3-SO₂NH₂ |

TABLE III-continued

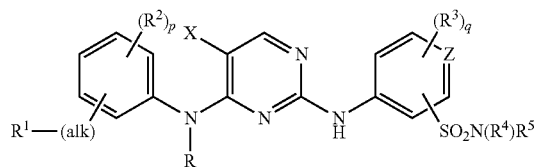

| # | R₁— | —alk— | (R²)ₚ | R | X | Z | (R³)q | SO₂NR⁴R⁵ |
|---|---|---|---|---|---|---|---|---|
| III-92 | 4-(2-methyl-imidazol-1-yl)- | —CH₂— | — | H | F | C | — | 4-SO₂NH₂ |
| III-93 | 4-(2-methyl-imidazol-1-yl)- | —CH₂— | — | H | F | C | 4-Me | 3-SO₂MHMe |
| III-94 | 4-(2-methyl-imidazol-1-yl)- | —CH₂— | — | H | F | C | — | 3-SO₂NH₂ |
| III-95 | 4-(1H-1,2,3-triazol-1-yl)- | —CH₂— | — | H | F | C | 4-Me | 3-SO₂NH₂ |
| III-96 | 4-(1H-1,2,3-triazol-1-yl)- | —CH₂— | — | H | F | C | — | 4-SO₂NH₂ |
| III-97 | 4-(1H-1,2,3-triazol-1-yl)- | —CH₂— | — | H | F | C | — | 3-SO₂NH₂ |
| III-98 | 4-(1H-1,2,3-triazol-1-yl)- | —CH₂— | — | H | F | C | 4-Me | 3-SO₂MHMe |
| III-99 | 4-(1H-1,2,4-triazol-1-yl)- | —CH₂— | — | H | F | C | — | 4-SO₂NH₂ |
| III-100 | 4-(1H-1,2,4-triazol-1-yl)- | —CH₂— | — | H | F | C | — | 3-SO₂NH₂ |
| III-101 | 4-(1H-1,2,4-triazol-1-yl)- | —CH₂— | — | H | F | C | 4-Me | 3-SO₂NH₂ |
| III-102 | 4-(1H-1,2,4-triazol-1-yl)- | —CH₂— | — | H | F | C | 4-Me | 3-SO₂MHMe |
| III-103 | 4-morpholin-1-yl- | —CH₂— | — | H | F | C | — | 3-SO₂NH₂ |
| III-104 | 4-morpholin-1-yl- | —CH₂— | — | H | F | C | 4-Me | 3-SO₂NH₂ |
| III-105 | 4-morpholin-1-yl- | —CH₂— | — | H | F | C | 4-Ome | 3-SO₂NH₂ |
| III-106 | 4-(3-methyl-1,2,4-oxadiazol-5-yl)- | —CH₂CH₂— | — | H | F | C | — | 3-SO₂NH₂ |
| III-107 | 4-(thiomorpholin-1-yl)- | —CH₂— | — | H | F | C | — | 3-SO₂NH₂ |
| III-108 | 4-(thiomorpholin-1-yl)- | —CH₂— | — | H | F | C | 4-Me | 3-SO₂NH₂ |
| III-109 | 4-(thiomorpholin-1-yl)- | —CH₂— | — | H | F | C | 4-Ome | 3-SO₂NH₂ |
| III-110 | 4-(S,S-dioxo-thiomorpholin-1-yl)- | —CH₂— | — | H | F | C | — | 3-SO₂NH₂ |
| III-111 | 4-(S,S-dioxo-thiomorpholin-1-yl)- | —CH₂— | — | H | F | C | 4-Me | 3-SO₂NH₂ |
| III-112 | 4-(S,S-dioxo-thiomorpholin-1-yl)- | —CH₂— | — | H | F | C | 4-Ome | 3-SO₂NH₂ |
| III-113 | 3-H₂NC(O)NH— | —CH₂— | — | H | F | C | — | 4-SO₂NH₂ |
| III-114 | 3-H₂NC(O)NH— | —CH₂— | — | H | F | C | — | 3-SO₂NH₂ |
| III-115 | 3-H₂NC(O)NH— | —CH₂— | — | H | F | C | 4-Me | 3-SO₂NH₂ |
| III-116 | 3-CH₃CH₂NHC(O)NH— | —CH₂— | — | H | F | C | — | 4-SO₂NH₂ |
| III-117 | 3-CH₃CH₂NHC(O)NH— | —CH₂— | — | H | F | C | — | 3-SO₂NH₂ |
| III-118 | 3-CH₃CH₂NHC(O)NH— | —CH₂— | — | H | F | C | 4-Me | 3-SO₂NH₂ |
| III-119 | 4-CH₃CH₂NHC(O)NH— | —CH₂— | — | H | F | C | — | 4-SO₂NH₂ |
| III-120 | 4-CH₃CH₂NHC(O)NH— | —CH₂— | — | H | F | C | — | 3-SO₂NH₂ |
| III-121 | 4-CH₃CH₂NHC(O)NH— | —CH₂— | — | H | F | C | 4-Me | 3-SO₂NH₂ |
| III-122 | 4-CH₃CH₂NHC(O)NH— | —CH₂CH₂— | — | H | F | C | — | 4-SO₂NH₂ |
| III-123 | 4-CH₃CH₂NHC(O)NH— | —CH₂CH₂— | — | H | F | C | — | 3-SO₂NH₂ |
| III-124 | 4-CH₃CH₂NHC(O)NH— | —CH₂CH₂— | — | H | F | C | 4-Me | 3-SO₂NH₂ |
| III-125 | 4-H₂NC(O)N(CH—₃CH₂CH₂)— | —CH₂— | — | H | F | C | — | 4-SO₂NH₂ |
| III-126 | 4-H₂NC(O)N(CH—₃CH₂CH₂)— | —CH₂— | — | H | F | C | — | 3-SO₂NH₂ |
| III-127 | 4-H₂NC(O)N(CH—₃CH₂CH₂)— | —CH₂— | — | H | F | C | 4-Me | 3-SO₂NH₂ |
| III-128 | 4-pyrindin-4-yl | —CH₂— | — | H | F | C | — | 3-SO₂NH₂ |
| III-129 | 4-pyrindin-4-yl | —CH₂— | — | H | F | C | — | 3-SO₂NH₂ |

TABLE IV

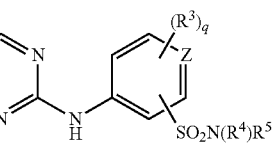
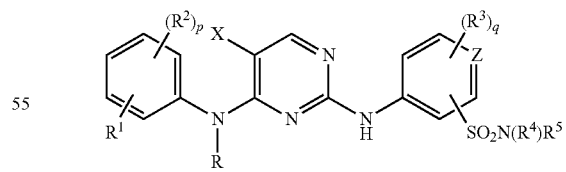

| # | R¹— | (R²)ₚ | R | X | Z | (R³)q | SO₂NR⁴R⁵ |
|---|---|---|---|---|---|---|---|
| IV-1 | 3-(oxazol-5-yl) | — | H | F | C | — | 3-SO₂NH₂ |
| IV-2 | 3-(oxazol-5-yl) | — | H | F | C | 4-Me | 3-SO₂NH₂ |
| IV-3 | 3-(oxazol-5-yl) | — | H | F | C | — | 4-SO₂NH₂ |
| IV-4 | 3-(oxazol-5-yl) | — | H | F | C | 4-Me | 3-SO₂MHMe |
| IV-5 | 4-(oxazol-5-yl) | — | H | F | C | — | 3-SO₂NH₂ |
| IV-6 | 4-(oxazol-5-yl) | — | H | F | C | 4-Me | 3-SO₂NH₂ |
| IV-7 | 4-(oxazol-5-yl) | — | H | F | C | 4-Me | 3-SO₂MHMe |
| IV-8 | 4-(oxazol-5-yl) | — | H | F | C | — | 4-SO₂NH₂ |
| IV-9 | 4-(N,N-dimethylsulfamoyl)- | — | H | F | C | — | 3-SO₂NH₂ |
| IV-10 | 4-(N,N-dimethylsulfamoyl)- | — | H | F | C | 4-Me | 3-SO₂NH₂ |
| IV-11 | 4-(N-methylsulfamoyl)- | — | H | F | C | — | 3-SO₂NH₂ |
| IV-12 | 4-(N-methylsulfamoyl)- | — | H | F | C | 4-Me | 3-SO₂NH₂ |

TABLE V

| # | A | R¹—alk—Y | (R²)$_p$ | (R³)$_q$ | NR⁴R⁵ |
|---|---|---|---|---|---|
| V-1 | pyriclin-3-yl | 6-((5-methylisoxazol-3-yl)-CH₂O)— | — | 4-Me | 3-SO₂NH₂ |
| V-2 | 3,4-dihydro-2H-benzo[b][1,4]oxazin-6-yl | 4-((pyriclin-2-yl)-CH₂-) | 3-oxo | 4-Me | 3-SO₂NH₂ |
| V-3 | 3,4-dihydro-2H-benzo[b][1,4]oxazin-6-yl | 4-(pyriclin-2-yl)—CH₂— | 3-oxo | — | 4-SO₂NH₂ |
| V-4 | 3,4-dihydro-2H-benzo[b][1,4]oxazin-6-yl | 4-methoxybenzyl | 2-Me, 3-oxo | — | 4-SO₂NH₂ |
| V-5 | 3,4-dihydro-2H-benzo[b][1,4]oxazin-6-yl | 4-methoxybenzyl | 2-Me, 3-oxo | — | 3-SO₂NH₂ |
| V-6 | 3,4-dihydro-2H-benzo[b][1,4]oxazin-6-yl | 4-NC—CH₂— | 3-oxo | — | 4-SO₂NH₂ |
| V-7 | 3,4-dihydro-2H-benzo[b][1,4]oxazin-6-yl | 4-NC—CH₂— | 3-oxo | — | 3-SO₂NH₂ |
| V-8 | 3,4-dihydro-2H-benzo[b][1,4]oxazin-6-yl | 4-NC—CH₂— | 3-oxo | 4-Me | 3-SO₂NH₂ |
| V-9 | 3,4-dihydro-2H-benzo[b][1,4]thiazin-6-yl | 4-methoxybenzyl | 2-Me, 3-oxo | 4-Me | 3-SO₂NH₂ |
| V-10 | 3,4-dihydro-2H-benzo[b][1,4]thiazin-6-yl | 4-methoxybenzyl | 2-Me, 3-oxo | — | 4-SO₂NH₂ |
| V-11 | 3,4-dihydro-2H-benzo[b][1,4]thiazin-6-yl | 4-NC—CH₂— | 3-oxo | — | 4-SO₂NH₂ |
| V-12 | 3,4-dihydro-2H-benzo[b][1,4]thiazin-6-yl | 4-NC—CH₂— | 3-oxo | — | 3-SO₂NH₂ |
| V-13 | 3,4-dihydro-2H-benzo[b][1,4]thiazin-6-yl | 4-NC—CH₂— | 3-oxo | 4-Me | 3-SO₂NH₂ |
| V-14 | 3,4-dihydro-2H-pyrido[3,2-b][1,4]oxazin-6-yl | 4-NC—CH₂— | 2,2,-diMe, 3-oxo | 4-Me | 3-SO₂NH₂ |
| V-15 | 3,4-dihydro-2H-pyrido[3,2-b][1,4]oxazin-6-yl | 4-NC—CH₂— | 2,2,-diMe, 3-oxo | 4-Cl | 3-SO₂NH₂ |
| V-16 | benzo[b]thiophen-5-yl | 2-NC-(CH₂)2- | — | 4-Me | 3-SO₂NH₂ |
| V-17 | 4H-pyrido[1,4]oxazin-6-yl | — | 2,2-diMe-3-oxo | — | 3-SO₂NH₂ |
| V-18 | 4H-pyrido[1,4]oxazin-7-yl | — | 2,2-diMe-3-oxo | 4-Me | 3-SO₂NH₂ |
| V-19 | piperidin-3-yl | 1-NCCH₂C(O)— | — | 4-Me | 4-Me 3-SO₂NH₂ |

TABLE VI

| # | (R²)$_p$ | R | X | Z | (R³)$_q$ | NR⁴R⁵ |
|---|---|---|---|---|---|---|
| VI-1 | 3-OH | H | F | C | 3-OMe | 4-SO₂NHMe |
| VI-2 | 3-Cl-4-OMe | H | F | C | 4-Cl | 3-SO₂NH₂ |
| VI-3 | 3,4-di-Cl | H | F | C | 4-Cl | 3-SO₂NH₂ |
| VI-4 | 3-Cl-4-OMe | H | F | C | 4-Me | 3-SO₂NH₂ |
| VI-5 | 4-Cl-3-OMe | H | F | C | 4-Me | 3-SO₂NH₂ |
| VI-6 | 3,4-di-Cl | H | F | C | 4-Me | 3-SO₂NH₂ |
| VI-7 | 3-Cl-4-OMe | H | F | C | — | 3-SO₂NHCH₂COOMe |
| VI-8 | 3,4-di-Cl | H | F | C | — | 3-SO₂NHCH₂COOMe |
| VI-9 | 3-Cl-4-OMe | H | F | C | — | 3-SO₂NH(1-Me-piperidin-4-yl) |
| VI-10 | 3,4-di-Cl | H | F | C | — | 3-SO₂NH(1-Me-piperidin-4-yl) |
| VI-11 | 4-Cl-3-OMe | H | F | C | 4-Cl | 3-SO₂NH₂ |
| VI-12 | 3-Cl-4-OMe | H | F | C | 4-Cl | 3-SO₂NHC(O)Me |
| VI-13 | 3-Cl-4-OMe | H | F | C | 4-Me-5-Cl | 3-SO₂NH₂ |
| VI-14 | 3-Cl-4-OCF₃ | H | F | C | 4-Me-5-Cl | 3-SO₂NH₂ |
| VI-15 | 3-Cl-4-OMe | H | F | C | 4-F-5-Me | 3-SO₂NH₂ |
| VI-16 | 3-Cl-4-OCF₃ | H | F | C | 4-F-5-Me | 3-SO₂NH₂ |
| VI-17 | 3-Cl-4-OMe | H | F | C | 4-Cl-5-Me | 3-SO₂NH₂ |
| VI-18 | 3-Cl-4-OCF₃ | H | F | C | 4-Cl-5-Me | 3-SO₂NH₂ |
| VI-19 | 3-Cl-4-OMe | Me | F | C | 4-Me | 3-SO₂NH₂ |
| VI-20 | 3-Cl-4-OMe | Me | F | C | 4-F-5-Me | 3-SO₂NH₂ |
| VI-21 | 3-Cl-4-OMe | Me | F | C | 4-Cl-5-Me | 3-SO₂NH₂ |
| VI-22 | 3-Cl-4-OMe | pr | F | C | 4-Me | 3-SO₂NH₂ |
| VI-23 | 3-Cl-4-OMe | pr | F | C | 4-F-5-Me | 3-SO₂NH₂ |
| VI-24 | 3-Cl-4-OMe | CH₂C(O)OEt | C(O)OEt | C | — | 3-SO₂NH₂ |
| VI-25 | 3-Cl-4-OMe | CH₂C(O)OEt | C(O)OEt | C | 4-Me | 3-SO₂NH₂ |
| VI-26 | 3-Cl-4-OMe | H | Br | C | — | 3-SO₂NH₂ |
| VI-27 | 3-Cl-4-OMe | H | Br | C | 4-Me | 3-SO₂NH₂ |
| VI-28 | 3-Cl-4-OMe | H | Me₃SiC≡C— | C | — | 3-SO₂NH₂ |
| VI-29 | 3-Cl-4-OMe | H | F | C | 4-OMe | 3-SO₂NH₂ |
| VI-30 | 3-Cl-4-OMe | H | F | C | 3-Me-4-OMe | 3-SO₂NH₂ |

TABLE VI-continued

| # | (R²)ₚ | R | X | Z | (R³)_q | NR⁴R⁵ |
|---|---|---|---|---|---|---|
| VI-31 | 3-Cl-4-OMe | H | F | N | — | 2-SO₂NH₂ |
| VI-32 | 4-OCF₃ | H | F | C | 4-Me | 3-SO₂NH₂ |
| VI-33 | 4-OCF₃ | H | F | C | — | 3-SO₂NH₂ |
| VI-34 | 4-OCF₃ | H | F | C | 4-MeO, 5-Me | 3-SO₂NH₂ |
| VI-35 | 4-t-butyl | H | F | C | — | 3-SO₂NH₂ |
| VI-36 | 4-t-butyl | H | F | C | 4-Me | 3-SO₂NH₂ |
| VI-37 | 4-t-butyl | H | F | C | 4-MeO, 5-Me | 3-SO₂NH₂ |
| VI-38 | 3-CF₃-4-Cl | H | F | C | 4-MeO, 5-Me | 3-SO₂NH₂ |
| VI-39 | 3-CF₃-4-Cl | H | F | C | 4-Me | 3-SO₂NH₂ |
| VI-40 | 3-CF₃-4-Cl | H | F | C | — | 3-SO₂NH₂ |
| VI-41 | 4-CF₃ | H | F | C | 4-Cl | 3-SO₂NH₂ |
| VI-42 | 4-OCF₃ | H | F | C | 4-Cl | 3-SO₂NH₂ |
| VI-43 | 4-t-butyl | H | F | C | 4-Cl | 3-SO₂NH₂ |
| VI-44 | 3-Cl-4-CF₃ | H | F | C | 4-Cl | 3-SO₂NH₂ |
| VI-45 | 3-Cl-4-MeO | H | F | C | 4-isopropyl | 3-SO₂NH₂ |
| VI-46 | 4-OCF₃ | H | F | C | 4-Me | 3-SO₂NH₂ |
| VI-47 | 4-OCF₃ | H | F | C | — | 3-SO₂NH₂ |
| VI-48 | 4-OCF₃ | H | F | C | 4-Cl | 3-SO₂NH₂ |
| VI-49 | 3-CH₂OC(O)NHMe | H | F | C | 4-Me | 3-SO₂NH₂ |
| VI-50 | 4-CF₃ | H | F | C | 4-Me | 3-SO₂NH₂ |
| VI-51 | 4-CF₃ | H | F | C | — | 3-SO₂NH₂ |
| VI-52 | 4-CH₂OH | H | F | C | 4-Me | 3-SO₂NH₂ |
| VI-53 | 4-HC≡C—CH₂O— | H | F | C | 4-Me | 3-SO₂NH₂ |
| VI-54 | 4-(CH₂=CH)— | H | F | C | 4-Me | 3-SO₂NH₂ |
| VI-55 | 4-HC≡C—CH₂O— | H | F | C | 4-Cl | 3-SO₂NH₂ |
| VI-56 | 4-HC≡C—CH₂O— | H | F | C | 4-Me | 3-SO₂NHC(O)Et |
| VI-57 | 3-HC≡C—CH₂O— | H | F | C | 4-Me | 3-SO₂NH₂ |
| VI-58 | 4-(HC≡C—CH₂O)-3-Me | H | F | C | 4-Me | 3-SO₂NH₂ |
| VI-59 | 4-(HC≡C—CH₂O)-3-Cl | H | F | C | 4-Me | 3-SO₂NH₂ |
| VI-60 | 4-(HC≡C—CH₂O)-3-F | H | F | C | 4-Me | 3-SO₂NH₂ |
| VI-61 | 4-MeC≡C—CH₂O— | H | F | C | 4-Me | 3-SO₂NH₂ |
| VI-62 | 4-prop-2-ynyloxy | H | F | C | 4-Me | 3-SO₂NHC(O)Et |
| VI-63 | 4-prop-2-ynyloxy | H | F | C | 4-isopropyl | 3-SO₂NH₂ |
| VI-64 | 4-diMe-carbamate-Et | H | F | C | — | 3-SO₂NHC(O)Et |
| VI-65 | 4-prop-2-ynylamine | H | F | C | 4-Me | 3-SO₂NH₂ |
| VI-66 | 4-diMe-carbamate-Et | H | F | C | — | 3-SO₂NHC(O)Et |
| VI-67 | 4-(di-prop-2-ynyl)amine | H | F | C | 4-Me | 3-SO₂NH₂ |
| VI-68 | 4-prop-2-ynyloxy | H | F | C | 4-Me | 3-SO₂NHMe |
| VI-69 | 4-prop-2-ynyloxy | H | F | C | 4-Me | 3-SO₂NH(1-Me-piperidin-4-yl) |
| VI-70 | 4-prop-2-ynyloxy | H | F | C | 4-(1-Me-piperizin-4-yl) | 3-SO₂NH₂ |
| VI-71 | 4-ethylurea | H | F | C | 4-Me | 3-SO₂NH₂ |
| VI-72 | 4-ethylurea | H | F | C | — | 3-SO₂NH₂ |
| VI-73 | 4-HC≡C—CH₂OC(O)NHCH₂ | H | F | C | 4-Me | 3-SO₂NH₂ |
| VI-74 | 4-HC≡C—CH₂OC(O)NHCH₂ | H | F | C | — | 3-SO₂NH₂ |
| VI-75 | 4-HC≡C—CH₂NHSO₂— | H | F | C | — | 3-SO₂NH₂ |
| VI-76 | 4-HC≡C—CH₂NHSO₂— | H | F | C | 4-Me | 3-SO₂NH₂ |
| VI-77 | 4-HC≡C—CH₂NHSO₂— | H | F | C | — | 4-SO₂NH₂ |
| VI-78 | 4-HC≡C—CH₂O | H | F | C | — | 3-SO₂NHCH₂C≡CH |
| VI-79 | 3-HC≡C—CH₂NHSO₂— | H | F | C | 4-Me | 3-SO₂NH₂ |
| VI-80 | 3-HC≡C—CH₂NHSO₂— | H | F | C | — | 4-SO₂NH₂ |
| VI-81 | 3-HC≡C—CH₂NHSO₂— | H | F | C | — | 3-SO₂NH₂ |
| VI-82 | 4-(F(CH₂)₃)— | H | F | C | — | 4-SO₂NH₂ |
| VI-83 | 4-(F(CH₂)₃)— | H | F | C | — | 3-SO₂NH₂ |
| VI-84 | 4-(F(CH₂)₃)— | H | F | C | 4-Me | 3-SO₂NH₂ |
| VI-85 | 4-(OH(CH₂)₃)— | H | F | C | — | 4-SO₂NH₂ |
| VI-86 | 4-(OH(CH₂)₃)— | H | F | C | — | 3-SO₂NH₂ |
| VI-87 | 4-(OH(CH₂)₃)— | H | F | C | 4-Me | 3-SO₂NH₂ |
| VI-88 | 4-(OH(CH₂)₄)— | H | F | C | — | 4-SO₂NH₂ |
| VI-89 | 4-(OH(CH₂)₄)— | H | F | C | — | 3-SO₂NH₂ |
| VI-90 | 4-(OH(CH₂)₄)— | H | F | C | 4-Me | 3-SO₂NH₂ |
| VI-91 | 4-(F(CH₂)₄)— | H | F | C | — | 4-SO₂NH₂ |
| VI-92 | 4-(F(CH₂)₄)— | H | F | C | — | 3-SO₂NH₂ |
| VI-93 | 4-(F(CH₂)₄)— | H | F | C | 4-Me | 3-SO₂NH₂ |
| VI-94 | 4-HSCH₂C(O)— | H | F | C | — | 4-SO₂NH₂ |
| VI-95 | 4-HSCH₂C(O)— | H | F | C | 4-Me | 3-SO₂NH₂ |
| VI-96 | 3-CN-4-Me | H | F | C | — | 3-SO₂NHBu |
| VI-97 | 3-Cl-4-F | H | F | C | — | 3-SO₂NHBu |

TABLE VI-continued

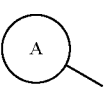

| # | $(R^2)_p$ | R | X | Z | $(R^3)_q$ | $NR^4R^5$ |
|---|---|---|---|---|---|---|
| VI-98 | 3-CN-4-F | H | F | C | — | 3-$SO_2NH_2$ |
| VI-99 | 3-CN-4-Me | H | F | C | — | 3-$SO_2NH_2$ |
| VI-100 | 4-OH | H | F | C | 4-F | 3-$SO_2NH_2$ |
| VI-101 | 4-OH | H | F | C | — | 3-$SO_2NH_2$ |
| VI-102 | 4-OH | H | F | C | 4-Me | 3-$SO_2NH_2$ |
| VI-103 | 3-Me-4-$CH_2CH_2$CN | H | F | C | 4-Me | 3-$SO_2$NHC(O)Et |
| VI-104 | 3-Me-4-$CH_2CH_2$CN | H | F | C | 4-Me | 3-$SO_2$N(Na)C(O)Et |
| VI-105 | 3,4-di-Cl | Me | F | C | 6-Ome | 3-$SO_2NEt_2$ |
| VI-106 | 3-Cl-4-Ome | H | F | C | — | 4-$SO_2NH_2$ |
| VI-107 | 3-Cl-4-Ome | H | F | C | — | 3-$SO_2NH_2$ |
| VI-108 | 3-Cl-4-Ome | H | F | C | 6-Ome | 3-$SO_2NEt_2$ |
| VI-109 | 3,4-di-Cl | H | F | C | — | 4-$SO_2NH_2$ |
| VI-110 | 3,4-di-Cl | H | F | C | — | 3-$SO_2NH_2$ |
| VI-111 | 4-$OCH_2CH_2$Ome | H | F | C | 4-Cl | 3-$SO_2NH_2$ |
| VI-112 | 4-$OCH_2CH_2$Ome | H | F | C | 4-Me | 3-$SO_2NH_2$ |
| VI-113 | 3-$H_2NSO_2$— | H | F | C | — | 3-$SO_2NH_2$ |
| VI-114 | 3-$H_2NSO_2$-4-Me | H | F | C | 4-Me | 3-$SO_2NH_2$ |
| VI-115 | 3-$H_2NSO_2$-4-Cl | H | F | C | 4-Cl | 3-$SO_2NH_2$ |
| VI-116 | 3-Cl-4-MeO | H | F | C | 4-(4-Me-piperazin-1-yl) | 3-$SO_2NH_2$ |

TABLE VII

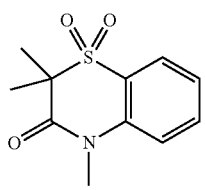

| # | A | $(R^2)_p$ | R | X | $(R^3)_q$ | $NR^4R^5$ |
|---|---|---|---|---|---|---|
| VII-1 | (2S,4R)-pyrrolidin-4-yl | 1-($CNCH_2C(O)$)-2-C(O)OME | H | F | 4-Me | 3-$SO_2NH_2$ |
| VII-2 | (2S,4S)-pyrrolidin-4-yl | 1-($CNCH_2C(O)$)-2-C(O)OME | H | F | 4-Me | 3-$SO_2NH_2$ |
| VII-3 | piperidin-3-yl | 1-benzyl-4-Me | H | F | 4-Me | 3-$SO_2NH_2$ |
| VII-4 | piperidin-3-yl | 4-Me | H | F | 4-Me | 3-$SO_2NH_2$ |
| VII-5 | piperidin-3-yl | 1-C(O)$CH_2$CN-4-Me | H | F | 4-Me | 3-$SO_2NH_2$ |
| VII-6 | pyridin-5-yl | 2-OMe | H | F | — | 3-$SO_2NH_2$ |
| VII-7 | pyridin-6-yl | 2-$NH_2$-3-OMe | H | F | — | 3-$SO_2NH_2$ |
| VII-8 | pyridin-6-yl | 2-$NH_2$-3-OMe | H | F | 4-Cl | 3-$SO_2NH_2$ |
| VII-9 | pyridin-6-yl | 2-$NH_2$-3-OMe | H | F | 4-Me | 3-$SO_2NH_2$ |
| VII-10 | pyridin-6-yl | 2-$NH_2$-3-OMe | H | F | 4-Cl | 3-$SO_2NHCH_2$COOEt |
| VII-11 | [structure] | | H | F | — | 3-$SO_2NH_2$ |

TABLE VII-continued

[Structure: pyrimidine core with A-ring connected via N(R), X substituent, and NH-phenyl-SO₂N(R⁴)R⁵ group; (R²)p on A ring, (R³)q on phenyl ring]

| # | A | (R²)p | R | X | (R³)q | NR⁴R⁵ |
|---|---|---|---|---|---|---|
| VII-12 | [2,2-dimethyl-4-methyl-3-oxo-benzothiazine 1,1-dioxide structure] | | H | F | — | 4-SO₂NH₂ |
| VII-13 | 1,2,3,4-tetrahydroisoquinolin-6-yl | 2-(ethylsulfonyl) | H | F | — | 4-SO₂NH₂ |
| VII-14 | 1,2,3,4-tetrahydroisoquinolin-6-yl | 2-(ethylsulfonyl) | H | F | — | 3-SO₂NH₂ |
| VII-15 | 1,2,3,4-tetrahydroisoquinolin-6-yl | 2-(ethylsulfonyl) | H | F | 4-Me | 3-SO₂NH₂ |
| VII-16 | 1,2,3,4-tetrahydroisoquinolin-7-yl | — | H | F | 4-Me | 3-SO₂NH₂ |
| VII-17 | 1,2,3,4-tetrahydroisoquinolin-7-yl | 2-C(O)NHMe | H | F | 4-Me | 3-SO₂NH₂ |
| VII-18 | 1,2,3,4-tetrahydroisoquinolin-7-yl | 2-C(O)NMe2 | H | F | 4-Me | 3-SO₂NH₂ |
| VII-19 | 1,2,3,4-tetrahydroquinolin-6-yl | 1-C(O)NHMe | H | F | 4-Me | 3-SO₂NH₂ |
| VII-20 | 1,2,3,4-tetrahydroquinolin-6-yl | 1-C(O)NHMe | H | F | — | 3-SO₂NH₂ |
| VII-21 | 1,2,3,4-tetrahydroquinolin-6-yl | 2-oxo | H | F | 4-Me | 3-SO₂NH₂ |
| VII-22 | 1H-indazol-5-yl | 1-(3-methoxypropyl) | H | F | — | 3-SO₂NH₂ |
| VII-23 | 1H-indazol-5-yl | 1-(2-methoxyethyl) | H | F | — | 3-SO₂NH₂ |
| VII-24 | 2,3-dihydrobenzodioxin6-yl | — | H | F | — | 4-SO₂N-(1-pyrrolidinyl) |
| VII-25 | 2,3-dihydrobenzodioxin-6-yl | — | H | F | 3-OMe | 4-SO₂NHMe |
| VII-26 | 2,3-dihydrobenzofuran-5-yl | 2-C(O)Nme2 | H | F | 4-Me | 3-SO₂NH₂ |
| VII-27 | 2,3-dihydrobenzofuran-5-yl | 2-C(O)Nme2 | H | F | 4-Cl | 3-SO₂NH₂ |
| VII-28 | 2,3-dihydrobenzopyran-6-yl | 4-NH₂ | H | F | — | 3-SO₂NH₂ |
| VII-29 | 2,3-dihydrobenzopyran-6-yl | 4-NH₂ | H | F | — | 4-SO₂NH₂ |
| VII-30 | 2H-benzo[b][1,4]oxazin-3(4H)-one | — | H | Me | Me | 3-SO₂NH₂ |
| VII-31 | 2H-benzo[b][1,4]oxazin-3(4H)-one | — | H | Me | — | 4-SO₂NH₂ |
| VII-32 | 2H-benzo[b][1,4]oxazin-3(4H)-one | — | H | Me | — | 3-SO₂NH₂ |
| VII-33 | 2H-benzo[b][1,4]thiazin-3(4H)-one | Me (N) | H | Me | Me | 3-SO₂NH₂ |
| VII-34 | 2H-benzo[b][1,4]thiazin-3(4H)-one | Me (N) | H | Me | — | 4-SO₂NH₂ |
| VII-35 | 2H-benzo[b][1,4]thiazin-3(4H)-one | Me (N) | H | Me | — | 3-SO₂NH₂ |
| VII-36 | 3,4-dihydro-2H-benzo[b][1,4]oxazin-6-yl | 3-oxo | H | F | 4-Me | 3-SO₂NH₂ |
| VII-37 | 3,4-dihydro-2H-benzo[b][1,4]oxazin-6-yl | 2,2-diMe, 3-oxo | H | F | 3-OMe | 4-SO₂NHMe |
| VII-38 | 3,4-dihydro-2H-benzo[b][1,4]oxazin-6-yl | 2,2-diF, 3-oxo | H | F | 4-OMe-5-Me | 3-SO₂NH₂ |
| VII-39 | 3,4-dihydro-2H-benzo[b][1,4]oxazin-6-yl | 2,2-diMe, 3-oxo | H | NH₂ | — | 3-SO₂NH₂ |
| VII-40 | 3,4-dihydro-2H-benzo[b][1,4]oxazin-6-yl | 3-oxo, 4-Me | H | F | — | 4-SO₂NH₂ |
| VII-41 | 3,4-dihydro-2H-benzo[b][1,4]oxazin-6-yl | 3-oxo, 4-Me | H | F | — | 3-SO₂NH₂ |
| VII-42 | 3,4-dihydro-2H-benzo[b][1,4]oxazin-6-yl | 2,2,-diMe, 3-oxo, 4-Me | H | F | — | 3-SO₂NH₂ |
| VII-43 | 3,4-dihydro-2H-benzo[b][1,4]oxazin-6-yl | 2,2-diMe, 3-oxo, 4-Me | H | F | — | 4-SO₂NH₂ |
| VII-44 | 3,4-dihydro-2H-benzo[b][1,4]thiazin-6-yl | 3-oxo | H | F | 4-Me | 3-SO₂NH₂ |
| VII-45 | 3,4-dihydro-2H-benzo[b][1,4]thiazin-6-yl | 3-oxo, 4-Me | H | F | 4-Me | 3-SO₂NH₂ |
| VII-46 | 3,4-dihydro-2H-benzo[b][1,4]thiazin-6-yl | 3-oxo, 4-Me | NC—CH₂— | F | 4-Me | 3-SO₂NH₂ |
| VII-47 | 3,4-dihydro-2H-benzo[b][1,4]thiazin-6-yl | 3-oxo, 4-Me | NC—CH₂— | F | — | 4-SO₂NH₂ |
| VII-48 | 3,4-dihydro-2H-benzo[b][1,4]thiazin-6-yl | 3-oxo, 4-Me | H | F | — | 4-SO₂NH₂ |
| VII-49 | 3,4-dihydro-2H-benzo[b][1,4]thiazin-6-yl | 3-oxo, 4-Me | H | F | — | 3-SO₂NH₂ |
| VII-50 | 3,4-dihydro-2H-benzo[b][1,4]thiazin-6-yl | 3-oxo, 4-Me | H | F | — | 4-SO₂-piperidin-1-yl |
| VII-51 | 3,4-dihydro-2H-pyrido[3,2-b][1,4]oxazin-6-yl | 2,2,-diMe, 3-oxo | H | F | — | 3-SO₂NH₂ |

TABLE VII-continued

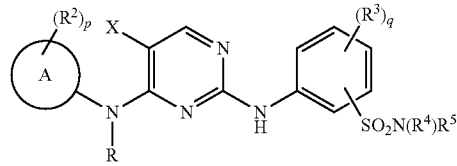

| # | A | (R²)ₚ | R | X | (R³)_q | NR⁴R⁵ |
|---|---|---|---|---|---|---|
| VII-52 | 3,4-dihydro-2H-pyrido[3,2-b][1,4]oxazin-6-yl | 3-oxo | H | F | — | 4-SO₂NH₂ |
| VII-53 | benzofuran-5-yl | 2-CN | H | F | 4-Me | 3-SO₂NH₂ |
| VII-54 | benzofuran-5-yl | 2-C(O)NH₂ | H | F | — | 3-SO₂NH₂ |
| VII-55 | benzomorpholin-6-yl | 1-((pyridine-3-yl)-CH₂)— | H | F | — | 3-SO₂NH₂ |
| VII-56 | benzomorpholin-6-yl | 1-((pyridine-3-yl)-CH₂)— | H | F | 4-Me | 3-SO₂NH₂ |
| VII-57 | benzothiophen-5-yl | — | H | F | 4-Me | 3-SO₂NH₂ |
| VII-58 | benzothiophen-5-yl | — | H | F | — | 3-SO₂NH₂ |
| VII-59 | chroman-6-yl | 4-NHAc | H | F | — | 4-SO₂NH₂ |
| VII-60 | indolin-5-yl | 1-(methylsulfonyl) | H | F | — | 3-SO₂NH₂ |
| VII-61 | indolin-5-yl | 1-(methylsulfonyl) | H | F | 4-Me | 3-SO₂NH₂ |
| VII-62 | indolin-5-yl | 1-(methylsulfonyl) | H | F | 4-Me | 3-SO₂NHMe |
| VII-63 | indolin-5-yl | 1-(methylsulfonyl) | H | F | — | 4-SO₂NH₂ |
| VII-64 | quinolin-2-yl | — | H | F | 4-Me | 3-SO₂NH₂ |
| VII-65 | quinolin-3-yl | — | H | F | 4-Me | 3-SO₂NH₂ |
| VII-66 | quinolin-3-yl | — | H | F | — | 3-SO₂NH₂ |
| VII-67 | quinolin-5-yl | — | H | F | 4-Me | 3-SO₂NH₂ |
| VII-68 | quinolin-5-yl | — | H | F | — | 3-SO₂NH₂ |
| VII-69 | quinolin-6-yl | — | H | F | 4-Me | 3-SO₂NH₂ |
| VII-70 | quinolin-6-yl | — | H | F | — | 3-SO₂NH₂ |
| VII-71 | quinolin-6-yl | 2-Me | H | F | 4-Me | 3-SO₂NH₂ |
| VII-72 | quinolin-6-yl | 2-Me | H | F | — | 3-SO₂NH₂ |
| VII-73 | quinolin-6-yl | 2-OH-4-Me | H | F | 4-Me | 3-SO₂NH₂ |
| VII-74 | quinolin-6-yl | 2-OH-4-Me | H | F | — | 3-SO₂NH₂ |
| VII-75 | quinolin-6-yl | 2-dimethylamino | H | F | 4-Me | 3-SO₂NH₂ |
| VII-76 | quinolin-6-yl | 2-dimethylamino | H | F | — | 3-SO₂NH₂ |
| VII-77 | quinolin-8-yl | — | H | F | 4-Me | 3-SO₂NH₂ |
| VII-78 | quinolin-8-yl | — | H | F | — | 3-SO₂NH₂ |
| VII-79 | quinolin-8-yl | — | H | F | 4-F | 3-SO₂NH₂ |
| VII-80 | quinolin-8-yl | 2-Me | H | F | 4-Me | 3-SO₂NH₂ |
| VII-81 | quinolin-8-yl | 2-Me | H | F | — | 3-SO₂NH₂ |
| VII-82 | bicyclo[2.2.1]hept-1-en-4-yl | 5-C(O)NH₂ | H | F | 4-Me | 3-SO₂NH₂ |
| VII-83 | bicyclo[2.2.1]hept-1-en-4-yl | 5-C(O)NH₂ | H | F | 4-OMe-5-Me | 3-SO₂NH₂ |

TABLE VIII

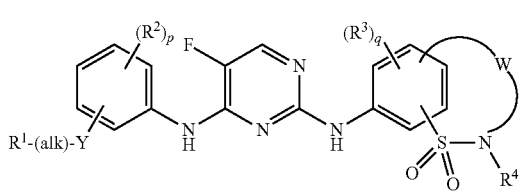

| # | R¹— | -alk-Y— | (R²)ₚ | (R³)_q | SO₂ position | R⁴ | W | W position |
|---|---|---|---|---|---|---|---|---|
| VIII-1 | 4-(5-methylisoxazol-3-yl)— | —CH₂—O— | — | — | 3 | H | —C(O)— | 4 |
| VIII-2 | 4-NC— | —CH₂CH₂— | 3-F | 5-Me | 3 | H | —CH=N— | 4 |
| VIII-3 | — | — | 3-Cl-4-MeO | 5-Me | 3 | H | —CH=N— | 4 |

TABLE IX

Structure: $R^1$-(alk)-Y attached to ring A (with $(R^2)_p$), connected via NH to a 5-fluoropyrimidine, connected via NH to a phenyl ring bearing $(R^3)_q$ and $SO_2N(R^4)R^5$.

| # | A | $R^1$-alk-Y | $(R^2)_p$ | $(R^3)_q$ | $SO_2NR^4R^5$ |
|---|---|---|---|---|---|
| IX-1 | 1H-indol-5yl | — | 1-prop-2-ynyl | 4-Me | 3-SO$_2$NH$_2$ |
| IX-2 | 1H-indol-5yl | — | 1-prop-2-ynyl | — | 3-SO$_2$NH$_2$ |
| IX-3 | 1H-indol-6-yl | — | 1-prop-2-ynyl | 4-Me | 3-SO$_2$NH$_2$ |
| IX-4 | 1H-indol-6-yl | — | 1-prop-2-ynyl | — | 3-SO$_2$NH$_2$ |
| IX-5 | indol-5-yl | 1-(NC—CH$_2$)— | — | — | 3-SO$_2$NH$_2$ |
| IX-6 | indol-5-yl | 1-(NC—CH$_2$)— | — | — | 4-SO$_2$NH$_2$ |
| IX-7 | indol-5-yl | 1-(NC—CH$_2$)— | — | 4-Cl | 3-SO$_2$NH$_2$ |
| IX-8 | indol-5-yl | 1-(NC—CH$_2$)— | — | 4-Me | 3-SO$_2$NH$_2$ |
| IX-9 | 1H-indol-6-yl | — | 3-C(O)NH$_2$ | 4-Me | 3-SO$_2$NH$_2$ |
| IX-10 | 1H-indol-6-yl | — | 3-C(O)NH$_2$ | 4-Cl | 3-SO$_2$NH$_2$ |
| IX-11 | 1H-indol-6-yl | 3-(NC—CH$_2$)— | — | 4-Me | 3-SO$_2$NH$_2$ |
| IX-12 | 1H-indol-6-yl | 3-(NC—CH$_2$)— | — | — | 3-SO$_2$NH$_2$ |
| IX-13 | 1H-indol-5-yl | 3-(NC—CH$_2$)— | — | — | 3-SO$_2$NH$_2$ |
| IX-14 | 1H-indol-5-yl | 3-(NC—CH$_2$)— | — | 4-Me | 3-SO$_2$NH$_2$ |
| IX-15 | 1H-indol-7-yl | 3-(NC—CH$_2$)— | — | — | 3-SO$_2$NH$_2$ |
| IX-16 | 1H-indol-7-yl | 3-(NC—CH$_2$)— | — | 4-Me | 3-SO$_2$NH$_2$ |
| IX-17 | 1H-indol-6-yl | 3-(NC—CH$_2$)— | — | 4-(4-Me-piperazin-1-yl) | 3-SO$_2$NH$_2$ |
| IX-18 | 1H-indol-7-yl | 3-(NC—CH$_2$)— | — | 4-(4-Me-piperazin-1-yl) | 3-SO$_2$NH$_2$ |
| IX-19 | 1H-indol-6-yl | 3-(NC—CH$_2$)— | — | 4-Me | 3-SO$_2$NH(1-methylpiperadin-4-yl) |
| IX-20 | indol-5-yl | — | 1-Me-3-(NC—CH$_2$)— | 4-Me | 3-SO$_2$NH$_2$ |
| IX-21 | benzofuran-5-yl | 2-NC | — | 4-Cl | 3-SO$_2$NH$_2$ |
| IX-22 | benzofuran-5-yl | 2-NC | — | 4-isopropyl | 3-SO$_2$NH$_2$ |
| IX-23 | phenyl | 4-(4-acetyl-piperazin-1-yl)-C$^O$— | — | — | 3-SO$_2$NH$_2$ |
| IX-24 | phenyl | 4-(4-acetyl-piperazin-1-yl)-C$^O$— | — | 4-Me | 3-SO$_2$NH$_2$ |
| IX-25 | phenyl | 4-(4-acetyl-piperazin-1-yl)-C$^O$— | — | 4-Me | 3-SO$_2$NHMe |
| IX-26 | phenyl | 4-(4-acetyl-piperazin-1-yl)-C$^O$— | — | — | 4-SO$_2$NH$_2$ |
| IX-27 | phenyl | 4-(4-acetyl-piperazin-1-yl)-C$^O$— | — | 4-Me | 3-SO$_2$NH$_2$ |
| IX-28 | phenyl | 4-(4-acetyl-piperazin-1-yl)-C$^O$— | — | — | 3-SO$_2$NH$_2$ |
| IX-29 | phenyl | 4-(4-methylsulfonyl-piperazin-1-yl)-C$^O$— | — | — | 3-SO$_2$NH$_2$ |
| IX-30 | phenyl | 4-(4-methylsulfonyl-piperazin-1-yl)-C$^O$— | — | 4-Me | 3-SO$_2$NH$_2$ |
| IX-31 | phenyl | 4-(4-methylsulfonyl-piperazin-1-yl)-C$^O$— | — | 4-Me | 3-SO$_2$NHMe |
| IX-32 | phenyl | 4-(4-methylsulfonyl-piperazin-1-yl)-C$^O$— | — | — | 4-SO$_2$NH$_2$ |
| IX-33 | phenyl | 4-(thiomorpholin-1-yl)-C$^O$— | — | 4-Me | 3-SO$_2$NHMe |
| IX-34 | phenyl | 4-(thiomorpholin-1-yl)-C$^O$— | — | — | 3-SO$_2$NH$_2$ |
| IX-35 | phenyl | 4-(thiomorpholin-1-yl)-C$^O$— | — | 4-Me | 3-SO$_2$NH$_2$ |
| IX-36 | phenyl | 4-(thiomorpholin-1-yl)-C$^O$— | — | — | 4-SO$_2$NH$_2$ |
| IX-37 | phenyl | 4-(S,S-dioxo-thiomorpholin-1-yl)-C$^O$— | — | — | 3-SO$_2$NH$_2$ |
| IX-38 | phenyl | 4-(S,S-dioxo-thiomorpholin-1-yl)-C$^O$— | — | 4-Me | 3-SO$_2$NH$_2$ |
| IX-39 | phenyl | 4-(S,S-dioxo-thiomorpholin-1-yl)-C$^O$— | — | 4-Me | 3-SO$_2$NHMe |
| IX-40 | phenyl | 4-(S,S-dioxo-thiomorpholin-1-yl)-C$^O$— | — | — | 4-SO$_2$NH$_2$ |
| IX-41 | phenyl | 4-CH$_3$C$^O$SCH$_2$C$^O$— | — | — | 4-SO$_2$NH$_2$ |
| IX-42 | phenyl | 4-CH$_3$C$^O$SCH$_2$C$^O$— | — | — | 3-SO$_2$NH$_2$ |
| IX-43 | phenyl | 4-CH$_3$C$^O$SCH$_2$C$^O$— | — | 4-Me | 3-SO$_2$NH$_2$ |
| IX-44 | phenyl | 4-(4-Me-piperazin-1-yl)- | 3,5-di-Me | — | 4-SO$_2$NH$_2$ |
| IX-45 | pyrrolidin-3-yl | 1- —CH$_2$C$^O$— | — | 4-Me | 3-SO$_2$NH$_2$ |
| IX-46 | thiophen-2-yl | 5-MeOC$^O$— | — | 4-Me | 3-SO$_2$NH$_2$ |
| IX-47 | thiophen-2-yl | 5-MeOC$^O$— | — | — | 3-SO$_2$NH$_2$ |
| IX-48 | thiophen-2-yl | 5-MeOC$^O$— | — | 4-F | 3-SO$_2$NH$_2$ |
| IX-49 | thiophen-2-yl | 5-MeOC$^O$— | — | — | 4-SO$_2$NH$_2$ |
| IX-50 | phenyl | — | 3,4-di-Ome | 3-OMe | 4-SO$_2$NHMe |
| IX-51 | phenyl | — | 3,5-di-OMe | 3-OMe | 4-SO$_2$NHMe |
| IX-52 | phenyl | — | 3-CF$_3$-4-Cl | 3-OMe | 4-SO$_2$NHMe |
| IX-53 | phenyl | — | 3-Cl-4-OCF$_3$ | 3-OMe | 4-SO$_2$NHMe |
| IX-54 | phenyl | 4-pyridin-2-yl-CH$_2$—O— | 3-Cl | 4-Me | 3-SO$_2$NHMe |

TABLE X

| # | Structure |
|---|---|
| X-1 | (3,4-dichlorophenyl)amino-pyrimidine-4-carboxylate methyl ester with 2-methoxy-5-(N,N-diethylsulfamoyl)phenylamino substituent |
| X-2 | 2,2-dimethyl-3-oxo-3,4-dihydro-2H-benzo[1,4]oxazin-6-ylamino-pyrimidine-4-carboxylate methyl ester with 2-methoxy-5-(N,N-diethylsulfamoyl)phenylamino substituent |
| X-3 | 5-fluoro-N4-((2-methyl-1H-indol-6-yl)methyl)-N2-(3-sulfamoylphenyl)pyrimidine-2,4-diamine |

TABLE XI

| CAS Reg. No. | Structure |
|---|---|
| 845817-97-2 | N4-(4-chloro-3-(trifluoromethyl)phenyl)-5-fluoro-N2-(4-methoxy-2-(N-methylsulfamoyl)phenyl)pyrimidine-2,4-diamine |
| 841290-42-4 | N4-(2,2-dimethyl-3-oxo-3,4-dihydro-2H-benzo[1,4]oxazin-6-yl)-5-fluoro-N2-(4-methoxy-2-(N-methylsulfamoyl)phenyl)pyrimidine-2,4-diamine |
| 841290-41-3 | N4-(2,3-dihydrobenzo[1,4]dioxin-6-yl)-5-fluoro-N4-methyl-N2-(4-methoxy-2-(N-methylsulfamoyl)phenyl)pyrimidine-2,4-diamine |

D. Methods of the Invention

The present invention provides 2,4-substituted pyrimidinediamine compounds and prodrugs thereof, as described herein, for use in therapy for the conditions as described herein. The present invention further provides use of the compounds of the present invention in the manufacture of a medicament for the treatment of conditions in which targeting of the JAK pathway or inhibition of JAK kinases, particularly JAK3, may be therapeutically useful. These include conditions where the function of lymphocytes, macrophages, or mast cells is involved. Conditions in which targeting of the JAK pathway or inhibition of the JAK kinases, particularly JAK3 may be therapeutically useful include, leukemia, lymphoma, transplant rejection (e.g. pancreas islet transplant rejection), bone marrow transplant applications (e.g. graft-versus-host disease)), autoimmune diseases (e.g. rheumatoid arthritis, etc.), inflammation (e.g. asthma, etc.) and other conditions as described in greater detail herein.

As noted previously, numerous conditions can be treated using the 2,4-substituted pyrimidinediamine compounds, prodrugs thereof, and methods of treatment as described herein. As used herein, and as well understood in the art, "treatment" is an approach for obtaining beneficial or desired results, including clinical results. For the purposes of this invention, beneficial or desired results can include one or more, but are not limited to, alleviation or amelioration of one or more symptoms, diminishment of extent of a condition, including a disease, stabilized (i.e., not worsening) state of a condition, including diseases, preventing spread of disease, delay or slowing of condition, including disease, progression, amelioration or palliation of the condition, including disease, state, and remission (whether partial or total), whether detectable or undetectable. Preferred are compounds that are potent and can be administered locally at very low doses, thus minimizing systemic adverse effects.

The compounds described herein are potent and selective inhibitors of JAK kinases, and particularly selective for cytokine signaling pathways containing JAK3. As a consequence of this activity, the compounds may be used in a variety of in vitro, in vivo and ex vivo contexts to regulate or inhibit JAK kinase activity, signaling cascades in which JAK kinases play a role, and the biological responses effected by such signaling cascades. For example, in one embodiment, the compounds may be used to inhibit JAK kinase, either in vitro or in vivo, in virtually any cell type expressing the JAK kinase. For example, in hematopoietic cells, in which, for example JAK3 is predominantly expressed. They may also be used to regulate signal transduction cascades in which JAK kinases, particularly JAK3, play a role. Such JAK-dependent signal transduction cascades include, but are not limited to, the signaling cascades of cytokine receptors that involve the common gamma chain, such as, for example, the IL-4, IL-7, IL-5, IL-9, IL-15 and IL-21, or IL-2, IL-4, IL-7, IL-9, IL-15 and IL-21 receptor signaling cascades. The compounds may also be used in vitro or in vivo to regulate, and in particular inhibit, cellular or biological responses affected by such JAK-dependent signal transduction cascades. Such cellular or biological responses include, but are not limited to, IL-4/ramos CD23 upregulation, IL-2 mediated T-cell proliferation, etc. Importantly, the compounds may be used to inhibit JAK kinases in vivo as a therapeutic approach towards the treatment or prevention of diseases mediated, either wholly or in part, by a JAK kinase activity (referred to herein as "JAK kinase mediated diseases"). Non-limiting examples of JAK kinase mediated diseases that may be treated or prevented with the compounds, include, but are not limited to allergies, asthma, autoimmune diseases such as transplant rejection (e.g., kidney, heart, lung, liver, pancreas, skin; host versus graft reaction (HVGR), graft versus host reaction (GVHR) etc.), rheumatoid arthritis, and amyotrophic lateral sclerosis, T-cell mediated autoimmune diseases such as multiple sclerosis, psoraiasis and Sjogren's syndrome, Type II inflammatory diseases such as vascular inflammation (including vasculitis, arteritis, atherosclerosis and coronary artery disease), diseases of the central nervous system such as stroke, pulmonary diseases such as bronchitis obliteraus and primary pulmonary hypertension, and solid, delayed Type IV hypersensitivity reactions, and hematologic malignancies such as leukemia and lymphomas.

Examples of diseases that are mediated, at least in part, by JAK kinases that can be treated or prevented according to the methods include, but are not limited to, allergies, asthma, autoimmune diseases such as transplant rejection (e.g., kidney, heart, lung, liver, pancreas, skin, host versus graft reaction (HVGR), etc.), rheumatoid arthritis, and amyotrophic lateral sclerosis, multiple sclerosis, psoriasis and Sjogren's syndrome, Type II inflammatory disease such as vascular inflammation (including vasculitis, ateritis, atherosclerosis and coronary artery disease), diseases of the central nervous system such as stroke, pulmonary diseases such as bronchitis obliterous and primary and primary pulmonary hypertension, delayed or cell-mediated, Type IV hypersensitivity and solid and hematologic malignancies such as leukemias and lyphomas.

JAK kinase mediated disease include, for example, cell proliferative disorders, such as hematopoietic neoplasms, including lymphoid neoplasms, and myeloid neoplasms. "Cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is neoplasm or tumor, which is an abnormal growth of tissue. Cancer refers to any of various malignant neoplasms characterized by the proliferation of cells that have the capability to invade surrounding tissue and/or metastasize to new colonization sites.

"Hematopoietic neoplasm" refers to a cell proliferative disorder arising from cells of the hematopoietic lineage. Generally, hematopoiesis is the physiological process whereby undifferentiated cells or stem cells develop into various cells found in the peripheral blood. In the initial phase of development, hematopoietic stem cells, typically found in the bone marrow, undergo a series of cell divisions to form multipotent progenitor cells that commit to two main developmental pathways: the lymphoid lineage and the myeloid lineage. The committed progenitor cells of the myeloid lineage differentiate into three major sub-branches comprised of the erythroid, megakaryocyte, and granulocyte/monocyte developmental pathways. An additional pathway leads to formation of dendritic cells, which are involved in antigen presentation. The erythroid lineage gives rise to red blood cells while the megakaryocytic lineage gives rise to blood platelets. Committed cells of the granulocyte/monocyte lineage split into granulocyte or monocyte developmental pathways, the former pathway leading to formation of neutrophils, eosinophils, and basophils and the latter pathway giving rise to blood monocytes and macrophages.

Committed progenitor cells of the lymphoid lineage develop into the B cell pathway, T cell pathway, or the non-T/B cell pathway. Similar to the myeloid lineage, an additional lymphoid pathway appears to give rise to dendritic cells involved in antigen presentation. The B cell progenitor cell develops into a precursor B cell (pre-B), which differentiates into B cells responsible for producing immunoglobulins. Progenitor cells of the T cell lineage differentiate into precursor T cells (pre-T) that, based on the influence of certain cytokines, develop into cytotoxic or helper/suppressor T cells involved in cell mediated immunity. Non-T/B cell pathway leads to generation of natural killer (NK) cells. Neoplasms of hematopoietic cells can involve cells of any phase of hematopoiesis, including hematopoietic stem cells, multipotent progenitor cells, oligopotent committed progenitor cells, precursor cells, and mature differentiated cells. The categories of hematopoietic neoplasms can generally follow the descriptions and diagnostic criteria employed by those of skill in the art (see, e.g., International Classification of Disease and Related Health Problems (ICD 10), World Health Organization (2003)). Hematopoietic neoplasms can also be characterized based on the molecular features, such as cell surface markers and gene expression profiles, cell phenotype exhibited by the aberrant cells, and/or chromosomal aberrations (e.g., deletions, translocations, insertions, etc.) characteristic of certain hematopoietic neoplasms, such as the Philadelphia chromosome found in chronic myelogenous leukemia. Other classifications include National Cancer Institute Working Formulation (Cancer, 1982, 49:2112-2135) and Revised European-American Lymphoma Classification (REAL).

"Lymphoid neoplasm" refers a proliferative disorder involving cells of the lymphoid lineage of hematopoiesis. Lymphoid neoplasms can arise from hematopoietic stem cells as well as lymphoid committed progenitor cells, precursor cells, and terminally differentiated cells. These neoplasms can be subdivided based on the phenotypic attributes of the aberrant cells or the differentiated state from which the abnormal cells arise. Subdivisions include, among others, B cell neoplasms, T cell neoplasms, NK cell neoplasms, and Hodgkin's lymphoma.

"Myeloid neoplasm" refers to proliferative disorder of cells of the myeloid lineage of hematopoiesis. Neoplasms can arise from hematopoietic stem cells, myeloid committed progenitor cells, precursor cells, and terminally differentiated cells. Myeloid neoplasms can be subdivided based on the phenotypic attributes of the aberrant cells or the differentiated state from which the abnormal cells arise. Subdivisions include, among others, myeloproliferative diseases, myelodysplastic/myeloproliferative diseases, myelodysplastic syndromes, acute myeloid leukemia, and acute biphenotypic leukemia.

Generally, cell proliferative disorders treatable with the compounds disclosed herein relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, among others, breast cancer, ovarian cancer, renal cancer, gastrointestinal cancer, kidney cancer, bladder cancer, pancreatic cancer, lung squamous carcinoma, and adenocarcinoma.

In some embodiments, the cell proliferative disorder treated is a hematopoietic neoplasm, which is aberrant growth of cells of the hematopoietic system. Hematopoietic malignancies can have its origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. For instance, cells capable of developing specific subtypes of acute myeloid leukemia (AML) upon transplantation display the cell surface markers of hematopoietic stem cells, implicating hematopoietic stem cells as the source of leukemic cells. Blast cells that do not have a cell marker characteristic of hematopoietic stem cells appear to be incapable of establishing tumors upon transplantation (Blaire et al., 1997, *Blood* 89:3104-3112). The stem cell origin of certain hematological malignancies also finds support in the observation that specific chromosomal abnormalities associated with particular types of leukemia can be found in normal cells of hematopoietic lineage as well as leukemic blast cells. For instance, the reciprocal translocation t(9q34;22q11) associated with approximately 95% of chronic myelogenous leukemia appears to be present in cells of the myeloid, erythroid, and lymphoid lineage, suggesting that the chromosomal aberration originates in hematopoietic stem cells. A subgroup of cells in certain types of CML displays the cell marker phenotype of hematopoietic stem cells.

Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition. Moreover, some chromosomal aberrations associated with subtypes of leukemia are not found in the cell population with a marker phenotype of hematopoietic stem cells, but are found in a cell population displaying markers of a more differentiated state of the hematopoietic pathway (Turhan et al., 1995, *Blood* 85:2154-2161). Thus, while committed progenitor cells and other differentiated cells may have only a limited potential for cell division, leukemic cells may have acquired the ability to grow unregulated, in some instances mimicking the self-renewal characteristics of hematopoietic stem cells (Passegue et al., *Proc. Natl. Acad. Sci. USA,* 2003, 100:11842-9).

In some embodiments, the hematopoietic neoplasm treated is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and Nk-cell neoplasms are further subdivided into precursor T-cell neoplasm and mature (peripheral) T-cell neoplasms. Exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with the compounds include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma. In various embodiments, any of the lymphoid neoplasms that are associated with aberrant Syk activity can be treated with the Syk inhibitory compounds.

In some embodiments, the hematopoietic neoplasm treated is a myeloid neoplasm. This group comprises a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (e.g., Philadelphia chromosome positive (t(9;22)(qq34;q11)), chronic neutrophilic leukemia, chronic eosinophilic leukemia/hypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome with t(9;12)(q22;p12) (TEL-Syk fusion; see, e.g., Kuno et al., 2001, *Blood* 97:1050). In various embodiments, any of the myeloid neoplasms that are associated with aberrant Syk activity can be treated with the Syk inhibitory compounds.

In some embodiments, the Syk inhibitory compounds can be used to treat Acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8;21)(q22;q22), AML1(CBF-alpha)/ETO, Acute promyelocytic leukemia (AML with t(15;17)(q22;q11-12) and variants, PML/RAR-alpha), AML with abnormal bone marrow eosinophils (inv(16)(p13q22) or t(16;16)(p13;q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, Acute myelomonocytic leukemia, Acute monocytic leukemia, Acute erythroid leukemia, Acute megakaryocytic leukemia, Acute basophilic leukemia, and Acute panmyelosis with myelofibrosis.

Jak mediated diseases also include a variety of autoimmune diseases. Such autoimmune disease include, but are not limited to, those autoimmune diseases that are frequently designated as single organ or single cell-type autoimmune disorders and those autoimmune disease that are frequently designated as involving systemic autoimmune disorder. Non-limiting examples of diseases frequently designated as single organ or single cell-type autoimmune disorders include: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy. Non-limiting examples of diseases often designated as involving systemic autoimmune disorder include: systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid. Additional autoimmune diseases, which can be β-cell (humoral) based or T-cell based, include Cogan's syndrome, ankylosing spondylitis, Wegener's granulomatosis, autoimmune alopecia, Type I or juvenile onset diabetes, and thyroiditis.

The types of autoimmune diseases that may be treated or prevented with JAK inhibitory compounds, as described herein, generally include those disorders involving tissue injury that occurs as a result of a humoral and/or cell-mediated response to immunogens or antigens of endogenous and/or exogenous origin. Such diseases are frequently referred to as diseases involving the nonanaphylactic (i.e., Type II, Type III and/or Type IV) hypersensitivity reactions.

Type I hypersensitivity reactions generally result from the release of pharmacologically active substances, such as histamine, from mast and/or basophil cells following contact with a specific exogenous antigen. Such Type I reactions play a role in numerous diseases, including allergic asthma, allergic rhinitis, etc. Type II hypersensitivity reactions (also referred to as cytotoxic, cytolytic complement-dependent or cell-stimulating hypersensitivity reactions) result when immunoglobulins react with antigenic components of cells or tissue, or with an antigen or hapten that has become intimately coupled to cells or tissue. Diseases that are commonly associated with Type II hypersensitivity reactions include, but are not limited, to autoimmune hemolytic anemia, erythroblastosis fetalis and Goodpasture's disease. Type III hypersensitivity reactions, (also referred to as toxic complex, soluble complex, or immune complex hypersensitivity reactions) result from the deposition of soluble circulating antigen-immunoglobulin complexes in vessels or in tissues, with accompanying acute inflammatory reactions at the site of immune complex deposition. Non-limiting examples of prototypical Type III reaction diseases include the Arthus reaction, rheumatoid arthritis, serum sickness, systemic lupus erythematosis, certain types of glomerulonephritis, multiple sclerosis and bullous pemphingoid. Type IV hypersensitivity reactions (frequently called cellular, cell-mediated, delayed, or tuberculin-type hypersensitivity reactions) are caused by sensitized T-lymphocytes which result from contact with a specific antigen. Non-limiting examples of diseases cited as involving Type IV reactions are contact dermatitis and allograft rejection.

Autoimmune diseases associated with any of the above nonanaphylactic hypersensitivity reactions may be treated or prevented with inhibitors of JAK kinase according to the invention described herein. In particular, the methods may be used to treat or prevent those autoimmune diseases frequently characterized as single organ or single cell-type autoimmune disorders including, but not limited to: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, as well as those autoimmune diseases frequently characterized as involving systemic autoimmune disorder, which include but are not limited to: systemic lupus erythematosis (SLE), rheumatoid arthritis, Sjogren's syndrome, Reiter's syndrome, polymyositis-dermatomyositis, systemic sclerosis, polyarteritis nodosa, multiple sclerosis and bullous pemphigoid.

It will be appreciated by skilled artisans that many of the above-listed autoimmune diseases are associated with severe symptoms, the amelioration of which provides significant therapeutic benefit even in instances where the underlying autoimmune disease may not be ameliorated.

JAK mediated disease also include inflammation and inflammatory diseases (e.g., osteoarthritis, inflammatory bowel disease, ulcerative colitis, Crohn's disease, idiopathic inflammatory bowel disease, irritable bowel syndrome, spastic colon, etc.), low grade scarring (e.g., scleroderma, increased fibrosis, keloids, post-surgical scars, pulmonary fibrosis, vascular spasms, migraine, reperfusion injury and post myocardial infarction), and sicca complex or syndrome. All of these diseases may be treated or prevented according to the methods described herein.

In one embodiment, this invention provides a method of inhibiting an activity of a JAK kinase, comprising contacting the JAK kinase with an amount of a compound effective to inhibit an activity of the JAK kinase wherein the compound is selected from the compounds of this invention, as described herein, and the compounds of Table XI (CAS Reg. No. 845817-97-2, CAS Reg. No. 841290-42-4, and CAS Reg. No. 841290-41-3).

In another embodiment, this invention provides a method of inhibiting an activity of a JAK kinase, comprising contacting in vitro a JAK3 kinase with an amount of a compound effective to inhibit an activity of the JAK kinase wherein the compound is selected from the compounds of the invention, as described herein (including compounds described in Tables I-X), and the compounds of Table XI (CAS Reg. No. 845817-97-2, CAS Reg. No. 841290-42-4, and CAS Reg. No. 841290-41-3). In certain embodiments of the methods described herein, the method is carried out in vivo.

In a specific embodiment, the compounds can be used to treat and/or prevent rejection in organ and/or tissue transplant recipients (i.e., treat and/or prevent allograft rejection). Allografts may be rejected through either a cell-mediated or humoral immune reaction of the recipient against transplant (histocompatibility) antigens present on the membranes of the donor's cells. The strongest antigens are governed by a complex of genetic loci termed human leukocyte group A (HLA) antigens. Together with the ABO blood groups antigens, they are the chief transplantation antigens detectable in humans. Preferably, the compounds of the invention are used in conjunction with transplant of a kidney, heart, lung, liver, pancreas, small intestine, large intestine, skin, in order to prevent or ameliorate a host versus graft reaction (HVGR) or a graft versus host reaction (GVHR).

Rejection following transplantation can generally be broken into three categories: hyperacute, occurring hours to days following transplantation; acute, occurring days to months following transplantation; and chronic, occurring months to years following transplantation.

Hyperacute rejection is caused mainly by the production of host antibodies that attack the graft tissue. In a hyperacute rejection reaction, antibodies are observed in the transplant vascular very soon after transplantation. Shortly thereafter, vascular clotting occurs, leading to ischemia, eventual necrosis and death. The graft infarction is unresponsive to known immunosuppressive therapies. Because HLA antigens can be identified in vitro, pre-transplant screening is used to significantly reduce hyperacute rejection. As a consequence of this screening, hyperacute rejection is relative uncommon today.

Acute rejection is thought to be mediated by the accumulation of antigen specific cells in the graft tissue. The T-cell-mediated immune reaction against these antigens (i.e., HVGR or GVHR) is the principle mechanism of acute rejection. Accumulation of these cells leads to damage of the graft tissue. It is believed that both CD4+ helper T-cells and CD8+ cytotoxic T-cells are involved in the process, and that the antigen is presented by donor and host dendritic cells. The CD4+ helper T-cells help recruit other effector cells, such as macrophages and eosinophils, to the graft. Accessing T-cell activation signal transduction cascades (for example, CD28, CD40L and CD2 cascades) are also involved.

The cell-mediated acute rejection may be reversed in many cases by intensifying immunotherapy. After successful reversal, severely damaged elements of the graft heal by fibrosis and the remainder of the graft appears normal. After resolution of acute rejection, dosages of immunosuppressive drugs can be reduced to very low levels.

Chronic rejection, which is a particular problem in renal transplants, often progresses insidiously despite increased immunosuppressive therapy. It is thought to be due, in large part, to cell-mediated Type IV hypersensitivity. The pathologic profile differs from that of acute rejection. The arterial endothelium is primarily involved, with extensive proliferation that may gradually occlude the vessel lumen, leading to ischemia, fibrosis, a thickened intima and atherosclerotic changes. Chronic rejection is mainly due to a progressive obliteration of graft vasculature, and resembles a slow, vasculitic process.

In Type IV hypersensitivity, CD8 cytotoxic T-cells and CD4 helper T cells recognize either intracellular or extracellular synthesized antigen when it is complexed, respectively, with either Class I or Class II MHC molecules. Macrophages function as antigen-presenting cells and release IL-1, which promotes proliferation of helper T-cells. Helper T-cells release interferon gamma and IL-2, which together regulate delayed hyperactivity reactions mediated by macrophage activation and immunity mediated by T cells. In the case of organ transplant, the cytotoxic T-cells destroy the graft cells on contact.

Since JAK kinases play a critical role in the activation of T-cells, the 2,4-substituted pyrimidinediamine compounds described herein can be used to treat and/or prevent many aspects of transplant rejection, and are particularly useful in the treatment and/or prevention of rejection reactions that are mediated, at least in part, by T-cells, such as HVGR or GVHR. The 2,4-substituted pyrimidinediamine compounds can also be used to treat and/or prevent chronic rejection in transplant recipients, and in particular in renal transplant recipients.

In another embodiment, this invention provides a method of treating a T-cell mediated autoimmune disease, comprising administering to a patient suffering from such an autoimmune disease an amount of a compound effective to treat the autoimmune disease wherein the compound is selected from the compounds of the invention, as described herein, and the compounds of Table XI (CAS Reg. No. 845817-97-2, CAS Reg. No. 841290-42-4, and CAS Reg. No. 841290-

41-3). In certain embodiments of the methods the autoimmune disease is multiple sclerosis (MS), psoraisis, or Sjogran's syndrome.

Therapy using the 2,4-substituted pyrimidinediamine compounds described herein can be applied alone, or it can be applied in combination with or adjunctive to other common immunosuppressive therapies, such as, for example, mercaptopurine, corticosteroids such as prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil and azathioprine, and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. These various agents can be used in accordance with their standard or common dosages, as specified in the prescribing information accompanying commercially available forms of the drugs (see also, the prescribing information in the 2006 Edition of *The Physician's Desk Reference*), the disclosures of which are incorporated herein by reference. Azathioprine is currently available from Salix Pharmaceuticals, Inc. under the brand name AZASAN; mercaptopurine is currently available from Gate Pharmaceuticals, Inc. under the brand name PURINETHOL; prednisone and prednisolone are currently available from Roxane Laboratories, Inc.; Methyl prednisolone is currently available from Pfizer; sirolimus (rapamycin) is currently available from Wyeth-Ayerst under the brand name RAPAMUNE; tacrolimus is currently available from Fujisawa under the brand name PROGRAF; cyclosporine is current available from Novartis under the brand dame SANDIMMUNE and Abbott under the brand name GENGRAF; IMPDH inhibitors such as mycophenolate mofetil and mycophenolic acid are currently available from Roche under the brand name CELLCEPT and Novartis under the brand name MYFORTIC; azathioprine is currently available from Glaxo Smith Kline under the brand name IMURAN; and antibodies are currently available from Ortho Biotech under the brand name ORTHOCLONE, Novartis under the brand name SIMULECT (basiliximab) and Roche under the brand name ZENAPAX (daclizumab).

In another embodiment, the 2,4-substituted pyrimidinediamine compounds could be administered either in combination or adjunctively with an inhibitor of a Syk kinase. Syk kinase is a tyrosine kinase known to play a critical role in Fey receptor signaling, as well as in other signaling cascades, such as those involving B-Cell receptor signaling (Tumer et al., (2000), *Immunology Today* 21:148-154) and integrins beta(1), beta (2) and beta (3) in neutrophils (Mocsavi et al., (2002), *Immunity* 16:547-558). For example, Syk kinase plays a pivotal role in high affinity IgE receptor signaling in mast cells that leads to activation and subsequent release of multiple chemical mediators that trigger allergic attacks. However, unlike the JAK kinases, which help regulate the pathways involved in delayed, or cell-mediated Type IV hypersensitivity reactions, Syk kinase helps regulate the pathways involved in immediate IgE-mediated, Type I hypersensitivity reactions. Certain compounds that affect the Syk pathway may or may not also affect the JAK pathways.

Suitable Syk inhibitory compounds are described, for example, in Ser. No. 10/355,543 filed Jan. 31, 2003 (publication no. 2004/0029902); WO 03/063794; Ser. No. 10/631, 029 filed Jul. 29, 2003; WO 2004/014382; Ser. No. 10/903, 263 filed Jul. 30, 2004; PCT/US2004/24716 filed Jul. 30, 2004 (WO005/016893); Ser. No. 10/903,870 filed Jul. 30, 2004; PCT/US2004/24920 filed Jul. 30, 2004; Ser. No. 60/630,808 filed Nov. 24, 2004; Ser. No. 60/645,424 filed Jan. 19, 2005; and Ser. No. 60/654,620, filed Feb. 18, 2005, the disclosures of which are incorporated herein by reference. The 2,4-substituted pyrimidinediamine described herein and Syk inhibitory compounds could be used alone, or in combination with one or more conventional transplant rejection treatments, as described above.

In a specific embodiment, the 2,4-substituted pyrimidinediamine compounds can be used to treat or prevent these diseases in patients that are either initially non-responsive to (resistant), or that become non-responsive to, treatment with a Syk inhibitory compound, or one of the other current treatments for the particular disease. The 2,4-substituted pyrimidinediamine compounds could also be used in combination with Syk inhibitory compounds in patients that are Syk-compound resistant or non-responsive. Suitable Syk-inhibitory compounds with which the 2,4-substituted pyrimidinediamine compounds can be administered are provided supra.

In another embodiment, this invention provides a method of treating a T-cell mediated autoimmune disease, comprising administering to a patient suffering from such an autoimmune disease an amount of a compound effective to treat the autoimmune disease wherein the compound is selected from the compounds of the invention, as described herein, and the compounds of Table XI (CAS Reg. No. 845817-97-2, CAS Reg. No. 841290-42-4, and CAS Reg. No. 841290-41-3) and the compound is administered in combination with, or adjunctively to, a compound that inhibits Syk kinase with an $IC_{50}$ in the range of at least 10 μM.

In another embodiment, this invention provides a method of treating or preventing allograft transplant rejection in a transplant recipient, comprising administering to the transplant recipient an amount of a compound effective to treat or prevent the rejection wherein the compound is selected from the compounds of the invention, as described herein, and the compounds of Table XI (CAS Reg. No. 845817-97-2, CAS Reg. No. 841290-42-4, and CAS Reg. No. 841290-41-3).

In another embodiment, this invention provides a method of treating or preventing allograft transplant rejection in a transplant recipient, in which the rejection is acute rejection, comprising administering to the transplant recipient an amount of a compound effective to treat or prevent the rejection wherein the compound is selected from the compounds of the invention, as described herein, and the compounds of Table XI (CAS Reg. No. 845817-97-2, CAS Reg. No. 841290-42-4, and CAS Reg. No. 841290-41-3).

In another embodiment, this invention provides a method of treating or preventing allograft transplant rejection in a transplant recipient, in which the rejection is chronic rejection, comprising administering to the transplant recipient an amount of a compound effective to treat or prevent the rejection wherein the compound is selected from the compounds of the invention, as described herein, and the compounds of Table XI (CAS Reg. No. 845817-97-2, CAS Reg. No. 841290-42-4, and CAS Reg. No. 841290-41-3).

In another embodiment, this invention provides a method of treating or preventing allograft transplant rejection in a transplant recipient, in which the rejection is mediated by HVGR or GVHR, comprising administering to the transplant recipient an amount of a compound effective to treat or prevent the rejection wherein the compound is selected from the compounds of this invention, as described herein, and the compounds of Table XI (CAS Reg. No. 845817-97-2, CAS Reg. No. 841290-42-4, and CAS Reg. No. 841290-41-3).

In another embodiment, this invention provides a method of treating or preventing allograft transplant rejection in a transplant recipient, in which the allograft transplant is selected from a kidney, a heart, a liver and a lung, comprising administering to the transplant recipient an amount of a compound effective to treat or prevent the rejection wherein the compound is selected from the compounds of this invention, as described herein, and the compounds of Table XI (CAS Reg. No. 845817-97-2, CAS Reg. No. 841290-42-4, and CAS Reg. No. 841290-41-3).

In another embodiment, this invention provides a method of treating or preventing allograft transplant rejection in a transplant recipient, in which the allograft transplant is selected from a kidney, a heart, a liver and a lung, comprising administering to the transplant recipient an amount of a compound effective to treat or prevent the rejection wherein the compound is selected from the compounds of the invention, as described herein, and the compounds of Table XI (CAS Reg. No. 845817-97-2, CAS Reg. No. 841290-42-4, and CAS Reg. No. 841290-41-3), in which the compound is administered in combination with, or adjunctively to, another immunosuppressant.

In another embodiment, this invention provides a method of treating or preventing allograft transplant rejection in a transplant recipient, in which the allograft transplant is selected from a kidney, a heart, a liver and a lung, comprising administering to the transplant recipient an amount of a compound effective to treat or prevent the rejection wherein the compound is selected from the compounds of the invention, as described herein, and the compounds of Table XI (CAS Reg. No. 845817-97-2, CAS Reg. No. 841290-42-4, and CAS Reg. No. 841290-41-3), in which the compound is administered in combination with, or adjunctively to, another immunosuppressant, in which the immunosuppressant is selected from cyclosporine, tacrolimus, sirolimus, an inhibitor of IMPDH, mycophenolate, mycophanolate mofetil, an anti-T-Cell antibody and OKT3.

The 2,4-substituted pyrimidinediamine compounds described herein are cytokine moderators of IL-4 signaling. As a consequence, the 2,4-substituted pyrimidinediamine compounds could slow the response of Type I hypersensitivity reactions. Thus, in a specific embodiment, the 2,4-substituted pyrimidinediamine compounds could be used to treat such reactions, and therefore the diseases associated with, mediated by or caused by such hypersensitivity reactions (for example, allergies), prophylactically. For example, an allergy sufferer could take one or more of the JAK selective compounds described herein prior to expected exposure to allergens to delay the onset or progress, or eliminate altogether, an allergic response.

When used to treat or prevent such diseases, the 2,4-substituted pyrimidinediamine compounds may be administered singly, as mixtures of one or more 2,4-substituted pyrimidinediamine compounds or in mixture or combination with other agents useful for treating such diseases and/or the symptoms associated with such diseases. The 2,4-substituted pyrimidinediamine compounds may also be administered in mixture or in combination with agents useful to treat other disorders or maladies, such as steroids, membrane stabilizers, 5-lipoxygenase (5LO) inhibitors, leukotriene synthesis and receptor inhibitors, inhibitors of IgE isotype switching or IgE synthesis, IgG isotype switching or IgG synthesis, β-agonists, tryptase inhibitors, aspirin, cyclooxygenase (COX) inhibitors, methotrexate, anti-TNF drugs, retuxin, PD4 inhibitors, p38 inhibitors, PDE4 inhibitors, and antihistamines, to name a few. The 2,4-substituted pyrimidinediamine compounds may be administered per se in the form of prodrugs or as pharmaceutical compositions, comprising an active compound or prodrug.

In another embodiment, this invention provides a method of treating or preventing a Type IV hypersensitivity reaction, comprising administering to a subject an amount of a compound of effective to treat or prevent the hypersensitivity reaction wherein the compound is selected from the compounds of this invention, as described herein, and the compounds of Table XI (CAS Reg. No. 845817-97-2, CAS Reg. No. 841290-42-4, and CAS Reg. No. 841290-41-3).

In another embodiment, this invention provides a method of treating or preventing a Type IV hypersensitivity reaction, which is practical prophylactically, comprising administering to a subject an amount of a compound of effective to treat or prevent the hypersensitivity reaction wherein the compound is selected from the compounds of this invention, as described herein, and the compounds of Table XI (CAS Reg. No. 845817-97-2, CAS Reg. No. 841290-42-4, and CAS Reg. No. 841290-41-3) and is administered prior to exposure to an allergen.

In another embodiment, this invention provides a method of inhibiting a signal transduction cascade in which JAK3 kinase plays a role, comprising contacting a cell expressing a receptor involved in such a signaling cascade with a compound wherein the compound is selected from the compounds of this invention, as described herein, and the compounds of Table XI (CAS Reg. No. 845817-97-2, CAS Reg. No. 841290-42-4, and CAS Reg. No. 841290-41-3).

In another embodiment, this invention provides a method of treating or preventing a JAK kinase-mediated disease, comprising administering to a subject an amount of compound effective to treat or prevent the JAK kinase-mediated disease wherein the compound is selected from the compounds of this invention, as described herein, and the compounds of Table XI (CAS Reg. No. 845817-97-2, CAS Reg. No. 841290-42-4, and CAS Reg. No. 841290-41-3).

In another embodiment, this invention provides a method of treating or preventing a JAK kinase-mediated disease, in which the JAK-mediated disease is HVGR or GVHR, comprising administering to a subject an amount of compound effective to treat or prevent the JAK kinase-mediated disease wherein the compound is selected from the compounds of the invention, as described herein, and the compounds of Table XI (CAS Reg. No. 845817-97-2, CAS Reg. No. 841290-42-4, and CAS Reg. No. 841290-41-3).

In another embodiment, this invention provides a method of treating or preventing a JAK kinase-mediated disease, in which the JAK-mediated disease is acute allograft rejection, comprising administering to a subject an amount of compound effective to treat or prevent the JAK kinase-mediated disease wherein the compound is selected from the compounds of the invention, as described herein, and the compounds of Table XI (CAS Reg. No. 845817-97-2, CAS Reg. No. 841290-42-4, and CAS Reg. No. 841290-41-3).

In another embodiment, this invention provides a method of treating or preventing a JAK kinase-mediated disease, in which the JAK-mediated disease is chronic allograft rejection, comprising administering to a subject an amount of compound effective to treat or prevent the JAK kinase-mediated disease wherein the compound is selected from the compounds of the invention, as described herein, and the compounds of Table XI (CAS Reg. No. 845817-97-2, CAS Reg. No. 841290-42-4, and CAS Reg. No. 841290-41-3).

Active compounds of the invention typically inhibit the JAK/Stat pathway. The activity of a specified compound as an inhibitor of a JAK kinase may be assessed in vitro or in vivo. In some embodiments, the activity of a specified compound can be tested in a cellular assay. Suitable assays include assays that determine inhibition of either the phosphorylation activity or ATPase activity of a JAK kinase. Thus, a compound is said to inhibit an activity of a JAK kinase if it inhibits the phosphorylation or ATPase activity of a JAK kinase with an $IC_{50}$ of about 20 µM or less.

One means of assaying for such inhibition is detection of the effect of the 2,4-substituted pyrimidinediamine compounds on the upregulation of downstream gene products. In the Ramos/IL4 assay, B-cells are stimulated with the cytokine Interleukin-4 (IL-4) leading to the activation of the JAK/Stat pathway through phosphorylation of the JAK family kinases, JAK1 and JAK3, which in turn phosphorylate and activate the transcription factor Stat-6. One of the genes upregulated by activated Stat-6 is the low affinity IgE receptor, CD23. To study the effect of inhibitors (e.g., the 2,4-substituted pyrimidinediamine compounds described herein) on the JAK1 and JAK3 kinases, human Ramos B cells are stimulated with human IL-4. Twenty to 24 hours post stimulation, cells are stained for upregulation of CD23 and analyzed using flow cytometry (FACS). A reduction of the amount of CD23 present compared to control conditions indicates the test compound actively inhibits the JAK kinase pathway. An exemplary assay of this type is described in greater detail in Example 41

The activity of the active compounds of the invention may further be characterized by assaying the effect of the 2,4-substituted pyrimidinediamine compounds described herein on the proliferative response of primary human T-cells. In this assay, primary human T-cells derived from peripheral blood and pre-activated through stimulation of the T-cell receptor and CD28, proliferate in culture in response to the cytokine Interleukin-2 (IL-2). This proliferative response is dependent on the activation of JAK1 and JAK3 tyrosine kinases, which phosphorylate and activate the transcription factor Stat-5. The primary human T-cells are incubated with the 2,4-substituted pyrimidinediamine compounds in the presence of IL-2 for 72 hours and at the assay endpoint intracellular ATP concentrations are measured to assess cell viability. A reduction in cell proliferation compared to control conditions is indicative of inhibition of the JAK kinase pathway. An exemplary assay of this type is described in greater detail in Example 42

The activity of the compounds of the invention may additionally be characterized by assaying the effect of the 2,4-substituted pyrimidinediamine compounds described herein on A549 lung epithelial cells and U937 cells. A549 lung epithelial cells and U937 cells up-regulate ICAM-1 (CD54) surface expression in response to a variety of different stimuli. Therefore, using ICAM-1 expression as readout, test compound effects on different signaling pathways can be assessed in the same cell type. Stimulation with IL-1β through the IL-1β receptor activates the TRAF6/NFκB pathway resulting in up-regulation of ICAM-1. IFNγ induces ICAM-1 up-regulation through activation of the JAK1/JAK2 pathway. The up-regulation of ICAM-1 can be quantified by flow cytometry across a compound dose curve and $EC_{50}$, values are calculated. An exemplary assays of this type are described in greater detail in Examples 43 and 44

Active compounds as described herein generally inhibit the JAK kinase pathway with an $IC_{50}$ in the range of about 1 mM or less, as measured in the assays described herein. Of course, skilled artisans will appreciate that compounds which exhibit lower $IC_{50}$s, for example on the order of 100 µM, 75 µM, 50 µM, 40 µM, 30 µM, 20 µM, 15 µM, 10 µM, 5 µM, 1 µM, 500 nM, 100 nM, 10 nM, 1 nM, or even lower, may be particularly useful in therapeutic applications. In instances where activity specific to a particular cell type is desired, the compound may be assayed for activity with the desired cell type and counter-screened for a lack of activity against other cell types. The desired degree of "inactivity" in such counter screens, or the desired ratio of activity vs. inactivity may vary for different situations, and may be selected by the user.

The 2,4-substituted pyrimidinediamine active compounds also typically inhibit IL-4 stimulated expression of CD23 in B-cells with an $IC_{50}$ in the range of about 20 µM or less, typically in the range of about 10 µM, 1 µM, 500 nM, 100 nM, 10 nM, 1 nM, or even lower. A suitable assay that can be used is the assay described in Example 41 "Assay for Ramos B-Cell Line Stimulated with IL-4." In certain embodiments, the active 2,4-substituted pyrimidinediamine compounds have an $IC_{50}$ of less than or equal to 5 µM, greater than 5 µM but less than 20 µM, greater than 20 µM, or greater than 20 µM but less than 50 µM in the assay described in Example 41

Additionally, the 2,4-substituted pyrimidinediamine active compounds also typically inhibit an activity of an human primary T-cells with an $IC_{50}$ in the range of about 20 µM or less, typically in the range of about 10 µM, 1 µM, 500 nM, 100 nM, 10 nM, 1 nM, or even lower. The $IC_{50}$ against human primary T-cells can be determined in a standard in vitro assay with isolated human primary T-cells. A suitable assay that can be used is the assay described in Example 42 "Primary Human T-cell Proliferation Assay Stimulated with IL-2." In certain embodiments, the active 2,4-substituted pyrimidinediamine compounds have an $IC_{50}$ of less than or equal to 5 µM, greater than 5 µM but less than 20 µM, greater than 20 µM, or greater than 20 µM but less than 50 µM in the assay described in Example 42

The 2,4-substituted pyrimidinediamine active compounds also typically inhibit expression of ICAM1 (CD54) induced by IFNγ exposure in U937 or A549 cells with an $IC_{50}$ in the range of about 20 µM or less, typically in the range of about 10 µM, 1 µM, 500 nM, 100 nM, 10 nM, 1 nM, or even lower. The $IC_{50}$ against expression of ICAM (CD54) in IFNγ stimulated cells can be determined in a functional cellular assay with an isolated A549 or U937 cell line. Suitable assays that can be used are the assays described in Examples 43 and 44 "A549 Epithelial Line Stimulated with IFNγ," or "U937 IFNγ ICAM1 FACS Assay," respectively. In certain embodiments, the active 2,4-substituted pyrimidinediamine compounds have an $IC_{50}$ of less than or equal to 20 µM, greater than 20 µM, or greater than 20 µM but less than 50 µM in the assays described in Example 43 or Example 44

E. Pharmaceutical Compositions of the Invention

Pharmaceutical compositions comprising the 2,4-substituted pyrimidinediamine compounds described herein (or prodrugs thereof) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the active compounds into preparations which can be used pharmaceutically.

The 2,4-substituted pyrimidinediamine compound or prodrug may be formulated in the pharmaceutical compositions per se, or in the form of a hydrate, solvate, N-oxide or pharmaceutically acceptable salt, as described herein. Typically, such salts are more soluble in aqueous solutions than the corresponding free acids and bases, but salts having lower solubility than the corresponding free acids and bases may also be formed.

In one embodiment, this invention provides a pharmaceutical formulation comprising a compound selected from the compounds of the invention, as described herein, and the compounds of Table XI (CAS Reg. No. 845817-97-2, CAS Reg. No. 841290-42-4, and CAS Reg. No. 841290-41-3) or a prodrug thereof, and at least one pharmaceutically acceptable excipient, diluent, preservative, or stabilizer, or mixtures thereof.

In another embodiment, the methods may be practiced as a therapeutic approach towards the treatment of the conditions described herein. Thus, in a specific embodiment, the 2,4-substituted pyrimidinediamine compounds (and the various forms described herein, including pharmaceutical formulations comprising the compounds (in the various forms)) may be used to treat the conditions described herein in animal subjects, including humans. The methods generally comprise administering to the subject an amount of a compound of the invention, or a salt, prodrug, hydrate or N-oxide thereof, effective to treat the condition. In one embodiment, the subject is a mammal, including, but not limited to, bovine, horse, feline, canine, rodent, or primate. In another embodiment, the subject is a human The compounds can be provided in a variety of formulations and dosages. The compounds may be provided in a pharmaceutically acceptable form including, where the compound or prodrug may be formulated in the pharmaceutical compositions per se, or in the form of a hydrate, solvate, N-oxide or pharmaceutically acceptable salt, as described herein. Typically, such salts are more soluble in aqueous solutions than the corresponding free acids and bases, but salts having lower solubility than the corresponding free acids and bases may also be formed. It is to be understood that reference to the compound, 2,4-substituted pyrimidinediamine compound, or "active" in discussions of formulations is also intended to include, where appropriate as known to those of skill in the art, formulation of the prodrugs of the 2,4-substituted pyrimidinediamine compounds.

In one embodiment, the compounds are provided as non-toxic pharmaceutically acceptable salts, as noted previously. Suitable pharmaceutically acceptable salts of the compounds of this invention include acid addition salts such as those formed with hydrochloric acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The pharmaceutically acceptable salts of the present invention may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope solvates of the 2,4-substituted pyrimidinediamine compounds and salts thereof, for example, hydrates.

The 2,4-substituted pyrimidinediamine compounds may have one or more asymmetric centers, and may accordingly exist both as enantiomers and as diastereoisomers. It is to be understood that all such isomers and mixtures thereof are encompassed within the scope of the present invention.

The 2,4-substituted pyrimidinediamine compounds may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, urethral (e.g., urethral suppository) or topical routes of administration (e.g., gel, ointment, cream, aerosol, etc.) and may be formulated, alone or together, in suitable dosage unit formulations containing conventional non-toxic pharmaceutically acceptable carriers, adjuvants, excipients and vehicles appropriate for each route of administration. In addition to the treatment of warm-blooded animals such as mice, rats, horses, cattle, sheep, dogs, cats, monkeys, etc., the compounds of the invention may be effective in humans.

The pharmaceutical compositions for the administration of the 2,4-substituted pyrimidinediamine compounds may conveniently be presented in dosage unit form and may be prepared by any of the methods well known in the art of pharmacy. The pharmaceutical compositions can be, for example, prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired therapeutic effect. For example, pharmaceutical compositions of the invention may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the JAK-selective compound(s) or prodrug(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings. Additionally, the pharmaceutical compositions containing the 2,4-substituted pyrmidinediamine as active ingredient or prodrug thereof in a form suitable for oral use, may also include, for example, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient (including prodrug) in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents (e.g., corn starch, or alginic acid); binding agents (e.g. starch, gelatin or acacia); and lubricating agents (e.g. magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. The pharmaceutical compositions of the invention may also be in the form of oil-in-water emulsions.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound or prodrug, as is well known.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent. Among the acceptable vehicles and solvents that may be employed are water, Ringer's solution and isotonic sodium chloride solution. The 2,4-substituted pyrimidinediamine compounds may also be administered in the form of suppositories for rectal or urethral administration of the drug. In particular embodiments, the compounds may be formulated as urethral suppositories, for example, for use in the treatment of fertility conditions, particularly in males, e.g., for the treatment of testicular dysfunction.

According to the invention, 2,4-substituted pyrimidinediamine compounds can be used for manufacturing a composition or medicament, including medicaments suitable for rectal or urethral administration. The invention also relates to methods for manufacturing compositions including 2,4-substituted pyrimidinediamine compounds in a form that is suitable for urethral or rectal administration, including suppositories.

For topical use, creams, ointments, jellies, gels, solutions or suspensions, etc., containing the 2,4-substituted pyrimidinediamine compounds may be employed. In certain embodiments, the 2,4-substituted pyrimidinediamine compounds may be formulated for topical administration with polyethylene glycol (PEG). These formulations may optionally comprise additional pharmaceutically acceptable ingredients such as diluents, stabilizers and/or adjuvants. In particular embodiments, the topical formulations are formulated for the treatment of allergic conditions and/or skin conditions including psoriasis, contact dermatitis and atopic dermatitis, among others described herein.

According to the invention, 2,4-substituted pyrimidinediamine compounds can be used for manufacturing a composition or medicament, including medicaments suitable for topical administration. The invention also relates to methods for manufacturing compositions including 2,4-substituted pyrimidinediamine compounds in a form that is suitable for topical administration.

According to the present invention, 2,4-substituted pyrimidinediamine compounds can also be delivered by any of a variety of inhalation devices and methods known in the art, including, for example: U.S. Pat. Nos. 6,241,969; 6,060,069; 6,238,647; 6,335,316; 5,364,838; 5,672,581; WO96/32149; WO95/24183; U.S. Pat. Nos. 5,654,007; 5,404,871; 5,672,581; 5,743,250; 5,419,315; 5,558,085; WO98/33480; U.S. Pat. Nos. 5,364,833; 5,320,094; 5,780,014; 5,658,878; 5,518,998; 5,506,203; 5,661,130; 5,655,523; 5,645,051; 5,622,166; 5,577,497; 5,492,112; 5,327,883; 5,277,195; U.S. Pat. App. No. 20010041190; U.S. Pat. App. No. 20020006901; and U.S. Pat. App. No. 20020034477.

Included among the devices which may be used to administer particular examples of the 2,4-substituted pyrimidinediamine compounds are those well-known in the art, such as, metered dose inhalers, liquid nebulizers, dry powder inhalers, sprayers, thermal vaporizers, and the like. Other suitable technology for administration of particular 2,4-substituted pyrimidinediamine compounds includes electro-hydrodynamic aerosolizers.

In addition, the inhalation device is preferably practical, in the sense of being easy to use, small enough to carry conveniently, capable of providing multiple doses, and durable. Some specific examples of commercially available inhalation devices are Turbohaler (Astra, Wilmington, DE), Rotahaler (Glaxo, Research Triangle Park, NC), Diskus (Glaxo, Research Triangle Park, NC), the Ultravent nebulizer (Mallinckrodt), the Acorn II nebulizer (Marquest Medical Products, Totowa, NJ) the Ventolin metered dose inhaler (Glaxo, Research Triangle Park, NC), or the like. In one embodiment, 2,4-substituted pyrimidinediamine compounds can be delivered by a dry powder inhaler or a sprayer.

As those skilled in the art will recognize, the formulation of 2,4-substituted pyrimidinediamine compounds, the quantity of the formulation delivered, and the duration of administration of a single dose depend on the type of inhalation device employed as well as other factors. For some aerosol delivery systems, such as nebulizers, the frequency of administration and length of time for which the system is activated will depend mainly on the concentration of 2,4-substituted pyrimidinediamine compounds in the aerosol. For example, shorter periods of administration can be used at higher concentrations of 2,4-substituted pyrimidinediamine compounds in the nebulizer solution. Devices such as metered dose inhalers can produce higher aerosol concentrations, and can be operated for shorter periods to deliver the desired amount of 2,4-substituted pyrimidinediamine compounds in some embodiments. Devices such as dry powder inhalers deliver active agent until a given charge of agent is expelled from the device. In this type of inhaler, the amount of 2,4-substituted pyrimidinediamine compounds in a given quantity of the powder determines the dose delivered in a single administration. The formulation of 2,4-substituted pyrimidinediamine is selected to yield the desired particle size in the chosen inhalation device.

Formulations of 2,4-substituted pyrimidinediamine compounds for administration from a dry powder inhaler may typically include a finely divided dry powder containing 2,4-substituted pyrimidinediamine compounds, but the powder can also include a bulking agent, buffer, carrier, excipient, another additive, or the like. Additives can be included in a dry powder formulation of 2,4-substituted pyrimidinediamine compounds, for example, to dilute the powder as required for delivery from the particular powder inhaler, to facilitate processing of the formulation, to provide advantageous powder properties to the formulation, to facilitate dispersion of the powder from the inhalation device, to stabilize to the formulation (e.g., antioxidants or buffers), to provide taste to the formulation, or the like. Typical additives include mono-, di-, and polysaccharides; sugar alcohols and other polyols, such as, for example, lactose, glucose, raffinose, melezitose, lactitol, maltitol, trehalose, sucrose, mannitol, starch, or combinations thereof; surfactants, such as sorbitols, diphosphatidyl choline, or lecithin; or the like.

The present invention also relates to a pharmaceutical composition including 2,4-substituted pyrimidinediamine compounds suitable for administration by inhalation. According to the invention, 2,4-substituted pyrimidinediamine compounds can be used for manufacturing a composition or medicament, including medicaments suitable for administration by inhalation. The invention also relates to methods for manufacturing compositions including 2,4-substituted pyrimidinediamine compounds in a form that is suitable for administration, including administration by inhalation. For example, a dry powder formulation can be manufactured in several ways, using conventional techniques, such as described in any of the publications mentioned above and incorporated expressly herein by reference, and for example, Baker, et al., U.S. Pat. No. 5,700,904, the entire disclosure of which is incorporated expressly herein by reference. Particles in the size range appropriate for maximal deposition in the lower respiratory tract can be made by micronizing, milling, or the like. And a liquid formulation can be manufactured by dissolving the 2,4-substituted pyrimidinediamine compounds in a suitable solvent, such as water, at an appropriate pH, including buffers or other excipients.

Pharmaceutical compositions comprising the 2,4-substituted pyrimidinediamine compounds described herein (or prodrugs thereof) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the active compounds into preparations which can be used pharmaceutically.

For ocular administration, the 2,4-substituted pyrimidinediamine compound(s) or prodrug(s) may be formulated as a solution, emulsion, suspension, etc. suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851.

For prolonged delivery, the 2,4-substituted pyrimidinediamine compound(s) or prodrug(s) can be formulated as a depot preparation for administration by implantation or intramuscular injection. The active ingredient may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

Alternatively, other pharmaceutical delivery systems may be employed. Liposomes and emulsions are well-known examples of delivery vehicles that may be used to deliver active compound(s) or prodrug(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

The 2,4-substituted pyrimidinediamine compound(s) or prodrug(s) described herein, or compositions thereof, will generally be used in an amount effective to achieve the intended result, for example in an amount effective to treat or prevent the particular condition being treated. The compound(s) may be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. As another specific example, therapeutic benefit in the context of transplantation rejection includes the ability to alleviate an acute rejection episode, such as for example, HVGR or GVHR, or the ability to prolong the time period between onset of acute rejection episodes and/or onset of chronic rejection. Therapeutic benefit also includes halting or slowing the progression of the disease, regardless of whether improvement is realized.

The amount of compound administered will depend upon a variety of factors, including, for example, the particular condition being treated, the mode of administration, the severity of the condition being treated and the age and weight of the patient, the bioavailability of the particular active compound, etc. Determination of an effective dosage is well within the capabilities of those skilled in the art.

As known by those of skill in the art, the preferred dosage of 2,4-substituted pyrimidinediamine compounds will also depend on the age, weight, general health and severity of the condition of the individual being treated. Dosage may also need to be tailored to the sex of the individual and/or where administered by inhalation, the lung capacity of the individual. Dosage may also be tailored to individuals suffering from more than one condition or those individuals who have additional conditions which affect lung capacity and the ability to breathe normally, for example, emphysema, bronchitis, pneumonia, respiratory infections, etc. Dosage, and frequency of administration of the compounds or prodrugs thereof, will also depend on whether the compounds are formulated for treatment of acute episodes of a condition or for the prophylactic treatment of a disorder. For example, acute episodes of allergic conditions, including allergy-related asthma, transplant rejection, etc. A skilled practitioner will be able to determine the optimal dose for a particular individual.

For prophylactic administration, the compound may be administered to a patient at risk of developing one of the previously described conditions. For example, if it is unknown whether a patient is allergic to a particular drug, the compound may be administered prior to administration of the drug to avoid or ameliorate an allergic response to the drug. Alternatively, prophylactic administration may be applied to avoid the onset of symptoms in a patient diagnosed with the underlying disorder. For example, a compound may be administered to an allergy sufferer prior to expected exposure to the allergen. Compounds may also be administered prophylactically to healthy individuals who are repeatedly exposed to agents known to one of the above-described maladies to prevent the onset of the disorder. For example, a compound may be administered to a healthy individual who is repeatedly exposed to an allergen known to induce allergies, such as latex, in an effort to prevent the individual from developing an allergy. Alternatively, a compound may be administered to a patient suffering from asthma prior to partaking in activities which trigger asthma attacks to lessen the severity of, or avoid altogether, an asthmatic episode.

In the context of transplant rejection, the compound may be administered while the patient is not having an acute rejection reaction to avoid the onset of rejection and/or prior to the appearance of clinical indications of chronic rejection.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, etc. Determination of an effective dosage is well within the capabilities of those skilled in the art.

Effective dosages may be estimated initially from in vitro assays. For example, an initial dosage for use in animals may be formulated to achieve a circulating blood or serum concentration of active compound that is at or above an $IC_{50}$ of the particular compound as measured in as in vitro assay. Calculating dosages to achieve such circulating blood or serum concentrations taking into account the bioavailability of the particular compound is well within the capabilities of skilled artisans. For guidance, the reader is referred to Fingl & Woodbury, "General Principles," In: Goodman and Gilman's The Pharmaceutical Basis of Therapeutics, Chapter 1, pp. 1-46, latest edition, Pergamagon Press, and the references cited therein.

Initial dosages can also be estimated from in vivo data, such as animal models Animal models useful for testing the efficacy of compounds to treat or prevent the various diseases described above are well-known in the art. Suitable animal models of hypersensitivity or allergic reactions are described in Foster, (1995) Allergy 50(21Suppl):6-9, discussion 34-38 and Tumas et al., (2001), J. Allergy Clin. Immunol. 107(6):1025-1033. Suitable animal models of allergic rhinitis are described in Szelenyi et al., (2000), Arzneimittelforschung 50(11):1037-42; Kawaguchi et al., (1994), Clin. Exp. Allergy 24(3):238-244 and Sugimoto et al., (2000), Immunopharmacology 48(1):1-7. Suitable animal models of allergic conjunctivitis are described in Carreras et al., (1993), Br. J. Ophthalmol. 77(8):509-514; Saiga et al., (1992), Ophthalmic Res. 24(1):45-50; and Kunert et al., (2001), Invest. Ophthalmol. Vis. Sci. 42(11):2483-2489. Suitable animal models of systemic mastocytosis are described in O'Keefe et al., (1987), J. Vet. Intern. Med. 1(2):75-80 and Bean-Knudsen et al., (1989), Vet. Pathol. 26(1):90-92. Suitable animal models of hyper IgE syndrome are described in Claman et al., (1990), Clin. Immunol. Immunopathol. 56(1):46-53. Suitable animal models of B-cell lymphoma are described in Hough et al., (1998), Proc. Natl. Acad. Sci. USA 95:13853-13858 and Hakim et al., (1996), J. Immunol. 157(12):5503-5511. Suitable animal models of atopic disorders such as atopic dermatitis, atopic eczema and atopic asthma are described in Chan et al., (2001), J. Invest. Dermatol. 117(4):977-983 and Suto et al., (1999), Int. Arch. Allergy Immunol. 120(Suppl 1):70-75. Suitable animal models of transplant rejection, such as models of HVGR are described in O'Shea et al., (2004), Nature Reviews Drug Discovery 3:555-564; Cetkovic- Curlje & Tibbles, (2004), *Current Pharmaceutical Design* 10:1767-1784; and Chengelian et al., (2003), *Science* 302:875-878. Ordinarily skilled artisans can routinely adapt such information to determine dosages suitable for human administration.

Dosage amounts will typically be in the range of from about 0.0001 or 0.001 or 0.01 mg/kg/day to about 100 mg/kg/day, but may be higher or lower, depending upon, among other factors, the activity of the compound, its bioavailability, the mode of administration and various factors discussed above. Dosage amount and interval may be adjusted individually to provide plasma levels of the compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of active compound(s) may not be related to plasma concentration. Skilled artisans will be able to optimize effective local dosages without undue experimentation.

Preferably, the compound(s) will provide therapeutic or prophylactic benefit without causing substantial toxicity. Toxicity of the compound(s) may be determined using standard pharmaceutical procedures. The dose ratio between toxic and therapeutic (or prophylactic) effect is the therapeutic index. Compounds(s) that exhibit high therapeutic indices are preferred.

The foregoing disclosure pertaining to the dosage requirements for the 2,4-substituted pyrimidinediamine compounds is pertinent to dosages required for prodrugs, with the realization, apparent to the skilled artisan, that the amount of prodrug(s) administered will also depend upon a variety of factors, including, for example, the bioavailability of the particular prodrug(s) the conversation rate and efficiency into active drug compound under the selected route of administration, etc. Determination of an effective dosage of prodrug(s) for a particular use and mode of administration is well within the capabilities of those skilled in the art.

Effective dosages may be estimated initially from in vitro activity and metabolism assays. For example, an initial dosage of prodrug for use in animals may be formulated to achieve a circulating blood or serum concentration of the metabolite active compound that is at or above an $IC_{50}$ of the particular compound as measured in as in vitro assay, such as the in vitro CHMC or BMMC and other in vitro assays described in U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO2004/014382), U.S. application Ser. No. 10/903,263 filed Jul. 30, 2004, and international application Serial No. PCT/US2004/24716 (WO005/016893). Calculating dosages to achieve such circulating blood or serum concentrations taking into account the bioavailability of the particular prodrug via the desired route of administration is well within the capabilities of skilled artisans. For guidance, the reader is referred to Fingl & Woodbury, "General Principles," *In: Goodman and Gilman's The Pharmaceutical Basis of Therapeutics*, Chapter 1, pp. 1-46, latest edition, Pagamonon Press, and the references cited therein.

Also provided are kits for administration of the 2,4-substituted pyrimidinediamine, prodrug thereof or pharmaceutical formulations comprising the compound, that may include a dosage amount of at least one 2,4-substituted pyrimidinediamine or a composition comprising at least one 2,4-substituted pyrimidinediamine as disclosed herein. Kits may further comprise suitable packaging and/or instructions for use of the compound. Kits may also comprise a means for the delivery of the at least one 2,4-substituted pyrimidinediamine or compositions comprising at least one 2,4-substituted pyrimidinediamine, such as an inhaler, spray dispenser (e.g. nasal spray), syringe for injection or pressure pack for capsules, tables, suppositories, or other device as described herein.

Additionally, the compounds of the present invention may be assembled in the form of kits. The kit provides the compound and reagents to prepare a composition for administration. The composition may be in a dry or lyophilized form, or in a solution, particularly a sterile solution. When the composition is in a dry form, the reagent may comprise a pharmaceutically acceptable diluent for preparing a liquid formulation. The kit may contain a device for administration or for dispensing the compositions, including, but not limited to syringe, pipette, transdermal patch, or inhalant.

The kits may include other therapeutic compounds for use in conjunction with the compounds described herein. In one embodiment, the therapeutic agents are immunosuppressant or anti-allergen compounds. These compounds may be provided in a separate form, or mixed with the compounds of the present invention.

The kits will include appropriate instructions for preparation and administration of the composition, side effects of the compositions, and any other relevant information. The instructions may be in any suitable format, including, but not limited to, printed matter, videotape, computer readable disk, or optical disc.

In one embodiment, this invention provides a kit comprising a compound selected from the compounds of the invention, as described herein, and the compounds of Table XI (CAS Reg. No. 845817-97-2, CAS Reg. No. 841290-42-4, and CAS Reg. No. 841290-41-3) or a prodrug thereof, packaging and instructions for use.

In another embodiment, this invention provides a kit comprising the pharmaceutical formulation comprising a compound selected from the compounds of the invention, as described herein, and the compounds of Table XI (CAS Reg. No. 845817-97-2, CAS Reg. No. 841290-42-4, and CAS Reg. No. 841290-41-3) or a prodrug thereof, and at least one pharmaceutically acceptable excipient, diluent, preservative, or stabilizer, or mixtures thereof, packaging, and instructions for use.

In another aspect of the invention, kits for treating an individual who suffers from or is susceptible to the conditions described herein are provided, comprising a container comprising a dosage amount of an 2,4-substituted pyrimidinediamine or composition as disclosed herein, and instructions for use. The container may be any of those known in the art and appropriate for storage and delivery of oral, intravenous, topical, rectal, urethral, or inhaled formulations.

Kits may also be provided that contain sufficient dosages of the 2,4-substituted pyrimidinediamine or composition to provide effective treatment for an individual for an extended period, such as a week, 2 weeks, 3, weeks, 4 weeks, 6 weeks or 8 weeks or more.

F. General Synthesis of the Compounds of the Invention

The 2,4-pyrimidinediamine compounds and prodrugs of the invention may be synthesized via a variety of different synthetic routes using commercially available starting materials and/or starting materials prepared by conventional synthetic methods. Suitable exemplary methods that may be routinely adapted to synthesize the 2,4-pyrimidinediamine compounds and prodrugs of the invention are found in U.S.

Pat. No. 5,958,935, the disclosure of which is incorporated herein by reference. Specific examples describing the synthesis of numerous 2,4-pyrimidinediamine compounds and prodrugs, as well as intermediates therefore, are described in copending U.S. application Ser. No. 10/355,543, filed Jan. 31, 2003 (US2004/0029902A1), the contents of which are incorporated herein by reference. Suitable exemplary methods that may be routinely used and/or adapted to synthesize active 2,4-substituted pyrimidinediamine compounds can also be found in international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO2004/014382), U.S. application Ser. No. 10/903,263 filed Jul. 30, 2004, and international application Serial No. PCT/US2004/24716 (WO005/016893), the disclosures of which are incorporated herein by reference. All of the compounds described herein (including prodrugs) may be prepared by routine adaptation of these methods.

Specific exemplary synthetic methods for the 2,4-substituted pyrimidinediamines described herein are also described in Examples 1-40, below. Those of skill in the art will also be able to readily adapt these examples for the synthesis of additional 2,4-substituted pyrimidinediamines as described herein.

A variety of exemplary synthetic routes that can be used to synthesize the 2,4-pyrimidinediamine compounds of the invention are described in Schemes (I)-(VII), below. These methods may be routinely adapted to synthesize the 2,4-substituted pyrimidinediamine compounds and prodrugs described herein.

In one exemplary embodiment, the compounds can be synthesized from substituted or unsubstituted uracils as illustrated in Scheme (I), below:

In Scheme (I), ring A, $R^1$, $(R^2)_p$, alk, $(R^3)_q$, $R^4$, $R^5$, X, Y and Z are as defined herein. According to Scheme (I), uracil A-1 is dihalogenated at the 2- and 4-positions using a standard halogenating agent such as $POCl_3$ (or other standard halogenating agent) under standard conditions to yield 2,4-dichloropyrimidine A-2. Depending upon the X substituent, in pyrimidinediamine A-2, the chloride at the C4 position is more reactive towards nucleophiles than the chloride at the C2 position. This differential reactivity can be exploited to synthesize 2,4-pyrimidinediamines A-7 by first reacting 2,4-dichloropyrimidine A-2 with one equivalent of amine A-3, yielding 4N-substituted-2-chloro-4-pyrimidineamine A-4, followed by amine A-5 to yield a 2,4-pyrimidinediamine derivative A-6, where N4 nitrogen can be selectively alkylated to give compounds of formula A-7.

Typically, the C4 halide is more reactive towards nucleophiles, as illustrated in the Scheme. However, as will be recognized by skilled artisans, the identity of X substituent may alter this reactivity. For example, when X is trifluoromethyl, a 50:50 mixture of 4N-substituted-4-pyrimidineamine A-4 and the corresponding 2N-substituted-2-pyrimidineamine is obtained. The regioselectivity of the reaction can also be controlled by adjusting the solvent and other synthetic conditions (such as temperature), as is well-known in the art.

The reactions depicted in Scheme (I) may proceed more quickly when the reaction mixtures are heated via microwave. When heating in this fashion, the following conditions may be used: heat to 175° C. in ethanol for 5-20 min. in a Smith Reactor (Personal Chemistry, Uppsala, Sweden) in a sealed tube (at 20 bar pressure).

The uracil 1 starting materials may be purchased from commercial sources or prepared using standard techniques of organic chemistry. Commercially available uracils that

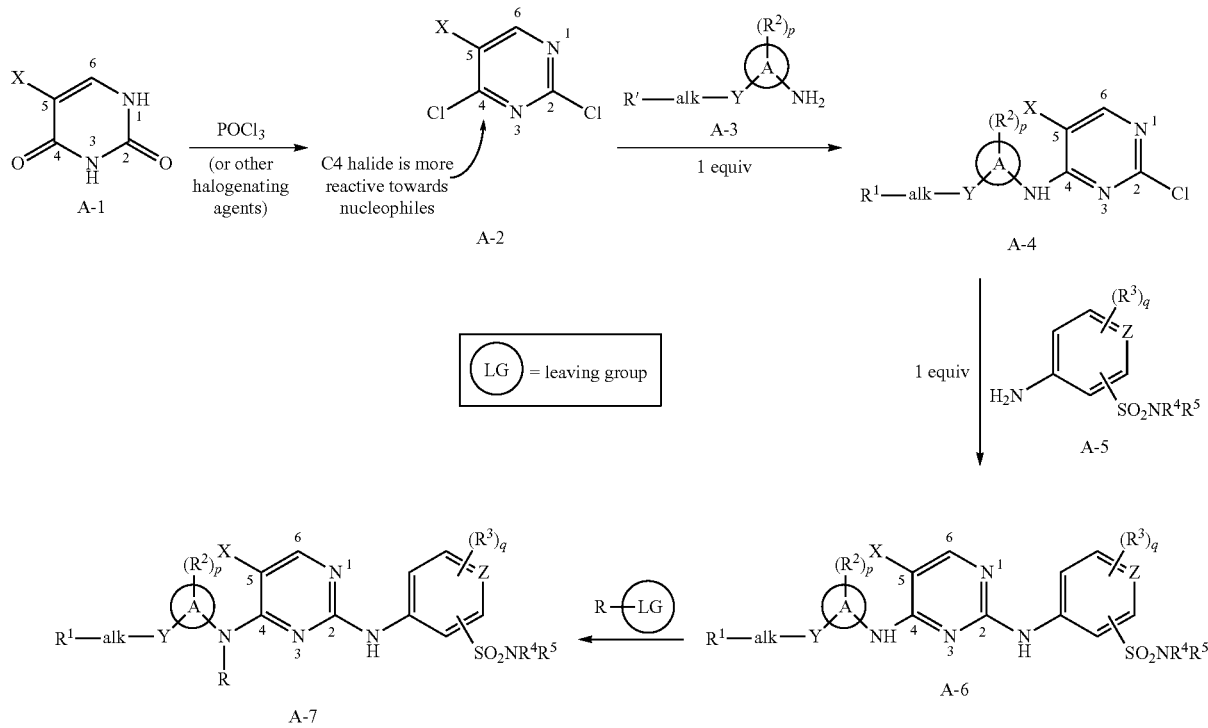

Scheme (I)

can be used as starting materials in Scheme (I) include, by way of example and not limitation, uracil (Aldrich #13,078-8; CAS Registry 66-22-8); 5-bromouracil (Aldrich #85,247-3; CAS Registry 51-20-7; 5-fluorouracil (Aldrich #85,847-1; CAS Registry 51-21-8); 5-iodouracil (Aldrich #85,785-8; CAS Registry 696-07-1); 5-nitrouracil (Aldrich #85,276-7; CAS Registry 611-08-5); 5-(trifluoromethyl)-uracil (Aldrich #22,327-1; CAS Registry 54-20-6). Additional 5-substituted uracils are available from General Intermediates of Canada, Inc., Edmonton, CA and/or Interchim, Cedex, France, or may be prepared using standard techniques. Myriad textbook references teaching suitable synthetic methods are provided infra.

Amines A-3 and A-5 may be purchased from commercial sources or, alternatively, may be synthesized utilizing standard techniques. For example, suitable amines may be synthesized from nitro precursors using standard chemistry. Specific exemplary reactions are provided in the Examples section. See also Vogel, 1989, *Practical Organic Chemistry*, Addison Wesley Longman, Ltd. and John Wiley & Sons, Inc.

Skilled artisans will recognize that in some instances, amines A-3 and A-5 and/or substituent X on uracil A-1 may include functional groups that require protection during synthesis. The exact identity of any protecting group(s) used will depend upon the identity of the functional group being protected, and will be apparent to those of skill in the art. Guidance for selecting appropriate protecting groups, as well as synthetic strategies for their attachment and removal, may be found, for example, in Greene & Wuts, *Protective Groups in Organic Synthesis*, 3d Edition, John Wiley & Sons, Inc., New York (1999) and the references cited therein (hereinafter "Greene & Wuts").

Thus, protecting group refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, as mentioned above, and additionally, in Harrison et al., *Compendium of Synthetic Organic Methods*, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated to form acetate and benzoate esters or alkylated to form benzyl and trityl ethers, as well as alkyl ethers, tetrahydropyranyl ethers, trialkylsilyl ethers (e.g., TMS or TIPPS groups) and allyl ethers.

A specific embodiment of Scheme (I) utilizing 5-fluorouracil (Aldrich #32,937-1) as a starting material is illustrated in Scheme (Ia), below:

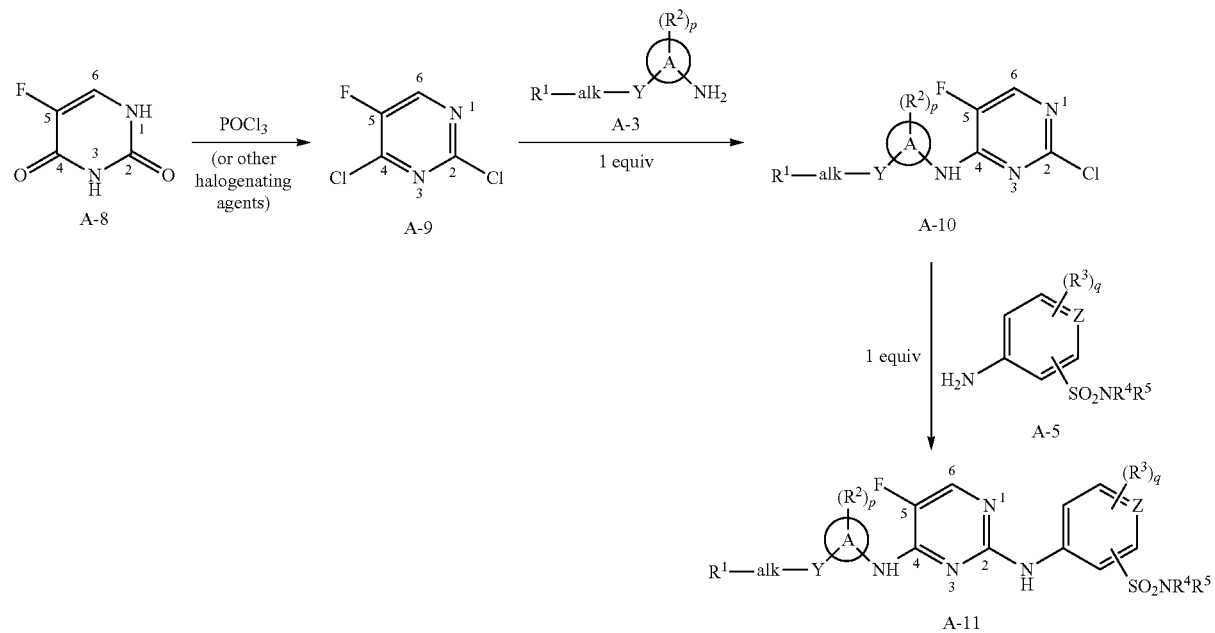

Scheme (Ia)

In Scheme (Ia), ring A, $R^1$, $(R^2)_p$, alk, $(R^3)_q$, $R^4$, $R^5$, Y and Z are as previously defined for Scheme (I). Asymmetric 2N,4N-disubstituted-5-fluoro-2,4-pyrimidinediamine A-11 may be obtained by reacting 2,4-dichloro-5-fluoropyrimidine A-9 with one equivalent of amine A-3 (to yield 2-chloro-N4-substituted-5-fluoro-4-pyrimidineamine A-10) followed by one or more equivalents of amine A-5.

In another exemplary embodiment, the 2,4-pyrimidinediamine compounds of the invention may be synthesized from substituted or unsubstituted cytosines as illustrated in Schemes (IIa) and (IIb), below:

Scheme (IIa)

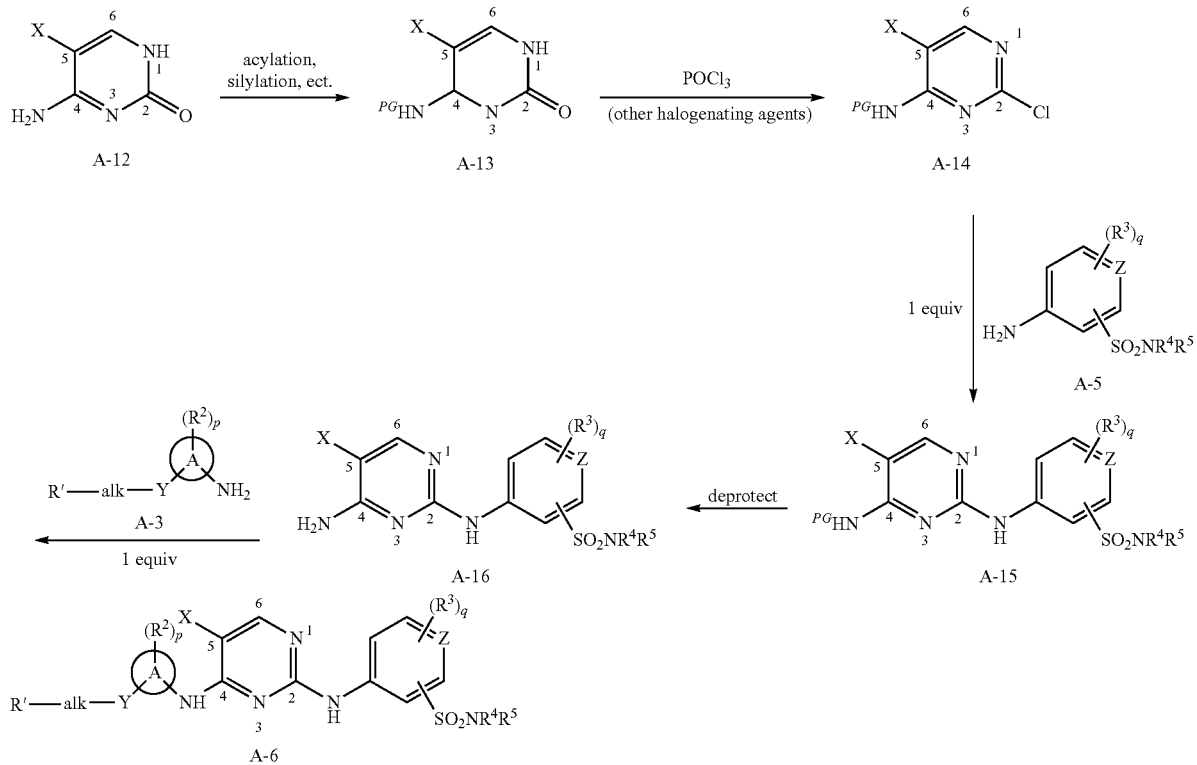

Scheme (IIb)

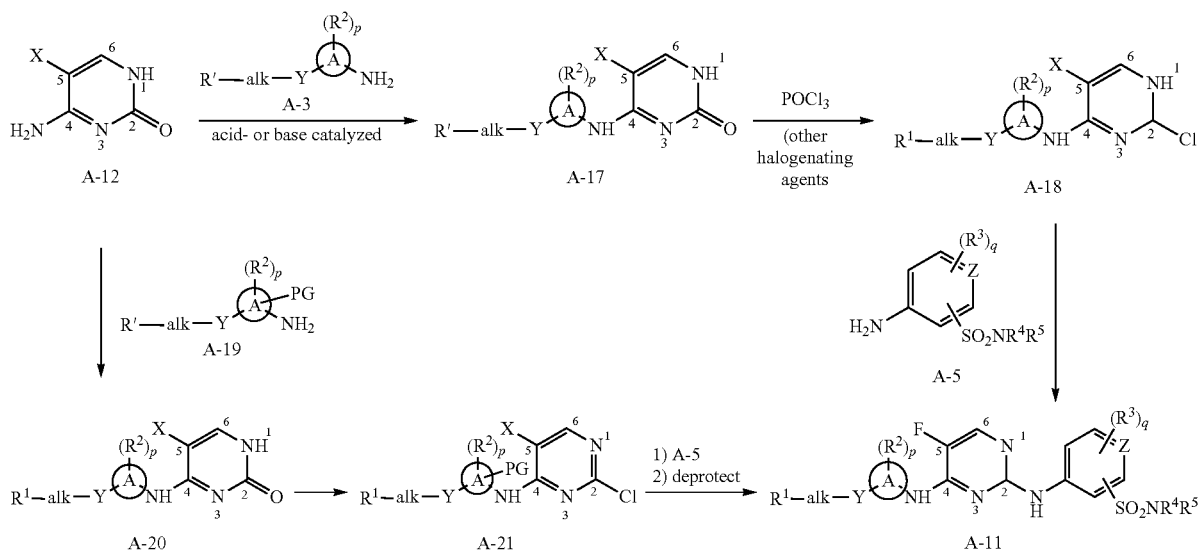

In Schemes (IIa) and (IIb), ring A, IV, $(R^2)_p$, alk, $(R^3)_q$, $R^4$, $R^5$, X, Y and Z are as previously defined for Scheme (I) and PG represents a protecting group. Referring to Scheme (IIa), the C4 exocyclic amine of cytosine A-12 is first protected with a suitable protecting group PG to yield N4-protected cytosine A-13. For specific guidance regarding protecting groups useful in this context, see Vorbrüggen and Ruh-Pohlenz, 2001, *Handbook of Nucleoside Synthesis*, John Wiley & Sons, NY, pp. 1-631 ("Vorbrüggen"). Protected cytosine A-13 is halogenated at the C2 position using a standard halogenation reagent under standard conditions to yield 2-chloro-4N-protected-4-pyrimidineamine A-14. Reaction with amine A-5 gives A-15, which on deprotection of the C4 exocyclic amine, gives A-16. Reaction of A-16 with amine A-3 yields 2,4-pyrimidinediamine derivative A-6.

Alternatively, referring to Scheme (IIb), cytosine A-12 may be reacted with amine A-3 or protected amine A-19 to yield N4-substituted cytosine A-17 or A-20, respectively. These substituted cytosines may then be halogenated as previously described, deprotected (in the case of N4-substituted cytosine A-20) and reacted with amine A-5 to yield a 2,4-pyrimidinediamine A-11.

Commercially-available cytosines that may be used as starting materials in Schemes (IIa) and (IIb) include, but are not limited to, cytosine (Aldrich #14,201-8; CAS Registry 71-30-7); $N^4$-acetylcytosine (Aldrich #37,791-0; CAS Registry 14631-20-0); 5-fluorocytosine (Aldrich #27,159-4; CAS Registry 2022-85-7); and 5-(trifluoromethyl)-cytosine. Other suitable cytosines useful as starting materials in Schemes (IIa) are available from General Intermediates of Canada, Inc., Edmonton, CA and/or Interchim, Cedex, France, or may be prepared using standard techniques. Myriad textbook references teaching suitable synthetic methods are provided infra.

In still another exemplary embodiment, the 2,4-pyrimidinediamine compounds of the invention may be synthesized from substituted or unsubstituted 2-amino-4-pyrimidinols as illustrated in Scheme (III), below:

Alternatively, the 2,4-pyrimidinediamine compounds of the invention may be prepared from substituted or unsubstituted 4-amino-2-pyrimidinols as illustrated in Scheme (IV), below:

Scheme (IV)

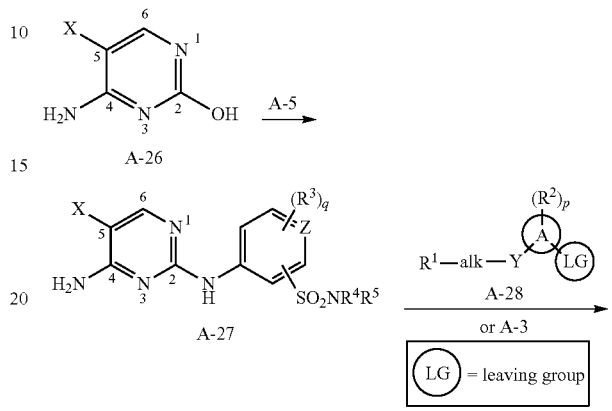

Scheme (III)

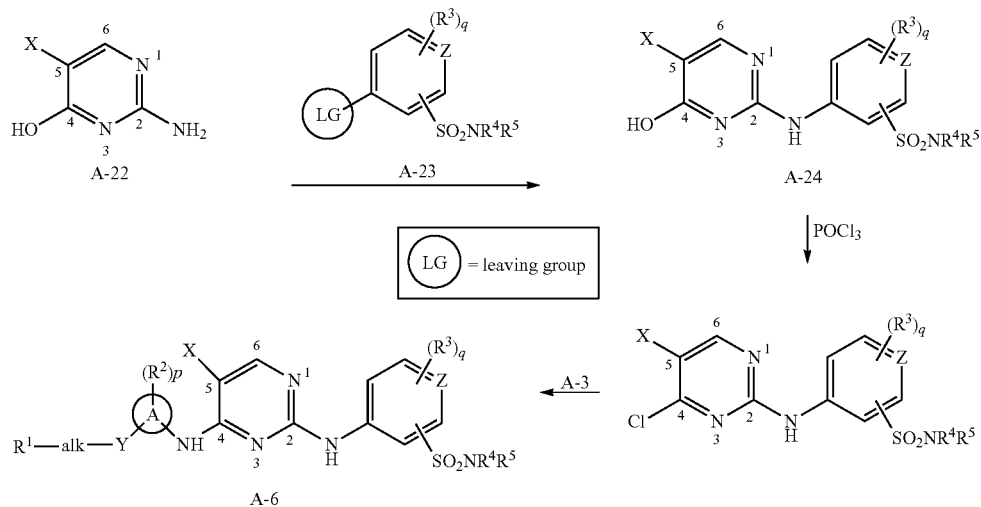

In Scheme (III), ring A, IV, $(R^2)_p$, alk, $(R^3)_q$, $R^4$, $R^5$, X, Y and Z are as previously defined for Scheme (I) and LG is a leaving group as discussed in more detail in connection with Scheme IV, infra. Referring to Scheme (III), 2-amino-4-pyrimidinol A-22 is reacted with arylating agent A-23 to yield N2-substituted-4-pyrimidinol A-24, which is then halogenated as previously described to yield N2-substituted-4-halo-2-pyrimidineamine A-25. Further reaction with amine A-3 affords a 2,4-pyrimidinediamine derivative A-6.

Suitable commercially-available 2-amino-4-pyrimidinols A-22 that can be used as starting materials in Scheme (III) are available from General Intermediates of Canada, Inc., Edmonton, CA and/or Interchim, Cedex, France, or may be prepared using standard techniques. Myriad textbook references teaching suitable synthetic methods are provided infra.

-continued

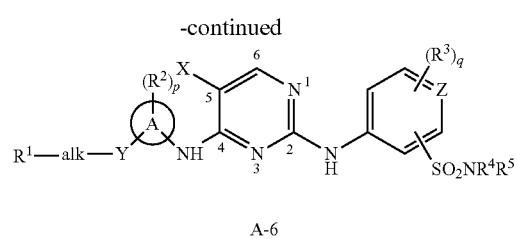

A-6

In Scheme (IV), ring A, IV, $(R^2)_p$, alk, $(R^3)_q$, $R^4$, $R^5$, X, Y and Z are as previously defined for Scheme (I). Referring to Scheme (IV), the C2-hydroxyl of 4-amino-2-pyrimidinol A-26 is more reactive towards nucleophiles than the C4-amino such that reaction with amine A-5 yields N2-substituted-2,4-pyrimidinediamine A-27. Subsequent reaction with compound A-28, which includes a suitable leaving group, or amine A-3 yields a 2,4-pyrimidinediamine derivative A-6. Compound A-28 may include virtually any leaving group that can be displaced by the C4-amino of N2-substituted-2,4-pyrimidinediamine A-27. Suitable leaving groups include, but are not limited to, halogens, methanesulfonyloxy (mesyloxy; "OMs"), trifluoromethanesulfonyloxy ("OTf") and p-toluenesulfonyloxy (tosyloxy; "OTs"), benzene sulfonyloxy ("besylate") and m-nitro benzene sulfonyloxy ("nosylate"). Other suitable leaving groups will be apparent to those of skill in the art.

Substituted 4-amino-2-pyrimidinol starting materials may be obtained commercially or synthesized using standard techniques. Myriad textbook references teaching suitable synthetic methods are provided infra.

In still another exemplary embodiment, the 2,4-pyrimidinediamine compounds of the invention can be prepared from 2-chloro-4-aminopyrimidines or 2-amino-4-chloropyrimidines as illustrated in Scheme (V), below:

Alternatively, 4-chloro-2-pyrimidineamines A-29 may be prepared as illustrated in Scheme (Va):

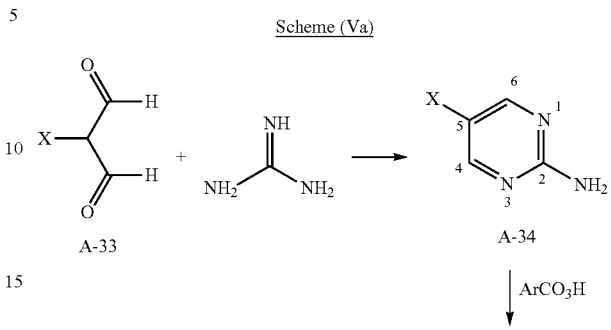

Scheme (Va)

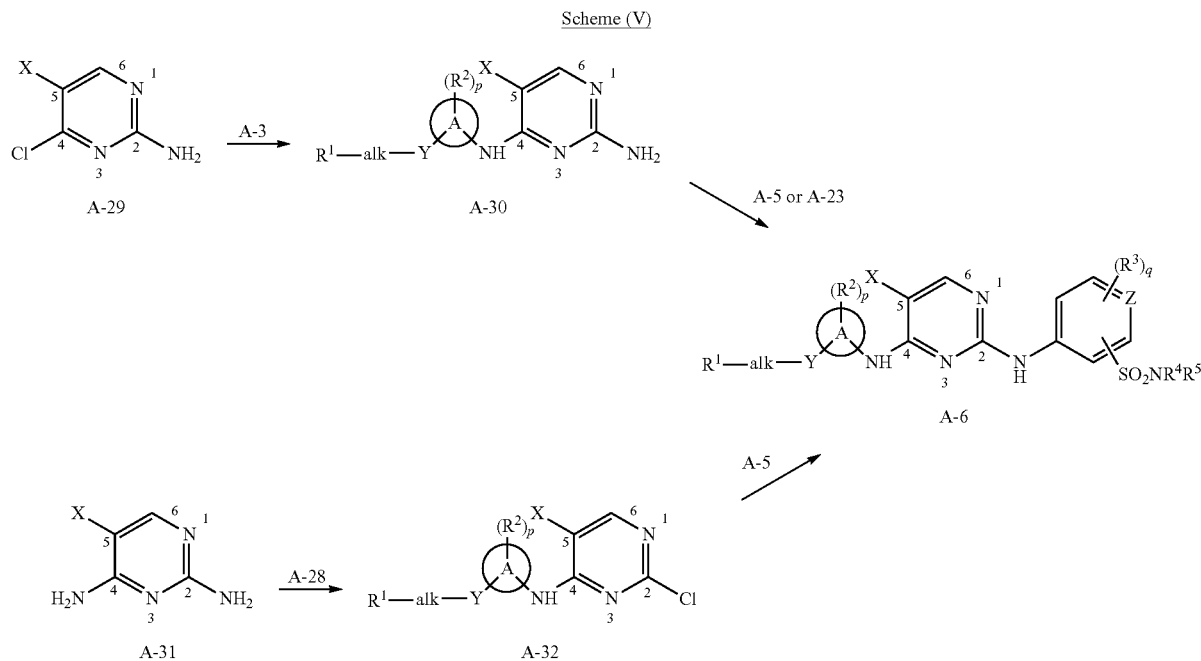

Scheme (V)

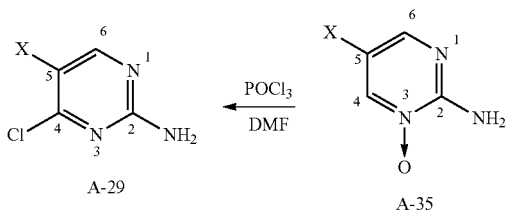

In Scheme (V), ring A, $R^1$, $(R^2)_p$, alk, $(R^3)_q$, $R^4$, $R^5$, X, Y and Z are as defined for Scheme (I) and leaving group is as defined for Scheme (IV). Referring to Scheme (V), 2-amino-4-chloropyrimidine A-29 is reacted with amine A-3 to yield 4N-substituted-2,4-pyrimidinediamine A-30 which, following reaction with compound A-23 or amine A-5, yields a N2,N4-2,4-pyrimidinediamine derivative A-6. Alternatively, 2-chloro-4-amino-pyrimidine A-31 may be reacted with compound A-28 to give compound A-32 which on reaction with amine A-5 yields A-6.

A variety of pyrimidines A-29 and A-31 suitable for use as starting materials in Scheme (V) are commercially available from General Intermediates of Canada, Inc., Edmonton, CA and/or Interchim, Cedex, France, or may be prepared using standard techniques. Myriad textbook references teaching suitable synthetic methods are provided infra.

In Scheme (Va), X is as previously defined for Scheme I. In Scheme (Va), dialdehyde A-33 is reacted with guanidine to yield 2-pyrimidineamine A-34. Reaction with a peracid such as m-chloroperbenzoic acid, trifluoroperacetic acid or urea hydrogen peroxide complex yields N-oxide A-35, which is then halogenated to give 4-chloro-2-pyrimidineamine A-29. The corresponding 4-halo-2-pyrimidineamines may be obtained by using suitable halogenation reagents.

In yet another exemplary embodiment, the 2,4-pyrimidinediamine compounds of the invention can be prepared from substituted or unsubstituted uridines as illustrated in Scheme (VI), below:

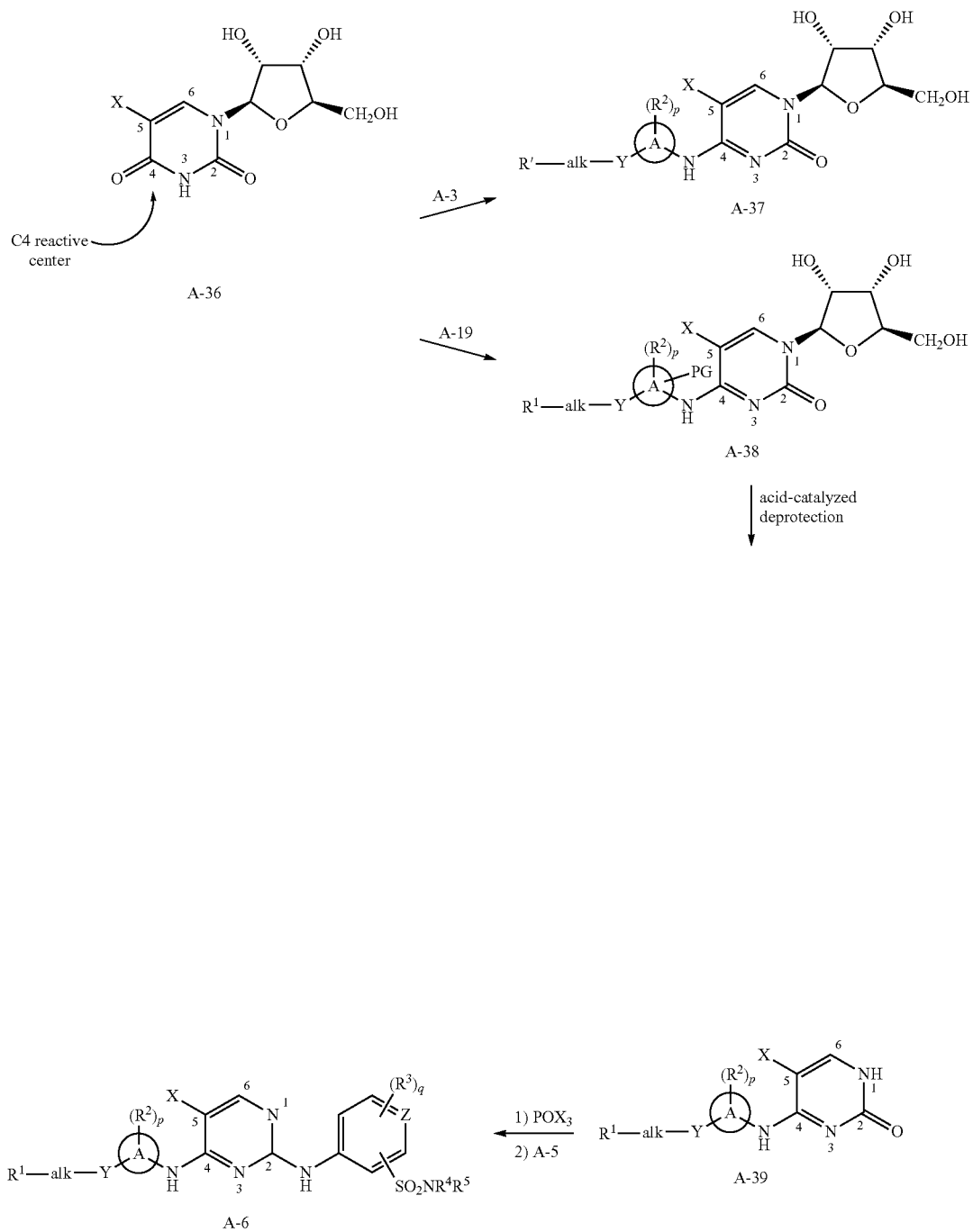

In Scheme (VI), ring A, IV, $(R^2)_p$, alk, $(R^3)_q$, $R^4$, $R^5$, X, Y and Z are as previously defined for Scheme (I) and PG represents a protecting group, as discussed in connection with Scheme (IIb). According to Scheme (VI), uridine A-36 has a C4 reactive center such that reaction with amine A-3 or protected amine A-19 yields N4-substituted cytidine A-37 or A-38, respectively. Acid-catalyzed deprotection of N4-substituted A-37 or A-38 (when "PG" represents an acid-labile protecting group) yields N4-substituted cytosine A-39, which may be subsequently halogenated at the C2-position and reacted with amine A-5 to yield a 2,4-pyrimidinediamine derivative A-6.

Cytidines may also be used as starting materials in an analogous manner, as illustrated in Scheme (VII), below:

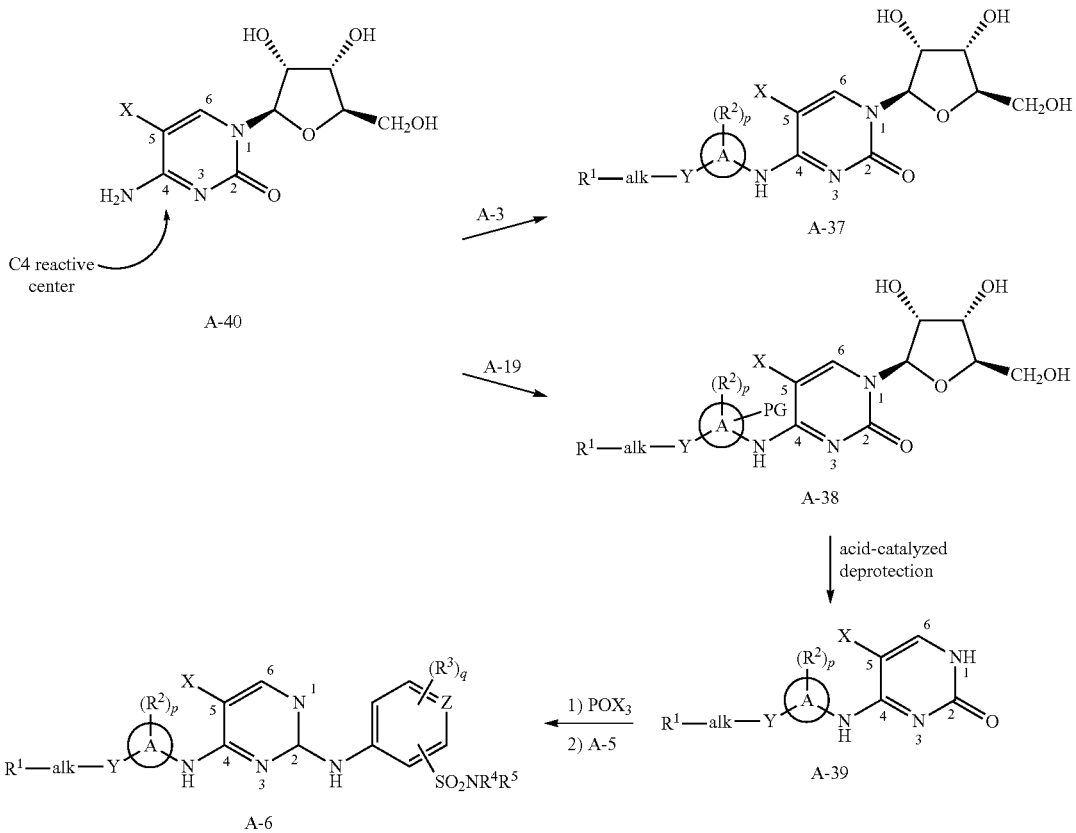

Scheme (VII)

In Scheme (VII), ring A, IV, $(R^2)_p$, alk, $(R^3)_q$, $R^4$, $R^5$, X, Y and Z are as previously defined in Scheme (I) and PG represents a protecting group as discussed above. Referring to Scheme (VII), like uridine A-36, cytidine A-40 has a C4 reactive center such that reaction with amine A-3 or protected amine A-19 yields N4-substituted cytidine A-37 or A-38, respectively. These cytidines A-37 and A-38 are then treated as previously described for Scheme (VI) to yield a 2,4-pyrimidinediamine derivative A-6.

Although Schemes (VI) and (VII) are exemplified with ribosylnucleosides, skilled artisans will appreciate that the corresponding 2'-deoxyribo and 2',3'-dideoxyribo nucleosides, as well as nucleosides including sugars or sugar analogs other than ribose, would also work.

Numerous uridines and cytidines useful as starting materials in Schemes (VI) and (VII) are known in the art, and include, by way of example and not limitation, 5-trifluoromethyl-2'-deoxycytidine (Chem. Sources #ABCR F07669; CAS Registry 66,384-66-5); 5-bromouridine (Chem. Sources Int'l 2000; CAS Registry 957-75-5); 5-iodo-2'-deoxyuridine (Aldrich #1-775-6; CAS Registry 54-42-2); 5-fluorouridine (Aldrich #32,937-1; CAS Registry 316-46-1); 5-iodouridine (Aldrich #85,259-7; CAS Registry 1024-99-3); 5-(trifluoromethyl)uridine (Chem. Sources Int'l 2000; CAS Registry 70-00-8); 5-trifluoromethyl-2'-deoxyuridine (Chem. Sources Int'l 2000; CAS Registry 70-00-8). Additional uridines and cytidines that can be used as starting materials in Schemes (VI) and (VII) are available from General Intermediates of Canada, Inc., Edmonton, CA and/or Interchim, Cedex, France, or may be prepared using standard techniques. Myriad textbook references teaching suitable synthetic methods are provided infra.

Although many of the synthetic schemes discussed above do not illustrate the use of protecting groups, skilled artisans will recognize that in some instances certain substituents, such as, for example, $R^2$ and/or $R^4$, may include functional groups requiring protection. The exact identity of the protecting group used will depend upon, among other things, the identity of the functional group being protected and the reaction conditions used in the particular synthetic scheme, and will be apparent to those of skill in the art. Guidance for selecting protecting groups, their attachment and removal suitable for a particular application can be found, for example, in Greene & Wuts, supra.

Prodrugs as described herein may be prepared by routine modification of the above-described methods. Alternatively, such prodrugs may be prepared by reacting a suitably protected 2,4-pyrimidinediamine 6 with a suitable progroup. Conditions for carrying out such reactions and for deprotecting the product to yield a prodrugs as described herein are well-known.

Myriad references teaching methods useful for synthesizing pyrimidines generally, as well as starting materials described in Schemes (I)-(VII), are known in the art. For specific guidance, the reader is referred to Brown, D. J., "The Pyrimidines", in *The Chemistry of Heterocyclic Compounds, Volume* 16 (Weissberger, A., Ed.), 1962, Interscience Publishers, (A Division of John Wiley & Sons), New York ("Brown I"); Brown, D. J., "The Pyrimidines", in *The Chemistry of Heterocyclic Compounds, Volume* 16, *Supplement I* (Weissberger, A. and Taylor, E. C., Ed.), 1970, Wiley-Interscience, (A Division of John Wiley & Sons), New York (Brown II"); Brown, D. J., "The Pyrimidines", in *The Chemistry of Heterocyclic Compounds, Volume* 16, *Supplement II* (Weissberger, A. and Taylor, E. C., Ed.), 1985, An Interscience Publication (John Wiley & Sons), New York ("Brown III"); Brown, D. J., "The Pyrimidines" in *The Chemistry of Heterocyclic Compounds, Volume* 52 (Weissberger, A. and Taylor, E. C., Ed.), 1994, John Wiley & Sons, Inc., New York, pp. 1-1509 (Brown IV"); Kenner, G. W. and Todd, A., in *Heterocyclic Compounds*, Volume 6, (Elderfield, R. C., Ed.), 1957, John Wiley, New York, Chapter 7 (pyrimidines); Paquette, L. A., *Principles of Modern Heterocyclic Chemistry*, 1968, W. A. Benjamin, Inc., New York, pp. 1-401 (uracil synthesis pp. 313, 315; pyrimidinediamine synthesis pp. 313-316; amino pyrimidinediamine synthesis pp. 315); Joule, J. A., Mills, K. and Smith, G. F., *Heterocyclic Chemistry*, 3$^{rd}$ Edition, 1995, Chapman and Hall, London, UK, pp. 1-516; Vorbrüggen, H. and Ruh-Pohlenz, C., *Handbook of Nucleoside Synthesis*, John Wiley & Sons, New York, 2001, pp. 1-631 (protection of pyrimidines by acylation pp. 90-91; silylation of pyrimidines pp. 91-93); Joule, J. A., Mills, K. and Smith, G. F., *Heterocyclic Chemistry*, 4$^{th}$ Edition, 2000, *Blackwell Science, Ltd*, Oxford, UK, pp. 1-589; and *Comprehensive Organic Synthesis*, Volumes 1-9 (Trost, B. M. and Fleming, I., Ed.), 1991, Pergamon Press, Oxford, UK.

Those of skill in the art will appreciate that the 2,4-substituted pyrimidinediamine compounds described herein may include functional groups that can be masked with progroups to create prodrugs. Such prodrugs are usually, but need not be, pharmacologically inactive until converted into their active drug form. Indeed, many of the 2,4-substituted pyrimidinediamine compounds described in this invention include promoieties that are hydrolyzable or otherwise cleavable under conditions of use. For example, ester groups commonly undergo acid-catalyzed hydrolysis to yield the parent carboxylic acid when exposed to the acidic conditions of the stomach, or base-catalyzed hydrolysis when exposed to the basic conditions of the intestine or blood. Thus, when administered to a subject orally, 2,4-substituted pyrimidinediamine compounds that include ester moieties may be considered prodrugs of their corresponding carboxylic acid, regardless of whether the ester form is pharmacologically active.

The mechanism by which the progroup(s) metabolizes is not critical, and can be caused by, for example, hydrolysis under the acidic conditions of the stomach, as described above, and/or by enzymes present in the digestive tract and/or tissues or organs of the body. Indeed, the progroup(s) can be selected to metabolize at a particular site within the body. For example, many esters are cleaved under the acidic conditions found in the stomach. Prodrugs designed to cleave chemically in the stomach to the active 2,4-substituted pyrimidinediamine can employ progroups including such esters. Alternatively, the progroups may be designed to metabolize in the presence of enzymes such as esterases, amidases, lipolases, phosphatases including ATPases and kinase etc. Progroups including linkages capable of metabolizing in vivo are well-known, and include, by way of example and not limitation, ethers, thioethers, silylethers, silylthioethers, esters, thioesters, carbonates, thiocarbonates, carbamates, thiocarbamates, ureas, thioureas, carboxamides, etc. In some instances, a "precursor" group that is oxidized by oxidative enzymes such as, for example, cytochrome P450 of the liver, to a metabolizable group, can be selected.

In the prodrugs, any available functional moiety may be masked with a progroup to yield a prodrug. Functional groups within the 2,4-substituted pyrimidinediamine compounds that may be masked with progroups for inclusion in a promoiety include, but are not limited to, amines (primary and secondary), hydroxyls, sulfanyls (thiols), carboxyls, etc. Myriad progroups suitable for masking such functional groups to yield promoieties that are cleavable under the desired conditions of use are known in the art. All of these progroups, alone or in combinations, may be included in the prodrugs.

In some embodiments of the 2,4-substituted pyrimidinediamine compounds and methods of using the compounds, the progroup(s) can be attached to any available primary or secondary amine, including, for example, the N2 nitrogen atom of the 2,4-pyrimidinediamine moiety, the N4 nitrogen atom of the 2,4-pyrimidinediamine moiety, and/or a primary or secondary nitrogen atom included in a substituent on the 2,4-pyrimidinediamine compound.

In particular embodiments of the 2,4-substituted pyrimidinediamine compounds and methods of using the compounds, the prodrugs described herein are 2,4-substituted pyrimidinediamine compounds that are substituted at the N4 nitrogen of the 2,4-pyrimidinediamine moiety with a substituted or unsubstituted nitrogen-containing bicyclic ring that includes at least one progroup at one or more of: the nitrogen atom(s) of the bicyclic ring, the N2 nitrogen of the 2,4-pyrimidinediamine moiety and/or the N4 nitrogen of the 2,4-pyrimidinediamine moiety.

As noted above, the identity of the progroup is not critical, provided that it can be metabolized under the desired conditions of use, for example under the acidic conditions found in the stomach and/or by enzymes found in vivo, to yield a the biologically active group, e.g., the 2,4-substituted pyrimidinediamines as described herein. Thus, skilled artisans will appreciate that the progroup can comprise virtually any known or later-discovered hydroxyl, amine or thiol protecting group. Non-limiting examples of suitable protecting groups can be found, for example, in *Protective Groups in Organic Synthesis*, Greene & Wuts, 2nd Ed., John Wiley & Sons, New York, 1991 (especially pages 10-142 (alcohols, 277-308 (thiols) and 309-405 (amines) the disclosure of which is incorporated herein by reference).

Additionally, the identity of the progroup(s) can also be selected so as to impart the prodrug with desirable characteristics. For example, lipophilic groups can be used to decrease water solubility and hydrophilic groups can be used to increase water solubility. In this way, prodrugs specifically tailored for selected modes of administration can be obtained. The progroup can also be designed to impart the prodrug with other properties, such as, for example, improved passive intestinal absorption, improved transport-mediated intestinal absorption, protection against fast metabolism (slow-release prodrugs), tissue-selective delivery, passive enrichment in target tissues, targeting-specific transporters, etc. Groups capable of imparting prodrugs with these characteristics are well-known, and are described, for example, in Ettmayer et al., 2004, J. Med. Chem. 47(10): 2393-2404, the disclosure of which is incorporated by reference. All of the various groups described in these references can be utilized in the prodrugs described herein.

As noted above, progroup(s) may also be selected to increase the water solubility of the prodrug as compared to the active drug. Thus the progroup(s) may include or may be a group(s) suitable for imparting drug molecules with improved water solubility. Such groups are well-known, and include, by way of example and not limitation, hydrophilic groups such as alkyl, aryl, arylalkyl, or cycloheteroalkyl groups substituted with one or more of an amine, alcohol, a carboxylic acid, a phosphorous acid, a sulfoxide, a sugar, an amino acid, a thiol, a polyol, an ether, a thioether and a quaternary amine salt.

The suitability of any particular progroup for a desired mode of administration can be confirmed in biochemical assays. For example, if a prodrug is to be administered by injection into a particular tissue or organ, and the identities of the various enzyme(s) expressed in the tissue or organ are known, the particular prodrug can be tested for metabolism in biochemical assays with the isolated enzyme(s). Alternatively, the particular prodrug can be tested for metabolism to the active 2,4-substituted pyrimidinediamine compound with tissue and/or organ extracts. Using tissue and/or organ extracts can be of particular convenience when the identity (ies) of the enzymes expressed in the target tissues or organs are unknown, or in instances when the isolated enzymes are not conveniently available. Skilled artisans will be able to readily select progroups having metabolic properties (such as kinetics) suitable for particular applications using such in vitro tests. Of course, specific prodrugs could also be tested for suitable metabolism in in vivo animal models.

Numerous references teach the use and synthesis of prodrugs, including, for example, Ettmayer et al., ibid and Bungaard et al., (1989) *J. Med. Chem.* 32(12): 2503-2507. Additionally, the preparation and use of prodrugs of 2,4-pyrimidinediamines is specifically taught in U.S. Provisional Patent Application 60/654,620, filed Feb. 18, 2005, entitled "Pyrimidinediamine Prodrugs and their Uses," the disclosure of which is hereby incorporated by reference in its entirety.

IV. EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications fall within the scope of the appended claims.

In the examples below as well as throughout the application, the following abbreviations have the following meanings. If not defined, the terms have their generally accepted meanings.

TFA=Trifluoroacetic acid
MeOH=Methanol
EtOH=Ethanol
mL=Milliliter
mmol=Millimole
DCM or $CH_2Cl_2$=methylene chloride
M=Molar
DMSO=dimethylsulfoxie
s=Singlet
d=Doublet
t=Triplet
q=Quartet
m=Multiplet
dd=double doublet
br=Broad
MS=mass spectrum
LC=liquid chromatography
Pd/C=palladium over carbon
HCl=hydrochloric acid
uL=Microliter
h=Hour
$K_2CO_3$=potassium carbonate
g=Gram
d=Days
RT or rt=room temperature
mg=Milligram
aq=Aqueous
THF=tetrahydrofuran
NaOH=sodium hydroxide
EtOAc=ethyl acetate
$NH_3$=Ammonia
DMF=dimethylformamide
DMAP=dimethylaminopyridine
TEA=Triethylamine
tBuOH=tert-butanol
$Cs_2CO_3$=cesium carbonate
iPrOH=Isopropanol
$H_2O_2$=hydrogen peroxide
HPLC=high pressure liquid chromatography
$Na_2SO_4$=sodium sulfate
psi=pound per square inch
$NH_4Cl$=ammonium chloride
$Cu_2O$=cuprous oxide
N=Normal
$NH_4OH$=ammonium hydroxide
$POCl_3$=phosphorous oxychloride
$H_2O$=Water
NaOMe=sodium methoxide
$NaHCO_3$=sodium bicarbonate
µM=Micromolar Example 1

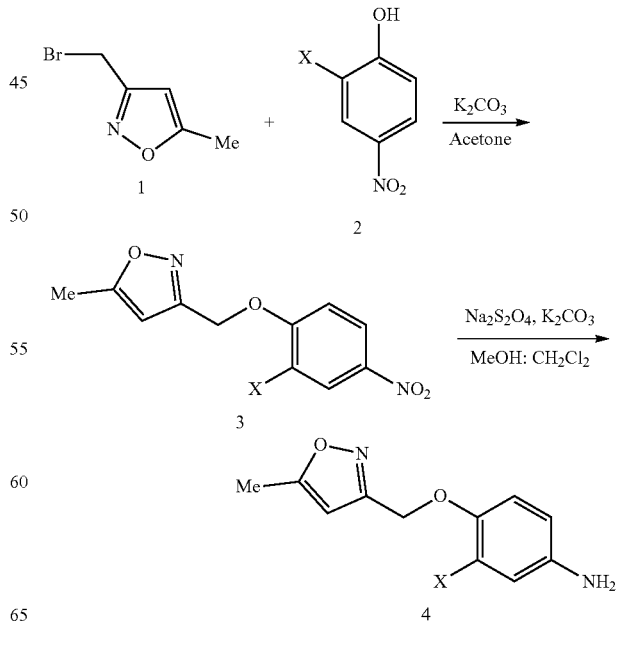

5-methyl-3-(4-nitrophenoxymethyl)isoxazole (3, X=H)

To a dry reaction flask equipped with a reflux condenser, a magnetic stirring bar and a rubber septum with a N2 inlet was placed 4-nitrophenol (2, X=H) (1.57 g, 11.36 mmol), anhydrous $K_2CO_3$ (1.58 g, 12 mmol) and tetrabutylammonium iodide (200 mg) in dry acetone (100 mL). The reaction mixture was stirred at room temperature for 30 minutes. To this heterogeneous mixture was added 3-(bromomethyl)-5-methylisoxazole (2.0 g, 11.36 mmol) at room temperature and then the reaction mixture was refluxed for over night. After cooling it to room temperature, the reaction mixture was filtered, washed with acetone (50 mL) and the combined filtrates were concentrated under reduced pressure. The resulting solid was purified by silica gel column, eluted with hexanes then polarity was increased gradually up to 40% EtOAc in hexanes to give 2.59 g (97%) of the desired 5-methyl-3-(4-nitrophenoxymethyl)isoxazole (3, X=H). $^1$H NMR ($CDCl_3$): δ 8.19 (d, 2H, J=9.3 Hz), 7.04 (d, 2H, J=9.6 Hz), 6.18 (s, 1H), 5.20 (s, 2H), 2.44 (s, 3H); LCMS (m/z): 235 (MH$^+$).

3-(4-Aminophenoxymethyl)-5-methylisoxazole (4, X=H)

The 5-methyl-3-(4-nitrophenoxymethyl)isoxazole (3, X=H) (2.59 g, 11.07 mmol) was dissolved in MeOH:$CH_2Cl_2$ (1:1, 600 mL). An aqueous solution of (77 mL) sodium hydrosulfite (11.93 g, 68.5 mmol) and $K_2CO_3$ (9.55 g, 69 mmol) was added dropwise under nitrogen for 30 min. The reaction was allowed to stir at room temperature for 2 h, and the organic solvents were removed under reduced pressure, diluted with water (200 mL), extracted with $CH_2Cl_2$ (3×300 mL), dried over anhydrous $Na_2SO_4$ and solvent was removed under reduced pressure. The resulting product was finally dried under high vacuum to afford 1.03 g (46%) of the 5-methyl-3-(4-aminophenoxymethyl)isoxazole (4, X=H). $^1$H NMR ($CDCl_3$): δ 6.78 (d, 2H, J=8.7 Hz), 6.61 (d, 2H, J=8.4 Hz), 6.07 (s, 1H), 5.01 (s, 2H), 3.44 (s, 2H), 2.40 (s, 3H); LCMS (m/z): 205 (MH$^+$).

The following compounds were made in a similar fashion to the example 1.

5-Methyl-3-(2-methyl-4-nitrophenoxymethyl)isoxazole (3, X=CH$_3$)

$^1$H NMR ($CDCl_3$): δ 8.08 (d, 1H, J=2.7 Hz), 8.04 (s, 1H), 6.96 (d, 1H, J=8.7 Hz), 6.08 (s, 1H), 5.21 (s, 2H), 2.44 (s, 3H), 2.30 (s, 3H); LCMS (m/z): 249 (MH$^+$).

3-(2-Fluoro-4-nitrophenoxymethyl)-5-methylisoxazole (3, X=F)

LCMS: purity: 98%; MS (m/e): 254 (MH$^+$).

3-(4-Amino-2-methylphenoxymethyl)-5-methylisoxazole (4, X=CH$_3$)

$^1$H NMR ($CDCl_3$): δ 6.70 (d, 1H, J=8.7 Hz), 6.52 (d, 1H, J=2.7 Hz), 6.45 (dd, 1H, J=2.7 and 8.4 Hz), 6.07 (s, 1H), 5.00 (s, 2H), 3.39 (s, 2H), 2.41 (s, 3H), 2.17 (s, 3H); LCMS (m/z): 219 (MH$^+$).

3-(4-Amino-2-fluorophenoxymethyl)-5-methylisoxazole (4, X=F)

LCMS: purity: 89%; MS: 224 (MH$^+$).

Example 2

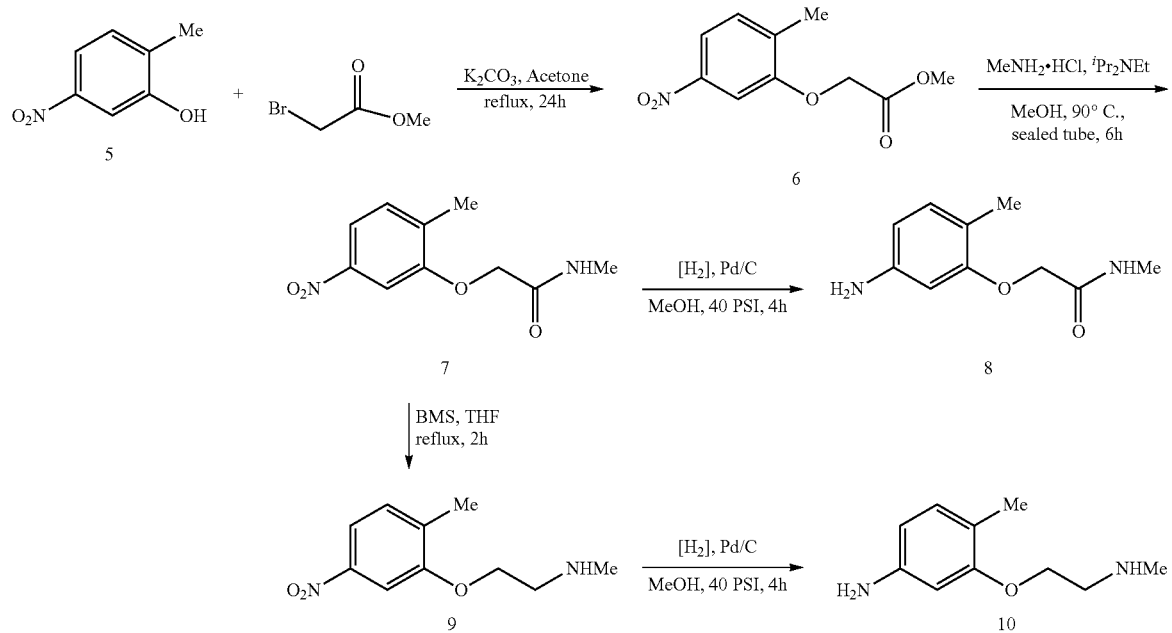

4-methyl-3-methoxycarbonylmethyleneoxynitrobenzene (6)

A reaction flask equipped with a reflux condenser, a magnetic stirrer bar and nitrogen inlet was charged with 2-methyl-5-nitrophenol (5) (5.0 g, 32.6 mmol), $K_2CO_3$ (4.51 g, 32.6 mmol) and acetone (35 mL). To this heterogeneous mixture was added methyl bromoacetate (2.7 mL, 29.34 mmol) at room temperature and then refluxed for 24 hours.

Upon cooling, the reaction mixture was poured over ice water (200 mL). The solid crashed out, was filtered, washed with water (3×50 mL) and dried under a high vacuum to obtain 7.0 g of 4-methyl-3-methoxycarbonylmethyleneoxynitrobenzene (6). LCMS: purity: 95%; MS (m/z): 226 (MH+).

4-methyl-3-methylaminocarbonylmethyleneoxynitrobenzene (7)

A mixture of 4-methyl-3-methoxycarbonylmethyleneoxynitrobenzene (6) (7.0 g, 31 mmol), methylamine hydrochloride (20.93 g, 310 mmol) and diisopropylethyl amine (DIPEA) (28 mL, 155 mmol) in methanol (100 mL) was stirred in a pressure tube at 90° C. for 6 hours. The reaction was cooled to room temperature, and diluted with water (1 Liter). The solid obtained was filtered, washed with water (3×150 mL) and dried to obtain 6 g of 4-methyl-3-methylaminocarbonylmethyleneoxynitrobenzene (7). LCMS: purity: 98%; MS (m/z): 225 (MH+).

4-methyl-3-methylaminocarbonylmethyleneoxyaniline (8)

The hydrogenation of 4-methyl-3-methylaminocarbonylmethyleneoxynitrobenzene (7) (1.0 g) was conducted using 10% Pd/C (100 mg) in methanol (50 mL) at 40 PSI for 4 hours to give 0.8 g of 4-methyl-3-methylaminocarbonylmethyleneoxyaniline (8) after filtration of catalyst and removal of solvent under reduced pressure. LCMS: purity: 93%; MS (m/e): 195 (MH+).

4-methyl-3-(2-methylamino)ethyloxynitrobenzene (9)

A dry reaction flask equipped with a reflux condenser, a magnetic stirring bar and a nitrogen inlet was charged with 4-methyl-3-methylaminocarbonylmethyleneoxynitrobenzene (7) (0.5 g, 2.23 mmol) and THF (5 mL). The resulting suspension was cooled to 0° C. and to it was added borane methylsulfide complex (3.3 mL, 2M) over a period of 5 minutes and then the reaction mixture was brought to room temperature and then refluxed for 2 hours. After removal of solvent under vacuum, the addition of methanol was performed carefully (CAUTION! methanol reacts violently with the residual/unreacted borane methylsulfide complex). The resulting methanolic solution was stirred at room temperature for 30 minutes and methanol and volatiles were removed under reduced pressure. This process was repeated twice. The methanolic solution was then treated with 4N HCl (in dioxane (4.4 mmol, 1.1 mL) and then heated at 60° C. for 2.5 hours. The solvent was removed under a reduced pressure. The mixture was treated with 2M NH3/methanol (8.8 mmol, 4.4 mL) and the solvent was then removed under a reduced pressure. The residual product was chromatographed (silica gel, eluted with hexanes then 20% ethyl acetate in hexanes) to obtain 0.350 g of 4-methyl-3-(2-methylamino)ethyloxynitrobenzene (9). LCMS: purity: 92%; MS (m/z): 211 (MH+).

4-methyl-3-(2-methylamino)ethyloxyaniline (10)

The hydrogenation of 4-methyl-3-(2-methylamino)ethyloxynitrobenzene (9) (0.5 g) was conducted using 10% Pd/C (50 mg) in methanol (20 mL) at 40 psi for 4 hours to give 0.350 g of 4-methyl-3-(2-methylamino)ethyloxyaniline (10). LCMS: purity: 90%; MS (m/z): 181 (MH+).

Example 3

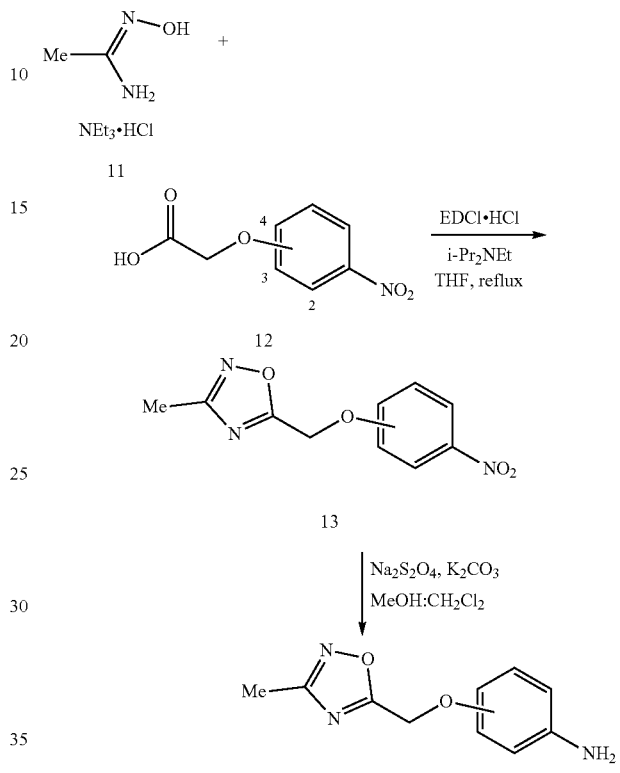

Acetamide Oxime.Triethylamine Hydrochloride Salt (11)

Hydroxylamine hydrochloride (3.38 g, 48.64 mmol) and triethyl amine (NEt3) (5.1 g, 7.0 mL, 50.4 mmol) were added to a stirred solution of acetonitrile (2.0 g, 2.54 mL, 48.72 mmol) in MeOH (10 mL) at room temperature and then refluxed for 3 days. The solvent was removed under reduced pressure and then dried under high vacuum to provide the desired acetamide oxime triethylamine hydrochloride salt (11) as a white crystalline solid.

3-Methyl-5-(4-nitrophenoxymethyl)-1,2,4-oxadiazole (13a)

A mixture of 4-nitrophenoxyacetic acid (12) (2.25 g, 11.4 mmol), acetamide oxime triethylamine hydrochloride salt (11, 5.85 g, 27.62 mmol), EDCl.HCl (4.37 g, 22.79 mmol) and diisopropylethylamine (7.42 g, 10 mL, 57.40 mmol) in anhydrous tetrohydrofuran (THF) (250 mL) was refluxed for 18 hours. The heterogeneous brown reaction mixture was then quenched with water and extracted with EtOAc (3×300 mL). The combined organic layers were washed successively with aqueous sodium bicarbonate (NaHCO3) and brine. The resulting organic phase was dried over anhydrous Na2SO4 and solvent was removed by using rotary evaporator. The resulting residue was purified by silica gel column chromatography to yield 1.62 g (60%) of the desired product, 3-methyl-5-(4-nitrophenoxymethyl)-1,2,4-oxadiazole (13a) as a white solid. $^1$H NMR (CDCl$_3$, 300 MHz): δ 8.24 (d, 2H, J=8.8 Hz), 7.08 (d, 2H, J=8.8 Hz), 5.36 (s, 2H), 2.44 (s, 3H); LCMS (m/z): 236 (MH$^+$).

5-(4-Aminophenoxymethyl)-3-methyl-1,2,4-oxadiazole (14a)

Prepared by following the procedure described in Example 1. $^1$H NMR (CDCl$_3$): δ 6.82 (d, 2H, J=8.8 Hz), 6.63 (d, 2H, J=8.8 Hz), 5.15 (s, 2H), 3.38 (br s, 2H), 2.41 (s, 3H); LCMS (m/z): 206 (MH$^+$).

The following compounds were made in a similar fashion to the example 3.

3-Methyl-5-(3-nitrophenoxymethyl)-1,2,4-oxadiazole (13b)

$^1$H NMR (CDCl$_3$, 300 MHz): δ 7.92 (dd, 1H, J=0.9 and 1.9 Hz), 7.89 (dd, 1H, J=0.9 and 2.1 Hz), 7.83 (t, 1H, J=2.1 Hz), 7.33 (m, 1H), 5.34 (s, 2H), 2.44 (s, 3H); LCMS (m/z): 236 (MH$^+$).

5-(3-Aminophenoxymethyl)-3-methyl-1,2,4-oxadiazole (14b)

$^1$H NMR (CDCl$_3$): δ 7.05 (t, 1H, J=8.4 Hz), 6.36-6.29 (m, 3H), 5.19 (s, 2H), 3.69 (br s, 2H), 2.42 (s, 3H); LCMS (m/z): 206 (MH$^+$).

3-Methyl-5-(4-nitrophenethyl)-1,2,4-oxadiazole $^1$H NMR (DMSO-d$_6$): δ 8.15-8.12 (d, J=9.0 Hz, 2H), 7.56-7.53 (d, J=9.0 Hz, 2H), 3.28-3.26 (m, 2H), 3.22-3.20 (m, 2H), and 2.28 (s, 3H).

4-[2-(3-Methyl-1,2,4-oxadiazol-5-yl)ethyl]aniline

LCMS: purity: 91%; MS (m/e): 204 (M+).

Example 4

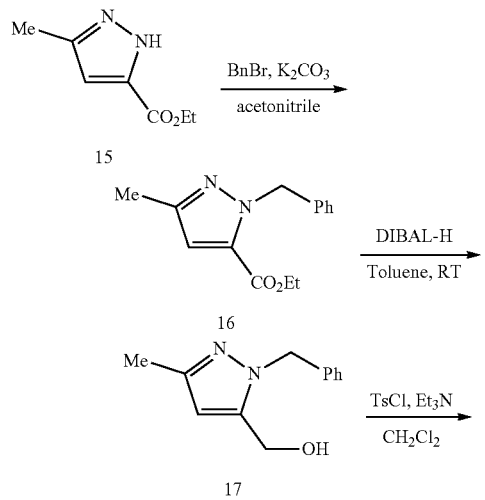

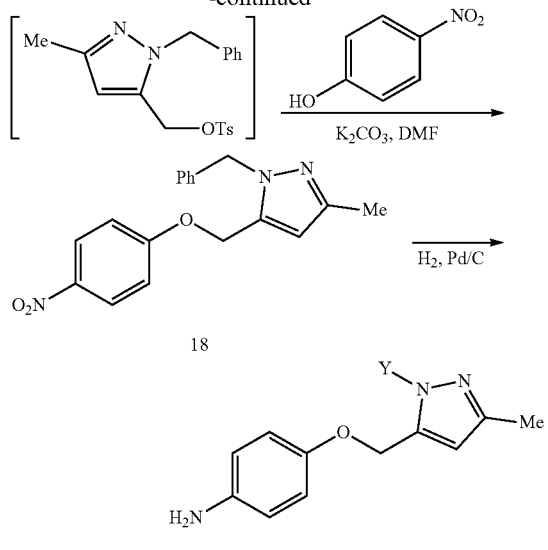

ethyl-1-benzyl-3-methylpyrazole-5-carboxylate (16)

An acetonitrile (8.0 mL) mixture of ethyl-3-methyl-1H-pyrazole-5-carboxylate (15) (0.50 g. 3.2 mmol), benzyl bromide (0.48 mL, 4.0 mmol), and K$_2$CO$_3$ (0.90 g, 6.5 mmol) was stirred at room temperature overnight. The reaction mixture was diluted with water (50 mL) and extracted with dichloromethane. The combined organic layers were washed with brine and dried over anhydrous magnesium sulfate. After removal of solvent under reduced pressure, the residue was purified by flash column chromatography [silica gel, eluting with mixtures of ethyl acetate and hexanes (0% ramped to 15% EtOAc/hexanes)] to yield 0.30 g of ethyl-1-benzyl-3-methylpyrazole-5-carboxylate (16). $^1$H NMR (CDCl$_3$): δ 7.30-7.22 (m, 5H), 6.65 (s, 1H), 5.71 (s, 2H), 4.28 (q, J=7.2 Hz, 2H), 2.32 (s, 3H), 1.32 (t, J=7.2 Hz, 3H); LCMS: purity: 99%; MS (m/z): 345 (MH$^+$).

4-[(1-benzyl-3-methylpyrazol-5-yl)methyleneoxy] nitrobenzene (18)

To a suspension of ethyl-1-benzyl-3-methylpyrazole-5-carboxylate (16) (0.30 g, 1.2 mmol) in anhydrous toluene (6.0 mL) at 0° C. was added a solution of diisobutyl aluminum hydride (DIBAL-H) (3.4 mL, 3.4 mmol, 1M in toluene) drop-wise. The reaction mixture was then stirred at room temperature for 1 hour. The reaction mixture was diluted with ether (50 mL) followed by addition of Rochelle's salt (50 mL, 0.5 M) and then stirred vigorously at room temperature for 2 hours. The aqueous layer was separated and extracted further with ether. The combined organic layers were washed with brine and dried over anhydrous magnesium sulfate. The crude product 17 (0.23 g) obtained after concentration was used without further purification.

The product 17 (0.23 g, 1.0 mmol) was suspended in anhydrous dichloromethane (8.0 mL), and to this solution were added triethylamine (0.29 mL, 2.1 mmol), 4-dimethylaminopyridine (5 mg, 0.04 mmol) and p-toluenesulfonyl-chloride (0.21 g, 1.1 mmol). The reaction mixture was then stirred at room temperature for 3.5 hours and then diluted with dichloromethane (10 mL) and saturated NH$_4$Cl (15 mL). The organic layer was separated, dried over anhydrous magnesium sulfate, and concentrated under vacuum. The crude product was passed through a pad of silica gel eluting with mixtures of ethyl acetate and hexanes (0% ramped to 5% EtOAc/hexanes) to give the tosylate as yellow oil (0.135 g). The tosylate (0.135 g, 0.379 mmol) was combined with 4-nitrophenol (66 mg, 0.47 mmol) and K$_2$CO$_3$ (0.10 g, 0.76 mmol) in anhydrous dimethylformamide (DMF) (2.0 mL). The mixture was then stirred at 65° C. overnight. The reaction mixture was cooled to room temperature and poured over water (20 mL) and the resulting solid of the desired product, 4-[(1-benzyl-3-methylpyrazol-5-yl)methyleneoxy]nitrobenzene (18) was isolated by suction filtration as a white solid (0.155 g). $^1$H NMR (CDCl$_3$): δ 8.16 (d, J=9.0 Hz, 2H), 7.29-7.25 (m, 3H), 7.11-7.06 (m, 2H), 6.83 (d, J=9.0 Hz, 2H), 6.20 (s, 1H), 5.39 (s, 2H), 4.96 (s, 2H), and 2.34 (s, 3H).

4-[(1-benzyl-3-methylpyrazol-5-yl)methyleneoxy]aniline (19, Y=Benzyl)

LCMS: purity: 85%; MS (m/e): 294 (MH+).

Example 5

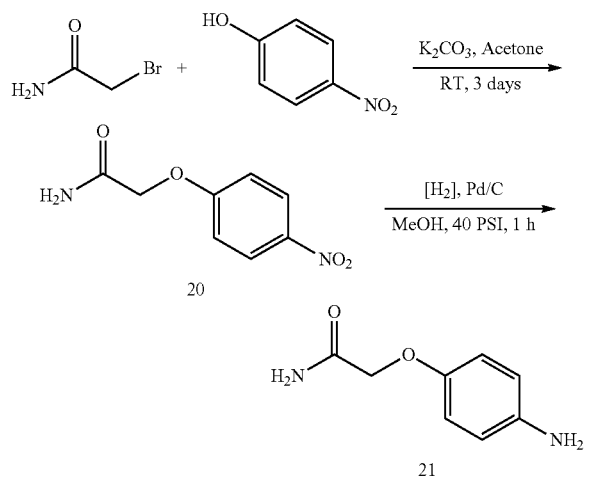

4-Aminocarbonylmethyleneoxynitrobenzene (20)

4-Nitrophenol (10 g), bromoacetamide (10 g) and K$_2$CO$_3$ (15 g) were suspended in acetone (30 mL). The yellow solution was stirred at room temperature for 3 days. The reaction mixture was diluted with distilled water and acetone was removed under reduced pressure. The light-yellow precipitate was collected by filtration, washed with water (3×100 mL) and dried to give 4-aminocarbonylmethyleneoxynitrobenzene (20) (11.5 g) as beige solid.

4-(aminocarbonylmethyleneoxy)aniline (21)

4-Aminocarbonylmethyleneoxynitrobenzene (20) (5 g) was dissolved in methanol (50 mL) and to it was added 10% Pd—C(500 mg). The reaction mixture was reacted under hydrogen atmosphere (~40 psi) for 1 h. The catalyst was filtered off through a pad of celite. The filtrate was concentrated under reduced pressure to give 4-(aminocarbonylmethoxy)aniline (21) as a white solid.

Example 6

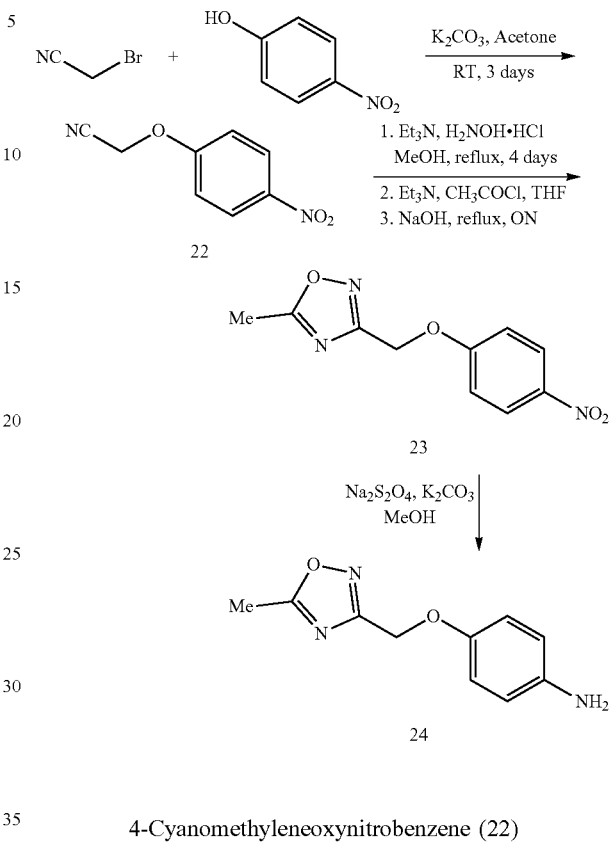

4-Cyanomethyleneoxynitrobenzene (22)

4-Nitrophenol (10 g), bromoacetonitrile (6 mL) and K$_2$CO$_3$ (15 g) were suspended in acetone (100 mL). The yellow solution was stirred at room temperature overnight. The reaction mixture was diluted with water (100 mL) and acetone was removed under reduced pressure. The light-yellow precipitate was collected by filtration, washed with distilled water (3×100 mL) and dried to give 4-cyanomethyleneoxynitrobenzene (22).

4-(5-methyl-1,2,4-oxadiazol-3-yl)methyleneoxynitrobenzene (23)

4-Cyanomethyleneoxynitrobenzene (22) (8 g) was dissolved in methanol (50 mL) and to the solution was added hydroxyamine HCl (3.4 g) and triethylamine (9.4 mL). The reaction mixture was refluxed for 4 days and the solvent was removed under reduced pressure. The residue was redissolved in THF (50 mL). To the solution was added acetyl chloride (AcCl) (23 mL) and triethylamine (50 mL). The reaction mixture was stirred at room temperature overnight, then was added water (30 mL) and NaOH (18 g). The reaction solution was refluxed overnight and diluted with water (200 mL). The aqueous solution was extracted with EtOAc (2×150 mL). After separation, the combined EtOAc layers were dried over anhydrous sodium sulfate and then solvent was removed under a reduced pressure. The resulting residue was purified by flash column chromatography) (EtOAc/hexanes=½ (v/v), 1/1, EtOAc) and recrystallized from EtOAc and hexanes to give 4-(5-methyl-1,2,4-oxadiazol-3-yl)methyleneoxynitrobenzene (23).

4-(5-methyl-1,2,4-oxadiazol-3-yl)methoxyaniline (24)

4-(5-Methyl-1,2,4-oxadiazol-3-yl)methyleneoxynitrobenzene (1 g) was dissolved in THF (40 mL) and water (40 mL). Sodium bisulfite (3.8 g), sodium bicarbonate (1.4 g), and $K_2CO_3$ (1.8 g) were added to the solution. The solution was stirred at room temperature for 30 minutes and diluted with water (80 mL). The aqueous solution was extracted with EtOAc (2×100 mL). The organic layers were then combined, dried over anhydrous sodium sulfate and solvent was removed under reduced pressure to give 4-(5-methyl-1,2,4-oxadiazol-3-yl)methoxyaniline (24).

Example 7

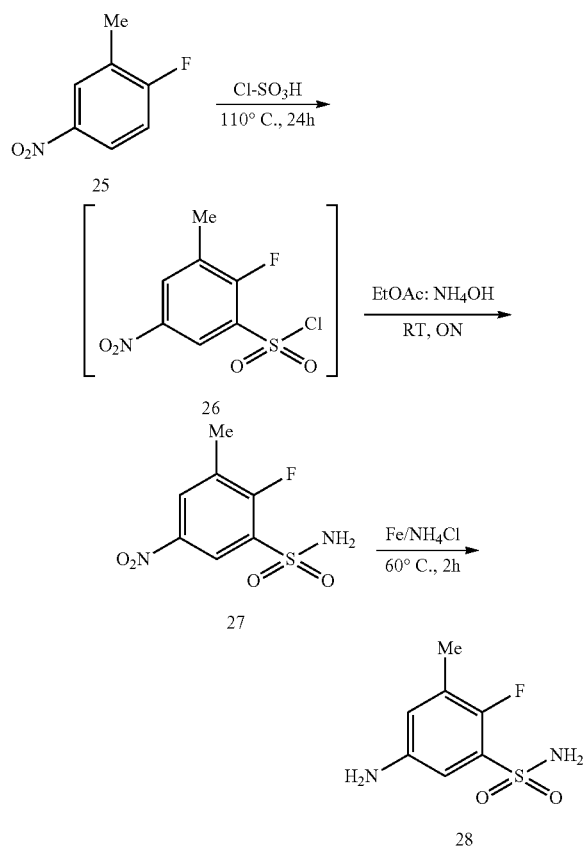

3-chlorosulfonyl-4-fluoro-5-methylnitrobenzene (26)

A dry reaction flask equipped with a stirring bar, a reflux condenser and nitrogen inlet was charged with 4-fluoro-3-methylnitrobenzene (25) (3.10 g, 20 mmol). To this at 0° C., was added dropwise chlorosulfonic acid (5.29 mL, 80 mmol) over a period of 15 minutes. After bringing the homogeneous solution to room temperature, it was stirred at 110° C. for 24 hours. The resulting slurry was then poured over ice water (100 gm), extracted with diethyl ether (3×75 mL), and the organic phase washed with water (75 mL), then dried over anhydrous sodium sulfate. The solvent was then removed under reduced pressure to afford the corresponding sulfonyl chloride derivative (26), which was used further without purification.

3-aminosulfonyl-4-fluoro-5-methylnitrobenzene (27)

The resulting oily residue of compound 26 was taken up in ethyl acetate (100 mL) and stirred with ammonium hydroxide (100 mL, 30% aqueous solution) overnight at room temperature. After the ethyl acetate layer was separated, the aqueous layer was extracted with ethyl acetate (2×50 mL). The organic layers were combined, dried over anhydrous sodium sulfate and the solvent was removed under vacuum. The dark oily residue was chromatographed (silica gel, hexanes then 10%, 20%, up to 50% ethyl acetate in hexanes to afford 3-aminosulfonyl-4-fluoro-5-methylnitrobenzene (27). LCMS: purity: 89%; MS (m/z): 235 (MH+).

Synthesis of 3-Aminosulfonyl-4-fluoro-5-methylaniline (28)

To a heterogeneous solution of 3-aminosulfonyl-4-fluoro-5-methylnitrobenzene (27) (0.5 g, 2 mmol) in of ethanol: water (50 mL, each) were added iron powder (1.08 g, 20 mmol), and ammonium chloride (1.08 g, 20 mmol) at room temperature. The resulting heterogeneous mixture was then stirred at 60° C. for 2 hours, filtered through celite (when hot), washed with ethanol (2×50 mL) and then the solvent was removed under reduced pressure. The residue upon dilution with water was extracted with ethyl acetate (3×50 mL), and the organic phase was dried over anhydrous sodium sulfate and concentrated under a reduced pressure to obtain 3-aminosulfonyl-4-fluoro-5-methylaniline (28). LCMS: purity: 85%; MS (m/z): 205 (MH+).

3-Aminosulfonyl-4-fluoroaniline

To a solution of 3-aminosulfonyl-4-fluoronitrobenzene (360 mg, 1.62 mmol) in dichloromethane (6 mL) and methanol (3 mL) was added 10% Pd/C (36 mg) and shaken under a hydrogen atmosphere at 50 psi for 15 minutes. The mixture was filtered through Celite and the cake was washed with methanol (5 mL). The combined organic solvent was concentrated under reduced pressure to give crude product, which was further purified by flash column chromatography (ethyl acetate: hexanes 1:1) to give 240 mg of 5-amino-2-fluorobenzensulfonamide as a light yellow solid. $^1$H NMR (DMSO-$d_6$): δ 7.38 (s, 2H), 7.03-6.94 (m, 2H), 6.70-6.66 (m, 1H), 5.33 (s, 1H).

The following compounds were made in a similar fashion to the example 7.

3-Aminosulfonyl-4-methylnitrobenzene

LCMS: purity: 95%; MS (m/e): 217 (MH+).

3-Aminosulfonyl-4-fluoronitrobenzene $^1$H NMR (DMSO-$d_6$): δ 8.53-8.50 (m, 2H), 8.04 (s, 2H), and 7.77-7.70 (m, 1H).

3-Aminosulfonyl-4-chloro-5-methylnitrobenzene

LCMS: purity: 86%; MS (m/e): 252 (MH+).

3-Aminosulfonyl-5-chloro-4-methylnitrobenzene

LCMS: purity: 96%; MS (m/e): 252 (MH+).

3-Aminosulfonyl-4-methylaniline

LCMS: purity: 87%; MS (m/e): 187 (MH+).

3-Aminosulfonyl-4-chloro-5-methylaniline

LCMS: purity: 98%; MS (m/e): 222 (MH+).

3-Aminosulfonyl-5-chloro-4-methylaniline

LCMS: purity: 97%; MS (m/e): 222 (MH+).

3-Aminosulfonyl-4-chloroaniline

LCMS: purity: 98%; MS (m/e): 239 (MH+).

Example 8

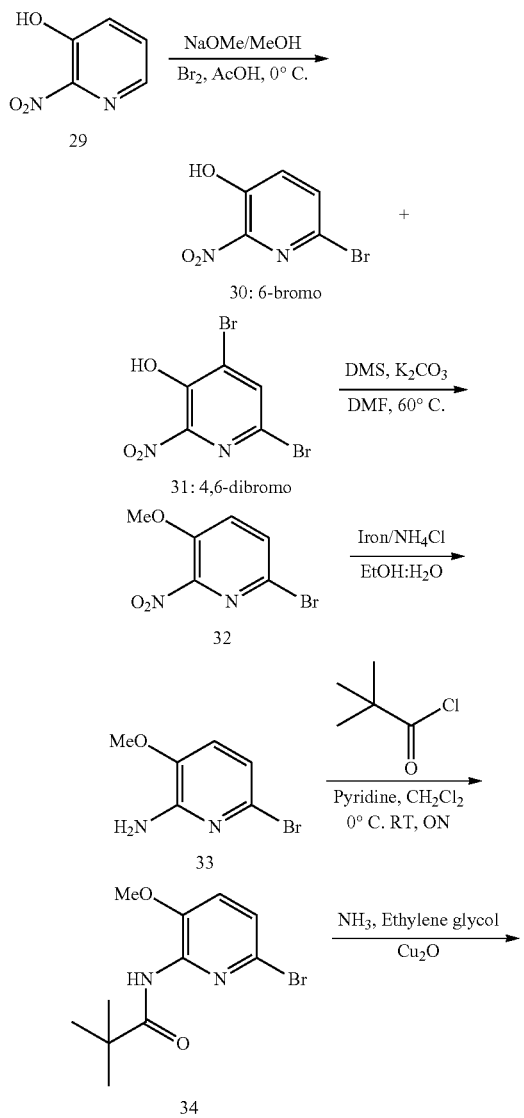

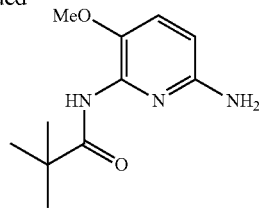

6-Bromo-3-hydroxy-2-nitropyridine (30)

A dry reaction flask equipped with a magnetic stirring bar and nitrogen inlet was charged with 3-hydroxy-2-nitropyridine (29) (28 g, 200 mmol) and methanol (560 mL). To this homogeneous mixture at room temperature was added sodium methoxide (25 wt %, in methanol; 181 mmol, 46.15 mL) over a period of 30 minutes. The resulting solution was cooled to 0° C. and to it was added bromine (10.31 mL, 200 mmol) over a period of 15 minutes. The reaction mixture was then stirred at 0° C. for an additional 30 minutes. The reaction was quenched with glacial acetic acid (3.5 mL), then the reaction mixture was concentrated to dryness, and then diluted with water (1 Liter). The solid obtained was filtered and washed with water (2×100 mL) to obtain 60:40 mixture of 6-bromo-3-hydroxy-2-nitropyridine (30): 4,6-dibromo-3-hydroxy-2-nitropyridine (31). LCMS: MS (m/z): 219 (MH$^+$) and 297 (MH$^+$), respectively. 60:40 mixture of 6-bromo-3-hydroxy-2-nitropyridine (30): 4,6-dibromo-3-hydroxy-2-nitropyridine (31) was used as such for the next experiment.

6-Bromo-3-methoxy-2-nitropyridine (32)

To a heterogeneous 60:40 mixture of 6-bromo-3-hydroxy-2-nitropyridine (30): 4,6-dibromo-3-hydroxy-2-nitropyridine (31) (2.18 g, 10 mmol), K$_2$CO$_3$ (2.08 g, 15 mmol) in N,N-dimethylformamide (DMF) (20 mL) was added dimethyl sulfate (DMS) (1.13 mL, 12 mmol) and the resulting mixture was stirred at 60° C. for 24 hours. The reaction mixture was poured over ice-water (100 mL), extracted with ethyl acetate (3×50 mL), and the organic phase was dried over anhydrous sodium sulfate. The solvent was then removed under reduced pressure to afford 6-bromo-3-methoxy-2-nitropyridine (32). LCMS: purity: 92%; MS (m/z): 233 (MH+).

2-Amino-6-bromo-3-methoxypyridine (33)

To a heterogeneous solution of 6-bromo-3-methoxy-2-nitropyridine (32) (2.32 g, 10 mmol) in of ethanol:water (40 mL, each) were added iron powder (2.8 g, 50 mmol), followed by ammonium chloride (2.64 g, 50 mmol) at room temperature. The resulting heterogeneous mixture was then stirred at 70-75° C. for 15 minutes, filtered through celite (when hot), washed with ethanol (2×50 mL) and solvent was then removed under reduced pressure. The residue upon dilution with water afforded a solid, which was isolated by filtration to give 2-amino-6-bromo-3-methoxypyridine (33). LCMS: purity: 95%, MS (m/z): 203 (MH$^+$).

6-Bromo-2-(tert-butylcarbonyl)amino-3-methoxypyridine (34)

A dry reaction flask equipped with a nitrogen inlet and magnetic stirring bar was charged with 2-amino-6-bromo- 3-methoxypyridine (33) (0.170 g, 0.84 mmol), pyridine (0.126 mL, 1.26 mmol) and $CH_2Cl_2$ (5 mL). To this at 0° C. was added pivaloyl chloride (0.113 mL, 0.92 mmol) and then the reaction mixture was stirred at room temperature overnight. The reaction was then quenched with water (25 mL), extracted with $CH_2Cl_2$ (2×25 mL), dried over anhydrous sodium sulfate and solvent was removed under reduced pressure to afford 6-bromo-2-(tert-butylcarbonyl)amino-3-methoxypyridine (34). LCMS: purity: 80%; MS (m/z): 287 (MH+).

6-Amino-2-(tert-butylcarbonyl)amino-3-methoxypyridine (35)

A pressure tube was charged with 6-bromo-2-(tert-butylcarbonyl)amino-3-methoxypyridine (34) (0.287 g), ethylene glycol (3 mL) and $Cu_2O$ (0.028 g) and cooled to −78° C. To this mixture, 1 mL of liquid ammonia was collected (at −78° C.), the pressure tube was sealed and then stirred at room temperature for 24 hours. The reaction mixture was again cooled to −78° C., the seal was removed and the reaction mixture diluted with water (10 mL). The aqueous solution was extracted with ethyl acetate (3×50 mL), dried over anhydrous sodium sulfate and solvent was removed under a reduced pressure. The resulting residue was chromatographed (silica gel, $CH_2Cl_2$ then 1% 2N $NH_3$/MeOH in $CH_2Cl_2$ to obtain 6-amino-2-(tert-butylcarbonyl)amino-3-methoxypyridine (35). LCMS: purity: 94%; MS (m/z): 224 $(MH^+)$.

Example 9

1:1) to give 740 mg of 3-(4-nitrophenyl)propionitrile (38) as a light orange solid. $^1$H NMR (DMSO-$d_6$): δ 8.20-8.17 (dd, J=8.7 Hz, 2H), 7.59-7.56 (d, J=9.0 Hz, 2H), and 3.06-3.01 (m, 2H).

3-(4-Aminophenyl)propionitrile (39)

3-(4-Nitrophenyl)propionitrile (38) (740 mg, 4.2 mmol) was reduced by using procedure described in Example 5 in methanol (100 mL) with 10% Pd/C as a catalyst to afford 3-(4-aminophenyl)propionitrile (39). $^1$H NMR (DMSO-$d_6$): δ 6.91-6.88 (d, J=9.0 Hz, 2H), 6.49-6.46 (d, J=9.0 Hz, 2H), 4.92 (s, 2H), and 2.66 (s, 4H).

(Cyanomethyl)Trimethylphosphonium Iodide

A solution of triphenylphosphine in toluene (1 mol $L^{-1}$, 40 mL, 40 mmol) at 0° C. under nitrogen was added to a mixture of toluene (20 mL) and tetrahydrofuran (20 mL). Iodoacetonitrile (2.8 mL, 38.7 mmol) was then added dropwise with vigorous stirring. The ice-bath was then removed and the mixture was stirred at room temperature for an additional of 40 hours. The mixture was filtered and the solid was washed with toluene and dried under reduced pressure to give 8 g of (cyanomethyl)trimethylphosphonium iodide as a light yellow solid. LCMS (m/z): 243.03 $(M^+)$.

Example 10

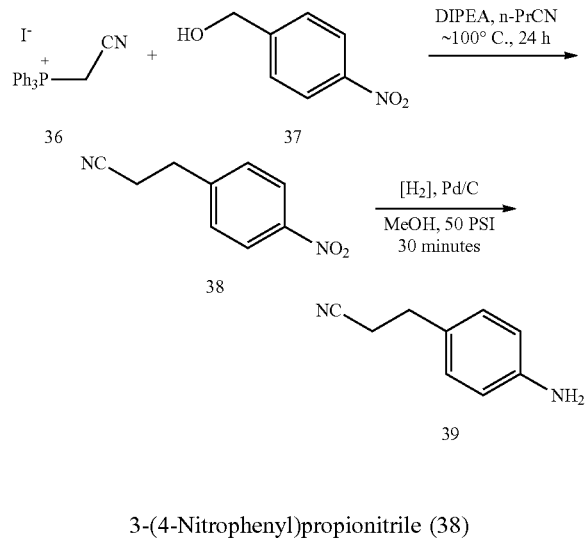

3-(4-Nitrophenyl)propionitrile (38)

To a mixture of 4-nitrobenzyl alcohol (37) (1 g, 6.53 mmol) and (cyanomethyl)trimethylphosphonium iodide (36) (4 g, 16.32 mmol) were added propionitrile (32 mL) and diisopropylethylamine (2.5 g, 19.58 mmol) at room temperature. The mixture was heated at ~100° C. for 24 hours. The reaction was quenched with water (1 mL), followed by addition of concentrated HCl (5 mL). The resulting reaction mixture was extracted with ethyl acetate (3×100 mL), washed with brine, dried over anhydrous sodium sulfate, and then concentrated under reduced pressure to give a dark brown solid. The crude solid product was purified by flash column chromatography (silica gel, ethyl acetate: hexanes

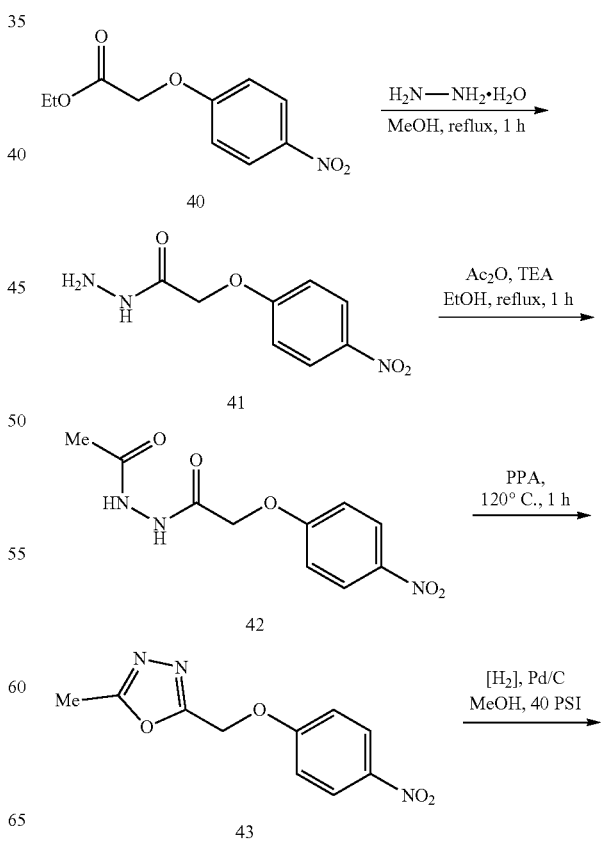

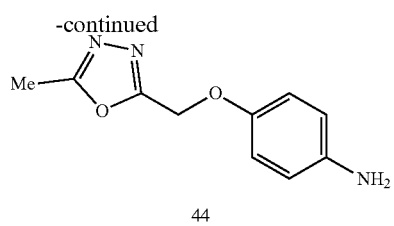

44

2-(4-Nitrophenoxy)acetylhydrazide (41)

To a solution of ethyl 2-(4-nitrophenoxy)acetate (40) (5 g, 24 mmol) in methanol (75 mL was added hydrazine hydrate (11.8 mL, 38 mmol) at room temperature and then the mixture was refluxed for 1 hour. The reaction solvent was removed under reduced pressure to afford a residue, which was washed with dichloromethane (30 mL), followed by with distilled water (30 mL) and ether (30 mL). The resulting solid was dried under reduced pressure to give 5.7 g of 2-(4-nitrophenoxy)acetylhydrazide (41) as a light yellow solid. $^1$H NMR (DMSO-$d_6$): δ 9.41 (s, 1H), 8.20-8.17 (d, J=9.0 Hz, 2H), 7.15-7.12 (d, J=9.0 Hz, 2H), 4.65 (s, 2H), 4.34 (d, J=6.0 Hz, 2H).

N'-Acetyl-2-(4-nitrophenoxy)acetylhydrazide (42)

To a solution of 2-(4-nitrophenoxy)acetylhydrazide (41) (5.7 g, 29.5 mmol) in ethyl alcohol (500 mL) were added acetic anhydride (3.9 mL, 41.3 mmol) and triethylamine (6.17 mL, 44.3 mmol) at room temperature. The reaction mixture was then refluxed for 1 hour and cooled to room temperature. Precipitate obtained was collected by filtration and washed with cold ethyl alcohol (2×50 mL) to yield 7.5 g of N'-acetyl-2-(4-nitrophenoxy)acetylhydrazide (42) as an off white solid. $^1$H NMR (DMSO-$d_6$): δ 9.84 (s, 1H), 8.21-8.18 (d, J=9.0 Hz, 2H), 7.17-7.14 (d, J=9.0 Hz, 2H), 4.77 (s, 2H), 1.90 (br s, 3H).

2-Methyl-5-[(4-nitrophenoxy)methyl]-1,3,4-oxadiazole (43)

A mixture of N'-acetyl-2-(4-nitrophenoxy)acetylhydrazide (42) (7.5 g, 29.4 mmol) was added to polyphosphoric acid (162 mL) was heated at 120° C. for 1 hour. The reaction mixture was then poured onto crushed ice and extracted with ethyl acetate (3×300 mL). The organic layer was dried over anhydrous sodium sulfate and solvent was removed under reduced pressure. The resulting residue was dissolved in dichloromethane (500 mL), washed with aqueous solution of sodium bicarbonate and brine. After drying over anhydrous sodium sulfate, the dichloromethane was removed under reduced pressure to give crude product, which was purified by flash column chromatography (ethyl acetate: hexanes 3:1 v/v) to give 2.4 g of 2-methyl-5[(4-nitrophenoxy)methyl]-1,3,4-oxadiazole (43) as a white solid. $^1$H NMR (DMSO-$d_6$): δ 8.23-8.20 (d, J=9.0 Hz, 2H), 7.28-7.25 (d, J=9.0 Hz, 2H), 5.54 (s, 2H), and 2.52 (s, 3H).

4-[(5-Methyl-1,3,4-oxadiazol-2-yl)methyleneoxy]benzeneamine (44)

2-Methyl-5-[(4-nitrophenoxy)methyl]-1,3,4-oxadiazole (43) (1.21 g, 5.13 mmol) was reduced by using procedure described in Example 5 to afford 1.02 g of [4-(5-methyl-1,3,4-oxadiazol-2-yl)methyleneoxy]benzeneamine (44) as a light brown oil. $^1$H NMR (CDCl$_3$): δ 6.85-6.82 (d, J=9.0 Hz, 2H), 6.65-6.62 (d, J=9.0 Hz, 2H), 5.132 (s, 2H), and 2.56 (s, 3H).

Example 11

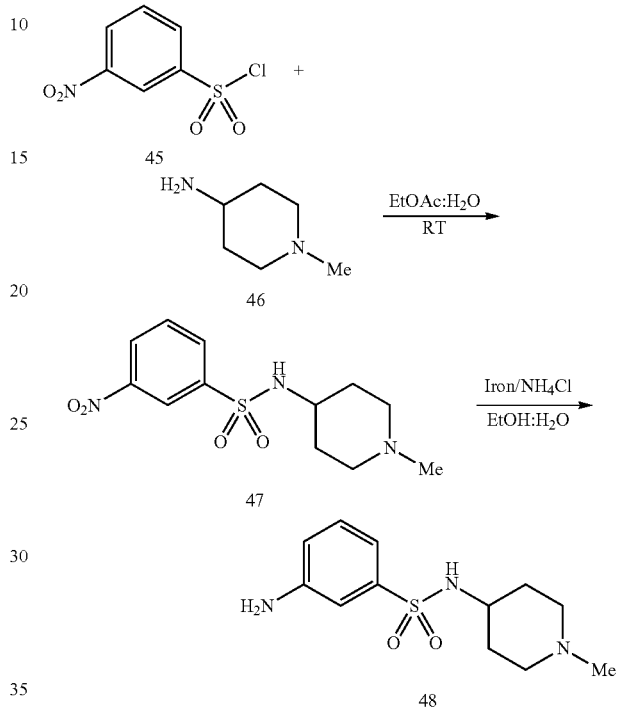

3-(N-4-Methylpiperidin-1-yl)aminosulfonylnitrobenzene (47)

To a solution of 3-chlorosulfonylnitrobenzene (45) (2.21 g, 10 mmol) in tetrahydrofuran (100 mL) at 0° C. were added diisopropylethyl amine (1.93 mL, 15 mmol) followed by N-methyl-4-aminopiperidine (46) (1.36 g, 12 mmol) and then the reaction mixture was stirred at room temperature for 2 hours. The reaction was quenched with water (50 mL), stirred for 30 minutes and the tetrahydrofuran layer was separated. The organic solution was concentrated under reduced pressure. The resulting residue was taken in dichloromethane (200 mL), washed with aqueous solution of sodium bicarbonate (2×100 mL) and then brine. The organic layer was dried over anhydrous sodium sulfate and solvent was removed under reduced pressure to afford the desired product, 3-(N-4-methylpiperidin-1-yl)aminosulfonylnitrobenzene (47). LCMS: purity: 93%; MS (m/e): 300 (MH+).

The following compounds were made in a similar fashion to the example 11 or by methods described herein or known to skilled artisans.

3-(N-4-Methylpiperidin-1-yl)aminosulfonylaniline (48)

LCMS: purity: 87%; MS (m/e): 270 (MH$^+$).

3-(N-Ethoxycarbonylmethylene)aminosulfonylnitrobenzene

LCMS: purity: 94%; MS (m/e): 289 (MH+).

3-(N-Ethoxycarbonylmethylene)aminosulfonylaniline

LCMS: purity: 88%; MS (m/e): 259 (MH+).

4-(2-N,N-Diethylaminoethyl)aminosulfonylnitrobenzene $^1$H NMR (CDCl$_3$): ε 8.35 (d, 2H, J=8.4 Hz), 8.05 (d, 2H, J=8.4 Hz), 5.02 (br s, 1H), 3.01 (t, 2H, J=6.0 Hz), 2.53 (t, 2H, J=6.0 Hz), 2.42 (q, 4H, J=7.2 Hz), 0.94 (t, 6H, J=6.9 Hz), LCMS (m/z): 302 (MH$^+$).

3-(2-N,N-Diethylaminoethyl)aminosulfonylnitrobenzene $^1$H NMR (CDCl$_3$): δ 8.69 (t, 1H, J=1.5 Hz), 8.41 (m, 1H), 8.18 (m, 1H), 7.72 (t, 1H, J=7.8 Hz), 2.99 (t, 2H, J=6.3 Hz), 2.50 (t, 2H, J=5.4 Hz), 2.39 (q, 4H, J=7.2 Hz), 0.92 (t, 6H, J=6.9 Hz), LCMS (m/z): 302 (MH$^+$).

4-(2-N,N-Diethylaminoethyl)aminosulfonylaniline $^1$H NMR (CDCl$_3$): δ 7.62 (d, 2H, J=8.4 Hz), 6.67 (d, 2H, J=8.4 Hz), 4.09 (s, 2H), 2.91 (t, 2H, J=6.3 Hz), 2.47 (t, 2H, J=5.4 Hz), 2.38 (q, 4H, J=7.2 Hz), 0.92 (t, 6H, J=7.2 Hz), LCMS (m/z): 272 (MH$^+$).

3-(2-N,N-Diethylaminoethyl)aminosulfonylaniline $^1$H NMR (CDCl$_3$): δ 7.27-7.13 (m, 3H), 6.82 (m, 1H), 3.91 (s, 2H), 2.94 (t, 2H, J=5.7 Hz), 2.45 (t, 2H, J=5.7 Hz), 2.36 (q, 4H, J=7.2 Hz), 0.91 (t, 6H, J=7.2 Hz), LCMS (m/z): 272 (MH$^+$).

Example 12

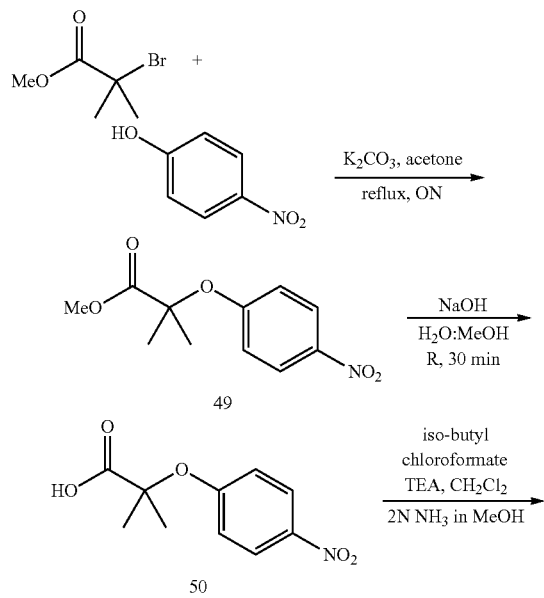

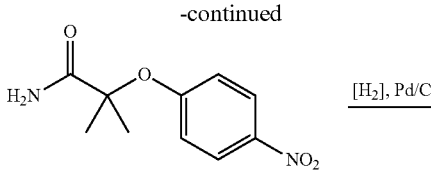

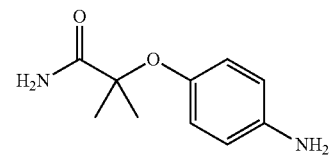

methyl 2-(4-nitrophenoxy)isobutyrate (49)

A heterogeneous mixture of 4-nitrophenol (5 g), methyl 2-bromoisobutyrate (5.6 mL) and K$_2$CO$_3$ (7.5 g) in acetone (60 mL) was refluxed overnight. The reaction mixture was then diluted with water (150 mL) and extracted with ethyl acetate (2×100 mL). The organic layers were evaporated to give methyl 2-(4-nitrophenoxy)isobutyrate (49).

2-(4-nitrophenoxy)isobutyric acid (50)

To a solution of methyl 2-(4-nitrophenoxy)isobutyrate (49) was in methanol (50 mL) and water (50 mL) was added sodium hydroxide (5 g) at room temperature. The solution was stirred at room temperature for 30 min, then acidified with 1N HCl aqueous to pH ~3. The aqueous solution was extracted with ethyl acetate (2×100 mL). The organic layers were combined, dried over anhydrous sodium sulfate and solvent was removed under a reduced pressure to give 2-(4-nitrophenoxy)isobutyric acid (50).

2-(4-nitrophenoxy)-2-methylpropanamide (51)

A mixture of 2-(4-nitrophenoxy)isobutyric acid (50) (5 g), isobutyl chloroformate (4.36 mL) and triethylamine (8 mL) in dichloromethane (20 mL) was stirred at room temperature for 1 hour. Then 2.0 M ammonia in methanol (20 mL) was added to the solution. The resulting solution was stirred at room temperature for 2 hours and then solvent was removed under reduced pressure. The mixture was purified by recrystallization from EtOAc and hexanes to give 2-(4-nitrophenoxy)-2-methylpropanamide (51).

2-(4-aminophenoxy)-2-methylpropanamide (52)

2-(4-Nitrophenoxy)-2-methylpropanamide (51) was dissolved in methanol (50 mL) and to the solution was added 10% Pd—C(500 mg). The reaction mixture was reacted under hydrogen atmosphere (~40 psi) for 1 hour. The catalyst was then filtered off over Celite. The filtrate was evaporated under reduced pressure to give 2-(4-aminophenoxy)-2-methylpropanamide as a white solid (52).

Example 13

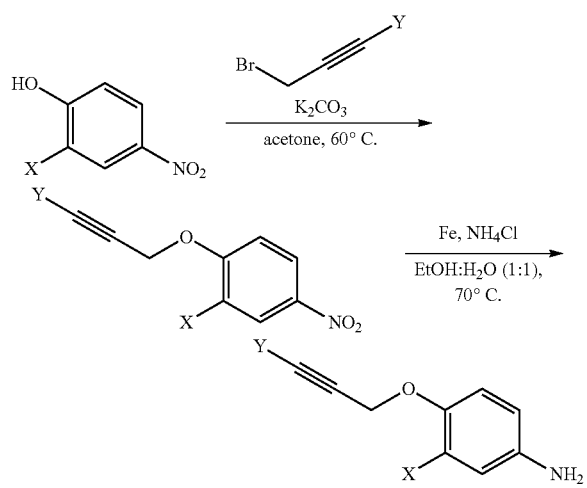

4-(Prop-2-ynyloxy)nitrobenzene (X=H, Y=H)

4-Nitrophenol (1.00 g, 7.19 mmol), propargyl bromide (80 wt % in toluene; 0.788 mL, 7.09 mmol), and $K_2CO_3$ (1.08 g, 7.84 mmol) were stirred in acetone (16.0 mL) at 60° C. for 18 h. The reaction mixture was cooled to room temperature and diluted with water (200 mL). 4-(prop-2-ynyloxy)nitrobenzene was isolated as a white solid by suction filtration (1.12 g). $^1$H NMR (CDCl$_3$): δ 8.22 (d, J=9.0 Hz, 2H), 7.05 (d, J=9.0 Hz, 2H), 4.80 (d, J=2.4 Hz, 2H), 2.59 (t, J=2.4 Hz, 1H).

4-(Prop-2-ynyloxy)aniline (X=H, Y=H)

4-(Prop-2-ynyloxy)nitrobenzene (0.910 g, 5.13 mmol), iron (1.42 g, 25.3 mmol), and NH$_4$Cl (0.719 g, 12.8 mmol) were vigorously stirred in EtOH/water (1:1, 55 mL) at 70° C. for 15 minutes. The reaction mixture was filtered hot through Celite and concentrated in vacuo. The residue was suspended in 10% 2N ammoniacal methanol in dichloromethane, sonicated, and filtered through Celite. Concentration gave 4-(prop-2-ynyloxy)aniline as a brown oil which was used without further purification. In general, isolated prop-2-ynyloxyanilines were unstable and were therefore used immediately after the second filtration. $^1$H NMR (CDCl$_3$): δ 6.82 (d, J=8.7 Hz, 2H), 6.64 (d, J=8.7 Hz, 2H), 4.61 (d, J=2.4 Hz, 2H), 2.50 (t, J=2.4 Hz, 1H).

The following compounds were made in a similar fashion to the example 13.

3-Methyl-4-(prop-2-ynyloxy)nitrobenzene (X=Me, Y=H)

$^1$H NMR (CDCl$_3$): δ 8.10 (dd, J=3.0 and 9.0 Hz, 1H), 7.01 (d, J=9.0 Hz, 1H), 4.83 (d, J=2.4 Hz, 2H), 2.58 (t, J=2.4 Hz, 1H), 2.31 (s, 3H).

3-Chloro-4-(prop-2-ynyloxy)nitrobenzene (X=Cl, Y=H)

$^1$H NMR (CDCl$_3$): δ 8.31 (d, J=2.7 Hz, 1H), 8.17 (dd, J=2.7 and 9.0 Hz, 1H), 7.17 (d, J=9.0 Hz, 1H), 4.90 (d, J=2.7 Hz, 2H), 2.63 (t, J=2.7 Hz, 1H).

3-Fluoro-4-(prop-2-ynyloxy)nitrobenzene (X=F, Y=H)

$^1$H NMR (CDCl$_3$): δ 8.07 (ddd, J=1.5, 2.7, and 9.3 Hz, 1H), 8.01 (dd, J=2.7 and 10.5 Hz, 1H), 7.20 (t, J=8.7 Hz, 1H), 4.89 (d, J=2.1 Hz, 2H), 6.23 (t, J=2.1 Hz, 1H).

4-(But-2-ynyloxy)nitrobenzene (X=H, Y=Me)

$^1$H NMR (CDCl$_3$): δ 8.21 (d, J=9.0 Hz, 2H), 7.03 (d, J=9.0 Hz, 2H), 4.75 (q, J=2.4 Hz, 2H), 1.88 (t, J=2.4 Hz, 3H).

3-(Prop-2-ynyloxy)nitrobenzene $^1$H NMR (CDCl$_3$): δ 7.87 (ddd, J=0.9, 2.1, and 8.1 Hz, 1H), 7.83 (t, J=2.1 Hz, 1H), 7.46 (t, J=8.4 Hz, 1H), 7.30 (ddd, J=0.6, 2.4, and 8.4 Hz, 1H), 4.79 (d, J=2.4 Hz, 2H), 2.58 (t, J=2.4 Hz, 1H).

Example 14

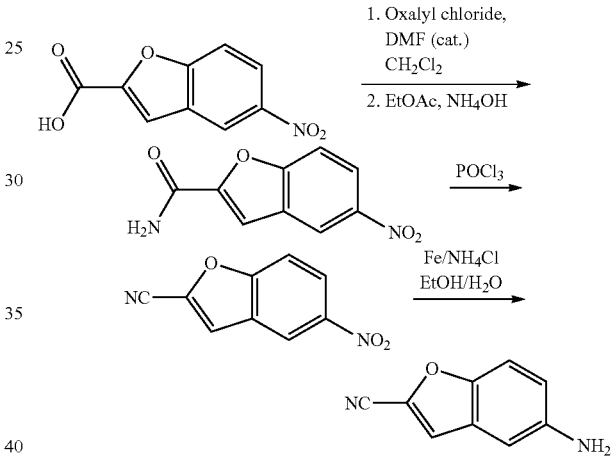

2-Aminocarbonyl-5-nitrobenzofuran

A dry reaction flask equipped with a magnetic stirring bar, nitrogen inlet and rubber septum was charged with 2-carboxy-5-nitrobenzofuran (0.414 g, 2 mmol) and CH$_2$Cl$_2$ (100 mL). To this was added DMF (0.1 mL) followed by a slow addition of oxaloyl chloride (0.519 mL, 6 mmol) over the period of 5 minutes at 0° C. The reaction mixture was further stirred for 30 minutes by the time the formation of a clear solution was observed. The resulting clear solution was concentrated under a reduced pressure and dried under high vacuum for 30 minutes. The resulting residue was suspended in EtOAc (25 mL), cooled to 10° C., to it was added NH$_4$OH (30% solution, 25 mL) and stirred at room temperature for 24 h. The organic phase was separated and dried over anhydrous sodium sulfate and solvent was removed to give 2-aminocarbonyl-5-nitrobenzofuran. $^1$H NMR (DMSO-d6): δ 8.75 (d, 1H, J=2.7 Hz), 8.28 (m, 2H), 7.86 (d, 1H, J=9.0 Hz), 7.83 (bs, 1H), 7.72 (s, 1H); LCMS: purity: 93%, MS (m/e): 206 (M$^+$).

2-Cyano-5-nitrobenzofuran

A heterogeneous solution of 2-aminocarbonyl-5-nitrobenzofuran (0.206 g, 1 mmol) in POCl$_3$ (5 mL) was heated at 100° C. for 24 to give a clear solution. The resulting clear solution was carefully poured over ice-water to give a solid mass which was isolated by filtration followed by washing with water to give 2-cyano-5-nitrobenzofuran. $^1$H NMR (DMSO-d6): δ 8.80 (d, 1H, J=2.4 Hz), 8.42 (dd, 1H, J=2.7 and 9.0 Hz), 8.27 (s, 1H), 7.99 (d, 1H, J=8.7 Hz); LCMS: purity: 98%, MS (m/e): 189 (MH$^+$).

5-Amino-2-cyanobenzofuran

A heterogeneous reaction mixture of 2-cyano-5-nitrobenzofuran (0.150 g, 0.789 mmol), iron powder (0.220 g, 3.9 mmol), NH$_4$Cl (0.221 g, 3.9 mmol) in EtOH/H$_2$O (5 mL each) was vigorously stirred at 60-70° C. for 1 hour. The resulting solution was filtered through a pad of Celite when hot and then washed with methanol. The filtrated was concentrated to dryness under a vacuum and resuspended into H$_2$O (20 mL), saturated and the solid was isolated by filtration to obtain 5-amino-2-cyanobenzofuran. $^1$H NMR (DMSO-d6): δ 7.80 (s, 1H), 7.36 (d, 1H, J=8.7 Hz), 6.86 (dd, 1H, J=2.7 and 9.0 Hz), 6.76 (d, 1H, J=2.1 Hz), 5.16 (bs, 2H); LCMS: purity: 95%, MS (m/e): 159 (MH$^+$).

Example 15

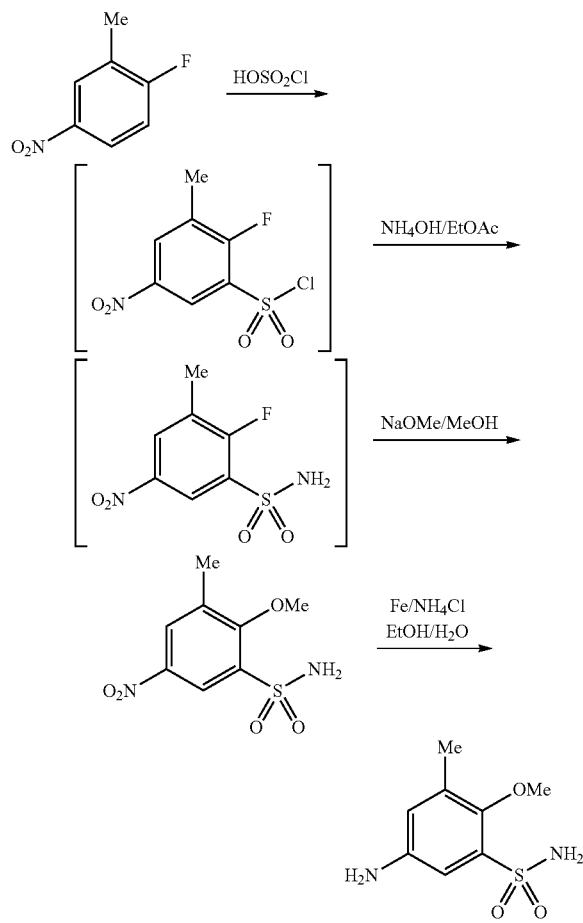

3-Aminosulfonyl-4-methoxy-5-methyl-aniline

A dry reaction flask equipped with a magnetic stirring bar, nitrogen inlet and reflux condenser was charged with 2-fluoro-5-nitrotoluene (6.20 g, 40 mmol) followed by chlorosulfonic acid (10.60 mL, 160 mmol) at 0° C., and then the reaction was stirred at 100° C. for 24 hours. After cooling it to the room temperature, the reaction was poured over ice-water (Caution!) and extracted with ethyl acetate (3×200 mL). Removal solvent under a reduced pressure afforded 3-chlorosulfonyl-4-fluoro-5-methylnitrobenzene intermediate, which was stirred in EtOAc (50 mL) and NH$_4$OH (30%, 50 mL) for 2-3 hours. The separated organic phase was then evaporated to afford a crude material, which was purified by column chromatography (silica gel, hexanes then 10-20% EtOAc in hexanes) to afford 3-aminosulfonyl-4-fluoro-5-methylnitrobenzene. LCMS: purity: 96%; MS (m/e): 235 (MH$^+$).

The resulting 3-aminosulfonyl-4-fluoro-5-methylnitrobenzene (0.940 g, 4 mmol) was stirred with 25% methanolic NaOMe (1.00 mL) at 60° C. for overnight. The resulting solution was then filtered through a pad of Celite, washed with methanol and the methanolic solution was concentrated to give 3-aminosulfonyl-4-methoxy-5-methylnitrobenzene. LCMS: purity: 100%, MS (m/e): 247 (MH$^+$).

The reduction of 3-aminosulfonyl-4-methoxy-5-methylnitrobenzene (0.740 g, 3 mmol) using iron powder (0.81 g, 15 mmol), NH$_4$Cl (0.81 g, 15 mmol) in ethanol (100 mL):water (25 mL) at 60° C. for 1 hour followed by filtration through a pad of Celite gave aqueous alcoholic solution. Concentration of it followed by dilution with water afforded a solid mass, which was isolated by filtration to give 3-aminosulfonyl-4-methoxy-5-methylaniline $^1$H NMR (DMSO-d6): δ 6.90 (bs, 1H), 6.55 (bs, 1H), 5.1 (bs, 2H), 3.65 (s, 3H), 2.15 (s, 3H), LCMS: purity: 94%, MS (m/e): 217 (MH$^+$).

The following compounds were made in a similar fashion to the methods described herein or known to skilled artisans.

4-(4-Nitrophenoxymethyl)-2-methylthiazole $^1$H NMR (CDCl$_3$, 300 MHz): δ 8.19 (d, 2H, J=9.0 Hz), 7.17 (s, 1H), 7.04 (d, 2H, J=9.3 Hz), 5.22 (s, 2H), 2.74 (s, 3H); LCMS (m/z): 251 (MH$^+$).

3-[(4-Nitrophenoxy)methyl]pyridine $^1$H NMR (CDCl$_3$, 300 MHz): δ 8.68 (d, 1H, J=2.1 Hz), 8.62 (dd, 1H, J=1.5 and 4.8 Hz), 8.21 (d, 2H, J=9.0 Hz), 7.76 (m, 1H), 7.35 (dd, 1H, J=4.5 and 7.8 Hz), 7.03 (d, 2H, J=9.0 Hz), 5.17 (s, 2H); LCMS (m/z): 231 (MH$^+$).

2-[(4-Nitrophenoxy)methyl]pyridine $^1$H NMR (CDCl$_3$, 300 MHz): δ 8.61 (d, 1H, J=4.8 Hz), 8.19 (d, 2H, J=9.0 Hz), 7.72 (m, 2H), 7.46 (d, 1H, J=7.8 Hz), 7.25 (m, 1H), 7.05 (d, 2H, J=9.3 Hz), 5.28 (s, 2H); LCMS (m/z): 231 (MH$^+$).

2-[(4-Nitrophenoxy)methyl]pyridine $^1$H NMR (CDCl$_3$, 300 MHz): δ 8.60 (d, 1H, J=4.5 Hz), 8.04 (m, 2H), 7.73 (m, 1H), 7.48 (d, 1H, J=8.1 Hz), 7.25 (m, 1H), 6.92 (d, 1H, J=9.3 Hz), 5.30 (s, 2H), 2.39 (s, 3H); LCMS (m/z): 245 (MH$^+$).

3-[(3-Nitrophenoxy)methyl]pyridine $^1$H NMR (CDCl$_3$, 300 MHz): δ 8.69 (d, 1H, J=2.1 Hz), 8.61 (d, 1H, J=4.5 Hz), 7.81 (m, 3H), 7.45 (t, 1H, J=8.1 Hz), 7.36-7.24 (m, 2H), 5.15 (s, 2H); LCMS (m/z): 231 (MH$^+$).

4-[(4-Nitrophenoxy)methyl]pyridine $^1$H NMR (CDCl$_3$, 300 MHz): δ 8.61 (d, 2H, J=5.4 Hz), 8.21 (d, 2H, J=9.0 Hz), 7.33 (d, 2H, J=5.4 Hz), 7.02 (d, 2H, J=9.0 Hz), 5.18 (s, 2H); LCMS (m/z): 231 (MH$^+$).

Example 16

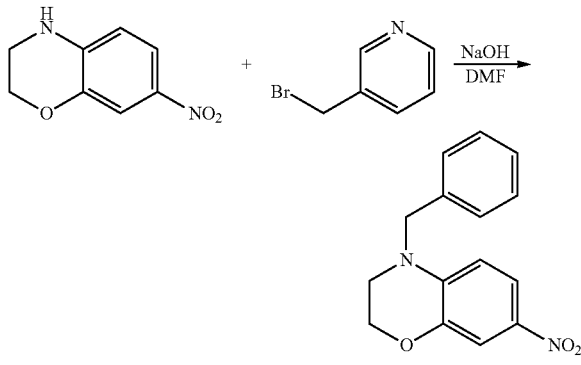

7-nitro-4-(3-pyridylmethyl)benz[1,4]oxazine

To a dry reaction flask equipped with a reflux condenser, a magnetic stirring bar and a rubber septum with a N2 inlet was placed 7-nitrobenz[1,4]oxazine (1.0 g, 5.55 mmol), tertabutyl ammonium chloride (56 mg), powdered NaOH (0.58 g) in dry DMF (10 mL). The reaction mixture was stirred at room temperature for 30 minutes. 3-(Bromomethyl)-pyridine hydrobromide (1.40 g, 5.55 mmol) was added. The reaction mixture was heated at 80° C. for over night, cooled to room temperature, poured in water (200 mL), left aside for 2 h, added ethyl acetate (200 mL). The organic layer was washed with water (2×200 mL), brine (200 mL), dried (Na$_2$SO$_4$) and concentrated. The solid was purified by silica gel column, eluted with EtOAc to give 0.67 g (44%) of the desired 7-nitro-4-(3-pyridylmethyl)benz[1,4]oxazine. $^1$H NMR (CDCl$_3$, 300 MHz): δ 8.56 (d, 1H, J=4.8 Hz), 8.53 (s, 1H), 7.72 (m, 2H), 7.53 (m, 1H), 7.28 (dd, 1H, J=5.1 and 7.8 Hz), 6.57 (d, 1H, J=9.0 Hz), 4.61 (s, 2H), 4.29 (t, 2H, J=4.2 Hz), 3.59 (t, 2H, J=4.5 Hz); LCMS (m/z): 272 (MH$^+$).

Example 17

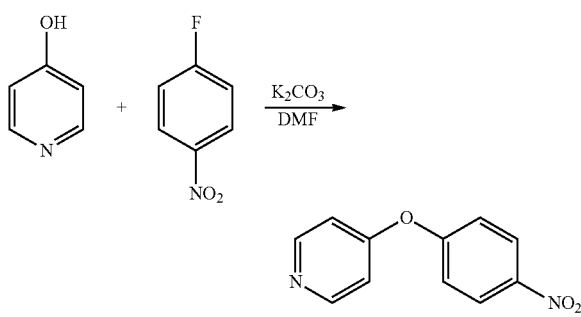

4-(4-pyridinyloxy)-1-nitrobenzene

To a solution of 4-hydroxypyridine (4.42 g, 45.8 mmol) and 1-fluoro-4-nitrobenzene (4.89 mL, 45.8 mmol) in anhydrous DMF (50 mL) was added anhydrous K$_2$CO$_3$ (13.0 g, 91.6 mmol) in one portion. The mixture was heated at the reflux temperature with stirring for 24 h, cooled to room temperature and poured in water (300 mL). The solid that separated was filtered, washed with water and dried well under high vacuum to yield 8.9 g (90%) of desired product, 4-(4-pyridinyloxy)-1-nitrobenzene.

$^1$H NMR (CDCl$_3$, 300 MHz): δ 8.36 (d, 2H, J=9.0 Hz), 8.11 (d, 2H, J=8.1 Hz), 7.83 (d, 2H, J=9.0 Hz), 6.27 (d, 2H, J=7.8 Hz); LCMS (m/z): 217 (MH$^+$).

Example 18

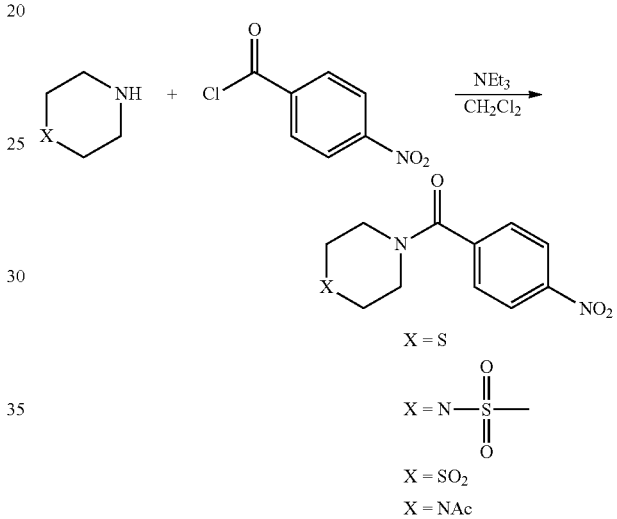

X = S

X = N—S(=O)$_2$—

X = SO$_2$

X = NAc

4-(4-nitrobenzoyl)thiomorpholine (X=S)

To a stirred solution of thiomorpholine (2.00 mL, 20 mmol) and Et$_3$N (5.0 mL) in CH$_2$Cl$_2$ (60 mL) was added drop wise a solution of 4-nitrobenzoyl chloride (3.71 g, 20 mmol) in CH$_2$Cl$_2$ (50 mL) at 0° C. The reaction was allowed to stir at room temperature for over night and then washed with a saturated NaHCO$_3$ solution (2×75 mL), and water (2×75 mL. The CH$_2$Cl$_2$ layer was dried (Na$_2$SO$_4$) and filtered and concentrated. Finally dried under high vacuum to afford 5.027 g (99%) of the 4-(4-nitrobenzoyl)thiomorpholine. $^1$H NMR (CDCl$_3$, 300 MHz): δ 8.28 (d, 2H, J=9.0 Hz), 7.54 (d, 2H, J=8.7 Hz), 4.04 (br s, 2H), 3.61 (br s, 2H), 2.75 (br s, 2H), 2.57 (br s, 2H); LCMS (m/z): 253 (MH$^+$).

The following compounds were made in a similar fashion to the example 18, methods described herein or known to skilled artisans.

1-Methanesulfonyl-4-(4-nitrobenzoyl)piperazine $^1$H NMR (CDCl$_3$, 300 MHz): δ 8.29 (d, 2H, J=8.4 Hz), 7.58 (d, 2H, J=8.4 Hz), 3.91 (br s, 2H), 3.52 (br s, 2H), 3.33 (br s, 2H), 3.23 (br s, 2H), 2.83 (s, 3H); LCMS (m/z): 314 (MH$^+$).

4-(4-Nitrobenzoyl)thiomorpholine-1,1-dioxide $^1$H NMR (CDCl$_3$, 300 MHz): δ 8.32 (d, 2H, J=8.4 Hz), 7.60 (d, 2H, J=9.0 Hz), 4.08 (br s, 4H), 3.08 (br s, 4H); LCMS (m/z): 285 (MH$^+$).

1-Acetyl-4-(4-nitrobenzoyl)piperazine $^1$H NMR (CDCl$_3$, 300 MHz): δ 8.29 (d, 2H, J=8.7 Hz), 7.58 (d, 2H, J=8.4 Hz), 3.59 (m, 8H), 2.14 (s, 3H); LCMS (m/z): 277 (MH$^+$).

4-(4-Aminophenoxymethyl)-2-methylthiazole $^1$H NMR (CDCl$_3$, 300 MHz): δ 7.10 (s, 1H), 6.81 (d, 2H, J=8.7 Hz), 6.62 (d, 2H, J=9.0 Hz), 5.06 (s, 2H), 3.43 (s, 2H), 2.72 (s, 3H); LCMS (m/z): 221 (MH$^+$).

3-[(4-Aminophenoxy)methyl]pyridine $^1$H NMR (CDCl$_3$, 300 MHz): δ 8.63 (d, 1H, J=2.1 Hz), 8.54 (d, 1H, J=5.1 Hz), 7.74 (d, 1H, J=7.5 Hz), 7.29 (dd, 1H, J=5.1 and 7.8 Hz), 6.79 (d, 2H, J=8.7 Hz), 6.63 (d, 2H, J=8.7 Hz), 4.99 (s, 2H), 3.44 (br s, 2H); LCMS (m/z): 201 (MH$^+$).

3-[(3-Aminophenoxy)methyl]pyridine $^1$H NMR (CDCl$_3$, 300 MHz): δ 8.64 (d, 1H, J=2.1 Hz), 7.75 (m, 1H), 7.29 (dd, 1H, J=4.8 and 7.8 Hz), 7.05 (t, 1H, J=8.4 Hz), 6.33 (m, 3H), 5.02 (s, 2H), 3.67 (br s, 2H); LCMS (m/z): 201 (MH$^+$).

2-[(4-Aminophenoxy)methyl]pyridine $^1$H NMR (CDCl$_3$, 300 MHz): δ 8.56 (m, 1H), 7.67 (m, 1H), 7.49 (d, 1H, J=7.8 Hz), 7.18 (m, 1H), 6.80 (d, 2H, J=8.7 Hz), 6.62 (d, 2H, J=8.7 Hz), 5.12 (s, 2H), 3.43 (br s, 2H); LCMS (m/z): 201 (MH$^+$).

4-[(4-Aminophenoxy)methyl]pyridine $^1$H NMR (CDCl$_3$, 300 MHz): δ 8.56 (d, 2H, J=6.0 Hz), 7.31 (d, 2H, J=6.0 Hz), 6.76 (d, 2H, J=8.7 Hz), 6.62 (d, 2H, J=8.6 Hz), 5.01 (s, 2H), 3.31 (br s, 2H); LCMS (m/z): 201 (MH$^+$).

2-[(4-Aminophenoxy-2-methyl)methyl]pyridine $^1$H NMR (CDCl$_3$, 300 MHz): δ 8.55 (d, 1H, J=4.8 Hz), 7.68 (m, 1H), 7.53 (d, 1H, J=7.5 Hz), 7.18 (m, 1H), 6.67 (d, 1H, J=8.4 Hz), 6.55 (d, 1H, J=3.0 Hz), 6.44 (dd, 1H, J=2.7 and 8.5 Hz), 5.11 (s, 2H), 3.23 (br s, 2H), 2.26 (s, 3H); LCMS (m/z): 215 (MH$^+$). 7-Amino-4-(3-pyridylmethyl)benzo[1,4]oxazine LCMS (m/z): 242 (MH$^+$).

Example 19

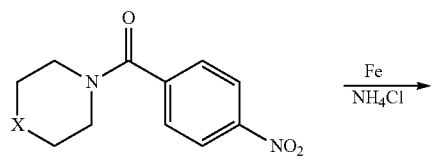

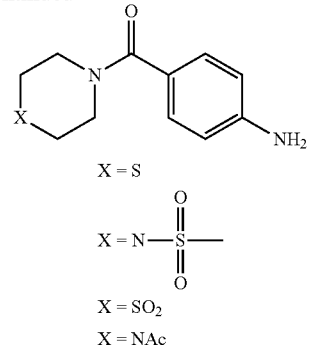

4-(4-aminobenzoyl)thiomorpholine

To a stirred solution of 4-(4-nitrobenzoyl)thiomorpholine (1.26 g, 5 mmol) in ethanol (80 mL) and water (20 mL) was added NH$_4$Cl (2.65 g) and heated to 80° C. To this heterogeneous reaction mixture at 80° C. was added iron powder (2.75 g) portion wise manner under a vigorous stirring in nitrogen atmosphere and the stirring was continued for 2 h. The reaction mixture was filtered through a Celite pad when hot and washed the pad with methanol. The filtrate was concentrated, diluted with water, extracted with CH$_2$Cl$_2$ (3×75 mL), dried (Na$_2$SO$_4$), filtered and concentrated. Finally dried under high vacuum to afford 1.11 g (100%) of the 4-(4-aminobenzoyl)thiomorpholine. $^1$H NMR (CDCl$_3$, 300 MHz): δ 7.21 (d, 2H, J=8.4 Hz), 6.64 (d, 2H, J=8.1 Hz), 3.86 (br s, 6H), 2.64 (t, 4H, J=4.5 Hz); LCMS (m/z): 223 (MH$^+$).

The following compounds were made in a similar fashion to the example 19.

1-Methanesulfonyl-4-(4-aminobenzoyl)piperazine $^1$H NMR (CDCl$_3$, 300 MHz): δ 7.26 (d, 2H, J=7.8 Hz), 6.65 (d, 2H, J=8.4 Hz), 3.92 (br s, 2H), 3.75 (t, 4H, J=4.8 Hz), 3.23 (t, 4H, J=4.8 Hz), 2.79 (s, 3H); LCMS (m/z): 284 (MH$^+$).

4-(4-Aminobenzoyl)thiomorpholine-1,1-dioxide $^1$H NMR (CDCl$_3$, 300 MHz): δ 7.27 (d, 2H, J=8.7 Hz), 6.65 (d, 2H, J=8.7 Hz), 4.09 (t, 4H, J=5.4 Hz), 3.97 (s, 2H), 3.05 (t, 4H, J=5.1 Hz), LCMS (m/z): 255 (MH$^+$).

1-Acetyl-4-(4-aminobenzoyl)piperazine $^1$H NMR (CDCl$_3$, 300 MHz): δ 7.26 (d, 2H, J=7.2 Hz), 6.65 (d, 2H, J=7.8 Hz), 3.90 (s, 2H), 3.60 (m, 8H), 2.12 (s, 3H); LCMS (m/z): 248 (MH$^+$).

4-(4-pyridinyloxy)aniline $^1$H NMR (DMSO d$_6$, 300 MHz): δ 7.76 (br s, 2H), 7.10 (br s, 2H), 6.61 (br s, 2H), 6.13 (br s, 2H), 5.37 (s, 2H); LCMS (m/z): 187 (MH$^+$).

1-Cyanomethoxy-2,3-dimethoxy-5-nitrobenzene

To a solution of 1.5 g of (±)-2,3-dimethoxy-5-nitrophenol in 25 mL of acetone at room temperature was added 7.8 g cesium carbonate and then 0.75 mL bromoacetonitrile was added slowly dropwise. The reaction mixture was filtered, the filtrate evaporated and the resulting residue was partitioned between 1N HCl solution and EtOAc. The aqueous phase was extracted with EtOAc and the combined organics washed with bicarbonate solution, brine then dried over MgSO$_4$. The solvent was removed by rotary evaporation and the crude material purified by column chromatography (hexanes/EtOAc) to yield 1.4 g 78% yield of the desired product 1-cyanomethoxy-2,3-dimethoxy-5-nitrobenzene. $^1$H NMR (DMSO-d6): δ 7.78 (d, 2H, J=4.5 Hz), 7.64 (d, 2H, J=4.5 Hz), 5.38 (s, 2H), 3.92 (s, 3H), 3.82 (s, 3H); LCMS: purity 93%; MS (m/e): 239 (MH$^+$).

3-Cyanomethoxy-4,5-dimethoxyaniline

A solution of 1.4 g of 1-cyanomethoxy-2,3-dimethoxy-5-nitrobenzene in 75 mL ethanol with 1.65 g of iron and 1.65 g of ammonium chloride was refluxed for 4 h, cooled to RT, diluted with DCM, filtered, extracted with DCM and the combined organic were dried with sodium sulfate and evaporated to give 1 g 82% of the desired product 3-cyanomethoxy-4,5-dimethoxyaniline, MS (m/e): 209 (MH$^+$).

The following compounds were made in a similar fashion to the above example. 3-(2-Fluoro-4-nitrophenyl)propionitrile $^1$H NMR (DMSO-d$_6$): δ 8.12-8.06 (t, 2H), 7.72-7.66 (t, 1H), 3.07-3.02 (t, 2H), 2.91-2.86 (t, 2H), LCMS: 196.10 (MH$^+$).

3-(4-Amino-2-fluorophenyl)propionitrile $^1$H NMR (DMSO-d$_6$): δ 8.41 (s, 2H), 7.13-7.07 (t, 1H), 6.57-6.54 (d, J=10.5 Hz, 2H), 2.77-2.71 (m, 4H), LCMS: 164.02 (MH$^+$).

3-(2-Methyl-4-nitrophenyl)propionitrile $^1$H NMR (DMSO-d$_6$): δ 8.06 (s, 1H), 8.03-8.00 (d, J=8.4 Hz, 1H), 7.50-7.48 (d, J=8.1 Hz, 1H), 3.03-2.98 (t, 2H), 2.88-2.83 (t, 2H), 2.41 (s, 3H), LCMS: 193.12 (MH+).

3-(2-Chloro-4-nitrophenyl)propionitrile

LCMS: 211.11 (MH+).

3-(4-Amino-2-chlorophenyl)propionitrile

LCMS: 181.04 (MH$^+$).

Example 20

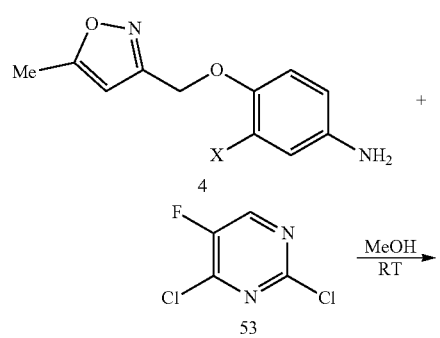

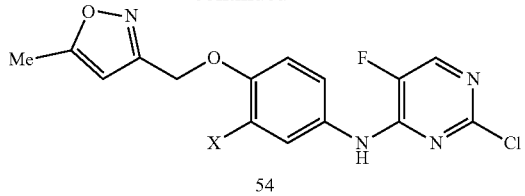

2-Chloro-5-fluoro-N4-[4-(5-methylisoxazol-3-yl)methyleneoxyphenyl]-4-pyrimidineamine (54, X=H)

5-Methyl-3-(4-aminophenoxymethyl)isoxazole (4, X=H, 1.94 g) 2,4-dichloro-5-fluoropyrimidine (53) (4.0 g) were dissolved in MeOH:H$_2$O (9:1, v/v, 400 mL). The reaction was allowed to stir at room temperature 24 hours, MeOH was removed under reduced pressure, the residue was basified with aqueous saturated solution of sodium bicarbonate (100 mL), water (300 mL), extracted with EA (3×300 mL), dried (Na$_2$SO$_4$) and solvent was removed under reduced pressure. The resulting residue was purified by silica gel column chromatography to provided 1.93 g of 2-chloro-5-fluoro-N4-[4-(5-methylisoxazol-3-yl)methyleneoxyphenyl]-4-pyrimidineamine (54, X=H) as a white solid. $^1$H NMR (DMSO-d6): δ 9.85 (s, 1H), 8.24 (d, 1H, J=3.6 Hz), 7.54 (d, 2H, J=8.7 Hz), 7.02 (d, 2H, J=9.0 Hz), 6.31 (s, 1H), 5.12 (s, 2H), 2.40 (s, 3H); LCMS (m/z): 335 (MH$^+$).

The following compounds were made in a similar fashion to the example 20.

2-Chloro-5-fluoro-N4-[3-methyl-4-(5-methylisoxazol-3-yl)methyleneoxyphenyl]-4-pyrimidineamine (54, X=CH$_3$)

$^1$H NMR (CDCl$_3$): δ 7.99 (d, 1H, J=3.0 Hz), 7.42 (dd, 1H, J=2.4 and 8.7 Hz), 7.30 (d, 1H, J=2.4 Hz), 6.89 (d, 2H, J=8.4 Hz), 6.09 (s, 1H), 5.10 (s, 2H), 2.44 (s, 3H), 2.26 (s, 3H); LCMS (m/z): 350 (MH$^+$).

2-Chloro-5-fluoro-N4-[3-fluoro-4-(5-methylisoxazol-3-yl)methyleneoxyphenyl]-4-pyrimidineamine (54, X=F)

LCMS: purity: 93%; MS (m/e): 354 (MH$^+$).

2-Chloro-5-fluoro-N4-[4-(3-methyl-1,2,4-oxadiazol-5-yl)methyleneoxyphenyl]-4-pyrimidineamine (11)

$^1$H NMR (DMSO-d6): δ 9.91 (s, 1H), 8.26 (d, 1H, J=3.5 Hz), 7.56 (d, 2H, J=8.8 Hz), 7.05 (d, 2H, J=8.8 Hz), 5.46 (s, 2H), 2.34 (s, 3H); LCMS (m/z): 336 (MH$^+$).

2-Chloro-5-fluoro-N4-[4-(3-methyl-1,2,4-oxadiazol-5-yl)ethylenephenyl]-4-pyrimidineamine $^1$H NMR (DMSO-d$_6$): δ 9.92 (s, 1H) 8.28-8.27 (d, J=3.0 Hz, 1H), 7.57-7.54 (d, J=9.0 Hz, 2H), 7.25-7.22 (d, J=9.0 Hz, 2H) 3.23-3.18 (m, 2H), 3.07-3.02 (m, 2H), 2.29 (s, 3H); LCMS (m/z): 334.27 (M$^+$).

2-Chloro-N4-(3-cyano-4-methylphenyl)-5-fluoro-4-pyrimidineamine

LCMS: 263.23 (MH$^+$).

2-Chloro-N4-(3-chloro-4-fluorophenyl)-5-fluoro-4-pyrimidineamine

LCMS: (m/z): 276.16 (MH+).

2-Chloro-N4-(3-cyano-4-fluorophenyl)-5-fluoro-4-pyrimidineamine

LCMS (m/z): 267.20 (MH+).

2-Chloro-5-fluoro-N4-(2-methylindol-5-ylmethylene)-4-pyrimidineamine

LCMS (m/z): 291.32 (MH+).

Example 21

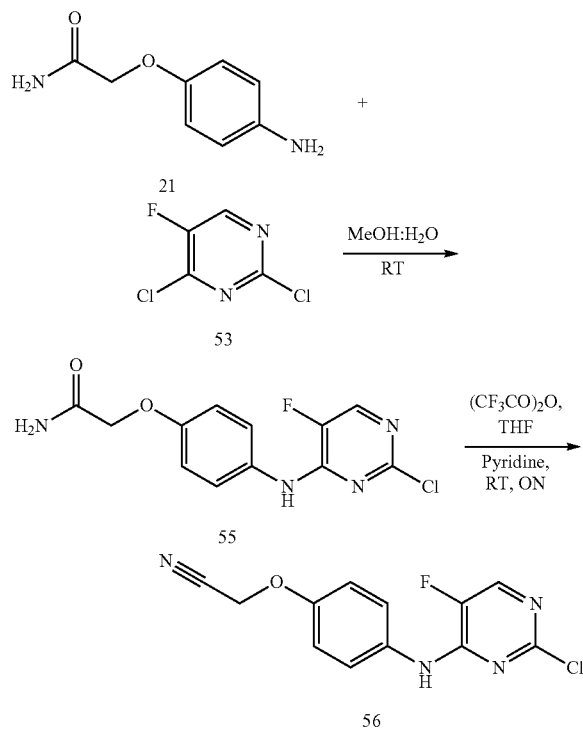

N4-(4-aminocarbonylmethyleneoxy)phenyl-2-chloro-5-fluoro-4-pyrimidineamine (55)

A mixture of 4-(aminocarbonylmethyleneoxy)aniline (21) (5 g) and 2,6-dichloro-5-fluoropyrimidine (53) (6 g) in methanol (10 mL) and water (1 mL) was stirred at room temperature overnight. Then methanol was removed under reduced pressure. The remaining aqueous solution was acidified with 1 N HCl (80 mL). The white precipitate was collected by filtration, washed with water (3×50 mL) and dried to give N4-(4-aminocarbonylmethyleneoxy)phenyl-2-chloro-5-fluoro-4-pyrimidineamine (55). $^1$H NMR (CDCl$_3$): δ 8.07 (d, 1H, J=2.7 Hz), 7.52 (t, 1H, J=2.4 Hz), 7.30 (d, 1H, J=8.1 Hz), 7.19 (m, 1H), 6.96 (br s, 1H), 6.79 (m, 1H), 5.29 (s, 2H), 2.44 (s, 3H); LCMS (m/z): 336 (MH+).

2-Chloro-N4-(4-cyanomethyleneoxy)phenyl-5-fluoro-4-pyrimidineamine (56)

To a solution of N4-(4-aminocarbonylmethyleneoxy)phenyl-2-chloro-5-fluoro-4-pyrimidineamine (55) (2 g) in THF (20 mL) was added trifluoroacetic anhydride (1.9 mL) and pyridine (1.65 mL) at room temperature. The reaction solution was stirred at room temperature overnight and then diluted with ethyl acetate (100 mL). The organic layer was washed with aqueous solution of potassium carbonate (2×100 mL), 1 N HCl (100 mL) and water (100 mL). The ethyl acetate layer was separated, dried over anhydrous sodium sulfate and solvent was evaporated under reduced pressure to give 2-chloro-N4-(4-cyanomethyleneoxy)phenyl-5-fluoro-4-pyrimidineamine (56).

The following compounds were made in a similar fashion to the example 21.

2-chloro-5-fluoro-N4-[4-(5-methyl-1,2,4-oxadiazol-3-yl)methoxy]phenyl-4-pyrimidineamine N4-[4-(1-aminocarbonyl-1-methyl)ethoxy]phenyl-2-chloro-5-fluoro-4-pyrimidineamine 2-chloro-N4-[4-(1-cyano-1-methyl)ethoxy]phenyl-5-fluoro-4-pyrimidineamine 2-Chloro-N4-[4-(cyanoethylene)phenyl]-5-fluoro-4-pyrimidineamine N4-[4-(1-Benzyl-3-methyl-(1H)-pyrazol-5-yl)methyleneoxyphenyl]-2-chloro-5-fluoro-4-pyrimidineamine LCMS: purity: 95%; MS (m/e): 424 (MH+).

2-Chloro-N4-[4-(1,3-dimethyl-(1H)-pyrazol-5-yl)methyleneoxyphenyl]-5-fluoro-4-pyrimidineamine LCMS: purity: 95%; MS (m/e): 424 (MH+).

2-Chloro-5-fluoro-N4-[4-(5-methyl-1,3,4-oxadiazol-2-yl)methyleneoxyphenyl]-4-pyrimidineamine $^1$H NMR (CDCl$_3$): δ 8.04-8.03 (d, J=3.0 Hz, 1H), 7.56-7.53 (d, J=9.0 Hz, 2H), 7.06-7.03 (d, J=9.0 Hz, 2H), 5.24 (s, 2H), and 2.58 (s, 3H).

N4-[2-(tert-Butylcarbonyl)amino-3-methoxypyrid-6-yl]-2-chloro-5-fluoro-4-pyrimidineamine (65)

A homogeneous mixture of 6-amino-2-(tert-butylcarbonyl)amino-3-methoxypyridine (35) (1.5 g, 6.72 mmol) and 2,4-dichloro-5-fluoropyrimidine (53) (1.68 g, 10 mmol) in methanol:water (20 mL, each) was stirred at 60° C. for 48 hours. The reaction mixture upon dilution with water (100 mL) gave a solid, which was isolated by filtration to obtain N4-[2-(tert-butylcarbonyl)amino-3-methoxypyrid-6-yl]-2-chloro-5-fluoro-4-pyrimidineamine LCMS: purity: 89%; MS (m/z): 354 (MH+).

Example 22

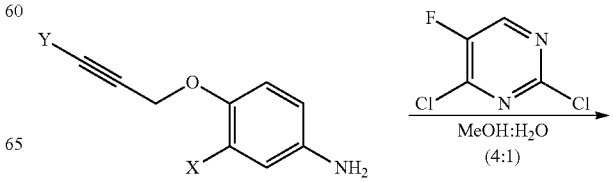

-continued

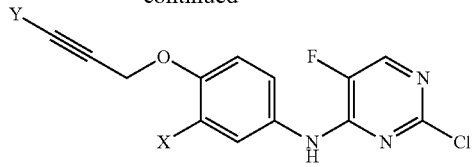

2-Chloro-5-fluoro-N4-[4-(prop-2-ynyloxy)phenyl]-4-pyrimidineamine (X=H, Y=H)

Crude 4-(prop-2-ynyloxy)aniline (0.750 g, 5.10 mmol) and 2,4-dichloro-5-fluoropyrimidine (1.27 g, 0.760 mmol) were stirred in MeOH/water (4:1, 35 mL) at room temperature for 18 h. The reaction mixture was diluted with EtOAc (200 mL) and washed with 1N HCl (50 mL) and brine (50 mL). The organic layer was dried (MgSO$_4$), filtered and concentrated in vacuo. The residue was purified by column chromatography (silica gel, hexanes ramped to EtOAc:hexanes (1:10)) to provide 2-chloro-5-fluoro-N4-[4-(prop-2-ynyloxy)phenyl]-4-pyrimidineamine as a light brown solid (0.514 g). $^1$H NMR (CDCl$_3$): δ 8.03 (d, J=2.7 Hz, 1H), 7.53 (d, J=8.7 Hz, 2H), 7.02 (d, J=8.7 Hz, 2H), 6.86 (s, 1H), 4.71 (d, J=2.4 Hz, 2H), 2.55 (t, J=2.4 Hz, 1H); LCMS: purity: 99%; MS (m/e): 279 (MH$^+$).

The following compounds were made in a similar fashion to the example 22, methods described herein or known to skilled artisans.

2-Chloro-5-fluoro-N4-[3-methyl-4-(prop-2-ynyloxy)phenyl]-4-pyrimidineamine (X=Me, Y=H)

$^1$H NMR (CDCl$_3$): δ 8.01 (d, J=2.7 Hz, 1H), 7.50 (dd, J=2.7 and 8.7 Hz, 1H), 7.50 (dd, J=2.7 and 8.7 Hz, 1H), 7.28 (d, J=2.1 Hz, 1H), 6.97 (d, J=8.7 Hz, 1H), 6.82 (s, 1H), 4.72 (d, J=2.4 Hz, 2H), 2.53 (t, J=2.4 Hz, 1H), 2.28 (s, 3H); LCMS: purity: 99%; MS (m/e): 293 (MH$^+$).

2-Chloro-N4-[3-chloro-4-(prop-2-ynyloxy)phenyl]-5-fluoro-4-pyrimidineamine (X=Cl, Y=H)

$^1$H NMR (CDCl$_3$): δ 8.06 (d, J=2.7 Hz, 1H), 7.66 (d, J=2.7 Hz, 1H), 7.54 (dd, J=3.0 and 9.3 Hz, 1H), 7.12 (d, J=9.3 Hz, 1H), 6.86 (s, 1H), 4.79 (d, J=2.4 Hz, 2H), 2.57 (t, J=2.4 Hz, 1H); LCMS: purity: 98%; MS (m/e): 313 (MH$^+$).

2-Chloro-5-fluoro-N4-[3-fluoro-4-(prop-2-ynyloxy)phenyl]-4-pyrimidineamine (X=F, Y=H)

$^1$H NMR (CDCl$_3$): δ 8.07 (d, J=2.7 Hz, 1H), 7.59 (dd, J=2.7 and 12.6 Hz, 1H), 7.28-7.24 (m, 1H), 7.13 (t, J=8.7 Hz, 1H), 6.89 (s, 1H), 4.78 (d, J=2.4 Hz, 2H), 2.56 (t, J=2.4 Hz, 1H); LCMS: purity: 99%; MS (m/e): 297 (MH$^+$).

N4-[4-(But-2-ynyloxy)phenyl]-2-chloro-5-fluoro-4-pyrimidineamine (X=H, Y=Me)

$^1$H NMR (CDCl$_3$): δ 8.02 (d, J=2.7 Hz, 1H), 7.52 (d, J=9.0 Hz, 2H), 7.00 (d, J=9.0 Hz, 2H), 6.85 (s, 1H), 4.66 (q, J=2.4 Hz, 2H), 1.89 (t, J=2.4 Hz, 3H); LCMS: purity: 98%; MS (m/e): 293 (MH$^+$).

2-Chloro-5-fluoro-N4-[3-(prop-2-ynyloxy)phenyl]-4-pyrimidineamine $^1$H NMR (CDCl$_3$): δ 8.08 (d, J=2.7 Hz, 1H), 7.49 (t, J=2.1 Hz, 1H), 7.31 (t, J=8.1 Hz, 1H), 7.16 (ddd, J=0.9, 2.1, and 8.1 Hz, 1H), 6.94 (s, 1H), 6.80 (ddd, J=0.9, 2.4, and 8.1 Hz, 1H), 4.74 (d, J=2.4 Hz, 2H), 2.57 (t, J=2.4 Hz, 1H); LCMS: purity: 98%; MS (m/e): 279 (MH$^+$).

2-Chloro-N4-(2-cyanobenzofuran-5-yl)-5-fluoro-4-pyrimidineamine $^1$H NMR (DMSO-d6): δ 10.14 (s, 1H), 8.32 (d, 1H, J=3.6 Hz), 8.14 (s, 1H), 8.12 (d, 1H, J=1.8 Hz), 7.77 (m, 2H); LCMS: purity: 94%, MS (m/e): 290 (MH$^+$).

2-Chloro-5-fluoro-N-[4-(3-pyridinylmethyl)benz[1,4]oxazin-7-yl]-4-pyrimidineamine $^1$H NMR (CDCl$_3$, 300 MHz): δ 8.56 (d, 1H, J=1.8 Hz), 8.52 (dd, 1H, J=1.5 and 4.6 Hz), 7.95 (d, 1H, J=3.0 Hz), 7.62 (m, 1H), 7.26 (m, 1H), 7.11 (d, 1H, J=2.7 Hz), 6.98 (dd, 1H, J=2.4 and 8.5 Hz), 6.90 (d, 1H, J=2.1 Hz), 6.60 (d, 1H, J=8.7 Hz), 4.29 (m, 2H), 3.36 (m, 2H); LCMS (m/z): 372 (MH$^+$).

2-Chloro-5-fluoro-N-[4-(3-pyridinyl)methyleneoxyphenyl]-4-pyrimidineamine $^1$H NMR (CDCl$_3$, 300 MHz): δ 8.66 (s, 1H), 8.58 (d, 1H, J=4.8 Hz), 8.00 (d, 1H, J=2.1 Hz), 7.77 (d, 1H, J=8.1 Hz), 7.52 (d, 2H, J=9.0 Hz), 7.32 (dd, 1H, J=5.1 and 7.6 Hz), 6.98 (d, 3H, J=8.4 Hz), 5.08 (s, 2H); LCMS (m/z): 331 (MH$^+$).

2-Chloro-5-fluoro-N-[4-(4-pyridinylmethyl)phenyl]-4-pyrimidineamine $^1$H NMR (CDCl$_3$, 300 MHz): δ 8.49 (d, 2H, J=6.0 Hz), 8.04 (d, 1H, J=3.0 Hz), 7.58 (d, 2H, J=8.4 Hz), 7.19 (d, 2H, J=8.1 Hz), 7.09 (d, 3H, J=5.4 Hz), 3.96 (s, 2H); LCMS (m/z): 315 (MH$^+$).

2-Chloro-5-fluoro-N-[3-(3-pyridinyl)methyleneoxyphenyl]-4-pyrimidineamine

LCMS (m/z): 331 (MH$^+$).

2-Chloro-5-fluoro-N-[4-(2-methylthiazol-4-yl)methyleneoxyphenyl]-4-pyrimidineamine $^1$H NMR (CDCl$_3$, 300 MHz): δ 8.00 (d, 1H, J=2.1 Hz), 7.50 (d, 2H, J=9.0 Hz), 7.15 (s, 1H), 6.99 (d, 2H, J=9.0 Hz), 6.89 (br s, 1H), 5.14 (s, 2H), 2.73 (s, 3H); LCMS (m/z): 351 (MH$^+$).

2-Chloro-5-fluoro-N-[4-(2-pyridinyl)methyleneoxyphenyl]-4-pyrimidineamine $^1$H NMR (CDCl$_3$, 300 MHz): δ 8.58 (d, 1H, J=4.5 Hz), 8.00 (d, 1H, J=3.0 Hz), 7.71 (m, 1H), 7.49 (m, 3H), 7.22 (m, 1H), 6.99 (d, 2H, J=9.0 Hz), 6.96 (br s, 1H), 5.19 (s, 2H); LCMS (m/z): 331 (MH$^+$).

2-Chloro-5-fluoro-N-[4-(4-pyridinyl)methyleneoxyphenyl]-4-pyrimidineamine $^1$H NMR (CDCl$_3$, 300 MHz): δ 8.60 (d, 2H, J=6.0 Hz), 8.01 (d, 1H, J=2.7 Hz), 7.52 (d, 2H, J=9.0 Hz), 7.35 (m, 2H), 6.96 (d, 2H, J=9.0 Hz), 6.92 (br s, 1H), 5.10 (s, 2H); LCMS (m/z): 331 (MH$^+$).

2-Chloro-5-fluoro-N-[4-(1-imidazolylmethyl)phenyl]-4-pyrimidineamine $^1$H NMR (DMSO-d$_6$, 300 MHz): δ 9.99 (s, 1H), 8.29 (d, 1H, J=3.6 Hz), 7.72 (s, 1H), 7.62 (d, 2H, J=8.4 Hz), 7.25 (d, 2H, J=8.1 Hz), 7.17 (s, 1H), 6.88 (s, 1H), 5.15 (s, 2H); LCMS (m/z): 304 (MH$^+$).

2-Chloro-5-fluoro-N-[4-(4-pyridinyloxy)phenyl]-4-pyrimidineamine

Prepared by using procedure described in Example 20. $^1$H NMR (DMSO-d$_6$, 300 MHz): δ 7.89 (d, 2H, J=7.5 Hz), 7.55 (s, 1H), 7.41 (d, 2H, J=7.8 Hz), 7.27 (d, 2H, J=6.9 Hz), 6.16 (d, 2H, J=6.3 Hz), 4.09 (s, 1H); LCMS (m/z): 317 (MH$^+$).

2-Chloro-5-fluoro-N-[4-(4-thiomorpholinyl)carbonylphenyl]-4-pyrimidineamine $^1$H NMR (DMSO-d$_6$, 300 MHz): δ 10.11 (s, 1H), 8.35 (d, 1H, J=3.3 Hz), 7.77 (d, 2H, J=8.7 Hz), 7.40 (d, 2H, J=8.7 Hz), 3.71 (br s, 4H), 2.64 (br s, 4H); LCMS (m/z): 353 (MH$^+$).

2-Chloro-5-fluoro-N-[4-(1-methanesulfonyl-4-piperazinyl)carbonylphenyl]-4-pyrimidineamine $^1$H NMR (DMSO-d$_6$, 300 MHz): δ 10.14 (s, 1H), 8.35 (d, 1H, J=2.7 Hz), 7.79 (d, 2H, J=8.1 Hz), 7.45 (d, 2H, J=7.8 Hz), 3.59 (br s, 4H), 3.16 (br s, 4H), 2.89 (s, 3H); LCMS (m/z): 414 (MH$^+$).

2-Chloro-5-fluoro-N-[4-(1-acetyl-4-piperazinyl)carbonylphenyl]-4-pyrimidineamine $^1$H NMR (DMSO-d$_6$, 300 MHz): δ 10.12 (s, 1H), 8.35 (d, 1H, J=3.3 Hz), 7.78 (d, 2H, J=8.4 Hz), 7.44 (d, 2H, J=8.7 Hz), 3.47 (br s, 8H), 2.01 (s, 3H); LCMS (m/z): 378 (MH$^+$).

2-Chloro-5-fluoro-N-[4-(1,1-dioxo-4-thiomorpholinyl)carbonylphenyl]-4-pyrimidineamine $^1$H NMR (DMSO-d$_6$, 300 MHz): δ 10.14 (s, 1H), 8.35 (d, 1H, J=3.3 Hz), 7.79 (d, 2H, J=8.4 Hz), 7.51 (d, 2H, J=7.5 Hz), 3.86 (br s, 4H), 3.25 (br s, 4H); LCMS (m/z): 385 (MH$^+$).

2-Chloro-5-fluoro-N-[4-(2-pyridinyl)-3-methylmethyleneoxyphenyl]-4-pyrimidineamine $^1$H NMR (DMSO-d$_6$, 300 MHz): δ 9.80 (s, 1H), 8.65 (d, 1H, J=5.1 Hz), 8.23 (d, 1H, J=4.5 Hz), 8.04 (t, 1H, J=7.8 Hz), 7.69 (d, 1H, J=7.8 Hz), 7.51 (t, 1H, J=6.3 Hz), 7.42 (d, 2H, J=9.0 Hz), 7.00 (d, 1H, J=8.4 Hz), 5.27 (s, 2H), 2.24 (s, 3H); LCMS (m/z): 345 (MH$^+$).

2-Chloro-N4-[3-chloro-4-(2-cyanoethyl)phenyl]-5-fluoro-4-pyrimidineamine

LCMS: 311.35 (MH$^+$).

2-Chloro-5-fluoro-N4-(quinolin-8-yl)-4-pyrimidineamine

LCMS: 275.22 (MH$^+$).

2-Chloro-5-fluoro-N4-(quinolin-2-yl)-4-pyrimidineamine

LCMS: 275.36 (MH$^+$).

2-Chloro-5-fluoro-N4-(quinolin-6-yl)-4-pyrimidineamine

LCMS: 275.28 (MH$^+$).

2-Chloro-5-fluoro-N4-(quinolin-3-yl)-4-pyrimidineamine

LCMS: 275.25 (MH$^+$).

2-Chloro-5-fluoro-N4-(2-methylquinolin-6-yl)-4-pyrimidineamine

LCMS: 289.38 (MI-1+).

N4-(Benzothiophene-5-yl)-2-chloro-5-fluoro-4-pyrimidineamine

LCMS: 280.26 (MH$^+$).

2-Chloro-5-fluoro-N4-(2-methylquinolin-8-yl)-4-pyrimidineamine

LCMS: 289.43 (MH$^+$).

2-Chloro-N4-[4-(2-cyanoethyl)phenyl]-5-methyl-4-pyrimidineamine

LCMS: 275.28 (MH$^+$).

N4-[(2S,4R)-1-t-Butoxycarbonyl-2-methoxycarbonyl-pyrrolidin-4-yl]-2-chloro-5-fluoro-4-pyrimidineamine

LCMS: 375.01 (MH$^+$).

N4-[(2S,4S)-1-t-Butoxycarbonyl-2-methylcarboxylate-pyrrolidine]-2-chloro-5-fluoro-4-pyrimidineamine

LCMS: 375.02 (MH$^+$).

2-Chloro-5-fluoro-N4-[(2S,4R)-2-methoxycarbonylpyrrolidin-4-yl]-4-pyrimidineamine

LCMS: 275.36 (MH$^+$).

2-Chloro-5-fluoro-N4-[(2S,4S)-2-methoxycarbonylpyrrolidin-4-yl]-4-pyrimidineamine

LCMS: 275.39 (MH$^+$).

2-Chloro-N4-[(2S,4R)-1-(2-cyanoacetyl)-2-methoxycarbonylpyrrolidin-4-yl]-5-fluoro-4-pyrimidineamine $^1$H NMR (DMSO-d$_6$): δ 8.38-8.36 (d, J=7.2 Hz, 1H), 8.13-8.11 (d, J=3.3 Hz, 1H), 4.61-4.59 (m, 1H), 4.52-4.47 (m, 1H), 4.06-4.04 (d, J=7.2 Hz, 1H), 3.85-3.80 (m, 1H), 3.64 (s, 3H), 3.51-3.46 (m, 1H), 2.43-2.34 (m, 1H), 2.20-2.13 (m, 1H), LCMS: 342.01 (MH$^+$).

2-Chloro-N4-[(2S,4S)-1-(2-cyanoacetyl)-2-methoxy-carbonylpyrrolidin-4-yl]-5-fluoro-4-pyrimidineamine ¹H NMR (DMSO-d₆): δ 8.20-8.18 (d, J=6.9 Hz, 1H), 8.13 (bs, 1H), 4.66-4.61 (m, 1H), 4.37-4.33 (m, 1H), 4.06-4.04 (bs, 2H), 3.90-3.84 (m, 1H), 3.63 (s, 3H), 3.47-3.37 (m, 1H), 2.56-2.54 (m, 1H), 2.07-1.98 (m, 1H), LCMS: 341.99 (MH⁺).

2-Chloro-N4-[4-(2-cyanoethyl)-3-methylphenyl]-5-fluoro-4-pyrimidineamine

LCMS: 291.05 (MH⁺).

2-Chloro-N4-[4-(2-cyanoethyl)-3-methylphenyl]-5-fluoro-4-pyrimidineamine

LCMS: 291.05 (MH⁺).

Example 23

2-Chloro-N4-(3-cyanomethyleneoxy-4,5-dimethoxy-phenyl)-5-fluoro-4-pyrimidineamine A suspension of 3-cyanomethoxy-4,5-dimethoxyaniline (1.5 g), 2,4-dichloro-5-fluopyrimidine and 1.3 g of sodium bicarbonate in 70 mL (4:1 EtOH/THF) was stirred overnight at room was diluted with 1 N HCl solution. The precipitate was collected by suction filtration, dried, triturated with ether, recollected by suction filtration and dried to yield 1.3 g 80% of the desired product 2-chloro-N4-(3-cyanomethoxy-4,5-dimethoxyphenyl)-5-fluoro-4-pyrimidineamine ¹H NMR (DMSO-d6): δ 8.18 (d, 1H, J=2.1 Hz), 7.28 (d, 1H, J=4.3 Hz), 7.18 (d, 1H, J=4.3 Hz), 5.09 (s, 2H), 3.77 (s, 3H), 3.64 (s, 3H); LCMS: purity 97%; MS (m/e): 339 (MH⁺).

Example 24

2-Chloro-5-methyl-N4-oxo-benz[1,4]oxazin-6-yl)-4-pyrimidineamine

A mixture of 250 mg of 6-Amino-3-oxo-4H-benz[1,4] oxazine and 460 mg of 2,4-Dichloro-5-methylpyrimidine in 15 mL methanol was stirred at RT overnight and was reduced in volume by rotary evaporation. The solution was filtered and the filtrate diluted with water and neutralized with sodium bicarbonate. The precipitate was collected by suction filtration washed with water and dried on the funnel to yield 75 mg 20% of the desired product 2-Chloro-5-methyl-N4-oxo-benz[1,4]oxazin-6-yl)-4-pyrimidineamine ¹H NMR (DMSO-d6): δ 7.98 (s, 1H), 7.08 (m, 2H), 6.91 (d, 1H J=6 Hz), 4.54 (s, 2H), 2.11 (s, 3H) purity 97%; MS (m/e) 291 (MH⁺).

Example 25

2-Chloro-5-methyl-N4-(4-methyl-3-oxo-benzo[1,4]thiazin-6-yl)-4-pyrimidineamine

A mixture of 1.3 g of 6-Amino-4-methyl-3-oxo-benzo[1,4]thiazine and 3.3 g of 2,4-Dichloro-5-methylpyrimidine in 100 mL methanol was stirred at RT overnight and was reduced in volume by rotary evaporation. The solution was filtered and the filtrate diluted with water and neutralized with sodium bicarbonate. The precipitate was collected by suction filtration washed with water and dried on the funnel to yield 660 mg 13% of the desired product 2-Chloro-5-methyl-N4-(4-methyl-3-oxo-benzo[1,4]thiazin-6-yl)-4-pyrimidineamine ¹H NMR (DMSO-d6): δ 8.93 (s, 1H), 8.06 (m, 2H), 7.62 (s, 1H), 7.37 (s, 1H), 3.51 (s, 2H), 2.16 (s, 3H) purity 97%; MS (m/e) 321 (MH⁺).

The following compounds were made in a similar fashion to the examples 20-25, methods described herein, or methods known to skilled artisans.

2-Chloro-N4-(4-cyanoethylene-2-methylphenyl)-5-fluoro-4-pyrimidineamine

¹H NMR (DMSO-d₆): δ 9.711 (s, 1H), 8.235-8.219 (d, J=4.8 Hz, 1H), 7.251-7.226 (d, J=7.5 Hz, 1H), 7.162-7.122 (m, 2H), 2.852-2.790 (m, 4H), 2.130 (s, 3H), LCMS: 291.36 (MH+).

2-Chloro-N4-(4-cyanoethylene-3-methoxyphenyl)-5-fluoro-4-pyrimidineamine

¹H NMR (DMSO-d₆): δ 9.959 (s, 1H), 8.305-8.293 (d, J=3.6 Hz, 1H), 7.410 (s, 1H), 7.285-7.262 (d, J=6.9 Hz, 1H), 7.192-7.164 (d, J=8.4 Hz, 1H), 3.784 (s, 3H), 2.808-2.726 (m, 4H), LCMS: 307.04 (MH+).

2-Chloro-5-fluoro-N4-(5-methoxycarbonyl-thio-phene-2-yl)-4-pyrimidineamine

¹H NMR (DMSO-d₆): δ 11.809 (s, 1H), 8.442-8.432 (d, J=3.0 Hz, 1H), 7.665-7.649 (d, J=4.8 Hz, 1H), 7.017-7.001 (d, J=4.8 Hz, 1H), 3.793 (s, 3H), LCMS: 288.25 (MH+).

2-Chloro-5-fluoro-N4-(2-hydroxy-4-methylquinolin-6-yl)-4-pyrimidineamine

¹H NMR (DMSO-d₆): δ 11.599 (s, 1H), 10.077 (s, 1H), 8.291-8.280 (d, J=3.3 Hz, 1H), 8.064 (s, 1H), 7.766-7.736 (d, J=9 Hz, 1H), 7.295-7.266 (d, J=8.7 Hz, 1H), 6.410 (s, 1H), 2.389 (s, 3H).

2-Chloro-N4-(4-cyanoethylene-3-trifluoromethylphenyl)-5-fluoro-4-pyrimidineamine ¹H NMR (DMSO-d₆): δ 10.223 (s, 1H), 8.372-8.360 (d, J=3.6 Hz, 1H), 8.138 (s, 1H), 8.004-7.975 (d, J=8.7 Hz, 1H), 7.599-7.571 (d, J=8.4 Hz, 1H), 3.047-2.999 (t, 2H), 2.885-2.837 (t, 2H), LCMS: 344.93 (MH+).

N4-[4-(2-Carboxyethylene)phenyl]-2-chloro-5-fluoro-4-pyrimidineamine

¹H NMR (DMSO-d₆): δ 12.075 (s, 1H), 9.908 (s, 1H), 8.271-8.260 (d, J=3.3 Hz, 1H), 7.548-7.520 (d, J=8.4 Hz, 2H), 7.221-7.193 (d, J=8.4 Hz, 2H), 2.818-2.767 (t, 2H), 2.549-2.497 (t, 2H).

N4-[4-(2-Aminocarboxylethylene)phenyl]-2-chloro-5-fluoro-4-pyrimidineamine

¹H NMR (DMSO-d₆): δ 8.269-8.257 (d, J=3.6 Hz, 1H), 7.540-7.512 (d, J=8.4 Hz, 2H), 7.266 (s, 1H), 7.197-7.169 (d, J=8.4 Hz, 2H), 6.740 (s, 1H), 2.796-2.745 (t, 2H), 2.365-2.313 (t, 2H), LCMS: 295.30 (MH+).

2-Chloro-N4-[3,4-dihydro-(1H)-quinolin-2-one-6-yl]-5-fluoro-4-pyrimidineamine ¹H NMR (DMSO-d$_6$): δ 9.963 (s, 1H), 7.919 (s, 1H), 7.260-7.215 (m, 2H), 6.766-6.739 (d, J=8.1 Hz, 1H), 2.845-2.796 (t, 2H), 2.442-2.392 (t, 2H), LCMS: 293.01 (MH+).

2-Chloro-N4-(2-N,N'-dimethylamino-quinolin-6-yl)-5-fluoro-4-pyrimidineamine

¹H NMR (DMSO-d$_6$): δ 10.015 (s, 1H), 8.273-8.261 (d, J=3.6 Hz, 1H), 7.955-7.925 (m, 2H), 7.705 (s, 1H), 7.532-7.502 (d, J=9 Hz, 1H), 7.077-7.047 (d, J=9.0 Hz, 1H), 3.138 (s, 6H).

N4-[(4R)-1-tert-Butoxycarbonyl-pyrrolidin-4-yl]-2-chloro-5-fluoro-4-pyrimidineamine ¹H NMR (DMSO-d$_6$): δ 8.330-8.309 (d, J=6.3 Hz, 1H), 8.093-8.081 (d, J=3.6 Hz, 1H), 4.462-4.444 (m, 1H), 3.587-3.528 (m, 1H), 3.436-3.378 (m, 1H), 3.208-3.154 (m, 1H), 2.138-2.095 (m, 1H), 1.958-1.914 (m, 1H), 1.395 (s, 9H).

2-Chloro-N4-[(4R)-1-(2-cyanoacetyl)-pyrrolidin-4-yl]-5-fluoro-4-pyrimidineamine ¹H NMR (DMSO-d$_6$): δ 8.320 (s, 1H), 8.113-8.092 (d, J=6.3 Hz, 1H), 4.543-4.001 (m, 1H), 3.908 (s, 2H), 3.718-3.543 (m, 1H), 3.520-3.299 (m, 3H), 2.208-1.979 (m, 2H), LCMS: 284.29 (MH+).

N4-(2-cyanoethylene-benzothiophene-5-yl)-2-chloro-5-fluoro-4-pyrimidineamine ¹H NMR (DMSO-d$_6$): δ 11.104 (s, 1H), 8.326-8.308 (d, J=5.4 Hz, 1H), 7.963-7.934 (d, J=8.7 Hz, 1H), 7.813 (s, 1H), 7.391-7.355 (d, J=9 Hz, 1H), 7.313 (s, 1H), 3.248-3.202 (t, 2H), 2.969-2.922 (t, 2H).

Example 26

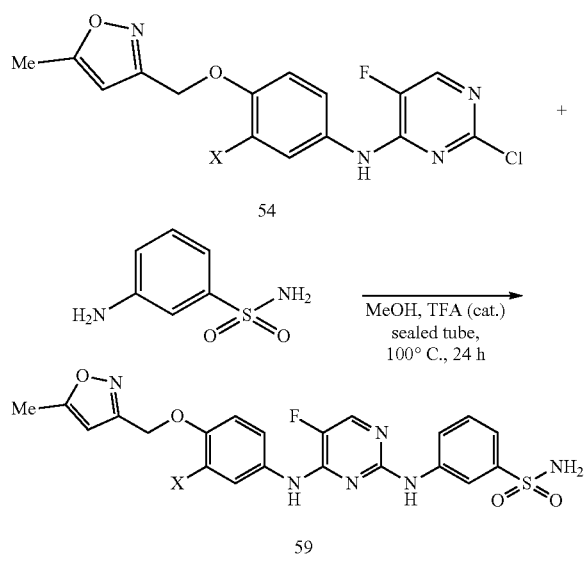

I-230: N2-(3-Aminosulfonylphenyl)-5-fluoro-N4-[4-(5-methylisoxazol-3-yl)methyleneoxyphenyl]-2,4-pyrimidinediamine (59, X=H)

A mixture of 2-chloro-5-fluoro-N-[4-(5-methylisoxazol-3-yl)methyleneoxyphenyl]-4-pyrimidineamine (54, X=H) (100 mg, 0.298 mmol), 3-aminobenzenesulfonamide (51.2 mg, 0.298 mmol) and trifluoroacetic acid (TFA) (2 drops) in MeOH (2 mL) were reacted in sealed reaction vial at 100° C. for 24 hours. The product was purified by column chromatography [silica gel column, eluted with CH$_2$Cl$_2$: 2M NH$_3$ in MeOH (1-3%)] to provide of N2-(3-aminosulfonylphenyl)-5-fluoro-N4-[4-(5-methylisoxazol-3-yl)methyleneoxyphenyl]-2,4-pyrimidinediamine (59, X=H). This reaction also works well in absence of trifluoroacetic acid.

¹H NMR (DMSO-d$_6$): δ 9.46 (s, 1H), 9.28 (s, 1H), 8.06 (d, 2H, J=1.2 Hz), 7.93 (m, 1H), 7.69 (d, 2H, J=9.3 Hz), 7.33 (m, 2H), 7.26 (s, 2H), 6.98 (d, 2H, J=9.0 Hz), 6.32 (s, 1H), 5.13 (s, 2H), 2.40 (s, 3H); LCMS (m/z): 471 (MH⁺).

The following compounds were made in a similar fashion to the example 26.

I-219: N2-(3-Aminosulfonyl-4-methylphenyl)-5-fluoro-N4-[4-(5-methylisoxazol-3-yl)methyleneoxyphenyl]-2,4-pyrimidinediamine ¹H NMR (CD$_3$OD): δ 8.08 (d, J=2.7 Hz, 1H), 7.87 (d, J=3.6 Hz, 1H), 7.72 (dd, J2.4 and 8.4 Hz, 1H), 7.57 (d, J=8.7 Hz, 2H), 7.16 (d, J=8.1 Hz, 1H), 6.99 (d, J=8.7 Hz, 2H), 6.25 (s, 1H), 5.13 (s, 2H), 2.60 (s, 3H), 2.44 (s, 3H); LCMS: purity: 94%; MS (m/z): 485 (MH⁺).

I-220: N2-(3-Aminosulfonyl-4-chlorophenyl)-5-fluoro-N4-[4-(5-methylisoxazol-3-yl)methyleneoxyphenyl]-2,4-pyrimidinediamine ¹H NMR (DMSO-d$_6$): δ 9.59 (s, 1H), 9.31 (s, 1H), 8.27 (d, J=1.8 Hz, 1H), 8.08 (d, J=3.6 Hz, 1H), 8.04-7.98 (m, 1H), 7.68 (d, J=9.0 Hz, 2H), 7.46 (s, 2H), 7.40 (d, J=8.7 Hz, 1H), 6.99 (d, J=9.0 Hz, 2H), 6.33 (s, 1H), 5.13 (s, 2H), 2.41 (s, 3H); LCMS: purity: 89%; MS (m/z): 506 (MH⁺).

I-221: N2-(3-Aminosulfonyl-4-methylphenyl)-N4-[3-chloro-4-(5-methylisoxazol-3-yl)methyleneoxyphenyl]-5-fluoro-2,4-pyrimidinediamine ¹H NMR (DMSO-d$_6$): δ 9.44 (s, 1H), 9.36 (s, 1H), 8.08 (d, J=3.6 Hz, 1H), 8.06-8.02 (m, 1H), 7.91-7.85 (m, 1H), 7.84 (d, J=1.8 Hz, 1H), 7.74 (dd, J=2.7 and 9.0 Hz, 1H), 7.26-7.13 (m, 4H), 6.33 (s, 1H), 5.22 (s, 2H), 2.59 (s, 3H), 2.41 (s, 3H); LCMS: purity: 99%; MS (m/z): 520 (MH⁺).

I-222: N2-(3-Aminosulfonyl-4-methylphenyl)-5-fluoro-N4-[3-fluoro-4-(5-methylisoxazol-3-yl)methyleneoxyphenyl]-2,4-pyrimidinediamine ¹H NMR (DMSO-d$_6$): δ 9.46 (s, 1H), 9.39 (s, 1H), 8.13-8.06 (m, 2H), 7.93-7.84 (m, 2H), 7.52 (d, J=9.3 Hz, 1H), 7.28-7.22 (m, 2H), 7.18 (d, J=8.4 Hz, 1H), 6.34 (s, 1H), 5.20 (s, 2H), 2.50 (s, 3H), 2.41 (s, 3H); LCMS: purity: 95%; MS (m/z): 503 (MH⁺).

1-233: N2-(3-Aminosulfonyl-4-fluorophenyl)-5-fluoro-N4-[4-(5-methylisoxazol-3-yl)methyleneoxyphenyl]-2,4-pyrimidinediamine ¹H NMR (DMSO-d$_6$): δ 9.42 (s, 1H), 9.27 (s, 1H), 8.05 (d, 2H, J=3.3 Hz), 7.95 (m, 1H), 7.66 (d, 2H, J=9.0 Hz), 7.54

(s, 2H), 7.21 (t, 1H, J=9.3 Hz), 6.98 (d, 2H, J=8.7 Hz), 6.32 (s, 1H), 5.12 (s, 2H), 2.40 (s, 3H); LCMS (m/z): 489 (MH$^+$).

I-234: N2-(3-Aminosulfonyl-4-methylphenyl)-5-fluoro-N4-[3-methyl-4-(5-methylisoxazol-3-yl)methyleneoxyphenyl]-2,4-pyrimidinediamine $^1$H NMR (DMSO-d$_6$): δ 9.33 (s, 1H), 9.15 (s, 1H), 8.05 (s, 1H), 8.02 (d, 1H, J=3.3 Hz), 7.90 (d, 1H, J=8.7 Hz), 7.52 (m, 2H), 7.22 (s, 2H), 7.12 (d, 1H, J=8.4 Hz), 6.98 (d, 1H, J=8.7 Hz), 6.33 (s, 1H), 5.13 (s, 2H), 2.49 (s, 3H), 2.41 (s, 3H), 2.16 (s, 3H); LCMS (m/z): 499 (MH$^+$).

I-235: 5-Fluoro-N2-[3-(N-methyl)aminosulfonyl-4-methylphenyl]-N4-[4-(5-methylisoxazol-3-yl)methyleneoxyphenyl]-2,4-pyrimidinediamine $^1$H NMR (DMSO d$_6$): δ 9.42 (s, 1H), 9.31 (s, 1H), 8.11 (d, 1H, J=3.0 Hz), 8.06 (s, 1H), 7.99 (d, 1H, J=8.4 Hz), 7.75 (d, 2H, J=8.4 Hz), 7.38 (q, 1H, J=4.8 Hz), 7.24 (d, 1H, J=8.4 Hz), 7.04 (d, 2H, J=8.7 Hz), 6.38 (s, 1H), 5.18 (s, 2H), 2.55 (d, 3H, J=1.8 Hz), 2.52 (s, 3H), 2.46 (s, 3H); LCMS (m/z): 499 (MH$^+$).

I-237: N2-(3-Aminosulfonyl-4-fluorophenyl)-5-fluoro-N4-[3methyl-4-(5-methylisoxazol-3-yl)methyleneoxyphenyl]-2,4-pyrimidinediamine $^1$H NMR (DMSO-d$_6$): δ 9.41 (s, 1H), 9.19 (s, 1H), 8.01 (m, 3H), 7.46 (m, 3H), 7.18 (t, 1H, J=9.6 Hz), 7.00 (d, 2H, J=9.0 Hz), 6.34 (s, 1H), 5.14 (s, 2H), 2.41 (s, 3H), 2.17 (s, 3H); LCMS (m/z): 503 (MH$^+$).

I-223: N2-(3-Aminosulfonyl-5-chloro-4-methylphenyl)-5-fluoro-N4-[3-fluoro-4-(5-methylisoxazol-3-yl)methyleneoxyphenyl]-2,4-pyrimidinediamine 1H NMR (DMSO-d$_6$): δ 9.71 (s, 1H), 9.50 (s, 1H), 8.25 (d, J=2.4 Hz, 1H), 8.14 (d, J=3.9 Hz, 1H), 8.04 (d, J=2.4 Hz, 1H), 7.79 (dd, J=2.7 and 13.5 Hz, 1H), 7.53-7.40 (m, 3H), 7.20 (t, J=9.3 Hz, 1H), 6.32 (s, 1H), 5.18 (s, 2H), 3.51 (s, 3H), 2.41 (s, 3H); LCMS: purity: 93%; MS (m/z): 538 (MH$^+$).

I-224: N2-(3-Aminosulfonyl-4-fluoro-5-methylphenyl)-5-fluoro-N4-[3-fluoro-4-(5-methylisoxazol-3-yl)methyleneoxyphenyl]-2,4-pyrimidinediamine $^1$H NMR (DMSO-d$_6$): δ 9.57 (s, 1H), 8.12 (d, J=4.2 Hz, 1H), 7.88-7.82 (m, 1H), 7.81-7.73 (m, 2H), 7.49-7.42 (m, 1H), 7.20 (t, J=9.0 Hz, 1H), 6.32 (s, 1H), 5.18 (s, 2H), 2.41 (s, 3H), 2.19 (s, 3H); LCMS: purity: 94%; MS (m/z): 521 (MH$^+$).

I-238: N2-(3-Aminosulfonylphenyl)-5-fluoro-N4-[3-methyl-4-(5-methylisoxazol-3-yl)methyleneoxyphenyl]-2,4-pyrimidinediamine $^1$H NMR (DMSO-d$_6$): δ 9.45 (s, 1H), 9.19 (s, 1H), 8.05 (d, 1H, J=3.6 Hz), 8.02-7.96 (m, 2H), 7.51 (m, 2H), 7.31 (d, 2H, J=4.8 Hz), 7.24 (s, 2H), 6.99 (d, 1H, J=8.4 Hz), 6.33 (s, 1H), 5.13 (s, 2H), 2.41 (s, 3H), 2.17 (s, 3H); LCMS (m/z): 485 (MH$^+$).

I-216: N2-(3-Aminosulfonyl-5-chloro-4-methylphenyl)-5-fluoro-N4-[3-methyl-4-(5-methylisoxazol-3-yl)methyleneoxyphenyl]-2,4-pyrimidinediamine LCMS: purity: 96%, MS (m/e): 520 (MH+).

I-217: N2-(3-Aminosulfonyl-4-fluoro-5-methylphenyl)-5-fluoro-N4-[3-methyl-4-(5-methylisoxazol-3-yl)methyleneoxyphenyl]-2,4-pyrimidinediamine LCMS: purity: 99%, MS (m/e): 504 (MH+).

V-1: N2-(3-Aminosulfonyl-4-methylphenyl)-5-fluoro-N4-[2-(5-methylisoxazol-3-yl)methyleneoxypyridin-5-yl]-2,4-pyrimidinediamine $^1$H NMR (DMSO-d$_6$): δ 9.33 (s, 1H), 9.21 (s, 1H), 8.14 (d, J=2.4 Hz, 1H), 8.05 (s, J=2.4 Hz, 2H), 7.81 (dd, J=2.4 and 8.7 Hz, 1H), 7.71 (dd, J=2.7 and 9.6 Hz, 1H), 7.24 (s, 2H), 7.12 (d, J=8.4 Hz, 1H), 6.46 (d, J=9.6 Hz, 1H), 6.11 (s, 1H), 5.13 (s, 2H), 2.48 (s, 3H), 2.34 (s, 3H); LCMS: purity: 87%; MS (m/z): 486 (MH$^+$).

I-240: N2-(4-Aminosulfonylphenyl)-5-fluoro-N4-[3methyl-4-(5-methylisoxazol-3-yl)methyleneoxyphenyl]-2,4-pyrimidinediamine $^1$H NMR (DMSO d$_6$, 300 MHz): δ 9.56 (s, 1H), 9.27 (s, 1H), 8.09 (d, 1H, J=3.6 Hz), 7.78 (d, 2H, J=8.7 Hz), 7.59 (d, 2H, J=8.4 Hz), 7.51 (s, 1H), 7.43 (d, 1H, J=8.7 Hz), 7.12 (s, 2H), 7.02 (d, 1H, J=8.4 Hz), 6.35 (s, 1H), 5.14 (s, 2H), 2.41 (s, 3H), 2.19 (s, 3H); LCMS (m/z): 485 (MH$^+$).

I-214: N2-(3-Aminosulfonyl-4-methylphenyl)-N4-[3-(5-methylisoxazol-3-yl)methyleneoxyphenyl]-2,4-pyrimidinediamine $^1$H NMR (DMSO-d$_6$): δ 9.45 (s, 1H), 9.37 (s, 1H), 8.14-8.05 (m, 2H). 7.93 (d, J=9.0 Hz, 1H), 7.53-7.49 (m, 1H), 7.46 (d, J=9.0 Hz, 1H), 7.27-7.20 (m, 3H), 7.16 (d, J=8.1 Hz, 1H), 6.73 (d, J=9.3 Hz, 1H), 6.31 (s, 1H), 5.12 (s, 2H), 2.49 (s, 3H), 2.40 (s, 3H); LCMS: purity: 96%; MS (m/z): 485 (MH$^+$).

I-206: N2-(3-Aminosulfonylphenyl)-5-fluoro-N4-[4-(2-morpholinoethyloxy)phenyl-2,4-pyrimidinediamine LCMS: purity: 93%; MS (m/z): 489 (MH$^+$).

I-207: 5-Fluoro-N2-(3-morpholinosulfonylphenyl)-N4-[4-(2-morpholinoethyloxy)phenyl]-2,4-pyrimidinediamine $^1$H NMR (DMSO-d6): δ 9.56 (s, 1H), 9.32 (s, 1H), 8.10 (d, 1H, J=3.9 Hz), 7.80 (d, 2H, J=8.1 Hz), 7.60 (3H, dd, J=2.4 Hz and 2.1 Hz), 7.12 (s, 2H), 6.96 (d, 2H, J=8.7 Hz), 3.58 (m, 3H), 3.32 (m, 8H), 3.30 (m, 8H), 2.70 (t, 2H, J=5.7 Hz); LCMS: purity: 93%; MS (m/z): 559 (MH$^+$).

I-208: N2-(3-Aminosulfonylphenyl)-5-fluoro-N4-[4-methyl-3-(2-morpholinocarbonylmethyleneoxy)phenyl]-2,4-pyrimidinediamine $^1$H NMR (DMSO-d6): δ 9.68 (s, 1H), 9.53 (s, 1H), 8.15 (d, 1H, J=3.9 Hz), 8.10 (s, 1H), 7.92 (m, 1H), 7.46 (s, 1H), 7.40 (m, 2H), 7.23 (m, 2H), 7.10 (d, 1H, J=8.4 Hz), 4.82 (s, 2H), 3.75 (bs, 4H), 3.50 (bs, 4H), 2.16 (s, 3H); LCMS: purity: 90%; MS (m/z): 503 (MH$^+$).

I-209: N2-(4-Aminosulfonylphenyl)-5-fluoro-N4-[4-methyl-3-(2-morpholinocarbonylmethyleneoxy)phenyl]-2,4-pyrimidinediamine $^1$H NMR (DMSO-d6): δ 9.85 (s, 1H), 9.64 (s, 1H), 8.18 (d, 1H, J=3.6 Hz), 7.80 (d, 2H, J=8.4 Hz), 7.65 (d, 2H, J=8.7 Hz), 7.38 (s, 1H), 7.16 (m, 2H), 4.80 (s, 2H), 3.51 (s, 4H), 3.43 (s, 4H), 2.18 (s, 3H); LCMS: purity: 88%; MS (m/z): 517 (MH$^+$).

I-203: N2-(3-Aminosulfonylphenyl)-5-fluoro-N4-[4-methyl-3-(2-morpholinoethyloxy)phenyl]-2,4-pyrimidinediamine $^1$H NMR (DMSO-d6): δ 9.48 (s, 1H), 9.26 (s, 1H), 8.10 (d, 1H, J=3.9 Hz), 7.97 (d, 1H, J=6.9 Hz), 7.36 (m, 3H), 7.25 (s, 2H), 7.09 (s, 1H), 4.03 (m, 2H), 3.55 (bs, 4H), 3.31 (bs, 4H), 2.71 (m, 2H), 2.13 (s, 3H); LCMS: purity: 87%; MS (m/z): 503 (MH$^+$).

VII-51: N2-(3-Aminosulfonylphenyl)-N4-[2,2-dimethyl-3-oxo-4H-5-pyrid[1,4]oxazin-7-yl]-5-fluoro-2,4-pyrimidinediamine $^1$H NMR (DMSO-d6): δ 11.11 (s, 1H), 9.63 (s, 1H), 9.48 (s, 1H), 8.42 (t, 1H, J=2.1 Hz), 8.13 (t, 2H, J=3.3 Hz), 7.95 (d, 1H, J=7.8 Hz), 7.87 (d, 1H, J=2.1 Hz), 7.41 (m, 2H), 7.25 (s, 1H), 1.45 (s, 6H); LCMS: purity: 92%; MS (m/z): 460 (MH$^+$).

VII-52: N2-(4-Aminosulfonylphenyl)-N4-[2,2-dimethyl-3-oxo-4H-5-pyrid[1,4]oxazin-7-yl]-5-fluoro-2,4-pyrimidinediamine $^1$H NMR (DMSO-d6): δ 11.14 (s, 1H), 9.70 (s, 1H), 9.53 (s, 1H), 8.16 (s, 1H), 7.81 (d, 2H, J=8.4 Hz), 7.66 (d, 2H, J=8.4 Hz), 7.11 (s, 2H), 1.45 (s, 6H); LCMS: purity: 95%; MS (m/z): 460 (MH$^+$).

VII-42: N2-(3-Aminosulfonylphenyl)-N4-[2,2,4-trimethyl-3-oxo-5-pyrid[1,4]oxazin-7-yl]-5-fluoro-2,4-pyrimidinediamine $^1$H NMR (DMSO-d6): δ 9.64 (s, 1H), 8.62 (s, 1H), 8.15 (d, 2H, J=3.9 Hz), 7.93 (t, 2H, J=7.2 Hz), 7.37 (m, 3H), 2.43 (s, 3H), 1.45 (s, 6H); LCMS: purity: 94%; MS (m/z): 474 (MH$^+$).

VII-43: N2-(4-Aminosulfonylphenyl)-N4-[2,2,4-trimethyl-3-oxo-5-pyrid[1,4]oxazin-5-yl]-5-fluoro-2,4-pyrimidinediamine $^1$H NMR (DMSO-d6): δ 11.14 (s, 1H), 9.70 (s, 1H), 9.53 (s, 1H), 8.16 (s, 1H), 7.81 (d, 2H, J=8.4 Hz), 7.66 (d, 2H, J=8.4 Hz), 7.11 (s, 2H), 2.43 (s, 3H), 1.45 (s, 6H); LCMS: purity: 90%; MS (m/z): 474 (MH$^+$).

I-204: N2-(3-Aminosulfonyl-4-methylphenyl)-5-fluoro-N4-[4-methyl-3-(2-morpholinoethyloxy)phenyl]2,4-pyrimidinediamine $^1$H NMR (DMSO-d6): δ 9.38 (s, 1H), 9.22 (s, 1H), 8.09 (d, 1H, J=1.5 Hz), 7.92 (d, 1H, J=2.4 Hz), 7.40 (d, 2H, J=8.1 Hz), 7.26 (s, 2H), 7.15 (s, 1H), 4.10 (t, 2H, J=5.7 Hz), 3.54 (bs, 4H), 2.69 (bs, 2H), 2.49 (s, 6H), 2.12 (s, 4H).

VI-111: N2-(3-Aminosulfonyl-4-chlorophenyl)-5-fluoro-N4-[4-(2-methoxyethyleneoxy)phenyl]-2,4-pyrimdinediamine LCMS: purity: 94%; MS (m/z): 468 (MH$^+$).

V-14: N2-(3-Aminosulfonyl-4-methylphenyl)-N4-[2,2-dimethyl-3-oxo-4-cyanomethyl-5-pyrid[1,4]oxazin-7-yl]-5-fluoro-2,4-pyrimidinediamine $^1$H NMR (DMSO-d6): δ 8.65 (s, 1H), 8.15 (d, 1H, J=3.6 Hz), 8.09 (s, 1H), 8.01 (s, 1H), 7.91 (m, 2H), 5.10 (s, 2H), 2.07 (s, 3H), 1.50 (s, 6H); LCMS: purity: 96%; MS (m/z): 513 (MH$^+$).

V-15: N2-(3-Aminosulfonyl-4-chlorophenyl)-N4-[2,2-dimethyl-3-oxo-4-cyanomethyl-5-pyrid[1,4]oxazin-7-yl]-5-fluoro-2,4-pyrimidinediamine $^1$H NMR (DMSO-d6): δ 8.66 (d, 1H, J=2.4 Hz), 8.27 (d, 1H, J=3.6 Hz), 8.19 (d, 1H, J=3.6 Hz), 8.10 (m, 1H), 7.48 (d, 2H, J=1.8 Hz), 5.10 (s, 2H), 1.52 (s, 6H); LCMS: purity: 96%; MS (m/z): 533 (MH$^+$).

VI-112: N2-(3-Aminosulfonyl-4-methylphenyl)-5-fluoro-N4-[4-(2-methoxyethyleneoxy)phenyl]-2,4-pyrimdinediamine LCMS: purity: 91%; MS (m/z): 448 (MH$^+$).

1-205: N2-(4-Aminosulfonylphenyl)-5-fluoro-N4-[4-(2-morpholinoethyloxy)phenyl)-2,4-pyrimidinediamine LCMS: purity: 87%; MS (m/z): 489 (MH$^+$).

VII-26: Racemic N2-(3-Aminosulfonyl-4-methylphenyl)-N4-[2-(N,N-dimethylaminocarbonyl)-2,3-dihydrobenzofuran-5-yl]-5-fluoro-2,4-pyrimidinediamine $^1$H NMR (DMSO-d6): δ 8.17 (d, 1H, J=4.8 Hz), 7.86 (s, 1H), 7.82 (d, 1H, J=2.1 Hz), 7.50 (s, 1H), 7.27 (t, 2H, J=8.4 Hz), 6.79 (d, 1H, J=8.4 Hz), 5.67 (t, 2H, J=8.1 Hz), 2.88 (s, 6H), 2.49 (s, 3H); LCMS: purity: 90%; MS (m/z): 487 (MH$^+$).

VII-27: Racemic N2-(3-Aminosulfonyl-4-chlorophenyl)-N4-[2-(N,N-dimethylaminocarbonyl)-2,3-dihydrobenzofuran-5-yl]-5-fluoro-2,4-pyrimidinediamine $^1$H NMR (DMSO-d6): δ 7.95 (dd, 2H, J=2.7 Hz and 2.4 Hz), 7.30 (dd, 3H, J=2.4 Hz and 2.4 Hz), 6.80 (d, 2H, J=8.7 Hz), 5.67 (t, 2H, J=7.5 Hz), 2.88 (s, 6H); LCMS: purity: 90%; MS (m/z): 507 (MH$^+$).

IX-9: N4-[3-(Aminocarbonyl)-1H-indol-6-yl]-N2-(3-aminosulfonyl-4-methylphenyl)-5-fluoro-2,4-pyrimidinediamine $^1$H NMR (DMSO-d6): δ 7.83 (d, 2H, J=7.8 Hz), 7.41 (s, 2H), 7.26 (s, 2H), 7.10 (d, 2H, J=8.4 Hz), 2.45 (s, 3H); LCMS: purity: 96%; MS (m/z): 456 (MH$^+$).

IX-10: N4-[3-(Aminocarbonyl)-1H-indol-6-yl]-N2-(3-aminosulfonyl-4-chlorophenyl)-5-fluoro-2,4-pyrimidinediamine $^1$H NMR (DMSO-d6): δ 8.18 (s, 1H), 8.12 (s, 1H), 8.03 (m, 2H), 7.44 (m, 3H), 7.15 (d, 1H, J=9.0 Hz); LCMS: purity: 87%; MS (m/z): 476 (MH$^+$).

IX-11: N2-(3-Aminosulfonyl-4-methylphenyl)-N4-(3-cyanomethyl-1H-indol-6-yl)-5-fluoro-2,4-pyrimidinediamine $^1$H NMR (DMSO-d6): δ 7.95 (d, 1H, J=8.4 Hz), 7.64 (s, 1H), 7.55 (d, 1H, J=8.4 Hz), 7.41 (m, 1H), 7.29 (s, 1H), 7.20 (s, 2H), 7.06 (d, 1H, J=8.7 Hz), 4.04 (s, 2H), 2.45 (s, 3H); LCMS: purity: 96%; MS (m/z): 452 (MH$^+$).

IX-12: N2-(3-Aminosulfonylphenyl)-N4-(3-cyanomethyl-1H-indol-6-yl)-5-fluoro-2,4-pyrimidinediamine $^1$H NMR (DMSO-d6): δ 8.08 (t, 1H, J=3.3 Hz), 8.01 (d, 1H, J=3.0 Hz), 7.65 (s, 1H), 7.55 (d, 2H, J=8.4 Hz), 7.43 (d, 1H, J=8.1 Hz), 7.26 (m, 3H), 4.04 (s, 2H); LCMS: purity: 93%; MS (m/z): 438 (MH$^+$).

IX-13: N2-(3-Aminosulfonylphenyl)-N4-(3-cyanomethyl-1H-indol-5-yl)-5-fluoro-2,4-pyrimidinediamine $^1$H NMR (DMSO-d6): δ 8.06 (d, 1H, J=3.9 Hz), 7.96 (d, 1H, J=8.4 Hz), 7.87 (s, 1H), 7.35 (m, 5H), 4.02 (s, 2H); LCMS: purity: 96%; MS (m/z): 438 (MH$^+$).

IX-14: N2-(3-Aminosulfonyl-4-methylphenyl)-N4-(3-cyanomethyl-1H-indol-5-yl)-5-fluoro-2,4-pyrimidinediamine $^1$H NMR (DMSO-d$_6$): δ 8.07 (s, 1H), 8.02 (d, 1H, J=3.9 Hz), 7.87 (s, 2H), 7.41 (s, 1H), 7.37 (s, 1H), 7.35 (s, 1H), 7.20 (s, 1H), 4.01 (s, 2H), 2.42 (s, 3H); LCMS: purity: 97%; MS (m/z): 452 (MH$^+$).

I-244: N2-[3-(2-N,N-Diethylaminoethyl)aminosulfonylphenyl)-5-fluoro-N4-[3-methyl-4-(5-methylisoxazol-3-yl)methyleneoxyphenyl]-2,4-pyrimidinediamine $^1$H NMR (DMSO d$_6$, 300 MHz): δ 9.45 (s, 1H), 9.20 (s, 1H), 8.05 (m, 3H), 7.50 (m, 2H), 7.34 (t, 1H, J=7.5 Hz), 7.26 (d, 2H, J=7.8 Hz), 7.00 (d, 1H, J=9.3 Hz), 6.33 (s, 1H), 5.13 (s, 2H), 2.79 (t, 2H, J=7.8 Hz), 2.41 (s, 3H), 2.38 (m, 6H), 2.17 (s, 3H), 0.85 (t, 6H, J=6.9 Hz); LCMS (m/z): 584 (MH$^+$).

I-245: N2-[4-(2-N,N-Diethylaminoethyl)aminosulfonylphenyl)-5-fluoro-N4-[3-methyl-4-(5-methylisoxazol-3-yl)methyleneoxyphenyl]-2,4-pyrimidinediamine $^1$H NMR (DMSO d$_6$): δ 9.62 (s, 1H), 9.28 (s, 1H), 8.09 (d, 1H, J=3.3 Hz), 7.80 (d, 2H, J=8.7 Hz), 7.55 (d, 2H, J=8.7 Hz), 7.52 (d, 1H, J=2.7 Hz), 7.40 (dd, 1H, J=2.4 and 8.5 Hz), 7.17 (br s, 1H), 7.01 (d, 1H, J=8.7 Hz), 6.34 (s, 1H), 5.13 (s, 2H), 2.71 (t, 2H, J=7.8 Hz), 2.41 (s, 3H), 2.38 (m, 6H), 2.18 (s, 3H), 0.83 (t, 6H, J=6.9 Hz); LCMS (m/z): 584 (MH$^+$).

I-239: 5-Fluoro-N2-[3-N-(methyl)aminosulfonyl-4-methylphenyl]-N4-[3-methyl-4-(5-methylisoxazol-3-yl)methyleneoxyphenyl]-2,4-pyrimidinediamine $^1$H NMR (DMSO d$_6$): δ 9.34 (s, 1H), 9.16 (s, 1H), 8.03 (d, 1H, J=3.9 Hz), 7.96 (m, 2H), 7.50 (m, 2H), 7.32 (q, 1H, J=4.5 Hz), 7.15 (d, 1H, J=9.0 Hz), 6.99 (d, 1H, J=8.4 Hz), 6.33 (s, 1H), 5.13 (s, 2H), 2.45 (s, 3H), 2.41 (d, 3H, J=3.3 Hz), 2.40 (s, 3H), 2.16 (s, 3H); LCMS (m/z): 513 (MH$^+$).

I-241: N2-[3-(2-N,N-Diethylaminoethyl)aminosulfonylphenyl)-5-fluoro-N4-[4-(5-methylisoxazol-3-yl)methyleneoxyphenyl]-2,4-pyrimidinediamine $^1$H NMR (DMSO d6): δ 9.45 (s, 1H), 9.28 (s, 1H), 8.05 (m, 2H), 7.98 (d, 1H, J=8.4 Hz), 7.67 (d, 2H, J=9 Hz), 7.36 (t, 1H, J=8.1 Hz), 7.26 (d, 2H, J=8.1 Hz), 6.98 (d, 2H, J=9.0 Hz), 6.32 (s, 1H), 5.12 (s, 2H), 2.79 (t, 2H, J=8.1 Hz), 2.40 (s, 3H), 2.37 (m, 6H), 0.84 (t, 6H, J=6.9 Hz); LCMS (m/z): 570 (MH$^+$).

I-246: N2-[4-(2-N,N-Diethylaminoethyl)aminosulfonylphenyl)-5-fluoro-N4-[4-(5-methylisoxazol-3-yl)methyleneoxyphenyl]-2,4-pyrimidinediamine $^1$H NMR (DMSO d$_6$): δ 9.60 (s, 1H), 9.34 (s, 1H), 8.10 (d, 1H, J=3.9 Hz), 7.81 (d, 2H, J=9.0 Hz), 7.63 (d, 2H, J=9.0 Hz), 7.57 (d, 2H, J=8.7 Hz), 7.15 (br s, 1H), 7.01 (d, 2H, J=9.3 Hz), 6.32 (s, 1H), 5.12 (s, 2H), 2.73 (t, 2H, J=7.5 Hz), 2.40 (s, 3H), 2.36 (m, 6H), 0.84 (t, 6H, J=6.9 Hz); LCMS (m/z): 570 (MH$^+$).

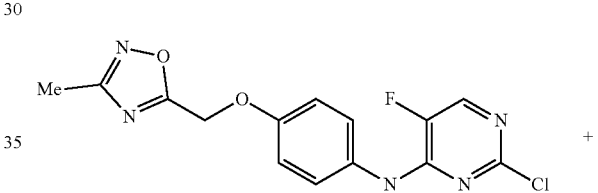

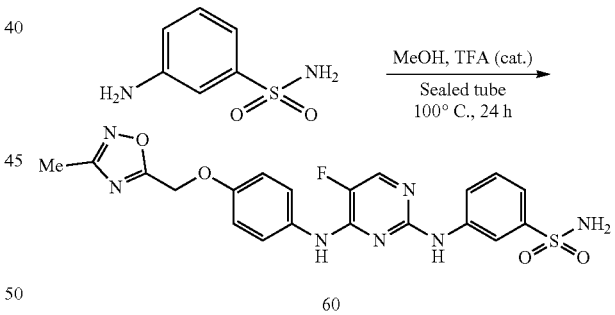

I-252: N2-(3-Aminosulfonylphenyl)-5-fluoro-N4-[4-(3-methyl-1,2,4-oxadiazol-5-yl)methyleneoxyphenyl]-2,4-pyrimidinediamine (60)

$^1$H NMR (DMSO-d6): δ 9.51 (s, 1H), 9.39 (s, 1H), 8.13 (d, 1H, J=2.1 Hz), 8.09 (s, 1H), 7.98 (d, 1H, J=6.9 Hz), 7.51 (br s, 2H), 7.41-7.25 (m, 4H), 6.73 (d, 2H, J=7.5 Hz), 5.45 (s, 2H), 2.35 (s, 3H); LCMS (m/z): 472 (MH$^+$).

I-253: N2-(4-Aminosulfonylphenyl)-5-fluoro-N4-[3-(3-methyl-1,2,4-oxadiazol-5-yl)methyleneoxyphenyl]-2,4-pyrimidinediamine $^1$H NMR (DMSO d$_6$, 300 MHz): δ 9.62 (s, 1H), 9.46 (s, 1H), 8.16 (d, 1H, J=2.1 Hz), 7.82 (d, 2H, J=7.5 Hz), 7.62 (d, 2H, J=7.2 Hz), 7.49 (d, 1H, J=8.1 Hz), 7.43 (s, 1H), 7.26 (t, 1H, J=8.1 Hz), 7.11 (br s, 2H), 6.76 (d, 1H, J=8.1 Hz), 5.46 (s, 2H), 2.34 (s, 3H); LCMS (m/z): 472 (MH$^+$).

I-231: N2-(4-Aminosulfonylphenyl)-5-fluoro-N4-[4-(3-methyl-1,2,4-oxadiazol-5-yl)methyleneoxyphenyl]-2,4-pyrimidinediamine $^1$H NMR (DMSO-d6): δ 9.62 (s, 1H), 9.46 (s, 1H), 8.16 (d, 1H, J=2.1 Hz), 7.82 (d, 2H, J=7.5 Hz), 7.62 (d, 2H, J=7.2 Hz), 7.49 (d, 1H, J=8.1 Hz), 7.43 (s, 1H), 7.26 (t, 1H, J=8.1 Hz), 7.11 (br s, 2H), 6.76 (d, 1H, J=8.1 Hz), 5.46 (s, 2H), 2.34 (s, 3H); LCMS (m/z): 472 (MH$^+$).

I-259: N2-(3-Aminosulfonyl-4-methylphenyl)-5-fluoro-N4-[4-(3-methyl-1,2,4-oxadiazol-5-yl)methyleneoxyphenyl]-2,4-pyrimidinediamine $^1$H NMR (DMSO d$_6$): δ 9.35 (s, 1H), 9.26 (s, 1H), 8.08 (s, 1H), 8.04 (d, 1H, J=3.3 Hz), 7.86 (d, 1H, J=7.5 Hz), 7.71 (d, 2H, J=8.7 Hz), 7.22 (s, 2H), 7.13 (d, 1H, J=8.4 Hz), 6.99 (d, 2H, J=9.0 Hz), 5.45 (s, 2H), 2.49 (s, 3H), 2.36 (s, 3H); LCMS (m/z): 486 (MH$^+$).

I-258: N2-(3-Aminosulfonylphenyl)-5-fluoro-N4-[4-(3-methyl-1,2,4-oxadiazol-5-yl)methyleneoxyphenyl]-2,4-pyrimidinediamine $^1$H NMR (DMSO d$_6$): δ 9.47 (s, 1H), 9.31 (s, 1H), 8.07 (d, 2H, J=3.0 Hz), 7.90 (d, 1H, J=6.6 Hz), 7.70 (d, 2H, J=8.7 Hz), 7.33 (m, 2H), 7.25 (s, 2H), 7.00 (d, 2H, J=9.0 Hz), 5.46 (s, 2H), 2.49 (s, 3H), 2.36 (s, 3H); LCMS (m/z): 472 (MH$^+$).

I-254: N2-(3-Aminosulfonyl-4-methylphenyl)-5-fluoro-N4-[3-(3-methyl-1,2,4-oxadiazol-5-yl)methyleneoxyphenyl]-2,4-pyrimidinediamine $^1$H NMR (DMSO d$_6$): δ 9.41 (s, 1H), 9.35 (s, 1H), 8.09 (m, 2H), 7.92 (dd, 2H, J=2.1 and 8.1 Hz), 7.51 (m, 2H), 7.22 (m, 5H), 6.74 (dd, 2H, J=2.1 and 8.2 Hz), 5.45 (s, 2H), 2.45 (s, 3H); LCMS (m/z): 486 (MH$^+$).

III-14: N2-(3-aminosulfonylphenyl)-N4-[4-(cyanoethylene)phenyl]-5-fluoro-2,4-pyrimidinediamine $^1$H NMR (DMSO-d$_6$): δ 9.52 (s, 1H), 9.37 (s, 1H), 8.11-8.10 (d, J=3 Hz, 2H), 7.98-7.95 (d, J=9.0 Hz, 1H), 7.77-7.74 (d, J=9.0 Hz, 2H), 7.39-7.32 (m, 2H), 7.26 (s, 2H), 7.23 (s, 2H), 2.86-2.79 (m, 4H); LCMS (m/z): 412.97 (MH$^+$).

III-15: N2-(3-Aminosulfonyl-4-methylphenyl)-N4-[4-(cyanoethylene)phenyl]-5-fluoro-2,4-pyrimidinediamine $^1$H NMR (DMSO-d$_6$): δ 9.40 (s, 1H), 9.32 (s, 1H), 8.10-8.06 (m, 2H), 7.92 (br s, 1H), 7.25-7.17 (m, 5H), 2.48 (s, 3H); LCMS (m/z): 427.01 (MH$^+$).

III-16: N2-(3-Aminosulfonyl-4-fluorophenyl)-N4-[4-(cyanoethylene)phenyl]-5-fluoro-2,4-pyrimidinediamine $^1$H NMR (DMSO-d$_6$): δ 9.47 (s, 1H), 9.36 (s, 1H), 8.09-8.08 (d, J=3.0 Hz, 1H) 8.06-8.04 (m, 1H), 8.02-7.98 (m, 1H), 7.75-7.72 (d, J=9.0 Hz, 2H), 7.54 (s, 2H), 7.28-7.22 (m, 3H), 2.86-2.81 (m, 4H); LCMS: (m/z): 430.98 (MH$^+$).

III-106: N2-(3-Aminosulfonylphenyl)-5-fluoro-N4-[4-(3-methyl-1,2,4-oxadiazol-5-yl)ethylenephenyl]-2,4-pyrimidinediamine $^1$H NMR (DMSO-d$_6$): δ 9.50 (s, 1H), 9.33 (s, 1H), 8.10 (br s, 2H), 7.97-7.94 (bd, J=9.0 Hz, 1H), 7.73-7.70 (d, J=9.0 Hz, 2H), 7.35 (m, 2H), 7.25 (s, 2H), 7.21-7.18 (d, J=9.0 Hz, 2H), 3.23-3.19 (m, 2H), 3.06-3.01 (m, 2H), 2.30 (s, 3H); LCMS (m/z): 469.88 (MH$^+$).

I-267: N2-(3-Aminosulfonyl-4-fluorophenyl)-5-fluoro-N4-[4-(3-methyl-1,2,4-oxadiazol-5-yl)ethylenephenyl]-2,4-pyrimidinediamine $^1$H NMR (DMSO-d$_6$): δ 9.411 (s, 1H), 9.30 (br s, 1H), 8.07-8.06 (d, J=3 Hz, 1H), 8.01 (m, 1H), 7.95 (m, 1H), 7.71-7.68 (d, J=9.0 Hz, 2H), 7.21-7.18 (d, J=9.0 Hz, 2H), 3.23-3.18 (m, 2H), 3.05-3.00 (m, 2H), 2.29 (s, 3H); LCMS (m/z): 488.41 (MH$^+$).

I-266: N2-(3-Aminosulfonyl-4-fluorophenyl)-5-fluoro-N4-[4-(3-methyl-1,2,4-oxadiazol-5-yl)methyleneoxyphenyl]-2,4-pyrimidinediamine $^1$H NMR (DMSO-d$_6$): δ 9.52 (s, 1H), 9.44 (s, 1H), 8.08-8.07 (d, J=3 Hz, 1H), 8.01-7.99 (m, 1H), 7.95-7.92 (m, 1H), 7.68-7.65 (d, J=9.0 Hz, 2H), 7.55 (s, 2H), 7.28-7.20 (m, 1H), 7.03-7.00 (d, J=9.0 Hz, 2H), 5.46 (s, 2H), 2.36 (s, 3H); LCMS (m/z): 490.36 (MH$^+$).

I-260: 5-Fluoro-N2-[3-N-(methyl)aminosulfonyl-4-methylphenyl)-N4-[4-(3-methyl-1,2,4-oxadiazol-5-yl)methyleneoxyphenyl]-2,4-pyrimidinediamine $^1$H NMR (DMSO d$_6$): δ 9.35 (s, 1H), 9.27 (s, 1H), 8.05 (d, 1H, J=3.6 Hz), 8.00 (d, 1H, J=2.4 Hz), 7.92 (dd, 1H, J=2.4 and 8.2 Hz), 7.71 (d, 2H, J=9.0 Hz), 7.31 (q, 1H, J=4.8 Hz), 7.18 (d, 1H, J=8.1 Hz), 7.00 (d, 2H, J=9.3 Hz), 5.45 (s, 2H), 2.45 (s, 3H), 2.41 (d, 3H, J=4.8 Hz), 2.35 (s, 3H), 2.46 (s, 3H); LCMS (m/z): 500 (MH$^+$).

I-255: 5-Fluoro-N2-[3-(N-methylaminosulfony)-4-methylphenyl]-N4-[3-(3-methyl-1,2,4-oxadiazol-5-yl)methyleneoxyphenyl]-2,4-pyrimidinediamine $^1$H NMR (DMSO d$_6$): δ 9.41 (s, 1H), 9.36 (s, 1H), 8.11 (d, 1H, J=3.6 Hz), 7.99 (m, 2H), 7.50 (m, 2H), 7.32 (q, 1H, J=4.8 Hz), 7.22 (t, 2H, J=8.1 Hz), 6.72 (dd, 1H, J=2.4 and 8.1 Hz), 5.43 (s, 2H), 2.44 (s, 3H), 2.41 (d, 3H, J=4.5 Hz), 2.35 (s, 3H); LCMS (m/z): 500 (MH$^+$).

I-261: N2-[3-(2-N,N-Diethylaminoethyl)aminosulfonylphenyl)-5-fluoro-N4-[3-(3-methyl-1,2,4-oxadiazol-5-yl)methyleneoxyphenyl]-2,4-pyrimidinediamine $^1$H NMR (DMSO d$_6$): δ 9.54 (s, 1H), 9.41 (s, 1H), 8.14 (d, 1H, J=3.3 Hz), 8.07 (s, 1H), 8.03 (d, 1H, J=8.4 Hz), 7.50 (m, 2H), 7.41 (t, 1H, J=8.1 Hz), 7.34 (br s, 1H), 7.25 (d, 2H, J=8.1 Hz), 6.74 (d, 1H, J=6.9 Hz), 5.45 (s, 2H), 2.79 (t, 2H, J=7.5 Hz), 2.35 (m, 9H), 0.84 (t, 6H, J=6.9 Hz); LCMS (m/z): 571 (MH$^+$).

I-256: N2-[4-(2-N,N-Diethylaminoethyl)amino-sulfonylphenyl)-5-fluoro-N4-[3-(3-methyl-1,2,4-oxadiazol-5-yl)methyleneoxyphenyl]-2,4-pyrimidinediamine $^1$H NMR (DMSO $d_6$): δ 9.68 (s, 1H), 9.47 (s, 1H), 8.17 (d, 1H, J=3.6 Hz), 7.85 (d, 2H, J=9.0 Hz), 7.60 (d, 2H, J=9.0 Hz), 7.44 (m, 2H), 7.27 (t, 2H, J=8.4 Hz), 6.76 (dd, 1H, J=2.4 and 8.1 Hz), 5.46 (s, 2H), 2.74 (t, 2H, J=7.8 Hz), 2.41 (m, 6H), 2.34 (s, 3H), 0.86 (t, 6H, J=7.2 Hz); LCMS (m/z): 571 (MH$^+$).

I-262: N2-[3-(2-N,N-Diethylaminoethyl)amino-sulfonylphenyl)-5-fluoro-N4-[4-(3-methyl-1,2,4-oxadiazol-5-yl)methyleneoxyphenyl]-2,4-pyrimidinediamine $^1$H NMR (DMSO $d_6$): δ 9.47 (s, 1H), 9.31 (s, 1H), 8.08 (d, 1H, J=3.9 Hz), 8.05 (s, 1H), 7.98 (d, 1H, J=8.4 Hz), 7.70 (d, 2H, J=9.0 Hz), 7.37 (t, 2H, J=7.8 Hz), 7.26 (d, 1H, J=8.1 Hz), 5.46 (s, 2H), 2.79 (t, 2H, J=7.5 Hz), 2.36 (m, 9H), 0.85 (t, 6H, J=6.9 Hz); LCMS (m/z): 571 (MH$^+$).

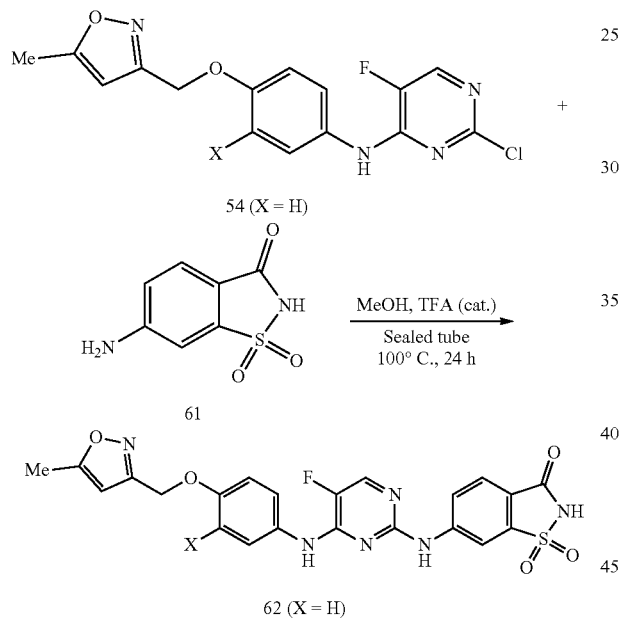

VIII-1: 5-Fluoro-N4-[4-(5-methylisoxazol-3-yl)methyleneoxyphenyl]-N2-(sacchrin-6-yl)-2,4-pyrimidinediamine:

$^1$H NMR (DMSO $d_6$, 300 MHz): δ 10.07 (s, 1H), 9.44 (s, 1H), 8.46 (s, 1H), 8.18 (d, 1H, J=3.6 Hz), 7.84 (d, 1H, J=8.4 Hz), 7.70 (d, 1H, J=8.7 Hz), 7.60 (d, 2H, J=9.3 Hz), 7.05 (d, 2H, J=9.0 Hz), 6.45 (br s, 1H), 6.33 (s, 1H), 5.15 (s, 2H), 2.41 (s, 3H); LCMS (m/z): 497 (MH$^+$).

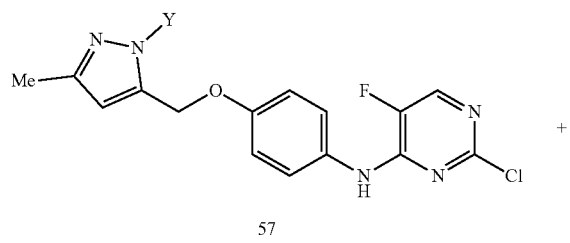

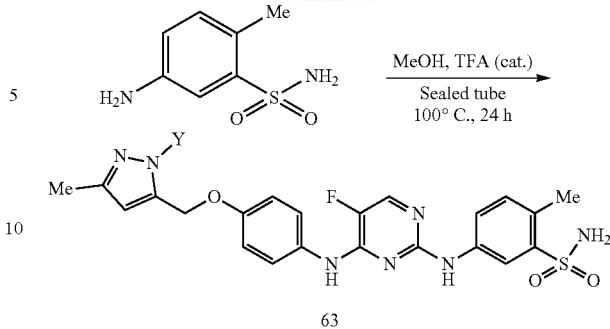

I-198: N2-(3-Aminosulfonyl-4-methylphenyl)-N4-[4-(1,3-dimethyl-(1H)-pyrazol-5-yl)methyleneoxyphenyl]-5-fluoro-2,4-pyrimidinediamine $^1$H NMR (DMSO-$d_6$): δ 9.33 (s, 1H), 9.22 (s, 1H), 8.09 (d, J=2.4 Hz, 1H), 8.03 (d, J=3.6 Hz, 1H), 7.85 (dd, J=2.1 and 8.4 Hz, 1H), 7.67 (d, J=8.7 Hz, 1H), 7.21 (s, 2H), 7.14 (d, J=8.1 Hz, 1H), 6.99 (d, J=8.7 Hz, 2H), 6.12 (s, 1H), 5.08 (s, 2H), 3.74 (s, 3H), 2.48 (s, 3H), 2.10 (s, 3H); LCMS: purity: 98%; MS (m/z): 498 (MH$^+$).

I-199: N2-(3-Aminosulfonyl-4-methylphenyl)-N4-[4-(1-benzyl-3-methyl-(1H)-pyrazol-5-yl)methyleneoxyphenyl]-5-fluoro-2,4-pyrimidinediamine $^1$H NMR (DMSO-$d_6$): δ 9.39 (s, 1H), 9.29 (s, 1H), 8.07 (d, J=2.1 Hz, 1H), 8.04 (d, J=3.9 Hz, 1H), 7.84 (dd, J=2.1 and 8.4 Hz, 1H), 7.64 (d, J=9.0 Hz, 2H), 7.33-7.22 (m, 5H), 7.18-7.11 (m, 3H), 6.90 (d, J=9.0 Hz, 2H), 6.19 (s, 1H), 5.28 (s, 2H), 5.06 (s, 2H), 2.49 (s, 3H), 2.13 (s, 3H); LCMS: purity: 98%; MS (m/z): 575 (MH$^+$).

I-197: N2-(3-Aminosulfonyl-4-methylphenyl)-5-fluoro-N4-[4-(3-methyl-(1H)-pyrazol-5-yl)methyleneoxyphenyl]-2,4-pyrimidinediamine A methanol (1.0 mL) suspension of N2-(3-aminosulfonyl-4-methylphenyl)-N4-[4-(1-benzyl-3-methyl-(1H)-pyrazol-5-yl)methyleneoxyphenyl]-5-fluoro-2,4-pyrimidinediamine (63, Y=benzyl, 50 mg, 0.087 mmol), 10% Pd/C (20 mg), and 4N HCl (30 µL, 0.12 mmol) was degassed under vacuum, back-filled with hydrogen, and stirred for 24 h under a balloon of hydrogen at room temperature. The reaction mixture was then filtered through Celite, and the filter cake was washed with methanol (10 mL). Removal of methanol under vacuum gave 43 mg of N2-(3-aminosulfonyl-4-methylphenyl)-5-fluoro-N4-[4-(3-methyl-(1H)-pyrazol-5-yl)methyleneoxyphenyl]-2,4-pyrimidinediamine as an off-white solid (63, Y=H). $^1$H NMR (DMSO-$d_6$): δ 12.45 (s, 1H), 9.33 (s, 1H), 9.21 (s, 1H), 8.09 (d, J=1.5 Hz, 1H), 8.02 (d, J=3.9 Hz, 1H), 7.86 (dd, J=2.1 and 8.1 Hz, 1H), 7.66 (d, J=9.0 Hz, 2H), 7.29-7.19 (m, 2H), 7.14 (d, J=8.1 Hz, 1H), 6.96 (d, J=9.0 Hz, 2H), 6.05 (s, 1H), 4.95 (s, 2H), 2.49 (s, 3H), 2.20 (s, 3H); LCMS: purity: 95%; MS (m/z): 484 (MH$^+$).

Example 27

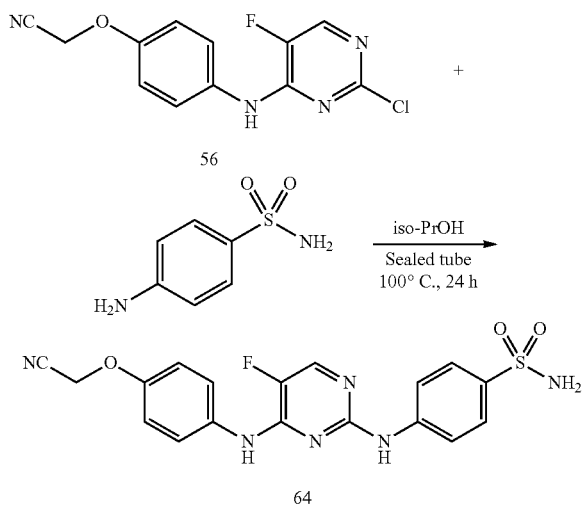

I-16: N2-(4-Aminosulfonyl)phenyl-N4-(4-cyanomethoxy)phenyl-5-fluoro-2,4-pyrimidinediamine 4-Nitrophenol (10 g), bromoacetamide (10 g) and K₂CO₃ (15 g) were suspended in acetone (30 mL). The yellow solution was stirred at rt for 3 d. The reaction mixture was diluted with water and acetone was removed under reduced pressure. The light-yellow precipitate was collected by filtration, washed with water and dried to give O-aminocarbonylmethyl-4-nitrophenol (11.5 g) as a beige solid.

O-Aminocarbonylmethyl-4-nitrophenol (5 g) was dissolved in methanol (50 mL) and to the solution was added 10% Pd—C(500 mg). The reaction mixture was reacted under hydrogen atmosphere (~40 psi) for 1 h. The catalyst was filtered off over celite. The filtrate was evaporated to give 4-(aminocarbonylmethoxy)analine as a white solid.

4-(Aminocarbonylmethoxy)analine (5 g) and 2,6-dichloro-5-fluoropyrimidine (6 g) were dissolved in methanol (10 mL) and water (1 mL). The reaction solution was stirred at rt overnight. Then methanol was removed under reduced pressure. The remaining aq. solution was acidified with 1 N HCl aq. (80 mL). The white precipitate was collected by filtration, washed with water and dried to give N4-(4-aminocarbonylmethoxy)phenyl-2-chloro-5-fluoro-4-pyrimidineamine as a solid.

N4-(4-Aminocarbonylmethoxy)phenyl-2-chloro-5-fluoro-4-pyrimidineamine (2 g) was dissolved in THF (20 mL). To this solution was added trifluoroacetic anhydride (1.9 mL) and pyridine (1.65 mL). The reaction solution was stirred at rt overnight. Then it was diluted with ethyl acetate (100 mL). The organic layer was washed with K₂CO₃ aq. (2×100 mL), 1 N HCl aq. (100 mL) and water (100 mL). The ethyl acetate layer was separated, dried and evaporated to give 2-chloro-N4-(4-cyanomethoxy)phenyl-5-fluoro-4-pyrimidineamine as a white solid.

2-Chloro-N4-(4-cyanomethoxy)phenyl-5-fluoro-4-pyrimidineamine (100 mg) and sulfanilamide (100 mg) were dissolved in isopropanol (1 mL). The solution was heated at 100° C. overnight, then diluted with methanol (5 mL) and sonicated. The precipitation was filtered off, washed with methanol and dried to give N2-(4-aminosulfonyl)phenyl-N4-(4-cyanomethoxy)phenyl-5-fluoro-2,4-pyrimidinediamine as a beige solid. $^1$H NMR (DMSO-d$_6$): δ 5.16 (s, 2H), 7.07 (d, J=9.0 Hz, 2H), 7.16 (br, 2H), 7.64 (d, J=8.7 Hz, 2H), 7.69 (d, J=9.0 Hz, 2H), 7.75 (d, J=8.7 Hz, 2H), 8.17 (d, J=4.2 Hz, 1H), 9.71 (br, 1H), 9.85 (br, 1H); $^{19}$F NMR (282 MHz, DMSO-d$_6$): δ −201.19; LCMS: purity: 95.05%; MS (m/e): 415.01 (MH⁺).

The following compounds were made in a similar fashion to the example 27.

I-17: N2-(3-Aminosulfonyl)phenyl-N4-(4-cyanomethoxy)phenyl-5-fluoro-2,4-pyrimidinediamine $^1$H NMR (DMSO-d$_6$): δ 5.16 (s, 2H), 7.06 (d, J=9.3 Hz, 2H), 7.31 (br, 2H), 7.42 (m, 2H), 7.68 (d, J=9.0 Hz, 2H), 7.87 (m, 1H), 7.94 (s, 1H), 8.19 (d, J=4.2 Hz, 1H), 9.90 (br, 1H), 9.97 (br, 1H); $^{19}$F NMR (282 MHz, DMSO-d$_6$): δ −200.94; LCMS: purity: 93.17%; MS (m/e): 415.54 (MH⁺).

I-91: N4-(3-Aminocarbonylmethoxy)phenyl-N2-(4-aminosulfonyl)phenyl-5-fluoro-2,4-pyrimidinediamine $^1$H NMR (DMSO-d$_6$): δ 4.43 (s, 2H), 6.72 (dd, J=2.1, 7.5 Hz, 1H), 7.16 (br, 2H), 7.26 (t, J=8.1 Hz, 1H), 7.36 (d, J=9.0 Hz, 1H), 7.44 (m, 2H), 7.54 (s, 1H), 7.65 (d, J=9.0 Hz, 2H), 7.79 (d, J=9.0 Hz, 2H), 8.22 (d, J=4.2 Hz, 1H), 9.82 (br, 1H), 9.91 (br, 1H); $^{19}$F NMR (282 MHz, DMSO-d$_6$): δ −200.39; LCMS: purity: 91.64%; MS (m/e): 433.00 (MH⁺).

I-88: N4-(3-Aminocarbonylmethoxy)phenyl-N2-(3-aminosulfonyl)phenyl-5-fluoro-2,4-pyrimidinediamine $^1$H NMR (DMSO-d$_6$): δ 4.41 (s, 2H), 6.66 (dd, J=2.4, 8.4 Hz, 1H), 7.23 (t, J=8.1 Hz, 1H), 7.26 (br, 2H), 7.35-7.54 (m, 6H), 7.94 (d, J=8.1 Hz, 1H), 8.09 (s, 1H), 8.16 (d, J=4.2 Hz, 1H), 9.62 (br, 2H); $^{19}$F NMR (282 MHz, DMSO-d$_6$): δ −201.09; LCMS: purity: 94.82%; MS (m/e): 433.46 (MH⁺).

I-3: N2-(4-Aminosulfonyl)phenyl-N4-(3-cyanomethoxy)phenyl-5-fluoro-2,4-pyrimidinediamine $^1$H NMR (DMSO-d$_6$): δ 5.14 (s, 2H), 6.81 (dd, J=2.7, 8.4 Hz, 1H), 7.13 (br, 2H), 7.32 (t, J=8.1 Hz, 1H), 7.49 (t, J=2.1 Hz, 1H), 7.54 (d, J=8.1 Hz, 1H), 7.63 (d, J=8.7 Hz, 2H), 7.80 (d, J=9.0 Hz, 2H), 8.18 (d, J=3.6 Hz, 1H), 9.55 (br, 1H), 9.62 (br, 1H); $^{19}$F NMR (282 MHz, DMSO-d$_6$): δ −201.17; LCMS: purity: 93.10%; MS (m/e): 415.56 (MH⁺).

I-4: N2-(3-Aminosulfonyl)phenyl-N4-(3-cyanomethoxy)phenyl-5-fluoro-2,4-pyrimidinediamine $^1$H NMR (DMSO-d$_6$): δ 5.14 (s, 2H), 6.81 (dd, J=2.4, 8.4 Hz, 1H), 7.29 (br, 2H), 7.32 (t, J=8.1 Hz, 1H), 7.40 (m, 2H), 7.52 (m, 2H), 7.92 (m, 1H), 8.01 (s, 1H), 8.20 (d, J=4.2 Hz, 1H), 9.78 (br, 2H); $^{19}$F NMR (282 MHz, DMSO-d$_6$): δ −200.81; LCMS: purity: 88.73%; MS (m/e): 415.58 (MH⁺).

III-3: N2-(4-Aminosulfonyl)phenyl-N4-(4-cyanomethyl)phenyl-5-fluoro-2,4-pyrimidinediamine $^1$H NMR (DMSO-d$_6$): δ 4.01 (s, 2H), 7.15 (br, 2H), 7.32 (d, J=9.0 Hz, 2H), 7.65 (d, J=8.7 Hz, 2H), 7.78 (d, J=8.7 Hz, 2H), 7.78 (d, J=9.0 Hz, 2H), 8.19 (d, J=3.6 Hz, 1H), 9.70 (br, 1H), 9.78 (br, 1H); $^{19}$F NMR (282 MHz, DMSO-d$_6$): δ −200.85; LCMS: purity: 89.03%; MS (m/e): 399.54 (MH$^+$).

III-4: N2-(3-Aminosulfonyl)phenyl-N4-(4-cyanomethyl)phenyl-5-fluoro-2,4-pyrimidinediamine $^1$H NMR (DMSO-d$_6$): δ 4.00 (s, 2H), 7.29 (br, 2H), 7.30 (d, J=8.4 Hz, 2H), 7.39 (m, 2H), 7.78 (d, J=8.1 Hz, 2H), 7.89 (m, 1H), 8.02 (s, 1H), 8.18 (d, J=3.9 Hz, 1H), 9.80 (br, 2H); $^{19}$F NMR (282 MHz, DMSO-d$_6$): δ −201.02; LCMS: purity: 98.20%; MS (m/e): 399.53 (MH$^+$).

I-18: N4-(4-Cyanomethoxy)phenyl-5-fluoro-N2-[4-(4-methylpiperazin-1-yl)sulfonyl]phenyl-2,4-pyrimidinediamine LCMS: purity: 99.80%; MS (m/e): 498.06 (MH$^+$).

I-19: N4-(4-Cyanomethoxy)phenyl-5-fluoro-N2-[3-(4-methylpiperazin-1-yl)sulfonyl]phenyl-2,4-pyrimidinediamine $^1$H NMR (DMSO-d$_6$): δ 2.12 (s, 3H), 2.34 (t, 4H), 2.87 (t, 4H), 5.15 (s, 2H), 7.05 (d, J=9.0 Hz, 2H), 7.18 (d, J=8.1 Hz, 1H), 7.45 (t, J=8.1 Hz, 1H), 7.74 (d, J=8.7 Hz, 2H), 7.98 (s, 1H), 8.11 (d, J=7.8 Hz, 1H), 8.11 (d, J=3.6 Hz, 1H), 9.38 (br, 1H), 9.53 (br, 1H); $^{19}$F NMR (282 MHz, DMSO-d$_6$): δ −202.15; LCMS: purity: 93.41%; MS (m/e): 498.39 (MH$^+$).

I-89: N4-(3-Aminocarbonylmethoxy)phenyl-5-fluoro-N2-[3-(4-methylpiperazin-1-yl)sulfonyl]phenyl-2,4-pyrimidinediamine $^1$H NMR (DMSO-d$_6$): δ 2.12 (s, 3H), 2.34 (t, 4H), 2.88 (t, 4H), 4.42 (s, 2H), 6.66 (dd, J=2.7, 8.4 Hz, 1H), 7.18-7.25 (m, 2H), 7.41-7.56 (m, 5H), 8.10 (m, 2H), 8.15 (d, J=3.9 Hz, 1H), 9.44 (br, 1H), 9.51 (br, 1H); $^{19}$F NMR (282 MHz, DMSO-d$_6$): δ −201.35; LCMS: purity: 86.95%; MS (m/e): 516.11 (MH$^+$).

I-5: N4-(3-Cyanomethoxy)phenyl-5-fluoro-N2-[3-(4-methylpiperazin-1-yl)sulfonyl]phenyl-2,4-pyrimidinediamine $^1$H NMR (DMSO-d$_6$): δ 2.12 (s, 3H), 2.34 (t, 4H), 2.87 (t, 4H), 5.14 (s, 2H), 6.78 (dd, J=2.4, 8.1 Hz, 1H), 7.20 (d, J=8.7 Hz, 1H), 7.31 (t, J=8.1 Hz, 1H), 7.46 (t, J=8.1 Hz, 1H), 7.54 (m, 2H), 8.00 (s, 1H), 8.10 (d, J=8.4 Hz, 1H), 8.16 (d, J=3.6 Hz, 1H), 9.48 (br, 1H), 9.55 (br, 1H); $^{19}$F NMR (282 MHz, DMSO-d$_6$): δ −201.35; LCMS: purity: 91.89%; MS (m/e): 498.06 (MH$^+$).

III-5: N4-(4-Cyanomethyl)phenyl-5-fluoro-N2-[3-(4-methylpiperazin-1-yl)sulfonyl]phenyl-2,4-pyrimidinediamine $^1$H NMR (DMSO-d$_6$): δ 2.12 (s, 3H), 2.34 (t, 4H), 2.87 (t, 4H), 3.99 (s, 2H), 7.19 (d, J=7.5 Hz, 1H), 7.30 (d, J=8.7 Hz, 2H), 7.46 (t, J=8.1 Hz, 1H), 7.81 (d, J=8.4 Hz, 2H), 8.00 (s, 1H), 8.10 (dd, J=1.5, 8.1 Hz, 1H), 8.14 (d, J=3.6 Hz, 1H), 9.48 (br, 1H), 9.56 (br, 1H); $^{19}$F NMR (282 MHz, DMSO-d$_6$): δ −201.59; LCMS: purity: 93.12%; MS (m/e): 482.06 (MH$^+$).

RI-6: N4-(3-Cyanomethoxy)phenyl-5-fluoro-N2-[4-(4-methylpiperazin-1-yl)sulfonyl]phenyl-2,4-pyrimidinediamine LCMS: purity: 99.63%; MS (m/e): 498.05 (MH$^+$).

III-6: N4-(4-Cyanomethyl)phenyl-5-fluoro-N2-[4-(4-methylpiperazin-1-yl)sulfonyl]phenyl-2,4-pyrimidinediamine LCMS: purity: 96.81%; MS (m/e): 482.03 (MH$^+$).

I-115: N4-(4-Aminocarbonylmethoxy)phenyl-N2-(4-aminosulfonyl)phenyl-5-fluoro-2,4-pyrimidinediamine $^1$H NMR (DMSO-d$_6$): δ 4.43 (s, 2H), 6.95 (d, J=8.7 Hz, 2H), 7.17 (br, 2H), 7.36 (br, 1H), 7.55 (br, 1H), 7.58 (d, J=9.3 Hz, 2H), 7.62 (d, J=8.4 Hz, 2H), 7.74 (d, J=8.7 Hz, 2H), 8.16 (d, J=3.9 Hz, 1H), 9.70 (br, 1H), 9.86 (br, 1H); $^{19}$F NMR (282 MHz, DMSO-d$_6$): δ −201.26; LCMS: purity: 95.49%; MS (m/e): 433.36 (MH$^+$).

I-111: N4-(4-Aminocarbonylmethoxy)phenyl-N2-(3-aminosulfonyl)phenyl-5-fluoro-2,4-pyrimidinediamine $^1$H NMR (DMSO-d$_6$): δ 4.42 (s, 2H), 6.93 (d, J=8.7 Hz, 2H), 7.31 (br, 2H), 7.41 (m, 3H), 7.52 (br, 1H), 7.60 (d, J=8.7 Hz, 2H), 7.87 (m, 1H), 7.94 (s, 1H), 8.17 (d, J=4.2 Hz, 1H), 9.84 (br, 1H), 9.94 (br, 1H); $^{19}$F NMR (282 MHz, DMSO-d$_6$): δ −201.04; LCMS: purity: 96.23%; MS (m/e): 433.39 (MH$^+$).

I-112: N4-(4-Aminocarbonylmethoxy)phenyl-5-fluoro-N2-[3-(4-methylpiperazin-1-yl)sulfonyl]phenyl-2,4-pyrimidinediamine $^1$H NMR (DMSO-d$_6$): δ 2.12 (s, 3H), 2.34 (t, 4H), 2.86 (t, 4H), 4.41 (s, 2H), 6.92 (d, J=9.0 Hz, 2H), 7.18 (d, J=8.4 Hz, 1H), 7.38 (br, 1H), 7.43 (t, J=8.1 Hz, 1H), 7.51 (br, 1H), 7.65 (d, J=9.0 Hz, 2H), 7.97 (s, 1H), 8.08 (d, J=3.6 Hz, 1H), 8.11 (d, J=8.4 Hz, 1H), 9.30 (br, 1H), 9.50 (br, 1H); $^{19}$F NMR (282 MHz, DMSO-d$_6$): δ −202.33; LCMS: purity: 77.73%; MS (m/e): 516.44 (MH$^+$).

I-65: Racemic N2-(3-Aminosulfonyl)phenyl-N4-[4-(1-cyano)ethoxy]phenyl-5-fluoro-2,4-pyrimidinediamine $^1$H NMR (DMSO-d$_6$): δ 1.69 (d, J=6.6 Hz, 3H), 5.41 (q, J=6.6 Hz, 1H), 7.06 (d, J=9.0 Hz, 2H), 7.25 (br, 2H), 7.31-7.41 (m, 2H), 7.77 (d, J=8.7 Hz, 2H), 7.94 (d, J=8.1 Hz, 1H), 8.09 (m, 2H), 9.35 (br, 1H), 9.49 (br, 1H); $^{19}$F NMR (282 MHz, DMSO-d$_6$): δ −202.36; LCMS: purity: 91.76%; MS (m/e): 429.05 (MH$^+$).

I-66: Racemic N2-(4-Aminosulfonyl)phenyl-N4-[4-(1-cyano)ethoxy]phenyl-5-fluoro-2,4-pyrimidinediamine $^1$H NMR (DMSO-d$_6$): δ 1.70 (d, J=6.6 Hz, 3H), 5.43 (q, J=6.6 Hz, 1H), 7.09 (d, J=9.0 Hz, 2H), 7.13 (br, 2H), 7.63 (d, J=8.7 Hz, 2H), 7.71 (d, J=9.0 Hz, 2H), 7.77 (d, J=8.7 Hz, 2H), 8.16 (d, J=3.9 Hz, 1H), 9.61 (br, 1H), 9.76 (br, 1H); $^{19}$F NMR (282 MHz, DMSO-d$_6$): δ −201.42; LCMS: purity: 96.39%; MS (m/e): 429.39 (MH$^+$).

I-116: Racemic N4-[4-(1-Aminocarbonyl)ethoxy]phenyl-N2-(4-aminosulfonyl)phenyl-5-fluoro-2,4-pyrimidinediamine $^1$H NMR (DMSO-d$_6$): δ 1.46 (d, J=6.6 Hz, 3H), 4.63 (q, J=6.6 Hz, 1H), 6.92 (d, J=9.0 Hz, 2H), 7.19 (br, 3H), 7.57 (d, J=7.8 Hz, 2H), 7.58 (br, 1H), 7.63 (d, J=9.0 Hz, 2H), 7.73 (d, J=7.5 Hz, 2H), 8.17 (d, J=4.2 Hz, 1H), 9.76 (br, 1H), 9.93 (br, 1H); $^{19}$F NMR (282 MHz, DMSO-d$_6$): δ −201.11; LCMS: purity: 94.25%; MS (m/e): 447.40 (MH$^+$).

I-117: Racemic N4-[4-(1-Aminocarbonyl)ethoxy]phenyl-N2-(3-aminosulfonyl)phenyl-5-fluoro-2,4-pyrimidinediamine $^1$H NMR (DMSO-d$_6$): δ 1.44 (d, J=6.6 Hz, 3H), 4.60 (q, J=6.6 Hz, 1H), 6.89 (d, J=8.7 Hz, 2H), 7.25 (br, 1H), 7.31 (br, 2H), 7.42 (m, 2H), 7.51 (br, 1H), 7.59 (d, J=8.7 Hz, 2H), 7.88 (m, 1H), 7.95 (s, 1H), 8.16 (d, J=4.5 Hz, 1H), 9.79 (br, 1H), 9.89 (br, 1H); $^{19}$F NMR (282 MHz, DMSO-d$_6$): δ 201.17; LCMS: purity: 95.18%; MS (m/e): 447.44 (MH$^+$).

I-125: N4-[4-(1-Aminocarbonyl-1-methyl)ethoxy]phenyl-N2-(4-aminosulfonyl)phenyl-5-fluoro-2,4-pyrimidinediamine $^1$H NMR (DMSO-d$_6$): δ 1.43 (s, 6H), 6.91 (d, J=8.7 Hz, 2H), 7.16 (br, 2H), 7.22 (br, 1H), 7.57 (br, 1H), 7.59 (d, J=8.7 Hz, 2H), 7.62 (d, J=9.9 Hz, 2H), 7.74 (d, J=8.4 Hz, 2H), 8.17 (d, J=4.9 Hz, 1H), 9.72 (br, 1H), 9.89 (br, 1H); $^{19}$F NMR (282 MHz, DMSO-d$_6$): δ −201.14; LCMS: purity: 98.31%; MS (m/e): 461.33 (MH$^+$).

I-21: N2-(3-Aminosulfonyl-4-chlorophenyl)-N4-(4-cyanomethoxy)phenyl-5-fluoro-2,4-pyrimidinediamine $^1$H NMR (DMSO-d$_6$): δ 5.16 (s, 2H), 7.06 (d, J=8.4 Hz, 2H), 7.42 (d, J=8.1 Hz, 1H), 7.47 (br, 2H), 7.74 (d, J=9.0 Hz, 2H), 8.02 (d, J=8.7 Hz, 1H), 8.10 (d, J=2.4 Hz, 1H), 8.26 (s, 1H), 9.42 (br, 1H), 9.63 (br, 1H); $^{19}$F NMR (282 MHz, DMSO-d$_6$): δ −201.94; LCMS: purity: 96.69%; MS (m/e): 449.34 (MH$^+$).

III-7: N2-(3-Aminosulfonyl-4-methyl)phenyl-N4-(4-cyanomethyl)phenyl-5-fluoro-2,4-pyrimidinediamine $^1$H NMR (DMSO-d$_6$): δ 2.51 (s, 3H), 4.00 (s, 2H), 7.21 (d, J=8.1 Hz, 1H), 7.29 (br, 2H), 7.30 (d, J=8.4 Hz, 2H), 7.76 (d, J=8.4 Hz, 2H), 7.81 (dd, J=2.1, 8.4 Hz, 1H), 8.01 (s, 1H), 8.16 (d, J=4.5 Hz, 1H), 9.75 (br s, 1H), 9.82 (br s, 1H); $^{19}$F NMR (282 MHz, DMSO-d$_6$): δ −201.31; LCMS: purity: 96.68%; MS (m/e): 413.66 (MH$^+$).

III-8: N2-(3-Aminosulfonyl-4-chloro)phenyl-N4-(4-cyanomethyl)phenyl-5-fluoro-2,4-pyrimidinediamine $^1$H NMR (DMSO-d$_6$): δ 4.01 (s, 2H), 7.32 (d, J=7.8 Hz, 2H), 7.44 (d, J=8.7 Hz, 1H), 7.49 (br, 2H), 7.79 (d, J=7.8 Hz, 2H), 8.00 (d, J=8.7 Hz, 1H), 8.16 (d, J=3.9 Hz, 1H), 8.24 (s, 1H), 9.68 (br s, 1H), 9.79 (br s, 1H); $^{19}$F NMR (282 MHz, DMSO-d$_6$): δ −201.00; LCMS: purity: 90.19%; MS (m/e): 433.00 (MH$^+$).

I-75: N2-(4-Aminosulfonyl)phenyl-N4-[4-(1-cyano-1-methyl)ethoxy]phenyl-5-fluoro-2,4-pyrimidinediamine $^1$H NMR (DMSO-d$_6$): δ 1.70 (s, 6H), 7.14 (br, 2H), 7.16 (d, J=9.0 Hz, 2H), 7.63 (d, J=8.4 Hz, 2H), 7.78 (d, J=9.0 Hz, 2H), 7.79 (d, J=8.7 Hz, 2H), 8.18 (d, J=3.9 Hz, 1H), 9.63 (br s, 1H), 9.74 (br s, 1H); $^{19}$F NMR (282 MHz, DMSO-d$_6$): δ −201.30; LCMS: purity: 94.43%; MS (m/e): 443.64 (MH$^+$).

I-274: 5-Fluoro-N4-[4-(5-methyl-1,2,4-oxadiazol-3-yl)methoxy]phenyl-N2-[3-(4-methylpiperazin-1-yl)sulfonyl]phenyl-2,4-pyrimidinediamine 4-Nitrophenol (10 g), bromoacetonitrile (6 mL) and K$_2$CO$_3$ (15 g) were suspended in acetone (100 mL). The yellow solution was stirred at rt overnight. The reaction mixture was diluted with water (100 mL) and acetone was removed under reduced pressure. The light-yellow precipitate was collected by filtration, washed with water and dried to give O-cyanomethyl-4-nitrophenol.

O-Cyanomethyl-4-nitrophenol (8 g) was dissolved in methanol (50 mL) and to the solution was added hydroxyamine HCl (3.4 g) and triethylamine (9.4 mL). The reaction mixture was refluxed for 4 d and the solvent was removed under reduced pressure. The residue was redissolved in THF (50 mL). To the solution was added AcCl (23 mL) and triethylamine (50 mL). The reaction mixture was stirred at rt overnight, then added water (30 mL) and NaOH (18 g). The reaction solution was refluxed overnight, then diluted with water (200 mL). The aq. solution was extracted with EtOAc (2×150 mL). After separation, the combined EtOAc layers were dried, evaporated. The residue was purified by flash column chromatography (EtOAc/hexanes=1/2, 1/1, EtOAc) and recrystallized from EtOAc and hexanes to give O-(5-methyl-1,2,4-oxadiazol-3-yl)methyl-4-nitrophenol.

O-(5-Methyl-1,2,4-oxadiazol-3-yl)methyl-4-nitrophenol (1 g) was dissolved in THF (40 mL) and water (40 mL). Sodium bisulfite (3.8 g), sodium bicarbonate (1.4 g), K$_2$CO$_3$ (1.8 g) were added to the solution. It was stirred at rt for 30 min, then diluted with water (80 mL). The aq. solution was extracted with EtOAc (2×100 mL). The organic layers were combined, dried, evaporated to give 4-(5-methyl-1,2,4-oxadiazol-3-yl)methoxyaniline 4-(5-Methyl-1,2,4-oxadiazol-3-yl)methoxyaniline and 2,6-dichloro-5-fluoropyrimidine (1 g) were dissolved in methanol (5 mL) and water (1 mL). The reaction solution was stirred at rt for 3d. Then solution was diluted with water (100 mL) and extracted with ethyl acetate (2×100 mL). The organic layers were evaporated to give 2-chloro-5-fluoro-N4-[4-(5-methyl-1,2,4-oxadiazol-3-yl)methoxy]phenyl-4-pyrimidineamine.

2-Chloro-5-fluoro-N4-[4-(5-methyl-1,2,4-oxadiazol-3-yl)methoxy]phenyl-4-pyrimidineamine (80 mg) and [3-(4-methylpiperazin-1-yl)sulfonyl]aniline (80 mg) were dissolved in isopropanol (1 mL) and TFA was added (5 drops). The solution was heated at 100° C. overnight, then evaporated. The residue was purified by flash column chromatography (2.0 M NH3/methanol in DCM=1-3%) and recrystallized from ethyl acetate and hexanes to give 5-fluoro-N4-[4-(5-methyl-1,2,4-oxadiazol-3-yl)methoxy]phenyl-N2-[3-(4-methylpiperazin-1-yl)sulfonyl]phenyl-2,4-pyrimidinediamine $^1$H NMR (DMSO-d$_6$): δ 2.12 (s, 3H), 2.35 (t, 4H), 2.61 (s, 3H), 2.87 (t, 4H), 5.22 (s, 2H), 7.01 (d, J=9.3 Hz, 2H), 7.18 (d, J=8.4 Hz, 1H), 7.43 (t, J=8.1 Hz, 1H), 7.68 (d, J=9.0 Hz, 2H), 7.98 (s, 1H), 8.10 (m, 2H), 9.32

(br, 1H), 9.51 (br, 1H); $^{19}$F NMR (282 MHz, DMSO-d$_6$): δ −202.24; LCMS: purity: 76.41%; MS (m/e): 555.37 (MH$^+$).

The following compounds were made in a similar fashion as described above.

I-275: N2-(4-Aminosulfonyl)phenyl-5-fluoro-N4-[4-(5-methyl-1,2,4-oxadiazol-3-yl)methoxy]phenyl-2,4-pyrimidinediamine LCMS: purity: 87.52%; MS (m/e): 472.33 (MH$^+$).

I-276: N2-(3-Aminosulfonyl)phenyl-5-fluoro-N4-[4-(5-methyl-1,2,4-oxadiazol-3-yl)methoxy]phenyl-2,4-pyrimidinediamine LCMS: purity: 84.90%; MS (m/e): 472.31 (MH$^+$).

I-20: N2-(3-Aminosulfonyl-4-methyl)phenyl-N4-(4-cyanomethoxy)phenyl-5-fluoro-2,4-pyrimidinediamine 2-Chloro-N4-(4-cyanomethoxy)phenyl-5-fluoro-4-pyrimidineamine (1 g) and 2-methyl-5-aminobenzenesulphonamide (1 g) were dissolved in isopropanol (10 mL) and TFA (10 drops). The solution was heated at 100° C. overnight, then diluted with DMF (30 mL). The solution was heated to 50° C. and added water until slightly cloudy. The solution was slowly cooled to rt. The beige precipitation was filtered off, washed with water and dried. The solid was resuspended in methanol and sonicated. The solid was filtered off, washed with methanol and dried to give N2-(3-aminosulfonyl-4-methyl)phenyl-N4-(4-cyanomethoxy)phenyl-5-fluoro-2,4-pyrimidinediamine (1.3 g). $^1$H NMR (DMSO-d$_6$): δ 2.50 (s, 3H), 5.16 (s, 2H), 7.05 (d, J=9.0 Hz, 2H), 7.20 (d, J=8.4 Hz, 1H), 7.26 (br, 2H), 7.72 (d, J=9.0 Hz, 2H), 7.85 (d, J=8.7 Hz, 1H), 8.03 (s, 1H), 8.96 (d, J=3.0 Hz, 1H), 9.56 (br, 2H); $^{19}$F NMR (282 MHz, DMSO-d6): δ −202.34; LCMS: purity: 95.79%; MS (m/e): 429.51 (MH$^+$).

I-76 945941: N2-(3-Aminosulfonyl)phenyl-N4-[4-(1-cyano-1-methyl)ethoxy]phenyl-5-fluoro-2,4-pyrimidinediamine 4-Nitrophenol (5 g), methyl 2-bromoisobutyrate (5.6 mL) and K$_2$CO$_3$ (7.5 g) were suspended in acetone (60 mL). The yellow solution was refluxed overnight. The reaction mixture was diluted with water (150 mL) and extracted with ethyl acetate (2×100 mL). The organic layers were evaporated to give methyl 2-(4-nitrophenoxy)isobutyrate.

Methyl 2-(4-nitrophenoxy)isobutyrate was dissolved in methanol (50 mL) and water (50 mL). Sodium hydroxide (5 g) was added. The solution was stirred at rt for 30 min, then acidified with 1N HCl aq. to pH ~3. The aq. Solution was extracted with ethyl acetate (2×100 mL). The organic layers were evaporated to give 2-(4-nitrophenoxy)isobutyric acid.

2-(4-Nitrophenoxy)isobutyric acid (5 g), isobutyl chloroformate (4.36 mL) and triethylamine (8 mL) were stirred in dichloromethane (20 mL) at rt for 1 h. Then 2.0 M ammonia in methanol (20 mL) was added to the solution. It was stirred at rt for 2 h and evaporated. The mixture was purified by recrystallization from EtOAc and hexanes to give 2-(4-nitrophenoxy)-2-methylpropanamide.

2-(4-Nitrophenoxy)-2-methylpropanamide was dissolved in methanol (50 mL) and to the solution was added 10% Pd—C(500 mg). The reaction mixture was reacted under hydrogen atmosphere (~40 psi) for 1 h. The catalyst was filtered off over celite. The filtrate was evaporated to give 2-(4-aminophenoxy)-2-methylpropanamide as a white solid.

2-(4-Aminophenoxy)-2-methylpropanamide and 2,6-dichloro-5-fluoropyrimidine (2 g) were dissolved in methanol (20 mL) and water (10 mL). The reaction solution was stirred at rt overnight. The solution was diluted with water (100 mL) and sonicated. The white precipitate was collected by filtration, washed with water and dried to give N4-[4-(1-aminocarbonyl-1-methyl)ethoxy]phenyl-2-chloro-5-fluoro-4-pyrimidineamine as a solid.

N4-[4-(1-Aminocarbonyl-1-methyl)ethoxy]phenyl-2-chloro-5-fluoro-4-pyrimidine amine (900 mg) was dissolved in THF (20 mL). To this solution was added trifluoroacetic anhydride (0.8 mL) and pyridine (0.7 mL). The reaction solution was stirred at rt overnight. Then it was diluted with ethyl acetate (100 mL). The organic layer was washed with K$_2$CO$_3$ aq. (2×100 mL), 1 N HCl aq. (100 mL) and water (2×100 mL). The ethyl acetate layer was separated, dried and evaporated to give 2-chloro-N4-[4-(1-cyano-1-methyl)ethoxy]phenyl-5-fluoro-4-pyrimidineamine as a white solid.

2-Chloro-N4-[4-(1-cyano-1-methyl)ethoxy]phenyl-5-fluoro-4-pyrimidineamine (100 mg) and 3-aminobenzenesulfonamide (100 mg) were dissolved in isopropanol (1 mL) and TFA (5 drops). The solution was heated at 100° C. overnight, then diluted with methanol (3 mL) and sonicated. The precipitation was filtered off, washed with methanol and dried to give N2-(3-aminosulfonyl)phenyl-N4-[4-(1-cyano-1-methyl)ethoxy]phenyl-5-fluoro-2,4-pyrimidinediamine as a beige solid. $^1$H NMR (DMSO-d$_6$): δ 1.69 (s, 6H), 7.13 (d, J=7.5 Hz, 2H), 7.29 (br, 2H), 7.38 (m, 2H), 7.80 (d, J=8.1 Hz, 2H), 7.91 (d, J=6.6 Hz, 1H), 8.02 (s, 1H), 8.16 (d, J=2.1 Hz, 1H), 9.70 (br, 1H), 9.75 (br, 1H); $^{19}$F NMR (282 MHz, DMSO-d$_6$): δ −201.30; LCMS: purity: 81.69%; MS (m/e): 443.02 (MH$^+$).

The following compounds were made in a similar fashion to the previous example or by methods described herein or know to skilled artisans.

I-126: N4-[4-(1-Aminocarbonyl-1-methy)ethoxy]phenyl-N2-(3-aminosulfonyl)phenyl-5-fluoro-2,4-pyrimidinediamine $^1$H NMR (DMSO-d$_6$): δ 1.41 (s, 6H), 6.88 (d, J=9.3 Hz, 2H), 7.25 (br, 2H), 7.34 (m, 3H), 7.53 (br, 1H), 7.69 (d, J=9.0 Hz, 2H), 7.95 (d, J=7.2 Hz, 1H), 8.07 (d, J=3.9 Hz, 1H), 8.09 (s, 1H), 9.29 (br, 1H), 9.47 (br, 1H); $^{19}$F NMR (282 MHz, DMSO-d$_6$): δ −202.34; LCMS: purity: 95.58%; MS (m/e): 461.31 (MH$^+$).

I-73: N2-(3-Aminosulfonyl-4-methyl)phenyl-N4-[4-(1-cyano-1-methyl)ethoxy]phenyl-5-fluoro-2,4-pyrimidinediamine $^1$H NMR (DMSO-d$_6$): δ 1.69 (s, 6H), 2.49 (s, 3H), 7.12 (d, J=9.0 Hz, 2H), 7.18 (d, J=8.4 Hz, 1H), 7.24 (br, 2H), 7.83 (d, J=9.0 Hz, 2H), 7.91 (d, J=8.1 Hz, 1H), 8.08 (s, 1H), 8.08 (d, J=2.7 Hz, 1H), 9.39 (br, 1H), 9.42 (br, 1H); $^{19}$F NMR (282 MHz, DMSO-d$_6$): δ −202.64; LCMS: purity: 97.27%; MS (m/e): 457.14 (MH$^+$).

I-67: Racemic N2-(3-Aminosulfonyl-4-methyl)phenyl-N4-[4-(1-cyano)ethoxy]phenyl-5-fluoro-2,4-pyrimidinediamine $^1$H NMR (DMSO-d$_6$): δ 1.70 (d, J=6.6 Hz, 3H), 2.48 (s, 3H), 5.41 (q, J=6.6 Hz, 1H), 7.05 (d, J=9.0 Hz, 2H), 7.17 (d, J=8.7 Hz, 1H), 7.22 (br, 2H), 7.76 (d, J=9.0 Hz, 2H), 7.89

(dd, J=2.4, 8.4 Hz, 1H), 8.07 (m, 2H), 9.32 (br, 1H), 9.39 (br, 1H); $^{19}$F NMR (282 MHz, DMSO-d$_6$): δ −202.64; LCMS: purity: 95.10%; MS (m/e): 443.46 (MH$^+$).

I-22: N2-(4-Aminosulfonyl)phenyl-N4-(4-cyanomethoxy-3-methyl)phenyl-5-fluoro-2,4-pyrimidinediamine $^1$H NMR (DMSO-d$_6$): δ 2.20 (s, 3H), 5.16 (s, 2H), 7.05 (d, J=9.0 Hz, 1H), 7.10 (br, 2H), 7.50 (dd, J=2.7, 8.7 Hz, 1H), 7.58 (d, J=2.7 Hz, 1H), 7.60 (d, J=8.7 Hz, 2H), 7.79 (d, J=8.4 Hz, 2H), 8.11 (d, J=3.3 Hz, 1H), 9.33 (br, 1H), 9.58 (br, 1H); $^{19}$F NMR (282 MHz, DMSO-d$_6$): δ −202.06; LCMS: purity: 95.53%; MS (m/e): 429.51 (MH$^+$).

I-23: N2-(3-Aminosulfonyl)phenyl-N4-(4-cyanomethoxy-3-methyl)phenyl-5-fluoro-2,4-pyrimidinediamine $^1$H NMR (DMSO-d$_6$): δ 2.17 (s, 3H), 5.17 (s, 2H), 7.07 (d, J=9.0 Hz, 1H), 7.30 (br, 2H), 7.40 (d, J=5.4 Hz, 2H), 7.51 (s, 1H), 7.55 (dd, J=2.7, 8.7 Hz, 1H), 7.93 (m, 2H), 8.17 (d, J=4.5 Hz, 1H), 9.80 (br, 1H), 9.92 (br, 1H); $^{19}$F NMR (282 MHz, DMSO-d$_6$): δ −201.02; LCMS: purity: 98.05%; MS (m/e): 429.64 (MH$^+$).

I-24: N2-(3-Aminosulfonyl-4-methyl)phenyl-N4-(4-cyanomethoxy-3-methyl)phenyl-5-fluoro-2,4-pyrimidinediamine $^1$H NMR (DMSO-d$_6$): δ 2.17 (s, 3H), 2.49 (s, 3H), 5.16 (s, 2H), 7.05 (d, J=8.7 Hz, 1H), 7.17 (d, J=8.4 Hz, 1H), 7.25 (br, 2H), 7.52 (d, J=2.1 Hz, 1H), 7.57 (d, J=8.7 Hz, 1H), 7.87 (dd, J=2.4, 8.4 Hz, 1H), 7.98 (s, 1H), 8.08 (d, J=3.9 Hz, 1H), 9.49 (br, 1H), 9.56 (br, 1H); $^{19}$F NMR (282 MHz, DMSO-d$_6$): δ −202.28; LCMS: purity: 96.81%; MS (m/e): 443.75 (MH$^+$).

I-113: N4-(4-Aminocarbonylmethoxy-3-methyl)phenyl-N2-(4-aminosulfonyl)phenyl-5-fluoro-2,4-pyrimidinediamine $^1$H NMR (DMSO-d$_6$): δ 2.24 (s, 3H), 4.45 (s, 2H), 6.81 (d, J=9.0 Hz, 1H), 7.16 (br, 2H), 7.36 (br, 2H), 7.38 (dd, J=2.1, 8.4 Hz, 1H), 7.46 (d, J=2.7 Hz, 1H), 7.62 (d, J=8.7 Hz, 2H), 7.74 (d, J=9.0 Hz, 2H), 8.15 (d, J=4.2 Hz, 1H), 9.66 (br, 1H), 9.88 (br, 1H); $^{19}$F NMR (282 MHz, DMSO-d$_6$): δ 201.17; LCMS: purity: 82.30%; MS (m/e): 447.04 (MH$^+$).

I-92: N4-(4-Aminocarbonylmethoxy-3-methyl)phenyl-N2-(3-aminosulfonyl)phenyl-5-fluoro-2,4-pyrimidinediamine $^1$H NMR (DMSO-d$_6$): δ 2.22 (s, 3H), 4.43 (s, 2H), 6.80 (d, J=8.4 Hz, 1H), 7.28 (br, 2H), 7.39 (m, 4H), 7.45 (br, 1H), 7.47 (dd, J=2.4 Hz, 1H), 7.94 (m, 2H), 8.12 (d, J=4.2 Hz, 1H), 9.62 (br, 1H), 9.78 (br, 1H); $^{19}$F NMR (282 MHz, DMSO-d$_6$): δ −201.45; LCMS: purity: 92.52%; MS (m/e): 447.44 (MH$^+$).

I-114: N4-(4-Aminocarbonylmethoxy-3,5-dimethyl)phenyl-N2-(4-aminosulfonyl)phenyl-5-fluoro-2,4-pyrimidinediamine $^1$H NMR (DMSO-d$_6$): δ 2.24 (s, 6H), 4.14 (s, 2H), 7.17 (br, 2H), 7.34 (s, 2H), 7.48 (br, 1H), 7.59 (br, 1H), 7.62 (d, J=9.0 Hz, 2H), 7.76 (d, J=8.7 Hz, 2H), 8.16 (d, J=3.9 Hz, 1H), 9.53 (br, 1H), 9.81 (br, 1H); $^{19}$F NMR (282 MHz, DMSO-d$_6$): δ −201.12; LCMS: purity: 93.05%; MS (m/e): 461.43 (MH$^+$).

I-93: N4-(4-Aminocarbonylmethoxy-3,5-dimethyl)phenyl-N2-(3-aminosulfonyl)phenyl-5-fluoro-2,4-pyrimidinediamine $^1$H NMR (DMSO-d$_6$): δ 2.23 (s, 6H), 4.13 (s, 2H), 7.25 (s, 2H), 7.33-7.40 (m, 4H), 7.47 (br, 1H), 7.59 (br, 1H), 7.99 (s, 1H), 8.04 (d, J=7.2 Hz, 1H), 8.08 (d, J=3.9 Hz, 1H), 9.19 (br, 1H), 9.48 (br, 1H); $^{19}$F NMR (282 MHz, DMSO-d$_6$): δ −202.22; LCMS: purity: 73.18%; MS (m/e): 461.58 (MH$^+$).

I-25: N2-(4-Aminosulfonyl)phenyl-N4-(4-cyanomethoxy-3,5-dimethyl)phenyl-5-fluoro-2,4-pyrimidinediamine $^1$H NMR (DMSO-d$_6$): δ 2.26 (s, 6H), 4.91 (s, 2H), 7.17 (br, 2H), 7.38 (s, 2H), 7.63 (d, J=8.7 Hz, 2H), 7.73 (d, J=8.7 Hz, 2H), 8.20 (d, J=4.2 Hz, 1H), 9.70 (br, 1H), 9.96 (br, 1H); $^{19}$F NMR (282 MHz, DMSO-d$_6$): δ −200.66; LCMS: purity: 96.84%; MS (m/e): 443.05 (MH$^+$).

I-26: N2-(3-Aminosulfonyl)phenyl-N4-(4-cyanomethoxy-3,5-dimethyl)phenyl-5-fluoro-2,4-pyrimidinediamine $^1$H NMR (DMSO-d$_6$): δ 2.26 (s, 6H), 4.90 (s, 2H), 7.25 (s, 2H), 7.32 (d, J=8.4 Hz, 1H), 7.37 (t, J=7.8 Hz, 1H), 7.44 (s, 2H), 7.99 (s, 1H), 8.04 (d, J=7.8 Hz, 1H), 8.09 (d, J=3.6 Hz, 1H), 9.25 (br, 1H), 9.50 (br, 1H); $^{19}$F NMR (282 MHz, DMSO-d$_6$): δ −202.11; LCMS: purity: 93.34%; MS (m/e): 443.04 (MH$^+$).

I-27: N2-(3-Aminosulfonyl-4-methyl)phenyl-N4-(4-cyanomethoxy-3,5-dimethyl)phenyl-5-fluoro-2,4-pyrimidinediamine $^1$H NMR (DMSO-d$_6$): δ 2.25 (s, 6H), 2.49 (s, 3H), 4.90 (s, 2H), 7.16 (d, J=8.1 Hz, 1H), 7.22 (s, 2H), 7.43 (s, 2H), 7.94 (dd, J=2.1, 8.1 Hz, 1H), 8.01 (d, J=2.4 Hz, 1H), 8.06 (d, J=3.6 Hz, 1H), 9.21 (br, 1H), 9.38 (br, 1H); $^{19}$F NMR (282 MHz, DMSO-d$_6$): δ −217.5; LCMS: purity: 96.48%; MS (m/e): 457.39 (MH$^+$).

I-28: N2-(4-Aminosulfonyl-3-methoxyphenyl)-N4-(4-cyanomethoxy)phenyl-5-fluoro-2,4-pyrimidinediamine $^1$H NMR (DMSO-d$_6$): δ 3.67 (s, 3H), 5.14 (s, 2H), 6.80 (s, 2H), 7.04 (d, J=9.0 Hz, 2H), 7.37 (m, 1H), 7.51 (m, 2H), 7.70 (d, J=9.3 Hz, 2H), 8.12 (d, 1H), 9.40 (br, 1H), 9.52 (br, 1H); $^{19}$F NMR (282 MHz, DMSO-d$_6$): δ −201.82; LCMS: purity: 89.30%; MS (m/e): 445.37 (MH$^+$).

III-9: N2-(4-Aminosulfonyl-3-methoxy)phenyl-N4-(4-cyanomethyl)phenyl-5-fluoro-2,4-pyrimidinediamine $^1$H NMR (DMSO-d$_6$): δ 3.70 (s, 3H), 4.00 (s, 2H), 6.82 (s, 2H), 7.30 (d, J=8.7 Hz, 2H), 7.39 (d, J=8.7 Hz, 1H), 7.52 (m, 2H), 7.78 (d, J=8.4 Hz, 2H), 8.17 (d, J=3.0 Hz, 1H), 9.51 (br, 1H), 9.56 (br, 1H); $^{19}$F NMR (282 MHz, DMSO-d$_6$): δ −201.21; LCMS: purity: 89.37%; MS (m/e): 429.14 (MH$^+$).

I-70: Racemic N2-(4-Aminosulfonyl-3-methoxy) phenyl-N4-[4-(1-cyano)ethoxy]phenyl-5-fluoro-2,4-pyrimidinediamine $^1$H NMR (DMSO-d$_6$): δ 3.69 (s, 3H), 5.41 (q, J=6.6 Hz, 1H), 6.80 (s, 2H), 7.06 (d, J=8.7 Hz, 2H), 7.37 (d, J=8.7 Hz, 1H), 7.50 (m, 2H), 7.72 (d, J=9.0 Hz, 2H), 8.13 (d, J=3.3 Hz, 1H), 9.41 (br, 1H), 9.53 (br, 1H); $^{19}$F NMR (282 MHz, DMSO-d$_6$): δ −201.75; LCMS: purity: 93.14%; MS (m/e): 459.17 (MH$^+$).

I-60: Racemic N2-(4-Aminosulfonyl)phenyl-N4-[4-(1-cyano)ethoxy-3-methyl]phenyl-5-fluoro-2,4-pyrimidinediamine $^1$H NMR (DMSO-d$_6$): δ 1.72 (d, J=6.6 Hz, 3H), 2.20 (s, 3H), 5.37 (q, J=6.6 Hz, 1H), 7.11 (d, J=8.7 Hz, 1H), 7.13 (br, 2H), 7.48 (dd, J=2.7, 8.4 Hz, 1H), 7.58 (d, J=2.7 Hz, 1H), 7.63 (d, J=9.0 Hz, 2H), 7.74 (d, J=8.7 Hz, 2H), 8.18 (d, J=4.2 Hz, 1H), 9.70 (br, 1H), 9.90 (br, 1H); $^{19}$F NMR (282 MHz, DMSO-d$_6$): δ −200.99; LCMS: purity: 97.08%; MS (m/e): 443.15 (MH$^+$).

I-61: Racemic N2-(3-Aminosulfonyl)phenyl-N4-[4-(1-cyano)ethoxy-3-methyl]phenyl-5-fluoro-2,4-pyrimidinediamine $^1$H NMR (DMSO-d$_6$): δ 1.72 (d, J=6.6 Hz, 3H), 2.18 (s, 3H), 5.36 (q, J=6.6 Hz, 1H), 7.10 (d, J=8.4 Hz, 1H), 7.29 (br, 2H), 7.40 (d, J=5.1 Hz, 2H), 7.53 (s, 1H), 7.56 (dd, J=2.1, 9.0 Hz, 1H), 7.94 (m, 2H), 8.17 (d, J=3.9 Hz, 1H), 9.75 (br, 1H), 9.89 (br, 1H); $^{19}$F NMR (282 MHz, DMSO-d$_6$): δ 201.06; LCMS: purity: 95.36%; MS (m/e): 443.64 (MH$^+$).

I-62: Racemic N2-(3-Aminosulfonyl-4-methyl)phenyl-N4-[4-(1-cyano)ethoxy-3-methyl]phenyl-5-fluoro-2,4-pyrimidinediamine $^1$H NMR (DMSO-d$_6$): δ 1.72 (d, J=6.6 Hz, 3H), 2.16 (s, 3H), 2.50 (s, 3H), 5.36 (q, J=6.6 Hz, 1H), 7.10 (d, J=8.7 Hz, 1H), 7.21 (d, J=8.4 Hz, 1H), 7.29 (br, 2H), 7.50 (s, 1H), 7.54 (d, J=8.7 Hz, 1H), 7.82 (dd, J=2.1, 8.1 Hz, 1H), 7.90 (d, 1H), 8.16 (d, J=4.5 Hz, 1H), 9.89 (br, 2H); $^{19}$F NMR (282 MHz, DMSO-d$_6$): δ −201.19; LCMS: purity: 93.72%; MS (m/e): 457.18 (MH$^+$).

I-94: N4-(4-Aminocarbonylmethoxy)phenyl-N2-(3-aminosulfonyl-4-methyl)phenyl-5-fluoro-2,4-pyrimidinediamine $^1$H NMR (DMSO-d$_6$): δ 2.49 (s, 3H), 4.40 (s, 2H), 6.91 (d, J=9.0 Hz, 2H), 7.15 (d, J=8.7 Hz, 1H), 7.22 (s, 2H), 7.38 (br, 1H), 7.51 (br, 1H), 7.67 (d, J=9.0 Hz, 2H), 7.87 (d, J=6.6 Hz, 1H), 8.03 (d, J=3.9 Hz, 1H), 8.09 (s, 1H), 9.23 (br, 1H), 9.35 (br, 1H); $^{19}$F NMR (282 MHz, DMSO-d$_6$): δ 203.07; LCMS: purity: 62.07%; MS (m/e): 447.05 (MH$^+$).

I-90: N4-(3-Aminocarbonylmethoxy)phenyl-N2-(3-aminosulfonyl-4-methyl)phenyl-5-fluoro-2,4-pyrimidinediamine $^1$H NMR (DMSO-d$_6$): δ 2.49 (s, 3H), 4.42 (s, 2H), 6.64 (dd, J=2.7, 8.4 Hz, 1H), 7.22 (m, 4H), 7.43 (m, 2H), 7.49 (s, 1H), 7.58 (s, 1H), 7.91 (dd, J=1.8, 8.7 Hz, 1H), 8.09 (d, J=3.0 Hz, 1H), 8.16 (d, J=1.8 Hz, 1H), 9.34 (br, 1H), 9.36 (br, 1H); $^{19}$F NMR (282 MHz, DMSO-d$_6$): δ −202.17; LCMS: purity: 83.29%; MS (m/e): 447.13 (MH$^+$).

I-118: N4-[4-(1-Aminocarbonyl)ethoxy]phenyl-N2-(3-aminosulfonyl-4-methyl)phenyl-5-fluoro-2,4-pyrimidinediamine $^1$H NMR (DMSO-d$_6$): δ 1.44 (d, J=6.6 Hz, 3H), 2.53 (s, 3H), 4.60 (q, J=6.6 Hz, 1H), 6.88 (d, J=8.7 Hz, 2H), 7.21 (d, J=8.1 Hz, 1H), 7.24 (br, 1H), 7.30 (s, 2H), 7.51 (br, 1H), 7.57 (d, J=9.0 Hz, 2H), 7.76 (d, J=8.1 Hz, 1H), 7.92 (s, 1H), 8.15 (d, J=4.8 Hz, 1H), 9.95 (br, 2H); $^{19}$F NMR (282 MHz, DMSO-d$_6$): δ −201.03; LCMS: purity: 89.00%; MS (m/e): 461.09 (MH$^+$).

I-127: N4-[4-(1-Aminocarbonyl-1-methyl)ethoxy]phenyl-N2-(3-aminosulfonyl-4-methyl)phenyl-5-fluoro-2,4-pyrimidinediamine $^1$H NMR (DMSO-d$_6$): δ 1.41 (s, 6H), 2.49 (s, 3H), 6.88 (d, J=8.7 Hz, 2H), 7.14 (d, J=8.7 Hz, 1H), 7.22 (s, 2H), 7.24 (s, 1H), 7.52 (s, 1H), 7.69 (d, J=9.0 Hz, 2H), 7.88 (dd, J=2.4, 8.1 Hz, 1H), 8.04 (d, J=3.6 Hz, 1H), 8.09 (d, J=1.8 Hz, 1H), 9.25 (br, 1H), 9.35 (br, 1H); $^{19}$F NMR (282 MHz, DMSO-d$_6$): δ −202.91; LCMS: purity: 92.68%; MS (m/e): 475.18 (MH$^+$).

I-95: N4-(4-Aminocarbonylmethoxy-3-methyl)phenyl-N2-(3-aminosulfonyl-4-methyl)phenyl-5-fluoro-2,4-pyrimidinediamine $^1$H NMR (DMSO-d$_6$): δ 2.22 (s, 3H), 2.49 (s, 3H), 4.42 (s, 2H), 6.78 (d, J=8.7 Hz, 1H), 7.14 (d, J=8.4 Hz, 1H), 7.20 (s, 2H), 7.35 (s, 1H), 7.39 (s, 1H), 7.48 (m, 2H), 7.90 (dd, J=2.4, 8.4 Hz, 1H), 8.01 (d, J=3.6 Hz, 1H), 8.06 (d, J=2.4 Hz, 1H), 9.14 (br, 1H), 9.32 (br, 1H); $^{19}$F NMR (282 MHz, DMSO-d$_6$): δ −203.12; LCMS: purity: 93.67%; MS (m/e): 461.16 (MH$^+$).

I-119: Racemic N4-[4-(1-Aminocarbonyl)ethoxy-3-methyl]phenyl-N2-(4-aminosulfonyl)phenyl-5-fluoro-2,4-pyrimidinediamine $^1$H NMR (DMSO-d$_6$): δ 1.47 (d, J=6.6 Hz, 3H), 2.22 (s, 3H), 4.64 (q, J=6.6 Hz, 1H), 6.80 (d, J=8.7 Hz, 1H), 7.18 (s, 1H), 7.27 (br, 2H), 7.32 (dd, J=2.4, 8.4 Hz, 1H), 7.42 (d, J=2.4 Hz, 1H), 7.51 (s, 1H), 7.66 (s, 4H), 8.29 (d, J=5.1 Hz, 1H), 10.32 (br, 1H), 10.63 (br, 1H); $^{19}$F NMR (282 MHz, DMSO-d$_6$): δ −199.40; LCMS: purity: 88.84%; MS (m/e): 461.14 (MH$^+$).

I-120: Racemic N4-[4-(1-Aminocarbonyl)ethoxy-3-methyl]phenyl-N2-(3-aminosulfonyl)phenyl-5-fluoro-2,4-pyrimidinediamine $^1$H NMR (DMSO-d$_6$): δ 1.45 (d, J=6.6 Hz, 3H), 2.19 (s, 3H), 4.58 (q, J=6.6 Hz, 1H), 6.76 (d, J=8.7 Hz, 1H), 7.26 (s, 1H), 7.31 (s, 2H), 7.41 (m, 5H), 7.86 (s, 1H), 7.93 (d, J=7.5 Hz, 1H), 8.17 (d, J=4.5 Hz, 1H), 9.87 (br, 1H), 10.03 (br, 1H); $^{19}$F NMR (282 MHz, DMSO-d6): δ −200.79; LCMS: purity: 87.27%; MS (m/e): 461.08 (MH$^+$).

I-96: N4-(4-Aminocarbonylmethoxy-3,5-dimethyl)phenyl-N2-(3-aminosulfonyl-4-methyl)phenyl-5-fluoro-2,4-pyrimidinediamine $^1$H NMR (DMSO-d$_6$): δ 2.21 (s, 6H), 2.48 (s, 3H), 4.12 (s, 2H), 7.14 (d, J=8.4 Hz, 1H), 7.23 (s, 2H), 7.38 (s, 2H), 7.46 (br, 1H), 7.60 (br, 1H), 7.91 (dd, J=8.4 Hz, 1H), 7.99 (d, 1H), 8.03 (d, J=3.6 Hz, 1H), 9.15 (br, 1H), 9.33 (br, 1H); $^{19}$F NMR (282 MHz, DMSO-d$_6$): δ −202.71; LCMS: purity: 83.51%; MS (m/e): 475.19 (MH$^+$).

I-121: Racemic N4-[4-(1-Aminocarbonyl)ethoxy-3-methyl]phenyl-N2-(3-aminosulfonyl-4-methyl)phenyl-5-fluoro-2,4-pyrimidinediamine $^1$H NMR (DMSO-d$_6$): δ 1.45 (d, J=6.6 Hz, 3H), 2.18 (s, 3H), 2.52 (s, 3H), 4.58 (q, J=6.6 Hz, 1H), 6.76 (d, J=9.6 Hz, 1H), 7.20 (d, J=8.4 Hz, 1H), 7.24 (s, 1H), 7.31 (s, 2H), 7.40 (br, 3H), 7.80 (d, J=8.4 Hz, 1H), 7.86 (s, 1H), 8.16 (d, J=4.8 Hz, 1H), 10.02 (br, 2H); $^{19}$F NMR (282 MHz, DMSO-d$_6$): δ −200.86; LCMS: purity: 87.82%; MS (m/e): 475.06 (MH$^+$).

I-122: Racemic N4-[4-(1-Aminocarbonyl)ethoxy-3,5-dimethyl]phenyl-N2-(4-aminosulfonyl)phenyl-5-fluoro-2,4-pyrimidinediamine $^1$H NMR (DMSO-d$_6$): δ 1.33 (d, J=6.6 Hz, 3H), 2.24 (s, 6H), 4.29 (q, J=6.6 Hz, 1H), 7.15 (br, 2H), 7.28 (br, 1H), 7.34 (s, 2H), 7.55 (br, 1H), 7.60 (d, J=9.0 Hz, 2H), 7.77 (d, J=9.0 Hz, 2H), 8.13 (d, J=3.9 Hz, 1H), 9.39 (br, 1H), 9.70 (br, 1H); $^{19}$F NMR (282 MHz, DMSO-d$_6$): δ −201.52; LCMS: purity: 89.76%; MS (m/e): 475.09 (MH$^+$).

I-123: Racemic N4-[4-(1-Aminocarbonyl)ethoxy-3,5-dimethyl]phenyl-N2-(3-aminosulfonyl)phenyl-5-fluoro-2,4-pyrimidinediamine $^1$H NMR (DMSO-d$_6$): δ 1.32 (d, J=6.6 Hz, 3H), 2.22 (s, 6H), 4.27 (q, J=6.6 Hz, 1H), 7.25 (s, 2H), 7.28 (br, 1H), 7.33 (m, 2H), 7.40 (s, 2H), 7.53 (br, 1H), 7.98 (s, 1H), 8.05 (m, 1H), 8.07 (d, J=3.6 Hz, 1H), 9.17 (br, 1H), 9.48 (br, 1H); $^{19}$F NMR (282 MHz, DMSO-d$_6$): δ −202.22; LCMS: purity: 90.76%; MS (m/e): 475.12 (MH$^+$).

I-124: Racemic N4-[4-(1-Aminocarbonyl)ethoxy-3,5-dimethyl]phenyl-N2-(3-aminosulfonyl-4-methyl)phenyl-5-fluoro-2,4-pyrimidinediamine $^1$H NMR (DMSO-d$_6$): δ 1.32 (d, J=6.6 Hz, 3H), 2.22 (s, 6H), 2.49 (s, 3H), 4.27 (q, J=6.6 Hz, 1H), 7.13 (d, J=8.4 Hz, 1H), 7.23 (s, 2H), 7.28 (s, 1H), 7.39 (s, 2H), 7.54 (s, 1H), 7.94 (dd, J=2.1, 8.4 Hz, 1H), 8.01 (d, J=2.4 Hz, 1H), 8.04 (d, J=3.6 Hz, 1H), 9.13 (br, 1H), 9.36 (br, 1H); $^{19}$F NMR (282 MHz, DMSO-d$_6$): δ −202.79; LCMS: purity: 96.27%; MS (m/e): 489.17 (MH$^+$).

I-63: Racemic N2-(4-Aminosulfonyl)phenyl-N4-[4-(1-cyano)ethoxy-3,5-dimethyl]phenyl-5-fluoro-2,4-pyrimidinediamine $^1$H NMR (DMSO-d$_6$): δ 1.71 (d, J=6.6 Hz, 3H), 2.27 (s, 6H), 5.01 (q, J=6.6 Hz, 1H), 7.16 (br, 2H), 7.39 (s, 2H), 7.64 (d, J=9.0 Hz, 2H), 7.74 (d, J=9.3 Hz, 2H), 8.20 (d, J=3.9 Hz, 1H), 9.72 (br, 1H), 9.98 (br, 1H); $^{19}$F NMR (282 MHz, DMSO-d$_6$): δ −200.54; LCMS: purity: 97.32%; MS (m/e): 457.15 (MH$^+$).

I-71: Racemic N2-(3-Aminosulfonyl)phenyl-N4-[4-(1-cyano)ethoxy-3,5-dimethyl]phenyl-5-fluoro-2,4-pyrimidinediamine $^1$H NMR (DMSO-d$_6$): δ 1.71 (d, J=6.6 Hz, 3H), 2.25 (s, 6H), 5.01 (q, J=6.6 Hz, 1H), 7.31 (s, 2H), 7.40 (s, 4H), 7.87 (s, 1H), 7.99 (m, 1H), 8.20 (d, J=4.2 Hz, 1H), 9.78 (br, 1H), 9.98 (br, 1H); $^{19}$F NMR (282 MHz, DMSO-d$_6$): δ −200.67; LCMS: purity: 99.05%; MS (m/e): 457.59 (MH$^+$).

I-72: Racemic N2-(3-Aminosulfonyl-4-methyl)phenyl-N4-[4-(1-cyano)ethoxy-3,5-dimethyl]phenyl-5-fluoro-2,4-pyrimidinediamine $^1$H NMR (DMSO-d$_6$): δ 1.71 (d, J=6.6 Hz, 3H), 2.25 (s, 6H), 2.50 (s, 3H), 5.01 (q, J=6.6 Hz, 1H), 7.21 (d, J=8.4 Hz, 1H), 7.30 (s, 2H), 7.40 (s, 2H), 7.89 (m, 2H), 8.16 (d, J=4.5 Hz, 1H), 9.74 (br, 1H), 9.83 (br, 1H); $^{19}$F NMR (282 MHz, DMSO-d$_6$): δ −201.19; LCMS: purity: 97.45%; MS (m/e): 471.60 (MH$^+$).

I-7: N2-(4-Aminosulfonyl-3-methoxy)phenyl-N4-(3-cyanomethoxy)phenyl-5-fluoro-2,4-pyrimidinediamine $^1$H NMR (DMSO-d$_6$): δ 3.72 (s, 3H), 5.13 (s, 2H), 6.80 (dd, J=9.3 Hz, 1H), 6.82 (br, 2H), 7.31 (t, J=8.1 Hz, 1H), 7.39 (d, 1H), 7.51 (m, 4H), 8.18 (d, J=3.6 Hz, 1H), 9.51 (br, 1H), 9.55 (br, 1H); $^{19}$F NMR (282 MHz, DMSO-d$_6$): δ −201.04; LCMS: purity: 91.71%; MS (m/e): 445.00 (MH$^+$).

I-77: N2-(4-Aminosulfonyl-3-methoxy)phenyl-N4-[4-(1-cyano-1-methyl)ethoxy]phenyl-5-fluoro-2,4-pyrimidinediamine $^1$H NMR (DMSO-d$_6$): δ 1.70 (s, 6H), 3.72 (s, 3H), 6.80 (s, 2H), 7.13 (d, J=8.7 Hz, 2H), 7.43 (m, 1H), 7.49 (m, 2H), 7.80 (d, J=8.7 Hz, 2H), 8.15 (d, J=3.6 Hz, 1H), 9.48 (br, 1H), 9.56 (br, 1H); $^{19}$F NMR (282 MHz, DMSO-d$_6$): δ −201.44; LCMS: purity: 84.88%; MS (m/e): 473.10 (MH$^+$).

I-29: N2-(4-Aminosulfonyl-3-methoxy)phenyl-N4-(4-cyanomethoxy-3-methyl)phenyl-5-fluoro-2,4-pyrimidinediamine $^1$H NMR (DMSO-d$_6$): δ 2.17 (s, 3H), 3.66 (s, 3H), 5.16 (s, 2H), 6.80 (br, 2H), 7.04 (d, J=8.4 Hz, 1H), 7.38 (s, 1H), 7.51 (m, 4H), 8.11 (d, J=3.6 Hz, 1H), 9.33 (br, 1H), 9.52 (br, 1H); $^{19}$F NMR (282 MHz, DMSO-d$_6$): δ −201.86; LCMS: purity: 70.82%; MS (m/e): 459.02 (MH$^+$).

I-32: N2-(4-Aminosulfonyl-3-methoxy)phenyl-N4-(4-cyanomethoxy-3,5-dimethyl)phenyl-5-fluoro-2,4-pyrimidinediamine $^1$H NMR (DMSO-d$_6$): δ 2.24 (s, 6H), 3.68 (s, 3H), 4.89 (s, 2H), 6.81 (s, 2H), 7.36 (dd, J=1.8, 8.4 Hz, 1H), 7.41 (s, 2H), 7.44 (d, J=1.5 Hz, 1H), 7.51 (d, J=8.7 Hz, 1H), 8.12 (d, J=3.9 Hz, 1H), 9.30 (br, 1H), 9.53 (br, 1H); $^{19}$F NMR (282 MHz, DMSO-d$_6$): δ −201.49; LCMS: purity: 70.55%; MS (m/e): 472.94 (MH$^+$).

I-64: Racemic N2-(4-Aminosulfonyl-3-methoxy)phenyl-N4-[4-(1-cyano)ethoxy-3-methyl]phenyl-5-fluoro-2,4-pyrimidinediamine $^1$H NMR (DMSO-d$_6$): δ 1.71 (d, J=6.6 Hz, 3H), 2.18 (s, 3H), 3.67 (s, 3H), 5.34 (q, J=6.6 Hz, 1H), 6.80 (br, 2H), 7.08 (d, J=8.4 Hz, 1H), 7.36 (d, J=8.7 Hz, 1H), 7.53 (m, 4H), 8.12 (d, J=2.7 Hz, 1H), 9.34 (br, 1H), 9.53 (br, 1H); $^{19}$F NMR (282 MHz, DMSO-d$_6$): δ −201.78; LCMS: purity: 77.96%; MS (m/e): 473.14 (MH$^+$).

I-33: N2-(3-Aminosulfonyl-4-fluoro)phenyl-N4-(4-cyanomethoxy)phenyl-5-fluoro-2,4-pyrimidinediamine ¹H NMR (DMSO-d₆): δ 5.16 (s, 2H), 7.07 (d, J=9.3 Hz, 2H), 7.31 (t, J=9.3 Hz, 1H), 7.61 (s, 2H), 7.64 (d, J=8.7 Hz, 2H), 7.88 (m, 2H), 8.20 (d, J=4.8 Hz, 1H), 10.04 (br, 2H); ¹⁹F NMR (282 MHz, DMSO-d₆): δ −200.77, −158.04; LCMS: purity: 97.97%; MS (m/e): 433.69 (MH⁺).

III-10: N2-(3-Aminosulfonyl-4-fluoro)phenyl-N4-(4-cyanomethyl)phenyl-5-fluoro-2,4-pyrimidinediamine ¹H NMR (DMSO-d₆): δ 4.00 (s, 2H), 7.28 (t, J=9.3 Hz, 1H), 7.31 (d, J=8.4 Hz, 2H), 7.59 (s, 2H), 7.75 (d, J=8.7 Hz, 2H), 7.92 (dd, J=3.6, 8.1 Hz, 1H), 7.97 (d, J=3.9 Hz, 1H), 8.17 (d, J=3.9 Hz, 1H), 9.77 (br, 2H); ¹⁹F NMR (282 MHz, DMSO-d₆): δ −201.13, −159.13; LCMS: purity: 99.78%; MS (m/e): 417.57 (MH⁺).

I-68: Racemic N2-(3-Aminosulfonyl-4-fluoro)phenyl-N4-[4-(1-cyano)ethoxy]phenyl-5-fluoro-2,4-pyrimidinediamine LCMS: purity: 89.22%; MS (m/e): 447.79 (MH⁺).

I-74: N2-(3-Aminosulfonyl-4-fluoro)phenyl-N4-[4-(1-cyano-1-methyl)ethoxy]phenyl-5-fluoro-2,4-pyrimidinediamine ¹H NMR (DMSO-d₆): δ 1.69 (s, 6H), 7.14 (d, J=9.0 Hz, 2H), 7.28 (t, J=9.3 Hz, 1H), 7.59 (s, 2H), 7.75 (d, J=8.7 Hz, 2H), 7.94 (m, 2H), 8.17 (d, J=3.9 Hz, 1H), 9.81 (br, 2H); ¹⁹F NMR (282 MHz, DMSO-d₆): δ −201.14, −159.13; LCMS: purity: 100%; MS (m/e): 461.72 (MH⁺).

I-34: N2-(3-Aminosulfonyl-4-fluoro)phenyl-N4-(4-cyanomethoxy-3-methyl)phenyl-5-fluoro-2,4-pyrimidinediamine ¹H NMR (DMSO-d₆): δ 2.16 (s, 3H), 5.17 (s, 2H), 7.07 (d, J=8.7 Hz, 1H), 7.27 (t, J=9.3 Hz, 1H), 7.46 (d, J=2.1 Hz, 1H), 7.54 (dd, J=2.4, 8.7 Hz, 1H), 7.60 (s, 2H), 7.92 (m, 2H), 8.16 (d, J=4.2 Hz, 1H), 9.82 (br, 1H), 9.90 (br, 1H); ¹⁹F NMR (282 MHz, DMSO-d₆): δ −201.08, −158.67; LCMS: purity: 99.77%; MS (m/e): 447.69 (MH⁺).

I-35: N2-(3-Aminosulfonyl-4-fluoro)phenyl-N4-(4-cyanomethoxy-3,5-dimethyl)phenyl-5-fluoro-2,4-pyrimidinediamine LCMS: purity: 96.22%; MS (m/e): 461.84 (MH⁺).

I-69: Racemic N2-(3-Aminosulfonyl-4-fluoro)phenyl-N4-[4-(1-cyano)ethoxy-3-methyl]phenyl-5-fluoro-2,4-pyrimidinediamine ¹H NMR (DMSO-d₆): δ 1.72 (d, J=6.6 Hz, 3H), 2.17 (s, 3H), 5.36 (q, J=6.6 Hz, 1H), 7.11 (d, J=9.0 Hz, 1H), 7.26 (t, J=9.3 Hz, 1H), 7.49 (s, 1H), 7.59 (m, 3H), 7.92 (m, 2H), 8.14 (d, J=4.2 Hz, 1H), 9.73 (br, 1H), 9.82 (br, 1H); ¹⁹F NMR (282 MHz, DMSO-d₆): δ −201.28, −158.94; LCMS: purity: 99.33%; MS (m/e): 461.74 (MH⁺).

Example 28

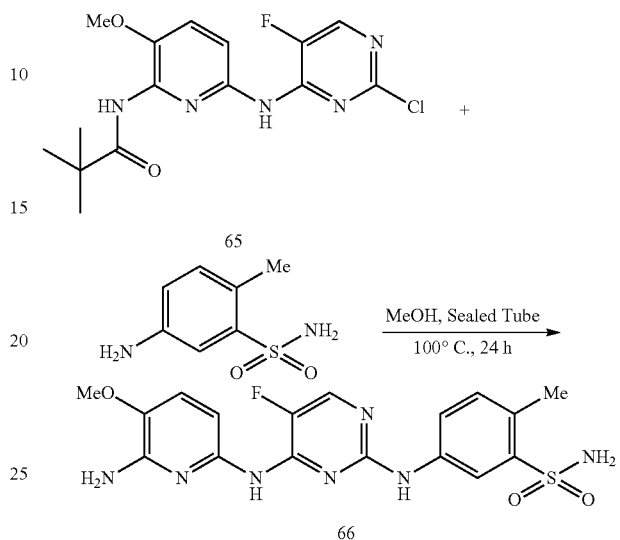

VII-9: N2-(3-Aminosulfonyl-4-methylphenyl)-N4-[2-amino-3-methoxypyrid-6-yl]-5-fluoro-2,4-pyrimidinediamine (66)

A mixture of N4-[2-(tert-butylcarbonyl)amino-3-methoxypyrid-6-yl]-2-chloro-5-fluoro-4-pyrimidineamine (65) (25 mg, 0.07 mmol) and 3-aminosulfonyl-4-methylaniline (15 mg) in methanol (1 mL) was shaken in a sealed tube at 100° C. for 48 h. The reaction mixture was then chromatographed (silica gel, CH₂Cl₂ then 2-4% 2N NH₃/MeOH in CH₂Cl₂) to obtain N2-(3-aminosulfonyl-4-methylphenyl)-N4-(2-amino-3-methoxypyrid-6-yl)-5-fluoro-2,4-pyrimidinediamine (66). (Note: The N-tert-butylcarbonyl group was cleaved during this reaction to give free amine function). LCMS: purity: 90%; MS (m/z): 420 (MH⁺).

The following compounds were made in a similar fashion to the example 28.

VII-7: N2-(3-Aminosulfonylphenyl)-N4-(2-amino-3-methoxypyrid-6-yl)-5-fluoro-2,4-pyrimidinediamine LCMS: purity: 92%; MS (m/z): 406 (MH⁺).

VII-8: N2-(3-Aminosulfonyl-4-chlorophenyl)-N4-(2-amino-3-methoxypyrid-6-yl)-5-fluoro-2,4-pyrimidinediamine LCMS: purity: 92%; MS (m/z): 440 (MH⁺).

VII-10: N4-(2-Amino-3-methoxypyrid-6-yl)-N2-[3-(ethoxycarbonylmethylene)aminosulfonylphenyl]-5-fluoro-2,4-pyrimidinediamine LCMS: purity: 93%; MS (m/z): 526 (MH⁺).

VI-96: N2-(3-Butylaminosulfonylphenyl)-N4-(3-cyano-4-methylphenyl)-5-fluoro-2,4-pyrimidinediamine $^1$H NMR (DMSO-d$_6$): δ 9.63 (s, 1H), 9.60 (s, 1H), 8.20-8.19 (d, J=3.0 Hz, 1H), 8.17-8.16 (d, J=3.0 Hz, 1H), 8.02-7.99 (d, J=9.0 Hz, 2H), 7.48-7.38 (m, 3H), 7.30-7.27 (d, J=9.0 Hz, 2H), 2.74-2.70 (m, 2H), 2.45 (s, 3H), 1.36-1.31 (m, 2H), 1.26-1.18 (m, 2H), 0.81-0.76 (m, 3H); LCMS (m/z): 455.02 (M$^+$).

VI-97: N2-(3-Butylaminosulfonylphenyl)-N4-(3-chloro-4-fluorophenyl)5-fluoro-2,4-pyrimidinediamine $^1$H NMR (DMSO-d$_6$): δ 9.60 (s, 1H), 9.55 (s, 1H), 8.17-8.16 (d, J=3.0 Hz, 1H), 8.03-8.00 (m, 2H), 7.97 (br s, 1H), 7.82-7.76 (m, 1H), 7.48-7.44 (m, 1H), 7.42 (s, 1H), 7.39-7.33 (m, 1H), 7.30-7.27 (br d, J=9.0 Hz, 1H), 2.76-2.70 (m, 2H), 1.37-1.29 (m, 2H), 1.26-1.18 (m, 2H), 0.81-0.76 (m, 3H); LCMS (m/z): 470.33 (M$^+$).

VI-98: N2-(3-Aminosulfonylphenyl)-N4-(3-cyano-4-fluorophenyl)-5-fluoro-2,4-pyrimidinediamine $^1$H NMR (DMSO-d$_6$): δ 9.72 (s, 1H), 9.66 (s, 1H), 8.39-8.36 (m, 1H), 8.20-8.19 (d, J=3.0 Hz, 1H), 8.08 (br s, 2H), 7.93-7.90 (d, J=9.0 Hz, 1H), 7.51-7.34 (m, 3H), 7.27 (s, 2H); LCMS (m/z): 403.18 (M$^+$).

VI-99: N2-(3-Aminosulfonylphenyl)-N4-(3-cyano-4-methylphenyl)-5-fluoro-2,4-pyrimidinediamine $^1$H NMR (DMSO-d$_6$): δ 9.63 (s, 1H), 9.59 (s, 1H), 8.21-8.20 (d, J=3.0 Hz, 1H), 8.17-8.16 (d, J=3.0 Hz, 1H), 8.07 (s, 1H), 8.00-7.94 (m, 2H), 7.45-7.34 (m, 3H), 7.27 (s, 2H), 2.45 (s, 3H); LCMS (m/z): 399.32 (M$^+$).

X-3: N2-(3-Aminosulfonylphenyl)-5-fluoro-N4-(2-methylindol-5-ylmethylene)-2,4-pyrimidinediamine $^1$H NMR (DMSO-d$_6$): δ 10.77 (s, 1H), 9.36 (s, 1H), 8.27 (s, 1H), 7.99 (m, 1H), 7.88-7.87 (d, J=3 Hz, 1H), 7.83-7.81 (d, J=6.0 Hz, 1H), 7.35-6.88 (m, 4H), 6.70-6.66 (d, J=12 Hz, 2H), 6.03 (s, 1H), 4.66-4.64 (d, J=6 Hz, 2H), 2.33 (s, 3H); LCMS (m/z): 427.20 (M$^+$).

Example 29

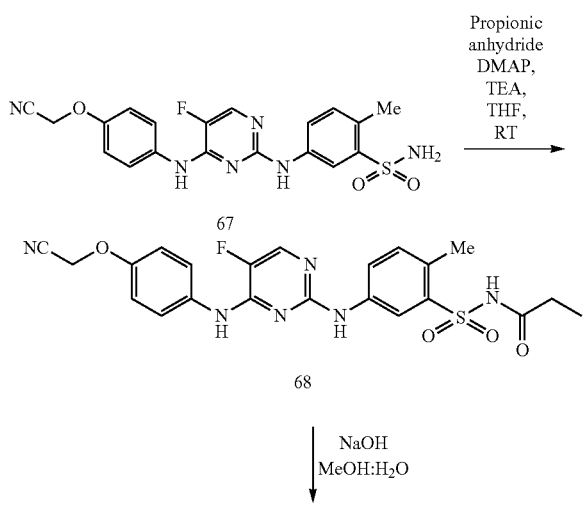

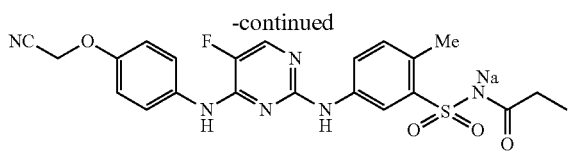

I-30: N4-(4-Cyanomethyleneoxy)phenyl-5-fluoro-N2-(4-methyl-3-propionylaminosulfonyl)phenyl-2,4-pyrimidinediamine (68)

N2-(3-Aminosulfonyl-4-methyl)phenyl-N4-(4-cyanomethyleneoxy)phenyl-5-fluoro-2,4-pyrimidinediamine (67) (400 mg), propionic anhydride (0.24 mL), N,N-dimethylaminopyridine (DMAP) (60 mg) and triethylamine (0.16 mL) were stirred in THF (15 mL) at room temperature overnight. The solution was diluted with ethyl acetate (100 mL) and washed with water (100 mL), and brine (100 mL). The organic layer was then evaporated. The residue was recrystallized from EtOAc and hexanes to give N4-(4-cyanomethyleneoxy)phenyl-5-fluoro-N2-(4-methyl-3-propionylaminosulfonyl)phenyl-2,4-pyrimidinediamine (68). $^1$H NMR (DMSO-d$_6$): δ 0.88 (t, J=7.5 Hz, 3H), 2.24 (q, J=7.5 Hz, 2H), 2.49 (s, 3H), 5.15 (s, 2H), 7.04 (d, J=9.3 Hz, 2H), 7.20 (d, J=8.1 Hz, 1H), 7.75 (d, J=9.0 Hz, 2H), 8.00 (dd, J=2.1, 8.1 Hz, 1H), 8.08 (d, J=3.9 Hz, 1H), 8.14 (s, 1H), 9.35 (br, 1H), 9.48 (br, 1H), 12.02 (br, 1H); $^{19}$F NMR (DMSO-d$_6$): δ −202.71; LCMS: purity: 95.67%; MS (m/z): 485.09 (MH$^+$).

I-31: N4-(4-Cyanomethyleneoxy)phenyl-5-fluoro-N2-(4-methyl-3-propionylaminosulfonyl)phenyl-2,4-pyrimidinediamine sodium salt (69)

N4-(4-Cyanomethoxy)phenyl-5-fluoro-N2-(4-methyl-3-propionylaminosulfonyl)phenyl-2,4-pyrimidinediamine (68) (583.5 mg) was dissolved in methanol (5 mL) and water (1 mL). To the solution was added 1 N NaOH aq. (1.2 mL). The solution was then evaporated and lyophilized to give N4-(4-cyanomethyleneoxy)phenyl-5-fluoro-N2-(4-methyl-3-propionylaminosulfonyl)phenyl-2,4-pyrimidinediamine sodium salt (69). $^1$H NMR (DMSO-d$_6$): δ 0.85 (t, J=7.5 Hz, 3H), 1.90 (q, J=7.5 Hz, 2H), 2.42 (s, 3H), 5.13 (s, 2H), 6.94 (d, J=8.1 Hz, 1H), 7.04 (d, J=9.0 Hz, 2H), 7.70 (d, J=7.5 Hz, 1H), 7.78 (d, J=9.0 Hz, 2H), 7.85 (d, J=2.1 Hz, 1H), 8.02 (d, J=3.9 Hz, 1H), 9.17 (br, 1H), 9.22 (br, 1H); $^{19}$F NMR (DMSO-d$_6$): δ −203.90; LCMS: purity: 100%; MS (m/z): 485.39 (MH$^+$).

The following compounds were made in a similar fashion to the example 29.

I-36: N2-(3-Acetylaminosulfonyl-4-methyl)phenyl-N4-(4-cyanomethyleneoxy)phenyl-5-fluoro-2,4-pyrimidinediamine $^1$H NMR (DMSO-d$_6$): δ 1.94 (s, 3H), 2.47 (s, 3H), 5.15 (s, 2H), 7.04 (d, J=9.0 Hz, 2H), 7.21 (d, J=8.4 Hz, 1H), 7.75 (d, J=9.0 Hz, 2H), 8.02 (dd, J=2.4, 8.4 Hz, 1H), 8.08 (d, J=3.6 Hz, 1H), 8.12 (d, J=2.1 Hz, 1H), 9.34 (br, 1H), 9.48 (br, 1H), 12.06 (br, 1H); $^{19}$F NMR (282 MHz, DMSO-d$_6$): δ 202.71; LCMS: purity: 99.34%; MS ((m/z): 471.71 (MH$^+$).

I-37: N4-(4-Cyanomethyleneoxy)phenyl-5-fluoro-N2-(3-isobutyrylaminosulfonyl-4-methyl)phenyl-2,4-pyrimidinediamine $^1$H NMR (DMSO-d$_6$): δ 0.94 (d, J=6.9 Hz, 6H), 2.47 (m, 1H), 2.47 (s, 3H), 5.15 (s, 2H), 7.04 (d, J=8.7 Hz, 2H), 7.19 (d, J=8.7 Hz, 1H), 7.75 (d, J=9.3 Hz, 2H), 7.97 (dd, J=2.4, 8.4 Hz, 1H), 8.07 (d, J=3.6 Hz, 1H), 8.15 (d, J=2.1 Hz, 1H), 9.34 (br, 1H), 9.47 (br, 1H), 12.02 (br, 1H); $^{19}$F NMR (DMSO-d$_6$): δ −202.77; LCMS: purity: 94.84%; MS (m/z): 499.74 (MH$^+$).

I-38: N2-(3-Acetylaminosulfonyl-4-methyl)phenyl-N4-(4-cyanomethyleneoxy)phenyl-5-fluoro-2,4-pyrimidinediamine sodium salt $^1$H NMR (DMSO-d$_6$): δ 1.63 (s, 3H), 2.42 (s, 3H), 5.13 (s, 2H), 6.95 (d, J=8.4 Hz, 1H), 7.03 (d, J=9.3 Hz, 2H), 7.71 (d, J=8.1 Hz, 1H), 7.78 (d, J=9.3 Hz, 2H), 7.84 (d, J=2.4 Hz, 1H), 8.02 (d, J=3.6 Hz, 1H), 9.18 (br, 1H), 9.22 (br, 1H); $^{19}$F NMR (282 MHz, DMSO-d$_6$): δ −203.87; LCMS: purity: 91.01%; MS (m/z): 471.18 (MH$^+$).

I-39: N4-(4-Cyanomethyleneoxy)phenyl-5-fluoro-N2-(3-isobutyrylaminosulfonyl-4-methyl)phenyl-2,4-pyrimidinediamine Sodium Salt $^1$H NMR (DMSO-d$_6$): δ 0.88 (d, J=6.9 Hz, 6H), 2.09 (p, J=6.9 Hz, 1H), 2.42 (s, 3H), 5.13 (s, 2H), 6.94 (d, J=7.8 Hz, 1H), 7.04 (d, J=8.7 Hz, 2H), 7.68 (d, J=5.7 Hz, 1H), 7.78 (d, J=9.3 Hz, 2H), 7.86 (s, 1H), 8.02 (d, J=3.9 Hz, 1H), 9.17 (br, 1H), 9.22 (br, 1H); $^{19}$F NMR (DMSO-d$_6$): δ −203.93; LCMS: purity: 91.73%; MS (m/z): 499.38 (MH$^+$).

I-48: N4-(4-Cyanomethoxy-3-fluorophenyl)-5-fluoro-N2-(4-methyl-3-propionylaminosulfonylphenyl)-2,4-pyrimidinediamine $^1$H NMR (DMSO-d$_6$): δ 0.89 (t, J=7.5 Hz, 3H), 2.24 (q, J=7.5 Hz, 2H), 2.48 (s, 3H), 5.20 (s, 2H), 7.25 (m, 2H), 7.58 (d, J=9.9 Hz, 1H), 7.94 (dd, J=2.7, 13.8 Hz, 1H), 8.02 (dd, J=2.7, 8.4 Hz, 1H), 8.12 (d, J=3.6 Hz, 1H), 8.16 (d, J=2.1 Hz, 1H), 9.50 (br, 1H), 9.58 (br, 1H), 12.03 (br, 1H); $^{19}$F NMR (282 MHz, DMSO-d$_6$): δ −171.26, −202.29; LCMS: purity: 95.69%; MS (m/e): 503.74 (MH$^+$).

I-49: N4-(4-Cyanomethoxy-3-fluorophenyl)-5-fluoro-N2-(4-methyl-3-propionylaminosulfonylphenyl)-2,4-pyrimidinediamine Sodium Salt $^1$H NMR (DMSO-d$_6$): δ 0.85 (t, J=7.5 Hz, 3H), 1.93 (q, 2H), 2.43 (s, 3H), 5.19 (s, 2H), 6.98 (d, J=7.8 Hz, 1H), 7.27 (t, J=9.3 Hz, 1H), 7.66 (d, J=9.9 Hz, 1H), 7.75 (d, 1H), 7.88 (m, 1H), 7.95 (d, 1H), 8.07 (d, J=3.6 Hz, 1H), 9.32 (br, 1H), 9.38 (br, 1H); LCMS: purity: 84.54%; MS (m/e): 503.45 (MH$^+$).

VI-12: N2-[3-(N-Acetyl)aminosulfonyl-4-chlorophenyl]-N4-(3-chloro-4-methoxyphenyl)-5-fluoro-2,4-pyrimidinediamine LCMS: purity: 89%, MS (m/e): 501 (MH$^+$).

I-264: 5-Fluoro-N4-[4-(3-methyl-1,2,4-oxadiazol-3-yl)methyleneoxyphenyl]-N2-[(3-N-propanamido)sulfonylphenyl)]-2,4-pyrimidinediamine $^1$H NMR (DMSO d$_6$, 300 MHz): δ 11.96 (s, 1H), 9.56 (s, 1H), 9.33 (s, 1H), 8.17 (s, 1H), 8.07 (m, 2H), 7.69 (d, 2H, J=8.7 Hz), 7.37 (m, 2H), 7.01 (d, 2H, J=9.0 Hz), 5.46 (s, 2H), 2.36 (s, 3H), 2.22 (q, 2H, J=7.5 Hz), 0.88 (t, 3H, J=7.5 Hz); LCMS (m/z): 528 (MH$^+$).

I-273: 5-Fluoro-N4-[4-(3-methyl-1,2,4-oxadiazol-3-yl)methyleneoxyphenyl]-N2-[(3-N-propanamido)sulfonylphenyl)]-2,4-pyrimidinediamine Sodium Salt $^1$H NMR (D$_2$O, 300 MHz): δ 7.61 (s, 1H), 7.51 (s, 1H), 7.45 (d, 1H, J=7.5 Hz), 7.26 (d, 1H, J=7.5 Hz), 7.11 (d, 2H, J=6.9 Hz), 7.00 (t, 1H, J=7.8 Hz), 6.67 (d, 2H, J=7.5 Hz), 5.16 (s, 2H), 2.26 (s, 3H), 2.03 (q, 2H, J=7.5 Hz), 0.86 (t, 3H, J=7.8 Hz); LCMS (m/z): 528 (MH$^+$).

III-68: 5-Fluoro-N4-[4-(4-pyridinylmethyl)phenyl]-N2-[(3-N-propanamido)sulfonylphenyl)]-2,4-pyrimidinediamine $^1$H NMR (DMSO d$_6$, 300 MHz): δ 11.95 (s, 1H), 9.55 (s, 1H), 9.37 (s, 1H), 8.44 (d, 2H, J=4.8 Hz), 8.17 (s, 1H), 8.09 (d, 1H, J=3.3 Hz), 8.04 (d, 1H, J=7.5 Hz), 7.70 (d, 2H, J=8.4 Hz), 7.34 (m, 2H), 7.22 (m, 4H), 3.94 (s, 2H), 2.21 (q, 2H, J=7.5 Hz), 0.88 (t, 3H, J=7.2 Hz); LCMS (m/z): 507 (MH$^+$).

III-69: 5-Fluoro-N4-[4-(4-pyridinylmethyl)phenyl]-N2-[(3-N-propanamido)sulfonylphenyl)]-2,4-pyrimidinediamine sodium salt $^1$H NMR (D20, 300 MHz): δ 8.06 (s, 2H), 7.46 (d, 1H, J=3.6 Hz), 7.33 (m, 2H), 7.08 (d, 1H, J=7.8 Hz), 6.79 (br s, 3H), 6.50 (d, 2H, J=8.1 Hz), 6.41 (t, 2H, J=7.8 Hz), 3.44 (s, 2H), 2.01 (q, 2H, J=7.5 Hz), 0.84 (t, 3H, J=7.2 Hz); LCMS (m/z): 507 (MH$^+$).=

I-232: N2-(3-Acetamidosulfonylphenyl)-5-fluoro-N4-[4-(5-methylisoxazol-3-yl)methyleneoxyphenyl]-2,4-pyrimidinediamine $^1$H NMR (DMSO d$_6$, 300 MHz): δ 12.05 (br s, 1H), 9.60 (s, 1H), 9.36 (s, 1H), 8.21 (s, 1H), 8.12 (s, 1H), 8.12 (s, 1H), 7.73 (d, 2H, J=8.7 Hz), 7.33 (m, 2H), 7.42 (s, 2H), 7.15 (s, 1H), 7.04 (d, 2H, J=8.7 Hz), 6.38 (s, 1H), 5.18 (s, 2H), 2.45 (s, 3H), 1.96 (s, 3H); LCMS (m/z): 513 (MH$^+$).

I-236: 5-Fluoro-N4-[4-(5-methylisoxazol-3-yl)methyleneoxyphenyl]-N2-(3-N-propanamido)sulfonylphenyl)]-2,4-pyrimidinediamine $^1$H NMR (DMSO d$_6$, 300 MHz): δ 11.96 (s, 1H), 9.55 (s, 1H), 9.31 (s, 1H), 8.17 (s, 1H), 8.06 (m, 2H), 7.68 (d, 2H, J=9.0 Hz), 7.37 (d, 2H, J=5.1 Hz), 6.99 (d, 2H, J=9.0 Hz), 6.33 (s, 1H), 5.13 (s, 2H), 2.41 (s, 3H), 2.21 (q, 2H, J=7.8 Hz), 0.88 (t, 3H), 2.46 (s, 3H J=7.5 Hz); LCMS (m/z): 527 (MH$^+$).

I-242: 5-Fluoro-N4-[4-(5-methylisoxazol-3-yl)methyleneoxyphenyl]-N2-(3-N-propanamido)sulfonylphenyl)]-2,4-pyrimidinediamine sodium salt $^1$H NMR (D$_2$O): δ 7.54 (d, 1H, J=2.1 Hz), 7.42 (br s, 2H), 7.21 (d, 1H, J=7.2 Hz), 6.98 (d, 2H, J=6.9 Hz), 6.83 (t, 1H, J=6.3 Hz), 6.55 (d, 2H, J=6.9 Hz), 5.99 (s, 1H), 4.86 (s, 2H), 2.23 (s, 3H), 2.01 (q, 2H, J=7.8 Hz), 0.83 (t, 3H), 2.46 (s, 3H J=7.5 Hz); LCMS (m/z): 527 (MH$^+$).

I-243: N2-(3-Acetamidosulfonylphenyl)-5-fluoro-N4-[4-(5-methylisoxazol-3-yl)methyleneoxyphenyl]-2,4-pyrimidinediamine sodium salt $^1$H NMR (D$_2$O): δ 7.59 (s, 1H), 7.47 (s, 2H), 7.22 (d, 1H, J=7.2 Hz), 7.08 (d, 2H, J=7.0 Hz), 6.94 (t, 1H, J=6.3 Hz), 6.67 (d, 2H, J=7.8 Hz), 6.05 (s, 1H), 4.94 (s, 2H), 2.24 (s, 3H), 1.77 (s, 3H); LCMS (m/z): 513 (MH$^+$).

I-228: 5-Fluoro-N4-[4-(5-methylisoxazol-3-yl)methyleneoxyphenyl]-N2-(4-methyl-3-propionylaminosulfonylphenyl)-2,4-pyrimidinediamine $^1$H NMR (DMSO-d$_6$): δ 12.00 (s, 1H), 9.43 (s, 1H), 9.25 (s, 1H), 8.16-8.13 (m, 1H), 8.04 (d, J=3.6 Hz, 1H), 8.00-7.95 (m, 1H), 7.68 (d, J=9.0 Hz, 2H), 7.17 (d, JH=9.0 Hz, 1H), 6.97 (d, J=9.0 Hz, 2H), 6.31 (s, 1H), 5.12 (s, 2H), 2.49 (s, 3H), 2.23 (q, J=7.2 Hz, 2H), 0.88 (t, J=7.2 Hz, 2H); LCMS: purity: 97%; MS (m/e): 542 (MH$^+$).

I-229: 5-Fluoro-N4-[4-(5-methylisoxazol-3-yl)methyleneoxyphenyl]-N2-(4-methyl-3-(2-methylpropionyl)aminosulfonylphenyl)-2,4-pyrimidinediamine $^1$H NMR (DMSO-d$_6$): δ 12.00 (s, 1H), 9.43 (s, 1H), 9.25 (s, 1H), 8.18-7.15 (m, 1H), 8.04 (d, J=3.6 Hz, 1H), 7.99-7.09 (m, 1H), 7.68 (d, J=9.0H, 2H), 7.17 (d, J=8.7 Hz, 1H), 6.97 (d, J=9.0 Hz, 2H), 6.31 (s, 1H), 5.12 (s, 2H), 2.48-2.46 (m, 4H), 2.41 (s, 3H), 0.93 (d, J=6.9 Hz, 6H); LCMS: purity: 94%; MS (m/e): 556 (MH$^+$).

Example 30

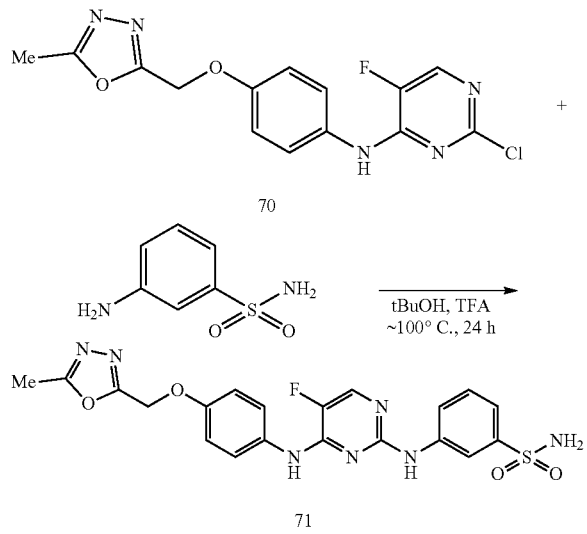

I-277: N2-(3-aminosulfonylphenyl)-5-fluoro-N4-[4-(5-methyl-1,3,4-oxadiazol-2-yl)methyleneoxyphenyl]-2,4-pyrimidinediamine (71)

2-Chloro-5-fluoro-N4-[4-(5-methyl-1,3,4-oxadiazol-2-yl)methyleneoxyphenyl]-4-pyrimidineamine (70) (100 mg, 0.3 mmol) was added to t-butanol (1 mL), followed by 3-aminobenzenesulfonamide (61.5 mg, 0.35 mmol) and a catalytic amount of acetic acid (10% by mole). The mixture was heated at 100° C. overnight and the solvent was removed under reduced pressure. The residue was dissolved in ethyl acetate and washed with saturated sodium bicarbonate. The organic layer was separated, dried with sodium sulfate, and then concentrated under reduced pressure. The crude product was purified by column chromatography (silica gel, ethyl acetate: hexanes 3:1) to give 20 mg of N2-(3-aminosulfonylphenyl)-5-fluoro-N4-[4-(5-methyl-1,3,4-oxadiazol-2-yl)methyleneoxyphenyl]-2,4-pyrimidinediamine (71) as a white solid. $^1$H NMR (DMSO-d$_6$): δ 9.47 (s, 1H), 9.30 (s, 1H), 8.08 (br s, 2H), 7.94 (br s, 1H), 7.73-7.70 (bd, J=9.0 Hz, 2H), 7.39-7.36 (d, J=9.0 Hz, 2H), 7.25 (br s, 2H), 7.04-7.01 (br s, J=9.0 Hz, 2H), 5.33 (br s, 2H), 2.55 (s, 3H); LCMS (m/z): 472.13 (MH$^+$).

The following compounds were made in a similar fashion to the example 30.

I-278: N2-(3-Aminosulfonyl-4-fluorophenyl)-5-fluoro-N4-[4-(5-methyl-1,3,4-oxadiazol-2-yl)methyleneoxyphenyl]-2,4-pyrimidinediamine $^1$H NMR (DMSO-d$_6$): δ 9.431 (s, 1H), 9.30 (s, 1H), 8.05 (br s, 2H), 7.97-7.94 (m, 1H), 7.71-7.68 (d, J=9.0 Hz, 2H), 7.54 (s, 2H), 7.27-7.21 (m, 1H), 7.05-7.02 (d, J=9.0 Hz, 2H), 5.34 (s, 2H), 2.53 (s, 3H); LCMS (m/z): 489.91 (MH$^+$).

I-279: N2-(3-Aminosulfonyl-4-methylphenyl)-5-fluoro-N4-[4-(5-methyl-1,3,4-oxadiazol-2-yl)methoxyphenyl]-2,4-pyrimidinediamine $^1$H NMR (DMSO-d$_6$): δ 9.36 (s, 1H), 9.26 (s, 1H), 8.09 (s, 1H), 8.05-8.04 (d, J=3.0 Hz, 1H), 7.89-7.86 (d, J=9.0 Hz, 1H), 7.73-7.70 (d, J=9.0 Hz, 2H), 7.22 (s, 2H), 7.18-7.15 (d, J=9.0 Hz, 1H), 7.03-7.00 (d, J=9.0 Hz, 2H), 5.33 (s, 2H), 2.53 (s, 3H); LCMS (m/z): 486.16 (MH$^+$).

Example 31

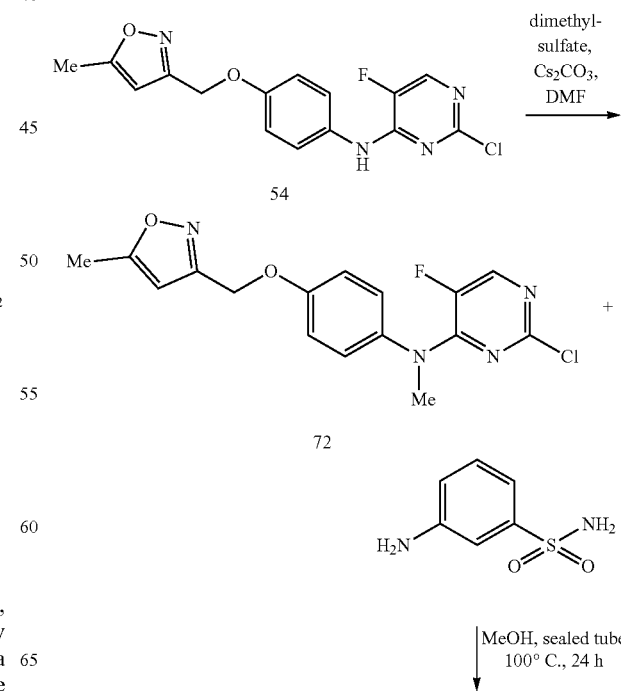

-continued

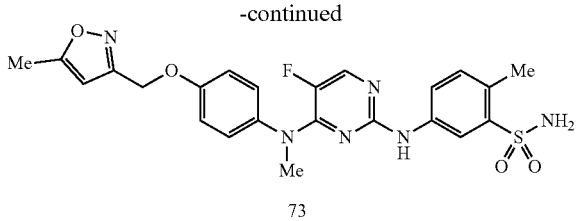

73

I-225: N2-(3-Aminosulfonyl-4-methylphenyl)-5-fluoro-N4-methyl-N4-[4-(5-methylisoxazol-3-yl)methyleneoxyphenyl]-2,4-pyrimidinediamine To a solution of N2-chloro-5-fluoro-N4-[4-(5-methyl-isoxazol-3-yl)methyleneoxyphenyl]-4-pyrimidineamine (54, 0.33 g, 1 mmol) in N,N-dimethylformamide (DMF) (1 mL) were added Cs$_2$CO$_3$ and dimethyl sulfate (DMS) (1.5 equivalents, each) and the reaction was stirred at room temperature for 24 h. The reaction was quenched with water and the solid obtained was collected by filtration to give N2-chloro-5-fluoro-N4-methyl-N4-[4-(5-methylisoxazol-3-yl)methyleneoxyphenyl]-4-pyrimidineamine (72), which was further reacted with 3-aminosulfonyl-4-methylaniline according to the procedure given in Example 18 to give N2-(3-aminosulfonyl-4-methylphenyl)-5-fluoro-N4-methyl-N4-[4-(5-methylisoxazol-3-yl)methyleneoxyphenyl]-2,4-pyrimidinediamine (73). $^1$H NMR (DMSO-d$_6$): δ 9.46 (s, 1H), 8.46 (s, 1H), 7.90 (d, J=5.4 Hz, 1H), 7.65 (d, J=6.6 Hz, 1H), 7.30-7.12 (m, 5H), 7.01 (d, J=8.4 Hz, 2H), 6.33 (s, 1H), 5.14 (s, 2H), 3.42 (s, 3H), 3.31 (s, 3H), 2.41 (s, 3H); LCMS: purity: 98%; MS (m/z): 499 (MH$^+$).

The following compounds were made in a similar fashion to the example 31.

I-227: N2-(3-Aminosulfonyl-4-methylphenyl)-5-fluoro-N4-methoxycarbonylmethyl-N4-[4-(5-methylisoxazol-3-yl)methyleneoxyphenyl]-2,4-pyrimidinediamine $^1$H NMR (CDCl$_3$): δ 8.29 (d, J=2.1 Hz, 1H), 7.78-7.52 (m, 2H), 7.21-7.15 (m, 3H), 7.06 (d, J=8.1 Hz, 1H), 6.87 (d, J=9.0 Hz, 2H), 6.03 (s, 1H), 5.46 (bs, 2H), 5.03 (s, 2H), 4.48 (s, 2H), 3.47 (s, 3H), 2.53 (s, 3H), 2.36 (s, 3H); LCMS: purity: 90%; MS (m/z): 557 (MH$^+$).

I-226: N2-(3-Aminosulfonyl-4-methylphenyl)-5-fluoro-N4-[3-fluoro-4-(5-methylisoxazol-3-yl)methyleneoxyphenyl]-N4-methyl-2,4-pyrimidinediamine $^1$H NMR (DMSO-d$_6$): δ 9.50 (s, 1H), 8.45 (d, J=2.1 Hz, 1H), 7.95 (d, J=5.7 Hz, 1H), 7.64 (dd, J=2.4 and 8.4 Hz, 1H), 7.32 (dd, J=2.7 and 12.3 Hz, 1H), 7.29-7.14 (m, 4H), 7.10 (d, J=9.0 Hz, 1H), 6.34 (s, 1H), 5.23 (s, 2H), 3.43 (s, 3H), 2.49 (s, 3H), 2.41 (s, 3H); LCMS: purity: 99%; MS (m/z): 517 (MH$^+$).

Example 32

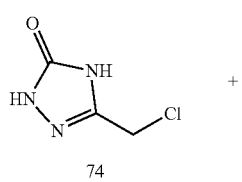

74

-continued

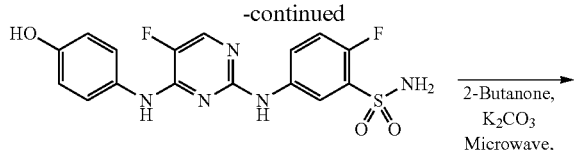

75

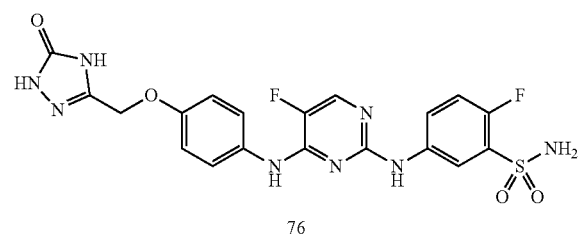

76

5-chloromethyl-2,4-dihydro-1,2,4-triazol-3-one (74)

Semicarbazide.HCl (5 g, 89 mmol), 2-chloro-1,1,1-trimethoxyethane (12.07 mL, 179 mmol) and methanol (50 mL) were combined and stirred at room temperature for 3 days, with the reaction monitored by $^1$H NMR. Additional 2-chloro-1,1,1-trimethoxyethane (8.77 mL) was added to complete the reaction. Methanol was then removed under vacuum. The resulting residue was extracted with ethyl acetate (500 mL) and washed with 1N HCl (2×100 mL). The aqueous phase was back extracted with ethyl acetate (5×100 mL). The organic layers were then combined, dried over anhydrous sodium sulfate, and solvent was removed under reduced pressure to give 3.1 g of 5-chloromethyl-2,4-dihydro-1,2,4-triazol-3-one (74) as a white powder. $^1$H NMR (DMSO-d$_6$): δ 11.65 (s, 1H), 11.50 (s, 1H), 4.48 (s, 2H); LCMS (m/z): 133.90 (M$^+$).

I-200: N2-(3-Aminosulfonyl-4-fluorophenyl)-5-fluoro-N4-[4-(2,4-dihydro-3-oxo-1,2,4-triazol-5-yl)methyleneoxyphenyl]-2,4-pyrimidinediamine (76)

To a solution of 5-chloromethyl-2,4-dihydro-1,2,4-triazol-3-one (35 mg, 0.26 mmol) in 2-butanone, were added N2-(3-aminosulfonyl-4-fluorophenyl)-5-fluoro-N4-(4-hydroxyphenyl)-2,4-pyrimidinediamine (100 mg, 0.25 mmol) and potassium carbonate (35 mg, 0.25 mmol). The resulting mixture was microwaved at 140° C. for 5 hours, and then additional of 5-chloromethyl-2,4-dihydro-1,2,4-triazol-3-one was added as needed The reaction solvent was removed under a reduced pressure, and the residual was purified by column chromatography (silica gel, dichloromethane:methanol 8:2 v/v) to give 25 mg of N2-(3-aminosulfonyl-4-fluorophenyl)-5-fluoro-N4-[4-(2,4-dihydro-3-oxo-1,2,4-triazol-5-yl)methoxyphenyl]-2,4-pyrimidinediamine (76) as a light yellow solid. $^1$H NMR (D$_2$O): δ 7.90-7.89 (d, J=3 Hz, 1H), 7.60-7.58 (d, J=6 Hz, 1H), 7.34 (bs, 2H), 7.24-7.18 (m, 2H), 7.05-7.02 (d, J=9.0 Hz, 2H), 6.65-6.62 (d, J=9.0 Hz, 2H), 5.11 (br s, 2H); LCMS (m/z): 491.05 (MH$^+$).

The following compounds were made in a similar fashion to the methods described in Example 32, or by methods described herein or known to skilled artisans.

VI-100: N2-(3-Aminosulfonyl-4-fluorophenyl)-5-fluoro-N4-(4-hydroxyphenyl)-2,4-pyrimidinediamine $^1$H NMR (DMSO-$d_6$): δ 7.99-7.97 (d, J=5.4 Hz, 1H), 7.80-7.77 (m, 1H), 7.74-7.69 (m, 1H), 7.34-7.31 (d, J=6.9 Hz, 2H), 7.27-7.21 (t, 2H), 6.81-6.78 (d, J=6.9 Hz, 2H), LCMS: 394.34 (MH$^+$).

VI-101: N2-(3-Aminosulfonylphenyl)-5-fluoro-N4-(4-hydroxyphenyl)-2,4-pyrimidinediamine $^1$H NMR (DMSO-$d_6$): δ 7.99-7.97 (d, J=5.4 Hz, 1H), 7.81-7.78 (m, 1H), 7.74-7.69 (m, 1H), 7.34-7.31 (d, J=6.9 Hz, 2H), 7.27-7.21 (t, 2H), 6.81-6.78 (d, J=6.9 Hz, 2H), LCMS: 376.38 (MH$^+$).

VI-102: N2-(3-Aminosulfonyl-4-methylphenyl)-5-fluoro-N4-[4-hydroxyphenyl]-2,4-pyrimidinediamine $^1$H NMR (DMSO-$d_6$): δ 7.96-7.94 (d, J=5.7 Hz, 1H), 7.87-7.86 (d, J=2.4 Hz, 1H), 7.62-7.58 (d, J=8.4 Hz, 1H), 7.37-7.29 (m, 4H), 6.80-6.77 (d, J=6.6 Hz, 2H), 2.66 (s, 3H), LCMS: 390.39 (MH$^+$).

I-201: N2-(3-Aminosulfonylphenyl)-5-fluoro-N4-[4-(2,4-dihydro-3-oxo-1,2,4-triazol-5-yl)methyleneoxyphenyl]-2,4-pyrimidinediamine $^1$H NMR (CD$_3$OD): δ 7.91-7.89 (d, J=4.0 Hz, 1H), 7.61-7.52 (m, 2H), 7.41-7.39 (m, 2H), 7.31-7.28 (d, J=9.0 Hz, 2H), 6.63-6.60 (d, J=9.0 Hz, 2H), 5.03 (s, 2H); LCMS: 473.58 (M$^+$).

I-202: N2-(3-Aminosulfonyl-4-methylphenyl)-5-fluoro-N4-[4-(2,4-dihydro-3-oxo-1,2,4-triazol-5-yl)methyleneoxyphenyl]-2,4-pyrimidinediamine $^1$H NMR (CD$_3$OD): δ 7.95-7.94 (d, J=3.0 Hz, 1H), 7.74 (s, 1H), 7.32-7.2 (m, 4H), 6.65-6.0 (m, 2H), 5.05 (s, 2H), 2.67 (s, 3H); LCMS (m/z): 487.53 (M$^+$).

IX-44: N2-(4-Aminosulfonylphenyl)-N4-[3,5-dimethyl-4-(4-methylpiperazin-1-yl]phenyl)-5-fluoro-2,4-pyrimidinediamine LCMS: purity: 94.62%; MS (m/e): 486.14 (MH$^+$).

I-40: N4-(4-Cyanomethoxy-3,5-dimethylphenyl)-5-fluoro-N2-[4-(4-methylpiperazin-1-yl)sulfonylphenyl]-2,4-pyrimidinediamine LCMS: purity: 92.80%; MS (m/e): 526.65 (MH$^+$).

I-41: N2-(4-Aminosulfonylphenyl)-N4-(3-chloro-4-cyanomethoxyphenyl)-5-fluoro-2,4-pyrimidinediamine $^1$H NMR (DMSO-$d_6$): δ 5.25 (s, 2H), 7.12 (br, 2H), 7.27 (d, J=9.0 Hz, 1H), 7.64 (d, J=8.7 Hz, 2H), 7.70 (dd, J=2.7, 9.0 Hz, 1H), 7.78 (d, J=8.7 Hz, 2H), 7.95 (d, J=2.4 Hz, 1H), 8.16 (d, J=3.6 Hz, 1H), 9.52 (br, 1H), 9.67 (br, 1H); $^{19}$F NMR (282 MHz, DMSO-$d_6$): δ -201.71; LCMS: purity: 75.54%; MS (m/e): 449.36 (MH$^+$).

I-42: N2-(3-Aminosulfonylphenyl)-N4-(3-chloro-4-cyanomethoxyphenyl)-5-fluoro-2,4-pyrimidinediamine $^1$H NMR (DMSO-$d_6$): δ 5.25 (s, 2H), 7.28 (m, 3H), 7.38 (m, 2H), 7.78 (dd, J=2.4, 8.7 Hz, 1H), 7.89 (d, J=2.4 Hz, 1H), 7.95 (d, J=7.8 Hz, 1H), 7.99 (s, 1H), 8.17 (d, J=3.6 Hz, 1H), 9.66 (br, 1H), 9.74 (br, 1H); $^{19}$F NMR (282 MHz, DMSO-$d_6$): δ -201.64; LCMS: purity: 88.17%; MS (m/e): 449.39 (MH$^+$).

I-43: N2-(3-Aminosulfonyl-4-methylphenyl)-N4-(3-chloro-4-cyanomethoxypheny)-5-fluoro-2,4-pyrimidinediamine $^1$H NMR (DMSO-$d_6$): δ 2.49 (s, 3H), 5.25 (s, 2H), 7.24 (m, 4H), 7.79 (dd, J=2.7, 9.0 Hz, 1H), 7.87 (m, 1H), 7.88 (d, J=2.7 Hz, 1H), 8.02 (d, J=2.1 Hz, 1H), 8.12 (d, J=3.9 Hz, 1H), 9.54 (br, 2H); $^{19}$F NMR (282 MHz, DMSO-$d_6$): δ -202.43; LCMS: purity: 91.27%; MS (m/e): 463.40 (MH$^+$).

I-97: N4-(4-Aminocarbonylmethoxy-3-chlorophenyl)-N2-(4-aminosulfonylphenyl)-5-fluoro-2,4-pyrimidinediamine $^1$H NMR (DMSO-$d_6$): δ 4.56 (s, 2H), 7.01 (d, J=8.7 Hz, 1H), 7.16 (br, 2H), 7.39 (br, 1H), 7.41 (br, 1H), 7.57 (dd, J=2.4, 9.0 Hz, 1H), 7.66 (d, J=8.7 Hz, 2H), 7.75 (d, J=8.7 Hz, 2H), 7.83 (d, J=2.4 Hz, 1H), 8.19 (d, J=3.9 Hz, 1H), 9.76 (br, 1H), 9.92 (br, 1H); $^{19}$F NMR (282 MHz, DMSO-$d_6$): δ 201.07; LCMS: purity: 82.15%; MS (m/e): 467.36 (MH$^+$).

I-98: N4-(4-Aminocarbonylmethoxy-3-chlorophenyl)-N2-(3-aminosulfonylphenyl)-5-fluoro-2,4-pyrimidinediamine $^1$H NMR (DMSO-$d_6$): δ 4.54 (s, 2H), 7.00 (d, J=8.7 Hz, 1H), 7.28 (br, 2H), 7.39 (m, 4H), 7.67 (dd, J=2.4, 8.7 Hz, 1H), 7.79 (d, J=2.4 Hz, 1H), 7.94 (dd, J=2.4, 7.2 Hz, 1H), 7.97 (s, 1H), 8.15 (d, J=3.9 Hz, 1H), 9.64 (br, 1H), 9.75 (br, 1H); $^{19}$F NMR (282 MHz, DMSO-$d_6$): δ -201.59; LCMS: purity: 82.05%; MS (m/e): 467.37 (MH$^+$).

I-99: N4-(4-Aminocarbonylmethoxy-3-chlorophenyl)-N2-(3-aminosulfonyl-4-methylphenyl)-5-fluoro-2,4-pyrimidinediamine $^1$H NMR (DMSO-$d_6$): δ 2.51 (s, 3H), 4.54 (s, 2H), 6.99 (d, J=9.0 Hz, 1H), 7.23 (dd, J=3.3, 8.7 Hz, 1H), 7.28 (br, 2H), 7.36 (br, 1H), 7.45 (br, 1H), 7.66 (d, J=9.0 Hz, 1H), 7.79 (d, J=2.4 Hz, 1H), 7.82 (dd, J=2.4, 8.1 Hz, 1H), 7.96 (s, 1H), 8.15 (d, J=4.2 Hz, 1H), 9.76 (br, 2H); $^{19}$F NMR (282 MHz, DMSO-$d_6$): δ -201.70; LCMS: purity: 80.53%; MS (m/e): 481.38 (MH$^+$).

I-100: N4-(4-Aminocarbonylmethoxy-3-fluorophenyl)-N2-(4-aminosulfonylphenyl)-5-fluoro-2,4-pyrimidinediamine $^1$H NMR (DMSO-$d_6$): δ 4.52 (s, 2H), 7.04 (t, J=9.0 Hz, 1H), 7.16 (br, 2H), 7.40 (m, 2H), 7.49 (br, 1H), 7.65 (d, J=8.7 Hz, 2H), 7.75 (d, J=2.7 Hz, 1H), 7.78 (d, J=9.0 Hz, 2H), 8.18 (d, J=3.6 Hz, 1H), 9.70 (br, 1H), 9.85 (br, 1H); $^{19}$F NMR (282 MHz, DMSO-$d_6$): δ -171.66, -201.16; LCMS: purity: 94.57%; MS (m/e): 451.63 (MH$^+$).

I-101: N4-(4-Aminocarbonylmethoxy-3-fluorophenyl)-N2-(3-aminosulfonylphenyl)-5-fluoro-2,4-pyrimidinediamine $^1$H NMR (DMSO-$d_6$): δ 4.50 (s, 2H), 7.02 (t, J=9.0 Hz, 1H), 7.29 (br, 2H), 7.40 (m, 3H), 7.46 (m, 2H), 7.78 (dd, J=2.4, 13.5 Hz, 1H), 7.94 (m, 1H), 8.02 (s, 1H), 8.16 (d, J=4.2 Hz, 1H), 9.69 (br, 1H), 9.79 (br, 1H); $^{19}$F NMR (282 MHz, DMSO-$d_6$): δ −171.60, −201.45; LCMS: purity: 91.91%; MS (m/e): 451.59 (MH$^+$).

I-102: N4-(4-Aminocarbonylmethoxy-3-fluorophenyl)-N2-(3-aminosulfonyl-4-methylphenyl)-5-fluoro-2,4-pyrimidinediamine $^1$H NMR (DMSO-$d_6$): δ 2.51 (s, 3H), 4.50 (s, 2H), 7.01 (t, J=9.3 Hz, 1H), 7.22 (m, 1H), 7.26 (br, 2H), 7.45 (m, 3H), 7.78 (dd, J=14.1 Hz, 1H), 7.84 (dd, J=2.4, 8.4 Hz, 1H), 8.02 (s, 1H), 8.12 (d, J=4.2 Hz, 1H), 9.68 (br, 2H); $^{19}$F NMR (282 MHz, DMSO-$d_6$): δ −171.61, −201.86; LCMS: purity: 83.32%; MS (m/e): 465.67 (MH$^+$).

I-44: N2-(4-Aminosulfonylphenyl)-N4-(4-cyanomethoxy-3-fluorophenyl)-5-fluoro-2,4-pyrimidinediamine $^1$H NMR (DMSO-$d_6$): δ 5.22 (s, 2H), 7.15 (br, 2H), 7.28 (t, J=9.0 Hz, 1H), 7.51 (d, J=8.1 Hz, 1H), 7.66 (d, J=8.7 Hz, 2H), 7.79 (d, J=9.0 Hz, 2H), 7.91 (dd, J=2.4, 13.5 Hz, 1H), 8.20 (d, J=3.9 Hz, 1H), 9.74 (br, 1H), 9.84 (br, 1H); $^{19}$F NMR (282 MHz, DMSO-$d_6$): δ −171.30, −201.07; LCMS: purity: 96.50%; MS (m/e): 433.69 (MH$^+$).

I-103: N4-(4-Aminocarbonylmethoxy-3-methoxyphenyl)-N2-(4-aminosulfonylphenyl)-5-fluoro-2,4-pyrimidinediamine $^1$H NMR (DMSO-$d_6$): δ 3.73 (s, 3H), 4.41 (s, 2H), 6.91 (d, J=8.4 Hz, 1H), 7.16 (br, 2H), 7.28 (m, 2H), 7.37 (br, 2H), 7.61 (d, J=8.7 Hz, 2H), 7.76 (d, J=7.8 Hz, 2H), 8.16 (d, 1H), 9.59 (br, 1H), 9.79 (br, 1H); $^{19}$F NMR (282 MHz, DMSO-$d_6$): δ −201.39; LCMS: purity: 86.59%; MS (m/e): 463.57 (MH$^+$).

I-104: N4-(4-Aminocarbonylmethoxy-3-methoxyphenyl)-N2-(3-aminosulfonylphenyl)-5-fluoro-2,4-pyrimidinediamine $^1$H NMR (DMSO-$d_6$): δ 3.72 (s, 3H), 4.40 (s, 2H), 6.89 (d, J=8.7 Hz, 1H), 7.27-7.41 (m, 8H), 7.93 (dd, J=2.4, 5.7 Hz, 1H), 7.99 (s, 1H), 8.13 (d, J=4.2 Hz, 1H), 9.60 (br, 1H), 9.73 (br, 1H); $^{19}$F NMR (282 MHz, DMSO-$d_6$): δ −201.60; LCMS: purity: 83.79%; MS (m/e): 463.01 (MH$^+$).

I-105: N4-(4-Aminocarbonylmethoxy-3-methoxyphenyl)-N2-(3-aminosulfonyl-4-methylphenyl)-5-fluoro-2,4-pyrimidinediamine $^1$H NMR (DMSO-$d_6$): δ 2.50 (s, 3H), 3.71 (s, 3H), 4.40 (s, 2H), 6.89 (d, J=8.7 Hz, 1H), 7.16 (d, J=8.4 Hz, 1H), 7.26 (br, 2H), 7.28 (d, J=2.4 Hz, 1H), 7.33 (m, 2H), 7.40 (m, 2H), 7.83 (dd, J=2.4, 8.1 Hz, 1H), 8.02 (s, 1H), 8.09 (d, J=3.9 Hz, 1H), 9.59 (br, 2H); LCMS: purity: 88.10%; MS (m/e): 477.53 (MH$^+$).

I-45: N2-(4-Aminosulfonylphenyl)-N4-(4-cyanomethoxy-3-methoxyphenyl)-5-fluoro-2,4-pyrimidinediamine $^1$H NMR (DMSO-$d_6$): δ 3.72 (s, 3H), 5.09 (s, 2H), 7.08 (d, J=8.7 Hz, 1H), 7.17 (br, 2H), 7.32 (dd, J=2.4, 8.7 Hz, 1H), 7.36 (d, J=2.4 Hz, 1H), 7.63 (d, J=9.0 Hz, 2H), 7.75 (d, J=8.7 Hz, 2H), 8.20 (d, J=4.2 Hz, 1H), 9.80 (br, 1H), 9.96 (br, 1H); $^{19}$F NMR (282 MHz, DMSO-$d_6$): δ −200.85; LCMS: purity: 98.23%; MS (m/e): 445.64 (MH$^+$).

I-46: N2-(3-Aminosulfonylphenyl)-N4-(4-cyanomethoxy-3-methoxyphenyl)-5-fluoro-2,4-pyrimidinediamine $^1$H NMR (DMSO-$d_6$): δ 3.73 (s, 3H), 5.08 (s, 2H), 7.06 (d, J=8.7 Hz, 1H), 7.28 (br, 2H), 7.37 (m, 4H), 7.93 (m, 1H), 8.00 (s, 1H), 8.15 (d, J=4.2 Hz, 1H), 9.62 (br, 1H), 9.72 (br, 1H); $^{19}$F NMR (282 MHz, DMSO-$d_6$): δ −201.58; LCMS: purity: 97.98%; MS (m/e): 445.10 (MH$^+$).

I-47: N2-(3-Aminosulfonyl-4-methylphenyl)-N4-(4-cyanomethoxy-3-methoxyphenyl)-5-fluoro-2,4-pyrimidinediamine $^1$H NMR (DMSO-$d_6$): δ 2.49 (s, 3H), 3.73 (s, 3H), 5.08 (s, 2H), 7.05 (d, J=8.7 Hz, 1H), 7.17 (d, J=9.0 Hz, 1H), 7.25 (br, 2H), 7.36 (d, J=2.1 Hz, 1H), 7.43 (dd, J=2.4, 8.4 Hz, 1H), 7.87 (dd, J=2.1, 7.8 Hz, 1H), 8.04 (d, 1H), 8.09 (d, J=3.9 Hz, 1H), 9.51 (br, 2H); $^{19}$F NMR (282 MHz, DMSO-$d_6$): δ −202.45; LCMS: purity: 92.72%; MS (m/e): 459.50 (MH$^+$).

I-106: N4-(4-Aminocarbonylmethoxy-3-hydroxymethylphenyl)-N2-(3-aminosulfonyl-4-methylphenyl)-5-fluoro-2,4-pyrimidinediamine $^1$H NMR (DMSO-$d_6$): δ 2.49 (s, 3H), 4.46 (s, 2H), 4.56 (d, J=5.4 Hz, 2H), 5.11 (t, J=5.4 Hz, 1H), 6.86 (d, J=8.7 Hz, 1H), 7.14 (d, J=8.1 Hz, 1H), 7.20 (br, 2H), 7.40 (br, 1H), 7.49 (br, 1H), 7.58 (d, J=2.7 Hz, 1H), 7.67 (dd, J=2.7, 9.0 Hz, 1H), 7.89 (dd, J=2.1, 8.1 Hz, 1H), 8.02 (d, J=3.6 Hz, 1H), 8.06 (d, J=1.2 Hz, 1H), 9.23 (br, 1H), 9.29 (br, 1H); $^{19}$F NMR (282 MHz, DMSO-$d_6$): δ −202.97; LCMS: purity: 82.44%; MS (m/e): 477.03 (MH$^+$).

I-50: N2-(3-Aminosulfonylphenyl)-N4-(4-cyanomethoxy-3-hydroxymethylphenyl)-5-fluoro-2,4-pyrimidinediamine $^1$H NMR (DMSO-$d_6$): δ 4.51 (d, J=5.4 Hz, 2H), 5.12 (t, J=5.4 Hz, 1H), 5.17 (s, 2H), 7.07 (d, J=8.7 Hz, 1H), 7.25 (br, 2H), 7.35 (m, 2H), 7.64 (d, J=2.7 Hz, 1H), 7.79 (dd, J=2.4, 8.7 Hz, 1H), 7.98 (d, J=8.1 Hz, 1H), 8.04 (s, 1H), 8.08 (d, J=3.6 Hz, 1H), 9.37 (br, 1H), 9.45 (br, 1H); $^{19}$F NMR (282 MHz, DMSO-$d_6$): δ −202.27; LCMS: purity: 82.62%; MS (m/e): 445.10 (MH$^+$).

I-51: N2-(3-Aminosulfonyl-4-methylphenyl)-N4-(4-cyanomethoxy-3-hydroxymethylphenyl)-5-fluoro-2,4-pyrimidinediamine $^1$H NMR (DMSO-$d_6$): δ 2.48 (s, 3H), 4.51 (d, J=5.7 Hz, 2H), 5.10 (t, J=5.4 Hz, 1H), 5.16 (s, 2H), 7.06 (d, J=8.7 Hz, 1H), 7.16 (d, J=8.7 Hz, 1H), 7.21 (br, 2H), 7.62 (d, J=2.7 Hz, 1H), 7.78 (dd, J=2.7, 9.0 Hz, 1H), 7.91 (dd, J=2.4, 8.4 Hz, 1H), 8.04 (d, J=3.6 Hz, 2H), 9.32 (br, 2H); $^{19}$F NMR (282 MHz, DMSO-d$_6$): δ −202.87; LCMS: purity: 87.82%, MS (m/e): 459.12 (MH$^+$).

I-52: N2-(4-Aminosulfonylphenyl)-N4-[4-cyanomethoxy-3-(1-cyanomethylpyrazol-3-yl)phenyl]-5-fluoro-2,4-pyrimidinediamine $^1$H NMR (DMSO-d$_6$): δ 5.25 (s, 2H), 5.48 (s, 2H), 6.80 (d, J=2.4 Hz, 1H), 7.06 (br, 2H), 7.23 (d, J=9.0 Hz, 1H), 7.52 (d, J=8.7 Hz, 2H), 7.78 (d, J=9.0 Hz, 2H), 7.90 (m, 2H), 8.06 (d, J=2.7 Hz, 1H), 8.13 (d, J=3.6 Hz, 1H), 9.53 (br, 1H), 9.56 (br, 1H); $^{19}$F NMR (282 MHz, DMSO-d$_6$): δ −201.76; LCMS: purity: 92.05%; MS (m/e): 520.46 (MH$^+$).

I-53: N2-(3-Aminosulfonylphenyl)-N4-[4-cyanomethoxy-3-(1-cyanomethylpyrazol-3-yl)phenyl]-5-fluoro-2,4-pyrimidinediamine $^1$H NMR (DMSO-d$_6$): δ 5.26 (s, 2H), 5.50 (s, 2H), 6.79 (d, J=1.5 Hz, 1H), 7.19-7.35 (m, 5H), 7.92 (m, 4H), 8.02 (d, J=2.4 Hz, 1H), 8.17 (d, J=3.9 Hz, 1H), 9.82 (br, 1H), 9.89 (br, 1H); $^{19}$F NMR (282 MHz, DMSO-d$_6$): δ −201.13; LCMS: purity: 94.31%; MS (m/e): 520.16 (MH$^+$).

I-54: N2-(3-Aminosulfonyl-4-methylphenyl]-N4-[4-cyanomethoxy-3-(1-cyanomethylpyrazol-3-yl)phenyl]-5-fluoro-2,4-pyrimidinediamine $^1$H NMR (DMSO-d$_6$): δ 2.45 (s, 3H), 5.25 (s, 2H), 5.50 (s, 2H), 6.79 (d, J=2.4 Hz, 1H), 6.98 (d, J=8.1 Hz, 1H), 7.23 (m, 3H), 7.86 (dd, J=2.4, 8.1 Hz, 1H), 7.92 (d, J=2.4 Hz, 1H), 7.97 (m, 2H), 8.02 (d, J=2.7 Hz, 1H), 8.09 (d, J=4.2 Hz, 1H), 9.53 (br, 1H), 9.66 (br, 1H); $^{19}$F NMR (282 MHz, DMSO-d$_6$): δ −202.24; LCMS: purity: 95.42%; MS (m/e): 534.28 (MH$^+$).

I-107: N4-(4-Aminocarbonylmethoxy-3-hydroxymethylphenyl]-N2-(3-aminosulfonylphenyl)-5-fluoro-2,4-pyrimidinediamine $^1$H NMR (DMSO-d$_6$): δ 4.47 (s, 2H), 4.56 (d, J=5.4 Hz, 2H), 5.12 (t, J=5.7 Hz, 1H), 6.86 (d, J=8.7 Hz, 1H), 7.24 (br, 2H), 7.32 (m, 2H), 7.41 (br, 1H), 7.49 (br, 1H), 7.59 (d, J=2.4 Hz, 1H), 7.67 (dd, J=3.0, 9.3 Hz, 1H), 7.97 (d, J=7.8 Hz, 1H), 8.05 (m, 2H), 9.28 (br, 1H), 9.42 (br, 1H); $^{19}$F NMR (282 MHz, DMSO-d$_6$): δ −202.45; LCMS: purity: 99.96%; MS (m/e): 463.68 (MH$^+$).

I-55: N2-(3-Aminosulfonylpyrid-4-yl)-N4-(4-cyanomethoxyphenyl)-5-fluoro-2,4-pyrimidinediamine $^1$H NMR (DMSO-d$_6$): δ 5.17 (s, 2H), 7.11 (d, J=9.0 Hz, 2H), 7.20 (d, J=7.5 Hz, 1H), 7.66 (d, J=8.7 Hz, 2H), 8.53 (d, J=3.3 Hz, 1H), 9.04 (dd, J=1.8, 7.5 Hz, 1H), 9.49 (d, J=1.8 Hz, 1H), 9.96 (br, 1H), 10.33 (br, 1H); $^{19}$F NMR (282 MHz, DMSO-d$_6$): δ −191.46; LCMS: purity: 90.38%; MS (m/e): 416.91 (MH$^+$).

I-143: N2-(4-Aminosulfonylphenyl)-5-fluoro-N4-(4-methylaminocarbonylmethoxyphenyl)-2,4-pyrimidinediamine $^1$H NMR (DMSO-d$_6$): δ 2.66 (d, J=4.5 Hz, 3H), 4.46 (s, 2H), 6.96 (d, J=9.0 Hz, 2H), 7.17 (br, 2H), 7.60 (d, J=8.7 Hz, 2H), 7.63 (d, J=8.7 Hz, 2H), 7.74 (d, J=8.7 Hz, 2H), 8.05 (q, J=4.5 Hz, 1H), 8.16 (d, J=4.2 Hz, 1H), 9.70 (br, 1H), 9.87 (br, 1H); $^{19}$F NMR (282 MHz, DMSO-d$_6$): δ −201.19; LCMS: purity: 97.92%; MS (m/e): 447.73 (MH$^+$).

I-144: N2-(3-Aminosulfonylphenyl)-5-fluoro-N4-(4-methylaminocarbonylmethoxyphenyl)-2,4-pyrimidinediamine $^1$H NMR (DMSO-d$_6$): δ 2.66 (d, J=4.8 Hz, 3H), 4.44 (s, 2H), 6.93 (d, J=8.7 Hz, 2H), 7.27 (br, 2H), 7.37 (m, 2H), 7.63 (d, J=8.4 Hz, 2H), 7.89 (q, J=3.6 Hz, 1H), 8.00 (br, 2H), 8.11 (d, J=3.9 Hz, 1H), 9.58 (br, 1H), 9.68 (br, 1H); $^{19}$F NMR (282 MHz, DMSO-d$_6$): δ −201.64; LCMS: purity: 98.07%; MS (m/e): 447.62 (MH$^+$).

I-145: N2-(3-Aminosulfonyl-4-methylphenyl)-5-fluoro-N4-(4-methylaminocarbonylmethoxyphenyl)-2,4-pyrimidinediamine $^1$H NMR (DMSO-d$_6$): δ 2.52 (s, 3H), 2.65 (d, J=4.8 Hz, 3H), 4.45 (s, 2H), 6.93 (d, J=9.0 Hz, 2H), 7.21 (d, J=8.4 Hz, 1H), 7.29 (br, 2H), 7.61 (d, J=9.0 Hz, 2H), 7.78 (dd, J=2.1, 8.1 Hz, 1H), 7.95 (s, 1H), 8.02 (q, J=4.5 Hz, 1H), 8.13 (d, J=4.5 Hz, 1H), 9.80 (br, 2H); $^{19}$F NMR (282 MHz, DMSO-d$_6$): δ −201.31; LCMS: purity: 94.30%; MS (m/e): 461.73 (MH$^+$).

I-128: N2-(4-Aminosulfonylphenyl)-N4-(4-dimethylaminocarbonylmethoxyphenyl)-5-fluoro-2,4-pyrimidinediamine $^1$H NMR (DMSO-d$_6$): δ 2.85 (s, 3H), 3.00 (s, 3H), 4.80 (s, 2H), 6.91 (d, J=8.7 Hz, 2H), 7.17 (br, 2H), 7.53 (d, J=8.4 Hz, 2H), 7.63 (d, J=8.4 Hz, 2H), 7.72 (d, J=8.4 Hz, 2H), 8.16 (d, J=3.9 Hz, 1H), 9.76 (br, 1H), 9.93 (br, 1H); $^{19}$F NMR (282 MHz, DMSO-d$_6$): δ −201.18; LCMS: purity: 95.72%; MS (m/e): 461.70 (MH$^+$).

I-129: N2-(3-Aminosulfonylphenyl)-N4-(4-dimethylaminocarbonylmethoxyphenyl)-5-fluoro-2,4-pyrimidinediamine $^1$H NMR (DMSO-d$_6$): δ 2.85 (s, 3H), 3.00 (s, 3H), 4.78 (s, 2H), 6.88 (d, J=8.4 Hz, 2H), 7.24 (br, 2H), 7.33 (m, 2H), 7.62 (d, J=8.7 Hz, 2H), 7.92 (d, J=7.8 Hz, 1H), 8.06 (d, J=2.7 Hz, 1H), 8.09 (s, 1H), 9.26 (br, 1H), 9.45 (br, 1H); $^{19}$F NMR (282 MHz, DMSO-d$_6$): δ −202.67; LCMS: purity: 89.45%; MS (m/e): 461.77 (MH$^+$).

I-130: N2-(3-Aminosulfonyl-4-methylphenyl)-N4-(4-dimethylaminocarbonylmethoxyphenyl)-5-fluoro-2,4-pyrimidinediamine $^1$H NMR (DMSO-d$_6$): δ 2.51 (s, 3H), 2.85 (s, 3H), 3.00 (s, 3H), 4.79 (s, 2H), 6.88 (d, J=9.0 Hz, 2H), 7.21 (d, J=8.4 Hz, 1H), 7.28 (br, 2H), 7.56 (d, J=9.0 Hz, 2H), 7.77 (dd, J=2.4, 8.4 Hz, 1H), 7.97 (d, J=2.1 Hz, 1H), 8.11 (d, J=4.5 Hz, 1H), 9.74 (br, 2H); $^{19}$F NMR (282 MHz, DMSO-d$_6$): δ 201.85; LCMS: purity: 97.67%; MS (m/e): 475.80 (MH$^+$).

I-56: N2-(3-Aminosulfonyl-4-methoxyphenyl)-N4-(4-cyanomethoxyphenyl)-5-fluoro-2,4-pyrimidinediamine $^1$H NMR (DMSO-d$_6$): δ 3.87 (s, 3H), 5.14 (s, 2H), 7.03 (br, 2H), 7.06 (d, J=9.3 Hz, 2H), 7.10 (d, J=8.7 Hz, 1H), 7.67 (d, J=9.0 Hz, 2H), 7.76 (dd, J=2.4, 9.0 Hz, 1H), 7.83 (s, 1H), 8.13 (d, J=4.2 Hz, 1H), 9.70 (br, 1H), 9.89 (br, 1H); $^{19}$F NMR (282 MHz, DMSO-d$_6$): δ −201.85; LCMS: purity: 90.15%; MS (m/e): 445.73 (MH$^+$).

I-57: N2-(4-Aminosulfonylphenyl)-N4-(4-cyanomethoxyphenyl-5)-methyl-2,4-pyrimidinediamine $^1$H NMR (DMSO-d$_6$): δ 2.16 (s, 3H), 5.18 (s, 2H), 7.12 (d, J=9.0 Hz, 2H), 7.24 (br, 2H), 7.52 (d, J=8.7 Hz, 2H), 7.58 (d, J=8.7 Hz, 2H), 7.64 (d, J=8.7 Hz, 2H), 7.91 (s, 1H), 9.64 (br, 1H), 10.38 (br, 1H); LCMS: purity: 96.78%; MS (m/e): 411.70 (MH$^+$).

I-58: N2-(3-Aminosulfonylphenyl)-N4-(4-cyanomethoxyphenyl)-5-methyl-2,4-pyrimidinediamine $^1$H NMR (DMSO-d$_6$): δ 2.10 (s, 3H), 5.15 (s, 2H), 7.04 (d, J=9.0 Hz, 2H), 7.23 (br, 2H), 7.29 (m, 2H), 7.67 (d, J=9.0 Hz, 2H), 7.87 (s, 1H), 7.99 (d, J=7.8 Hz, 1H), 8.04 (s, 1H), 8.28 (br, 1H), 9.27 (br, 1H); LCMS: purity: 95.23%; MS (m/e): 411.18 (MH+).

I-59: N2-(3-Aminosulfonyl-4-methylphenyl)-N4-(4-cyanomethoxyphenyl)-5-methyl-2,4-pyrimidinediamine $^1$H NMR (DMSO-d$_6$): δ 2.09 (s, 3H), 2.47 (s, 3H), 5.15 (s, 2H), 7.04 (d, J=9.0 Hz, 2H), 7.12 (d, J=8.4 Hz, 1H), 7.20 (br, 2H), 7.67 (d, J=8.7 Hz, 2H), 7.84 (s, 1H), 7.92 (dd, J=2.7, 8.1 Hz, 1H), 8.04 (d, J=2.1 Hz, 1H), 8.26 (br, 1H), 9.17 (br, 1H); LCMS: purity: 92.97%; MS (m/e): 425.72 (MH$^+$).

I-108: N4-(4-Aminocarbonylmethoxyphenyl)-N2-(4-aminosulfonylphenyl)-5-methyl-2,4-pyrimidinediamine $^1$H NMR (DMSO-d$_6$): δ 2.16 (s, 3H), 4.48 (s, 2H), 7.01 (d, J=8.1 Hz, 2H), 7.26 (br, 2H), 7.34 (br, 1H), 7.42 (d, J=8.4 Hz, 2H), 7.57 (d, J=8.4 Hz, 2H), 7.58 (br, 1H), 7.63 (d, J=8.4 Hz, 2H), 7.91 (s, 1H), 9.73 (br, 1H), 10.56 (br, 1H); LCMS: purity: 96.73%; MS (m/e): 429.17 (MH$^+$).

I-109: N4-(4-Aminocarbonylmethoxyphenyl)-N2-(3-aminosulfonylphenyl)-5-methyl-2,4-pyrimidinediamine $^1$H NMR (DMSO-d$_6$): δ 2.16 (s, 3H), 4.45 (s, 2H), 6.97 (d, J=9.0 Hz, 2H), 7.39 (m, 6H), 7.52 (d, J=7.5 Hz, 2H), 7.64 (s, 1H), 7.78 (d, J=9.3 Hz, 1H), 7.88 (s, 1H), 9.70 (br, 1H), 10.49 (br, 1H); LCMS: purity: 93.75%; MS (m/e): 429.22 (MH$^+$).

I-110: N4-(4-Aminocarbonylmethoxyphenyl)-N2-(3-aminosulfonyl-4-methylphenyl)-5-methyl-2,4-pyrimidinediamine $^1$H NMR (DMSO-d$_6$): δ 2.15 (s, 3H), 2.54 (s, 3H), 4.45 (s, 2H), 6.96 (d, J=8.7 Hz, 2H), 7.19 (d, J=8.4 Hz, 1H), 7.35 (br, 2H), 7.39 (br, 1H), 7.41 (d, J=9.0 Hz, 2H), 7.54 (br, 1H), 7.64 (dd, J=2.1, 8.1 Hz, 1H), 7.70 (d, J=2.1 Hz, 1H), 7.84 (s, 1H), 9.65 (br, 1H), 10.35 (br, 1H); LCMS: purity: 94.04%; MS (m/e): 443.12 (MH$^+$).

I-157: N4-(4-Allylaminocarbonylmethoxyphenyl)-N2-(4-aminosulfonylphenyl)-5-fluoro-2,4-pyrimidinediamine $^1$H NMR (DMSO-d$_6$): δ 3.77 (t, J=5.4 Hz, 2H), 4.50 (s, 2H), 5.02-5.13 (m, 2H), 5.78 (m, 1H), 6.96 (d, J=9.3 Hz, 2H), 7.11 (br, 2H), 7.60 (d, J=8.4 Hz, 2H), 7.63 (d, J=8.4 Hz, 2H), 7.79 (d, J=8.7 Hz, 2H), 8.09 (d, J=3.6 Hz, 1H), 8.27 (t, J=5.7 Hz, 1H), 9.34 (br, 1H), 9.56 (br, 1H); $^{19}$F NMR (282 MHz, DMSO-d$_6$): δ −202.14; LCMS: purity: 92.65%; MS (m/e): 473.14 (MH$^+$).

I-158: N4-(4-Allylaminocarbonylmethoxyphenyl)-N2-(3-aminosulfonylphenyl)-5-fluoro-2,4-pyrimidinediamine $^1$H NMR (DMSO-d$_6$): δ 3.76 (t, J=5.4 Hz, 2H), 4.49 (s, 2H), 5.02-5.13 (m, 2H), 5.80 (m, 1H), 6.94 (d, J=9.3 Hz, 2H), 7.27 (br, 2H), 7.37 (m, 2H), 7.65 (d, J=9.0 Hz, 2H), 7.90 (td, J=2.1, 6.6 Hz, 1H), 8.01 (s, 1H), 8.10 (d, J=4.2 Hz, 1H), 8.26 (t, J=4.5 Hz, 1H), 9.52 (br, 1H), 9.64 (br, 1H); $^{19}$F NMR (282 MHz, DMSO-d$_6$): δ −201.86; LCMS: purity: 98.60%; MS (m/e): 473.22 (MH$^+$).

I-159: N4-(4-Allylaminocarbonylmethoxyphenyl)-N2-(3-aminosulfonyl-4-methylphenyl)-5-fluoro-2,4-pyrimidinediamine $^1$H NMR (DMSO-d$_6$): δ 2.51 (s, 3H), 3.76 (t, J=5.4 Hz, 2H), 4.50 (s, 2H), 5.00-5.12 (m, 2H), 5.79 (m, 1H), 6.94 (d, J=9.3 Hz, 2H), 7.20 (d, J=9.0 Hz, 1H), 7.28 (br, 2H), 7.62 (d, J=9.0 Hz, 2H), 7.79 (dd, J=2.7, 8.4 Hz, 1H), 7.97 (s, 1H), 8.11 (d, J=4.2 Hz, 1H), 8.26 (t, J=6.0 Hz, 1H), 9.72 (br, 2H); $^{19}$F NMR (282 MHz, DMSO-d$_6$): δ −201.73; LCMS: purity: 92.70%; MS (m/e): 487.80 (MH$^+$).

I-131: N2-(4-Aminosulfonylphenyl)-N4-(3-chloro-4-dimethylaminocarbonylmethoxyphenyl)-5-fluoro-2,4-pyrimidinediamine $^1$H NMR (DMSO-d$_6$): δ 2.85 (s, 3H), 3.01 (s, 3H), 4.92 (s, 2H), 6.98 (d, J=9.0 Hz, 1H), 7.11 (br, 2H), 7.54 (dd, J=2.7, 9.3 Hz, 1H), 7.63 (d, J=8.7 Hz, 2H), 7.77 (d, J=8.7 Hz, 2H), 7.78 (s, 1H), 8.12 (d, J=3.3 Hz, 1H), 9.40 (br, 1H), 9.62 (br, 1H); $^{19}$F NMR (282 MHz, DMSO-d$_6$): δ −202.11; LCMS: purity: 92.42%; MS (m/e): 495.42 (MH$^+$).

I-132: N2-(3-Aminosulfonylphenyl)-N4-(3-chloro-4-dimethylaminocarbonylmethoxyphenyl)-5-fluoro-2,4-pyrimidinediamine $^1$H NMR (DMSO-d$_6$): δ 2.85 (s, 3H), 3.00 (s, 3H), 4.92 (s, 2H), 6.96 (d, J=9.0 Hz, 1H), 7.27 (br, 2H), 7.38 (m, 2H), 7.61 (dd, J=2.4, 9.0 Hz, 1H), 7.74 (d, J=2.4 Hz, 1H), 7.93 (d, J=7.5 Hz, 1H), 7.98 (s, 1H), 8.13 (d, J=4.2 Hz, 1H), 9.56 (br, 1H), 9.69 (br, 1H); $^{19}$F NMR (282 MHz, DMSO-d$_6$): δ −201.89; LCMS: purity: 96.46%; MS (m/e): 495.04 (MH$^+$).

I-133: N2-(3-Aminosulfonyl-4-methylphenyl)-N4-(3-chloro-4-dimethylaminocarbonylmethoxyphenyl)-5-fluoro-2,4-pyrimidinediamine $^1$H NMR (DMSO-d$_6$): δ 2.49 (s, 3H), 2.85 (s, 3H), 3.00 (s, 3H), 4.92 (s, 2H), 6.95 (d, J=9.0 Hz, 1H), 7.19 (d, J=8.4 Hz, 1H), 7.24 (br, 2H), 7.62 (dd, J=3.0, 9.3 Hz, 1H), 7.75 (d, J=2.4 Hz, 1H), 7.85 (dd, J=2.4, 8.4 Hz, 1H), 8.01 (d, J=2.4 Hz, 1H), 8.09 (d, J=3.6 Hz, 1H), 9.47 (br, 1H), 9.53 (br, 1H); $^{19}$F NMR (282 MHz, DMSO-d$_6$): δ −202.56; LCMS: purity: 93.71%; MS (m/e): 509.06 (MH$^+$).

I-210: N2-(4-Aminosulfonylphenyl)-5-fluoro-N4-[4-(2-morpholin-4-yl-2-oxo-ethoxy)phenyl]-2,4-pyrimidinediamine $^1$H NMR (DMSO-d$_6$): δ 3.47 (m, 4H), 3.54-3.60 (m, 4H), 4.83 (s, 2H), 6.93 (d, J=9.0 Hz, 2H), 7.16 (br, 2H), 7.55 (d, J=9.0 Hz, 2H), 7.63 (d, J=9.0 Hz, 2H), 7.73 (d, J=8.7 Hz, 2H), 8.16 (d, J=4.2 Hz, 1H), 9.72 (br, 1H), 9.90 (br, 1H); $^{19}$F NMR (282 MHz, DMSO-d$_6$): δ −201.25; LCMS: purity: 95.60%; MS (m/e): 503.81 (MH$^+$).

I-211: N2-(3-Aminosulfonylphenyl)-5-fluoro-N4-[4-(2-morpholin-4-yl-2-oxo-ethoxy)phenyl]-2,4-pyrimidinediamine $^1$H NMR (DMSO-d$_6$): δ 3.46 (m, 4H), 3.56-3.60 (m, 4H), 4.82 (s, 2H), 6.90 (d, J=9.0 Hz, 2H), 7.30 (br, 2H), 7.40 (m, 2H), 7.57 (d, J=9.0 Hz, 2H), 7.85 (m, 1H), 7.95 (s, 1H), 8.15 (d, J=4.5 Hz, 1H), 9.78 (br, 1H), 9.87 (br, 1H); $^{19}$F NMR (282 MHz, DMSO-d$_6$): δ −201.26; LCMS: purity: 94.18%; MS (m/e): 503.75 (MH$^+$).

I-212: N2-(3-Aminosulfonyl-4-methylphenyl)-5-fluoro-N4-[4-(2-morpholin-4-yl-2-oxo-ethoxy)phenyl]-2,4-pyrimidinediamine $^1$H NMR (DMSO-d$_6$): δ 3.46 (m, 4H), 3.56-3.61 (m, 4H), 4.82 (s, 2H), 6.89 (d, J=9.0 Hz, 2H), 7.22 (d, J=8.4 Hz, 1H), 7.29 (br, 2H), 7.56 (d, J=9.0 Hz, 2H), 7.75 (dd, J=2.7, 8.4 Hz, 1H), 7.94 (s, 1H), 8.14 (d, J=4.2 Hz, 1H), 9.86 (br, 2H); $^{19}$F NMR (282 MHz, DMSO-d$_6$): δ −201.34; LCMS: purity: 91.60%; MS (m/e): 517.75 (MH$^+$).

III-119: N2-(4-Aminosulfonylphenyl)-N4-(4-ethylaminocarbonylaminomethylphenyl]-5-fluoro-2,4-pyrimidinediamine $^1$H NMR (DMSO-d$_6$): δ 1.00 (t, J=7.2 Hz, 3H), 3.03 (q, J=7.2 Hz, 2H), 4.18 (s, 2H), 7.16 (br, 2H), 7.22 (d, J=8.7 Hz, 2H), 7.63 (d, J=8.7 Hz, 4H), 7.76 (d, J=9.0 Hz, 2H), 8.16 (d, J=3.6 Hz, 1H), 9.63 (br, 1H), 9.76 (br, 1H); $^{19}$F NMR (282 MHz, DMSO-d$_6$): δ −201.17; LCMS: purity: 100%; MS (m/e): 460.54 (MH$^+$).

III-120: N2-(3-Aminosulfonylphenyl]-N4-(4-ethylaminocarbonylaminomethylphenyl)-5-fluoro-2,4-pyrimidinediamine $^1$H NMR (DMSO-d$_6$): δ 1.00 (t, J=7.2 Hz, 3H), 3.03 (q, J=7.2 Hz, 2H), 4.16 (s, 2H), 7.20 (d, J=8.4 Hz, 2H), 7.28 (br, 2H), 7.38 (m, 2H), 7.66 (d, J=8.4 Hz, 2H), 7.92 (m, 1H), 8.00 (s, 1H), 8.14 (d, J=4.2 Hz, 1H), 9.66 (br, 1H), 9.74 (br, 1H); $^{19}$F NMR (282 MHz, DMSO-d$_6$): δ −201.25; LCMS: purity: 97.96%; MS (m/e): 460.17 (MH$^+$).

III-121: N2-(3-Aminosulfonyl-4-methylphenyl)-N4-(4-ethylaminocarbonylaminomethylphenyl)-5-fluoro-2,4-pyrimidinediamine $^1$H NMR (DMSO-d$_6$): δ 1.00 (t, J=7.2 Hz, 3H), 3.03 (p, J=7.2 Hz, 2H), 4.16 (d, J=5.7 Hz, 2H), 5.85 (t, J=5.4 Hz, 1H), 6.24 (t, J=6.0 Hz, 1H), 7.16 (d, J=6.9 Hz, 1H), 7.18 (d, J=8.1 Hz, 2H), 7.22 (br, 2H), 7.71 (d, J=8.4 Hz, 2H), 7.90 (dd, J=2.4, 8.1 Hz, 1H), 8.06 (d, J=3.9 Hz, 1H), 8.10 (d, J=2.1 Hz, 1H), 9.30 (br, 1H), 9.37 (br, 1H); $^{19}$F NMR (282 MHz, DMSO-d$_6$): δ −202.63; LCMS: purity: 88.98%; MS (m/e): 474.75 (MH$^+$).

I-146: N2-(4-Aminosulfonylphenyl)-N4-(3-chloro-4-methylaminocarbonylmethoxyphenyl)-5-fluoro-2,4-pyrimidinediamine $^1$H NMR (DMSO-d$_6$): δ 2.67 (d, J=4.8 Hz, 3H), 4.57 (s, 2H), 7.02 (d, J=9.0 Hz, 1H), 7.14 (br, 2H), 7.60 (dd, J=2.7, 9.0 Hz, 1H), 7.65 (d, J=9.0 Hz, 2H), 7.77 (d, J=9.0 Hz, 2H), 7.86 (d, J=2.7 Hz, 1H), 7.91 (d, J=5.1 Hz, 1H), 8.16 (d, J=3.9 Hz, 1H), 9.58 (br, 1H), 9.75 (br, 1H); $^{19}$F NMR (282 MHz, DMSO-d$_6$): δ −201.52; LCMS: purity: 97.14%; MS (m/e): 481.41 (MH$^+$).

I-147: N2-(3-Aminosulfonylphenyl)-N4-(3-chloro-4-methylaminocarbonylmethoxyphenyl)-5-fluoro-2,4-pyrimidinediamine $^1$H NMR (DMSO-d$_6$): δ 2.67 (d, J=4.5 Hz, 3H), 4.56 (s, 2H), 7.00 (d, J=8.7 Hz, 1H), 7.28 (br, 2H), 7.39 (m, 2H), 7.68 (dd, J=2.4, 8.7 Hz, 1H), 7.80 (d, J=2.4 Hz, 1H), 7.89 (d, J=4.2 Hz, 1H), 7.94 (d, J=2.1, 7.2 Hz, 1H), 7.98 (s, 1H), 8.15 (d, J=3.9 Hz, 1H), 9.62 (br, 1H), 9.73 (br, 1H); $^{19}$F NMR (282 MHz, DMSO-d$_6$): δ −201.68; LCMS: purity: 97.93%; MS (m/e): 481.40 (MH$^+$).

I-148: N2-(3-Aminosulfonyl-4-methylphenyl)-N4-(3-chloro-4-methylaminocarbonylmethoxyphenyl)-5-fluoro-2,4-pyrimidinediamine $^1$H NMR (DMSO-d$_6$): δ 2.51 (s, 3H), 2.67 (d, J=4.8 Hz, 3H), 4.56 (s, 2H), 7.00 (d, J=9.3 Hz, 1H), 7.22 (d, J=8.7 Hz, 1H), 7.28 (br, 2H), 7.65 (dd, J=2.4, 8.7 Hz, 1H), 7.79 (d, J=2.7 Hz, 1H), 7.82 (dd, J=2.4, 8.1 Hz, 1H), 7.89 (d, J=4.2 Hz, 1H), 7.95 (d, J=2.4 Hz, 1H), 8.15 (d, J=4.5 Hz, 1H), 9.79 (br, 2H); $^{19}$F NMR (282 MHz, DMSO-d$_6$): δ −201.59; LCMS: purity: 93.21%; MS (m/e): 495.44 (MH$^+$).

I-213: 5-Fluoro-N4-(4-methoxycarbonylmethoxyphenyl)-N2-(4-methyl-3-propionylaminosulfonylphenyl)-2,4-pyrimidinediamine LCMS: purity: 94.24%; MS (m/e): 518.82 (MH$^+$).

I-134: N2-(4-Aminosulfonylphenyl)-N4-(3-chloro-4-dimethylaminocarbonylmethoxyphenyl)-5-methyl-2,4-pyrimidinediamine $^1$H NMR (DMSO-d$_6$): δ 2.15 (s, 3H), 2.86 (s, 3H), 3.01 (s, 3H), 4.97 (s, 2H), 7.03 (d, J=9.3 Hz, 1H), 7.24 (br, 2H), 7.37 (dd, J=2.4, 9.0 Hz, 1H), 7.58 (d, J=9.0 Hz, 2H), 7.65 (d, J=3.0 Hz, 1H), 7.69 (d, J=8.7 Hz, 2H), 7.93 (s, 1H), 9.66 (br, 1H), 10.53 (br, 1H); LCMS: purity: 93.31%; MS (m/e): 491.44 (MH$^+$).

I-135: N2-(3-Aminosulfonylphenyl)-N4-(3-chloro-4-dimethylaminocarbonylmethoxyphenyl)-5-methyl-2,4-pyrimidinediamine $^1$H NMR (DMSO-d$_6$): δ 2.14 (s, 3H), 2.86 (s, 3H), 3.01 (s, 3H), 4.96 (s, 2H), 7.00 (d, J=9.0 Hz, 1H), 7.34 (br, 2H), 7.40-7.49 (m, 3H), 7.59 (d, J=2.7 Hz, 1H), 7.70 (s, 1H), 7.84 (d, J=7.2 Hz, 1H), 7.89 (s, 1H), 9.44 (br, 1H), 10.24 (br, 1H); LCMS: purity: 96.97%; MS (m/e): 491.47 (MH$^+$).

I-136: N2-(3-Aminosulfonyl-4-methylphenyl)-N4-(3-chloro-4-dimethylaminocarbonylmethoxyphenyl)-5-methyl-2,4-pyrimidinediamine $^1$H NMR (DMSO-d$_6$): δ 2.13 (s, 3H), 2.52 (s, 3H), 2.86 (s, 3H), 3.01 (s, 3H), 4.96 (s, 2H), 6.98 (d, J=9.0 Hz, 1H), 7.24 (d, J=8.7 Hz, 1H), 7.34 (br, 2H), 7.42 (dd, J=2.4, 8.4 Hz, 1H), 7.59 (d, J=2.4 Hz, 1H), 7.71 (d, J=8.4 Hz, 1H), 7.75

(s, 1H), 7.84 (s, 1H), 9.40 (br, 1H), 10.13 (br, 1H); LCMS: purity: 93.42%; MS (m/e): 505.10 (MH$^+$).

I-137: N2-(4-Aminosulfonylphenyl)-N4-(4-dimethylaminocarbonylmethoxy-3-fluorophenyl)-5-methyl-2,4-pyrimidinediamine $^1$H NMR (DMSO-d$_6$): δ 2.15 (s, 3H), 2.86 (s, 3H), 3.00 (s, 3H), 4.93 (s, 2H), 7.06 (t, J=9.0 Hz, 1H), 7.23 (d, J=16.2 Hz, 1H), 7.26 (br, 2H), 7.50 (d, J=12.9 Hz, 1H), 7.59 (d, J=8.7 Hz, 2H), 7.66 (d, J=8.7 Hz, 2H), 7.92 (s, 1H), 9.66 (br, 1H), 10.51 (br, 1H); $^{19}$F NMR (282 MHz, DMSO-d$_6$): δ 172.68; LCMS: purity: 98.26%; MS (m/e): 475.63 (MH$^+$).

I-138: N2-(3-Aminosulfonylphenyl)-N4-(4-dimethylaminocarbonylmethoxy-3-fluorophenyl)-5-methyl-2,4-pyrimidinediamine $^1$H NMR (DMSO-d$_6$): δ 2.15 (s, 3H), 2.86 (s, 3H), 3.00 (s, 3H), 4.93 (s, 2H), 7.04 (t, J=9.3 Hz, 1H), 7.23 (d, J=8.7 Hz, 1H), 7.36 (br, 2H), 7.39-7.49 (m, 3H), 7.69 (s, 1H), 7.83 (d, J=6.9 Hz, 1H), 7.89 (s, 1H), 9.57 (br, 1H), 10.36 (br, 1H); $^{19}$F NMR (282 MHz, DMSO-d$_6$): δ −172.80; LCMS: purity: 98.80%; MS (m/e): 475.57 (MH$^+$).

I-139: N2-(3-Aminosulfonyl-4-methylphenyl)-N4-(4-dimethylaminocarbonylmethoxy-3-fluorophenyl)-5-methyl-2,4-pyrimidinediamine $^1$H NMR (DMSO-d$_6$): δ 2.14 (s, 3H), 2.53 (s, 3H), 2.85 (s, 3H), 3.00 (s, 3H), 4.92 (s, 2H), 7.02 (t, J=9.0 Hz, 1H), 7.24 (d, J=8.1 Hz, 2H), 7.34 (br, 2H), 7.48 (d, J=12.9 Hz, 1H), 7.71 (d, J=8.4 Hz, 1H), 7.76 (s, 1H), 7.84 (s, 1H), 9.44 (br, 1H), 10.17 (br, 1H); $^{19}$F NMR (282 MHz, DMSO-d$_6$): δ 172.82; LCMS: purity: 96.33%; MS (m/e): 489.12 (MH$^+$).

I-149: N2-(4-Aminosulfonylphenyl)-N4-(3-chloro-4-methylaminocarbonylmethoxyphenyl)-5-methyl-2,4-pyrimidinediamine $^1$H NMR (DMSO-d$_6$): δ 2.15 (s, 3H), 2.68 (d, J=4.5 Hz, 3H), 4.61 (s, 2H), 7.08 (d, J=9.0 Hz, 1H), 7.26 (br, 2H), 7.42 (dd, J=2.7, 9.0 Hz, 1H), 7.60 (d, J=9.0 Hz, 2H), 7.68 (d, J=8.7 Hz, 2H), 7.71 (d, J=1.8 Hz, 1H), 7.93 (s, 2H), 9.60 (br, 1H), 10.45 (br, 1H); LCMS: purity: 90.13%; MS (m/e): 476.99 (MH$^+$).

I-150: N2-(3-Aminosulfonylphenyl)-N4-(3-chloro-4-methylaminocarbonylmethoxyphenyl)-5-methyl-2,4-pyrimidinediamine $^1$H NMR (DMSO-d$_6$): δ 2.15 (s, 3H), 2.68 (d, J=4.8 Hz, 3H), 4.60 (s, 2H), 7.04 (d, J=9.0 Hz, 1H), 7.36 (br, 2H), 7.46 (m, 4H), 7.63 (d, J=2.4 Hz, 1H), 7.83 (d, J=8.7 Hz, 1H), 7.92 (s, 2H), 9.66 (br, 1H), 10.50 (br, 1H); LCMS: purity: 85.98%; MS (m/e): 476.96 (MH$^+$).

I-151: N2-(3-Aminosulfonyl-4-methylphenyl)-N4-(3-chloro-4-methylaminocarbonylmethoxyphenyl)-5-methyl-2,4-pyrimidinediamine $^1$H NMR (DMSO-d$_6$): δ 2.14 (s, 3H), 2.67 (d, J=4.5 Hz, 3H), 4.60 (s, 2H), 7.03 (d, J=9.3 Hz, 1H), 7.24 (d, J=7.8 Hz, 1H), 7.36 (br, 2H), 7.45 (d, J=9.3 Hz, 1H), 7.63 (d, J=2.4 Hz, 1H), 7.69 (d, J=9.3 Hz, 1H), 7.71 (s, 1H), 7.86 (s, 1H), 7.91 (d, J=4.8 Hz, 1H), 9.60 (br, 1H), 10.32 (br, 1H); LCMS: purity: 98.01%; MS (m/e): 491.00 (MH$^+$).

Example 33

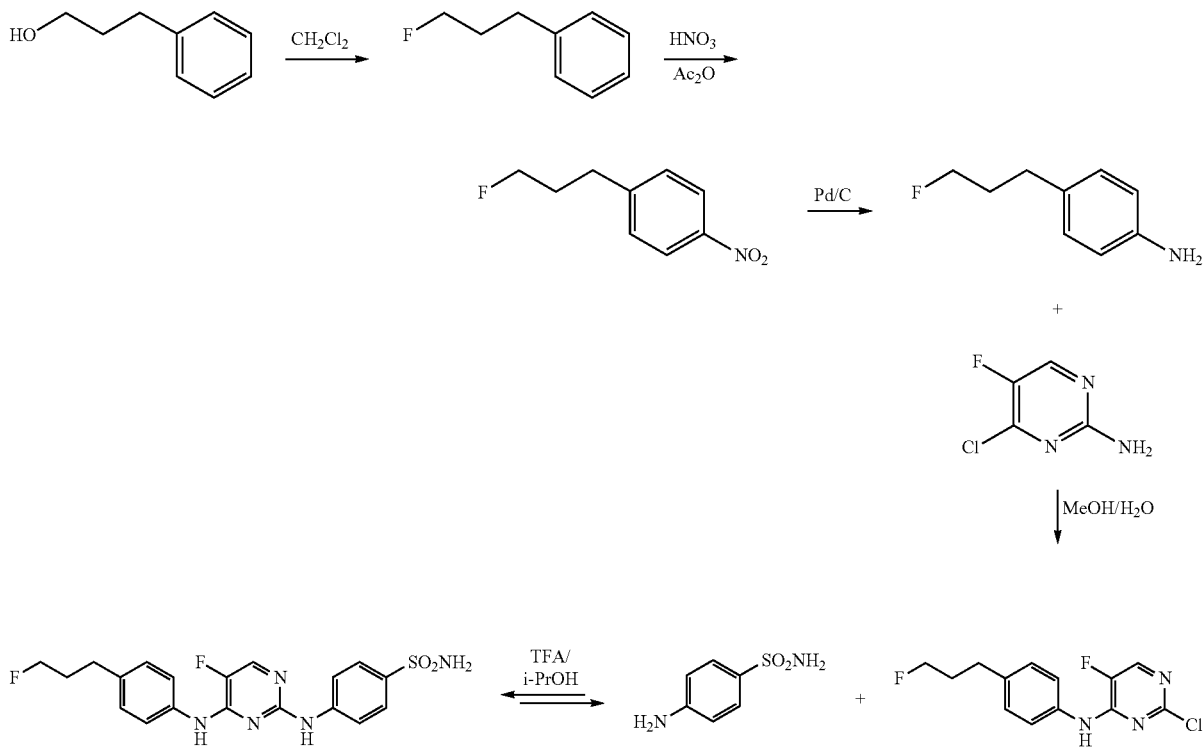

VI-82: N2-(4-Aminosulfonylphenyl)-5-fluoro-N4-[4-(3-fluoropropyl)phenyl]-2,4-pyrimidinediamine 3-Phenyl-1-propanol (1 mL) and (diethylamino)sulfur trifluoride (1.2 mL) were dissolved in dichloromethane (10 mL). The reaction solution was stirred at rt for 3 d. The reaction mixture was passed through a short silica gel column and washed with dichloromethane. The collected solution was evaporated to give 1-fluoro-3-phenylpropane as light yellow oil. $^1$H NMR (DMSO-d$_6$): δ 1.84-2.02 (m, 2H), 2.65 (t, J=7.5 Hz, 2H), 4.34 (t, J=5.7 Hz, 1H), 4.50 (t, J=5.7 Hz, 1H), 7.20 (m, 5H); $^{19}$F NMR (282 MHz, DMSO-d$_6$): δ −79.22.

1-Fluoro-3-phenylpropane was dissolved in acetic anhydride (10 mL) and to the solution was added acetic acid (1 mL) and fuming nitric acid (1 mL) at 0° C. The reaction mixture was reacted at rt and to 60° C. for 1 h, then diluted with ethyl acetate (100 mL). The organic solution was washed with water (3×100 mL) and brine (100 mL), and evaporated to give 1-fluoro-3-(4-nitrophenyl)propane.

1-Fluoro-3-(4-nitrophenyl)propane was dissolved in methanol (50 mL) and to the solution was added 10% Pd—C. The reaction mixture was reacted under hydrogen atmosphere (~40 psi) for 1 h. The catalyst was filtered off over celite. The filtrate was evaporated to give 4-(3-fluoropropyl)analine.

4-(3-Fluoropropyl)aniline and 2,6-dichloro-5-fluoropyrimidine (1.5 g) were dissolved in methanol (5 mL) and water (1 mL). The reaction solution was stirred at rt for 3 d. The reaction solution was diluted with water (100 mL) and extracted with ethyl acetate (2×100 mL). The organic layers were evaporated and purified by flash column chromatography (EtOAc/hexanes=¼, ½) to give 2-chloro-5-fluoro-N4-[4-(3-fluoropropyl)phenyl]-4-pyrimidineamine.

2-Chloro-5-fluoro-N4-[4-(3-fluoropropyl)phenyl]-4-pyrimidineamine (100 mg) and sulfanilamide (100 mg) were suspended in isopropanol (1 mL) and TFA (5 drops). The solution was heated at 100° C. overnight. The solution was evaporated and purified by flash column chromatography (2.0 M NH$_3$/MeOH in dichloromethane=1-3%) and recrystallized from ethyl acetate to give N2-(4-aminosulfonylphenyl)-5-fluoro-N4-[4-(3-fluoropropyl)phenyl]-2,4-pyrimidinediamine $^1$H NMR (DMSO-d$_6$): δ 1.89-2.02 (m, 2H), 2.67 (t, J=8.1 Hz, 2H), 4.38 (t, J=5.7 Hz, 1H), 4.53 (t, J=5.7 Hz, 1H), 7.11 (br, 2H), 7.19 (d, J=8.1 Hz, 2H), 7.60 (d, J=8.7 Hz, 2H), 7.65 (d, J=8.1 Hz, 2H), 7.80 (d, J=8.7 Hz, 2H), 8.12 (d, J=3.9 Hz, 1H), 9.38 (br, 1H), 9.57 (br, 1H); $^{19}$F NMR (282 MHz, DMSO-d$_6$): δ −201.79; LCMS: purity: 91.96%; MS (m/e): 420.74 (MH$^+$).

The following compounds were made in a similar fashion to the above example or by methods described herein or known to skilled artisans.

VI-83: N2-(3-Aminosulfonylphenyl)-5-fluoro-N4-[4-(3-fluoropropyl)phenyl]-2,4-pyrimidinediamine $^1$H NMR (DMSO-d$_6$): δ 1.88-2.01 (m, 2H), 2.65 (t, J=7.8 Hz, 2H), 4.37 (t, J=6.0 Hz, 1H), 4.52 (t, J=6.0 Hz, 1H), 7.17 (d, J=8.4 Hz, 2H), 7.24 (br, 2H), 7.37 (m, 2H), 7.70 (d, J=8.7 Hz, 2H), 7.95 (d, J=7.8 Hz, 1H), 8.09 (d, J=3.3 Hz, 2H), 9.32 (br, 1H), 9.48 (br, 1H); $^{19}$F NMR (282 MHz, DMSO-d$_6$): δ −202.10; LCMS: purity: 93.78%; MS (m/e): 420.78 (MH$^+$).

VI-84: N2-(3-Aminosulfonyl-4-methylphenyl)-5-fluoro-N4-[4-(3-fluoropropyl)phenyl]-2,4-pyrimidinediamine $^1$H NMR (DMSO-d$_6$): δ 1.88-1.98 (m, 2H), 2.65 (t, J=7.8 Hz, 2H), 4.36 (t, J=6.0 Hz, 1H), 4.52 (t, J=6.0 Hz, 1H), 7.17 (m, 5H), 7.70 (d, J=8.1 Hz, 2H), 7.88 (dd, J=2.4, 8.4 Hz, 1H), 8.05 (d, J=3.9 Hz, 1H), 8.10 (d, J=2.1 Hz, 1H), 9.27 (br, 1H), 9.37 (br, 1H); $^{19}$F NMR (282 MHz, DMSO-d$_6$): δ 202.68; LCMS: purity: 97.85%; MS (m/e): 434.92 (MH$^+$).

VI-85: N2-(4-Aminosulfonylphenyl)-5-fluoro-N4-[4-(3-hydroxypropyl)phenyl]-2,4-pyrimidinediamine $^1$H NMR (DMSO-d$_6$): δ 1.72 (p, J=7.2 Hz, 2H), 2.61 (t, J=7.5 Hz, 2H), 3.42 (t, J=6.3 Hz, 2H), 4.47 (br, 1H), 7.11 (br, 2H), 7.16 (d, J=8.4 Hz, 2H), 7.60 (d, J=9.0 Hz, 2H), 7.62 (d, J=8.4 Hz, 2H), 7.80 (d, J=9.0 Hz, 2H), 8.11 (d, J=3.9 Hz, 1H), 9.36 (br, 1H), 9.57 (br, 1H); $^{19}$F NMR (282 MHz, DMSO-d$_6$): δ −201.84; LCMS: purity: 97.76%; MS (m/e): 418.20 (MH$^+$).

VI-86: N2-(3-Aminosulfonylphenyl)-5-fluoro-N4-[4-(3-hydroxypropyl)phenyl]-2,4-pyrimidinediamine $^1$H NMR (DMSO-d$_6$): δ 1.71 (p, J=7.5 Hz, 2H), 2.58 (t, J=7.5 Hz, 2H), 3.41 (q, J=6.0 Hz, 2H), 4.44 (t, J=5.1 Hz, 1H), 7.14 (d, J=7.8 Hz, 2H), 7.24 (br, 2H), 7.34 (m, 2H), 7.67 (d, J=8.1 Hz, 2H), 7.95 (d, J=7.2 Hz, 1H), 8.08 (d, J=3.6 Hz, 2H), 9.29 (br, 1H), 9.47 (br, 1H); $^{19}$F NMR (282 MHz, DMSO-d$_6$): δ −202.16; LCMS: purity: 89.77%; MS (m/e): 418.18 (MH$^+$).

VI-87: N2-(3-Aminosulfonyl-4-methylphenyl)-5-fluoro-N4-[4-(3-hydroxypropyl)phenyl]-2,4-pyrimidinediamine LCMS: purity: 94.51%; MS (m/e): 432.66 (MH$^+$).

I-152: N2-(3-Aminosulfonyl-4-chlorophenyl)-N4-(3-chloro-4-methylaminocarbonylmethoxyphenyl)-5-fluoro-2,4-pyrimidinediamine $^1$H NMR (DMSO-d$_6$): δ 2.67 (d, J=4.8 Hz, 3H), 4.56 (s, 2H), 7.01 (d, J=9.0 Hz, 1H), 7.42 (d, J=8.7 Hz, 1H), 7.47 (br, 2H), 7.69 (dd, J=2.7, 8.7 Hz, 1H), 7.80 (d, J=2.4 Hz, 1H), 7.88 (br, 1H), 8.02 (dd, J=2.7, 8.7 Hz, 1H), 8.12 (d, J=3.9 Hz, 1H), 8.20 (d, J=2.4 Hz, 1H), 9.51 (br, 1H), 9.72 (br, 1H); $^{19}$F NMR (282 MHz, DMSO-d$_6$): δ −201.67; LCMS: purity: 91.37%; MS (m/e): 515.31 (MH$^+$).

I-140: N2-(3-Aminosulfonyl-4-chlorophenyl)-N4-(3-chloro-4-dimethylaminocarbonylmethoxyphenyl)-5-fluoro-2,4-pyrimidinediamine $^1$H NMR (DMSO-d$_6$): δ 2.85 (s, 3H), 3.01 (s, 3H), 4.93 (s, 2H), 6.96 (d, J=9.0 Hz, 1H), 7.41 (d, J=9.0 Hz, 1H), 7.46 (br, 2H), 7.61 (dd, J=2.4, 9.0 Hz, 1H), 7.72 (d, J=2.7 Hz, 1H), 8.01 (dd, J=2.7, 9.0 Hz, 1H), 8.10 (d, J=3.6 Hz, 1H), 8.20 (d, J=2.4 Hz, 1H), 9.43 (br, 1H), 9.67 (br, 1H); $^{19}$F NMR (282 MHz, DMSO-d$_6$): δ −202.04; LCMS: purity: 91.74%; MS (m/e): 529.35 (MH$^+$).

I-141: N2-(3-Aminosulfonyl-4-chlorophenyl)-N4-(3-chloro-4-dimethylaminocarbonylmethoxyphenyl)-5-methyl-2,4-pyrimidinediamine $^1$H NMR (DMSO-d$_6$): δ 2.13 (s, 3H), 2.87 (s, 3H), 3.01 (s, 3H), 4.97 (s, 2H), 7.00 (d, J=8.7 Hz, 1H), 7.44 (d, J=8.7 Hz, 2H), 7.54 (br, 2H), 7.58 (d, J=2.4 Hz, 1H), 7.88 (m, 2H), 7.96 (s, 1H), 9.26 (br, 1H), 10.12 (br, 1H); LCMS: purity: 97.43%; MS (m/e): 525.37 (MH$^+$).

I-142: N2-(3-Aminosulfonyl-4-chlorophenyl)-N4-(4-dimethylaminocarbonylmethoxy-3-fluorophenyl)-5-methyl-2,4-pyrimidinediamine $^1$H NMR (DMSO-d$_6$): δ 2.14 (s, 3H), 2.86 (s, 3H), 3.00 (s, 3H), 4.94 (s, 2H), 7.04 (t, J=9.3 Hz, 1H), 7.25 (d, J=8.7 Hz, 1H), 7.45 (d, J=9.0 Hz, 1H), 7.46 (dd, 1H), 7.55 (br, 2H), 7.89 (m, 2H), 7.96 (s, 1H), 9.39 (br, 1H), 10.26 (br, 1H); $^{19}$F NMR (282 MHz, DMSO-d$_6$): δ −172.86; LCMS: purity: 99.33%; MS (m/e): 509.19 (MH$^+$).

I-153: N2-(3-Aminosulfonyl-4-chlorophenyl)-N4-(3-chloro-4-methylaminocarbonylmethoxyphenyl)-5-methyl-2,4-pyrimidinediamine $^1$H NMR (DMSO-d$_6$): δ 2.09 (s, 3H), 2.68 (d, J=4.5 Hz, 3H), 4.56 (s, 2H), 7.00 (d, J=9.0 Hz, 1H), 7.35 (d, J=9.0 Hz, 1H), 7.43 (br, 2H), 7.67 (d, J=8.7 Hz, 1H), 7.71 (s, 1H), 7.89 (s, 2H), 8.07 (d, J=8.7 Hz, 1H), 8.21 (s, 1H), 8.33 (s, 1H), 9.44 (br, 1H); LCMS: purity: 98.98%; MS (m/e): 511.34 (MH$^+$).

VI-88: N2-(4-Aminosulfonylphenyl)-5-fluoro-N4-[4-(4-hydroxybutyl)phenyl]-2,4-pyrimidinediamine $^1$H NMR (DMSO-d$_6$): δ 1.44 (m, 2H), 1.60 (m, 2H), 2.57 (t, J=7.5 Hz, 2H), 3.41 (q, J=6.0 Hz, 2H), 4.37 (t, J=5.1 Hz, 1H), 7.11 (br, 2H), 7.16 (d, J=8.7 Hz, 2H), 7.60 (d, J=8.7 Hz, 2H), 7.62 (d, J=8.4 Hz, 2H), 7.80 (d, J=9.0 Hz, 2H), 8.11 (d, J=3.6 Hz, 1H), 9.36 (br, 1H), 9.57 (br, 1H); $^{19}$F NMR (282 MHz, DMSO-d$_6$): δ −201.84; LCMS: purity: 90.99%; MS (m/e): 432.24 (MH$^+$).

VI-89: N2-(3-Aminosulfonylphenyl)-5-fluoro-N4-[4-(4-hydroxybutyl)phenyl]-2,4-pyrimidinediamine $^1$H NMR (DMSO-d$_6$): δ 1.43 (m, 2H), 1.59 (m, 2H), 2.55 (t, J=7.5 Hz, 2H), 3.40 (q, J=5.8 Hz, 2H), 4.36 (t, J=4.8 Hz, 1H), 7.13 (d, J=8.4 Hz, 2H), 7.21 (br, 2H), 7.33 (m, 2H), 7.67 (d, J=8.4 Hz, 2H), 7.95 (d, J=6.9 Hz, 2H), 8.08 (d, J=3.9 Hz, 2H), 9.29 (br, 1H), 9.47 (br, 1H); $^{19}$F NMR (282 MHz, DMSO-d$_6$): δ −202.14; LCMS: purity: 92.80%; MS (m/e): 432.24 (MH$^+$).

VI-90: N2-(3-Aminosulfonyl-4-methylphenyl)-5-fluoro-N4-[4-(4-hydroxybutyl)phenyl]-2,4-pyrimidinediamine LCMS: purity: 91.08%; MS (m/e): 446.51 (MH$^+$).

VI-91: N2-(4-Aminosulfonylphenyl)-5-fluoro-N4-[4-(4-fluorobutyl)phenyl]-2,4-pyrimidinediamine $^1$H NMR (DMSO-d$_6$): δ 1.64-1.69 (m, 4H), 2.62 (t, J=6.9 Hz, 2H), 4.38 (t, J=5.7 Hz, 1H), 4.54 (t, J=6.0 Hz, 1H), 7.11 (br, 2H), 7.18 (d, J=8.7 Hz, 2H), 7.60 (d, J=9.3 Hz, 2H), 7.63 (d, J=8.4 Hz, 2H), 7.80 (d, J=9.0 Hz, 2H), 8.12 (d, J=3.9 Hz, 1H), 9.37 (br, 1H), 9.58 (br, 1H); $^{19}$F NMR (282 MHz, DMSO-d$_6$): δ −201.85; LCMS: purity: 89.65%; MS (m/e): 434.59 (MH$^+$).

VI-92: N2-(3-Aminosulfonylphenyl)-5-fluoro-N4-[4-(4-fluorobutyl)phenyl]-2,4-pyrimidinediamine $^1$H NMR (DMSO-d$_6$): δ 1.64-1.68 (m, 4H), 2.59 (t, J=6.9 Hz, 2H), 4.37 (t, J=6.3 Hz, 1H), 4.53 (t, J=5.4 Hz, 1H), 7.15 (d, J=8.1 Hz, 2H), 7.24 (br, 2H), 7.34 (m, 2H), 7.68 (d, J=7.8 Hz, 2H), 7.95 (d, J=7.2 Hz, 1H), 8.08 (d, J=2.4 Hz, 2H), 9.30 (br, 1H), 9.47 (br, 1H); $^{19}$F NMR (282 MHz, DMSO-d$_6$): δ −202.13; LCMS: purity: 91.90%; MS (m/e): 434.60 (MH$^+$).

VI-93: N2-(3-Aminosulfonyl-4-methylphenyl)-5-fluoro-N4-[4-(4-fluorobutyl)phenyl]-2,4-pyrimidinediamine $^1$H NMR (DMSO-d$_6$): δ 1.63-1.68 (m, 4H), 2.60 (t, J=6.9 Hz, 2H), 4.37 (t, J=5.7 Hz, 1H), 4.53 (t, J=5.1 Hz, 1H), 7.16 (d, J=8.7 Hz, 2H), 7.18 (d, J=8.1 Hz, 1H), 7.26 (br, 2H), 7.61 (d, J=8.4 Hz, 2H), 7.80 (d, J=7.5 Hz, 1H), 7.98 (s, 1H), 8.13 (d, J=4.5 Hz, 1H), 9.75 (br, 2H); $^{19}$F NMR (282 MHz, DMSO-d$_6$): δ −201.39; LCMS: purity: 84.96%; MS (m/e): 448.68 (MH$^+$).

I-154: N2-(4-Aminosulfonylphenyl)-N4-(3-fluoro-4-methylaminocarbonylmethoxyphenyl)-5-methyl-2,4-pyrimidinediamine $^1$H NMR (DMSO-d$_6$): δ 2.15 (s, 3H), 2.66 (d, J=4.2 Hz, 3H), 4.58 (s, 2H), 7.10 (t, J=9.0 Hz, 1H), 7.26 (br, 3H), 7.57 (dd, J=2.4, 12.9 Hz, 1H), 7.61 (d, J=8.7 Hz, 2H), 7.66 (d, J=9.3 Hz, 2H), 7.93 (s, 1H), 8.02 (d, J=3.9 Hz, 1H), 9.59 (br, 1H), 10.44 (br, 1H); $^{19}$F NMR (282 MHz, DMSO-d$_6$): δ 171.80; LCMS: purity: 99.32%; MS (m/e): 461.58 (MH$^+$).

I-155: N2-(3-Aminosulfonylphenyl)-N4-(3-fluoro-4-methylaminocarbonylmethoxyphenyl)-5-methyl-2,4-pyrimidinediamine $^1$H NMR (DMSO-d$_6$): δ 2.15 (s, 3H), 2.66 (d, J=4.5 Hz, 3H), 4.56 (s, 2H), 7.06 (t, J=9.3 Hz, 1H), 7.29 (d, J=8.7 Hz, 1H), 7.34 (br, 2H), 7.40 (t, J=7.8 Hz, 1H), 7.50 (d, J=7.5 Hz, 1H), 7.53 (d, J=12.0 Hz, 1H), 7.72 (s, 1H), 7.84 (d, J=8.4 Hz, 1H), 7.90 (s, 1H), 7.98 (d, 1H), 9.50 (br, 1H), 10.26 (br, 1H); $^{19}$F NMR (282 MHz, DMSO-d$_6$): δ −171.83; LCMS: purity: 99.44%; MS (m/e): 461.52 (MH$^+$).

I-156: N2-(3-Aminosulfonyl-4-methylphenyl)-N4-(3-fluoro-4-methylaminocarbonylmethoxyphenyl)-5-methyl-2,4-pyrimidinediamine $^1$H NMR (DMSO-d$_6$): δ 2.14 (s, 3H), 2.54 (s, 3H), 2.65 (d, J=4.8 Hz, 3H), 4.56 (s, 2H), 7.06 (t, J=9.0 Hz, 1H), 7.22 (d, J=8.7 Hz, 1H), 7.28 (d, J=8.4 Hz, 1H), 7.36 (br, 2H), 7.51 (dd, J=10.8 Hz, 1H), 7.69 (d, J=7.8 Hz, 1H), 7.72 (s, 1H), 7.86 (s, 1H), 7.99 (d, 1H), 9.58 (br, 1H), 10.35 (br, 1H); $^{19}$F NMR (282 MHz, DMSO-d$_6$): δ −171.83; LCMS: purity: 98.38%; MS (m/e): 475.67 (MH$^+$).

III-32: N4-(4-Aminocarbonylaminomethylphenyl)-N2-(4-aminosulfonylphenyl)-5-fluoro-2,4-pyrimidinediamine $^1$H NMR (DMSO-d$_6$): δ 4.17 (s, 2H), 6.47 (br, 1H), 7.17 (br, 2H), 7.23 (d, J=8.7 Hz, 2H), 7.62 (d, J=9.0 Hz, 2H), 7.63 (d, J=8.4 Hz, 2H), 7.77 (d, J=9.0 Hz, 2H), 8.15 (d, J=3.9 Hz, 1H), 9.60 (br, 1H), 9.73 (br, 1H); $^{19}$F NMR (282 MHz, DMSO-d$_6$): δ −201.32; LCMS: purity: 96.25%; MS (m/e): 432.11 (MH$^+$).

III-33: N4-(4-Aminocarbonylaminomethylphenyl)-N2-(3-aminosulfonylphenyl)-5-fluoro-2,4-pyrimidinediamine $^1$H NMR (DMSO-d$_6$): δ 4.15 (s, 2H), 6.46 (br, 1H), 7.21 (d, J=8.1 Hz, 2H), 7.28 (br, 2H), 7.39 (d, J=4.8 Hz, 2H), 7.67

(d, J=7.5 Hz, 2H), 7.92 (m, 1H), 8.01 (s, 1H), 8.15 (d, J=3.6 Hz, 1H), 9.68 (br, 1H), 9.75 (br, 1H); $^{19}$F NMR (282 MHz, DMSO-d$_6$): δ −201.24; LCMS: purity: 95.09%; MS (m/e): 432.51 (MH$^+$).

III-34: N4-(4-Aminocarbonylaminomethylphenyl)-N2-(3-aminosulfonyl-4-methylphenyl)-5-fluoro-2,4-pyrimidinediamine $^1$H NMR (DMSO-d$_6$): δ 2.52 (s, 3H), 4.15 (s, 2H), 6.42 (br, 1H), 7.20 (d, J=8.4 Hz, 1H), 7.21 (d, J=8.1 Hz, 2H), 7.26 (br, 2H), 7.66 (d, J=8.4 Hz, 2H), 7.83 (d, J=8.1 Hz, 1H), 8.01 (s, 1H), 8.13 (d, J=4.2 Hz, 1H), 9.70 (br, 2H); $^{19}$F NMR (282 MHz, DMSO-d$_6$): δ −201.66; LCMS: purity: 85.70%; MS (m/e): 446.65 (MH$^+$).

IX-41: N4-(4-Acetylthiomethylcarbonylphenyl)-N2-(4-aminosulfonylphenyl)-5-fluoro-2,4-pyrimidinediamine $^1$H NMR (DMSO-d$_6$): δ 2.36 (s, 3H), 4.11 (s, 2H), 7.15 (br, 2H), 7.27 (d, J=8.4 Hz, 2H), 7.63 (d, J=8.7 Hz, 2H), 7.65 (d, J=8.7 Hz, 2H), 7.76 (d, J=9.0 Hz, 2H), 8.18 (d, J=3.9 Hz, 1H), 9.69 (br, 1H), 9.81 (br, 1H); $^{19}$F NMR (282 MHz, DMSO-d$_6$): δ −200.96; LCMS: purity: 78.34%; MS (m/e): 448.42 (M-28).

IX-42: N4-(4-Acetylthiomethylcarbonylphenyl)-N2-(3-aminosulfonylphenyl)-5-fluoro-2,4-pyrimidinediamine $^1$H NMR (DMSO-d$_6$): δ 2.35 (s, 3H), 4.09 (s, 2H), 7.24 (d, J=8.4 Hz, 2H), 7.25 (br, 2H), 7.36 (m, 2H), 7.70 (d, J=8.7 Hz, 2H), 7.91 (m, 1H), 8.05 (s, 1H), 8.13 (d, J=3.6 Hz, 1H), 9.53 (br, 1H), 9.60 (br, 1H); $^{19}$F NMR (282 MHz, DMSO-d$_6$): δ −201.56; LCMS: purity: 84.49%; MS (m/e): 448.41 (M-28).

IX-43: N4-(4-Acetylthiomethylcarbonylphenyl)-N2-(3-aminosulfonyl-4-methylphenyl)-5-fluoro-2,4-pyrimidinediamine $^1$H NMR (DMSO-d$_6$): δ 2.36 (s, 3H), 4.10 (s, 2H), 7.20 (d, J=8.1 Hz, 1H), 7.25 (d, J=8.4 Hz, 2H), 7.28 (br, 2H), 7.64 (d, J=8.7 Hz, 2H), 7.79 (dd, J=2.4, 8.4 Hz, 1H), 7.96 (s, 1H), 8.17 (d, J=4.2 Hz, 1H), 9.86 (br, 1H), 9.89 (br, 1H); $^{19}$F NMR (282 MHz, DMSO-d$_6$): δ −201.03; LCMS: purity: 85.44%; MS (m/e): 462.21 (M-28).

III-44: N4-(4-Acrylamidomethylphenyl)-N2-(4-aminosulfonylphenyl)-5-fluoro-2,4-pyrimidinediamine $^1$H NMR (DMSO-d$_6$): δ 4.33 (d, J=6.0 Hz, 2H), 5.61 (dd, J=2.4, 9.9 Hz, 1H), 6.11 (dd, J=2.4, 17.1 Hz, 1H), 6.27 (dd, J=9.6, 17.1 Hz, 1H), 7.12 (br, 2H), 7.23 (d, J=8.7 Hz, 2H), 7.62 (d, J=8.7 Hz, 2H), 7.70 (d, J=8.1 Hz, 2H), 7.81 (d, J=8.7 Hz, 2H), 8.13 (d, J=3.6 Hz, 1H), 8.59 (t, J=5.7 Hz, 1H), 9.43 (br, 1H), 9.58 (br, 1H); $^{19}$F NMR (282 MHz, DMSO-d$_6$): δ −201.60; LCMS: purity: 93.70%; MS (m/e): 443.22 (MH$^+$).

III-45: N4-(4-Acrylamidomethylphenyl)-N2-(3-aminosulfonylphenyl)-5-fluoro-2,4-pyrimidinediamine $^1$H NMR (DMSO-d$_6$): δ 4.32 (d, J=6.0 Hz, 2H), 5.61 (dd, J=2.1, 9.9 Hz, 1H), 6.11 (dd, J=2.4, 17.1 Hz, 1H), 6.28 (dd, J=10.2, 17.4 Hz, 1H), 7.22 (d, J=8.1 Hz, 2H), 7.25 (br, 2H), 7.34 (m, 2H), 7.74 (d, J=8.4 Hz, 2H), 7.95 (d, J=7.5 Hz, 1H), 8.10 (s, 1H), 8.10 (d, J=3.6 Hz, 1H), 8.57 (t, 1H), 9.38 (br, 1H), 9.49 (br, 1H); $^{19}$F NMR (282 MHz, DMSO-d$_6$): δ −202.04; LCMS: purity: 91.76%; MS (m/e): 443.57 (MH$^+$).

III-46: N4-(4-Acrylamidomethylphenyl)-N2-(3-aminosulfonyl-4-methylphenyl)-5-fluoro-2,4-pyrimidinediamine $^1$H NMR (DMSO-d$_6$): δ 4.32 (d, J=6.3 Hz, 2H), 5.61 (dd, J=2.4, 9.9 Hz, 1H), 6.12 (dd, J=2.4, 17.1 Hz, 1H), 6.28 (dd, J=9.9, 17.1 Hz, 1H), 7.15 (d, J=8.1 Hz, 1H), 7.21 (d, J=8.4 Hz, 2H), 7.22 (br, 2H), 7.74 (d, J=8.4 Hz, 2H), 7.89 (dd, J=2.1, 8.1 Hz, 1H), 8.07 (d, J=3.9 Hz, 1H), 8.10 (d, J=2.1 Hz, 1H), 8.56 (t, J=5.4 Hz, 1H), 9.34 (br, 1H), 9.38 (br, 1H); $^{19}$F NMR (282 MHz, DMSO-d$_6$): δ 202.59; LCMS: purity: 88.19%; MS (m/e): 457.48 (MH$^+$).

IX-15: N2-(3-Aminosulfonylphenyl)-N4-(3-cyanomethyl-1H-indol-7-yl)-5-fluoro-2,4-pyrimidinediamine $^1$H NMR (DMSO-d6): δ 8.07 (s, 1H), 7.88 (s, 1H), 7.50 (d, 1H, J=8.1 Hz), 7.16 (m, 6H), 4.08 (s, 2H); LCMS: purity: 93%; MS (m/e): 438 (MH$^+$).

IX-16: N2-(3-Aminosulfonyl-4-methylphenyl)-N4-(3-cyanomethyl-1H-indol-7-yl)-5-fluoro-2,4-pyrimidinediamine $^1$H NMR (DMSO-d6): δ 8.05 (d, 1H, J=3.3 Hz), 7.88 (s, 1H), 7.50 (d, 1H, J=7.5 Hz), 7.39 (d, 1H, J=7.8 Hz), 7.28 (s, 1H), 7.23 (d, 2H, J=7.8 Hz), 7.07 (t, 1H, J=7.8 Hz), 6.75 (d, 1H, J=8.4 Hz), 4.08 (s, 2H), 2.39 (s, 3H); LCMS: purity: 92%; MS (m/e): 452 (MI-1+).

I-9: N2-[3-Aminosulfonyl-4-(4-methylpiperazin-1-yl)phenyl]-5-fluoro-N4-(4-cyanomethyleneoxyphenyl)-2,4-pyrimidinediamine $^1$H NMR (DMSO-d6): δ 8.07 (d, 1H, J=4.62 Hz), 7.95 (bs, 1H), 7.70 (bs, 2H), 7.44 (d, 1H, J=9.3 Hz), 7.06 (d, 2H, J=9 Hz), 5.14 (s, 2H), 3.15 (s, 4H), 2.90 (bs, 4H), 2.27 (s, 3H); LCMS: purity: 91%; MS (m/e): 514 (MH$^+$).

I-251: N2-[3-Aminosulfonyl-4-(4-methylpiperazin-1-yl)phenyl]-5-fluoro-N4-[2-fluoro-4-(5-methyl-isoxazol-3-yl)methyleneoxyphenyl]-2,4-pyrimidinediamine $^1$H NMR (DMSO-d6): δ 8.07 (bs, 1H), 7.98 (d, 1H, J=9 Hz), 7.87 (d, 1H, J=13.8 Hz), 7.53 (d, 1H, J=9.3 Hz), 7.42 (d, 1H, J=8.7 Hz), 7.20 (t, 1H, J=9 Hz), 6.33 (s, 1H), 5.18 (s, 2H), 3.15 (s, 4H), 2.90 (s, 4H), 2.41 (s, 3H), 2.28 (s, 3H); LCMS: purity: 98%; MS (m/e): 588 (MH$^+$).

I-10: N2-[3-Aminosulfonyl-4-(4-methylpiperazine-1-yl)phenyl]-5-fluoro-N4-(4-cyanomethyleneoxy-3-fluorophenyl)-2,4-pyrimidinediamine $^1$H NMR (DMSO-d6): δ 8.10 (t, 2H, J=3.6 Hz), 7.92 (m, 2H), 7.58 (d, 1H, J=3.3 Hz), 7.45 (d, 1H, J=8.7 Hz), 7.26 (t, 1H, J=8.7 Hz), 5.19 (s, 2H), 3.15 (s, 4H), 2.90 (s, 4H), 2.22 (s, 3H); LCMS: purity: 94%; MS (m/e): 531 (MH$^+$).

I-11: N2-(3-Aminosulfonyl-4-methylphenyl)-5-fluoro-N4-(4-cyanomethyleneoxy-3-fluorophenyl)-2,4-pyrimidinediamine ¹H NMR (DMSO-d6): δ 8.10 (t, 2H, J=3.6 Hz), 7.92 (m, 2H), 7.59 (d, 1H, J=9.0 Hz), 7.24 (m, 2H), 5.20 (s, 2H), 2.45 (s, 3H); LCMS: purity: 94%; MS (m/e): 447 (MH⁺).

I-12: N2-(3-Aminosulfonylphenyl)-5-fluoro-N4-(4-cyanomethyleneoxy-3-fluorophenyl)-2,4-pyrimidinediamine ¹H NMR (DMSO-d6): δ 8.13 (t, 1H, J=3.9 Hz), 8.10 (s, 1H), 7.95 (m, 2H), 7.60 (d, 1H, J=8.7 Hz), 7.36 (m, 3H), 5.20 (s, 2H); LCMS: purity: 95%; MS (m/e): 433 (MH⁺).

IX-20: N2-(3-Aminosulfonyl-4-methylphenyl)-N4-(3-cyanomethyl-1-methyl-indol-5-yl)-5-fluoro-2,4-pyrimidinediamine ¹H NMR (DMSO-d6): δ 9.32 (s, 1H), 9.21 (s, 1H), 8.08 (s, 1H), 8.02 (d, 1H, J=3.9 Hz), 7.89 (s, 1H), 7.46 (s, 1H), 7.34 (s, 1H), 7.21 (s, 2H), 4.02 (s, 2H), 3.75 (s, 3H), 2.47 (s, 3H); LCMS: purity: 99%; MS (m/e): 467 (MH⁺).

III-103: N2-(3-Aminosulfonylphenyl)-5-fluoro-N4-(4-N-morpholinomethylenephenyl)-2,4-pyrimidinediamine ¹H NMR (DMSO-d6): δ 8.10 (m, 2H), 7.96 (m, 2H), 7.76 (d, 1H, J=8.1 Hz), 7.35 (m, 1H), 7.25 (m, 2H), J=5.7 Hz), 3.57 (bs, 4H), 3.43 (bs, 2H), 2.28 (bs, 4H); LCMS: purity: 96%; MS (m/e): 459 (MH⁺).

III-104: N2-(3-Aminosulfonyl-4-methylphenyl)-5-fluoro-N4-(4-N-morpholinomethylenephenyl)-2,4-pyrimidinediamine ¹H NMR (DMSO-d6): δ 8.08 (t, 1H, J=3.6 Hz), 7.92 (d, 1H, J=8.1 Hz), 7.57 (d, 1H, J=8.1 Hz), 7.25 (d, 1H, J=7.5 Hz), 7.16 (d, 1H, J=8.1 Hz), 3.57 (bs, 4H), 3.44 (s, 2H), 2.36 (s, 4H), 2.07 (s, 3H); LCMS: purity: 99%; MS (m/e): 473 (MH⁺).

III-105: N2-(3-Aminosulfonyl-4-methyleneoxyphenyl)-5-fluoro-N4-(4-N-morpholinomethylenephenyl)-2,4-pyrimidinediamine ¹H NMR (DMSO-d6): δ 8.05 (d, 1H, J=3.6 Hz), 7.98 (m, 1H), 7.89 (m, 1H), 7.59 (d, 1H, J=8.4 Hz), 7.24 (d, 1H, J=8.1 Hz), 7.06 (m, 1H), 6.97 (s, 2H), 3.85 (s, 3H), 3.56 (bs, 4H), 3.42 (s, 2H), 2.34 (bs, 4H); LCMS: purity: 95%; MS (m/e): 489 (MH⁺).

III-110: N2-(3-Aminosulfonylphenyl)-5-fluoro-N4-{4-[(1,1-dioxothiomorpholin-4-yl-)methyl]phenyl}-2,4-pyrimidinediamine ¹H NMR (DMSO-d6): δ 8.12 (d, 2H, J=3.6 Hz), 7.95 (m, 1H), 7.78 (d, 2H, J=8.4 Hz), 7.37 (m, 2H), 7.28 (d, 2H), 3.64 (s, 2H), 3.10 ((bs, 4H), 2.87 (bs, 4H); LCMS: purity: 97%; MS (m/e): 507 (MH⁺).

III-111: N2-(3-Aminosulfonyl-4-methylphenyl)-5-fluoro-N4-{4-[(1,1-dioxothiomorpholin-4-yl-)methyl]phenyl}-2,4-pyrimidinediamine ¹H NMR (DMSO-d6): δ 8.1 (d, 2H, J=2.4 Hz), 8.08 (d, 1H, J=3.9 Hz), 7.90 (m, 1H), 7.78 (d, 2H, J=8.7 Hz), 7.22 (m, 3H), 3.64 (s, 2H), 3.10 (bs, 4H), 2.45 (s, 3H), 2.88 (bm, 4H); LCMS: purity: 98%; MS (m/e): 521 (MH⁺).

III-112: N2-(3-Aminosulfonyl-4-methyloxyphenyl)-5-fluoro-N4-{4-[(1,1-dioxothiomorpholin-4-yl-)methyl]phenyl}-2,4-pyrimidinediamine ¹H NMR (DMSO-d6): δ 8.06 (d, 1H, J=3.6 Hz), 7.99 (bs, 1H), 7.97 (m, 2H), 7.28 (d, 2H, J=7.8 Hz), 7.08 (d, 1H, J=9 Hz), 6.96 (s, 1H), 3.85 (s, 3H), 3.65 (s, 2H), 3.12 (s, 4H), 2.90 (s, 4H); LCMS: purity: 91%; MS (m/e): 537 (MH⁺).

III-107: N2-(3-Aminosulfonylphenyl)-5-fluoro-N4-(4-thiomorpholinomethylenephenyl)-2,4-pyrimidinediamine ¹H NMR (DMSO-d6): δ 8.10 (m, 2H), 7.95 (m, 1H), 7.75 (d, 2H, J=8.4 Hz), 7.36 (d, 2H, J=7.2 Hz), 7.24 (t, 2H, J=8.7 Hz), 3.46 (s, 2H), 2.6 (s, 4H), 2.48 (s, 4H); LCMS: purity: 96%; MS (m/e): 475 (MH+).

III-108: N2-(3-Aminosulfonyl-4-methylphenyl)-5-fluoro-N4-(4-thiomorpholinomethylenephenyl)-2,4-pyrimidinediamine ¹H NMR (DMSOd-6): δ 8.07 (t, 2H, J=5.1 Hz), 7.89 (dd, 1H, J=8.4 Hz, J=1.8 Hz), 7.50 (d, 2H, J=8.4 Hz), 7.23 (d, 2H, J=8.4 Hz), 7.16 (d, 1H, J=8.1 Hz), 3.46 (s, 2H), 2.6 (s, 4H), 2.49 (s, 3H), 2.48 (s, 4H); LCMS: purity: 88%; MS (m/e): 489 (MH⁺).

III-109: N2-(3-Aminosulfonyl-4-methyoxyphenyl)-5-fluoro-N4-(4-thiomorpholinomethylenephenyl)-2,4-pyrimidinediamine ¹H NMR (DMSO-d6): δ 8.08 (d, 1H, J=8.06 Hz), 7.87 (bs, 1H), 7.78 (bs, 1H), 7.73 (d, 1H, J=8.1 Hz), 7.23 (d, 1H, J=8.1 Hz), 7.01 (s, 2H), 3.77 (s, 3H), 3.45 (s, 2H), 2.60 (s, 4H), 2.21 (s, 4H); LCMS: purity: 99%; MS (m/e): 505 (MH⁺).

II-9: N2-(3-Aminosulfonylphenyl)-5-fluoro-N4-(N-methylpyrrolidin-3-yloxyphenyl)-2,4-pyrimidinediamine ¹H NMR (DMSO-d6): δ 8.07 (t., 2H, J=4.8 Hz), 7.94 (d, 1H, J=6.6 Hz), 7.66 (d, 2H, J=8.4 Hz), 7.33 (d, 2H, J=7.5 Hz), 7.25 (s, 1H), 6.85 (d, 2H, J=8.1 Hz), 4.83 (s, 1H), 2.76 (m, 2H), 2.62 (m, 2H), 2.35 (m, 2H), 2.26 (s, 3H); LCMS: purity: 90%; MS (m/e): 446 (MH⁺)

II-10: N2-(3-Aminosulfonyl-4-methylphenyl)-5-fluoro-N4-(N-methylpyrrolidin-3-yloxyphenyl)-2,4-pyrimidinediamine ¹H NMR (DMSOd-6): δ 8.06 (m, 2H), 7.93 (d, 1H, J=6.9 Hz), 7.66 (d, 2H, J=9.3 Hz), 7.33 (m, 2H), 6.85 (d, 2H, J=9.0 Hz), 4.83 (s, 1H), 2.75 (m, 2H), 2.62 (m, 2H), 2.49 (s, 3H), 2.35 (m, 2H), 2.25 (s, 3H); LCMS: purity: 90%; MS (m/e): 473 (MH⁺).

IX-27: N2-(3-Aminosulfonyl-4-methylphenyl)-5-fluoro-N4-[4-(4-methylpiperazin-1-ylcarbonyl)phenyl]-2,4-pyrimidinediamine ¹H NMR (DMSO-d₆): δ 9.53 (s, 1H), 9.46 (s, 1H), 8.12 (s, 2H), 7.89 (t, 3H, J=9.0 Hz), 7.25 (m, 3H), 3.49 (s, 4H), 2.31 (s, 3H), 2.19 (s, 3H); LCMS: purity: 92%; MS (m/e): 500 (MH⁺).

IX-28: N2-(3-Aminosulfonylphenyl)-5-fluoro-N4-[4-(4-methylpiperazin-1-ylcarbonyl)phenyl]-2,4-pyrimidinediamine $^1$H NMR (DMSO-d6): δ 95.3 (s, 1H), 8.16 (d, 1H, J=11.4 Hz), 7.92 (d, 2H, J=8.1 Hz), 7.35 (m, 3H), 7.26 (s, 3 Hz), 3.49 (s, 4H), 2.2 (s, 3H); LCMS: purity: 86%; MS (m/e): 486 (MH$^+$)

II-5: N2-(3-Aminosulfonyl-4-methylphenyl)-5-fluoro-N4-{3-methyl-4-[(1-methylpiperidin-4-yl)oxy]phenyl}-2,4-pyrimidinediamine $^1$H NMR (CD$_3$OD): δ 6.92 (d, J=2.4 Hz, 1H), 6.73 (d, J=3.9 Hz, 1H), 6.61 (dd, J=2.4 and 8.4 Hz, 1H), 6.29 (dd, J=2.7 and 8.4 Hz, 1H), 6.23-6.20 (m, 1H), 6.01 (d, J=8.4 Hz, 1H), 5.79 (d, J=8.7 Hz, 1H), 3.35-3.25 (m, 1H), 1.69-1.56 (m, 2H), 1.46 (s, 3H), 1.38-1.27 (m, 2H), 1.21 (s, 3H), 1.09 (s, 3H), 0.96-0.86 (m, 2H), 0.81-0.70 (m, 2H); LCMS: purity: 92%, MS (m/e): 501 (MH$^+$).

II-6: N2-(3-Aminosulfonyl-4-methylphenyl)-5-fluoro-N4-{4-[(1-methylpiperidin-4-yl)oxy]-3-trifluoromethylphenyl}-2,4-pyrimidinediamine $^1$H NMR (DMSO-d$_6$): δ 9.39 (s, 1H), 9.37 (s, 1H), 8.09-8.01 (m, 3H), 7.81 (dd, J=2.4 and 8.7 Hz, 1H), 7.77 (d, J=2.7 Hz, 1H), 7.27-7.21 (m, 3H), 7.11 (d, J=8.4 Hz, 1H), 4.62-4.51 (m, 1H), 2.57-2.42 (m, 5H), 2.28-2.00 (m, 2H), 2.16 (s, 3H), 1.98-1.86 (m, 2H), 1.75-1.63 (m, 2H); LCMS: purity: 97% (m/e): 555 (MH$^+$).

II-7: N2-(3-Aminosulfonyl-4-methylphenyl)-5-fluoro-N4-{4-[(1-methylpiperidin-4-yl)oxy]phenyl}-2,4-pyrimidinediamine $^1$H NMR (DMSO-d$_6$): δ 9.31 (s, 1H), 9.18 (s, 1H), 8.07 (d, J=2.4 Hz, 1H), 8.02 (d, J=3.9 Hz, 1H), 7.85 (dd, J=2.7 and 8.4 Hz, 1H), 7.62 (d, J=8.7 Hz, 2H), 7.21 (s, 2H), 7.13 (d, J=8.7 Hz, 1H), 6.90 (d, J=8.7 Hz, 2H), 4.34-4.25 (m, 1H), 2.65-2.57 (m, 2H), 2.49 (s, 3H), 2.17 (s, 3H), 2.20-2.10 (m, 2H), 1.98-1.87 (m, 2H), 1.69-1.55 (m, 2H); LCMS: purity: 95 MS (m/e): 487 (MH$^+$).

II-3: Racemic N2-(3-aminosulfonyl-4-methylphenyl)-N4-{3-chloro-4-[(1-methylpiperidin-3-yl)oxy]phenyl}-5-fluoro-2,4-pyrimidinediamine $^1$H NMR (CD$_3$OD): δ 8.04 (d, J=2.4 Hz, 1H), 7.89 (d, J=3.6 Hz, 1H), 7.76 (dd, J=2.4 and 8.4 Hz, 1H), 7.71 (d, J=2.7 Hz, 1H), 7.55 (dd, J=2.7 and 9.0 Hz, 1H), 7.18 (d, J=8.4 Hz, 1H), 7.07 (d, J=9.0 Hz, 1H), 4.36-4.27 (m, 1H), 3.03-2.95 (m, 1H), 2.71-2.64 (m, 1H), 2.59 (s, 3H), 2.32 (s, 3H), 2.30-2.25 (m, 1H), 2.24-2.12 (m, 1H), 2.10-2.02 (m, 1H), 1.96-1.84 (m, 1H), 1.72-1.48 (m, 2H); LCMS: purity: 90% (m/e): 522 (MH$^+$).

II-4: Racemic N2-(3-aminosulfonyl-4-methylphenyl)-5-fluoro-N4-{4-[(1-methylpiperidin-3-yl)oxy]phenyl}-2,4-pyrimidinediamine $^1$H NMR (CD$_3$OD): δ 8.05 (d, J=2.4 Hz, 1H), 7.83 (d, J=3.6 Hz, 1H), 7.71 (dd, J=2.4 and 8.1 Hz, 1H), 7.51 (d, J=9.3 Hz, 2H), 7.11 (d, J=8.1 Hz, 1H), 6.90 (d, J=9.0 Hz, 2H), 4.41-4.30 (m, 1H), 2.89-2.78 (m, 1H), 2.58 (s, 3H), 2.35-2.18 (m, 5H), 2.00-1.80 (m, 3H), 1.68-1.46 (m, 2H); LCMS: purity: 96% (m/e): 487 (MH$^+$).

II-8: N2-(3-Aminosulfonyl-4-methylphenyl)-5-fluoro-N4-{3-chloro-4-[(1-methylpiperidin-4-yl)oxy]phenyl}-2,4-pyrimidinediamine $^1$H NMR (DMSO-d$_6$): δ 9.41 (s, 1H), 9.31 (bs, 1H), 8.07 (d, J=3.6 Hz, 1H), 8.04 (d, J=2.1 Hz, 1H), 7.86 (dd, J=2.1 and 8.1 Hz, 1H), 7.80 (d, J=2.4 Hz, 1H), 7.66 (dd, J=2.7 and 9.0 Hz, 1H), 7.23 (bs, 2H), 7.18-7.12 (m, 2H), 4.43-4.35 (m, 1H), 2.64-2.55 (m, 2H), 2.50 (s, 3H), 2.24-2.14 (m, 5H), 1.96-1.86 (m, 2H), 1.74-1.63 (m, 2H); LCMS: purity: 98%; MS (m/e): 522 (MH$^+$).

II-1: Racemic N2-(3-aminosulfonyl-4-methylphenyl)-5-fluoro-N4-{3-[(1-methylpiperidin-3-yl)oxy]phenyl}-2,4-pyrimidinediamine $^1$H NMR (DMSO-d$_6$): δ 9.40 (s, 1H), 9.27 (s, 1H), 8.09 (d, J=3.6 Hz, 1H), 8.06 (d, J=2.4 Hz, 1H), 7.93 (dd, J=2.4 and 8.4 Hz, 1H), 7.57-7.49 (m, 1H), 7.32 (t, J=2.1 Hz, 1H), 7.23 (s, 2H), 7.17 (dd, J=2.4 and 8.4 Hz, 2H), 6.63 (dd, J=1.8 and 7.8 Hz, 1H), 4.36-4.24 (m, 1H), 2.94-2.84 (m, 1H), 2.61-2.52 (m, 1H), 2.49 (s, 3H), 2.17 (S, 3H), 2.06-1.91 (m, 2H), 1.76-1.63 (m, 1H), 1.58-1.42 (m, 1H), 1.40-1.19 (m, 2H); LCMS: purity: 90%; (m/e): 487 (MH$^+$).

II-2: N2-(3-Aminosulfonyl-4-methylphenyl)-5-fluoro-N4-{3-[(1-methylpiperidin-4-yl)oxy]phenyl}-2,4-pyrimidinediamine $^1$H NMR (DMSO-d$_6$): δ 9.42 (s, 1H), 9.25 (s, 1H), 8.10-8.07 (m, 2H), 7.92 (dd, J=2.4 Hz, 1H), 7.56-7.50 (m, 1H), 7.28 (t, J=1.8 Hz, 1H), 7.22 (s, 2H), 7.20-7.15 (m, 4H), 6.63 (dd, J=2.4 and 8.1 Hz, 1H), 4.31-4.20 (m, 1H), 2.67-2.55 (m, 2H), 2.50 (s, 3H), 2.15-2.05 (m, 2H), 1.98-1.86 (m, 2H), 1.68-1.54 (m, 2H); LCMS: purity: 98%; MS (m/e): 487 (MH$^+$).

VII-16: N2-(3-Aminosulfonyl-4-methylphenyl)-5-fluoro-N4-(1,2,3,4-tetrahydroisoquin-7-yl)-2,4-pyrimidinediamine $^1$H NMR (DMSO-d$_6$): δ 9.35 (s, 1H), 9.19 (s, 1H), 8.07 (d, J=2.4 Hz, 1H), 8.04 (d, J=3.3 Hz, 1H), 7.90 (dd, J=1.8 and 8.1 Hz, 1H), 7.46 (dd, J=2.1 and 8.4 Hz, 1H), 7.42-7.38 (m, 1H), 7.22 (bs, 2H), 7.16 (d, J=8.4 Hz, 1H), 6.99 (d, J=8.7 Hz, 1H), 5.74 (s, 1H), 3.81 (s, 2H), 2.95 (t, J=6.0 Hz, 2H), 2.43 (s, 3H); LCMS: purity: 97%; MS (m/e): 429 (MH$^+$).

VII-17: N2-(3-Aminosulfonyl-4-methylphenyl)-5-fluoro-N4-[2-(methylaminocarbonyl)-1,2,3,4-tetrahydroisoquin-7-yl]-2,4-pyrimidinediamine $^1$H (DMSO-d$_6$): δ 9.81-9.69 (m, 2H), 8.14 (d, J=4.5 Hz, 1H), 7.95 (d, J=1.5 Hz, 1H), 7.84 (dd, J=2.4 and 8.1 Hz, 1H), 7.51-7.44 (m, 2H), 7.27 (s, 2H), 7.23 (d, J=8.4 Hz, 1H), 7.10 (d, J=8.7 Hz, 1H), 4.43 (s, 2H), 3.52 (t, J=5.7 Hz, 2H), 2.73 (t, J=5.7 Hz, 2H), 2.59 (s, 3H), 2.46 (s, 3H); LCMS: purity: 92%; MS (m/e): 487 (MH$^+$).

VII-18: N2-(3-Aminosulfonyl-4-methylphenyl)-5-fluoro-N4-[2-(dimethylaminocarbonyl)-1,2,3,4-tetrahydroisoquin-7-yl]-2,4-pyrimidinediamine $^1$H NMR (DMSO-d$_6$): δ 9.72-9.63 (m, 2H), 8.13 (d, J=4.2 Hz, 1H), 7.97 (s, 1H), 7.85 (dd, J=2.4 and 8.1 Hz, 1H), 7.57

(s, 1H), 7.48-7.44 (m, 1H), 7.27 (s, 2H), 7.20 (d, J=8.1 Hz, 1H), 7.10 (d, J=8.1 Hz, 1H), 4.26 (s, 2H), 3.39 (t, J=5.4 Hz, 2H), 2.81 (t, J=5.4 Hz, 2H), 2.78 (s, 6H), 2.46 (s, 3H); LCMS: purity: 98%; MS (m/e): 501 (MH$^+$).

VII-3: Racemic N2-(3-aminosulfonyl-4-methylphenyl)-N4-(1-benzyl-4-methylpiperidin-3-yl)-5-fluoro-2,4-pyrimidinediamine $^1$H NMR (CDCl$_3$): δ 8.56 (d, J=2.1 Hz, 1H), 7.62 (d, J=3.6 Hz, 1H), 7.25 (dd, J=2.1 and 8.4 Hz, 1H), 7.21-7.10 (m, 5H), 7.07 (d, J=8.1 Hz, 1H), 5.81-5.70 (m), 5.35-5.22 (m), 4.46-4.37 (m), 3.47 (d, J=13.2 Hz), 3.35 (d, J=13.2 Hz), 2.79-2.68 (m), 2.67-2.56 (m), 2.51 (s), 2.27 (d, J=11.1 Hz), 2.14-2.00 (m), 1.85-1.69 (m), 1.49-1.38 (m), 1.24-1.15 (m), 0.89-0.86 (m); LCMS: purity: 98%; MS (m/e): 485 (MH$^+$).

VII-4: Racemic N2-(3-aminosulfonyl-4-methylphenyl)-5-fluoro-N4-(4-methylpiperidin-3-yl)-2,4-pyrimidinediamine $^1$H NMR (CD$_3$OD): δ 8.67 (d, J=2.4 Hz, 1H), 7.75 (d, J=3.9 Hz, 1H), 7.43 (dd, J=2.4 Hz, 1H), 7.21 (d, J=8.7 Hz, 1H), 4.63-4.57 (m), 3.06-2.95 (m), 2.94-2.88 (m), 2.74-2.63 (m), 2.49 (s), 2.14-2.00 (m), 1.66-1.55 (m), 1.52-1.40 (m), 1.32-1.26 (m), 0.99-0.88 (m); LCMS: purity: 98%; MS (m/e): 395 (MH$^+$).

VII-5: Racemic N2-(3-aminosulfonyl-4-methylphenyl)-N4-(1-cyanomethylenecarbonyl-4-methylpiperidin-3-yl)-5-fluoro-2,4-pyrimidinediamine $^1$H NMR (DMSO-d$_6$): δ 9.30 (s, 1H), 8.53-8.48 (m, 1H), 8.24 (s, 1H), 7.89 (d, J=3.9 Hz, 1H), 7.62-7.56 (m, 1H), 7.22-7.14 (m, 3H), 4.51-4.42 (m), 4.21-4.14 (m), 4.10-4.02 (m), 3.99-3.90 (m), 3.66-3.52 (m), 3.35-3.28 (m), 3.15-3.00 (m), 2.96-2.84 (m), 2.49 (s), 2.14-1.99 (m), 1.86-1.62 (m), 1.53-1.40 (m), 0.87 (d, J=6.6 Hz); LCMS: purity: 99%; MS (m/e): 463 (MH$^+$).

VI-49: N2-(3-Aminosulfonyl-4-methylphenyl)-5-fluoro-N4-[3-(methylaminocarbonyloxymethyl)phenyl]-2,4-pyrimidinediamine $^1$H NMR (DMSO-d$_6$): δ 9.72 (s, 1H), 9.66 (s, 1H), 8.16 (d, J=4.2 Hz, 1H), 7.99 (s, 1H), 7.85 (dd, J=1.8 and 8.4 Hz, 1H), 7.74 (d, J=7.8 Hz, 1H), 7.68 (s, 1H), 7.32 (t, J=7.8 Hz, 1H), 7.27 (s, 2H), 7.19 (d, J=8.1 Hz, 1H), 7.12-7.04 (m, 2H), 4.98 (s, 2H), 2.57 (d, J=4.2 Hz, 3H), 2.50 (s, 3H); LCMS: purity: 96%; MS (m/e): 461 (MH$^+$).

VII-19: N2-(3-Aminosulfonyl-4-methylphenyl)-5-fluoro-N4-[1-(methylaminocarbonyl)-1,2,3,4-tetrahydroquin-6-yl]-2,4-pyrimidinediamine $^1$H NMR (DMSO-d$_6$): δ 9.98-9.84 (m, 2H), 8.16 (d, J=4.8 Hz, 1H), 7.92-7.88 (m, 1H), 7.81 (dd, J=2.1 and 8.1 Hz, 1H), 7.46-7.38 (m, 3H), 7.31 (s, 2H), 7.24 (d, J=8.1 Hz, 1H), 6.60 (s, 1H), 3.55 (t, J=6.0 Hz, 2H), 2.64 (s, 3H), 2.59 (t, J=6.0 Hz, 2H), 2.52 (s, 3H), 1.812 (t, J=6.0 Hz, 2H); LCMS: purity: 94%; MS (m/e): 487 (MH$^+$).

VI-50: N2-(3-Aminosulfonyl-4-methylphenyl)-5-fluoro-N4-(4-trifluoromethylphenyl)-2,4-pyrimidinediamine $^1$H NMR (DMSO-d$_6$): δ 9.70 (s, 1H), 9.49 (s, 1H), 8.17 (d, J=3.6 Hz, 1H), 8.13 (s, 1H), 8.07 (d, J=8.7 Hz, 2H), 7.84 (d, J=8.4 Hz, 1H), 7.63 (d, J=8.5 Hz, 2H), 7.28-7.18 (m, 3H), 2.50 (s, 3H); LCMS: purity: 99%; MS (m/e): 442 (MH$^+$).

VI-51: N2-(3-Aminosulfonylphenyl)-5-fluoro-N4-(4-trifluoromethylphenyl)-2,4-pyrimidinediamine $^1$H NMR (DMSO-d$_6$): δ 9.74 (s, 1H), 9.61 (s, 1H), 8.21 (d, J=3.6 Hz, 1H), 8.13 (s, 1H), 8.07 (d, J=8.7 Hz, 2H), 7.89 (d, J=7.8 Hz, 2H), 7.64 (d, J=8.78 Hz, 2H), 7.45-7.34 (m, 2H), 7.27 (s, 2H); LCMS: purity: 99%; MS (m/e): 428 (MH$^+$).

VI-52: N2-(3-Aminosulfonyl-4-methylphenyl)-5-fluoro-N4-(4-hydroxymethylphenyl)-2,4-pyrimidinediamine $^1$H NMR (DMSO-d$_6$): δ 9.38 (s, 1H), 9.30 (s, 1H), 8.11 (d, J=2.4 Hz, 1H), 8.07 (d, J=3.9 Hz, 1H), 7.90 (dd, J=2.4 and 8.4 Hz, 1H), 7.75 (d, J=8.4 Hz, 2H), 7.26 (d, J=8.4 Hz, 2H), 7.23 (s, 2H), 7.177 (d, J=8.7 Hz, 1H), 5.10 (t, J=5.7 Hz, 1H), 4.46 (d, J=5.7 Hz, 2H) 2.50 (s, 3H); LCMS: purity: 95%; MS (m/e): 404 (MH$^+$).

VI-53: N2-(3-Aminosulfonyl-4-methylphenyl)-5-fluoro-N4-[4-(prop-2-ynyloxy)phenyl]-2,4-pyrimidinediamine 2-Chloro-5-fluoro-N4-[4-(prop-2-ynyloxy)phenyl]-4-pyrimidineamine (0.514 g, 1.85 mmol), 3-(aminosulfonyl)-4-methylaniline (0.689 g, 3.70 mmol), and trifluoroacetic acid (0.186 mL, 2.41 mmol) were combined with iPrOH (6.0 mL) in a sealed vial and heated at 100° C. for 3 h. The reaction mixture was cooled to room temperature and diluted with 1N HCl (80 mL). N2-(3-Aminosulfonyl-4-methylphenyl)-5-fluoro-N4-[4-(prop-2-ynyloxy)phenyl]-2,4-pyrimidinediamine VI-53) was isolated as a white solid by suction filtration (0.703 g). $^1$H NMR (DMSO-d$_6$): δ 10.08 (bs, 2H), 8.19 (d, J=4.5 Hz, 1H), 7.89 (s, 1H), 7.74 (dd, J=2.4 and 8.4 Hz, 1H), 7.58 (d, J=8.7 Hz, 2H), 7.32 (bs, 2H), 7.23 (d, J=8.4 Hz, 1H), 6.97 (d, J=8.4 Hz, 2H), 4.79 (d, J=2.1 Hz, 2H), 3.59-3.55 (m, 1H), 2.53 (s, 3H); LCMS: purity: 97%; MS (m/e): 428 (MH$^+$).

VI-54: N2-(3-Aminosulfonyl-4-methylphenyl)-5-fluoro-N4-(4-vinylphenyl)-2,4-pyrimidinediamine $^1$H NMR (DMSO-d$_6$): δ 9.42 (s, 1H), 9.40 (s, 1H), 8.12 (d, J=2.4 Hz, 1H), 8.09 (d, J=3.3 Hz, 1H), 7.89 (dd, J=2.4 and 8.4 Hz, 1H), 7.82 (d, J=8.4 Hz, 2H), 7.42 (d, J=8.4 Hz, 2H), 7.23 (s, 2H), 7.18 (d, J=8.4 Hz, 2H), 7.23 (s, 2H), 7.18 (d, J=8.4 Hz, 1H), 6.69 (dd, J=10.8 and 17.4 Hz, 1H), 5.73 (d, J=17.4 Hz, 1H), 5.16 (d, J=11.4 Hz, 1H), 2.50 (s, 3H); LCMS: purity: 96%; MS (m/e): 400 (MH$^+$).

VI-55: N2-(3-Aminosulfonyl-4-chlorophenyl)-5-fluoro-N4-[4-(prop-2-ynyloxy)phenyl]-2,4-pyrimidinediamine $^1$H NMR (DMSO-d$_6$): δ 9.58 (s, 1H), 9.31 (s, 1H), 8.26 (d, J=2.4 Hz, 1H), 8.06 (d, J=3.6 Hz, 1H), 8.02 (dd, J=2.4 and 9.0 Hz, 1H), 7.68 (d, J=8.7 Hz, 2H), 7.45 (s, 2H), 7.39 (d, J=8.7 Hz, 1H), 6.96 (d, J=9.0 Hz, 2H), 4.78 (d, J=2.4 Hz, 2H), 3.55 (t, J=2.4 Hz, 1H); LCMS: purity: 97%; MS (m/e): 449 (MH$^+$).

VII-20: N2-(3-Aminosulfonylphenyl)-5-fluoro-N4-[1-(methylaminocarbonyl)-1,2,3,4-tetrahydroquin-6-yl]-2,4-pyrimidinediamine ¹H NMR (CD₃OD): δ 8.17 (t, J=1.5 Hz, 1H), 7.93 (d, J=3.9 Hz, 1H), 7.79 (ddd, J=1.2, 2.4, and 8.1 Hz, 1H), 7.56 (dd, J=2.4 and 8.7 Hz, 1H), 7.48-7.34 (m, 4H), 7.30 (d, J=9.0 Hz, 1H), 3.67 (t, J=6.3 Hz, 2H), 2.80 (s, 3H), 2.73 (t, J=6.3 Hz, 2H), 1.91 (t, J=6.3 Hz, 2H); LCMS: purity: 99%; MS (m/e): 472 (MH⁺).

III-59: N2-(3-Aminosulfonyl-4-methylphenyl)-5-fluoro-N4-{4-[2-(methylaminocarbonyloxy)ethyl]phenyl}-2,4-pyrimidinediamine ¹H NMR (DMSO-d₆): δ 9.44 (s, 1H), 9.37 (s, 1H), 8.10-8.05 (m, 2H), 7.87 (dd, J=2.1 and 8.1 Hz, 1H), 7.69 (d, J=8.4 Hz, 1H), 7.22 (s, 2H), 7.21-7.14 (m, 3H), 6.96-6.90 (m, 1H), 4.13 (t, J=6.6 Hz, 2H), 2.82 (t, J=6.6 Hz, 2H), 2.54 (d, J=4.5 Hz, 3H), 2.50 (s, 3H); LCMS: purity: 94%; MS (m/e): 476 (MH⁺).

III-60: N2-(3-Aminosulfonylphenyl)-5-fluoro-N4-{4-[2-(methylaminocarbonyloxy)ethyl]phenyl}-2,4-pyrimidinediamine ¹H NMR (DMSO-d₆): δ 9.85 (s, 1H), 9.75 (s, 1H), 8.17 (d, J=3.9 Hz, 1H), 7.98 (s, 1H), 7.93-7.87 (m, 1H), 7.65 (d, J=8.1 Hz, 2H), 7.42-7.38 (m, 2H), 7.29 (s, 2H), 7.21 (d, J=7.8 Hz, 2H), 6.97-6.90 (m, 1H), 4.13 (t, J=6.6 Hz, 2H), 2.83 (t, J=6.6 Hz, 2H), 2.54 (d, J=3.6 Hz, 3H); LCMS: purity: 98%; MS (m/e): 461 (MH⁺).

III-61: N2-(3-Aminosulfonyl-4-chlorophenyl)-5-fluoro-N4-{4-[2-(methylaminocarbonyloxy)ethyl]phenyl}-2,4-pyrimidinediamine ¹H NMR (DMSO-d₆): δ 9.60 (s, 1H), 9.36 (s, 1H), 8.29 (d, J=2.7 Hz, 1H), 8.10 (d, J=3.3 Hz, 1H), 8.03 (dd, J=2.4 and 9.0 Hz, 1H), 7.70 (d, J=8.1 Hz, 2H), 7.45 (s, 2H), 7.41 (d, J=8.7 Hz, 1H), 7.20 (d, J=8.1 Hz, 2H), 6.96-6.90 (m, 1H), 4.13 (t, J=7.2 Hz, 2H), 2.83 (t, J=6.9 Hz, 2H), 2.54 (d, J=4.5 Hz, 3H); LCMS: purity: 95%; MS (m/e): 496 (MH⁺).

III-56: N2-(3-Aminosulfonyl-4-methylphenyl)-N4-{4-[2-(dimethylaminocarbonyloxy)ethyl]phenyl}-5-fluoro-2,4-pyrimidinediamine ¹H (DMSO-d₆): δ 9.71 (bs, 2H), 8.13 (d, J=4.2 Hz, 1H), 8.01 (s, 1H), 7.81 (dd, J=1.8 and 7.8 Hz, 1H), 7.66 (d, J=8.1 Hz, 2H), 7.27 (s, 2H), 7.24-7.16 (m, 3H), 4.15 (t, J=6.6 Hz, 2H), 2.86 (t, J=6.6 Hz, 2H), 2.78 (s, 6H), 2.51 (s, 3H); LCMS: purity: 98%; MS (m/e): 490 (MH⁺).

III-57: N2-(3-Aminosulfonylphenyl)-N4-{4-[2-(dimethylaminocarbonyloxy)ethyl]phenyl}-5-fluoro-2,4-pyrimidinediamine ¹H NMR (DMSO-d₆): δ 9.77 (s, 1H), 9.67 (s, 1H), 8.16 (d, J=4.2 Hz, 1H), 8.01 (s, 1H), 7.94-7.86 (m, 1H), 7.67 (d, J=8.1 Hz, 2H), 7.41-7.36 (m, 2H), 7.29 (s, 2H), 7.21 (d, J=8.7 Hz, 2H), 4.14 (t, J=6.6 Hz, 2H), 2.85 (t, J=6.6 Hz, 2H), 2.79 (s, 6H); LCMS: purity: 97%; MS (m/e): 475 (MH⁺).

III-58: N2-(3-Aminosulfonyl-4-chlorophenyl)-N4-{4-[2-(dimethylaminocarbonyloxy)ethyl]phenyl}-5-fluoro-2,4-pyrimidinediamine ¹H NMR (DMSO-d₆): δ 9.87 (s, 1H), 9.68 (s, 1H), 8.20 (d, J=2.7 Hz, 1H), 8.16 (d, J=4.2 Hz, 1H), 7.97 (dd, J=2.7 and 8.7 Hz, 1H), 7.66 (d, J=8.4 Hz, 2H), 7.49 (s, 2H), 7.42 (d, J=9.0 Hz, 1H), 7.22 (d, J=8.7 Hz, 2H), 4.15 (t, J=6.6 Hz, 2H), 2.86 (t, J=6.6 Hz, 2H), 2.78 (s, 6H); LCMS: purity: 98%; MS (m/e): 510 (MH⁺).

III-53: N4-{4-[2-(Aminocarbonyloxy)ethyl]phenyl}-N2-(3-aminosulfonyl-4-methylphenyl)-5-fluoro-2,4-pyrimidinediamine ¹H NMR (DMSO-d₆): δ 10.00 (s, 2H), 8.19 (d, J=4.5 Hz, 1H), 7.93 (d, J=2.1 Hz, 1H), 7.77 (dd, J=2.1 and 8.4 Hz, 1H), 7.62 (d, J=8.4 Hz, 2H), 7.30 (s, 2H), 7.22 (d, J=8.4 Hz, 3H), 6.44 (bs, 2H), 4.10 (t, J=6.6 Hz, 2H), 2.84 (t, J=6.6 Hz, 2H), 2.53 (s, 3H); LCMS: purity: 96%; MS (m/e): 461 (MH⁺).

III-54: N4-{4-[2-(Aminocarbonyloxy)ethyl]phenyl}-N2-(3-aminosulfonylphenyl)-5-fluoro-2,4-pyrimidinediamine ¹H NMR (DMSO-d₆): δ 9.77 (s, 1H), 9.67 (s, 1H), 8.16 (d, J=4.2 Hz, 1H), 8.01 (s, 1H), 7.96-7.89 (m, 1H), 7.67 (d, J=8.4 Hz, 2H), 7.44-7.36 (m, 2H), 7.29 (s, 2H), 7.21 (d, J=8.1 Hz, 2H), 4.09 (t, J=6.6 Hz, 2H), 2.83 (t, J=6.6 Hz, 2H); LCMS: purity: 93%; MS (m/e): 447 (MH⁺).

III-55: N4-{4-[2-(Aminocarbonyloxy)ethyl]phenyl}-N2-(3-aminosulfonyl-4-chlorophenyl)-5-fluoro-2,4-pyrimidinediamine ¹H NMR (DMSO-d₆): δ 9.76 (s, 1H), 9.56 (s, 1H), 8.24 (d, J=2.4 Hz, 1H), 8.13 (d, J=3.9 Hz, 1H), 7.99 (dd, J=2.4 and 8.7 Hz, 1H), 7.68 (d, J=8.7 Hz, 2H), 7.48 (s, 2H), 7.43 (d, J=9.0 Hz, 1H), 7.22 (d, J=8.4 Hz, 2H), 4.10 (t, J=6.6 Hz, 2H), 2.83 (t, J=6.6 Hz, 2H); LCMS: purity: 97%; MS (m/e): 482 (MH⁺).

III-56: 5-Fluoro-N2-(4-methyl-3-propionylaminosulfonylphenyl)-N4-[4-(prop-2-ynyloxy)phenyl]-2,4-pyrimidinediamine ¹H NMR (DMSO-d₆): δ 12.01 (s, 1H), 9.44 (s, 1H), 9.26 (s, 1H), 8.16 (d, J=2.4 Hz, 1H), 8.06 (dd, J=0.3 and 3.3 Hz, 1H), 8.00 (dd, J=2.1 and 7.8 Hz, 1H), 7.69 (d, J=8.7 Hz, 2H), 7.19 (d, J=8.4 Hz, 1H), 6.95 (d, J=8.7 Hz, 2H), 4.77 (d, J=2.1 Hz, 2H), 3.56 (t, J=2.1 Hz, 1H), 2.49 (s, 3H), 2.24 (q, J=7.2 Hz, 2H), 0.89 (t, J=7.2 Hz, 3H); LCMS: purity: 98%; MS (m/e): 484 (MH⁺).

VI-57: N2-(3-Aminosulfonyl-4-methylphenyl)-5-fluoro-N4-[3-(prop-2-ynyloxy)phenyl]-2,4-pyrimidinediamine ¹H NMR (DMSO-d₆): δ 9.45 (s, 1H), 9.35 (s, 1H), 8.12-8.07 (m, 2H), 7.93 (dd, J=2.1 and 8.4 Hz, 1H), 7.49 (d, J=8.1 Hz, 1H), 7.42 (t, J=2.1 Hz, 1H), 7.27-7.16 (m, 4H), 6.69 (dd, J=2.7 and 8.7 Hz, 1H), 4.77 (d, J=2.4 Hz, 2H), 3.58 (t, J=2.4 Hz, 1H), 2.49 (s, 3H); LCMS: purity: 98%; MS (m/e): 428 (MH⁺).

VI-58: N2-(3-Aminosulfonyl-4-methylphenyl)-5-fluoro-N4-[3-methyl-4-(prop-2-ynyloxy)phenyl]-2,4-pyrimidinediamine ¹H NMR (DMSO-d₆): δ 10.09-9.90 (m, 2H), 8.17 (d, J=4.5 Hz, 1H), 7.87 (s, 1H), 7.80 (dd, J=2.1 and 8.4 Hz, 1H), 7.49-7.42 (m, 2H), 7.32 (s, 2H), 7.20 (d, J=8.1 Hz, 1H), 6.99

(d, J=8.4 Hz, 1H), 4.81 (d, J=2.1 Hz, 2H), 3.57 (t, J=2.1 Hz, 1H), 2.52 (s, 3H), 2.13 (s, 3H); LCMS: purity: 99%; MS (m/e): 442 (MH$^+$).

VI-59: N2-(3-Aminosulfonyl-4-methylphenyl)-N4-[3-chloro-4-(prop-2-ynyloxy)phenyl]-5-fluoro-2,4-pyrimidinediamine $^1$H (DMSO-d$_6$): δ 10.06 (s, 1H), 8.22 (d, J=4.5 Hz, 1H), 7.89 (d, J=2.1 Hz, 1H), 7.82-7.75 (m, 2H), 7.65 (dd, J=2.4 and 9.0 Hz, 1H), 7.32 (s, 2H), 7.24 (d, J=8.1 Hz, 1H), 7.19 (d, J=8.7 Hz, 1H), 4.90 (d, J=2.1 Hz, 2H), 3.63 (t, J=2.1 Hz, 1H), 2.52 (s, 3H); LCMS: purity: 99%; MS (m/e): 463 (MH$^+$).

VI-60: N2-(3-Aminosulfonyl-4-methylphenyl)-5-fluoro-N4-[3-fluoro-4-(prop-2-ynyloxy)phenyl]-2,4-pyrimidinediamine $^1$H NMR (DMSO-d$_6$): δ 9.94 (s, 2H), 8.19 (d, J=4.5 Hz, 1H), 7.96 (s, 1H), 7.82 (d, J=8.4 Hz, 1H), 7.75 (d, J=13.2 Hz, 1H), 7.48 (d, J=8.7 Hz, 1H), 7.31 (s, 2H), 7.23 (d, J=7.8 Hz, 1H), 7.17 (d, J=9.6 Hz, 1H), 4.88-4.86 (m, 2H), 3.64-3.61 (m, 1H), 2.53 (s, 3H); LCMS: purity: 98%; MS (m/e): 446 (MH$^+$).

VI-61: N2-(3-Aminosulfonyl-4-methylphenyl)-N4-[4-(but-2-ynyloxy)phenyl]-5-fluoro-2,4-pyrimidinediamine $^1$H NMR (DMSO-d$_6$): δ 10.10 (s, 2H), 8.19 (d, J=4.8 Hz, 1H), 7.90 (d, J=2.1 Hz, 1H), 7.73 (dd, J=1.8 and 8.1 Hz, 1H), 7.57 (d, J=9.0 Hz, 2H), 7.32 (s, 2H), 7.23 (d, J=8.1 Hz, 1H), 6.95 (d, J=9.0 Hz, 2H), 4.74-4.70 (m, 2H), 2.53 (s, 3H), 1.83 (t, J=2.1 Hz, 3H); LCMS: purity: 98%; MS (m/e): 442 (MH$^+$).

VIII-2: N4-(3-Chloro-4-cyanomethyleneoxyphenyl)-5-fluoro-N2-(5-methyl-2H-1,1-dioxide-1,2,4-benzothiadiazin-7-yl)-2,4-pyrimidinediamine $^1$H NMR (DMSO-d$_6$): δ 11.50 (bs, 1H), 9.57 (s, 1H), 8.17 (d, 1H, J=2.7 Hz), 8.04 (s, 1H), 7.88 (d, 1H), 7.79 (m, 2H), 7.57 (dd, 1H, J=1.2 and 9.0 Hz), 7.27 (t, 1H, J=9.6 Hz), 5.20 (s, 2H), 2.31 (s, 3H); LCMS: purity: 100%; MS (m/e): 472 (MH$^+$).

VI-26: N2-(3-aminosulfonylphenyl)-5-bromo-N4-(3-chloro-4-methoxyphenyl)-2,4-pyrimidinediamine $^1$H NMR (DMSO-d6): δ 9.61 (s, 1H), 8.64 (s, 1H), 8.21 (s, 1H), 7.91 (m, 2H), 7.63 (d, 1H, J=2.7 Hz), 7.53 (dd, 1H, J=2.4 and 6.3 Hz), 7.30 (m, 3H), 7.13 (d, 1H, J=9.3 Hz), 3.86 (s, 3H); LCMS: purity:100%; MS (m/e): 484 (M$^+$), 486 (M+2).

VI-27: N2-(3-aminosulfonyl-4-methylphenyl)-5-bromo-N4-(3-chloro-4-methoxyphenyl)-2,4-pyrimidinediamine $^1$H NMR (DMSO-d6): δ 10.01 (s, 1H), 9.15 (s, 1H), 8.28 (s, 1H), 7.84 (s, 1H), 7.72 (dd, 1H, J=1.8 and 8.4 Hz), 7.61 (d, 1H, J=2.4 Hz), 7.47 (dd, 1H, J=2.1 and 9.0 Hz), 7.29 (bs, 2H), 7.12 (m, 2H), 3.86 (s, 3H); LCMS: purity: 97%, MS (m/e): 498 (M$^+$), 500 (M+2).

VI-28: N2-(3-Aminosulfonylphenyl)-N4-(3-chloro-4-methoxyphenyl)-5-trimethylsilylacetylene-2,4-pyrimidinediamine LCMS: purity: 98%, MS (m/e): 502 (M$^+$).

VII-82: (1R,2R,3S,4S) N4-(3-Aminocarbonylbicyclo[2.2.1]hept-5-en-2-yl)-N2-(3-aminosulfonyl-4-methylphenyl)-5-fluoro-2,4-pyrimidinediamine $^1$H NMR (DMSO-d6): δ 9.30 (s, 1H), 8.19 (d, 1H, J=1.5 Hz), 7.88 (m, 2H), 7.68 (bs, 1H), 7.46 (bd, 1H, J=7.8 Hz), 7.19 (m, 4H), 6.30 (bs, 2H), 4.13 (t, 1H, J=7.5 Hz), 2.85 (bs, 1H), 2.77 (bs, 1H), 2.53 (m, 1H), 2.12 (d, 1H, J=8.4 Hz), 1.40 (d, 1H, J=8.1 Hz); LCMS: purity: 97%, MS (m/e): 433 (MH$^+$).

I-13: N2-(3-Aminosulfonylphenyl)-5-bromo-N4-(4-cyanomethyleneoxyphenyl)-2,4-pyrimidinediamine $^1$H NMR (DMSO-d6): δ 9.91 (s, 1H), 9.02 (s, 1H), 8.27 (d, 1H, J=0.9 Hz), 7.85 (m, 2H), 7.53 (d, 2H, 8.1 Hz), 7.34 (m, 4H), 7.07 (d, 2H, J=8.1 Hz), 5.18 (s, 2H); LCMS: purity: 100%, MS (m/e): 475 (M$^+$), 477 (M+2).

I-14: N2-(3-Aminosulfonyl-4-methylphenyl)-5-bromo-N4-(4-cyanomethyleneoxyphenyl)-2,4-pyrimidinediamine $^1$H NMR (DMSO-d6): δ 10.05 (s, 1H), 9.23 (s, 1H), 8.28 (s, 1H), 7.82 (s, 1H), 7.74 (dd, 1H, J=2.1 and 8.4 Hz), 7.51 (d, 2H, J=8.7 Hz), 7.29 (bs, 2H), 7.11 (m, 3H), 5.11 (s, 2H), 2.45 (s, 3H); LCMS: purity: 98%, MS (m/e): 491 (M+2).

VI-29: N2-(3-Aminosulfonyl-4-methoxyphenyl)-N4-(3-chloro-4-methoxyphenyl)-5-fluoro-2,4-pyrimidinediamine $^1$H NMR (DMSO-d6): δ 9.03 (s, 1H), 9.33 (s, 1H), 8.09 (s, 1H), 7.12 (d, 1H, J=1.8 Hz), 7.07 (d, 1H, J=2.1 Hz), 7.01 (m, 2H), 6.80 (dd, 1H, J=1.2 and 9.0 Hz), 6.60 (d, 1H, J=8.7 Hz), 4.22 (s, 3H), 4.15 (s, 3H); LCMS: purity: 99%, MS (m/e): 453 (M+).

I-15: N2-(3-Aminosulfonylphenyl)-N4-(4-cyanomethyleneoxyphenyl)-5-trimethylsilylacetylene-2,4-pyrimidinediamine $^1$H NMR (DMSO-d6): δ 9.48 (s, 1H), 8.08 (s, 1H), 7.93 (s, 1H), 7.67 (m, 2H), 7.29 (m, 3H), 7.07 (m, 3H), 6.82 (m, 2H), 4.91 (s, 2H), 0.00 (s, 9H); LCMS: purity: 89%, MS (m/e): 494 (MH$^+$).

VII-38: N2-(3-Aminosulfonyl-4-methoxy-5-methylphenyl)-N4-(2,2-difluoro-4H-benz[1,4]oxazin-3-on-6-yl)-5-fluoro-2,4-pyrimidinediamine $^1$H NMR (DMSO-d6): δ 9.55 (s, 1H), 9.29 (s, 1H), 8.10 (bd, 1H), 7.82 (bs, 1H), 7.86 (bs, 1H), 7.57 (bd, 1H, J=8.1 Hz), 7.42 (bs, 2H), 7.25 (bd, 1H, J=8.7 Hz), 7.02 (bs, 2H), 3.75 (s, 3H), 2.16 (s, 3H); LCMS: purity: 88%, MS (m/e): 511 (MH$^+$).

VI-30: N2-(3-Aminosulfonyl-4-methoxy-5-methylphenyl)-N4-(3-chloro-4-methoxyphenyl)-5-fluoro-2,4-pyrimidinediamine $^1$H NMR (DMSO-d6): δ 9.31 (bs, 2H), 8.06 (bd, 1H, J=3.6 Hz), 7.39 (m, 4H), 7.11 (d, 1H, J=8.7 Hz), 7.02 (bs, 2H), 3.83 (s, 3H), 3.76 (s, 3H), 2.18 (s, 3H); LCMS: purity: 100%, MS (m/e): 468 (M$^+$).

VII-83: (1R,2R,3S,4S) N2-(3-Aminosulfonyl-4-methoxy-5-methylphenyl)-N4-(3-aminocarbonylbicyclo[2.2.1]hept-5-ene-2-yl)-5-fluoro-2,4-pyrimidinediamine $^1$H NMR (DMSO-d6): δ 9.20 (s, 1H), 7.96 (d, 1H, =2.1 Hz), 7.86 (d, 1H, J=3.3 Hz), 7.78 (d, 1H, J=2.1 Hz), 7.65 (bs, 1H), 7.40 (bdd, 1H, J=7.8 Hz), 7.16 (bs, 1H), 6.98 (bs, 2H), 6.28 (bs, 2H), 4.16 (t, 1H, J=7.5 Hz), 3.76 (s, 3H), 2.84 (s, 1H), 2.74 (s, 1H), 2.53 (m, 1H), 2.25 (s, 3H), 2.13 (d, 1H, J=8.4 Hz), 1.39 (d, 1H, J=8.1 Hz); LCMS: purity: 100%, MS (m/e): 463 (MH$^+$).

VI-31: N2-(3-Aminosulfonylpyrid-4-yl)-N4-(3-chloro-4-methoxyphenyl)-5-fluoro-2,4-pyrimidinediamine LCMS: purity: 100%, MS (m/e): 425 (MH$^+$).

II-19: N2-(3-Aminocarbonyl-5-methylphenyl)-5-fluoro-N2-[4-(1-methylpyrazol-3-yl)amidophenyl)-2,4-pyrimidinediamine $^1$H NMR (DMSO-d6): δ 10.67 (s, 1H), 9.70 (s, 1H), 9.63 (s, 1H), 8.18 (d, 1H, J=3.6 Hz), 8.11 (d, 1H, J=2.4 Hz), 7.97 (m, 4H), 7.90 (dd, 1H, J=2.4 and 8.4 Hz), 7.58 (d, 1H, J=2.1 Hz), 7.27 (m, 2H), 7.24 (m, 1H), 6.58 (d, 1H, J=2.1 Hz), 3.78 (s, 3H), 2.52 (s, 3H); LCMS: purity: 91%, MS (m/e): 497 (MH$^+$).

II-20: N2-(3-Aminocarbonyl-5-methylphenyl)-5-fluoro-N2-[4-(1-ethylpyrazol-5-yl)amidophenyl)-2,4-pyrimidinediamine LCMS: purity: 97%, MS (m/e): 511 (M+).

II-21: N2-(3-Aminocarbonyl-5-methylphenyl)-5-fluoro-N2-[4-(1-methylpyrazol-5-yl)amidophenyl)-2,4-pyrimidinediamine $^1$H NMR (DMSO-d6): δ 10.21 (s, 1H), 9.91 (s, 1H), 9.77 (s, 1H), 8.22 (d, 1H, J=2.4 Hz), 8.07 (s, 1H), 7.96 (m, 6H), 7.38 (d, 1H, J=1.5 Hz), 7.27 (m, 3H), 6.23 (s, 1H), 2.52 (s, 3H), 2.49 (s, 3H); LCMS: purity: 96%, MS (m/e): 497 (M$^+$).

II-22: N2-(3-Aminocarbonyl-5-methylphenyl)-5-fluoro-N2-[4-(1H-pyrazol-5-yl)amidophenyl)-2,4-pyrimidinediamine LCMS: purity: 91%, MS (m/e): 483 (MH$^+$).

VI-24: N2-(3-Aminosulfonylphenyl)-5-carboethoxy-N4-(N-carboethoxymethylene-N-3-chloro-4-methoxyphenyl)-2,4-pyrimidinediamine LCMS: purity: 94%; MS (m/e): 564 (M$^+$).

VI-25: N2-(3-Aminosulfonyl-4-methylphenyl)-5-carboethoxy-N4-(N-carboethoxymethylene-N-3-chloro-4-methoxyphenyl)-2,4-pyrimidinediamine LCMS: purity: 97%, MS (m/e): 579 (MH$^+$).

VIII-3: N4-(3-Chloro-4-methoxyphenyl)-5-fluoro-N2-(5-methyl-2H-1,1-dioxo-1,2,4-benzothiadiazin-7-yl)-2,4-pyrimidinediamine LCMS: purity: 96%, MS (m/e): 463 (M$^+$).

VI-33: N2-(3-aminosulfonylphenyl)-5-fluoro-N4-(4-trofluoromethoxyphenyl)-2,4-pyrimidinediamine $^1$H NMR (DMSO-d6): δ 9.57 (s, 1H), 9.55 (s, 1H), 8.15 (d, 1H, J=3.6 Hz), 8.12 (bs, 1H), 7.92 (m, 3H), 7.36 (m, 6H); LCMS: purity: 98%, MS (m/e): 444 (MH$^+$).

VII-53: N2-(3-Aminosulfonyl-4-methylphenyl)-N4-(2-cyanobenzofuran-5-yl)-5-fluoro-2,4-pyrimidinediamine $^1$H NMR (DMSO-d6): δ 9.53 (s, 1H), 9.42 (s, 1H), 8.29 (d, 1H, J=1.8 Hz), 8.10 (m, 2H), 7.90 (m, 2H), 7.69 (d, 1H, J=9.0 Hz), 7.23 (bs, 1H), 7.13 (d, 1H, J=8.1 Hz), 7.10 (m, 2H), 5.23 (s, 2H), 2.37 (s, 3H); LCMS: purity: 97%, MS (m/e): 439 (MH$^+$).

VI-32: N2-(3-aminosulfonyl-4-methylphenyl)-5-fluoro-N4-(4-trofluoromethoxyphenyl)-2,4-pyrimidinediamine LCMS: purity: 100%, MS (m/e): 458 (MH$^+$).

I-263: N2-[4-(2-N,N-Diethylaminoethyl)aminosulfonylphenyl)-5-fluoro-N4-[4-(3-methyl-1,2,4-oxadiazol-5-yl)methyleneoxyphenyl]-2,4-pyrimidinediamine $^1$H NMR (DMSO d$_6$, 300 MHz): δ 9.61 (s, 1H), 9.36 (s, 1H), 8.11 (d, 1H, J=3.6 Hz), 7.82 (d, 2H, J=8.7 Hz), 7.66 (d, 2H, J=8.7 Hz), 7.58 (d, 2H, J=8.7 Hz), 7.15 (br s, 1H), 7.03 (d, 2H, J=8.7 Hz), 5.46 (s, 2H), 2.74 (br s, 2H), 2.36 (m, 9H), 0.85 (t, 6H, J=6.6 Hz); LCMS (m/z): 571 (MH$^+$).

I-280: N2-(3-Aminosulfonyl-4-methylphenyl)-5-fluoro-N4-[4-(2-methylthiazol-4-yl)methyleneoxyphenyl]-2,4-pyrimidinediamine $^1$H NMR (DMSO d$_6$, 300 MHz): δ 9.32 (s, 1H), 9.21 (d, 1H, J=1.8 Hz), 8.02 (d, 1H, J=3.9 Hz), 7.87 (dd, 1H, J=2.1 and 8.2 Hz), 7.68 (d, 2H, J=9.0 Hz), 7.52 (s, 1H), 7.21 (s, 2H), 7.13 (m, 1H), 6.98 (d, 2H, J=8.7 Hz), 5.08 (s, 2H), 2.65 (s, 3H), 2.48 (s, 3H); LCMS (m/z): 501 (MH$^+$).

I-281: N2-(3-Aminosulfonylphenyl)-5-fluoro-N4-[4-(2-methylthiazol-4-yl)methyleneoxyphenyl]-2,4-pyrimidinediamine $^1$H NMR (DMSO d$_6$, 300 MHz): δ 9.44 (s, 1H), 9.25 (s, 1H), 8.06 (d, 2H, J=3.9 Hz), 7.93 (m, 1H), 7.67 (d, 1H, J=9.0 Hz), 7.52 (s, 1H), 7.32 (m, 2H), 7.24 (s, 2H), 6.99 (d, 2H, J=8.7 Hz), 5.08 (s, 2H), 2.66 (s, 3H); LCMS (m/z): 487 (MH$^+$).

I-282: 5-Fluoro-N2-[3-(N-methylaminosulfony)-4-methylphenyl]-N4-[4-(2-methylthiazol-4-yl)methyleneoxyphenyl]-2,4-pyrimidinediamine ¹H NMR (DMSO d₆, 300 MHz): δ 9.34 (s, 1H), 9.22 (s, 1H), 8.04 (d, 1H, J=3.6 Hz), 8.00 (d, 1H, J=1.8 Hz), 7.93 (dd, 1H, J=2.4 and 8.1 Hz), 7.67 (d, 2H, J=9.0 Hz), 7.52 (s, 1H), 7.31 (q, 1H, J=5.1 Hz), 7.18 (d, 1H, J=8.4 Hz), 6.99 (d, 2H, J=9.0 Hz), 5.08 (s, 2H), 2.65 (s, 3H), 2.45 (s, 3H), 2.41 (d, 3H, J=4.5 Hz); LCMS (m/z): 515 (MH⁺).

I-283: N2-[3-(2-N,N-Diethylaminoethyl)aminosulfonylphenyl)-5-fluoro-N4-[4-(2-methylthizol-4-yl)methyleneoxyphenyl]-2,4-pyrimidinediamine ¹H NMR (DMSO d₆, 300 MHz): δ 9.46 (s, 1H), 9.26 (s, 1H), 8.06 (d, 2H, J=5.1 Hz), 7.99 (m, 1H), 7.66 (d, 2H, J=9.0 Hz), 7.52 (s, 1H), 7.36 (t, 1H, J=8.1 Hz), 7.26 (m, 2H), 6.99 (d, 2H, J=9.0 Hz), 5.08 (s, 2H), 2.78 (t, 2H, J=7.8 Hz), 2.65 (s, 3H), 2.37 (m, 6H), 0.84 (t, 6H, J=6.9 Hz); LCMS (m/z): 586 (MH⁺).

I-284: N2-[4-(2-N,N-Diethylaminoethyl)aminosulfonylphenyl)-5-fluoro-N4-[4-(2-methylthizol-4-yl)methyleneoxyphenyl]-2,4-pyrimidinediamine ¹H NMR (DMSO d₆, 300 MHz): δ 9.59 (s, 1H), 9.32 (s, 1H), 8.09 (d, 1H, J=3.6 Hz), 7.82 (d, 2H, J=9.0 Hz), 7.58 (m, 5H), 7.15 (br s, 1H), 7.01 (d, 2H, J=9.0 Hz), 5.09 (s, 2H), 2.72 (br s, 2H), 2.65 (s, 3H), 2.38 (m, 6H), 0.84 (t, 6H, J=6.9 Hz); LCMS (m/z): 586 (MH⁺).

I-265: N2-(3-Aminosulfonyl-4-chloro-5-methylphenyl)-5-fluoro-N4-[4-(3-methyl-1,2,4-oxadiazol-5-yl)methyleneoxyphenyl]-2,4-pyrimidinediamine ¹H NMR (DMSO d₆, 300 MHz): δ 9.50 (s, 1H), 9.31 (s, 1H), 8.07 (m, 2H), 8.00 (s, 1H), 7.67 (d, 2H, J=8.7 Hz), 7.40 (s, 2H), 7.00 (d, 2H, J=9.3 Hz), 5.44 (s, 2H), 2.36 (s, 3H), 2.24 (s, 3H); LCMS (m/z): 520 (MH⁺).

I-285: N2-(4-Aminosulfonylphenyl)-5-fluoro-N4-[4-(2-methylthiazol-4-yl)methyleneoxyphenyl]-2,4-pyrimidinediamine ¹H NMR (DMSO d₆, 300 MHz): δ 9.57 (s, 1H), 9.34 (s, 1H), 8.09 (d, 1H, J=3.9 Hz), 7.79 (d, 2H, J=8.7 Hz), 7.63 (d, 2H, J=6.3 Hz), 7.60 (d, 2H, J=6.6 Hz), 7.54 (s, 1H), 7.13 (s, 2H), 7.02 (d, 2H, J=9.0 Hz), 5.09 (s, 2H), 2.66 (s, 3H); LCMS (m/z): 487 (MH⁺).

III-70: N2-(3-Aminosulfonylphenyl)-5-fluoro-N4-[4-(4-pyridinylmethyl)phenyl]-2,4-pyrimidinediamine ¹H NMR (DMSO d₆, 300 MHz): δ 9.47 (s, 1H), 9.36 (s, 1H), 8.44 (d, 2H, J=5.7 Hz), 8.09 (d, 1H, J=3.6 Hz), 8.07 (s, 1H), 7.93 (m, 1H), 7.71 (d, 2H, J=8.4 Hz), 7.25 (m, 8H), 3.94 (s, 2H); LCMS (m/z): 451 (MH⁺).

III-74: N2-(3-Aminosulfonyl-4-methylphenyl)-5-fluoro-N4-[4-(4-pyridinylmethyl)phenyl]-2,4-pyrimidinediamine ¹H NMR (DMSO d₆, 300 MHz): δ 9.35 (s, 1H), 9.31 (s, 1H), 8.44 (d, 2H, J=5.7 Hz), 8.07 (d, 1H, J=2.4 Hz), 8.06 (d, 1H, J=3.6 Hz), 7.87 (dd, 1H, J=2.4 and 8.1 Hz), 7.71 (d, 2H, J=8.4 Hz), 7.20 (m, 5H), 7.09 (m, 2H), 3.93 (s, 2H), 2.36 (s, 3H); LCMS (m/z): 465 (MH⁺).

III-75: 5-Fluoro-N2-[3-(N-methylaminosulfony)-4-methylphenyl]-5-fluoro-N4-[4-(4-pyridinylmethyl)phenyl]-2,4-pyrimidinediamine ¹H NMR (DMSO d₆, 300 MHz): δ 9.37 (s, 1H), 9.33 (s, 1H), 8.44 (d, 2H, J=5.7 Hz), 8.07 (d, 1H, J=3.6 Hz), 7.98 (d, 1H, J=2.1), 7.93 (dd, 1H, J=2.1 and 8.4 Hz), 7.70 (d, 2H, J=8.1 Hz), 7.32 (q, 1H, J=4.8 Hz), 7.24 (d, 2H, J=5.4 Hz), 7.19 (d, 2H, J=8.1 Hz), 7.11 (d, 1H, J=8.1 Hz), 3.94 (s, 2H), 2.44 (s, 3H), 2.40 (d, 3H, J=5.1 Hz); LCMS (m/z): 479 (MH⁺).

III-71: N2-(4-Aminosulfonylphenyl)-5-fluoro-N4-[4-(4-pyridinylmethyl)phenyl]-2,4-pyrimidinediamine ¹H NMR (DMSO d₆, 300 MHz): δ 9.58 (s, 1H), 9.42 (s, 1H), 8.45 (d, 2H, J=6.0 Hz), 8.13 (d, 1H, J=3.9 Hz), 7.79 (d, 2H, J=8.7 Hz), 7.67 (d, 2H, J=8.4 Hz), 7.61 (d, 2H, J=9.0 Hz), 7.24 (m, 4H), 7.14 (br s, 2H), 3.96 (s, 2H); LCMS (m/z): 451 (MH⁺).

I-188: N2-(3-Aminosulfonylphenyl)-5-fluoro-N4-[4-(3-pyridinyl)methyleneoxyphenyl]-2,4-pyrimidinediamine ¹H NMR (DMSO d₆, 300 MHz): δ 9.46 (s, 1H), 9.27 (s, 1H), 8.66 (s, 1H), 8.53 (d, 1H, J=3.6 Hz), 8.06 (d, 2H, J=2.7 Hz), 7.93 (m, 1H), 7.86 (d, 1H, J=8.1 Hz), 7.68 (d, 2H, J=9.0 Hz), 7.41 (dd, 1H, J=4.8 and 7.6 Hz), 7.32 (m, 2H), 7.25 (s, 2H), 7.00 (d, 2H, J=9.3 Hz), 5.15 (s, 2H); LCMS (m/z): 467 (MH⁺).

I-189: N2-(3-Aminosulfonyl-4-methylphenyl)-5-fluoro-N4-[4-(3-pyridinyl)methyleneoxyphenyl]-2,4-pyrimidinediamine ¹H NMR (DMSO d₆, 300 MHz): δ 9.30 (s, 1H), 9.27 (s, 1H), 8.66 (s, 1H), 8.53 (d, 1H, J=3.6 Hz), 8.08 (d, 1H, J=1.5 Hz), 8.03 (d, 1H, J=3.6 Hz), 7.86 (d, 2H, J=8.4 Hz), 7.69 (d, 2H, J=9.0 Hz), 7.42 (dd, 1H, J=5.1 and 7.8 Hz), 7.22 (s, 1H), 7.11 (m, 2H), 6.99 (d, 2H, J=8.7 Hz), 5.15 (s, 2H), 2.36 (s, 3H); LCMS (m/z): 481 (MH⁺).

I-190: 5-Fluoro-N2-[3-(N-methylaminosulfony)-4-methylphenyl]-5-fluoro-N4-[4-(3-pyridinyl)methyleneoxyphenyl]-2,4-pyrimidinediamine ¹H NMR (DMSO d₆, 300 MHz): δ 9.29 (s, 1H), 9.18 (s, 1H), 8.60 (s, 1H), 8.46 (d, 1H, J=4.5 Hz), 7.98 (d, 1H, J=3.6 Hz), 7.93 (s, 1H), 7.87 (d, 1H, J=8.4 Hz), 7.80 (d, 1H, J=7.5 Hz), 7.62 (d, 2H, J=8.7 Hz), 7.35 (dd, 1H, J=4.5 and 7.6 Hz), 7.26 (q, 1H, J=5.1 Hz), 7.10 (d, 1H, J=8.4 Hz), 6.93 (d, 2H, J=8.7 Hz), 5.08 (s, 2H), 2.39 (s, 3H), 2.35 (d, 3H, J=4.8 Hz); LCMS (m/z): 495 (MH⁺).

III-1: 5-Fluoro-N2-[3-(N-methylaminosulfony)-4-methylphenyl]-5-fluoro-N4-(4-cyanomethylphenyl)-2,4-pyrimidinediamine ¹H NMR (DMSO d₆, 300 MHz): δ 9.41 (s, 2H), 8.11 (d, 1H, J=3.6 Hz), 8.02 (d, 1H, J=2.1 Hz), 7.95 (dd, 1H, J=1.8 and 8.2 Hz), 7.82 (d, 2H, J=8.7 Hz), 7.29 (d, 3H, J=8.4 Hz), 7.21 (d, 1H, J=8.1 Hz), 3.99 (s, 2H), 2.46 (s, 3H), 2.42 (d, 3H, J=2.4 Hz); LCMS (m/z): 427 (MH⁺).

I-182: N2-(3-Aminosulfonylphenyl)-5-fluoro-N4-[3-(3-pyridinyl)methyleneoxyphenyl]-2,4-pyrimidinediamine ¹H NMR (DMSO d₆, 300 MHz): δ 9.52 (s, 1H), 9.34 (s, 1H), 8.65 (d, 1H, J=1.8 Hz), 8.53 (dd, 1H, J=1.5 and 4.6 Hz), 8.12 (d, 1H, J=3.6 Hz), 8.08 (s, 1H), 7.98 (d, 1H, J=7.8 Hz), 7.84 (d, 1H, J=7.8 Hz), 7.47 (s, 2H), 7.41 (m, 1H), 7.32 (m, 2H), 7.24 (m, 3H), 6.75 (m, 1H), 5.13 (s, 2H); LCMS (m/z): 467 (MH⁺).

I-183: N2-(3-Aminosulfonyl-4-methylphenyl)-5-fluoro-N4-[3-(3-pyridinyl)methyleneoxyphenyl]-2,4-pyrimidinediamine ¹H NMR (DMSO d₆, 300 MHz): δ 9.42 (s, 1H), 9.31 (s, 1H), 8.65 (d, 1H, J=2.1 Hz), 8.52 (dd, 1H, J=1.5 and 4.7 Hz), 8.09 (m, 2H), 7.93 (dd, 1H, J=2.7 and 8.4 Hz), 7.84 (d, 1H, J=7.5 Hz), 7.47 (m, 2H), 7.41 (dd, 1H, J=4.8 and 7.6 Hz), 7.21 (m, 3H), 7.14 (d, 1H, J=8.4 Hz), 6.73 (m, 1H), 5.11 (s, 2H), 2.44 (s, 3H); LCMS (m/z): 481 (MH⁺).

I-184: 5-Fluoro-N2-[3-(N-methylaminosulfony)-4-methylphenyl]-5-fluoro-N4-[3-(3-pyridinyl)methyleneoxyphenyl]-2,4-pyrimidinediamine ¹H NMR (DMSO d₆, 300 MHz): δ 9.42 (s, 1H), 9.33 (s, 1H), 8.64 (s, 1H), 8.52 (d, 1H, J=4.5 Hz), 8.11 (d, 1H, J=3.6 Hz), 7.98 (d, 2H, J=8.1 Hz), 7.83 (d, 1H, J=7.5 Hz), 7.47 (s, 2H), 7.41 (m, 1H), 7.31 (q, 1H, J=4.8 Hz), 7.23 (t, 1H, J=8.1 Hz), 7.17 (d, 1H, J=8.1 Hz), 6.73 (d, 1H, J=9.0 Hz), 5.10 (s, 2H), 2.49 (s, 3H), 2.41 (d, 3H, J=4.5 Hz), LCMS (m/z): 495 (MH⁺).

III-2: N2-[4-(2-N,N-Diethylaminoethyl)aminosulfonylphenyl)-5-fluoro-N4-(4-cyanomethylphenyl)-2,4-pyrimidinediamine ¹H NMR (DMSO d₆, 300 MHz): δ 9.67 (s, 1H), 9.52 (s, 1H), 8.16 (d, 1H, J=3.3 Hz), 7.85 (d, 2H, J=8.7 Hz), 7.79 (d, 2H, J=8.1 Hz), 7.61 (d, 2H, J=8.7 Hz), 7.31 (d, 2H, J=8.4 Hz), 7.16 (br s, 1H), 4.01 (s, 2H), 2.74 (t, 2H, J=7.2 Hz), 2.36 (q, 6H, J=7.2 Hz), 0.85 (t, 6H, J=6.9 Hz); LCMS (m/z): 498 (MH⁺).

VII-55: N2-(3-Aminosulphonylphenyl)-5-fluoro-N4-[4-(3-pyridinylmethyl)benzo[1,4]oxazin-7-yl]-2,4-pyrimidinediamine ¹H NMR (DMSO d₆, 300 MHz): δ 9.41 (s, 1H), 9.07 (s, 1H), 8.56 (s, 1H), 7.47 (d, 1H, J=3.9 Hz), 8.01 (m, 3H), 7.72 (d, 1H, J=8.1 Hz), 7.36 (dd, 1H, J=4.5 and 7.6 Hz), 7.31-7.11 (m, 6H), 6.65 (d, 1H, J=8.7 Hz), 4.51 (s, 2H), 4.25 (t, 2H, J=4.5 Hz), 3.39 (t, 2H, J=4.2 Hz); LCMS (m/z): 508 (MH⁺).

VII-56: N2-(3-Aminosulphonylphenyl)-5-fluoro-N4-[4-(3-pyridinylmethyl)benzo[1,4]oxazin-7-yl]-2,4-pyrimidinediamine ¹H NMR (DMSO d₆, 300 MHz): δ 9.30 (s, 1H), 9.03 (s, 1H), 8.56 (s, 1H), 8.46 (d, 1H, J=3.6 Hz), 8.05 (d, 1H, J=1.8 Hz), 7.98 (d, 1H, J=3.6 Hz), 7.91 (dd, 1H, J=2.1 and 8.4 Hz), 7.71 (d, 1H, J=7.5 Hz), 7.35 (dd, 1H, J=4.5 and 9.7 Hz), 7.21 (s, 2H), 7.19-7.05 (m, 3H), 6.64 (d, 1H, J=8.7 Hz), 4.49 (s, 2H), 4.24 (t, 2H, J=4.5 Hz), 3.37 (t, 2H, J=4.5 Hz), 2.47 (s, 3H); LCMS (m/z): 522 (MH⁺).

I-185: N2-(4-Aminosulfonylphenyl)-5-fluoro-N4-[3-(3-pyridinyl)methyleneoxyphenyl]-2,4-pyrimidinediamine ¹H NMR (DMSO d₆, 300 MHz): δ 9.64 (s, 1H), 9.42 (s, 1H), 8.64 (s, 1H), 8.51 (d, 1H, J=4.5 Hz), 8.16 (d, 1H, J=3.6 Hz), 7.84 (m, 3H), 7.63 (d, 2H, J=8.7 Hz), 7.42 (m, 3H), 7.26 (t, 1H, J=7.8 Hz), 7.13 (s, 2H), 6.77 (d, 1H, J=8.1 Hz), 5.13 (s, 2H), LCMS (m/z): 467 (MH⁺).

I-186: N2-[4-(2-N,N-Diethylaminoethyl)aminosulfonylphenyl)-5-fluoro-N4-[3-(3-pyridinyl)methyleneoxyphenyl]-2,4-pyrimidinediamine ¹H NMR (DMSO d₆, 300 MHz): δ 9.69 (s, 1H), 9.43 (s, 1H), 8.64 (s, 1H), 8.51 (d, 1H, J=4.5 Hz), 8.16 (d, 1H, J=3.6 Hz), 7.84 (m, 3H), 7.59 (d, 2H, J=8.7 Hz), 7.40 (m, 3H), 7.26 (t, 1H, J=8.1 Hz), 7.18 (br s, 1H), 6.78 (d, 1H, J=8.1 Hz), 5.13 (s, 2H), 2.72 (s, 2H), 2.37 (q, 6H, J=6.9 Hz), 0.85 (t, 6H, J=6.9 Hz), LCMS (m/z): 566 (MH⁺).

I-160 942988: N2-(3-Aminosulfonyl-4-methylphenyl)-5-fluoro-N4-[4-(2-pyridinyl)methyleneoxyphenyl]-2,4-pyrimidinediamine ¹H NMR (DMSO d₆, 300 MHz): δ 9.32 (s, 1H), 9.21 (s, 1H), 8.56 (d, 1H, J=4.5 Hz), 8.09 (d, 1H, J=2.1 Hz), 8.02 (d, 1H, J=3.6 Hz), 7.83 (m, 2H), 7.68 (d, 2H, J=9.0 Hz), 7.50 (d, 1H, J=7.8 Hz), 7.33 (dd, 1H, J=5.1 and 7.0 Hz), 7.21 (s, 2H), 7.12 (d, 1H, J=8.4 Hz), 6.98 (d, 1H, J=8.7 Hz), 5.73 (s, 2H), 2.48 (s, 3H); LCMS (m/z): 481 (MH⁺).

I-191: N2-[4-(2-N,N-Diethylaminoethyl)aminosulfonylphenyl)-5-fluoro-N4-[4-(3-pyridinyl)methyleneoxyphenyl]-2,4-pyrimidinediamine ¹H NMR (DMSO d₆, 300 MHz): δ 9.61 (s, 1H), 9.34 (s, 1H), 8.66 (s, 1H), 8.53 (d, 1H, J=3.9 Hz), 8.10 (d, 1H, J=3.6 Hz), 7.86 (d, 1H, J=9.3 Hz), 7.81 (d, 2H, J=8.7 Hz), 7.62 (d, 2H, J=9.0 Hz), 7.56 (d, 1H, J=9.0 Hz), 7.41 (dd, 1H, J=5.1 and 7.8 Hz), 7.21 (br s, 1H), 7.02 (d, 2H, J=9.0 Hz), 5.18 (s, 2H), 2.72 (bs s, 2H), 2.34 (m, 6H), 0.83 (t, 6H, J=7.5 Hz), LCMS (m/z): 566 (MH⁺).

III-66: N2-(3-Aminosulfonyl-4-methoxyphenyl)-5-fluoro-N4-[4-(4-pyridinylmethyl)phenyl]-2,4-pyrimidinediamine ¹H NMR (DMSO d₆, 300 MHz): δ 9.27 (s, 1H), 9.17 (s, 1H), 8.44 (d, 2H, J=4.2 Hz), 8.04 (d, 1H, J=3.9 Hz), 7.97 (s, 1H), 7.86 (d, 1H, J=8.7 Hz), 7.72 (d, 2H, J=8.1 Hz), 7.24 (d, 2H, J=4.5 Hz), 7.19 (d, 2H, J=8.1 Hz), 7.01 (d, 1H, J=9.0 Hz), 6.95 (s, 2H), 3.93 (s, 2H), 3.83 (s, 3H); LCMS (m/z): 481 (MH⁺).

III-67: N2-[4-(2-N,N-Diethylaminoethyl)aminosulfonylphenyl)-5-fluoro-N4-[4-(4-pyridinylmethyl)phenyl]-2,4-pyrimidinediamine ¹H NMR (DMSO d₆, 300 MHz): δ 9.47 (s, 1H), 9.36 (s, 1H), 8.44 (d, 2H, J=5.1 Hz), 8.09 (d, 1H, J=3.3 Hz), 8.05 (s, 1H), 7.98 (d, 1H, J=7.5 Hz), 7.71 (d, 2H, J=7.8 Hz), 7.25 (m, 7H), 3.94 (s, 2H), 2.79 (t, 2H, J=7.2 Hz), 2.37 (q, 6H, J=6.9 Hz), 0.85 (t, 6H, J=6.6 Hz); LCMS (m/z): 550 (MH$^+$).

I-161: 5-Fluoro-N2-[3-(N-methylaminosulfony)-4-methylphenyl]-5-fluoro-N4-[4-(2-pyridinyl)methyleneoxyphenyl]-2,4-pyrimidinediamine $^1$H NMR (DMSO d$_6$, 300 MHz): δ 9.33 (s, 1H), 9.23 (s, 1H), 8.57 (d, 1H, J=4.8 Hz), 8.04 (d, 1H, J=3.9 Hz), 8.01 (d, 1H, J=2.1 Hz), 7.93 (dd, 1H, J=2.4 and 8.1 Hz), 7.82 (m, 1H), 7.68 (d, 2H, J=8.7 Hz), 7.51 (d, 1H, J=7.8 Hz), 7.32 (m, 2H), 7.16 (d, 1H, J=8.4 Hz), 6.98 (d, 2H, J=8.7 Hz), 5.17 (s, 2H), 2.46 (s, 3H), 2.42 (d, 3H, J=4.8 Hz); LCMS (m/z): 495 (MH$^+$).

I-162: N2-(3-Aminosulfonylphenyl)-5-fluoro-N4-[4-(2-pyridinyl)methyleneoxyphenyl]-2,4-pyrimidinediamine $^1$H NMR (DMSO d$_6$, 300 MHz): δ 9.43 (s, 1H), 9.25 (s, 1H), 8.57 (d, 1H, J=5.4 Hz), 8.06 (d, 2H, J=3.9 Hz), 7.93 (m, 1H), 7.82 (m, 1H), 7.68 (d, 2H, J=9.0 Hz), 7.51 (d, 1H, J=7.8 Hz), 7.31 (m, 3H), 7.24 (s, 2H), 6.99 (d, 2H, J=9.0 Hz), 5.17 (s, 2H); LCMS (m/z): 467 (MH$^+$).

I-193: N2-(3-Aminosulfonylphenyl)-5-fluoro-N4-[4-(4-pyridinyl)methyleneoxyphenyl]-2,4-pyrimidinediamine $^1$H NMR (DMSO d$_6$, 300 MHz): δ 9.45 (s, 1H), 9.27 (s, 1H), 8.56 (d, 2H, J=5.7 Hz), 8.06 (d, 2H, J=3.6 Hz), 7.93 (d, 1H, J=7.2 Hz), 7.68 (d, 2H, J=8.7 Hz), 7.42 (d, 1H, J=6.0 Hz), 7.28 (m, 4H), 6.98 (d, 2H, J=8.7 Hz), 5.18 (s, 2H); LCMS (m/z): 467 (MH$^+$).

I-194: N2-(3-Aminosulfonyl-4-methylphenyl)-5-fluoro-N4-[4-(4-pyridinyl)methyleneoxyphenyl]-2,4-pyrimidinediamine $^1$H NMR (DMSO d$_6$, 300 MHz): δ 9.33 (s, 1H), 9.23 (s, 1H), 8.56 (d, 2H, J=4.8 Hz), 8.07 (d, 1H, J=1.8 Hz), 8.02 (d, 1H, J=3.9 Hz), 7.86 (dd, 1H, J=2.4 and 8.2 Hz), 7.68 (d, 2H, J=9.3 Hz), 7.42 (d, 2H, J=5.4 Hz), 7.22 (s, 2H), 7.11 (d, 1H, J=8.4 Hz), 6.97 (d, 2H, J=9.3 Hz), 5.18 (s, 2H), 2.48 (s, 3H); LCMS (m/z): 481 (MH$^+$).

III-72: N2-[4-(2-N,N-Diethylaminoethyl)aminosulfonylphenyl)-5-fluoro-N4-[4-(4-pyridinylmethyl)phenyl]-2,4-pyrimidinediamine $^1$H NMR (DMSO d$_6$, 300 MHz): δ 9.63 (s, 1H), 9.43 (s, 1H), 8.45 (d, 2H, J=6.0 Hz), 8.13 (d, 1H, J=3.6 Hz), 7.82 (d, 2H, J=8.7 Hz), 7.67 (d, 2H, J=8.4 Hz), 7.57 (d, 2H, J=8.7 Hz), 7.23 (t, 4H, J=9.3 Hz), 7.18 (br s, 1H), 3.96 (s, 2H), 2.71 (t, 2H, J=6.0 Hz), 2.37 (q, 6H, J=6.9 Hz), 0.84 (t, 6H, J=6.5 Hz); LCMS (m/z): 550 (MH$^+$).

I-187: N2-[3-(2-N,N-Diethylaminoethyl)aminosulfonylphenyl)-5-fluoro-N4-[3-(3-pyridinyl)methyleneoxyphenyl]-2,4-pyrimidinediamine $^1$H NMR (DMSO d$_6$, 300 MHz): δ 9.54 (s, 1H), 9.37 (s, 1H), 8.65 (d, 1H, J=1.8 Hz), 8.52 (dd, 1H, J=1.5 and 4.8 Hz), 8.13 (d, 1H, J=3.6 Hz), 8.05 (d, 1H, J=1.2 Hz), 8.02 (m, 1H), 7.84 (m, 1H), 7.47 (m, 2H), 7.43-7.34 (m, 2H), 7.31 (br s, 1H), 7.24 (m, 2H), 6.74 (dd, 1H, J=2.4 and 7.9 Hz), 5.12 (s, 2H), 2.78 (br s, 2H), 2.35 (q, 6H, J=7.2 Hz), 0.84 (t, 6H, J=6.9 Hz); LCMS (m/z): 566 (MH$^+$).

I-163: N2-(4-Aminosulfonylphenyl)-5-fluoro-N4-[4-(2-pyridinyl)methyleneoxyphenyl]-2,4-pyrimidinediamine $^1$H NMR (DMSO d$_6$, 300 MHz): δ 9.57 (s, 1H), 9.34 (s, 1H), 8.57 (d, 1H, J=4.5 Hz), 8.09 (d, 1H, J=3.6 Hz), 7.84 (d, 1H, J=7.5 Hz), 7.79 (d, 2H, J=8.7 Hz), 7.61 (t, 4H, J=6.6 Hz), 7.52 (d, 1H, J=7.8 Hz), 7.33 (t, 1H, J=8.7 Hz), 7.13 (s, 2H), 7.02 (d, 2H, J=9.0 Hz), 5.18 (s, 2H); LCMS (m/z): 467 (MH$^+$).

I-164: N2-(3-Aminosulfonylpyrid-4-yl)-5-fluoro-N4-[4-(2-pyridinyl)methyleneoxyphenyl]-2,4-pyrimidinediamine $^1$H NMR (DMSO d$_6$, 300 MHz): δ 9.29 (s, 1H), 9.28 (s, 1H), 8.69 (d, 1H, J=7.5 Hz), 8.56 (m, 1H), 8.45 (d, 1H, J=3.3 Hz), 8.36 (s, 1H), 7.83 (m, 1H), 7.58 (d, 2H, J=9.0 Hz), 7.52 (d, 1H, J=8.1 Hz), 7.34 (m, 1H), 7.06 (d, 2H, J=9.0 Hz), 6.91 (d, 1H, J=7.8 Hz), 5.18 (s, 2H); LCMS (m/z): 468 (MH$^+$).

I-165: N2-[4-(2-N,N-Diethylaminoethyl)aminosulfonylphenyl)-5-fluoro-N4-[4-(2-pyridinyl)methyleneoxyphenyl]-2,4-pyrimidinediamine LCMS (m/z): 566 (MH$^+$).

I-166: N2-[3-(2-N,N-Diethylaminoethyl)aminosulfonylphenyl)-5-fluoro-N4-[4-(2-pyridinyl)methyleneoxyphenyl]-2,4-pyrimidinediamine $^1$H NMR (DMSO d$_6$, 300 MHz): δ 9.45 (s, 1H), 9.28 (s, 1H), 8.56 (d, 1H, J=4.5 Hz), 8.14 (s, 1H), 8.05 (m, 2H), 7.98 (d, 1H, J=8.4 Hz), 7.82 (m, 1H), 7.67 (d, 2H, J=9.0 Hz), 7.51 (d, 1H, J=7.8 Hz), 7.33 (t, 2H, J=7.8 Hz), 7.25 (d, 1H, J=7.8 Hz), 6.99 (d, 2H, J=8.7 Hz), 5.17 (s, 2H), 2.79 (t, 2H, J=7.5 Hz), 2.38 (q, 6H, J=6.9 Hz), 0.85 (t, 6H, J=7.2 Hz); LCMS (m/z): 566 (MH$^+$).

I-195: 5-Fluoro-N2-[3-(N-methylaminosulfony)-4-methylphenyl]-5-fluoro-N4-[4-(4-pyridinyl)methyleneoxyphenyl]-2,4-pyrimidinediamine $^1$H NMR (DMSO d$_6$, 300 MHz): δ 9.35 (s, 1H), 9.25 (s, 1H), 8.56 (d, 2H, J=4.5 Hz), 8.05 (d, 1H, J=2.4 Hz), 7.99 (s, 1H), 7.92 (d, 1H, J=7.8 Hz), 7.68 (d, 2H, J=8.7 Hz), 7.43 (d, 2H, J=5.1 Hz), 7.33 (q, 1H, J=4.8 Hz), 7.15 (d, 1H, J=7.8 Hz), 6.98 (d, 2H, J=7.8 Hz), 5.18 (s, 2H), 2.45 (s, 3H), 2.41 (d, 3H, J=4.2 Hz); LCMS (m/z): 495 (MH$^+$).

III-81: N2-(3-Aminosulfonylphenyl)-5-fluoro-N4-[4-(1-imidazolylmethyl)phenyl]-2,4-pyrimidinediamine $^1$H NMR (DMSO d$_6$, 300 MHz): δ 9.49 (s, 1H), 9.42 (s, 1H), 8.11 (m, 3H), 7.93 (m, 1H), 7.77 (d, 3H, J=8.4 Hz), 7.25 (m, 6H), 6.89 (s, 1H), 5.14 (s, 2H); LCMS (m/z): 440 (MH$^+$).

III-82: N2-(3-Aminosulfonyl-4-methylphenyl)-5-fluoro-N4-[4-(1-imidazolylmethyl)phenyl]-2,4-pyrimidinediamine $^1$H NMR (DMSO d$_6$, 300 MHz): δ 9.38 (s, 2H), 8.14 (s, 1H), 8.08 (s, 2H), 7.86 (dd, 1H, J=1.8 and 8.2 Hz), 7.78 (s, 1H), 7.74 (d, 2H, J=4.5 Hz), 7.20 (m, 4H), 7.11 (d, 1H, J=8.1 Hz), 6.89 (d, 1H, J=0.9 Hz), 5.14 (s, 2H), 2.49 (s, 3H); LCMS (m/z): 454 (MH$^+$).

IX-33: 5-Fluoro-N2-[3-(N-methylaminosulfony)-4-methylphenyl]-5-fluoro-N4-[4-(4-thiomorpholino)carbonylphenyl]-2,4-pyrimidinediamine $^1$H NMR (DMSO d$_6$, 300 MHz): δ 9.52 (s, 1H), 9.47 (s, 1H), 8.14 (d, 1H, J=3.9 Hz), 8.05 (d, 1H, J=2.1 Hz), 7.92 (m, 3H), 7.34 (m, 3H), 7.23 (d, 1H, J=8.1 Hz), 3.72 (br s, 4H), 2.64 (br s, 4H), 2.47 (s, 3H), 2.41 (d, 3H, J=4.8 Hz); LCMS (m/z): 517 (MH$^+$).

IX-34: N2-(3-Aminosulfonylphenyl)-5-fluoro-N4-[4-(4-thiomorpholinyl)carbonylphenyl]-2,4-pyrimidinediamine $^1$H NMR (DMSO d$_6$, 300 MHz): δ 9.59 (s, 1H), 9.57 (s, 1H), 8.17 (d, 1H, J=3.3 Hz), 8.12 (s, 1H), 7.91 (d, 3H, J=8.4 Hz), 7.37 (m, 4H), 7.28 (s, 2H), 3.73 (br s, 4H), 2.65 (br s, 4H); LCMS (m/z): 489 (MH$^+$).

IX-35: N2-(3-Aminosulfonyl-4-methylphenyl)-5-fluoro-N4-[4-(4-thiomorpholinyl)carbonylphenyl]-2,4-pyrimidinediamine $^1$H NMR (DMSO d$_6$, 300 MHz): δ 9.53 (s, 1H), 9.48 (s, 1H), 8.13 (t, 2H, J=2.1 Hz), 7.92 (d, 2H, J=8.4 Hz), 7.87 (dd, 1H, J=2.4 and 8.2 Hz), 7.35 (d, 2H, J=8.7 Hz), 7.25 (s, 2H), 7.20 (d, 1H, J=8.1 Hz), 3.73 (br s, 4H), 2.65 (br s, 4H), 2.46 (s, 3H); LCMS (m/z): 489 (MH$^+$).

IX-23: N4-[4-(1-Acetyl-4-piperizinyl)carbonylphenyl]-N2-(3-Aminosulfonylphenyl)-5-fluoro-2,4-pyrimidinediamine $^1$H NMR (DMSO d$_6$, 300 MHz): δ 9.58 (s, 2H), 8.17 (d, 1H, J=3.6 Hz), 8.13 (s, 1H), 7.91 (m, 3H), 7.38 (m, 5H), 7.25 (br s, 1H), 3.72 (br s, 4H), 2.48 (br s, 8H), 2.02 (s, 3H); LCMS (m/z): 514 (MH$^+$).

IX-24: N4-[4-(1-Acetyl-4-piperizinyl)carbonylphenyl]-N2-(3-Aminosulfonyl-4-methylphenyl)-5-fluoro-2,4-pyrimidinediamine $^1$H NMR (DMSO d$_6$, 300 MHz): δ 9.54 (s, 1H), 9.48 (s, 1H), 8.14 (d, 2H, J=3.0 Hz), 7.93 (d, 2H, J=8.1 Hz), 7.87 (d, 1H, J=7.8 Hz), 7.38 (d, 2H, J=7.8 Hz), 7.25 (s, 2H), 7.19 (d, 1H, J=8.4 Hz), 3.49 (br s, 8H), 2.50 (s, 3H), 2.05 (s, 3H); LCMS (m/z): 528 (MH$^+$).

IX-25: N4-[4-(1-Acetyl-4-piperizinyl)carbonylphenyl]-5-fluoro-N2-[3-(N-methylaminosulfony)-4-methylphenyl]-2,4-pyrimidinediamine $^1$H NMR (DMSO d$_6$, 300 MHz): δ 9.55 (s, 1H), 9.48 (s, 1H), 8.15 (d, 1H, J=3.3 Hz), 8.05 (s, 1H), 7.92 (d, 3H, J=8.1 Hz), 7.38 (d, 2H, J=8.4 Hz), 7.35 (q, 1H, J=5.4 Hz), 7.23 (d, 1H, J=8.1 Hz), 3.49 (br s, 8H), 2.47 (s, 3H), 2.41 (d, 3H, J=4.8 Hz), 2.02 (s, 3H); LCMS (m/z): 542 (MH$^+$).

IX-29: N2-(3-Aminosulfonylphenyl)-5-fluoro-N4-[4-(1-methanesulfonyl-4-piperizinyl)carbonylphenyl]-2,4-pyrimidinediamine $^1$H NMR (DMSO d$_6$, 300 MHz): δ 9.60 (s, 2H), 8.18 (d, 1H, J=3.6 Hz), 8.15 (s, 1H), 7.93 (m, 3H), 7.38 (m, 4H), 7.28 (s, 2H), 3.60 (br s, 4H), 3.17 (br s, 4H), 2.90 (s, 3H), 2.91 (s, 3H); LCMS (m/z): 550 (MH$^+$).

IX-30: N2-(3-Aminosulfonyl-4-methylphenyl)-5-fluoro-N4-[4-(1-methanesulfonyl-4-piperizinyl)carbonylphenyl]-2,4-pyrimidinediamine $^1$H NMR (DMSO d$_6$, 300 MHz): δ 9.55 (s, 1H), 9.48 (s, 1H), 8.13 (m, 2H), 7.94 (d, 2H, J=9.0 Hz), 7.85 (dd, 1H, J=2.4 and 8.5 Hz), 7.38 (d, 1H, J=8.7 Hz), 7.24 (s, 2H), 7.20 (d, 1H, J=8.4 Hz), 3.61 (br s, 4H), 3.17 (br s, 4H), 2.90 (s, 3H), 2.50 (s, 3H); LCMS (m/z): 564 (MH$^+$).

IX-31: 5-Fluoro-N2-[3-(N-methylaminosulfony)-4-methylphenyl]-5-fluoro-N4-[4-(1-methanesulfonyl-4-piperizinyl)carbonylphenyl]-2,4-pyrimidinediamine $^1$H NMR (DMSO d$_6$, 300 MHz): δ 9.56 (s, 1H), 9.49 (s, 1H), 8.16 (d, 1H, J=3.3 Hz), 8.05 (d, 1H, J=2.1 Hz), 7.92 (m, 1H), 7.39 (d, 2H, J=8.4 Hz), 7.34 (q, 1H, J=5.1 Hz), 7.23 (d, 1H, J=8.1 Hz), 3.61 (br s, 4H), 3.17 (br s, 4H), 2.90 (s, 3H), 2.41 (d, 3H, J=4.2 Hz); LCMS (m/z): 578 (MH$^+$).

III-83: 5-Fluoro-N2-[3-(N-methylaminosulfony)-4-methylphenyl]-5-fluoro-N4-[4-(1-imidazolylmethyl)phenyl]-2,4-pyrimidinediamine $^1$H NMR (DMSO d$_6$, 300 MHz): δ 9.41 (s, 2H), 8.09 (d, 1H, J=3.3 Hz), 8.00 (d, 1H, J=2.1 Hz), 7.92 (dd, 1H, J=2.4 and 8.5 Hz), 7.75 (d, 3H, J=8.1 Hz), 7.32 (q, 1H, J=4.5 Hz), 7.22 (d, 3H, J=8.7 Hz), 7.13 (d, 1H, J=8.4 Hz), 6.94 (br s, 1H), 5.15 (s, 2H), 2.46 (s, 3H), 2.41 (d, 3H, J=4.5 Hz); LCMS (m/z): 468 (MH$^+$).

IX-37: N2-(3-Aminosulfonylphenyl)-N4-[4-(1,1-dioxo-4-thiomorpholinyl)carbonylphenyl]-5-fluoro-2,4-pyrimidinediamine $^1$H NMR (DMSO d$_6$, 300 MHz): δ 9.61 (s, 1H), 9.59 (s, 1H), 8.18 (d, 1H, J=3.3 Hz), 8.13 (s, 1H), 7.92 (d, 3H, J=8.7 Hz), 7.45 (d, 2H, J=8.4 Hz), 7.39 (m, 2H), 7.28 (s, 2H), 3.89 (br s, 4H), 3.26 (br s, 4H); LCMS (m/z): 521 (MH$^+$).

IX-38: N2-(3-Aminosulfonyl-4-methylphenyl)-N4-[4-(1,1-dioxo-4-thiomorpholinyl)carbonylphenyl]-5-fluoro-2,4-pyrimidinediamine $^1$H NMR (DMSO d$_6$, 300 MHz): δ 9.54 (s, 1H), 9.48 (s, 1H), 8.14 (m, 2H), 7.94 (d, 2H, J=8.1 Hz), 7.85 (d, 1H, J=8.5 Hz), 7.44 (d, 2H, J=7.8 Hz), 7.24 (s, 2H), 7.20 (d, 1H, J=8.1 Hz), 3.88 (br s, 4H), 3.25 (br s, 4H), 2.50 (s, 3H); LCMS (m/z): 535 (MH$^+$).

IX-39: N4-[4-(1,1-dioxo-4-thiomorpholinyl)carbonylphenyl]-5-Fluoro-N2-[3-(N-methylaminosulfony)-4-methylphenyl]-2,4-pyrimidinediamine $^1$H NMR (DMSO d$_6$, 300 MHz): δ 9.55 (s, 1H), 9.49 (s, 1H), 8.15 (d, 1H, J=3.9 Hz), 8.05 (d, 1H, J=2.1 Hz), 7.93 (m, 3H), 7.75 (d, 3H, J=8.1 Hz), 7.44 (d, 2H, J=8.4 Hz), 7.34 (q, 1H, J=5.2 Hz), 7.24 (d, 1H, J=8.1 Hz), 3.88 (br s, 4H), 3.26 (br s, 4H), 2.47 (s, 3H), 2.41 (d, 3H, J=4.5 Hz); LCMS (m/z): 549 (MH$^+$).

II-16: N2-(3-Aminosulfonyl-4-methylphenyl)-5-fluoro-N4-[4-(4-pyridyloxy)phenyl]-2,4-pyrimidinediamine $^1$H NMR (DMSO d$_6$, 300 MHz): δ 9.56 (s, 1H), 9.48 (s, 1H), 8.14 (d, 2H, J=2.4 Hz), 8.00 (d, 2H, J=8.7 Hz), 7.93 (d, 2H, J=8.1 Hz), 7.83 (d, 1H, J=8.1 Hz), 7.46 (d, 2H, J=8.7 Hz), 7.23 (d, 3H, J=7.2 Hz), 6.22 (d, 2H, J=7.5 Hz), 2.48 (s, 3H); LCMS (m/z): 467 (MH$^+$).

II-17: N2-(3-Aminosulfonylphenyl)-5-fluoro-N4-[4-(4-pyridyloxy)phenyl]-2,4-pyrimidinediamine $^1$H NMR (DMSO d$_6$, 300 MHz): δ 9.59 (s, 2H), 8.17 (d, 1H, J=3.3 Hz), 8.13 (s, 1H), 7.99 (d, 2H, J=8.7 Hz), 7.94 (d, 2H, J=7.8 Hz), 7.88 (d, 1H, J=8.1 Hz), 7.45 (m, 2H), 7.37 (m, 1H), 7.27 (s, 2H), 6.22 (d, 2H, J=7.5 Hz)); LCMS (m/z): 453 (MH$^+$).

II-18: 5-Fluoro-N2-[3-(N-methylaminosulfony)-4-methylphenyl]-5-fluoro-N4-[4-(4-pyridyloxy)phenyl]-2,4-pyrimidinediamine $^1$H NMR (DMSO d$_6$, 300 MHz): δ 9.58 (s, 1H), 9.49 (s, 1H), 8.15 (d, 1H, J=3.9 Hz), 8.05-7.88 (m, 6H), 7.46 (d, 2H, J=8.7 Hz), 7.34 (q, 1H, J=5.1 Hz), 7.26 (d, 1H, J=8.7 Hz), 6.22 (d, 2H, J=7.8 Hz), 2.47 (s, 3H), 2.41 (d, 3H, J=4.8 Hz); LCMS (m/z): 481 (MH$^+$).

IX-36: N2-(4-Aminosulfonylphenyl)-5-fluoro-N4-[4-(4-thiomorpholinyl)carbonylphenyl]-2,4-pyrimidinediamine $^1$H NMR (DMSO d$_6$, 300 MHz): δ 9.68 (s, 1H), 9.61 (s, 1H), 8.20 (d, 1H, J=3.6 Hz), 7.86 (d, 2H, J=8.7 Hz), 7.81 (d, 2H, J=9.0 Hz), 7.63 (d, 2H, J=8.7 Hz), 7.37 (d, 2H, J=8.1 Hz), 7.12 (s, 2H), 3.74 (br s, 4H), 2.65 (br s, 4H); LCMS (m/z): 489 (MH$^+$).

IX-32: N2-(4-Aminosulfonylphenyl)-5-fluoro-N4-[4-(1-methanesulfonyl-4-piperazinyl)carbonylphenyl]-2,4-pyrimidinediamine $^1$H NMR (DMSO d$_6$, 300 MHz): δ 9.69 (s, 1H), 9.64 (s, 1H), 8.20 (d, 1H, J=3.6 Hz), 7.90 (d, 2H, J=8.7 Hz), 7.82 (d, 2H, J=9.0 Hz), 7.65 (d, 2H, J=9.0 Hz), 7.41 (d, 2H, J=8.4 Hz), 7.13 (s, 2H), 3.61 (br s, 4H), 3.17 (br s, 4H), 2.91 (s, 3H); LCMS (m/z): 550 (MH$^+$).

IX-40: N2-(4-Aminosulfonylphenyl)-N4-[4-(1,1-dioxo-4-thiomorpholinyl)carbonylphenyl]-5-fluoro-2,4-pyrimidinediamine $^1$H NMR (DMSO d$_6$, 300 MHz): δ 9.67 (s, 1H), 9.66 (s, 1H), 8.18 (d, 1H, J=3.5 Hz), 7.92 (d, 2H, J=9.0 Hz), 7.80 (d, 2H, J=8.2 Hz), 7.66 (d, 2H, J=8.7 Hz), 7.43 (d, 2H, J=9.0 Hz), 7.13 (s, 2H), 3.63 (br s, 4H), 3.15 (br s, 4H); LCMS (m/z): 521 (MH$^+$).

IX-26: N4-[4-(1-Acetyl-4-piperizinyl)carbonylphenyl]-N2-(4-aminosulfonylphenyl)-5-fluoro-2,4-pyrimidinediamine $^1$H NMR (DMSO d$_6$, 300 MHz): δ 9.69 (s, 1H), 9.65 (s, 1H), 8.19 (d, 1H, J=3.6 Hz), 7.87 (d, 2H, J=8.1 Hz), 7.82 (d, 2H, J=9.0 Hz), 7.63 (d, 2H, J=8.7 Hz), 7.41 (d, 2H, J=8.4 Hz), 7.13 (s, 2H), 3.49 (br s, 8H), 2.02 (s, 3H); LCMS (m/z): 514 (MH$^+$).

I-167: N2-(3-Aminosulfonylphenyl)-5-fluoro-N4-[(4-((pyridin-2-yl)methoxy)-3-methylphenyl)]-2,4-pyrimidinediamine $^1$H NMR (DMSO d$_6$, 300 MHz): δ 9.44 (s, 1H), 9.19 (s, 1H), 8.56 (d, 1H, J=3.9 Hz), 8.05 (d, 1H, J=3.6 Hz), 8.02 (s, 1H), 7.98 (m, 1H), 7.84 (t, 1H, J=7.5 Hz), 7.51 (m, 3H), 7.30 (m, 5H), 6.92 (d, 2H, J=7.8 Hz), 5.19 (s, 2H), 2.25 (s, 3H); LCMS (m/z): 481 (MH$^+$).

I-168: N2-(3-Amino-4-methylsulfonylphenyl)-5-fluoro-N4-[(4-((pyridin-2-yl)methoxy)-3-methylphenyl)]-2,4-pyrimidinediamine $^1$H NMR (DMSO d$_6$, 300 MHz): δ 9.33 (s, 1H), 9.15 (s, 1H), 8.57 (d, 1H, J=4.5 Hz), 8.05 (s, 1H), 8.02 (d, 1H, J=3.6 Hz), 7.89 (m, 1H), 7.82 (d, 1H, J=7.5 Hz), 7.52 (m, 3H), 7.33 (m, 1H), 7.22 (s, 2H), 7.11 (d, 1H, J=8.1 Hz), 6.93 (d, 1H, J=9.6 Hz), 5.19 (s, 2H), 2.49 (s, 3H), 2.25 (s, 3H); LCMS (m/z): 495 (MH$^+$).

III-73: N2-(3-Aminosulfonylphenyl)-5-fluoro-N4-[4-(4-pyridylmethyl)phenyl]-2,4-pyrimidinediamine Hydrochloride Salt N2-(3-Aminosulfonylphenyl)-5-fluoro-N4-[4-(4-pyridylmethyl)phenyl]-2,4-pyrimidinediamine III-70, 50 mg) was dissolved in methanol (10 mL), 4N HCl (in dioxane, 63.5 μL) was added and stirred the reaction mixture at room temperature for 1 h and concentrated under reduced pressure. Finally washed the solid with hexanes and dried well under high vacuum resulted HCl salt in quantitative yield. $^1$H NMR (DMSO d$_6$, 300 MHz): δ 9.92 (s, 1H), 9.82 (s, 1H), 8.81 (d, 2H, J=5.4 Hz), 8.20 (d, 1H, J=4.5 Hz), 7.98 (s, 1H), 7.93 (d, 1H, J=5.4 Hz), 7.87 (d, 2H, J=7.8 Hz), 7.72 (d, 2H, J=8.7 Hz), 7.42-7.28 (m, 5H), 4.26 (s, 2H); LCMS (m/z): 451 (MH$^+$).

The following three compounds were made in a similar fashion as described above.

III-129: N2-(3-Aminosulfonylphenyl)-5-fluoro-N4-[4-(4-pyridylmethyl)phenyl]-2,4-pyrimidinediamine Methanesulfonic Acid Salt $^1$H NMR (DMSO d$_6$, 300 MHz): δ 9.61 (s, 1H), 9.55 (s, 1H), 8.79 (d, 2H, J=6.0 Hz), 8.15 (s, 1H), 8.04 (s, 1H), 7.90 (br s, 3H), 7.76 (d, 2H, J=7.5 Hz), 7.36-7.26 (m, 6H), 4.23 (s, 2H), 2.31 (s, 3H); LCMS (m/z): 451 (MH$^+$).

III-128: N2-(3-Aminosulfonylphenyl)-5-fluoro-N4-[4-(4-pyridylmethyl)phenyl]-2,4-pyrimidinediamine p-Toluenesulfonic Acid Salt $^1$H NMR (DMSO d$_6$, 300 MHz): δ 9.55 (s, 1H), 9.47 (s, 1H), 8.77 (d, 2H, J=5.7 Hz), 8.13 (d, 1H, J=3.6 Hz), 8.06 (s, 1H), 7.88 (m, 3H), 7.77 (d, 2H, J=8.7 Hz), 7.45 (d, 2H, J=7.8 Hz), 7.34 (d, 2H, J=5.7 Hz), 7.25 (m, 3H), 7.08 (d, 2H, J=8.1 Hz), 4.22 (s, 2H), 2.27 (s, 3H); LCMS (m/z): 451 (MH$^+$).

I-196: N2-(3-Aminosulfonylphenyl)-5-fluoro-N4-4-[(2-pyridinyl)methyleneoxyphenyl]-2,4-pyrimidinediamine Hydrochloride Salt $^1$H NMR (DMSO d$_6$, 300 MHz): δ 9.98 (s, 1H), 9.88 (s, 1H), 8.69 (d, 1H, J=4.8 Hz), 8.18 (d, 1H, J=3.9 Hz), 8.10 (t, 1H, J=8.4 Hz), 7.92 (s, 1H), 7.85 (d, 1H, J=7.8 Hz), 7.73 (d, 1H, J=7.8 Hz), 7.61 (m, 3H), 7.38 (m, 4H), 7.03 (d, 2H, J=9.0 Hz), 5.29 (s, 2H); LCMS (m/z): 467 (MH⁺).

Example 34

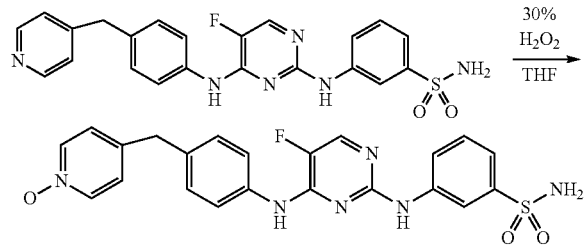

III-80: Preparation of N2-(3-Aminosulfonylphenyl)-5-fluoro-N4-[4-(1-oxido-4-pyridylmethyl)phenyl]-2,4-pyrimidinediamine A mixture of N2-(3-Aminosulfonylphenyl)-5-fluoro-N4-[4-(4-pyridylmethyl)phenyl]-2,4-pyrimidinediamine (50 mg) and methyltrioxorhenium (VII) (5 mg) in THF (15 mL) was treated with 30% aq. H₂O₂ (23 µW. After 24 h stirring, 30% aq. H₂O₂ (23 µL) was added and stirred for 24 h. The reaction mixture was filtered through Celite, washed the bed with methanol and concentrated. The residue was purified by HPLC yielded 10 mg of desired product. ¹H NMR (DMSO d₆, 300 MHz): δ 9.47 (s, 1H), 9.35 (s, 1H), 8.10 (m, 4H), 7.92 (m, 1H), 7.73 (d, 2H, J=8.4 Hz), 7.32-7.18 (m, 8H), 3.91 (s, 2H); LCMS (m/z): 467 (MH⁺).

Example 35

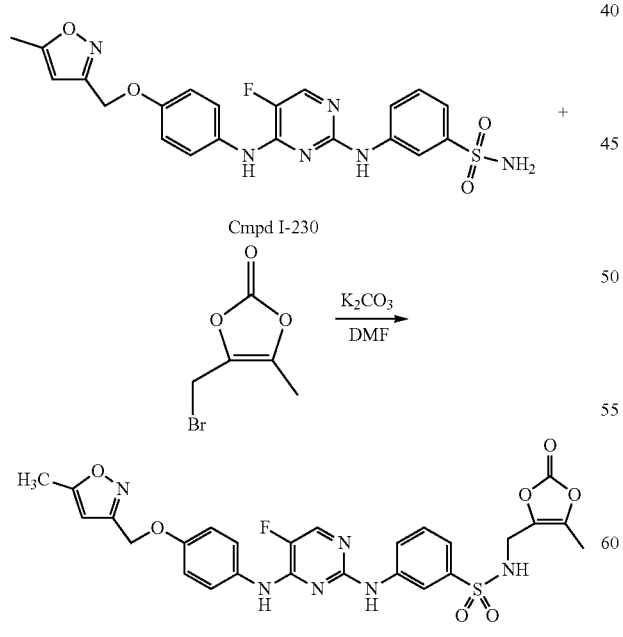

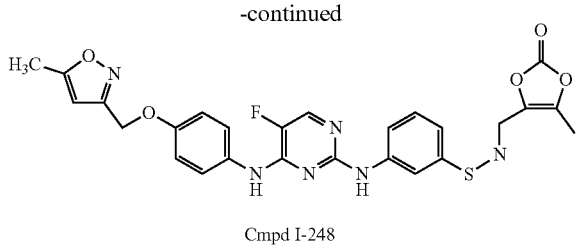

Cmpd I-248

A mixture of N2-(3-aminosulfonylphenyl)-5-fluoro-N4-[4-(5-methylisoxazol-3-yl)methyleneoxyphenyl]-2,4-pyrimidinediamine (1-230, 0.627 mg, 1.33 mmol), 4-bromomethyl-5-methyl-1,3-dioxolene-2-one (0.283 mg, 1.33 mmol) and anhydrous K₂CO₃ (0.202 g, 1.33 mmol) in DMF (5 mL) were stirred at r. t. for 3 days. The reaction mixture was poured in water (50 mL), filtered the solid and dried well. Purified by HPLC to provide desired 1-247 (14 mg) and 1-248 (14 mg) products.

I-247: N2-{3-[(N-5-Methyl-1,3-dioxolene-2-one-4-yl)methylene]aminosulfonylphenyl}-5-fluoro-N4-[4-(5-methylisoxazol-3-yl)methyleneoxyphenyl]-2,4-pyrimidinediamine ¹H NMR (DMSO d₆, 300 MHz): δ 9.49 (s, 1H), 9.29 (s, 1H), 8.22 (s, 1H), 8.08 (d, 2H, J=3.9 Hz), 7.93 (m, 1H), 7.69 (d, 2H, J=9.3 Hz), 7.33 (t, 1H, J=7.8 Hz), 7.24 (d, 1H, J=8.4 Hz), 6.98 (d, 2H, J=9.0 Hz), 6.32 (s, 1H), 5.12 (s, 2H), 3.87 (d, 2H, J=5.1 Hz), 2.40 (s, 3H), 1.94 (s, 3H); LCMS (m/z): 583 (MH⁺).

I-248: N2-{3-[N—N-Di-[(5-Methyl-1,3-dioxolene-2-one-4-yl)methylene]]aminosulfonylphenyl}-5-fluoro-N4-[4-(5-methylisoxazol-3-yl)methyleneoxyphenyl]-2,4-pyrimidinediamine ¹H NMR (DMSO d₆, 300 MHz): δ 9.48 (s, 1H), 9.32 (s, 1H), 8.19 (s, 1H), 8.12 (s, 1H), 8.08 (d, 1H, J=3.3 Hz), 8.03 (d, 1H, J=9.6 Hz), 7.81 (d, 2H, J=9.0 Hz), 7.39 (t, 1H, J=8.1 Hz), 7.29 (d, 1H, J=7.8 Hz), 6.99 (d, 2H, J=9.0 Hz), 6.32 (s, 1H), 5.73 (s, 1H), 5.12 (s, 2H), 4.25 (s, 3H), 2.40 (s, 3H), 2.04 (s, 5H); LCMS (m/z): 695 (MH⁺).

The following compounds were made in a similar fashion to the example 35 or by methods described herein or known to skilled artisans.

I-249: N2-{3-[N—N-Di-[(5-t-Butyl-1,3-dioxolene-2-one-4-yl)methylene]]aminosulfonylphenyl}-5-fluoro-N4-[4-(5-methylisoxazol-3-yl)methyleneoxyphenyl]-2,4-pyrimidinediamine ¹H NMR (DMSO d₆, 300 MHz): δ 9.48 (s, 1H), 9.31 (s, 1H), 8.20 (s, 1H), 8.12 (s, 1H), 8.07 (d, 1H, J=3.9 Hz), 7.93 (d, 1H, J=8.7 Hz), 7.66 (d, 2H, J=9.0 Hz), 7.36 (t, 1H, J=7.8 Hz), 7.21 (d, 1H, J=7.8 Hz), 6.98 (d, 2H, J=8.7 Hz), 6.32 (s, 1H), 5.12 (s, 2H), 4.39 (s, 4H), 2.40 (s, 3H), 1.20 (s, 18H); LCMS (m/z): 779 (MH⁺).

I-250: N2-{3-[(N-5-t-Butyl-1,3-dioxolene-2-one-4-yl)methylene]aminosulfonylphenyl}-5-fluoro-N4-[4-(5-methylisoxazol-3-yl)methyleneoxyphenyl]-2,4-pyrimidinediamine ¹H NMR (DMSO d₆, 300 MHz): δ 9.47 (s, 1H), 9.28 (s, 1H), 8.29 (t, 1H, J=6.0 Hz), 8.12 (s, 1H), 8.07 (d, 1H, J=3.9

Hz), 7.92 (m, 1H), 7.68 (d, 2H, J=9.0 Hz), 7.34 (t, 1H, J=7.8 Hz), 7.25 (d, 1H, J=8.1 Hz), 6.98 (d, 2H, J=9.0 Hz), 6.32 (s, 1H), 5.12 (s, 2H), 3.93 (d, 2H, J=6.0 Hz), 2.40 (s, 3H), 1.11 (s, 9H); LCMS (m/z): 625 (MH$^+$).

I-257: N2-{3-[(N-5-Methyl-1,3-dioxolene-2-one-4-yl)methylene]aminosulfonylphenyl}-5-fluoro-N4-[4-(3-methyl-1,2,4-oxadiazol-5-yl)methyleneoxyphenyl]-2,4-pyrimidinediamine $^1$H NMR (DMSO d$_6$, 300 MHz): δ 9.49 (s, 1H), 9.32 (s, 1H), 8.38 (s, 1H), 8.22 (s, 1H), 8.08 (d, 2H, J=2.1 Hz), 7.94 (d, 1H, J=7.8 Hz), 7.70 (d, 2H, J=8.1 Hz), 7.35 (t, 1H, J=7.8 Hz), 7.25 (m, 1H), 7.01 (d, 2H, J=8.4 Hz), 5.46 (s, 2H), 3.87 (s, 2H), 2.36 (s, 3H), 1.94 (s, 3H); LCMS (m/z): 584 (MH$^+$).

III-17: N2-(3-Aminosulfonyl-4-methylphenyl)-5-fluoro-N4-[4-(2-cyanoethyl)-3-fluorophenyl]-2,4-pyrimidinediamine $^1$H NMR (DMSO-d$_6$): δ 9.51 (s, 2H), 8.11 (s, 2H), 7.92-7.89 (d, J=8.4 Hz, 1H), 7.87-7.82 (d, J=12.9 Hz, 1H), 7.60-7.58 (d, J=8.4 Hz, 1H), 7.32-7.19 (m, 4H), 7.09 (s, 1H), 3.29 (s, 3H), 2.88-2.86 (bd, J=6 Hz, 2H), 2.82-2.80 (bd, J=5.7 Hz, 2H), LCMS: 445.01 (MH$^+$).

III-18: N2-(3-Aminosulfonylphenyl)-N4-[4-(2-cyanoethyl)-3-fluorophenyl]-5-fluoro-2,4-pyrimidinediamine $^1$H NMR (DMSO-d$_6$): δ 9.62 (s, 1H), 9.55 (s, 1H), 8.16-8.15 (d, J=3.9 Hz, 1H) 8.10 (s, 1H), 7.98-7.96 (d, J=6.9 Hz, 1H), 7.87-7.83 (dd, J=12.9 Hz, 1H), 7.61-7.58 (dd, J=8.4 Hz, 1H), 7.43-7.23 (m, 5H), 2.93-2.77 (m, 4H), LCMS: 430.98 (MH$^+$).

III-19: N2-(3-Aminosulfonyl-4-methylphenyl)-N4-[4-(2-cyanoethyl)-3-methylphenyl]-5-fluoro-2,4-pyrimidinediamine $^1$H NMR (DMSO-d$_6$): δ 9.39 (s, 1H), 9.24 (s, 1H), 8.06-8.05 (d, J=3.9 Hz, 1H), 7.95-7.91 (dd, J=8.7 Hz, 1H), 7.63-7.59 (dd, J=8.1 Hz, 1H), 7.55 (s, 1H), 7.21 (s, 2H), 7.14 (s, 1H), 2.86-2.83 (t, 2H), 2.79-2.74 (t, 2H), LCMS: 441.49 (MH$^+$).

III-20: N2-(3-Aminosulfonylphenyl)-N4-[4-(2-cyanoethyl)-3-methylphenyl]-5-fluoro-2,4-pyrimidinediamine $^1$H NMR (DMSO-d$_6$): δ 9.50 (s, 1H), 9.28 (s, 1H), 8.10 (bs, 1H), 8.04 (bs, 1H), 7.60 (d, 1H), 7.55 (s, 1H), 7.25 (s, 1H), 7.15 (s, 1H), 6.98 (s, 2H), 2.86 (m, 2H), 2.79 (s, 2H), 2.29 (s, 3H), LCMS: 427.45 (MH$^+$).

III-21: N2-(3-Aminosulfonyl-4-methylphenyl)-N4-[3-chloro-4-(2-cyanoethyl)phenyl]-5-fluoro-2,4-pyrimidinediamine $^1$H NMR (DMSO-d$_6$): δ 9.49 (s, 1H), 9.47 (s, 1H), 8.13-8.12 (d, J=3.6 Hz, 1H), 8.06-8.06 (d, J=2.1 Hz, 1H), 7.92-7.90 (dd, J=8.4 Hz, 1H), 7.88-7.88 (d, J=2.1 Hz, 1H), 7.85-7.82 (dd, J=8.4 Hz, 1H), 7.37-7.34 (d, J=8.4 Hz, 1H), 7.23 (s, 2H), 7.19 (s, 1H), 3.00-2.95 (t, 2H), 3.84-2.80 (t, 2H), 2.48 (s, 3H), LCMS: 460.94 (MH$^+$).

III-22: N2-(3-Aminosulfonylphenyl)-N4-[3-chloro-4-(2-cyanoethyl)phenyl]-5-fluoro-2,4-pyrimidinediamine $^1$H NMR (DMSO-d$_6$): δ 9.60 (s, 1H), 9.50 (s, 1H), 8.16-8.15 (d, J=3.3 Hz, 1H), 8.05, (s, 1H), 8.00-7.97 (d, J=9 Hz, 1H), 7.89-7.88 (d, J=2.1 Hz, 1H), 7.85-7.82 (d, J=8.1 Hz, 1H), 7.44-7.38 (t, 1H), 7.37 (s, 1H), 7.34 (s, 2H), 7.32 (s, 1H), 3.00-2.95 (t, 2H), 2.84-2.79 (t, 2H), LCMS: 446.93 (MH$^+$).

VII-1: N2-(3-Aminosulfonyl-4-methylphenyl)-N4-[(2S,4R)-1-(2-cyanoacetyl)-2-methoxycarbonylpyrrolidin-4-yl]-5-fluoro-2,4-pyrimidinediamine $^1$H NMR (DMSO-d$_6$): δ 9.34 (s, 1H), 8.41-8.40 (d, J=2.1 Hz, 1H), 7.92-7.90 (d, J=3.9 Hz, 1H), 7.76-7.73 (d, J=6.3 Hz, 1H), 7.67-7.63 (dd, J=7.8 Hz, 1H), 7.20 (s, 2H), 7.17 (s, 1H), 4.73 (bs, 1H), 4.53-4.47 (t, 1H), 4.03 (bs, 2H), 3.91-3.85 (m, 1H), 3.65 (s, 1H), 3.55-3.51 (d, J=10.8 Hz, 1H), 2.43-2.36 (m, 1H), 2.20-2.15 (m, 1H), LCMS: 492.20 (MH$^+$).

VII-2: N2-(3-Aminosulfonyl-4-methylphenyl)-N4-[(2S,4S)-1-(2-cyanoacetyl)-2-methoxycarbonylpyrrolidin-4-yl]-5-fluoro-2,4-pyrimidinediamine $^1$H NMR (DMSO-d$_6$): δ 9.37 (s, 1H), 8.69 (s, 1H), 7.93-7.92 (d, J=3.3 Hz, 1H), 7.59-7.56 (d, J=7.5 Hz, 1H), 7.46-7.43 (dd, J=8.4 Hz, 1H), 7.19 (s, 1H), 7.17 (s, 2H), 4.84-4.82 (m, 1H), 4.39-4.33 (t, 1H), 3.94-3.89 (t, 1H), 3.64 (s, 3H), 3.44-3.38 (t, 1H), 2.63-2.59 (m, 1H), 2.07-2.00 (m, 1H), LCMS: 492.79 (MH$^+$).

VII-77: N2-(3-Aminosulfonyl-4-methylphenyl)-5-fluoro-N4-(quinolin-8-yl)-2,4-pyrimidinediamine $^1$H NMR (DMSO-d$_6$): δ 9.71 (s, 1H), 9.66 (s, 1H), 9.00-8.98 (d, J=7.2 Hz, 1H), 8.94-8.93 (d, J=3.6 Hz, 1H), 8.45-8.42 (d, J=8.1 Hz, 1H), 8.25-8.24 (d, J=3.0 Hz, 1H), 8.21-8.21 (d, J=2.1 Hz, 1H), 7.91-7.87 dd, J=7.8 Hz, 1H), 7.68-7.67 (d, J=3.9 Hz, 1H), 7.66 (s, 2H), 7.28 (s, 2H), 2.53 (s, 3H), LCMS: 425.68 (MH$^+$).

VII-78: N2-(3-Aminosulfonylphenyl)-5-fluoro-N4-(quinolin-8-yl)-2,4-pyrimidinediamine $^1$H NMR (DMSO-d$_6$): δ 9.78 (s, 1H), 9.74-9.74 (d, J=2.7 Hz, 1H), 9.00-8.97 (dd, J=6.9 Hz, 1H), 8.95-8.93 (dd, J=3.9 Hz, 1H), 8.46-8.42 (dd, J=8.4 Hz, 1H), 8.28-8.27 (d, J=3.3 Hz, 1H), 8.23 (s, 1H), 7.93-7.91 (d, J=8.1 Hz, 1H), 7.68-7.63 (m, 3H), 7.49-7.38 (m, 2H), 7.303 (s, 1H), LCMS: 411.60 (MH+).

VII-79: N2-(3-Aminosulfonyl-4-fluorophenyl)-5-fluoro-N4-(quinolin-8-yl)-2,4-pyrimidinediamine $^1$H NMR (DMSO-d$_6$): δ 9.73 (s, 2H), 8.96 (s, 1H), 8.94-8.94 (d, J=2.4 Hz, 1H), 8.45-8.43 (d, J=6.9 Hz, 1H), 8.26-8.25 (d, J=3.0 Hz, 1H), 8.19-8.16 (dd, J=6 Hz, 1H), 7.99-7.94 (m, 1H), 7.68-7.63 (m, 3H), 7.59 (s, 2H), 7.37-7.31 (t, 1H), LCMS: 429.40 (MH$^+$).

VII-69: N2-(3-Aminosulfonyl-4-methylphenyl)-5-fluoro-N4-(quinolin-6-yl)-2,4-pyrimidinediamine $^1$H NMR (DMSO-d$_6$): δ 9.69 (s, 1H), 9.48 (s, 1H), 8.76-8.74 (dd, J=4.2 Hz, 1H), 8.61-8.61 (d, J=2.1 Hz, 1H), 8.21-8.19 (d, J=7.2 Hz, 1H), 8.16-8.15 (d, J=3.6 Hz, 1H), 8.12-8.11 (d, J=2.4 Hz, 1H), 8.10-8.06 (dd, J=9.0 Hz, 1H), 7.95-7.92 (d, J=9.3 Hz, 1H), 7.94-7.91 (d, J=8.4 Hz, 1H), 7.50-7.46 (m, 1H), 7.25 (s, 2H), 7.17-7.14 (d, J=8.4 Hz, 1H), LCMS: 425 (MH$^+$).

VII-70: N2-(3-Aminosulfonylphenyl)-5-fluoro-N4-(quinolin-6-yl)-2,4-pyrimidinediamine $^1$H NMR (DMSO-d$_6$): δ 9.96 (s, 1H), 9.68 (s, 1H), 8.95-8.94 (d, J=4.2 Hz, 1H), 8.82 (s, 1H), 8.61-8.59 (d, J=7.5 Hz, 1H), 8.28-8.24 (m, 2H), 8.12-8.07 (m, 2H), 7.99-7.96 (m, 1H), 7.78-7.75 (m, 1H), 7.40-7.38 (m, 2H), 7.28 (s, 2H), LCMS: 411.11 (MH$^+$).

VII-57: N2-(3-Aminosulfonyl-4-methylphenyl)-N4-(benzothiophen-5-yl)-5-fluoro-2,4-pyrimidinediamine $^1$H NMR (DMSO-d$_6$): δ 9.44 (s, 1H), 9.40 (s, 1H), 8.41-8.40 (s, 1H), 8.09 (s, 1H), 8.08 (s, 1H), 7.93 (s, 1H), 7.90 (s, 1H), 7.76-7.74 (d, J=5.4 Hz, 1H), 7.72-7.68 (d, J=6.6 Hz, 1H), 7.37-7.35 (d, J=5.4 Hz, 1H), 7.23 (s, 2H), 7.13-7.10 (d, J=8.4 Hz, 1H), LCMS: 430.37 (MH$^+$).

VII-58: N2-(3-Aminosulfonylphenyl)-N4-(benzothiophen-5-yl)-5-fluoro-2,4-pyrimidinediamine $^1$H NMR (DMSO-d$_6$): δ 9.51 (s, 1H), 9.48 (s, 1H), 8.40 (s, 1H), 8.13-8.12 (d, J=3.6 Hz, 1H), 8.06 (s, 1H), 7.94 (m, 1H), 7.94-7.91 (d, J=9 Hz, 1H), 7.76-7.74 (d, J=5.7 Hz, 1H), 7.72-7.68 (dd, J=2.4 Hz, 1H), 7.38-7.36 (d, J=5.7 Hz, 1H), 7.33-7.32 (m, 2H), 7.25 (s, 2H), LCMS: 416.39 (MH$^+$).

VII-71: N2-(3-Aminosulfonyl-4-methylphenyl)-5-fluoro-N4-(2-methylquinolin-6-yl)-2,4-pyrimidinediamine $^1$H NMR (DMSO-d$_6$): δ 9.62 (s, 1H), 9.47 (s, 1H), 8.55 (s, 1H), 8.15-8.13 (d, J=3.6 Hz, 1H), 8.10 (s, 2H), 8.05-8.01 (dd, J=9.3 Hz, 1H), 7.95-7.91 (dd, J=8.1 Hz, 1H), 7.85-7.82 (d, J=9.3 Hz, 1H), 7.38-7.36 (d, J=8.4 Hz, 1H), 7.25 (s, 2H), 7.17-7.14 (d, J=8.4 Hz, 1H), 2.62 (s, 3H), 2.51 (s, 3H), LCMS: 439.41 (MH$^+$).

VII-72: N2-(3-Aminosulfonylphenyl)-5-fluoro-N4-(2-methylquinolin-6-yl)-2,4-pyrimidinediamine $^1$H NMR (DMSO-d$_6$): δ 9.55 (s, 1H), 8.55 (s, 1H), 8.16-8.16 (d, J=3.3 Hz, 1H), 8.13 (s, 1H), 8.10-8.08 (d, J=4.5 Hz, 1H), 8.04 (bs, 1H), 8.01 (bs, 1H), 7.85-7.82 (d, J=8.7 Hz, 1H), 7.38-7.33 (m, 3H), 2.62 (s, 3H), LCMS: 425.57 (MH$^+$).

VII-65: N2-(3-Aminosulfonyl-4-methylphenyl)-5-fluoro-N4-(quinolin-3-yl)-2,4-pyrimidinediamine $^1$H NMR (DMSO-d$_6$): δ 9.47 (s, 1H), 9.19 (s, 1H), 8.86 (s, 1H), 8.15-8.12 (m, 2H), 7.92-7.84 (m, 4H), 7.61-7.52 (m, 2H), 7.17-7.14 (d, J=8.1 Hz, 1H), 2.42 (s, 3H), LCMS: 425.79 (MH$^+$).

VII-66: N2-(3-Aminosulfonylphenyl)-5-fluoro-N4-(quinolin-3-yl)-2,4-pyrimidinediamine $^1$H NMR (DMSO-d$_6$): δ 9.46 (s, 1H), 9.14 (s, 1H), 8.80 (s, 1H), 8.12-8.08 (m, 2H), 7.95-7.84 (m, 4H), 7.59-7.53 (m, 3H), 7.34-7.32 (m, 3H), LCMS: 411.44 (MH$^+$).

VII-67: N2-(3-Aminosulfonyl-4-methylphenyl)-5-fluoro-N4-(quinolin-5-yl)-2,4-pyrimidinediamine $^1$H NMR (DMSO-d$_6$): δ 9.15 (s, 1H), 8.89-8.87 (d, J=3.3 Hz, 1H), 8.34-8.31 (d, J=8.4 Hz, 1H), 8.08-8.07 (d, J=3.6 Hz, 1H), 7.96-7.93 (d, J=8.7 Hz, 1H), 7.88 (s, 1H), 7.81-7.75 (t, 1H), 7.66-7.64 (d, J=6.9 Hz, 1H), 7.50-7.46 (m, 2H), 7.36 (s, 1H), 7.34 (s, 1H), 6.70-6.68 (d, J=8.1 Hz, 1H), 2.38 (s, 3H), LCMS: 425.71 (MH$^+$).

VII-68: N2-(3-Aminosulfonylphenyl)-5-fluoro-N4-(quinolin-5-yl)-2,4-pyrimidinediamine $^1$H NMR (DMSO-d$_6$): δ 9.15 (s, 1H), 8.85 (s, 1H), 8.40-8.38 (d, J=7.8 Hz, 1H), 8.00 (s, 1H), 7.87-7.83 (m, 2H), 7.77-7.67 (m, 2H), 7.53-7.50 (d, J=7.8 Hz, 1H), 7.47-7.42 (m, 2H), 7.17-7.14 (d, J=7.5 Hz, 1H), 6.95-6.90 (t, 1H), LCMS: 411.58 (MH$^+$).

VII-80: N2-(3-Aminosulfonyl-4-methylphenyl)-5-fluoro-N4-(2-methylquinolin-8-yl)-2,4-pyrimidinediamine $^1$H NMR (DMSO-d$_6$): δ 9.81 (s, 1H), 9.71 (s, 1H), 8.91 (s, 1H), 8.34-8.31 (d, J=8.4 Hz, 1H), 8.24-8.23 (d, J=3.3 Hz, 1H), 8.17 (s, 1H), 7.87-7.85 (d, J=6.9 Hz, 1H), 7.63-7.51 (m, 3H), 7.27-7.24 (m, 3H), 2.73 (s, 3H), 2.53 (s, 3H), LCMS: 439.16 (MH$^+$).

VII-81: N2-(3-Aminosulfonylphenyl)-5-fluoro-N4-(2-methylquinolin-8-yl)-2,4-pyrimidinediamine $^1$H NMR (DMSO-d$_6$): δ 9.84 (s, 1H), 9.81 (s, 1H), 8.87 (s, 1H), 8.35-8.33 (d, J=8.4 Hz, 1H), 8.28-8.27 (d, J=3.3 Hz, 1H), 8.18 (s, 1H), 7.90-7.88 (m, 1H), 7.65-7.62 (m, 1H), 7.58-7.53 (m, 2H), 7.45-7.39 (m, 2H), 7.30 (s, 2H), 2.74 (s, 3H), LCMS: 425.06 (MH$^+$).

VII-64: N2-(3-Aminosulfonyl-4-methylphenyl)-5-fluoro-N4-(quinolin-2-yl)-2,4-pyrimidinediamine $^1$H NMR (DMSO-d$_6$): δ 9.59 (s, 1H), 8.31 (s, 1H), 8.22-8.21 (d, J=3.3 Hz, 1H), 8.10 (s, 1H), 8.00-7.97 (dd, J=8.1 Hz, 1H), 7.96-7.89 (d, J=8.1 Hz, 1H), 7.81-7.78 (d, J=8.1 Hz, 1H), 7.71-7.65 (t, 1H), 7.48-7.43 (t, 1H), 7.25 (s, 2H), 7.19-7.16 (d, J=8.4 Hz, 1H), 7.09 (s, 1H), 2.54 (s, 3H), LCMS: 425.87 (MH$^+$).

III-13: N2-(3-Aminosulfonyl-4-chlorophenyl)-N4-[4-(2-cyanoethyl)phenyl]-5-fluoro-2,4-pyrimidinediamine $^1$H NMR (DMSO-d$_6$): δ 10.52 (s, 1H), 8.25-8.24 (d, J=2.7 Hz, 1H), 8.10-8.09 (d, J=3.9 Hz, 1H), 8.03-7.99 (dd, J=8.7 Hz, 1H), 7.75-7.73 (d, J=8.4 Hz, 2H), 7.40-7.37 (d, J=8.7 Hz, 1H), 7.26-7.23 (d, J=8.4 Hz, 2H), 2.85-2.78 (m, 4H), LCMS: 447.45 (MH$^+$).

III-11: N2-(3-Aminosulfonyl-4-methylphenyl)-N4-(4-cyanoethylenephenyl)-5-methyl-2,4-pyrimidinediamine $^1$H NMR (DMSO-d$_6$): δ 9.17 (s, 1H), 8.22 (s, 1H), 8.07-8.07 (d, J=2.1 Hz, 1H), 7.96-7.92 (dd, J=8.4 Hz, 1H), 7.86 (s, 1H), 7.69-7.66 (d, J=8.4 Hz, 2H), 7.23-7.20 (d, J=8.7 Hz, 2H), 7.16-7.11 (m, 2H), 2.85-2.80 (m, 4H), 2.10 (s, 3H), LCMS: 424.01 (MH$^+$).

III-12: N2-(3-Aminosulfonyl-4-chlorophenyl)-N4-[4-(2-cyanoethyl)phenyl]-5-methyl-2,4-pyrimidinediamine $^1$H NMR (DMSO-d$_6$): δ 9.45 (s, 1H), 9.41 (s, 1H), 8.30-8.25 (m, 2H), 8.09-8.05 (d, J=8.7 Hz, 1H), 7.88 (s, 1H), 7.67-7.64 (d, J=8.4 Hz, 2H), 7.42 (s, 2H), 7.37-7.34 (d, J=8.7 Hz, 2H), 7.25-7.22 (d, J=8.4 Hz, 2H), 2.88-2.79 (m, 4H), 2.11 (s, 3H), LCMS: 443.51 (MH$^+$).

VI-103: N4-[4(2-Cyanoethyl)-3-methylphenyl]-5-fluoro-N2-(4-methyl-3-propionylaminosulfonylphenyl)-2,4-pyrimidinediamine $^1$H NMR (DMSO-d$_6$): δ 9.40 (s, 1H), 9.23 (s, 1H), 8.10-8.03 (m, 2H), 8.00-7.69 (d, J=8.4 Hz, 1H), 7.62-7.59 (d, J=8.1 Hz, 1H), 7.56 (s, 1H), 7.17-7.12 (t, 2H), 6.66-6.64 (d, J=5.1 Hz, 2H), 2.85-2.83 (m, 2H), 2.78-2.75 (m, 2H), 2.45 (s, 3H), 2.27 (s, 3H), 2.16-2.11 (q, 2H), 0.90-0.85 (t, 3H), LCMS: 497.50 (MH$^+$).

VI-104: N4-[4-(2-Cyanoethyl)-3-methylphenyl]-5-fluoro-N2-(4-methyl-3-propionylaminosulfonylphenyl)-2,4-pyrimidinediamine Sodium Salt $^1$H NMR (DMSO-d$_6$): δ 9.18 (s, 1H), 9.15 (s, 1H), 8.03-8.02 (d, J=3.6 Hz, 1H), 7.81 (s, 1H), 7.78 (s, 1H), 7.64-7.62 (d, J=8.1 Hz, 1H), 7.60 (s, 1H), 7.16-7.13 (d, J=8.4 Hz, 1H), 6.96-6.93 (d, J=7.8 Hz, 1H), 2.85-2.83 (m, 2H), 2.78-2.76 (m, 2H), 2.41 (s, 1H), 2.28 (s, 1H), 1.94-1.87 (q, 2H), 0.87-0.82 (t, 3H), LCMS: 497.44 (MH$^+$).

V11-39: 5-Amino-N2-(3-amionsulfonylphenyl)-N4-(2,2-dimethyl-3-oxo-4H-benz[1,4]oxazin-6-yl)-2,4-pyrimidinediamine $^1$H NMR (DMSO-d$_6$): δ 10.55 (s, 1H), 8.86 (s, 1H), 8.21 (s, 1H), 8.07 (s, 1H), 7.95 (d, 1H, J=8.0 Hz), 7.61 (d, 1H, J=1.3 Hz), 7.39 (dd, 1H, J=1.3 and 8.8 Hz), 7.30-7.21 (m, 5H), 6.87 (d, 1H, J=8.8 Hz), 1.39 (s, 6H). LCMS: ret. time: 3.51 min.; purity: 99%; MS (m/e): 456 (MH$^+$).

VII-22: N2-(3-Aminosulfonylphenyl)-5-fluoro-N4-[1-(3-methoxypropyl)indazolin-5-yl]-2,4-pyrimidinediamine $^1$H NMR (DMSO-d$_6$): δ 9.48 (s, 1H), 9.41 (s, 1H), 8.20 (s, 1H), 8.10 (d, 1H, J=3.8 Hz), 8.05 (s, 1H), 7.99 (s, 1H), 7.99-7.96 (m, 1H), 7.64 (d, 1H, J=9.1 Hz), 7.58 (d, 1H, J=9.1 Hz), 7.31-7.25 (app m, 4H), 4.42 (t, 2H, J=6.7 Hz), 3.32 (s, 3H), 3.23 (t, 2H, J=6.7 Hz), 2.04 (qt, 2H, J=6.7 Hz). LCMS: ret. time: 4.59 min.; purity: 99%; MS (m/e): 472 (MH$^+$).

VII-23: N2-(3-Aminosulfonylphenyl)-5-fluoro-N4-[1-(2-methoxyethyl)indazolin-5-yl]-2,4-pyrimidinediamine $^1$H NMR (DMSO-d$_6$): δ 9.47 (s, 1H), 9.40 (s, 1H), 8.16 (s, 1H), 8.10 (d, 1H, J=3.5 Hz), 8.05 (s, 1H), 7.99-7.95 (m, 2H), 7.65 (d, 1H, J=9.8 Hz), 7.60 (d, 1H, J=8.8 Hz), 7.33-7.25 (m, 4H), 4.54 (t, 2H, J=5.3 Hz), 3.75 (t, 2H, J=5.3 Hz), s, 3H), 3.30 (s, 3H). LCMS: ret. time: 4.31 min.; purity: 99%; MS (m/e): 458 (MH$^+$).

I-1: N2-(4-Aminosulphonylphenyl)-N4-(3-cyanomethoxy-4,5-dimethoxyphenyl)-5-fluoro-2,4-pyrimidinediamine $^1$H NMR (DMSO-d6): δ 8.16 (d, 1H, J=2.2 Hz), 7.77 (d, 2H, J=8.3 Hz), 7.60 (d, 2H, J=8.3 Hz), 7.24 (m, 1H), 7.15 (m, 1H), 5.10 (s, 2H), 3.82 (s, 3H), 3.66 (s, 3H); LCMS: purity 90%; MS (m/e): 475 (MH$^+$).

I-2: N2-(3-Aminosulphonyl-4-methylphenyl)-N4-(3-cyanomethoxy-4,5-dimethoxyphenyl)-5-fluoro-2,4-pyrimidinediamine $^1$H NMR (DMSO-d6): δ 8.10 (m, 2H), 7.89 (dd, 1H, J=2.1 and J=5.6 Hz), 7.25 (m, 1H), 7.15 (m, 2H), 5.12 (s, 2H), 3.74 (s, 3H), 3.68 (s, 3H), 2.48 (s, 3H); LCMS: purity 99%; MS (m/e): 489 (MH+).

V-4: Racemic N2-(4-Aminosulphonylphenyl)-5-fluoro-N4-[2-methyl-3-oxo-4-(4-methoxybenzyl)-benz[1,4]oxazin-6-yl]-2,4-pyrimidinediamine Purity 90%; MS (m/e): 565 (MH$^+$).

V-5: Racemic N2-(3-Aminosulphonylphenyl)-5-fluoro-N4-[2-methyl-3-oxo-4-(4-methoxybenzyl)-benz[1,4]oxazin-6-yl]-2,4-pyrimidinediamine purity 90%; MS (m/e): 565 (MH$^+$).

V-6: N2-(4-Aminosulphonylphenyl)-5-fluoro-N4-(3-oxo-4-cyanomethyl-benz[1,4]oxazin-6-yl]-2,4-pyrimidinediamine $^1$H NMR (DMSO-d6): δ 8.20 (d, 1H, J=3.9 Hz), 7.74 (d, 2H, J=8.4 Hz), 7.63 (d, 2H, J=8.4 Hz), 7.53 (m, 2H), 7.07 (m, 1H), 5.00 (s, 2H), 4.77 (s, 2H); purity 92%; MS (m/e): 470 (MH$^+$).

V-7: N2-(3-Aminosulphonylphenyl)-5-fluoro-N4-(3-oxo-4-cyanomethyl-benz[1,4]oxazin-6-yl]-2,4-pyrimidinediamine $^1$H NMR (DMSO-d6): δ 8.18 (d, 1H, J=3.3 Hz), 8.05 (s, 1H), 7.82 (s, 1H), 7.54 (m, 2H), 7.38 (m, 2H), 4.99 (s, 2H), 4.76 (s, 2H); purity 90%; MS (m/e): 470 (MH$^+$).

VII-11: N2-(3-Aminosulphonylphenyl)-5-fluoro-N4-(2,2,4-trimethyl-1,1,3-trioxo-benzo[1,4]thiazin-6-yl)-2,4-pyrimidinediamine $^1$H NMR (DMSO-d6): δ 8.28 (d, 1H, 3.3 Hz), 8.13 (s, 1H), 7.98 (m, 4H), 7.89 (m, 1H), 7.80 (m, 1H), 7.77 (m, 1H), 7.40 (m, 2H), 3.34 (s, 3H), 1.43 (s, 6H); purity 91%; MS (m/e): 521 (MH$^+$).

VII-12: N2-(4-Aminosulphonylphenyl)-5-fluoro-N4-(2,2,4-trimethyl-1,1,3-trioxo-benzo[1,4]thiazin-6-yl)-2,4-pyrimidinediamine Purity 90%; MS (m/e): 521 (MH$^+$).

V-11: N2-(4-Aminosulphonylphenyl)-5-fluoro-N4-(3-oxo-4-cyanomethyl-benzo[1,4]thiazin-6-yl)-2,4-pyrimidinediamine $^1$H NMR (DMSO-d6): δ 8.21 (d, 1H, J=3.2 Hz), 7.80 (m, 3H), 7.64 (m, 2H), 7.42 (m, 1H), 7.13 (s, 1H), 5.00 (s, 2H), 3.66 (s, 2H); purity 93%; MS (m/e): 486 (MH$^+$).

V-12: N2-(3-Aminosulphonylphenyl)-5-fluoro-N4-(3-oxo-4-cyanomethyl-benzo[1,4]thiazin-6-yl)-2,4-pyrimidinediamine $^1$H NMR (DMSO-d6): δ 8.18 (d, 1H, J=3.4 Hz), 8.14 (s, 1H), 7.88 (m, 1H), 7.80 (m, 1H), 7.38 (m, 3H) 7.27 (s, 1H), 4.99 (s, 2H), 3.65 (s, 2H); purity 93%; MS (m/e): 486 (MH$^+$).

V-8: N2-(3-Aminosulphonyl-4-methylphenyl)-5-fluoro-N4-[3-oxo-4-cyanomethyl-benz[1,4]oxazin-6-yl]-2,4-pyrimidinediamine $^1$H NMR (DMSO-d6): δ 8.11 (m, 2H), 7.80 (m, 1H), 7.61 (m, 2H), 7.18 (s, 1H), 7.02 (d, 1H, J=8.4 Hz), 5.00 (s, 2H), 4.75 (s, 2H), 3.54 (s, 3H); purity 95%; MS (m/e): 484 (MH$^+$).

V-13: N2-(3-Aminosulphonyl4-methylphenyl)-5-fluoro-N4-(3-oxo-4-cyanomethyl-benzo[1,4]thiazin-6-yl)-2,4-pyrimidinediamine $^1$H NMR (DMSO-d6): δ 8.17 (d, 1H, J=3.4 Hz), 8.11 (s, 1H), 7.64 (m, 2H), 7.27 (m, 1H), 7.19 (m, 2H), 4.96 (s, 2H), 4.75 (s, 2H), 3.65 (s, 3H); purity 95%; MS (m/e): 500 (MH$^+$).

VII-46: N2-(4-Aminosulphonylphenyl)-5-fluoro-N4-(2,2,4-trimethyl-1,1,3-trioxo-benzo[1,4]thiazin-6-yl)-2,4-pyrimidinediamine Purity 90%; MS (m/e): 514 (MH$^+$).

VII-47: N2-(4-Aminosulphonylphenyl)-N4-cyanomethyl-5-fluoro-N4-[3-oxo-4-methyl-benzo[1,4]thiazin-6-yl]-2,4-pyrimidinediamine $^1$H NMR (DMSO-d6): δ 8.21 (d, 1H, J=4.8 Hz), 7.88 (d, 2H, J=8.7 Hz), 7.69 (d, 2H, J=8.7 Hz), 7.46 (d, 1H, J=7.2 Hz), 7.33 (bs, 1H), 7.04 (m, 1H), 5.00 (s, 2H), 3.56 (s, 2H), 3.31 (s, 3H); purity 99%; MS (m/e): 500 (MH$^+$).

V-9: (R/S)—N2-(3-Aminosulphonyl-4-methylphenyl)-5-fluoro-N4-[2-methyl-3-oxo-4-(4-methoxybenzyl)-benzo[1,4]thiazin-6-yl]-2,4-pyrimidinediamine $^1$H NMR (DMSO-d6): δ 8.10 (d, 1H, J=2.2 Hz), 7.82 (m, 1H), 7.63 (m, 2H), 7.16 (m, 3H), 7.04 (d, 2H, J=8.1 Hz), 6.78 (d, 2H, J=8.1 Hz), 5.00 (m, 2H), 3.76 (q, 1H, J=6.6 Hz), 3.63 (s, 3H), 3.34 (s, 3H), 1.36 (d, 3H, J=6.6 Hz); purity 90%; MS (m/e): 595 (MH$^+$).

V-10: (R/S)—N2-(4-Aminosulphonylphenyl)-5-fluoro-N4-[2-methyl-3-oxo-4-(4-methoxybenzyl)-benzo[1,4]thiazin-6-yl]-2,4-pyrimidinediamine $^1$H NMR (DMSO-d6): δ 8.15 (d, 1H, J=3.6 Hz), 7.78 (d, 2H, J=8.4 Hz), 7.65 (m, 2H), 7.52 (bs, 1H), 7.34 (d, 1H, J=8.4 Hz), 7.13 (s, 1H), 7.07 (d, 2H, J=8.4 Hz), 6.79 (d, 2H, J=8.4 Hz), 5.06 (s, 2H), 3.79 (q, 1H, J=6.9 Hz), 3.64 (s, 3H), 1.38 (d, 3H, J=6.9 Hz); purity 99%; MS (m/e): 581 (MH$^+$).

V-2: N2-(3-Aminosulphonyl-4-methylphenyl)-5-fluoro-N4-[3-oxo-4-(2-pyridylmethy)-benz[1,4]oxazin-6-yl]-2,4-pyrimidinediamine Purity 90%; MS (m/e): 536 (MH$^+$).

V-3: N2-(3-Aminosulphonyl-4-methylphenyl)-5-fluoro-N4-[3-oxo-4-(2-pyridylmethy)-benz[1,4]oxazin-6-yl]-2,4-pyrimidinediamine Purity 90%; MS (m/e): 522 (MH$^+$).

VII-36: N2-(3-Aminosulphonylphenyl)-5-fluoro-N4-(3-oxo-4-cyanomethyl-benzo[1,4]thiazin-6-yl)-2,4-pyrimidinediamine (LCMS (m/z): 445 (MH$^+$).

VII-44: N2-(3-Aminosulphonyl-4-methyl-phenyl)-5-fluoro-N4-(3-oxo-4H-benzo[1,4]thiazin-6-yl)-2,4-pyrimidinediamine LCMS (m/z): 461 (MH$^+$).

VII-45: N2-(3-Aminosulphonyl-4-methyl-phenyl)-5-fluoro-N4-(3-oxo-4H-benzo[1,4]thiazin-6-yl)-2,4-pyrimidinediamine LCMS (m/z): 475 (MH$^+$).

I-268: N2-(4-Aminosulfonylphenyl)-5-fluoro-N4-(4-[3-methyl-1,2,4-oxadiazol-5-yl]methyleneoxyphenyl)-2,4-pyrimidinediamine $^1$H NMR (DMSO-d$_6$): δ 9.58 (s, 1H), 9.37 (s, 1H), 7.79 (d, 2H, J=8.7 Hz), 7.86 (d, 2H, J=8.7 Hz), 7.62 (d, 2H, J=8.7 Hz), 7.12 (s, 2H), 7.03 (d, 2H, J=8.7 Hz), 5.47 (s, 2H), 2.36 (s, 3H); LCMS: purity: 100%; MS (m/e): 472.4 (MH$^+$).

I-271: N2-(5-N,N-Diethylaminosulfonyl-2-methoxyphenyl)-5-fluoro-N4-(4-[3-methyl-1,2,4-oxadiazol-5-yl]methyleneoxyphenyl)-2,4-pyrimidinediamine LCMS: purity: 91.7%; MS (m/e): 558.5 (MH$^+$).

I-272: 5-Fluoro-N4-(4-[3-methyl-1,2,4-oxadiazol-5-yl]methyleneoxyphenyl)-N2-(5-piperidinesulfonylphenyl)-2,4-pyrimidinediamine LCMS: purity: 100%; MS (m/e): 558.5 (MH$^+$).

VII-48: N2-(4-Aminosulfonylphenyl)-5-fluoro-N4-(4-methyl-3-oxo-benz[1,4]thiazin-6-yl)-2,4-pyrimidinediamine LCMS: purity: 96.5%; MS (m/e): 461.4 (MH$^+$).

VII-49: N2-(3-Aminosulfonylphenyl)-5-fluoro-N4-(4-methyl-3-oxo-benz[1,4]thiazin-6-yl)-2,4-pyrimidinediamine LCMS: purity: 97.4%; MS (m/e): 461.4 (MH$^+$).

VII-40: N2-(4-Aminosulfonylphenyl)-5-fluoro-N4-(4-methyl-3-oxo-benz[1,4]oxazin-6-yl)-2,4-pyrimidinediamine LCMS: purity: 97.1%; MS (m/e): 445.1 (MH$^+$).

VII-41: N2-(3-Aminosulfonylphenyl)-5-fluoro-N4-(4-methyl-3-oxo-benz[1,4]oxazin-6-yl)-2,4-pyrimidinediamine LCMS: purity: 97.1%; MS (m/e): 445.1 (MH$^+$).

VII-50: 5-Fluoro-N4-(4-methyl-3-oxo-benz[1,4]
thiazin-6-yl)-N2-(3-piperidinosulfonylphenyl)-2,4-
pyrimidinediamine LCMS: purity: 100%; MS (m/e): 529.4 (MH+).

VII-54: N2-(3-Aminosulfonylphenyl)-N4-(2-ami-
nocarbonylbenzofurane-5-yl)-5-fluoro-2,4-pyrimi-
dinediamine LCMS: purity: 84.5%; MS (m/e): 443.4 (MH+).

IX-5: N2-(3-Aminosulfonylphenyl)-N4-(1-cyanom-
ethyleneindol-5-yl)-5-fluoro-2,4-pyrimidinediamine LCMS: purity: 92.6%; MS (m/e): 438.3 (MH+).

VII-59: N2-(4-Aminosulfonylphenyl)-N4-(4-N-tert-
butoxycarbonylamino-3,4-dihydro-2H-1-benzopy-
ran-6-yl)-5-fluoro-2,4-pyrimidinediamine LCMS: purity: 97.7%; MS (m/e): 473.4 (MH+).

IX-6: N2-(4-Aminosulfonylphenyl)-N4-(1-cyanom-
ethyleneindol-5-yl)-5-fluoro-2,4-pyrimidinediamine LCMS: purity: 100%; MS (m/e): 438.4 (MH+).

IX-7: N2-(3-Aminosulfonyl-4-chlorophenyl)-N4-(1-
cyanomethyleneindol-5-yl)-5-fluoro-2,4-pyrimidin-
ediamine LCMS: purity: 100%; MS (m/e): 452.4 (MH+).

IX-8: N2-(3-Aminosulfonyl-4-methylphenyl)-N4-(1-
cyanomethyleneindol-5-yl)-5-fluoro-2,4-pyrimidin-
ediamine LCMS: purity: 100%; MS (m/e): 472.4 (MH+).

Example 36

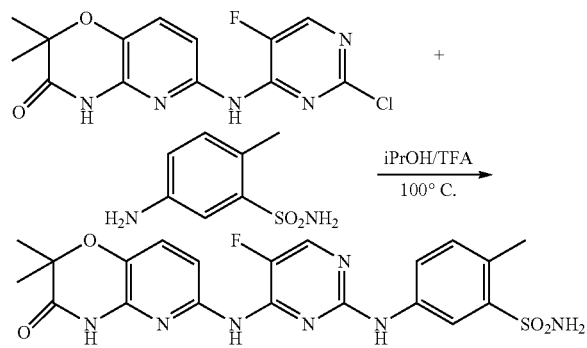

V-18: N-2-(3-aminosulfonyl-4-methylphenyl)-N4-
[2,2-dimethyl-3-oxo-4H-pyrid[1,4]oxazin-7-yl]-5-
fluoro-2,4-pyrimidinediamine A heterogeneous mixture of N4-[2,2-dimethyl-3-oxo-4H-pyrid[1,4]oxazin-7-yl]-2-chloro-5-fluoro-4-pyrimidineamine (40 mg, 0.123 mmol), 4-methyl-aminobenzene-3-sulfonamide (25.5 mg, 0.148 mmol) and trifluoroacetic acid (504) in MeOH (2 mL) was heated in sealed reaction vial at 100° C. for 24 h. The resulting reaction mixture was purified by silica gel column chromatography using 1-3% 2N NH3/MeOH in CH2Cl2 to provide desired 20.0 mg (34%) of N2-(3-aminosulfony-4-methylphenyl)-N4-[2,2-dimethyl-3-oxo-4H-pyrid[1,4]oxazin-7-yl]-5-fluoro-2,4-pyrimidinediamine ¹HNMR (DMSO-d6): δ 11.08 (s, 1H), 9.46 (s, 1H), 8.12 (d, 1H, J=3.6 Hz), 8.07 (d, 1H, J=2.1 Hz), 7.88 (m, 1H), 7.64 (d, 1H, J=8.4 Hz), 7.38 (d, 1H, J=10.2 Hz), 7.24 (s, 2H), 7.16 (d, 1H, J=8.1 Hz), 2.49 (s, 3H), 1.43 (s, 6H): LCMS: purity: 97%; MS (m/e): 475 (MH+).

Example 37

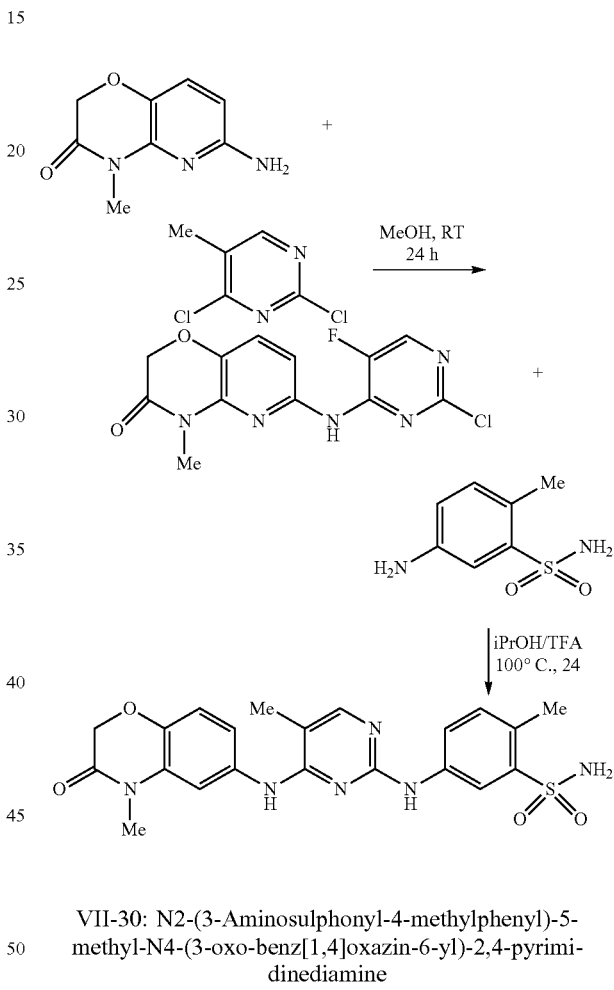

VII-30: N2-(3-Aminosulphonyl-4-methylphenyl)-5-
methyl-N4-(3-oxo-benz[1,4]oxazin-6-yl)-2,4-pyrimi-
dinediamine A mixture of 250 mg of 6-Amino-3-oxo-4H-benz[1,4]oxazine and 460 mg of 2,4-dichloro-5-methylpyrimidine in 15 mL methanol was stirred overnight at RT and solvent volume was reduced by using rotary evaporation. The solution was filtered and the filtrate diluted with water and neutralized with sodium bicarbonate. The precipitate was collected by suction filtration washed with water and dried on the funnel to yield 75 mg (20%) of the desired product 2-chloro-5-methyl-N4-oxo-benz[1,4]oxazin-6-yl)-4-pyrimidineamine ¹H NMR (DMSO-d6): δ 7.98 (s, 1H), 7.08 (m, 2H), 6.91 (d, 1H J=6 Hz), 4.54 (s, 2H), 2.11 (s, 3H) purity 97%; MS (m/e) 291 (MH+).

A heterogeneous mixture of 2-chloro-5-methyl-N4-oxo-benz[1,4]oxazin-6-yl)-4-pyrimidineamine (25 mg) and 3-aminosulfonyl-4-methylaniline (40 mg) in iPrOH: TFA (4:1; v/v) was heated in a sealed tube for 24 h. The resulting reaction mixture was diluted with water, acidified with 2N HCl and the solid obtained was filtered. The solid upon taking into methanol:water was neutralized by aqueous solution of sodium bicarbonate and the resulting solid was isolated by filtration to give N2-(3-aminosulphonyl-4-methylphenyl)-5-methyl-N4-(3-oxo-benz[1,4]oxazin-6-yl)-2,4-pyrimidinediamine. $^1$H NMR (DMSO-d$_6$): δ 7.86 (s, 1H), 7.80 (s, 1H), 7.77 (m, 1H), 7.31 (bs, 2H), 7.12 (m, 2H), 6.95 (m, 1H), 4.58 (s, 2H), 2.11 (s, 3H); purity 99%; MS (m/e): 441 (MH$^+$).

Example 38

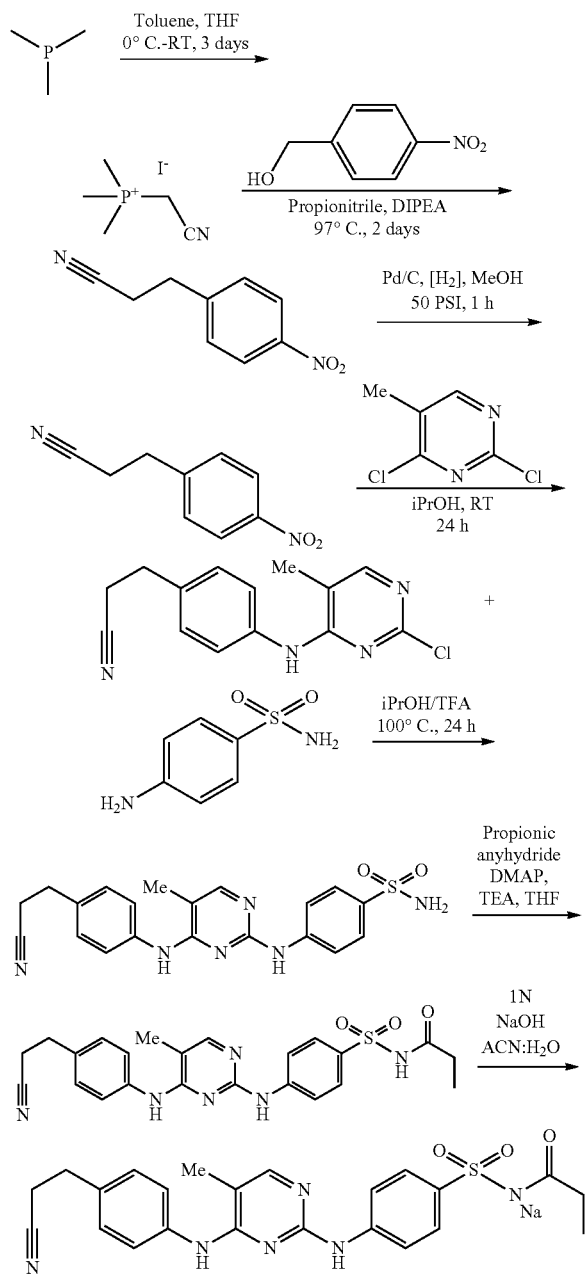

III-27: N2-(4-Aminosulfonylphenyl)-N4-(4-cyanoethylenephenyl)-5-methyl-2,4-pyrimidinediamine and its Prodrug A solution of triphenylphosphine in toluene (1 mol L-1, 40 mL, 40 mmol) at 0° C. under nitrogen was added to a mixture of toluene (20 mL) and tetrahydrofuran (20 ml). Iodoacetonitrile (2.8 mL, 38.7 mmol) was then added drop wise with vigorous stirring. Ice-bath was removed and the mixture was stirred at room temperature for an additional of 40 h. The mixture was filtered and the solid was washed with toluene and recrystallized from acetonitrile to give 8 g of (cyanomethyl)trimethylphosphonium iodide as a white solid. LCMS: 243.03 (M$^+$).

Propionitrile (32 mL), diisopropylethylamine (2.5 g, 19.58 mmol) were added to a mixture of 4-nitrobenzyl alcohol (1 g, 6.53 mmol) and (cyanomethyl)trimethylphosphonium iodide (4 g, 16.32 mmol). The mixture was heated at 97° C. for 24 h. Water (1 mL) was added to the mixture and followed by conc. HCl (5 mL). Ethyl acetate (3×100 mL) was used to extract the product. Organic layer was washed with brine, dried with sodium sulfate, concentrated to give dark brown solid. The crude product was purified by flash column chromatography (Ethyl acetate: Hexanes 1:1) to give 740 mg of 3-(4-nitrophenyl)propionitrile as a light orange solid. $^1$H NMR (DMSO-d$_6$): δ 8.20-8.17 (dd, J=8.7 Hz, 2H), 7.59-7.56 (d, J=9.0 Hz, 2H), 3.06-3.01 (m, 2H).

3-(4-Nitrophenyl)propionitrile (740 mg, 4.2 mmol) was dissolved in methanol (100 mL), 10% Pd/C was added and the mixture was shaken under a hydrogen atmosphere (50 psi) at room temperature for 30 minutes. The mixture was filtered through Celite, and washed with 20 mL of methanol. The combined organic solvent was concentrated under reduced pressure to give crude materials which was further purified by flash column chromatography (Ethyl acetate: Hexanes 1:1) to yield 520 mg of 3-(4-Aminophenyl)propionitrile as a light yellow oil. $^1$H NMR (DMSO-d$_6$): δ 6.91-6.88 (d, J=9.0 Hz, 2H), 6.49-6.46 (d, J=9.0 Hz, 2H), 4.92 (s, 2H), 2.66 (s, 4H).

3-(4-Aminophenyl)propionitrile (152 mg, 1.0 mmol) was dissolved in isopropyl alcohol (2 mL), 2,4-dichloro-5-methylpyrimidine (300 mg, 1.8 mmol) was added to the solution. The mixture was stirred for 48 hours. All the solvent was removed under reduced pressure, saturated sodium bicarbonate was added, aqueous layer was extracted with ethyl acetate. Ethyl acetate was dried with sodium sulfate, filtered, concentrated under reduced pressure to give crude product. Crude was further purified by column chromatography (Ethyl Acetate:Hexanes, 1:1 to 3:1) to give 70 mg of 2-Chloro-N4-(4-cyanoethylenephenyl)-5-methyl-4-pyrimidineamine as a colorless oil. $^1$H NMR (DMSO-d$_6$): δ 8.80 (s, 1H), 8.00 (s, 1H), 7.55-7.52 (d, J8.Hz, 2H), 7.271-7.244 (d, J=8.1 Hz, 2H), 2.85-2.80 (m, 4H), 2.15 (s, 3H); LCMS: 275.28 (MH$^+$).

2-Chloro-N4-(4-cyanoethylenephenyl)-5-methyl-4-pyrimidineamine (70 mg, 0.25 mmol) was dissolved in isopropyl alcohol (2 mL). Trifluoroacetic acid (2 drops) and 4-aminosulfonylaniline (70 mg, 0.4 mmol) was added to the solution, the mixture was heated at 100° C. for 48 hours. Solvent was removed under reduced pressure, saturated sodium bicarbonate was added, and extracted with ethyl acetate. Organic layer was dried with sodium sulfate, filtered and concentrated to give crude product. The crude product was sonicated with dichloromethane and acetone respectively to give 120 mg of N2-(4-Aminosulfonylphenyl)-N4-(4-cyanoethylenephenyl)-5-methyl-2,4-pyrimidinediamine as an off-white solid. $^1$H NMR (DMSO-d$_6$): δ 8.39 (s, 1H), 8.35 (s, 1H), 8.10 (s, 1H), 7.91 (s, 1H), 7.81-7.78 (d, J=8.7 Hz, 2H), 7.63-7.60 (d, J=8.4 Hz, 2H), 7.57-7.55 (d, J=8.7 Hz, 2H), 7.26-7.23 (d, J=8.4 Hz, 2H), 7.07 (s, 2H), 2.88-2.81 (m, 4H), 2.11 (s, 3H); LCMS: 409.01 (MH+).

N2-(4-Aminosulfonylphenyl)-N4-(4-cyanoethylenephenyl)-5-methyl-2,4-pyrimidinediamine (70 mg, 0.17 mmol) was added to THF (2 mL), DMAP (10 mg, 0.5 equitant), triethylamine (0.028 mL, 1.2 equivalents), and propionic anhydride (0.024 mL, 1.1equivalents). The mixture was shaken overnight, all the solvent was removed under reduced pressure. The residue was extracted with dichloromethane, the organic layer was washed with water, dried, and concentrated under reduced pressure to give 20 mg of a prodrug of the compound described above, N4-(4-Cyanoethylenephenyl)-5-methyl-N2-(4-propionylaminosulfonylphenyl)-2,4-pyrimidinediamine, as an off white solid. ¹H NMR (DMSO-d₆): δ 11.79 (s, 1H), 9.55 (s, 1H), 8.39 (s, 1H), 7.92 (s, 1H), 7.84-7.81 (d, J=7.8 Hz, 2H), 7.65-7.62 (d, J=8.7 Hz, 2H), 7.61-7.59 (d, J=7.5 Hz, 2H), 7.27-7.24 (d, J=7.5 Hz, 2H), 2.86-2.82 (m, 4H), 2.21-2.13 (q, 2H), 2.12 (s, 3H), 0.90-0.85 (t, 2H); LCMS: 465.02 (MH+).

N4-(4-Cyanoethylenephenyl)-5-methyl-N2-(4-propionylaminosulfonylphenyl)-2,4-pyrimidinediamine (20 mg, 0.04 mmol) was dissolved in acetonitrile and water, 1N NaOH was added drop wise. The solution was lyophilized over 48 hours to give the sodium salt of prodrug 111-27, as a light yellow solid. ¹H NMR (DMSO-d₆): δ 9.07 (s, 1H), 8.24 (s, 1H), 7.87 (s, 1H), 7.65-7.63 (d, J=6.6 Hz, 2H), 7.60-7.57 (d, J=7.2 Hz, 2H), 7.50-7.48 (d, J=7.2 Hz, 2H), 7.24-7.22 (d, J=6.9 Hz, 2H), 2.87-2.81 (m, 4H), 2.10 (s, 3H), 1.89-1.86 (q, 2H), 0.87-0.82 (t, 3H); LCMS: 465.02 (MH+).

Example 39

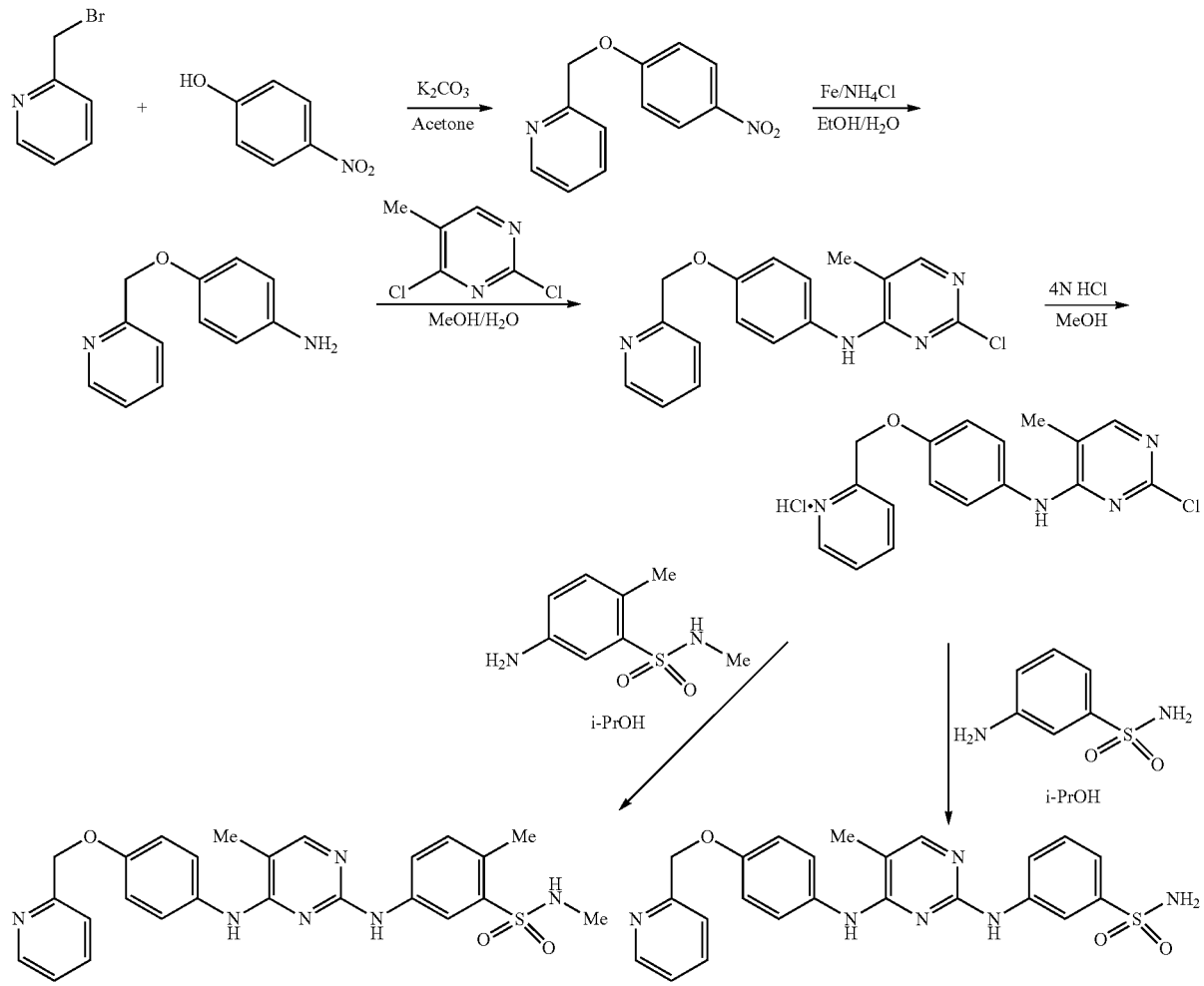

I-179: N2-(3-Aminosulfonylphenyl)-5-methyl-N4-[4-(2-pyridinyl)methyleneoxyphenyl]-2,4-pyrimidinediamine A dry reaction flask was charged with 4-nitrophenol (3.858 g, 27.75 mmol), anhydrous K₂CO₃ (8.29 g, 60 mmol) and acetone (250 mL). To this heterogeneous mixture was added 2-pyridylmethylbromide hydrobromide (7.0 g, 27.75 mmol) and refluxed for 24 h. From the resulting reaction mixture, 200 mL of acetone was removed under reduced pressure. The resulting residue was then diluted with ice-water (1 liter), the solid crushed out was filtered, washed with water and dried well to give 2-[(4-nitrophenoxy)methyl]pyridine (6.05 g, 95% yield). ¹H NMR (CDCl₃): δ 8.61 (d, 1H, J=4.8 Hz), 8.19 (d, 2H, J=9.0 Hz), 7.72 (m, 2H), 7.46 (d, 1H, J=7.8 Hz), 7.25 (m, 1H), 7.05 (d, 2H, J=9.3 Hz), 5.28 (s, 2H); LCMS (m/z): 231 (MH+).

2-[(4-Nitrophenoxy)methyl]pyridine (2.30 g, 10 mmol) was dissolved in ethanol (160 mL) and water (40 mL). NH₄Cl (5.30 g) was added to the above mixture and heated to 70-80° C. To this reaction mixture was added iron powder (5.50 g) in portion wise manner under a vigorous stirring and the stirring was continued for 2 h. The reaction mixture was filtered through a Celite pad when hot and washed the filter bed with MeOH. The filtrate was concentrated, diluted with water, extracted with CH₂Cl₂ (3×75 mL), dried and concentrated to provide 2-[(4-aminophenoxy)methyl]pyridine as brown solid (1.735 g) in 86% yield. ¹H NMR (CDCl₃): δ 8.56 (m, 1H), 7.67 (m, 1H), 7.49 (d, 1H, J=7.8 Hz), 7.18 (m, 1H), 6.80 (d, 2H, J=8.7 Hz), 6.62 (d, 2H, J=8.7 Hz), 5.12 (s, 2H), 3.43 (br s, 2H); LCMS (m/z): 201 (MH⁺).

A mixture of 2-[(4-aminophenoxy)methyl]pyridine (0.794 g, 3.97 mmol) and 2.4-dichloro-5-methylpyridine (0.65 g, 3.97 mmol) in a mixture of methanol (49 mL) and water (16 mL) was stirred at room temperature for 48 h. The reaction mixture was concentrated under reduced pressure to remove MeOH (30 mL) and then diluted with ice-water (200 mL). The resulting mixture was kept aside for 1 h, the solid that separated was filtered, washed with water and dried to afford 2-chloro-5-methyl-N-[4-(2-pyridinyl)methyleneoxyphenyl]-4-pyrimidineamine (1.21 g, 93% yield). ¹H NMR (DMSO-d₆): δ 8.60 (s, 1H), 8.56 (d, 1H, J=4.8 Hz), 7.94 (d, 1H, J=0.9 Hz), 7.81 (m, 1H), 7.52 (s, 1H), 7.48 (d, 2H, J=9.3 Hz), 7.31 (dd, 1H, J=4.8 and 7.5 Hz), 7.02 (d, 2H, J=9.0 Hz), 5.17 (s, 2H), 2.14 (s, 3H); LCMS (m/z): 327 (MH⁺).

2-Chloro-5-methyl-N-[4-(2-pyridinyl)methyleneoxyphenyl]-4-pyrimidineamine (1.21 g) was dissolved in MeOH (65 mL), added 4N HCl (in dioxane, 2.12 mL) drop wise, stirred at room temperature for 1 h, removed the solvents under reduced pressure and finally dried under high vacuum to provide hydrochloride salt in quantitative yield, which was used in the next step as such.

A mixture of 2-chloro-5-methyl-N-[4-(2-pyridinyl)methyleneoxyphenyl]-4-pyrimidineamine hydrochloride (54 mg, 0.149 mmol) and 3-aminobenzenesulfonamide (25.6 mg, 0.149 mmol) in i-PrOH (2 mL) were reacted in sealed reaction vial at 100° C. for 24 hours. The product was purified by column chromatography [silica gel column, eluted with CH₂Cl₂: 2M NH₃ in MeOH (4-5%)] to provide N2-(3-aminosulfonylphenyl)-5-methyl-N4-[4-(2-pyridinyl)methyleneoxyphenyl]-2,4-pyrimidinediamine (I-179; 55.4 mg) in 80% yield. ¹H NMR (DMSO-d₆): δ 9.23 (s, 1H), 8.57 (d, 1H, J=4.5 Hz), 8.21 (s, 1H), 8.00 (m, 2H), 7.84 (s, 1H), 7.81 (dd, 1H, J=1.8 and 7.8 Hz), 7.58 (d, 2H, J=8.7 Hz), 7.52 (d, 1H, J=8.1 Hz), 7.33 (dd, 1H, J=5.1 and 6.9 Hz), 7.22 (m, 4H), 6.98 (d, 2H, J=8.7 Hz), 5.17 (s, 2H), 2.08 (s, 3H); LCMS (m/z): 463 (MH⁺).

The following compounds were made in a similar fashion to that for 1-179.

I-180: 5-Methyl-N2-[3-(N-methylaminosulfony)-4-methylphenyl]-N4-[4-(2-pyridinyl)methyleneoxyphenyl]-2,4-pyrimidinediamine ¹H NMR (DMSO-d₆): δ 9.12 (s, 1H), 8.56 (d, 1H, J=3.6 Hz), 8.17 (s, 1H), 7.97 (m, 2H), 7.82 (m, 2H), 7.59 (d, 2H, J=8.7 Hz), 7.51 (d, 1H, J=7.8 Hz), 7.31 (m, 2H), 7.09 (d, 1H, J=9.0 Hz), 6.98 (d, 2H, J=9.0 Hz), 5.17 (s, 2H), 2.43 (s, 3H), 2.41 (d, 3H, J=4.8 Hz), 2.08 (s, 3H); LCMS (m/z): 491 (MH⁺).

I-181: N2-(4-Aminosulfonylphenyl)-5-methyl-N4-[4-(2-pyridinyl)methyleneoxyphenyl]-2,4-pyrimidinediamine ¹H NMR (DMSO-d₆): δ 9.35 (s, 1H), 8.57 (d, 1H, J=4.5 Hz), 8.30 (s, 1H), 7.86-7.76 (m, 4H), 7.53 (m, 5H), 7.33 (dd, 1H, J=4.8 and 6.7 Hz), 7.09 (s, 2H), 7.02 (d, 2H, J=8.7 Hz), 5.18 (s, 2H), 2.09 (s, 3H); LCMS (m/z): 463 (MH⁺).

Example 40

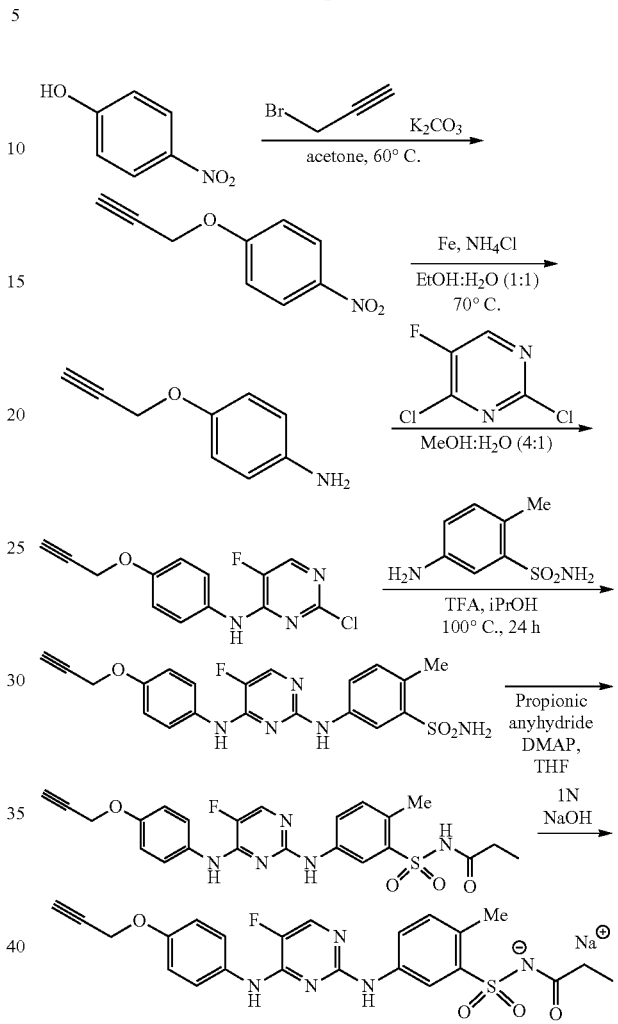

VI-53: N2-(3-Aminosulfonyl-4-methylphenyl)-5-fluoro-N4-[4-(prop-2-ynyloxy)phenyl]-2,4-pyrimidinediamine and its prodrug 4-Nitrophenol (1.00 g, 7.19 mmol), propargyl bromide (80 wt % in toluene; 0.788 mL, 7.09 mmol), and K₂CO₃ (1.08 g, 7.84 mmol) were stirred in acetone (16.0 mL) at 60° C. for 18 h. The reaction mixture was cooled to room temperature and diluted with water (200 mL). 4-(prop-2-ynyloxy)nitrobenzene was isolated as a white solid by suction filtration (1.12 g). ¹H NMR (CDCl₃): δ 8.22 (d, J=9.0 Hz, 2H), 7.05 (d, J=9.0 Hz, 2H), 4.80 (d, J=2.4 Hz, 2H), 2.59 (t, J=2.4 Hz, 1H).

4-(Prop-2-ynyloxy)nitrobenzene (0.910 g, 5.13 mmol), iron (1.42 g, 25.3 mmol), and NH₄Cl (0.719 g, 12.8 mmol) were vigorously stirred in EtOH/water (1:1, 55 mL) at 70° C. for 15 minutes. The reaction mixture was filtered hot through Celite and concentrated in vacuo. The residue was suspended in 10% 2N ammoniacal methanol in dichloromethane, sonicated, and filtered through Celite. Concentration gave 4-(prop-2-ynyloxy)aniline as a brown oil which was used without further purification. In general, isolated prop-2-ynyloxyanilines were unstable and were therefore used immediately after the second filtration. $^1$H NMR (CDCl$_3$): δ 6.82 (d, J=8.7 Hz, 2H), 6.64 (d, J=8.7 Hz, 2H), 4.61 (d, J=2.4 Hz, 2H), 2.50 (t, J=2.4 Hz, 1H).

Crude 4-(prop-2-ynyloxy)aniline (0.750 g, 5.10 mmol) and 2,4-dichloro-5-fluoropyrimidine (1.27 g, 0.760 mmol) were stirred in MeOH/water (4:1, 35 mL) at room temperature for 18 h. The reaction mixture was diluted with EtOAc (200 mL) and washed with 1N HCl (50 mL) and brine (50 mL). The organic layer was dried (MgSO$_4$), filtered and concentrated in vacuo. The residue was purified by column chromatography (silica gel, hexanes ramped to EtOAc: hexanes (1:10)) to provide 2-chloro-5-fluoro-N4-[4-(prop-2-ynyloxy)phenyl]-4-pyrimidineamine as a light brown solid (0.514 g). $^1$H NMR (CDCl$_3$): δ 8.03 (d, J=2.7 Hz, 1H), 7.53 (d, J=8.7 Hz, 2H), 7.02 (d, J=8.7 Hz, 2H), 6.86 (s, 1H), 4.71 (d, J=2.4 Hz, 2H), 2.55 (t, J=2.4 Hz, 1H); LCMS: purity: 99%; MS (m/e): 279 (MH$^+$).

2-Chloro-5-fluoro-N4-[4-(prop-2-ynyloxy)phenyl]-4-pyrimidineamine (0.514 g, 1.85 mmol), 3-(aminosulfonyl)-4-methylaniline (0.689 g, 3.70 mmol), and trifluoroacetic acid (0.186 mL, 2.41 mmol) were combined with iPrOH (6.0 mL) in a sealed vial and heated at 100° C. for 3 h. The reaction mixture was cooled to room temperature and diluted with 1N HCl (80 mL). N2-(3-Aminosulfonyl-4-methylphenyl)-5-fluoro-N4-[4-(prop-2-ynyloxy)phenyl]-2,4-pyrimidinediamine (VI-53) was isolated as a white solid by suction filtration (0.703 g). $^1$H NMR (DMSO-d$_6$): δ 10.08 (bs, 2H), 8.19 (d, J=4.5 Hz, 1H), 7.89 (s, 1H), 7.74 (dd, J=2.4 and 8.4 Hz, 1H), 7.58 (d, J=8.7 Hz, 2H), 7.32 (bs, 2H), 7.23 (d, J=8.4 Hz, 1H), 6.97 (d, J=8.4 Hz, 2H), 4.79 (d, J=2.1 Hz, 2H), 3.59-3.55 (m, 1H), 2.53 (s, 3H); LCMS: purity: 97%; MS (m/e): 428 (MH$^+$).

N2-(3-Aminosulfonyl-4-methylphenyl)-5-fluoro-N4-[4-(prop-2-ynyloxy)phenyl]-2,4-pyrimidinediamine (0.200 g, 0.467 mmol), DMAP (40 mg, 0.33 mmol)) and triethylamine (0.118 mL, 0.847 mmol) were stirred in THF (6.0 mL). Propionic anhydride (0.180 mL, 1.40 mmol) was added to the solution dropwise. The reaction mixture was stirred at rt overnight. The solution was diluted with ethyl acetate (50 mL) and washed with water (5×25 mL) and brine (10 mL). The organic layer was dried (MgSO$_4$), filtered, and evaporated. The residue was suspended in ethyl acetate (25 mL), sonicated and filtered off to give a prodrug of VI-53, 5-fluoro-N2-(4-methyl-3-propionylaminosulfonylphenyl)-N4-[4-(prop-2-ynyloxy)phenyl]-2,4-pyrimidinediamine (VI-56; 0.20 g). $^1$H NMR (DMSO-d$_6$): δ 12.01 (s, 1H), 9.44 (s, 1H), 9.26 (s, 1H), 8.16 (d, J=2.4 Hz, 1H), 8.06 (dd, J=0.3 and 3.3 Hz, 1H), 8.00 (dd, J=2.1 and 7.8 Hz, 1H), 7.69 (d, J=8.7 Hz, 2H), 7.19 (d, J=8.4 Hz, 1H), 6.95 (d, J=8.7 Hz, 2H), 4.77 (d, J=2.1 Hz, 2H), 3.56 (t, J=2.1 Hz, 1H), 2.49 (s, 3H), 2.24 (q, J=7.2 Hz, 2H), 0.89 (t, J=7.2 Hz, 3H); LCMS: purity: 98%; MS (m/e): 484 (MH$^+$).

5-Fluoro-N2-(4-methyl-3-propionylaminosulfonylphenyl)-N4-[4-(prop-2-ynyloxy)phenyl]-2,4-pyrimidinediamine (0.125 g, 0.258 mmol) was suspended in acetonitrile (1.5 mL) and water (1.5 mL) and cooled in an ice bath. A solution of 1N NaOH aq. (0.260 mL) was added dropwise. The reaction mixture was stirred until it became clear, filtered through glass wool, and lyophilized to give the sodium salt of the prodrug VI-56 (independently designated as VI-62). $^1$H NMR (DMSO-d$_6$): δ 9.17 (bs, 2H), 8.01 (d, J=3.6 Hz, 1H), 7.89 (s, 1H), 7.78-7.69 (m, 3H), 6.99-6.92 (m, 3H), 4.76 (d, J=2.1 Hz, 1H), 2.43 (s, 3H), 1.95 (q, J=7.2 Hz, 2H), 0.86 (t, J=7.2 Hz, 3H); LCMS: purity: 98%; MS (m/e): 484 (MH+).

The following compounds were made in a similar fashion to the example 40 or by methods described herein or known to skilled artisans.

VII-31: N2-(4-Aminosulphonylphenyl)-5-methyl-N4-(3-oxo-benz[1,4]oxazin-6-yl)-2,4-pyrimidinediamine $^1$H NMR (DMSO-d$_6$): δ 7.93 (s, 1H), 7.60 (m, 4H), 7.24 (bs, 2H), 7.08 (m, 1H), 7.02 (m, 1H) 7.27 (s, 1H), 4.61 (s, 2H), 2.14 (s, 3H); purity 99%; MS (m/e): 427 (MH$^+$).

VII-33: N2-(3-Aminosulphonyl-4-methylphenyl)-5-methyl-N4-(4-methyl-3-oxo-benzo[1,4]thiazin-6-yl)-2,4-pyrimidinediamine $^1$H NMR (DMSO-d6): δ 7.91 (s, 1H), 7.80 (s, 1H), 7.66 (m, 1H), 7.48 (s, 1H), 7.35 (m, 2H), 7.12 (m, 1H), 3.52 (s, 2H), 3.11 (s, 3H), 2.16 (s, 3H); purity 95%; MS (m/e): 471 (MH$^+$).

VII-34: N2-(4-Aminosulphonylphenyl)-5-methyl-N4-(4-methyl-3-oxo-benzo[1,4]thiazin-6-yl)-2,4-pyrimidinediamine $^1$H NMR (DMSO-d6): δ 7.96 (s, 1H), 7.64 (m, 4H), 7.46 (s, 1H), 7.40 (s, 2H), 7.18 (s, 2H), 3.53 (s, 2H), 3.26 (s, 3H), 2.16 (s, 3H); purity 90%; MS (m/e): 457 (MH$^+$).

VII-32: N2-(3-Aminosulphonylphenyl)-5-methyl-N4-(3-oxo-benz[1,4]oxazin-6-yl)-2,4-pyrimidinediamine $^1$H NMR (DMSO-d6): δ 7.91 (s, 1H), 7.82 (m, 1H), 7.65 (s, 1H), 7.51 (m, 1H), 7.36 (m, 3H), 7.04 (s, 1H), 6.98 (m, 1H), 4.60 (s, 2H), 2.14 (s, 3H); purity 96%; MS (m/e): 427 (MH$^+$).

VII-35: N2-(3-Aminosulphonylphenyl)-5-methyl-N4-(4-methyl-3-oxo-benzo[1,4]thiazin-6-yl)-2,4-pyrimidinediamine $^1$H NMR (DMSO-d6): δ 7.95 (s, 1H), 7.73 (m, 2H), 7.38 (m, 7H), 3.52 (s, 2H), 3.16 (s, 3H), 2.17 (s, 3H); purity 90%; MS (m/e): 456 (MH$^+$).

VI-63: N2-[3-Aminosulfonyl-4-(2-propyl)phenyl]-5-fluoro-N4-[4-(prop-2-ynyloxy)phenyl]-2,4-pyrimidinediamine $^1$H NMR (DMSO-d$_6$): δ 10.40-9.84 (m, 2H), 8.15 (d, J=4.8 Hz, 1H), 7.89 (s, 1H), 7.77 (dd, J=1.8 and 8.1 Hz, 1H), 7.61 (d, J=8.7 Hz, 2H), 7.43 (d, J=8.7 Hz, 1H), 7.39 (s, 2H), 6.95 (d, J=9.0 Hz, 2H), 4.77 (d, J=1.8 Hz, 2H), 3.77 (q, J=6.9 Hz, 1H), 3.56 (t, J=1.8 Hz, 1H), 1.20 (d, J=6.9 Hz, 6H), LCMS: purity: 98%; MS (m/e): 456 (MH$^+$).

VI-64: N4-{4-[2-(Dimethylaminocarbonyloxy)ethyl]phenyl}-5-fluoro-N2-(3-propionylaminosulfonylphenyl)-2,4-pyrimidinediamine $^1$H NMR (DMSO-d$_6$): δ 11.95 (s, 1H), 9.58 (s, 1H), 9.36 (s, 1H), 8.20 (s, 1H), 8.12-8.04 (m, 2H), 7.71 (d, J=8.4 Hz, 2H), 7.42-7.36 (m, 3H), 7.20 (d, J=8.4 Hz, 2H), 4.15 (t, J=6.3 Hz, 2H), 2.85 (t, J=7.2 Hz, 2H), 2.79 (s, 6H), 2.22 (q, J=7.5 Hz, 2H), 0.89 (t, J=7.5 Hz, 3H); LCMS: purity: 97%; MS (m/e): 531 (MH$^+$).

VI-65: N2-(3-Aminosulfonyl-4-methylphenyl)-5-fluoro-N4-[4-(prop-2-ynylamino)phenyl]-2,4-pyrimidinediamine $^1$H NMR (DMSO-d$_6$): δ 9.27 (s, 1H), 9.02 (s, 1H), 8.08 (s, 1H), 7.96 (d, J=3.0 Hz, 1H), 7.92 (d, J=8.1 Hz, 1H), 7.47 (d, J=8.4 Hz, 2H), 7.19 (s, 2H), 7.13 (d, J=9.0 Hz, 1H), 6.63 (d, J=8.7 Hz, 2H), 5.85 (t, J=6.0 Hz, 1H), 3.85 (s, 2H), 3.06-3.04 (m, 1H), 2.48 (s, 3H); LCMS: purity: 98%; MS (m/e): 427 (MH$^+$).

VI-66: N4-{4-[2-(Dimethylaminocarbonyloxy)ethyl]phenyl}-5-fluoro-N2-(3-propionylaminosulfonylphenyl)-2,4-pyrimidinediamine sodium salt 1H NMR (DMSO-d$_6$): δ 9.27 (s, 1H), 9.25 (s, 1H), 8.06 (d, J=3.9 Hz, 1H), 7.86-7.82 (m, 2H), 7.74 (d, J=8.4 Hz, 2H), 7.27-7.11 (m, 4H), 4.14 (t, J=6.6 Hz, 2H), 2.84 (t, J=6.6 Hz, 2H), 2.79 (s, 6H), 1.91 (q, J=7.5 Hz, 2H), 0.85 (t, J=7.5 Hz, 3H); LCMS: purity: 97%.

VI-67: N2-(3-Aminosulfonyl-4-methylphenyl)-N4-{4-[bis(prop-2-ynyl)amino]phenyl}-5-fluoro-2,4-pyrimidinediamine $^1$H NMR (DMSO-d$_6$): δ 9.34 (s, 1H), 9.17 (s, 1H), 8.09 (d, J=2.1 Hz, 1H), 8.01 (d, J=3.6 Hz, 1H), 7.91 (dd, J=2.1 Hz, 1H), 7.63 (d, J=8.7 Hz, 2H), 7.22 (s, 2H), 7.16 (d, J=8.7 Hz, 1H), 6.91 (d, J=9.3 Hz, 2H), 4.11 (d, J=2.12 Hz, 4H), 3.17 (t, J=2.1 Hz, 2H), 2.50 (s, 3H); LCMS: purity: 98%; MS (m/e): 465 (MH$^+$).

VI-68: 5-Fluoro-N2-(4-methyl-3-methylaminosulfonylphenyl)-N4-[4-(prop-2-ynyloxy)phenyl]-2,4-pyrimidinediamine $^1$H NMR (DMSO-d$_6$): δ 9.75 (s, 2H), 8.13 (d, J=3.9 Hz, 1H), 7.93-7.89 (m, 1H), 7.84 (dd, J=2.4 and 8.4 Hz, 1H), 7.63 (d, J=9.0 Hz, 2H), 7.41-7.34 (m, 1H), 7.24 (d, J=8.1 Hz, 1H), 6.96 (d, J=9.0 Hz, 2H), 4.78 (d, J=2.4 Hz, 2H), 3.57 (t, J=2.4 Hz, 1H), 2.49 (s, 3H), 2.40 (d, J=4.8 Hz, 3H); LCMS: purity: 96%; MS (m/e): 443 (MH$^+$).

VI-69: 5-Fluoro-N2-{[4-methyl-3-((1-methylpiperidin-4-yl)aminosulfonyl)]phenyl}-N4-[4-(prop-2-ynyloxy)phenyl]-2,4-pyrimidinediamine 1H NMR (DMSO-d$_6$): δ 9.34 (s, 1H), 9.25 (s, 1H), 8.09-8.06 (m, 1H), 8.03 (d, J=3.9 Hz, 1H), 7.96-7.87 (m, 1H), 7.69 (d, J=9.0 Hz, 2H), 7.67-7.63 (m, 1H), 7.18 (d, J=8.4 Hz, 1H), 6.94 (d, J=9.0 Hz, 2H), 4.77 (d, J=2.1 Hz, 2H), 3.58-3.55 (m, 1H), 3.00-2.86 (m, 1H), 2.80-2.70 (m, 2H), 2.49 (s, 3H), 2.20 (s, 3H), 2.13-2.99 (m, 2H), 1.66-1.40 (m, 4H); LCMS: purity: 96%; MS (m/e): 526 (MH$^+$).

VI-70: N2-[3-Aminosulfonyl-4-(1-methylpiperazin-4-yl)phenyl]-5-fluoro-N4-[4-(prop-2-ynyloxy)phenyl]-2,4-pyrimidinediamine 1H NMR (DMSO-d$_6$): δ 9.38 (s, 1H), 9.25 (s, 1H), 8.09 (d, J=2.1 Hz, 1H), 8.04 (d, J=3.6 Hz, 1H), 7.93 (dd, J=2.4 and 8.7 Hz, 1H), 7.69 (d, J=8.7 Hz, 2H), 7.41 (d, J=8.7 Hz, 1H), 6.96 (d, J=9.0 Hz, 2H), 6.84 (s, 4H), 4.77 (d, J=2.1 Hz, 2H), 3.55 (t, J=2.1 Hz, 1H), 2.94-2.86 (m, 4H), 2.53-2.44 (m, 4H), 2.25 (s, 3H); LCMS: purity: 93%; MS (m/e): 512 (MH$^+$).

VI-71: N4-{4-[2-(Aminocarbonylamino)ethyl]phenyl}-N2-(3-aminosulfonyl-4-methylphenyl)-5-fluoro-2,4-pyrimidinediamine $^1$H NMR (DMSO-d$_6$): δ 9.37 (s, 1H), 9.27 (s, 1H), 8.12-8.09 (m, 1H), 8.07-8.03 (m, 1H), 7.92-7.87 (m, 1H), 7.72 (d, J=7.8 Hz, 2H), 7.21 (s, 2H), 7.19-7.11 (m, 3H), 5.91-5.85 (m, 1H), 5.40 (s, 2H), 3.21-3.16 (m, 2H), 2.65 (t, J=7.5 Hz, 2H), 2.48 (s, 3H); LCMS: purity: 87%; MS (m/e): 461 (MH$^+$).

VI-72: N4-{4-[2-(Aminocarbonylamino)ethyl]phenyl}-N2-(3-aminosulfonylphenyl)-5-fluoro-2,4-pyrimidinediamine $^1$H NMR (DMSO-d$_6$): δ 9.50 (s, 1H), 9.34 (s, 1H), 8.12-8.06 (m, 2H), 7.98-7.94 (m, 1H), 7.71 (d, J=8.1 Hz, 2H), 7.39-7.32 (m, 2H), 7.25 (s, 2H), 7.15 (d, =8.4 Hz, 2H), 5.89 (s, 1H), 3.24-3.16 (m, 2H), 2.65 (t, J=6.6 Hz, 2H); LCMS: purity: 92%; MS (m/e): 447 (MH$^+$).

VI-73: N2-(3-Aminosulfonyl-4-methylphenyl)-5-fluoro-N4-{4-[(prop-2-ynyloxy)carbonylaminomethyl]phenyl}-2,4-pyrimidinediamine $^1$H NMR (DMSO-d$_6$): δ 9.72 (bs, 2H), 8.13 (d, J=4.2 Hz, 1H), 8.00 (s, 1H), 7.93-7.86 (m, 1H), 7.82 (dd, J=2.1 and 8.1 Hz, 1H), 7.68 (d, J=8.4 Hz, 2H), 7.27 (s, 2H), 7.23-7.16 (m, 3H), 4.63 (d, J=2.1 Hz, 2H), 4.16 (d, J=5.7 Hz, 2H), 3.48 (t, J=2.4 Hz, 1H), 2.42 (s, 3H); LCMS: purity: 95%; MS (m/e): 486 (MH$^+$).

VI-74: N2-(3-Aminosulfonylphenyl)-5-fluoro-N4-{4-[(prop-2-ynyloxy)carbonylaminomethyl]phenyl}-2,4-pyrimidinediamine 1H NMR (DMSO-d$_6$): δ 9.73 (s, 1H), 9.66 (s, 1H), 8.15 (d, J=4.2 Hz, 1H), 8.02 (s, 1H), 7.95-7.87 (m, 2H), 7.69 (d, J=8.4 Hz, 2H), 7.41-7.36 (m, 2H), 7.29 (s, 2H), 7.21 (d, J=8.4 Hz, 2H), 4.63 (d, J=2.1 Hz, 2H), 4.16 (d, J=5.7 Hz, 2H), 3.48 (t, J=2.1 Hz, 2H); LCMS: purity: 97%; MS (m/e): 471 (MH$^+$).

IX-1: N2-(3-Aminosulfonyl-4-methylphenyl)-5-fluoro-N4-[1-(propyn-3-yl)indol-5-yl]-2,4-pyrimidinediamine $^1$H NMR (DMSO-d$_6$): δ 10.00 (s, 1H), 9.88 (s, 1H), 8.14 (d, J=4.5 Hz, 1H), 7.88-7.78 (m, 3H), 7.50 (d, J=8.7 Hz, 1H), 7.41 (d, J=2.7 Hz, 1H), 7.38 (dd, J=1.8 and 9.0 Hz, 1H), 7.29 (s, 2H), 7.09 (d, J=8.7 Hz, 1H), 6.43 (d, J=3.0 Hz, 1H), 5.09 (d, J=2.7 Hz, 2H), 3.42 (t, J=2.7 Hz, 1H), 2.51 (s, 3H); LCMS: purity: 98%; MS (m/e): 451 (MH$^+$).

IX-2: N2-(3-Aminosulfonylphenyl)-5-fluoro-N4-[1-(propyn-3-yl)indol-5-yl]-2,4-pyrimidinediamine $^1$H NMR (DMSO-d$_6$): δ 10.03 (bs, 2H), 8.18 (d, J=4.5 Hz, 1H), 7.97-7.92 (m, 1H), 7.87-7.82 (m, 2H), 7.51 (d, J=8.7 Hz, 1H), 7.42-7.36 (m, 3H), 7.32-7.26 (m, 3H), 6.44 (d, J=3.3 Hz, 1H), 5.10 (d, J=2.4 Hz, 2H), 3.43 (t, J=2.4 Hz, 2H); LCMS: purity: 97%; MS (m/e): 437 (MH$^+$).

VI-75: N2-(3-Aminosulfonylphenyl)-5-fluoro-N4-[4-(prop-2-ynylaminosulfonyl)phenyl]-2,4-pyrimidinediamine $^1$H NMR (DMSO-d$_6$): δ 9.84 (s, 1H), 9.70 (s, 1H), 8.23 (d, J=3.6 Hz, 1H), 8.14-8.06 (m, 3H), 8.02 (t, J=6.0 Hz, 1H), 7.97-7.92 (m, 1H), 7.72 (d, J=8.7 Hz, 2H), 7.47-7.37 (m, 2H), 7.30 (s, 2H), 3.67 (dd, J=2.4 and 5.7 Hz, 2H), 3.07 (t, J=2.4 Hz, 1H); LCMS: purity: 96%; MS (m/e): 478 (MH$^+$).

VI-76: N2-(3-Aminosulfonyl-4-methylphenyl)-5-fluoro-N4-[4-(prop-2-ynylaminosulfonyl)phenyl]-2,4-pyrimidinediamine 1H NMR (DMSO-d$_6$): δ 9.86 (s, 1H), 9.64 (s, 1H), 8.21 (d, J=3.9 Hz, 1H), 8.13-8.08 (m, 2H), 8.06-8.00 (m, 2H), 7.87 (dd, J=2.4 and 8.4 Hz, 1H), 7.70 (d, J=8.7 Hz, 2H), 7.28 (s, 2H), 7.23 (d, J=8.4 Hz, 1H), 3.67 (dd, J=2.4 and 6.0 Hz, 2H), 3.07 (t, J=2.7 Hz, 1H), 2.52 (s, 3H); LCMS: purity: 96%; MS (m/e): 492 (MH$^+$).

VI-77: N2-(4-Aminosulfonylphenyl)-5-fluoro-N4-[4-(prop-2-ynylaminosulfonyl) phenyl]-2,4-pyrimidinediamine 1H NMR (DMSO-d$_6$): δ 9.89 (s, 1H), 9.81 (s, 1H), 8.26 (d, J=3.3 Hz, 1H), 8.10-8.03 (m, 3H), 7.84 (d, J=9.0, 2H), 7.73 (d, J=9.0 Hz, 2H), 7.68 (d, J=9.0 Hz, 2H), 7.17 (s, 2H), 3.68 (dd, J=2.7 and 5.7 Hz, 2H), 3.06 (t, J=2.7 Hz, 1H); LCMS: purity: 96 MS (m/e): 477 (MH$^+$).

VI-78: 5-Fluoro-N2-[3-(prop-2-ynylaminosulfonyl)phenyl]-N4-[4-(prop-2-ynyloxy)phenyl]-2,4-pyrimidinediamine 1H NMR (DMSO-d$_6$): δ 9.76 (s, 1H), 9.66 (s, 1H), 8.14 (d, J=4.2 Hz, 1H), 8.07 (t, J=6.3 Hz, 1H), 7.99-7.94 (m, 2H), 7.64 (d, J=9.0 Hz, 2H), 7.45-7.32 (m, 2H), 6.96 (d, J=9.0 Hz, 2H), 4.78 (d, J=1.8 Hz, 2H), 3.67-3.63 (m, 2H), 3.62-3.56 (m, 1H); LCMS: purity: 96%; MS (m/e): 452 (MH$^+$).

IX-3: N2-(3-Aminosulfonyl-4-methylphenyl)-5-fluoro-N4-[1-(propyn-3-yl)indol-6-yl]-2,4-pyrimidinediamine 1H NMR (DMSO-d$_6$): δ 9.90 (s, 1H), 9.74 (s, 1H), 8.13 (d, J=4.2 Hz, 1H), 7.96 (s, 1H), 7.86-7.79 (m, 2H), 7.52 (d, J=8.1 Hz, 1H), 7.40-7.36 (m, 2H), 7.27 (s, 2H), 7.07 (d, J=8.1 Hz, 1H), 6.45 (d, J=3.0 Hz, 1H), 5.01 (d, J=2.4 Hz, 1H), 3.38 (t, J=2.4 Hz, 1H), 2.49 (s, 3H); LCMS: purity: 91%; MS (m/e): 451 (MH$^+$).

IX-4: N2-(3-Aminosulfonylphenyl)-5-fluoro-N4-[1-(propyn-3-yl)indol-6-yl]-2,4-pyrimidinediamine $^1$H NMR (DMSO-d$_6$): δ 9.70-9.58 (m, 2H), 8.12 (d, J=3.9 Hz, 1H), 8.02 (s, 1H), 7.95 (d, J=7.8 Hz, 1H), 7.85 (s, 1H), 7.52 (d, J=9.0 Hz, 1H), 7.42-7.25 (m, 6H), 6.44 (d, J=2.7 Hz, 1H), 5.03 (s, 2H), 3.38 (m, 1H); LCMS: purity: 92%; MS (m/e): 437 (MH$^+$).

VI-79: N2-(3-Aminosulfonyl-4-methylphenyl)-5-fluoro-N4-[3-(prop-2-ynylaminosulfonyl)phenyl]-2,4-pyrimidinediamine 1H NMR (DMSO-d$_6$): δ 9.92 (s, 1H), 9.64 (s, 1H), 8.32 (d, J=7.5 Hz, 1H), 8.19 (d, J=3.9 Hz, 1H), 8.14 (d, J=6.0 Hz, 1H), 8.06-8.03 (m, 1H), 8.00-7.97 (m, 1H), 7.81 (dd, J=2.1 and 8.4 Hz, 1H), 7.57-7.46 (m, 2H), 7.27 (s, 2H), 7.22 (d, J=8.7 Hz, 1H), 3.69 (dd, J=2.4 and 5.7 Hz, 2H), 3.06 (t, J=2.7 Hz, 1H), 2.44 (s, 3H); LCMS: purity: 96%; MS (m/e): 492 (MH$^+$).

VI-80: N2-(4-Aminosulfonylphenyl)-5-fluoro-N4-[3-(prop-2-ynylaminosulfonyl)phenyl]-2,4-pyrimidinediamine $^1$H NMR (DMSO-d$_6$): δ 9.77 (s, 1H), 9.63 (s, 1H), 8.33-8.27 (m, 1H), 8.21 (d, J=3.6 Hz, 1H), 8.15 (t, J=6.3 Hz, 1H), 7.99-7.96 (m, 1H), 7.79 (d, J=8.7 Hz, 2H), 7.64 (d, J=9.0 Hz, 2H), 7.59-7.48 (m, 2H), 7.12 (s, 2H), 3.71 (dd, J=2.4 and 5.7 Hz, 2H), 3.06 (t, J=2.4 Hz, 1H); LCMS: purity: 95%; MS (m/e): 477 (MH$^+$).

VI-81: N2-(3-Aminosulfonylphenyl)-5-fluoro-N4-[3-(prop-2-ynylaminosulfonyl)phenyl]-2,4-pyrimidinediamine $^1$H NMR (DMSO-d$_6$): δ 9.80 (s, 1H), 9.60 (s, 1H), 8.39-8.34 (m, 1H), 8.20 (d, J=3.6 Hz, 1H), 8.15 (t, J=6.0 Hz, 1H), 8.10-8.06 (m, 1H), 8.02-7.98 (m, 1H), 7.94-7.88 (m, 1H), 7.54 (t, J=8.1 Hz, 1H), 7.49-7.34 (m, 3H), 7.28 (s, 2H), 3.70 (dd, J=2.4 and 5.4 Hz, 2H), 3.07 (t, J=2.4 Hz, 1H); LCMS: purity: 98%; MS (m/e): 477 (MH$^+$).

III-84: N2-[4-(2-N,N-Diethylaminoethyl)aminosulfonylphenyl]-5-fluoro-N4-[4-(1-imidazolylmethyl)phenyl]-2,4-pyrimidinediamine $^1$H NMR (DMSO d$_6$, 300 MHz): δ 9.64 (s, 1H), 9.49 (s, 1H), 8.15 (d, 2H, J=3.6 Hz), 7.81 (d, 2H, J=8.4 Hz), 7.76 (s, 1H), 7.70 (d, 2H, J=8.1 Hz), 7.55 (d, 2H, J=8.4 Hz), 7.25 (d, 2H, J=8.4 Hz), 7.20 (s, 1H), 5.17 (s, 2H), 2.76 (t, 2H, J=7.2 Hz), 2.42 (m, 6H), 0.87 (t, 6H, J=7.2 Hz); LCMS (m/z): 539 (MH$^+$).

III-76: N2-(3-Aminosulfonylphenyl)-5-fluoro-N4-[4-(4-pyridinyl)phenethyl]-2,4-pyrimidinediamine $^1$H NMR (DMSO d$_6$, 300 MHz): δ 9.48 (s, 1H), 9.29 (s, 1H), 8.41 (d, 2H, J=5.1 Hz), 8.09 (d, 2H, J=2.4 Hz), 7.95 (m, 1H), 7.69 (d, 2H, J=8.4 Hz), 7.34 (d, 2H, J=5.1 Hz), 7.24 (d, 4H, J=6.0 Hz), 7.16 (d, 2H, J=8.4 Hz), 3.30 (d, 4H, J=1.2 Hz); LCMS (m/z): 465 (MH$^+$).

III-77: N2-(3-Aminosulfonyl-4-methylphenyl)-5-fluoro-N4-[4-(4-pyridinyl)phenethyl]-2,4-pyrimidinediamine $^1$H NMR (DMSO d$_6$, 300 MHz): δ 9.38 (s, 1H), 9.26 (s, 1H), 8.41 (d, 2H, J=4.5 Hz), 8.10 (s, 1H), 8.05 (d, 1H, J=3.3 Hz), 7.89 (d, 1H, J=8.1 Hz), 7.80 (d, 2H, J=7.8 Hz), 7.23 (m, 4H), 7.15 (m, 3H), 3.31 (d, 4H, J=1.2 Hz), 2.48 (s, 3H); LCMS (m/z): 479 (MH$^+$).

III-78: 5-Fluoro-N2-[3-N-(methyl)aminosulfonyl-4-methylphenyl]-N4-[4-(4-pyridinyl)phenethyl]-2,4-pyrimidinediamine $^1$H NMR (DMSO d$_6$, 300 MHz): δ 9.38 (s, 1H), 9.27 (s, 1H), 8.41 (d, 2H, J=5.1 Hz), 8.07 (d, 2H, J=3.9 Hz), 8.01 (s, 1H), 7.93 (m, 1H), 7.69 (d, 2H, J=8.4 Hz), 7.32 (q, 1H, J=4.8 Hz), 7.23 (d, 2H, J=5.4 Hz), 7.17 (t, 3H, J=8.1 Hz), 3.30 (s, 4H), 2.46 (s, 3H), 2.42 (d, 3H, J=4.5 Hz); LCMS (m/z): 493 (MH$^+$).

I-169: N2-(3-Aminosulfonylphenyl)-5-fluoro-N4-[4-(2-pyridinyl)-3-fluoromethyleneoxyphenyl]-2,4-pyrimidinediamine $^1$H NMR (DMSO d$_6$, 300 MHz): δ 9.56 (s, 1H), 9.40 (s, 1H), 8.56 (m, 1H), 8.11 (d, 1H, J=3.9 Hz), 8.08 (s, 1H), 7.95

(m, 1H), 7.88 (m, 1H), 7.84 (m, 2H), 7.52 (d, 1H, J=7.5 Hz), 7.48 (s, 1H), 7.35 (m, 2H), 7.26 (s, 2H), 7.16 (t, 1H, J=9.3 Hz), 5.23 (s, 2H); LCMS (m/z): 485 (MH$^+$).

I-170: 5-Fluoro-N2-[3-N-(methyl)aminosulfonyl-4-methylphenyl]-N4-[4-(2-pyridinyl)-3-methylmethyleneoxyphenyl]-2,4-pyrimidinediamine $^1$H NMR (DMSO d$_6$, 300 MHz): δ 9.32 (s, 1H), 9.15 (s, 1H), 8.57 (m, 1H), 8.03 (d, 1H, J=3.9 Hz), 7.94 (m, 2H), 7.83 (m, 1H), 7.52 (m, 3H), 7.33 (m, 2H), 7.14 (d, 1H, J=8.7 Hz), 6.93 (d, 1H, J=9.6 Hz), 5.18 (s, 2H), 2.45 (s, 3H), 2.41 (d, 3H, J=4.2 Hz), 2.25 (s, 3H); LCMS (m/z): 509 (MH$^+$).

I-171: N2-(3-Aminosulfonylphenyl)-5-fluoro-N4-[4-(2-pyridinyl)-3-chloromethyleneoxyphenyl]-2,4-pyrimidinediamine $^1$H NMR (DMSO d$_6$, 300 MHz): δ 9.53 (s, 1H), 9.37 (s, 1H), 8.57 (m, 1H), 8.10 (d, 1H, J=3.6 Hz), 8.03 (s, 1H), 7.96 (m, 1H), 7.85 (m, 2H), 7.72 (dd, 1H, J=2.4 and 9.0 Hz), 7.55 (d, 1H, J=8.1 Hz), 7.35 (m, 3H), 7.25 (s, 2H), 7.17 (d, 1H, J=9.3 Hz), 5.27 (s, 2H); LCMS (m/z): 501 (MH$^+$).

I-172: N2-(3-Aminosulfonyl-4-methylphenyl)-5-fluoro-N4-[4-(2-pyridinyl)-3-fluoromethyleneoxyphenyl]-2,4-pyrimidinediamine $^1$H NMR (DMSO d$_6$, 300 MHz): δ 9.44 (s, 1H), 9.37 (s, 1H), 8.56 (d, 1H, J=3.9 Hz), 8.09 (s, 1H), 8.07 (d, 1H, J=3.6 Hz), 7.90-7.81 (m, 3H), 7.51 (t, 2H, J=7.5 Hz), 7.34 (m, 1H), 7.24 (s, 1H), 7.15 (m, 2H), 5.23 (s, 2H), 2.49 (s, 3H); LCMS (m/z): 449 (MH$^+$).

I-173: 5-Fluoro-N2-[3-N-(methyl)aminosulfonyl-4-methylphenyl]-N4-[4-(2-pyridinyl)-3-fluoromethyleneoxyphenyl]-2,4-pyrimidinediamine $^1$H NMR (DMSO d$_6$, 300 MHz): δ 9.48 (s, 1H), 9.38 (s, 1H), 8.57 (m, 1H), 8.08 (d, 1H, J=3.0 Hz), 8.01 (s, 1H), 7.95 (dd, 1H, J=2.1 and 8.4 Hz), 7.83 (m, 2H), 7.51 (t, 2H, J=9.3 Hz), 7.35 (m, 2H), 7.19 (d, 1H, J=8.1 Hz), 7.14 (d, 1H, J=9.3 Hz), 5.23 (s, 2H), 2.46 (s, 3H), 2.41 (d, 1H, J=4.2 Hz), LCMS (m/z): 513 (MH$^+$).

I-174: N2-(3-Aminosulfonyl-4-methylphenyl)-5-fluoro-N4-[4-(2-pyridinyl)-3-chloromethyleneoxyphenyl]-2,4-pyrimidinediamine $^1$H NMR (DMSO d$_6$, 300 MHz): δ 9.42 (s, 1H), 9.34 (s, 1H), 8.57 (d, 1H, J=3.6 Hz), 8.07 (m, 1H), 7.86 (m, 3H), 7.73 (d, 1H, J=9.0 Hz), 7.55 (d, 1H, J=7.5 Hz), 7.34 (t, 1H, J=5.1 Hz), 7.24 (s, 2H), 7.16 (d, 2H, J=8.7 Hz), 5.26 (s, 2H), 2.49 (s, 3H); LCMS (m/z): 515 (MH$^+$).

IX-54: 5-Fluoro-N2-[3-N-(methyl)aminosulfonyl-4-methylphenyl]-N4-[4-(2-pyridinyl)-3-chloromethyleneoxyphenyl]-2,4-pyrimidinediamine $^1$H NMR (DMSO d$_6$, 300 MHz): δ 9.43 (s, 1H), 9.35 (s, 1H), 8.56 (m, 1H), 8.09 (d, 1H, J=3.0 Hz), 7.96 (m, 2H), 7.85 (m, 2H), 7.71 (dd, 1H, J=3.0 and 8.8 Hz), 7.55 (d, 1H, J=7.8 Hz), 7.34 (t, 2H, J=5.1 Hz), 7.17 (t, 2H, J=9.0 Hz), 5.26 (s, 2H), 2.45 (s, 3H), 2.41 (d, 1H, J=4.8 Hz), LCMS (m/z): 529 (MH$^+$).

II-11: N2-(3-Aminosulfonylphenyl)-5-fluoro-N4-[4-(3-pyridyloxy)phenyl]-2,4-pyrimidinediamine $^1$H NMR (DMSO d$_6$, 300 MHz): δ 9.57 (s, 1H), 9.52 (s, 1H), 8.43 (s, 1H), 8.39 (t, 1H, J=2.1 Hz), 8.18 (t, 2H, J=3.3 Hz), 7.99 (d, 1H, J=7.5 Hz), 7.93 (d, 2H, J=8.7 Hz), 7.44 (m, 4H), 7.32 (s, 2H), 7.13 (d, 2H, J=9.0 Hz); LCMS (m/z): 453 (MH$^+$).

III-85: 5-Fluoro-N2-[3-(N-methylaminosulfony)-4-methylphenyl]-N4-[4-(1-imidazolylmethyl)phenyl]-2,4-pyrimidinediamine hydrochloride $^1$H NMR (DMSO d$_6$, 300 MHz): δ 9.79 (s, 1H), 9.75 (s, 1H), 9.30 (s, 1H), 8.18 (d, 1H, J=3.0 Hz), 7.94 (s, 1H), 7.86 (d, 1H, J=8.1 Hz), 7.80 (d, 3H, J=8.1 Hz), 7.69 (s, 1H), 7.38 (d, 3H, J=8.4 Hz), 7.20 (d, 1H, J=8.4 Hz), 5.40 (s, 2H), 2.48 (s, 3H), 2.39 (d, 3H, J=4.2 Hz); LCMS (m/z): 468 (MH$^+$).

III-86: 5-Fluoro-N2-[3-(N-methylaminosulfony)-4-methylphenyl]-N4-[4-(1-imidazolylmethyl)phenyl]-2,4-pyrimidinediamine dihydrochloride $^1$H NMR (DMSO d$_6$, 300 MHz): δ 9.85 (s, 1H), 9.81 (s, 1H), 9.31 (s, 1H), 8.19 (d, 1H, J=4.2 Hz), 7.93 (s, 1H), 7.84 (d, 1H, J=8.1 Hz), 7.80 (d, 3H, J=8.1 Hz), 7.69 (s, 1H), 7.38 (d, 3H, J=8.4 Hz), 7.20 (d, 1H, J=8.4 Hz), 5.41 (s, 2H), 2.48 (s, 3H), 2.39 (d, 3H, J=4.2 Hz); LCMS (m/z): 468 (MH$^+$).

II-12: N2-(3-Aminosulfonyl-4-methylphenyl)-5-fluoro-N4-[4-(3-pyridyloxy)phenyl]-2,4-pyrimidinediamine $^1$H NMR (DMSO d$_6$, 300 MHz): δ 9.42 (s, 1H), 9.40 (s, 1H), 8.32 (m, 2H), 8.08 (d, 2H, J=3.0 Hz), 7.86 m, 2H), 7.39 (m, 2H), 7.23 (s, 2H), 7.09 (m, 4H), 2.36 (s, 3H), 7.13; LCMS (m/z): 467 (MH$^+$).

II-13: 5-Fluoro-N2-[3-N-(methylaminosulfonyl)-4-methylphenyl]-N4-[4-(3-pyridyloxy)phenyl]-2,4-pyrimidinediamine $^1$H NMR (DMSO d$_6$, 300 MHz): δ 9.43 (s, 1H), 9.40 (s, 1H), 8.35 (s, 1H), 8.32 (t, 1H, J=2.4 Hz), 8.09 (d, 1H, J=3.6 Hz), 8.00 (s, 1H), 7.93 (dd, 1H, J=1.8 and 8.2 Hz), 7.84 (d, 2H, J=8.7 Hz), 7.39 (m, 2H), 7.33 (q, 1H, J=4.2 Hz), 7.18 (d, 1H, J=8.4 Hz), 7.06 (d, 2H, J=8.7 Hz), 2.44 (s, 3H), 2.40 (d, 3H, J=4.5 Hz), LCMS (m/z): 481 (MH$^+$).

III-79: N2-(4-Aminosulfonylphenyl)-5-fluoro-N4-[4-(4-pyridinyl)phenethyl]-2,4-pyrimidinediamine $^1$H NMR (DMSO d$_6$, 300 MHz): δ 9.56 (s, 1H), 9.37 (s, 1H), 8.42 (d, 2H, J=4.2 Hz), 8.11 (d, 1H, J=3.6 Hz), 7.79 (d, 2H, J=8.4 Hz), 7.61 (t, 4H, J=9.3 Hz), 7.24 (d, 2H, J=5.1 Hz), 7.19 (d, 4H, J=8.1 Hz), 7.15 (s, 2H), 3.92 (s, 4H); LCMS (m/z): 465 (MH$^+$).

I-175: N2-(4-Aminosulfonylphenyl)-5-fluoro-N4-[4-(2-pyridinyl)-3-chloromethyleneoxyphenyl]-2,4-pyrimidinediamine $^1$H NMR (DMSO d$_6$, 300 MHz): δ 9.71 (s, 1H), 9.51 (s, 1H), 8.64 (d, 1H, J=4.1 Hz), 8.20 (d, 1H, J=3.6 Hz), 7.92 (m, 2H), 7.85 (d, 2H, J=8.7 Hz), 7.71 (d, 2H, J=9.3 Hz), 7.63 (d, 2H, J=8.7 Hz), 7.41 (m, 1H), 7.26 (d, 1H, J=9.3 Hz), 7.19 (s, 2H), 5.33 (s, 2H); LCMS (m/z): 501 (MH⁺).

I-176: N2-(4-Aminosulfonylphenyl)-5-fluoro-N4-[4-(2-pyridinyl)-3-methylmethyleneoxyphenyl]-2,4-pyrimidinediamine ¹H NMR (DMSO d₆, 300 MHz): δ 9.63 (s, 1H), 9.33 (s, 1H), 8.63 (m, 1H), 8.15 (d, 1H, J=3.9 Hz), 7.91 (t, 1H, J=7.8 Hz), 7.85 (d, 2H, J=8.7 Hz), 7.66 (d, 2H, J=8.4 Hz), 7.60 (m, 2H), 7.42 (m, 2H), 7.19 (s, 2H), 7.03 (d, 1H, J=8.4 Hz), 5.26 (s, 2H), 2.34 (s, 3H); LCMS (m/z): 481 (MH⁺).

II-14: N2-(4-Aminosulfonylphenyl)-5-fluoro-N4-[4-(3-pyridyloxy)phenyl]-2,4-pyrimidinediamine ¹H NMR (DMSO d₆, 300 MHz): δ 9.67 (s, 1H), 9.58 (s, 1H), 8.41 (d, 2H, J=12.3 Hz), 8.21 (d, 1H, J=3.3 Hz), 7.86 (d, 4H, J=6.9 Hz), 7.68 (d, 2H, J=9.0 Hz), 7.48 (s, 2H), 7.17 (m, 4H); LCMS (m/z): 453 (MH⁺).

III-87: N2-(3-Aminosulfonylphenyl)-5-fluoro-N4-[4-(1-imidazolyl)phenethyl]-2,4-pyrimidinediamine ¹H NMR (DMSO d₆, 300 MHz): δ 9.51 (s, 1H), 9.32 (s, 1H), 8.09 (d, 2H, J=3.6 Hz), 7.94 (s, 1H), 7.71 (d, 2H, J=8.4 Hz), 7.48 (s, 1H), 7.35 (m, 2H), 7.26 (s, 2H), 7.14 (s, 1H), 7.10 (d, 2H, J=8.4 Hz), 6.83 (s, 1H), 4.26 (t, 2H, J=6.9 Hz), 3.06 (t, 2H, J=7.2 Hz); LCMS (m/z): 454 (MH⁺).

III-88: N2-(3-Aminosulfonyl-4-methylphenyl)-5-fluoro-N4-[4-(1-imidazolyl)phenethyl]-2,4-pyrimidinediamine ¹H NMR (DMSO d₆, 300 MHz): δ 9.47 (s, 1H), 9.35 (s, 1H), 8.17 (s, 1H), 8.13 (d, 1H, J=3.0 Hz), 7.95 (dd, 1H, J=2.1 and 8.1 Hz), 7.78 (d, 2H, J=8.1 Hz), 7.54 (s, 1H), 7.29 (s, 2H), 7.24 (d, 1H, J=8.1 Hz), 7.20 (s, 2H), 7.16 (d, 2H, J=8.4 Hz), 6.90 (s, 1H), 4.26 (t, 2H, J=6.9 Hz), 3.06 (t, 2H, J=7.2 Hz), 2.53 (s, 3H); LCMS (m/z): 468 (MH⁺).

III-91: N2-(3-Aminosulfonyl-4-methylphenyl)-5-fluoro-N4-[4-(2-methyl-1-imidazolylmethyl)phenyl]-2,4-pyrimidinediamine ¹H NMR (DMSO d₆, 300 MHz): δ 9.39 (s, 2H), 8.08 (d, 1H, J=3.0 Hz), 7.89 (s, 1H), 7.87 (dd, 1H, J=2.1 and 8.2 Hz), 7.78 (d, 2H, J=8.4 Hz), 7.24 (s, 1H), 7.15 (s, 1H), 7.11 (d, 2H, J=8.4 Hz), 6.79 (s, 1H), 5.10 (s, 2H), 2.49 (s, 3H), 2.26 (s, 3H); LCMS (m/z): 468 (MH⁺).

III-89: 5-Fluoro-N2-[3-(N-methylaminosulfony)-4-methylphenyl]-N4-[4-(1-imidazolyl)phenethyl]-2,4-pyrimidinediamine ¹H NMR (DMSO d₆, 300 MHz): δ 9.40 (s, 1H), 9.29 (s, 1H), 8.08 (d, 1H, J=3.9 Hz), 8.02 (d, 1H, J=2.1 Hz), 7.95 (dd, 1H, J=1.8 and 8.4 Hz), 7.71 (d, 2H, J=8.4 Hz), 7.48 (s, 1H), 7.33 (q, 1H, J=4.5 Hz), 7.20 (d, 1H, J=8.4 Hz), 7.14 (s, 1H), 7.10 (d, 2H, J=8.4 Hz), 6.84 (s, 1H), 4.19 (t, 2H, J=7.2 Hz), 3.00 (t, 2H, J=7.2 Hz), 2.46 (s, 3H), 2.42 (d, 3H, J=4.8 Hz), LCMS (m/z): 482 (MH⁺).

I-177: N2-(4-Aminosulfonylphenyl)-5-fluoro-N4-[4-(2-pyridinyl)-3-fluoromethyleneoxyphenyl]-2,4-pyrimidinediamine ¹H NMR (DMSO d₆, 300 MHz): δ 9.72 (s, 1H), 9.54 (s, 1H), 8.64 (d, 1H, J=4.8 Hz), 8.21 (d, 1H, J=3.6 Hz), 7.92 (m, 2H), 7.88 (d, 2H, J=8.4 Hz), 7.70 (d, 2H, J=8.7 Hz), 7.60 (d, 1H, J=8.1 Hz), 7.50 (d, 1H, J=8.7 Hz), 7.41 (dd, 1H, J=5.1 and 6.7 Hz), 7.26 (t, 1H, J=9.3 Hz), 7.21 (s, 2H), 5.31 (s, 2H); LCMS (m/z): 485 (MH⁺).

III-92: N2-(4-Aminosulfonylphenyl)-5-fluoro-N4-[4-(2-methyl-1-imidazolylmethyl)phenyl]-2,4-pyrimidinediamine ¹H NMR (DMSO d₆, 300 MHz): δ 9.60 (s, 1H), 9.49 (s, 1H), 8.13 (t, 2H, J=3.6 Hz), 7.77 (d, 1H, J=9.0 Hz), 7.70 (d, 2H, J=8.4 Hz), 7.55 (d, 2H, J=8.7 Hz), 7.27 (s, 2H), 7.15 (s, 1H), 7.17 (s, 1H), 7.12 (d, 2H, J=8.4 Hz), 6.79 (s, 1H), 5.13 (s, 2H), 2.24 (s, 3H); LCMS (m/z): 454 (MH⁺).

III-99: N2-(4-Aminosulfonylphenyl)-5-fluoro-N4-{4-[1-(1,2,4-triazolyl)methyl]phenyl}-2,4-pyrimidinediamine ¹H NMR (DMSO d₆, 300 MHz): δ 9.60 (s, 1H), 9.49 (s, 1H), 8.64 (s, 1H), 8.15 (d, 1H, J=3.6 Hz), 7.98 (s, 1H), 7.80 (d, 2H, J=8.7 Hz), 7.74 (d, 2H, J=8.4 Hz), 7.62 (d, 2H, J=8.7 Hz), 7.27 (d, 2H, J=8.7 Hz), 7.14 (s, 2H), 5.39 (s, 2H); LCMS (m/z): 441 (MH⁺).

III-95: N2-(3-Aminosulfonyl-4-methylphenyl)-5-fluoro-N4-{4-[1-(1,2,3-triazolyl)methyl]phenyl}-2,4-pyrimidinediamine ¹H NMR (DMSO d₆, 300 MHz): δ 9.41 (s, 1H), 9.40 (s, 1H), 8.17 (s, 1H), 8.09 (d, 2H, J=3.6 Hz), 7.86 (dd, 1H, J=2.1 and 8.2 Hz), 7.79 (d, 2H, J=8.4 Hz), 7.73 (s, 1H), 7.26 (d, 2H, J=8.7 Hz), 7.24 (s, 1H), 7.12 (d, 1H, J=8.1 Hz), 5.74 (s, 2H), 2.48 (s, 3H); LCMS (m/z): 455 (MH⁺).

III-96: N2-4-Aminosulfonylphenyl-5-fluoro-N4-{4-[1-(1,2,3-triazolyl)methyl]phenyl}-2,4-pyrimidinediamine ¹H NMR (DMSO d₆, 300 MHz): δ 9.60 (s, 1H), 9.51 (s, 1H), 8.17 (d, 1H, J=0.9 Hz), 8.15 (d, 1H, J=3.6 Hz), 7.78 (t, 3H, J=5.4 Hz), 7.74 (s, 2H), 7.61 (d, 2H, J=8.7 Hz), 7.29 (d, 2H, J=8.4 Hz), 7.15 (s, 2H), 5.59 (s, 2H); LCMS (m/z): 441 (MH⁺).

III-100: N2-(3-Aminosulfonylphenyl)-5-fluoro-N4-{4-[1-(1,2,4-triazolyl)methyl]phenyl}-2,4-pyrimidinediamine ¹H NMR (DMSO d₆, 300 MHz): δ 9.50 (s, 1H), 9.44 (s, 1H), 8.64 (s, 1H), 8.63 (s, 1H), 8.11 (d, 1H, J=3.9 Hz), 8.09 (s, 1H), 7.97 (s, 1H), 7.93 (bs s, 1H), 7.78 (d, 2H, J=8.4 Hz), 7.33 (d, 2H, J=4.8 Hz), 7.26 (d, 4H, J=7.5 Hz), 5.37 (s, 2H); LCMS (m/z): 441 (MH⁺).

III-101: N2-(3-Aminosulfonyl-4-methylphenyl)-5-fluoro-N4-{4-[1-(1,2,4-triazolyl)methyl]phenyl}-2,4-pyrimidinediamine ¹H NMR (DMSO d₆, 300 MHz): δ 9.46 (s, 2H), 8.70 (s, 1H), 8.15 (d, 1H, J=3.3 Hz), 8.04 (s, 1H), 7.94 (dd, 1H, J=2.4 and 8.4 Hz), 7.84 (d, 2H, J=8.4 Hz), 7.30 (m, 3H), 7.19 (s, 1H), 7.17 (s, 1H), 5.44 (s, 2H), 2.55 (s, 3H); LCMS (m/z): 455 (MH⁺).

III-102: 5-Fluoro-N2-[3-(N-methylaminosulfony)-4-methylphenyl]-N4-{4-[1-(1,2,4-triazolyl)methyl]phenyl}-2,4-pyrimidinediamine ¹H NMR (DMSO d₆, 300 MHz): δ 9.42 (s, 1H), 9.40 (s, 1H), 8.64 (s, 1H), 8.09 (d, 1H, J=3.6 Hz), 8.01 (d, 1H, J=1.8 Hz), 7.97 (s, 1H), 7.93 (dd, 1H, J=2.4 and 8.1 Hz), 7.77 (d, 2H, J=8.7 Hz), 7.34 (q, 1H, J=4.8 Hz), 7.24 (d, 2H, J=8.4 Hz), 7.15 (d, 1H, J=8.4 Hz), 5.38 (s, 2H), 2.46 (s, 3H), 2.41 (d, 3H, J=4.8 Hz), LCMS (m/z): 469 (MH⁺).

VII-60: N2-(3-Aminosulfonylphenyl)-5-fluoro-N4-[4-(1-methylsulfonyl)indolin-5-yl]-2,4-pyrimidinediamine ¹H NMR (DMSO d₆, 300 MHz): δ 9.47 (s, 1H), 9.36 (s, 1H), 8.09 (d, 1H, J=3.3 Hz), 8.06 (s, 1H), 7.95 (d, 1H, J=7.8 Hz), 7.73 (s, 1H), 7.59 (d, 1H, J=8.4 Hz), 7.35 (m, 2H), 7.25 (s, 2H), 7.20 (d, 1H, J=8.4 Hz), 3.94 (t, 2H, J=8.7 Hz), 3.11 (t, 2H, J=8.1 Hz), 2.97 (s, 3H); LCMS (m/z): 479 (MH⁺).

VII-61: N2-(3-Aminosulfonyl-4-methylphenyl)-5-fluoro-N4-[4-(1-methylsulfonyl)indolin-5-yl]-2,4-pyrimidinediamine ¹H NMR (DMSO d₆, 300 MHz): δ 9.35 (s, 1H), 9.31 (s, 1H), 8.06 (m, 2H), 7.87 (dd, 1H, J=2.1 and 8.1 Hz), 7.72 (s, 1H), 7.58 (d, 1H, J=10.5 Hz), 7.18 (m, 4H), 3.94 (t, 2H, J=8.7 Hz), 3.10 (t, 2H, J=8.4 Hz), 2.96 (s, 3H), 2.48 (s, 3H); LCMS (m/z): 493 (MH⁺).

VII-62: 5-Fluoro-N2-[3-(N-methylaminosulfony)-4-methylphenyl]-N4-[4-(1-methylsulfonyl)indolin-5-yl]-2,4-pyrimidinediamine ¹H NMR (DMSO d₆, 300 MHz): δ 9.36 (s, 1H), 9.33 (s, 1H), 8.07 (d, 1H, J=3.6 Hz), 7.99 (d, 1H, J=2.1 Hz), 7.93 (dd, 1H, J=2.4 and 8.2 Hz), 7.71 (s, 1H), 7.57 (dd, 1H, J=2.1 and 8.7 Hz), 7.33 (q, 1H, J=4.8 Hz), 7.19 (d, 2H, J=8.4 Hz), 3.94 (t, 2H, J=8.7 Hz), 3.10 (t, 2H, J=8.4 Hz), 2.96 (s, 3H), 2.46 (s, 3H), 2.41 (d, 3H, J=4.8 Hz); LCMS (m/z): 507 (MH⁺).

III-93: 5-Fluoro-N2-[3-(N-methylaminosulfony)-4-methylphenyl]-N4-[4-(2-methyl-1-imidazolylmethyl)phenyl]-2,4-pyrimidinediamine ¹H NMR (DMSO d₆, 300 MHz): δ 9.39 (s, 2H), 8.09 (d, 1H, J=3.3 Hz), 8.00 (d, 1H, J=2.1 Hz), 7.92 (dd, 1H, J=2.4 and 8.1 Hz), 7.33 (q, 1H, J=5.1 Hz), 7.12 (m, 4H), 6.75 (s, 1H), 5.09 (s, 2H), 2.46 (s, 3H), 2.41 (d, 3H, J=4.5 Hz), 2.24 (s, 3H); LCMS (m/z): 482 (MH⁺).

III-97: N2-(3-Aminosulfonylphenyl)-5-fluoro-N4-{4-[1-(1,2,3-triazolyl)methyl]phenyl}-2,4-pyrimidinediamine ¹H NMR (DMSO d₆, 300 MHz): δ 9.58 (s, 1H), 9.52 (s, 1H), 8.24 (s, 1H), 8.18 (d, 1H, J=3.6 Hz), 8.17 (s, 1H), 7.98 (m, 1H), 7.86 (d, 2H, J=8.7 Hz), 7.80 (s, 1H), 7.40 (d, 2H, J=4.8 Hz), 7.33 (m, 4H), 5.64 (s, 2H); LCMS (m/z): 441 (MH⁺).

III-98: 5-Fluoro-N2-[3-(N-methylaminosulfony)-4-methylphenyl]-N4-{4-[1-(1,2,3-triazolyl)methyl]phenyl}-2,4-pyrimidinediamine ¹H NMR (DMSO d₆, 300 MHz): δ 9.43 (s, 1H), 9.41 (s, 1H), 8.17 (d, 1H, J=0.9 Hz), 8.09 (d, 1H, J=3.9 Hz), 8.00 (d, 1H, J=2.1 Hz), 7.92 (dd, 1H, J=2.4 and 8.1 Hz), 7.76 (t, 3H, J=8.7 Hz), 7.33 (q, 1H, J=5.1 Hz), 7.26 (d, 2H, J=9.0 Hz), 7.14 (d, 1H, J=8.4 Hz), 5.58 (s, 2H), 2.46 (s, 3H), 2.41 (d, 3H, J=4.8 Hz); LCMS (m/z): 469 (MH⁺).

III-90: N2-(4-Aminosulfonylphenyl)-5-fluoro-N4-[4-(1-imidazolyl)phenethyl]-2,4-pyrimidinediamine ¹H NMR (DMSO d₆, 300 MHz): δ 9.61 (s, 1H), 9.38 (s, 1H), 8.13 (d, 1H, J=3.9 Hz), 7.79 (d, 2H, J=8.7 Hz), 7.62 (t, 4H, J=9.0 Hz), 7.51 (s, 1H), 7.23 (s, 1H), 7.15 (s, 1H), 7.12 (d, 2H, J=8.4 Hz), 6.85 (s, 1H), 4.21 (t, 2H, J=6.9 Hz), 3.03 (t, 2H, J=6.9 Hz); LCMS (m/z): 454 (MH⁺).

VII-63: N2-(4-Aminosulfonylphenyl)-5-fluoro-N4-[4-(1-methylsulfonyl)indolin-5-yl]-2,4-pyrimidinediamine ¹H NMR (DMSO d₆, 300 MHz): δ 9.57 (s, 1H), 9.41 (s, 1H), 8.11 (d, 1H, J=3.6 Hz), 7.78 (d, 2H, J=8.4 Hz), 7.68 (s, 1H), 7.60 (d, 1H, J=8.4 Hz), 7.50 (d, 1H, J=8.4 Hz), 7.22 (d, 1H, J=9.0 Hz), 7.13 (s, 2H), 3.95 (t, 2H, J=5.4 Hz), 3.12 (t, 2H, J=8.1 Hz), 2.97 (s, 3H); LCMS (m/z): 479 (MH⁺).

IV-5: N2-(3-Aminosulfonylphenyl)-5-fluoro-N4-[4-(1,3-oxazol-5-yl)phenyl]-2,4-pyrimidinediamine ¹H NMR (DMSO d₆, 300 MHz): δ 9.58 (s, 1H), 9.57 (s, 1H), 8.39 (s, 1H), 8.16 (d, 1H, J=3.6 Hz), 8.13 (s, 1H), 7.97 (d, 2H, J=8.7 Hz), 7.93 (s, 1H), 7.67 (d, 2H, J=8.4 Hz), 7.59 (s, 1H), 7.39 (m, 2H), 7.27 (s, 2H); LCMS (m/z): 427 (MH⁺).

IV-6: N2-(3-Aminosulfonyl-4-methylphenyl)-5-fluoro-N4-[4-(1,3-oxazol-5-yl)phenyl]-2,4-pyrimidinediamine ¹H NMR (DMSO d₆, 300 MHz): δ 9.58 (s, 1H), 9.52 (s, 1H), 8.45 (s, 1H), 8.19 (t, 2H, J=3.9 Hz), 8.04 (d, 2H, J=8.4 Hz), 7.95 (dd, 1H, J=2.1 and 8.4 Hz), 7.72 (d, 2H, J=8.7 Hz), 7.65 (s, 1H), 7.30 (s, 2H), 7.27 (d, 1H, J=8.4 Hz), 2.57 (s, 3H); LCMS (m/z): 441 (MH⁺).

IV-1: N2-(3-Aminosulfonylphenyl)-5-fluoro-N4-[3-(1,3-oxazol-5-yl)phenyl]-2,4-pyrimidinediamine ¹H NMR (DMSO d₆, 300 MHz): δ 9.61 (s, 1H), 9.59 (s, 1H), 8.47 (s, 1H), 8.22 (d, 1H, J=3.0 Hz), 8.10 (d, 2H, J=9.9 Hz), 8.04 (d, 1H, J=7.8 Hz), 7.97 (m, 1H), 7.70 (s, 1H), 7.50 (d, 2H, J=4.8 Hz), 7.31 (m, 4H); LCMS (m/z): 427 (MH⁺).

IV-2: N2-(3-Aminosulfonyl-4-methylphenyl)-5-fluoro-N4-[3-(1,3-oxazol-5-yl)phenyl]-2,4-pyrimidinediamine ¹H NMR (DMSO d₆, 300 MHz): δ 9.55 (s, 1H), 9.50 (s, 1H), 8.46 (s, 1H), 8.18 (d, 1H, J=3.6 Hz), 8.12 (d, 1H, J=2.1 Hz), 8.09 (s, 1H), 7.95 (m, 2H), 7.69 (s, 1H), 7.49 (d, 2H, J=5.1 Hz), 7.29 (s, 2H), 7.06 (d, 1H, J=8.1 Hz), 2.52 (s, 3H); LCMS (m/z): 441 (MH⁺).

IV-7: 5-Fluoro-N2-[3-(N-methylaminosulfony)-4-methylphenyl]-N4-[4-(1,3-oxazol-5-yl)phenyl]-2,4-pyrimidinediamine ¹H NMR (DMSO d₆, 300 MHz): δ 9.54 (s, 1H), 9.48 (s, 1H), 8.39 (s, 1H), 8.13 (d, 1H, J=3.6 Hz), 8.06 (d, 1H, J=2.4

Hz), 7.97 (d, 2H, J=8.7 Hz), 7.92 (d, 1H, J=2.4 Hz), 7.66 (d, 2H, J=8.7 Hz), 7.59 (s, 1H), 7.33 (q, 1H, J=4.8 Hz), 7.24 (d, 1H, J=8.4 Hz), 2.47 (s, 3H), 2.42 (d, 3H, J=4.8 Hz), LCMS (m/z): 455 (MH+).

IV-8: N2-(4-Aminosulfonylphenyl)-5-fluoro-N4-[4-(1,3-oxazol-5-yl)phenyl]-2,4-pyrimidinediamine $^1$H NMR (DMSO d$_6$, 300 MHz): δ 9.65 (s, 1H), 9.59 (s, 1H), 8.41 (s, 1H), 8.18 (d, 1H, J=3.6 Hz), 7.98 (s, 1H), 7.81 (m, 4H), 7.64 (s, 1H), 7.55 (d, 2H, J=9.0 Hz), 7.47 (m, 1H); LCMS (m/z): 427 (MH+).

IV-3: N2-(4-Aminosulfonylphenyl)-5-fluoro-N4-[3-(1,3-oxazol-5-yl)phenyl]-2,4-pyrimidinediamine $^1$H NMR (DMSO d$_6$, 300 MHz): δ 9.68 (s, 1H), 9.62 (s, 1H), 8.40 (s, 1H), 8.19 (d, 1H, J=3.6 Hz), 7.93 (d, 2H, J=8.7 Hz), 7.83 (d, 2H, J=8.7 Hz), 7.66 (m, 5H), 7.13 (s, 2H); LCMS (m/z): 427 (MH+).

IV-4: 5-Fluoro-N2-[3-(N-methylaminosulfony)-4-methylphenyl]-N4-[3-(1,3-oxazol-5-yl)phenyl]-2,4-pyrimidinediamine $^1$H NMR (DMSO d$_6$, 300 MHz): δ 9.51 (s, 1H), 9.45 (s, 1H), 8.39 (s, 1H), 8.14 (d, 1H, J=3.6 Hz), 8.02 (s, 1H), 7.97-7.85 (m, 3H), 7.61 (s, 1H), 7.43 (d, 2H, J=5.1 Hz), 7.33 (q, 1H, J=4.8 Hz), 7.03 (d, 1H, J=8.1 Hz), 2.41 (d, 6H, J=4.8 Hz); LCMS (m/z): 455 (MH+).

II-15: N2-[3,5-bis(Aminosulfonyl)phenyl]-5-fluoro-N4-[4-(3-pyridyloxy)phenyl]-2,4-pyrimidinediamine $^1$H NMR (DMSO d$_6$, 300 MHz): δ 9.84 (s, 1H), 9.52 (s, 1H), 8.40 (d, 1H, J=1.5 Hz), 8.34 (m, 2H), 8.16 (t, 2H, J=3.6 Hz), 7.93 (d, 2H, J=8.7 Hz), 7.79 (t, 1H, J=1.5 Hz), 7.50 (s, 4H), 7.39 (m, 2H), 7.06 (d, 2H, J=9.0 Hz); LCMS (m/z): 532 (MH+).

III-94: N2-(3-Aminosulfonylphenyl)-5-fluoro-N4-[4-(2-methyl-1-imidazolylmethyl)phenyl]-2,4-pyrimidinediamine $^1$H NMR (DMSO d$_6$, 300 MHz): δ 9.48 (s, 1H), 9.41 (s, 1H), 8.10 (t, 2H, J=3.9 Hz), 7.92 (m, 1H), 7.78 (d, 2H, J=8.4 Hz), 7.33 (d, 2H, J=4.8 Hz), 7.25 (s, 2H), 7.11 (d, 3H, J=8.4 Hz), 6.76 (s, 1H), 5.09 (s, 2H), 2.24 (s, 3H); LCMS (m/z): 454 (MH+).

I-192: N2-(3-Aminosulfonylphenyl)-5-fluoro-N4-[4-(3-pyridinyl)-methylenethiophenyl]-2,4-pyrimidinediamine $^1$H NMR (DMSO d$_6$, 300 MHz): δ 9.60 (s, 1H), 9.49 (s, 1H), 8.48 (s, 1H), 8.45 (d, 1H, J=4.8 Hz), 8.19 (d, 1H, J=3.9 Hz), 8.16 (s, 1H), 7.98 (m, 1H), 7.86 (d, 2H, J=9.0 Hz), 7.74 (d, 1H, J=7.8 Hz), 7.42 (m, 2H), 7.34 (m, 4H), 7.18 (s, 2H), 4.26 (s, 2H); LCMS (m/z): 483 (MH+).

VI-94: N2-(4-aminosulfonyl)phenyl-5-fluoro-N4-(4-thiomethylcarbonyl)phenyl-2,4-pyrimidinediamine $^1$H NMR (DMSO-d$_6$): δ 2.81 (t, J=7.5 Hz, 1H), 3.74 (d, J=7.5 Hz, 2H), 7.11 (br, 2H), 7.30 (d, J=8.1 Hz, 2H), 7.62 (d, J=8.4 Hz, 2H), 7.68 (d, J=8.1 Hz, 2H), 7.80 (d, J=9.3 Hz, 2H), 8.13 (d, J=3.6 Hz, 1H), 9.42 (br, 1H), 9.59 (br, 1H); $^{19}$F NMR (282 MHz, DMSO-d$_6$): δ −201.61; LCMS: purity: 79.54%; MS (m/e): 406.05 (M-28).

VI-95: N2-(3-aminosulfonyl-4-methyl)phenyl-5-fluoro-N4-(4-thiomethylcarbonyl)phenyl-2,4-pyrimidinediamine $^1$H NMR (DMSO-d$_6$): δ 2.50 (s, 3H), 2.82 (t, J=7.5 Hz, 1H), 3.72 (d, J=7.2 Hz, 2H), 7.18 (d, J=8.7 Hz, 1H), 7.23 (br, 2H), 7.28 (d, J=8.4 Hz, 2H), 7.73 (d, J=8.7 Hz, 2H), 7.90 (dd, J=8.4 Hz, 1H), 8.07 (d, J=3.9 Hz, 1H), 8.11 (d, J=2.1 Hz, 1H), 9.33 (br, 1H), 9.40 (br, 1H); $^{19}$F NMR (282 MHz, DMSO-d$_6$): δ −202.55; LCMS: purity: 98.63%; MS (m/e): 420.06 (M-28).

III-41: N2-(4-aminosulfonyl)phenyl-N4-(4-cyclopropylcarbonylaminomethyl)phenyl-5-fluoro-2,4-pyrimidinediamine $^1$H NMR (DMSO-d$_6$): δ 0.65-0.72 (m, 4H), 1.61 (m, 1H), 4.26 (d, J=6.3 Hz, 2H), 7.12 (br, 2H), 7.22 (d, J=8.4 Hz, 2H), 7.62 (d, J=8.7 Hz, 2H), 7.70 (d, J=8.1 Hz, 2H), 7.81 (d, J=8.7 Hz, 2H), 8.13 (d, J=3.9 Hz, 1H), 8.54 (t, J=5.7 Hz, 1H), 9.42 (br, 1H), 9.58 (br, 1H); $^{19}$F NMR (282 MHz, DMSO-d$_6$): δ −201.16; LCMS: purity: 98.07%; MS (m/e): 457.29 (MH+).

III-42: N2-(3-aminosulfonyl)phenyl-N4-(4-cyclopropylcarbonylaminomethyl)phenyl-5-fluoro-2,4-pyrimidinediamine $^1$H NMR (DMSO-d$_6$): δ 0.65-0.72 (m, 4H), 1.60 (m, 1H), 4.24 (d, J=6.0 Hz, 2H), 7.20 (d, J=8.7 Hz, 2H), 7.26 (br, 2H), 7.35 (m, 2H), 7.71 (d, J=8.4 Hz, 2H), 7.94 (dt, J=2.1, 6.6 Hz, 1H), 8.06 (s, 1H), 8.11 (d, J=3.6 Hz, 1H), 8.52 (t, J=6.0 Hz, 1H), 9.47 (br, 1H), 9.56 (br, 1H); $^{19}$F NMR (282 MHz, DMSO-d$_6$): δ −201.79; LCMS: purity: 96.52%; MS (m/e): 457.46 (MH+).

III-43: N2-(3-aminosulfonyl-4-methyl)phenyl-N4-(4-cyclopropylcarbonylaminomethyl)phenyl-5-fluoro-2,4-pyrimidinediamine $^1$H NMR (DMSO-d$_6$): δ 0.66-0.72 (m, 4H), 1.63 (m, 1H), 2.52 (s, 3H), 4.25 (d, J=5.7 Hz, 2H), 7.20 (d, J=8.4 Hz, 2H), 7.22 (d, J=2.1 Hz, 1H), 7.28 (br, 2H), 7.66 (d, J=8.4 Hz, 2H), 7.81 (dd, J=2.4, 8.1 Hz, 1H), 7.97 (s, 1H), 8.15 (d, J=4.2 Hz, 1H), 8.54 (t, J=5.7 Hz, 1H), 9.80 (br, 2H); $^{19}$F NMR (282 MHz, DMSO-d$_6$): δ −201.18; LCMS: purity: 99.45%; MS (m/e): 471.57 (MH+).

III-125: N2-(4-aminosulfonyl)phenyl-N4-[4-(N-carbamoyl-N-propyl)aminomethyl]phenyl-5-fluoro-2,4-pyrimidinediamine $^1$H NMR (DMSO-d$_6$): δ 0.91 (t, J=7.5 Hz, 3H), 1.65 (q, J=7.5 Hz, 2H), 2.84 (m, 2H), 4.11 (s, 2H), 7.14 (br, 2H), 7.47 (d, J=8.7 Hz, 2H), 7.66 (d, J=8.7 Hz, 2H), 7.81 (d, J=8.7 Hz, 2H), 7.87 (d, J=8.4 Hz, 2H), 8.19 (d, J=3.6 Hz, 1H), 8.87 (br, 2H), 9.55 (br, 1H), 9.67 (br, 1H); $^{19}$F NMR (282 MHz, DMSO-d$_6$): δ −201.11; LCMS: purity: 100%; MS (m/e): 431.45 (M-42).

III-126: N2-(3-aminosulfonyl)phenyl-N4-[4-(N-carbamoyl-N-propyl)aminomethyl]phenyl-5-fluoro-2,4-pyrimidinediamine $^1$H NMR (DMSO-d$_6$): δ 0.91 (t, J=7.2 Hz, 3H), 1.65 (q, J=7.5 Hz, 2H), 2.84 (m, 2H), 4.09 (s, 2H), 7.28 (br, 2H), 7.36

(t, J=7.8 Hz, 1H), 7.41 (d, J=8.7 Hz, 1H), 7.46 (d, J=7.8 Hz, 2H), 7.90 (d, J=8.1 Hz, 2H), 7.95 (d, J=8.4 Hz, 1H), 8.09 (s, 1H), 8.16 (dd, J=1.2, 3.6 Hz, 1H), 8.94 (br, 2H), 9.50 (br, 1H), 9.58 (br, 1H); $^{19}$F NMR (282 MHz, DMSO-d$_6$): δ −201.56; LCMS: purity: 98.40%; MS (m/e): 431.15 (M-42).

III-127: N2-(3-aminosulfonyl-4-methyl)phenyl-N4-[4-(N-carbamoyl-N-propyl)aminomethyl]phenyl-5-fluoro-2,4-pyrimidinediamine $^1$H NMR (DMSO-d$_6$): δ 0.90 (t, J=7.2 Hz, 3H), 1.66 (q, J=7.5 Hz, 2H), 2.52 (s, 3H), 2.82 (m, 2H), 4.09 (s, 2H), 7.24 (d, J=8.7 Hz, 1H), 7.27 (br, 2H), 7.47 (d, J=8.7 Hz, 2H), 7.87 (d, J=8.7 Hz, 3H), 8.04 (s, 1H), 8.16 (d, J=3.6 Hz, 1H), 9.02 (br, 2H), 9.65 (br, 2H); $^{19}$F NMR (282 MHz, DMSO-d$_6$): δ −201.58; LCMS: purity: 96.79%; MS (m/e): 445.20 (M-42).

III-35: N2-(4-aminosulfonyl)phenyl-N4-(4-ethylcarbonylaminomethyl)phenyl-5-fluoro-2,4-pyrimidinediamine $^1$H NMR (DMSO-d$_6$): δ 1.03 (t, J=7.5 Hz, 3H), 2.15 (q, J=7.5 Hz, 2H), 4.24 (d, J=6.3 Hz, 2H), 7.13 (br, 2H), 7.21 (d, J=8.4 Hz, 2H), 7.61 (d, J=8.7 Hz, 2H), 7.67 (d, J=8.7 Hz, 2H), 7.80 (d, J=8.7 Hz, 2H), 8.13 (d, J=3.6 Hz, 2H), 8.26 (t, J=6.3 Hz, 1H), 9.41 (br, 1H), 9.58 (br, 1H); $^{19}$F NMR (282 MHz, DMSO-d$_6$): δ −201.68; LCMS: purity: 84.18%; MS (m/e): 445.55 (MH+).

III-36: N2-(3-aminosulfonyl)phenyl-N4-(4-ethylcarbonylaminomethyl)phenyl-5-fluoro-2,4-pyrimidinediamine $^1$H NMR (DMSO-d$_6$): δ 1.03 (t, J=7.5 Hz, 3H), 2.14 (q, J=7.5 Hz, 2H), 4.22 (d, J=6.0 Hz, 2H), 7.19 (d, J=8.4 Hz, 2H), 7.25 (br, 2H), 7.34 (m, 2H), 7.72 (d, J=8.4 Hz, 2H), 7.95 (dt, J=2.1, 7.8 Hz, 1H), 8.09 (s, 1H), 8.10 (d, J=3.6 Hz, 1H), 8.23 (t, J=6.0 Hz, 1H), 9.36 (br, 1H), 9.49 (br, 1H); $^{19}$F NMR (282 MHz, DMSO-d$_6$): δ −202.05; LCMS: purity: 90.32%; MS (m/e): 445.17 (MH+).

III-37: N2-(3-aminosulfonyl-4-methyl)phenyl-N4-(4-ethylcarbonylaminomethyl)phenyl-5-fluoro-2,4-pyrimidinediamine $^1$H NMR (DMSO-d$_6$): δ 1.03 (t, J=7.5 Hz, 3H), 2.14 (q, J=7.5 Hz, 2H), 2.49 (s, 3H), 4.22 (d, J=6.3 Hz, 2H), 7.16 (d, J=8.4 Hz, 1H), 7.18 (d, J=8.7 Hz, 2H), 7.22 (br, 2H), 7.72 (d, J=8.4 Hz, 2H), 7.89 (dd, J=2.1, 7.8 Hz, 1H), 8.06 (d, J=3.6 Hz, 1H), 8.09 (d, J=2.1 Hz, 1H), 8.23 (t, J=6.0 Hz, 1H), 9.32 (br, 1H), 9.38 (br, 1H); $^{19}$F NMR (282 MHz, DMSO-d$_6$): δ −202.60; LCMS: purity: 88.90%; MS (m/e): 459.62 (MH+).

III-113: N4-(3-aminocarbonylaminomethyl)phenyl-N2-(4-aminosulfonyl)phenyl-5-fluoro-2,4-pyrimidinediamine $^1$H NMR (DMSO-d$_6$): δ 4.18 (s, 2H), 6.49 (br, 1H), 7.02 (d, J=7.5 Hz, 1H), 7.14 (br, 2H), 7.30 (t, J=7.8 Hz, 1H), 7.59 (br, 2H), 7.63 (d, J=9.3 Hz, 2H), 7.77 (d, J=9.0 Hz, 2H), 8.18 (d, J=3.9 Hz, 1H), 9.70 (br, 1H), 9.77 (br, 1H); $^{19}$F NMR (282 MHz, DMSO-d$_6$): δ −200.91; LCMS: purity: 89.57%; MS (m/e): 432.18 (MH+).

III-114: N4-(3-aminocarbonylaminomethyl)phenyl-N2-(3-aminosulfonyl)phenyl-5-fluoro-2,4-pyrimidinediamine $^1$H NMR (DMSO-d$_6$): δ 4.16 (s, 2H), 6.47 (br, 1H), 6.98 (d, J=7.5 Hz, 1H), 7.28 (m, 3H), 7.40 (m, 2H), 7.63 (m, 2H), 7.92 (m, 1H), 7.99 (s, 1H), 8.17 (d, J=4.2 Hz, 1H), 9.78 (br, 2H); $^{19}$F NMR (282 MHz, DMSO-d$_6$): δ −200.79; LCMS: purity: 97.93%; MS (m/e): 432.14 (MH+).

III-115: N4-(3-aminocarbonylaminomethyl)phenyl-N2-(3-aminosulfonyl-4-methyl)phenyl-5-fluoro-2,4-pyrimidinediamine $^1$H NMR (DMSO-d$_6$): δ 2.49 (s, 3H), 4.17 (d, J=6.6 Hz, 2H), 5.53 (br, 2H), 6.43 (t, 1H), 6.94 (d, J=7.8 Hz, 1H), 7.23 (m, 4H), 7.68 (m, 2H), 7.90 (dd, J=6.0 Hz, 1H), 8.07 (d, J=3.6 Hz, 1H), 8.11 (d, 1H), 9.34 (br, 1H), 9.36 (br, 1H); $^{19}$F NMR (282 MHz, DMSO-d$_6$): δ −202.31; LCMS: purity: 86.53%; MS (m/e): 446.55 (MH+).

III-38: N2-(4-aminosulfonyl)phenyl-N4-(3-cyclopropylcarbonylaminomethyl)phenyl-5-fluoro-2,4-pyrimidinediamine $^1$H NMR (DMSO-d$_6$): δ 0.64-0.70 (m, 4H), 1.61 (m, 1H), 4.28 (d, J=6.0 Hz, 2H), 7.02 (d, J=6.9 Hz, 1H), 7.13 (br, 2H), 7.31 (t, J=7.8 Hz, 1H), 7.60 (d, J=8.1 Hz, 2H), 7.64 (m, 2H), 7.77 (d, J=8.7 Hz, 2H), 8.18 (d, J=3.9 Hz, 1H), 8.57 (t, J=6.0 Hz, 1H), 9.69 (br, 1H), 9.73 (br, 1H); $^{19}$F NMR (282 MHz, DMSO-d$_6$): δ −200.90; LCMS: purity: 98.26%; MS (m/e): 457.49 (MH+).

III-39: N2-(3-aminosulfonyl)phenyl-N4-(3-cyclopropylcarbonylaminomethyl)phenyl-5-fluoro-2,4-pyrimidinediamine $^1$H NMR (DMSO-d$_6$): δ 0.64-0.71 (m, 4H), 1.61 (m, 1H), 4.27 (d, J=5.7 Hz, 2H), 6.97 (d, J=7.2 Hz, 1H), 7.29 (m, 3H), 7.38 (m, 2H), 7.64 (s, 1H), 7.70 (d, J=9.0 Hz, 1H), 7.93 (d, J=6.9 Hz, 1H), 8.01 (s, 1H), 8.16 (d, J=3.9 Hz, 1H), 8.55 (t, J=6.0 Hz, 1H), 9.67 (br, 2H); $^{19}$F NMR (282 MHz, DMSO-d$_6$): δ −200.98; LCMS: purity: 93.15%; MS (m/e): 457.13 (MH+).

III-40: N2-(3-aminosulfonyl-4-methyl)phenyl-N4-(3-cyclopropylcarbonylaminomethyl)phenyl-5-fluoro-2,4-pyrimidinediamine $^1$H NMR (DMSO-d$_6$): δ 0.64-0.70 (m, 4H), 1.61 (m, 1H), 2.48 (s, 3H), 4.26 (d, J=5.7 Hz, 2H), 6.98 (d, J=8.1 Hz, 1H), 7.26 (m, 4H), 7.62 (s, 1H), 7.68 (d, J=8.4 Hz, 1H), 7.84 (d, J=8.4 Hz, 1H), 8.01 (s, 1H), 8.13 (d, J=4.2 Hz, 1H), 8.54 (t, 1H), 9.60 (br, 1H), 9.70 (br, 1H); $^{19}$F NMR (282 MHz, DMSO-d$_6$): δ −201.36; LCMS: purity: 98.87%; MS (m/e): 471.61 (MH+).

III-122: N2-(4-aminosulfonyl)phenyl-N4-[4-(2-ethylaminocarbonylamino)ethyl]phenyl-5-fluoro-2,4-pyrimidinediamine $^1$H NMR (DMSO-d$_6$): δ 0.97 (t, J=7.2 Hz, 3H), 2.67 (t, J=7.2 Hz, 2H), 2.98 (q, J=7.2 Hz, 2H), 3.22 (t, J=7.8 Hz, 2H), 7.16 (br, 2H), 7.17 (d, J=8.4 Hz, 2H), 7.62 (d, J=9.0 Hz, 2H), 7.64 (d, J=8.7 Hz, 2H), 7.78 (d, J=9.3 Hz, 2H), 8.14 (d, J=3.9 Hz, 1H), 9.50 (br, 1H), 9.67 (br, 1H); $^{19}$F NMR (282 MHz, DMSO-d$_6$): δ −201.40; LCMS: purity: 98.96%; MS (m/e): 474.56 (MH+).

III-123: N2-(3-aminosulfonyl)phenyl-N4-[4-(2-ethylaminocarbonylamino)ethyl]phenyl-5-fluoro-2,4-pyrimidinediamine $^1$H NMR (DMSO-d$_6$): δ 0.97 (t, J=7.2 Hz, 3H), 2.64 (t, J=7.2 Hz, 2H), 2.98 (t, J=6.0 Hz, 2H), 3.16 (m, 2H), 7.14 (d, J=8.1 Hz, 2H), 7.25 (br, 2H), 7.36 (m, 2H), 7.71 (d, J=8.1 Hz, 2H), 7.95 (d, J=6.6 Hz, 1H), 8.09 (d, J=3.3 Hz, 2H), 9.32 (br, 1H), 9.49 (br, 1H); $^{19}$F NMR (282 MHz, DMSO-d$_6$): δ −202.04; LCMS: purity: 96.25%; MS (m/e): 474.55 (MH+).

III-124: N2-(3-aminosulfonyl-4-methyl)phenyl-N4-[4-(2-ethylaminocarbonylamino)ethyl]phenyl-5-fluoro-2,4-pyrimidinediamine $^1$H NMR (DMSO-d$_6$): δ 0.96 (t, J=7.2 Hz, 3H), 2.51 (s, 3H), 2.64 (t, J=7.2 Hz, 2H), 2.98 (q, J=7.2 Hz, 2H), 3.20 (t, J=7.5 Hz, 2H), 7.15 (d, J=8.1 Hz, 2H), 7.20 (d, J=8.4 Hz, 1H), 7.26 (br, 2H), 7.66 (d, J=8.1 Hz, 2H), 7.82 (d, J=8.1 Hz, 1H), 8.01 (s, 1H), 8.12 (d, J=4.2 Hz, 1H), 9.67 (br, 2H); $^{19}$F NMR (282 MHz, DMSO-d$_6$): δ −201.42; LCMS: purity: 90.25%; MS (m/e): 488.16 (MH+).

III-116: N2-(4-aminosulfonyl)phenyl-N4-(3-ethylaminocarbonylaminomethyl)phenyl-5-fluoro-2,4-pyrimidinediamine $^1$H NMR (DMSO-d$_6$): δ 0.97 (t, J=7.2 Hz, 3H), 3.01 (p, J=6.6 Hz, 2H), 4.20 (d, J=6.0 Hz, 2H), 5.90 (t, J=5.4 Hz, 1H), 6.31 (t, J=6.0 Hz, 1H), 6.98 (d, J=8.1 Hz, 1H), 7.12 (br, 2H), 7.28 (t, J=7.5 Hz, 1H), 7.63 (d, J=8.7 Hz, 4H), 7.80 (d, J=8.7 Hz, 2H), 8.14 (d, J=3.6 Hz, 1H), 9.47 (br, 1H), 9.58 (br, 1H); $^{19}$F NMR (282 MHz, DMSO-d$_6$): δ −201.50; LCMS: purity: 84.70%; MS (m/e): 460.19 (MH+).

III-117: N2-(3-aminosulfonyl)phenyl-N4-(3-ethylaminocarbonylaminomethyl)phenyl-5-fluoro-2,4-pyrimidinediamine $^1$H NMR (DMSO-d$_6$): δ 0.97 (t, J=7.2 Hz, 3H), 3.02 (q, J=7.2 Hz, 2H), 4.18 (s, 2H), 6.32 (br, 1H), 6.96 (d, J=7.5 Hz, 1H), 7.29 (m, 3H), 7.39 (m, 2H), 7.65 (m, 2H), 7.93 (d, J=6.9 Hz, 1H), 8.02 (s, 1H), 8.16 (d, J=4.2 Hz, 1H), 9.70 (br, 2H); $^{19}$F NMR (282 MHz, DMSO-d$_6$): δ −200.97; LCMS: purity: 94.77%; MS (m/e): 460.13 (MH+).

III-118: N2-(3-aminosulfonyl-4-methyl)phenyl-N4-(3-ethylaminocarbonylaminomethyl)phenyl-5-fluoro-2,4-pyrimidinediamine $^1$H NMR (DMSO-d$_6$): δ 0.98 (t, J=7.2 Hz, 3H), 2.50 (s, 3H), 3.02 (p, J=6.6 Hz, 2H), 4.19 (d, J=6.0 Hz, 2H), 5.86 (t, J=5.7 Hz, 1H), 6.26 (t, J=5.7 Hz, 1H), 6.93 (d, J=7.8 Hz, 1H), 7.18 (d, J=8.4 Hz, 1H), 7.22 (br, 2H), 7.26 (d, J=7.8 Hz, 1H), 7.69 (m, 2H), 7.90 (dd, J=2.7, 8.7 Hz, 1H), 8.07 (d, J=3.6 Hz, 1H), 8.11 (d, J=2.1 Hz, 1H), 9.33 (br, 1H), 9.34 (br, 1H); $^{19}$F NMR (282 MHz, DMSO-d$_6$): δ −202.30; LCMS: purity: 98.09%; MS (m/e): 474.15 (MH+).

VII-13: N2-(4-aminosulfonyl)phenyl-N4-[(N-ethylsulfonyl)-1,2,3,4-tetrahydroisoquinolin-6-yl]-5-fluoro-2,4-pyrimidinediamine $^1$H NMR (DMSO-d$_6$): δ 1.22 (t, J=7.5 Hz, 3H), 2.86 (t, 2H), 3.13 (q, J=7.5 Hz, 2H), 3.50 (t, J=6.0 Hz, 2H), 4.40 (s, 2H), 7.13 (br, 2H), 7.15 (m, 1H), 7.57 (m, 2H), 7.61 (d, J=8.7 Hz, 2H), 7.78 (d, J=8.7 Hz, 2H), 8.14 (d, J=3.3 Hz, 1H), 9.40 (br, 1H), 9.61 (br, 1H); $^{19}$F NMR (282 MHz, DMSO-d$_6$): δ −201.54; LCMS: purity: 94.58%; MS (m/e): 507.37 (MH+).

VII-14: N2-(3-aminosulfonyl)phenyl-N4-[(N-ethylsulfonyl)-1,2,3,4-tetrahydroisoquinolin-6-yl]-5-fluoro-2,4-pyrimidinediamine $^1$H NMR (DMSO-d$_6$): δ 1.22 (t, J=7.2 Hz, 3H), 2.86 (t, 2H), 3.13 (q, J=7.5 Hz, 2H), 3.49 (t, 2H), 4.38 (s, 2H), 7.12 (d, J=9.0 Hz, 1H), 7.26 (br, 2H), 7.36 (d, J=8.7 Hz, 1H), 7.60 (m, 2H), 7.96 (d, 1H), 8.05 (s, 1H), 8.10 (d, J=3.9 Hz, 1H), 9.34 (br, 1H), 9.50 (br, 1H); $^{19}$F NMR (282 MHz, DMSO-d$_6$): δ −201.96; LCMS: purity: 82.10%; MS (m/e): 507.37 (MH+).

VII-15: N2-(3-aminosulfonyl-4-methyl)phenyl-N4-[(N-ethylsulfonyl)-1,2,3,4-tetrahydroisoquinolin-6-yl]-5-fluoro-2,4-pyrimidinediamine $^1$H NMR (DMSO-d$_6$): δ 1.22 (t, J=7.2 Hz, 3H), 2.85 (t, 2H), 3.13 (q, J=7.2 Hz, 2H), 3.50 (t, J=5.7 Hz, 2H), 4.38 (s, 2H), 7.12 (d, J=8.1 Hz, 1H), 7.16 (d, J=8.7 Hz, 1H), 7.24 (br, 2H), 7.59 (m, 2H), 7.89 (d, J=8.1 Hz, 1H), 8.07 (m, 2H), 9.30 (br, 1H), 9.39 (br, 1H); $^{19}$F NMR (282 MHz, DMSO-d$_6$): δ −202.55; LCMS: purity: 97.17%; MS (m/e): 521.14 (MH+).

III-23: N2-(3-Aminosulfonyl-4-methylphenyl)-N4-(4-cyanoethylene-2-methylphenyl)-5-fluoro-2,4-pyrimidinediamine $^1$H NMR (DMSO-d$_6$): δ 9.198 (s, 1H), 8.984 (s, 1H), 8.015 (bs, 2H), 7.722-7.695 (d, J=8.1 Hz, 1H), 7.259 (s, 1H), 7.179 (s, 2H), 7.126 (s, 1H), 7.098 (s, 1H), 6.965-6.938 (d, J=8.1 Hz, 1H), 2.865-2.792 (m, 4H), 2.438 (s, 3H), 2.171 (s, 3H), LCMS: 441.11 (MH$^+$).

III-24: N2-(3-Aminosulfonylphenyl)-N4-(4-cyanoethylene-2-methylphenyl)-5-fluoro-2,4-pyrimidinediamine $^1$H NMR (DMSO-d$_6$): δ 9.315 (s, 1H), 9.047 (s, 1H), 8.061-8.049 (d, J=3.6 Hz, 2H), 7.985 (s, 1H), 7.805-7.778 (d, J=8.1 Hz, 1H), 7.259-7.106 (m, 6H), 2.866-2.816 (m, 4H), 2.173 (s, 3H), LCMS: 427.38 (MH+).

III-25: N2-(3-Aminosulfonyl-4-methylphenyl)-N4-(4-cyanoethylene-3-methoxyphenyl)-5-fluoro-2,4-pyrimidinediamine $^1$H NMR (DMSO-d$_6$): δ 9.395 (s, 1H), 8.089 (s, 2H), 7.920-7.891 (d, J=8.7 Hz, 1H), 7.503-7.476 (d, J=8.1 Hz, 1H), 7.315 (s, 1H), 7.175-7.124 (t, 3H), 3.742 (s, 3H), 2.811-2.727 (m, 4H), LCMS: 457.07 (MH+).

III-26: N2-(3-Aminosulfonylphenyl)-N4-(4-cyanoethylene-2-methylphenyl)-5-fluoro-2,4-pyrimidinediamine $^1$H NMR (DMSO-d$_6$): δ 9.512 (s, 1H), 9.400 (bs, 1H), 8.123-8.090 (t, 2H), 7.988-7.963 (d, J=7.5 Hz, 1H), 7.500-7.472 (d, J=8.4 Hz, 1H), 7.370-7.249 (m, 4H), 7.160-7.132 (d, J=8.4 Hz, 1H), 3.753 (s, 3H), 2.812-2.708 (m, 4H), LCMS: 443.08 (MH+).

IX-46: N2-(3-Aminosulfonyl-4-methylphenyl)-5-fluoro-N4-(5-methoxycarbonyl-thiophene-2-yl)-2,4-pyrimidinediamine $^1$H NMR (DMSO-d$_6$): δ 11.120 (s, 1H), 9.541 (s, 1H), 8.194-8.183 (d, J=3.3 Hz, 1H), 8.139 (s, 1H), 7.618-7.604 (d, J=4.2 Hz, 1H), 7.261-7.234 (m, 3H), 6.996-6.983 (d, J=3.9 Hz, 1H), 3.773 (s, 3H), 2.527 (s, 3H), LCMS: 438.36 (MH+).

IX-47: N2-(3-Aminosulfonylphenyl)-5-fluoro-N4-(5-methoxycarbonyl-thiophene-2-yl)-2,4-pyrimidinediamine $^1$H NMR (DMSO-d$_6$): δ 11.158 (s, 1H), 9.642 (s, 1H), 8.228-8.218 (d, J=3 Hz, 1H), 8.128 (s, 1H), 8.020-7.996 (d, J=7.2 Hz, 1H), 7.452-7.413 (m, 2H), 7.279 (s, 2H), 7.004-6.992 (d, J=3.6 Hz, 1H), 3.773 (s, 3H), LCMS: 424.32 (MH+).

IX-48: N2-(3-Aminosulfonyl-4-fluorophenyl)-5-fluoro-N4-(5-methoxycarbonyl-thiophene-2-yl)-2,4-pyrimidinediamine $^1$H NMR (DMSO-d$_6$): δ 11.20 (bs, 1H), 9.332 (s, 1H), 8.075-8.057 (d, J=5.4 Hz, 3H), 7.573-7.559 (d, J=4.2 Hz, 3H), 7.304-7.244 (t, 1H), 6.789 (s, 1H), 3.740 (s, 3H), LCMS: 442.26 (MH+).

IX-49: N2-(4-Aminosulfonylphenyl)-5-fluoro-N4-(5-methoxycarbonyl-thiophene-2-yl)-2,4-pyrimidinediamine $^1$H NMR (DMSO-d$_6$): δ 11.166 (s, 1H), 9.437 (s, 1H), 8.053 (s, 1H), 7.930-7.901 (d, J=8.7 Hz, 2H), 7.692-7.664 (d, J=8.4 Hz, 2H), 7.591 (s, 1H), 7.113 (s, 2H), 6.808 (s, 1H), 3.757 (s, 3H), LCMS: 423.97 (MH+).

III-28: N4-(3-Chloro-4-cyanoethylene-phenyl)-5-fluoro-N2-(4-methyl-3-propionylaminosulfonylphenyl)-2,4-pyrimidinediamine $^1$H NMR (DMSO-d$_6$): δ 12.029 (s, 1H), 9.586 (s, 1H), 9.509 (s, 1H), 8.149-7.137 (m, 2H), 8.041-8.012 (d, J=8.7 Hz, 1H), 7.873 (s, 1H), 7.849-7.821 (d, J=8.4 Hz, 1H), 7.371-7.343 (d, J=8.4 Hz, 1H), 7.252-7.225 (d, J=8.1 Hz, 1H), 2.996-2.952 (t, 2H), 2.843-2.797 (t, 2H), 2.273-2.199 (q, 2H), 0.906-0.857 (t, 3H), LCMS: 517.38 (MH+).

III-29: N4-(3-Chloro-4-cyanoethylene-phenyl)-5-fluoro-N2-(4-methyl-3-propionylaminosulfonylphenyl)-2,4-pyrimidinediamine Sodium salt $^1$H NMR (DMSO-d$_6$): δ 9.395 (s, 1H), 9.306 (s, 1H), 8.097-8.085 (d, J=3.6 Hz, 1H), 7.922-7.875 (m, 2H), 7.840 (s, 1H), 7.780-7.754 (d, J=7.8 Hz, 1H), 7.375-7.347 (d, J=8.4 Hz, 1H), 6.997-6.970 (d, J=8.1 Hz, 1H), 2.991-2.945 (t, 2H), 2.837-2.788 (t, 2H), 2.421 (s, 3H), 1.938-1.863 (q, 2H), 0.873-0.824 (t, 3H), LCMS: 514.83 (MH+).

VII-73: N2-(3-Aminosulfonyl-4-methylphenyl)-5-fluoro-N4-(2-hydroxy-4-methylquinolin-6-yl)-2,4-pyrimidinediamine $^1$H NMR (DMSO-d$_6$): δ 11.527 (s, 1H), 9.460 (s, 1H), 9.356 (s, 1H), 8.077 (s, 2H), 8.030-8.010 (d, J=6.0 Hz, 1H), 7.889 (s, 1H), 7.850 (s, 1H), 7.297-7.268 (d, J=8.7 Hz, 1H), 7.219 (s, 2H), 7.076-7.048 (d, J=8.4 Hz, 1H), 6.382 (s, 1H), 3.146 (s, 3H), 2.339 (s, 2H), 2.076 (s, 1H), LCMS: 454.92 (MH+).

VII-74: N2-(3-Aminosulfonylphenyl)-5-fluoro-N4-(2-hydroxy-4-methylquinolin-6-yl)-2,4-pyrimidinediamine $^1$H NMR (DMSO-d$_6$): δ 11.531 (s, 1H), 9.502 (s, 1H), 9.468 (s, 1H), 8.117-7.900 (m, 3H), 7.303-7.243 (m, 3H), 3.150 (s, 3H), 2.352 (s, 2H), 2.074 (s, 1H), LCMS: 440.94 (MH+).

III-30: N4-(4-Cyanoethylene-3-trifluoromethylphenyl)-5-fluoro-N2-(4-methyl-3-aminosulfonylphenyl)-2,4-pyrimidinediamine $^1$H NMR (DMSO-d$_6$): δ 9.647 (s, 1H), 9.506 (s, 1H), 8.345-8.319 (d, J=7.8 Hz, 1H), 8.152-8.141 (d, J=3.3 Hz, 1H), 8.065 (s, 1H), 7.941 (s, 1H), 7.891-7.864 (d, J=8.1 Hz, 1H), 7.541-7.513 (d, J=8.4 Hz, 1H), 7.244 (s, 2H), 7.193-7.166 (d, J=8.1 Hz, 1H), 3.044-2.998 (t, 2H), 2.883-2.836 (t, 2H), LCMS: 495.62 (MH+).

III-31: N4-(4-Cyanoethylene-3-trifluoromethylphenyl)-5-fluoro-N2-(3-aminosulfonylphenyl)-2,4-pyrimidinediamine $^1$H NMR (DMSO-d$_6$): δ 9.603 (s, 1H), 8.341-8.313 (d, J=8.4 Hz, 1H), 8.175-8.164 (d, J=3.3 Hz, 1H), 8.059 (s, 1H), 7.948 (s, 2H), 7.546-7.517 (d, J=8.7 Hz, 1H), 7.385-7.348 (m, 2H), 3.044-2.996 (t, 2H), 2.882-2.834 (t, 2H), LCMS: 481.55 (MH+).

III-47: N4-[4-(2-Aminocarboxylethylene)phenyl]-5-fluoro-N2-(4-methyl-3-aminosulfonylphenyl)-2,4-pyrimidinediamine $^1$H NMR (DMSO-d$_6$): δ 9.374 (s, 1H), 9.258 (s, 1H), 8.115 (s, 1H), 8.056-8.044 (d, J=3.6 Hz, 1H), 7.909-7.881 (d, J=8.4 Hz, 1H), 7.699-7.670 (d, J=8.7 Hz, 2H), 7.269-7.128 (m, 6H), 6.740 (s, 1H), 2.799-2.748 (t, 2H), 2.370-2.319 (t, 2H), LCMS: 445.11 (MH+).

III-48: N4-[4-(2-Aminocarboxylethylene)phenyl]-N2-(3-aminosulfonylphenyl)-5-fluoro-2,4-pyrimidinediamine $^1$H NMR (DMSO-d$_6$): δ 9.486 (s, 1H), 9.301 (s, 1H), 8.094 (bs, 2H), 7.969-7.942 (d, J=8.1 Hz, 2H), 7.374-7.341 (m, 2H), 7.248 (bs, 3H), 7.164-7.137 (d, J=8.1 Hz, 2H), 6.743 (s, 1H), 2.800-2.750 (t, 2H), 2.370-2.321 (t, 2H), LCMS: 431.10 (MH+).

III-49: N4-[4-(2-Aminocarboxylethylene)phenyl]-N2-(4-aminosulfonylphenyl)-5-fluoro-2,4-pyrimidinediamine $^1$H NMR (DMSO-d$_6$): δ 9.594 (s, 1H), 9.372 (s, 1H), 8.125-8.112 (d, J=3.9 Hz, 1H), 7.818 (s, 1H), 7.788 (s, 1H), 7.627-7.591 (m, 4H), 7.283 (s, 1H), 7.191-7.163 (d, J=8.4 Hz, 2H), 6.735 (s, 1H), 2.821-2.773 (t, 2H), 2.391-2.342 (t, 2H), LCMS: 431.05 (MH+).

VII-21: N2-(3-Aminosulfonyl-4-methylphenyl)-N4-[3,4-dihydro-(1H)-quinolin-2-one-6-yl]-5-fluoro-2,4-pyrimidinediamine $^1$H NMR (DMSO-d$_6$): δ 9.981 (s, 1H), 9.306 (s, 1H), 8.042-8.017 (m, 2H), 7.898-7.869 (d, J=8.7 Hz, 1H), 7.565-

7.515 (m, 2H), 7.148-7.120 (d, J=8.4 Hz, 2H), 6.817-6.789 (d, J=8.4 Hz, 2H), 2.863-2.814 (t, 2H), LCMS: 443.05 (MH+).

VII-75: N2-(3-Aminosulfonyl-4-methylphenyl)-N4-(2-N,N'-dimethylamine-quinolin-6-yl)-5-fluoro-2,4-pyrimidinediamine $^1$H NMR (DMSO-d$_6$): δ 9.393 (s, 2H), 8.270 (s, 1H), 8.081 (bs, 2H), 7.944-7.903 (m, 2H), 7.789-7.781 (d, J=2.4 Hz, 1H), 7.508-7.478 (d, J=9 Hz, 1H), 7.124-7.065 (m, 3H), 3.146 (s, 6H), LCMS: 467.99 (MH+).

VII-76: N2-(3-Aminosulfonylphenyl)-N4-(2-N,N'-dimethylamine-quinolin-6-yl)-5-fluoro-2,4-pyrimidinediamine $^1$H NMR (DMSO-d$_6$): δ 9.518 (s, 1H), 9.446 (s, 1H), 8.266 (s, 1H), 8.118-8.017 (m, 3H), 7.953-7.921 (d, J=9.6 Hz, 1H), 7.82-7.76 (m, 2H), 7.516-7.485 (d, J=9.3 Hz, 1H) 7.331 (s, 2H), 7.265 (s, 2H), 7.099-7.068 (d, J=9.3 Hz, 1H), 3.147 (s, 6H).

III-51: N2-(3-Aminosulfonylphenyl)-N4-[(1-ethylpyrazolyl-5-aminocarbonylmethylene)phenyl]-5-fluoro-2,4-pyrimidinediamine $^1$H NMR (DMSO-d$_6$): δ 9.50 (s, 1H), 9.38 (s, 1H), 8.10 (s, 2H), 7.93 (bs, 2H), 7.75 (d, 2H, J=8.4 Hz), 7.50 (s, 1H), 7.36 (m, 5H), 6.15 (s, 1H), 3.98 (d, 2H, J=7.8 Hz), 3.66 (s, 2H), 1.24 (s, 3H): LCMS: purity: 99%; MS (m/e): 511 (MH$^+$).

III-52: N2-(3-Aminosulfonyl-4-methylphenyl)-5-N4-[(1-ethylpyrazolyl-5-aminocarbonylmethylene)phenyl]-5-fluoro-2,4-pyrimidinediamine $^1$H NMR (DMSO-d$_6$): δ 9.39 (s, 1H), 9.34 (s, 1H), 8.10 (d, 2H, J=10.8 Hz), 7.93 (d, 2H), 7.75 (d, 2H, J=7.8 Hz), 7.29 (m, 4H), 6.15 (s, 1H), 3.98 (d, 2H, J=6.9 Hz), 3.66 (s, 2H), 2.45 (s, 3H), 1.26 (t, 3H, J=6.3 Hz): LCMS: purity: 87%; MS (m/e): 525 (MH$^+$).

III-50: N2-(3-Aminosulfonylphenyl)-5-fluoro-N-4-[4(1-methylpyrazolyl-3-aminocarbonylmethylene)phenyl]-2,4-pyrimidinediamine $^1$H NMR (DMSO-d$_6$): δ 8.09 (s, 2H), 7.96 (d, 1H, J=6.6 Hz), 7.69 (d, 2H, J=8.1 Hz), 7.49 (s, 1H), 7.31 (m, 4H), 6.39 (s, 1H), 3.72 (s, 3H), 3.56 (s, 2H): LCMS: purity: 92%; MS (m/e): 497 (MH$^+$).

IV-12: N2-(3-Aminosulfonyl-4-methylphenyl)-5-fluoro-N4-[3-(N-methylaminosulfonyl)phenyl]-2,4-pyrimidinediamine $^1$HNMR (DMSO-d$_6$): δ 8.40 (d, 1H, J=7.8 Hz), 8.15 (d, 1H, J=3.6 Hz), 8.09 (s, 1H), 7.96 (s, 1H), 7.84 (m, 1H), 7.55 (t, 1H, J=7.8 Hz), 7.44 (d, 2H), 7.21 (m, 3H), 2.45 (s, 3H), 2.43 (s, 3H) LCMS: purity: 99%; MS (m/e): 467 (MH$^+$).

IV-9: N2-(3-Aminosulfonylphenyl)-5-fluoro-N4-[3-(N,N-dimethylaminosulfonyl)phenyl]-2,4-pyrimidinediamine $^1$HNMR (DMSO-d$_6$): δ 9.75 (s, 1H), 9.57 (s, 1H), 8.56 (bs, 1H), 8.19 (s, 1H, J=2.7 Hz), 8.10 (s, 1H), 7.89 (m, 2H), 7.62 (m, 3H), 7.38 (s, 3H), 7.27 (s, 1H), 2.62 (s, 6H): LCMS: purity: 98%; MS (m/e): 467 (MH$^+$).

IV-10: N2-(3-Aminosulfonyl-4-methylphenyl)-5-fluoro-N4-[3-(N,N-dimethylaminosulfonyl)phenyl]-2,4-pyrimidinediamine $^1$HNMR (DMSO-d$_6$): δ 9.71 (s, 1H), 9.46 (s, 1H), 8.59 (d, 1H, J=8.4 Hz), 8.16 (d, 1H, J=3.6 Hz), 8.11 (d, 1H, J=2.4 Hz), 7.85 (m, 2H), 7.58 (t, 1H, J=8.1 Hz), 7.39 (d, 1H, 8.7 Hz), 7.21 (m, 3H), 2.62 (s, 6H), 2.48 (s, 3H): LCMS: purity: 99%; MS (m/e): 481 (MH$^+$).

IV-11: N2-(3-Aminosulfonylhenyl)-5-fluoro-N4-[3-(N-methylaminosulfonyl)phenyl]-2,4-pyrimidinediamine $^1$HNMR (DMSO-d$_6$): δ 9.73 (s, 1H), 9.53 ((, 1H), 8.40 (d, 1H, J=8.7 Hz), 8.19 (s, 1H), 8.09 (s, 1H), 7.96 (m, 2H), 7.56 (m, 1H), 7.40 (m, 4H), 7.27 (s, 2H), 2.43 (s, 3H): LCMS: purity: 99%; MS (m/e): 453 (MH$^+$).

VI-34: N2-(3-Aminosulfonyl-4-methoxy-5-methylphenyl)-5-fluoro-N4-(4-trifluoromethylphenyl)-2,4-pyrimidinediamine $^1$H NMR (DMSO-d$_6$): δ 9.53 (s, 1H), 9.36 (s, 1H), 8.13 (d, 1H, J=3.6 Hz), 7.90 (d, 2H, J=9 Hz), 7.80 (s, 2H), 7.30 (d, 2H, J=8.7 Hz), 7.03 (s, 2H), 3.76 (s, 3H), 2.21 (s, 3H); LCMS: purity: 92%; MS (m/e): 488 (MH$^+$).

VI-35: N2-(3-Aminosulfonylphenyl)-N4-(4-tert-butylphenyl)-5-fluoro-2,4-pyrimidinediamine $^1$H NMR (DMSO-d$_6$): δ 9.47 (s, 1H), 9.32 (s, 1H), 8.09 (m, 2H), 7.94 (bd, 1H, J=6.9 Hz), 7.69 (d, 2H, J=9 Hz), 7.33 (m, 4H), 7.25 (s, 2H), 1.28 (s, 9H); LCMS: purity: 98%; MS (m/e): 416 (MH$^+$)

VI-36: N2-(3-Aminosulfonyl-4-methylphenyl)-N4-(4-tert-butylphenyl)-5-fluoro-2,4-pyrimidinediamine $^1$H NMR (DMSO-d$_6$): δ 9.35 (s, 1H), 9.28 (s, 1H), 8.11 (bs, 1H), 8.04 (d, 1H, J=3.3 Hz), 7.86 (bdd, 1H, J=8.1 Hz), 7.67 (d, 2H, J=8.4 Hz), 7.33 (d, 2H, J=8.4 Hz), 7.21 (bs, 2H), 7.12 (m, 1H), 2.38 (s, 3H), 1.22 (s, 9H); LCMS: purity: 99%; MS (m/e): 430 (MH$^+$).

VI-37: N2-(3-Aminosulfonyl-4-methoxy-5-methylphenyl)-N4-(4-tert-butylphenyl)-5-fluoro-2,4-pyrimidinediamine $^1$H NMR (DMSO-d$_6$): δ 8.28 (bs, 2H), 8.05 (d, 1H, J=3.9 Hz), 7.86 (d, 1H, J=2.4 Hz), 7.75 (bd, 1H), 7.64 (d, 2H, J=8.7 Hz), 7.33 (d, 2H, J=8.7 Hz), 7.01 (s, 2H), 3.75 (s, 3H), 3.31 (s, 3H), 1.27 (s, 9H); LCMS: purity: 96%; MS (m/e): 460 (MH$^+$).

VI-38: N2-(3-Aminosulfonylphenyl)-N4-(4-chloro-3-trifluoromethylphenyl)-5-fluoro-2,4-pyrimidinediamine $^1$H NMR (DMSO-d$_6$): δ 9.78 (s, 1H), 8.36 (bdd, 1H, J=9 Hz), 8.21 (bd, 1H, J=2.1 Hz), 8.10 (d, 1H, J=2.1 Hz), 8.07 (s, 1H), 7.89 (bd, 1H, J=6.9 Hz), 7.62 (d, 1H, J=9.3 Hz), 7.38 (m, 2H), 7.27 (m, 2H); LCMS: purity: 99%; MS (m/e): 463 (MH$^+$).

VI-39: N2-(3-Aminosulfonyl-4-methyl-phenyl)-N4-(4-chloro-3-trifluoromethylphenyl)-5-fluoro-2,4-pyrimidinediamine $^1$H NMR (DMSO-d$_6$): δ 9.74 (s, 1H), 9.51 (s, 1H), 8.38 (bd, 1H, J=8.7 Hz), 8.17 (d, 1H, J=2.4 Hz), 8.10 (s, 1H), 8.08 (s, 1H), 7.83 (d, 1H, J=8.1 Hz), 7.61 (d, 1H, J=8.7 Hz), 7.25 (s, 2H), 7.18 (d, 1H, J=8.1 Hz), 7.09 (s, 1H), 2.50 (s, 3H); LCMS: purity: 96%; MS (m/e): 477 (MH$^+$).

VI-40: N2-(3-Aminosulfonyl-4-methoxy-5-methylphenyl)-N4-(4-chloro-3-trifluoromethyl-phenyl)-5-fluoro-2,4-pyrimidinediamine $^1$H NMR (DMSO-d$_6$): δ 9.74 (s, 1H), 9.42 (s, 1H), 8.38 (bd, 1H, J=9 Hz), 8.17 (d, 1H, J=1.8 Hz), 8.08 (s, 1H), 7.81 (s, 1H), 7.75 (s, 1H), 7.61 (d, 1H, J=9 Hz), 7.04 (s, 2H), 3.77 (s, 3H), 2.21 (s, 1H); LCMS: purity: 93%; MS (m/e): 507 (MH$^+$).

VI-41: N2-(3-Aminosulfonyl-4-chlorophenyl)-5-fluoro-N4-(4-trifluorophenyl)-2,4-pyrimidinediamine LCMS: purity: 96%; MS (m/e): 463 (MH$^+$).

VI-42: N2-(3-Aminosulfonyl-4-chlorophenyl)-5-fluoro-N4-(4-trifluoromethoxyphenyl)-2,4-pyrimidinediamine $^1$H NMR (DMSO-d$_6$): δ 9.66 (s, 1H), 9.60 (s, 1H), 8.27 (d, 1H, J=1.8 Hz), 8.15 (bdd, 1H, J=2.7 Hz), 8.00 (bdd, 1H, J=1.5 and 9.0 Hz), 7.91 (d, 2H, J=8.1 Hz), 7.47 (s, 2H), 7.41 (d, 1H, J=8.7 Hz), 7.32 (d, 2H, J=8.7 Hz); LCMS: purity: 95%; MS (m/e): 478 (M).

IX-21: N2-(3-Aminosulfonyl-4-chlorophenyl)-N4-(2-cyanobenzofuran-5-yl)-5-fluoro-2,4-pyrimidinediamine LCMS: purity: 91%; MS (m/e): 460 (MH$^+$).

VI-43: N2-(3-Aminosulfonyl-4-chlorophenyl)-N4-(4-tert-butylphenyl)-5-fluoro-2,4-pyrimidinediamine $^1$H NMR (DMSO-d$_6$): δ 9.57 (s, 1H), 9.35 (s, 1H), 8.27 (d, 1H, J=2.7 Hz), 8.09 (d, 1H, J=3.6 Hz), 8.00 (dd, 1H, J=2.7 and 8.7 Hz), 7.66 (d, 2H, J=8.4 Hz), 7.44 (s, 2H), 7.36 (m, 3H), 1.22 (s, 9H); LCMS: purity: 94%; MS (m/e): 451 (MH$^+$).

VI-44: N2-(3-Aminosulfonyl-4-chlorophenyl)-N4-(3-chloro-4-trifluoromethyl-phenyl)-5-fluoro-2,4-pyrimidinediamine LCMS: purity: 87%; MS (m/e): 497 (MH$^+$).

III-62: N2-(3-Aminosulfonylphenyl)-N4-(4-benzylphenyl)-5-fluoro-2,4-pyrimidinediamine $^1$H NMR (DMSO-d$_6$): δ 9.53 (s, 1H), 9.36 (s, 1H), 8.10 (d, 1H, J=2.7 Hz), 8.02 (bs, 1H), 7.96 (bs, 1H), 7.83 (d, 1H, J=1.8 Hz), 7.69 (bdd, 1H, J=9.3 Hz), 7.47-7.31 (m, 9H), 7.26 (s, 1H), 7.18 (d, 1H, J=9 Hz); LCMS: purity: 96%; MS (m/e): 450 (M).

III-63: N2-(3-Aminosulfonyl-4-methylphenyl)-N4-(4-benzylphenyl)-5-fluoro-2,4-pyrimidinediamine $^1$H NMR (DMSO-d$_6$): δ 9.42 (s, 1H), 9.33 (s, 1H), 8.05 (m, 2H), 7.87 (m, 2H), 7.70 (bd, 1H, J=8.7 Hz), 7.46-7.14 (m, 10H), 5.19 (s, 2H), 2.45 (s, 3H); LCMS: purity: 99%; MS (m/e): 465 (MH$^+$).

III-64: N2-(3-Aminosulfonyl-4-chlorophenyl)-N4-(4-benzylphenyl)-5-fluoro-2,4-pyrimidinediamine $^1$H NMR (DMSO-d$_6$): δ 9.65 (s, 1H), 9.40 (s, 1H), 8.22 (d, 1H, J=2.1 Hz), 8.10 (d, 1H, J=3.6 Hz), 8.02 (dd, 1H, J=2.7 and 9 Hz), 7.81 (d, 1H, J=2.4 Hz), 7.70 (dd, 1H, J=2.7 and 9 Hz), 7.39 (m, 8H), 7.19 (d, 2H, J=9 Hz), 5.20 (s, 2H); LCMS: purity: 99%; MS (m/e): 485 (MH$^+$).

III-65: N2-(3-Aminosulfonyl-4-methoxy-5-methylphenyl)-N4-(4-benzylphenyl)-5-fluoro-2,4-pyrimidinediamine $^1$H NMR (DMSO-d$_6$): δ 9.37 (s, 2H), 8.08 (bs, 1H), 7.77 (m, 2H), 7.71 (bd, 1H, J=8.7 Hz), 7.37 (m, 5H), 7.18 (m, 2H), 7.03 (s, 2H), 5.18 (s, 2H), 3.75 (s, 3H), 2.16 (s, 3H); LCMS: purity: 94%; MS (m/e): 495 (MH$^+$).

VI-45: N2-(3-Aminosulfonyl-4-iso-propylphenyl)-N4-(3-chloro-4-methoxy-phenyl)-5-fluoro-2,4-pyrimidinediamine $^1$H NMR (DMSO-d$_6$): δ 10.25 (s, 2H), 8.25 (d, 1H, J=8.4 Hz), 7.79 (m, 2H), 7.74 (d, 1H, J=1.8 Hz), 7.57)dd, 1H, J=1.8 and 8.7 Hz), 7.45 (m, 3H), 7.12 (d, 1H, J=8.7 Hz), 3.83 (s, 3H), 3.77 (m, 1H), 1.19 (d, 6H, J=6.9 Hz); LCMS: purity: 95%; MS (m/e): 467 (MH$^+$). RIX-22: N2-(3-Aminosulfonyl-4-iso-propylphenyl)-N4-(2-cyanobenzofuran-5-yl)-5-fluoro-2,4-pyrimidinediamine $^1$H NMR (DMSO-d$_6$): δ 9.53 (s, 1H), 9.41 (s, 1H), 8.29 (d, 1H, J=1.8 Hz), 8.10 (d, 1H, J=3.6 Hz), 8.03 (d, 1H, J=2.4 Hz), 8.01 (d, 1H), 7.90 (d, 1H), 7.87 (d, 1H, J=2.1 Hz), 7.70 (d, 1H, J=8.7 Hz), 7.32 (m, 3H), 3.75 (m, 1H), 1.20 (d, 6H, J=6.6 Hz); LCMS: purity: 95%; MS (m/e): 467 (MH$^+$).

I-8: N2-(3-Aminosulfonyl-4-iso-propylphenyl)-N4-(4-cyanomethyleneoxyphenyl)-5-fluoro-2,4-pyrimidinediamine $^1$H NMR (DMSO-d$_6$): δ 9.71 (bs, 2H), 8.11 (d, 1H, J=4.2 Hz), 7.95 (d, 1H, J=2.1 Hz), 7.82 (dd, 1H, J=2.1 and 8.4 Hz), 7.71 (d, 2H, J=8.7 Hz), 7.40 (d, 1H, J=8.4 Hz), 7.36 (s, 2H), 7.03 (d, 2H, J=9.3 Hz), 5.25 (s, 2H), 3.75 (m, 1H), 1.19 (d, 6H, J=6.9 Hz); LCMS: purity: 99%; MS (m/e): 457 (MH$^+$).

N4-(4-Aminosulfonylmethylenephenyl)-N2-(3-aminosulfonyl-4-methyl-phenyl)-5-fluoro-2,4-pyrimidinediamine $^1$H NMR (DMSO-d$_6$): δ 9.43 (s, 1H), 9.41 (s, 1H), 8.09 (m, 2H), 7.92 (dd, 1H, J=2.4 and 8.4 Hz), 7.82 (d, 2H, J=8.4 Hz), 7.29 (d, 2H, J=8.4 Hz), 7.22 (s, 2H), 7.19 (d, 1H, J=7.2 Hz), 6.80 (s, 2H), 4.23 (s, 2H), 2.21 (s, 3H); LCMS: purity: 99%; MS (m/e): 468 (MH$^+$).

VI-46: N2-(3-Aminosulfonyl-4-methylphenyl)-5-fluoro-N4-(4-trifluoromethylmethyleneoxyphenyl)-2,4-pyrimidinediamine $^1$H NMR (DMSO-d$_6$): δ 10.26 (bs, 2H), 8.24 (d, 1H, J=8.1 Hz), 7.87 (s, 1H), 7.70 (bd, 1H, J=8.1 Hz), 7.60 (d, 2H, J=9

Hz), 7.34 (bs, 2H), 7.25 (d, 1H, J=8.1 Hz), 7.04 (d, 2H, J=9 Hz), 4.75 (q, 2H, J=8.7 Hz); LCMS: purity: 98%; MS (m/e): 472 (MH$^+$).

VI-47: N2-(3-Aminosulfonylphenyl)-5-fluoro-N4-(4-trifluoromethylmethyleneoxyphenyl)-2,4-pyrimidinediamine $^1$H NMR (DMSO-d$_6$): δ 10.20 (s, 1H), 10.09 (s, 1H), 8.23 (d, 1H, J=4.8 Hz), 7.89 (s, 1H), 7.84 (m, 1H), 7.62 (d, 2H, J=8.7 Hz), 7.45 (m, 2H), 7.34 (bs, 2H), 7.03 (d, 2H, J=8.7 Hz), 4.75 (q, 2H, J=9 Hz); LCMS: purity: 98%; MS (m/e): 458 (MH$^+$).

VI-48: N2-(3-Aminosulfonyl-4-chlorophenyl)-5-fluoro-N4-(4-trifluoromethylmethyleneoxyphenyl)-2,4-pyrimidinediamine $^1$H NMR (DMSO-d$_6$): δ 10.23 (s, 1H), 10.03 (s, 1H), 8.23 (d, 1H, J=4.5 Hz), 8.10 (d, 1H, J=2.1 Hz), 7.87 (dd, 1H, J=2.4 and 9 Hz), 7.62 (d, 2H, J=8.7 Hz), 7.54 (bs, 2H), 7.47 (d, 1H, J=9 Hz), 7.05 (d, 2H, J=8.7 Hz), 4.75 (q, 2H, J=6 Hz); LCMS: purity: 98%; MS (m/e): 492 (M). V-16: N2-(3-Aminosulfonyl-4-methylphenyl)-N4-(2-cyanoethylene-benzothiophen-5-yl)-5-fluoro-2,4-pyrimidinediamine $^1$H NMR (DMSO-d$_6$): δ 9.423 (s, 2H), 8.305 (s, 1H), 8.096-8.070 (m, 2H), 7.938-7.903 (d, J=8.4 Hz, 1H), 7.846-7.818 (d, J=8.4 Hz, 1H), 7.670-7.634 (d, J=8.7 Hz, 1H), 7.233-7.217 (m, 3H), 7.154-7.127 (d, J=8.1 Hz, 1H), 3.238-3.192 (t, 2H), 2.974-2.928 (t, 3H), 2.065 (s, 3H), LCMS: 482.90 (MH+).

IX-45: N2-(3-Aminosulfonyl-4-methylphenyl)-N4-[(4R)-1-(2-cyanoacetyl)-pyrrolidin-4-yl)-5-fluoro-2,4-pyrimidinediamine $^1$H NMR (DMSO-d$_6$): δ 9.324 (s, 1H), 8.540 (s, 1H), 7.904-7.891 (d, J=3.9 Hz, 1H), 7.670-7.650 (d, J=6 Hz, 1H), 7.579-7.557 (d, J=6.6 Hz, 1H), 7.185 (s, 1H), 7.158 (s, 1H), 4.673 (bs, 1H), 3.705 (bs, 1H), 3.552-3.457 (m, 2H), 3.371-3.355 (m, 1H), 2.186 (bs, 1H), 2.032-1.979 (m, 1H), LCMS: 434.42 (MH$^+$).

VI-113: N2,N4-Bis-(3-aminosulfonylphenyl)-5-fluoro-2,4-pyrimidinediamine $^1$H NMR (DMSO-d$_6$): δ 9.75 (s, 1H), 9.52 (s, 1H), 8.20 (m, 2H), 8.11 (d, 2H, J=7.2 Hz), 7.94 (d, 1H, J=8.1 Hz), 7.52 (m, 2H), 7.41 (m, 4H), 7.27 (s, 2H): LCMS: purity: 94%; MS (m/e): 440 (MH+).

VI-114: N2,N4-Bis-(3-aminosulfonyl-4-methylphenyl)-5-fluoro-2,4-pyrimidinediamine $^1$H NMR (DMSO-d$_6$): δ 9.61 (s, 1H), 9.33 (s, 1H), 8.23 (d, 2H, J=2.1 Hz), 8.11 (d, 2H, J=1.8 Hz), 8.02 (m, 1H), 7.88 (m, 1H), 7.40 (s, 2H), 7.31 (d, 1H, J=8.4 Hz), 7.24 (s, 2H), 7.21 (d, 1H, J=8.4 Hz), 2.55 (s, 6H): LCMS: purity: 89%; MS (ne): 468 (MH$^+$).

VI-115: N2,N4-Bis-(3-aminosulfonyl-4-chlorophenyl)-5-fluoro-2,4-pyrimidinediamine $^1$H NMR (DMSO-d$_6$): δ 9.86 (s, 1H), 9.64 (s, 1H), 8.34 (d, 1H, J=2.7 Hz), 8.28 (d, 1H, J=3.0 Hz), 8.24 (d, 1H, J=2.7 Hz), 8.20 (d, 1H, J=3.6 Hz), 8.01 (m, 1H), 7.63 (s, 1H), 7.57 (d, 1H, J=8.7 Hz), 7.49 (s, 1H), 7.46 (s, 1H): LCMS: purity: 91%; MS (m/e): 508 (MH$^+$).

IX-17: N2-[3-Aminosulfonyl-4-(4-methylpiperazine-1-yl)phenyl]-N4-(3-cyanomethylene-1H-indol-6-yl)-5-fluoro-2,4-pyrimidinediamine LCMS: purity: 94%; MS (n/e): 537 (MH$^+$).

IX-18: N2-[3-Aminosulfonyl-4-(4-methylpiperazine-1-yl)phenyl]-N4-(3-cyanomethylene-1H-indol-7-yl)-5-fluoro-2,4-pyrimidinediamine LCMS: purity: 96%; MS (ne): 537 (MH$^+$).

VI-116: N2-[3-Aminosulfonyl-4-(4-methylpiperazine-1-yl)phenyl]-N4-(3-chloro-4-methoxyphenyl)-5-fluoro-2,4-pyrimidinediamine LCMS: purity: 92%; MS (n/e): 523 (MH$^+$).

IX-19: N4-(3-cyanomethylene-1H-indol-5-yl)-5-fluoro-N2-[3-(1-methyl-4-aminopiperadine)sulfonyl-4-methylphenyl]-2,4-pyrimidinediamine LCMS: purity: 97%; MS (ne): 549 (MH$^+$).

I-78: N2-(3-Aminosulfonylphenyl)-N4-[4-(N-cyanoacetyl)aminophneyl]-5-fluoro-2,4-pyrimidinediamine $^1$H NMR (DMSO-d$_6$): δ 8.10 (s, 2H), 7.95 (s, 1H), 7.80 (s, 2H), 7.55 (s, 2H), 7.34 (s, 1H), 7.26 (s, 1H), 3.88 (s, 2H): LCMS: purity: 96%; MS (ne): 442 (MH$^+$).

I-79: N2-(3-Aminosulfonyl-4-methylphenyl)-N4-[4-(N-cyanoacetyl)aminophneyl]-5-fluoro-2,4-pyrimidinediamine $^1$H NMR (DMSO-d$_6$): δ 8.11 (s, 1H), 8.06 (s, 1H), 7.78 (d, 1H, J=8.7 Hz), 7.50 (d, 2H, J=8.7 Hz), 7.17 (m, 3H), 3.88 (s, 2H): LCMS: purity: 91%; MS (m/e): 456 (MH$^+$).

I-80: N2-(3-Aminosulfonylphenyl)-5-fluoroN4-[3-methyl-4-(N-cyanoacetyl)aminophneyl]-2,4-pyrimidinediamine $^1$H NMR (DMSO-d$_6$): δ 8.11 (d, 1H, J=3.6 Hz), 8.03 (s, 1H), 7.98 (d, 1H, J=6.6 Hz), 7.58 (s, 2H), 7.35 (d, 2H, J=9.0 Hz), 7.26 (s, 1H), 3.91 (s, 2H), 2.19 (s, 3H): LCMS: purity: 92%; MS (m/e): 456 (MH$^+$).

I-81: N2-(3-Aminosulfonyl-4-methylphenyl)-5-fluoroN4-[3-methyl4-(N-cyanoacetyl)aminophneyl]-2,4-pyrimidinediamine $^1$H NMR (DMSO-d$_6$): δ 8.07 (s, 1H), 7.89 (s, 1H), 7.60 (s, 1H), 7.23 (m, 5H), 3.90 (s, 2H), 2.49 (s, 3H), 2.18 (s, 3H): LCMS: purity: 98%; MS (m/e): 470 (MH$^+$).

I-82: N2-(3-Aminosulfonylphenyl)-N4-[3-chloro-4-(N-cyanoacetyl)aminophneyl]-5-fluoro-2,4-pyrimidinediamine $^1$H NMR (DMSO-d$_6$): δ 8.17 (d, 1H, J=3.6 Hz), 8.06 (s, 1H), 7.96 (d, 1H, J=5.4 Hz), 7.85 (d, 1H, J=8.7 Hz)), 7.59

(s, 1H), 7.40 (s, 1H), 7.36 (d, 1H, J=8.1 Hz), 7.26 (s, 1H), 3.97 (s, 2H): LCMS: purity: 97%; MS (m/e): 476 (MH$^+$).

I-83: N2-(3-Aminosulfonyl-4-methylphenyl)-N4-[3-chloro-4-(N-cyanoacetyl)aminophneyl]-5-fluoro-2,4-pyrimidinediamine $^1$H NMR (DMSO-d$_6$): δ 8.13 (d, 1H, J=3.3), 7.89 (d, 1H, J=2.1) 7.85 (m, 1H), 7.59 (d, 1H, J=9.0 Hz), 7.21 (m, 2H), 3.97 (s, 2H), 2.49 s, 3H): LCMS: purity: 90%; MS (m/e): 490 (MH$^+$).

I-84: N2-(3-Aminosulfonylphenyl)-5-fluoroN4-[3-methoxy-4-(N-cyanoacetyl)aminophneyl]-2,4-pyrimidinediamine $^1$H NMR (DMSO-d$_6$): δ 9.55 (s, 1H), 0.50 (s, 1H), 9.39 (s, 1H), 8.11 (s, 1H) 7.98 (d, 1H, J=7.2 Hz), 7.81 (d, 1H, J=8.4 Hz), 7.53 (d, 1H, J=9.3 Hz), 7.41 (s, 1H), 7.34 (s, 2H), 7.25 (s, 1H), 3.96 (s, 2H), 3.78 (s, 3H): LCMS: purity: 93%; MS (m/e): 472 (MH$^+$).

I-85: N2-(3-Aminosulfonyl-4-methylphenyl)-5-fluoroN4-[3-methoxy-4-(N-cyanoacetyl)aminophneyl]-2,4-pyrimidinediamine $^1$H NMR (DMSO-d$_6$): δ 9.55 (s, 1H), 9.39 (s, 1H), 9.35 (s, 1H), 8.08 (t, 3H, J=2.4) 7.92 (d, 1H, J=8.1 Hz), 7.81 (d, 1H, J=8.7 Hz), 7.53 (d, 1H, J=9.6 Hz), 7.41 (s, 1H), 7.23 (s, 2H), 7.17 (d, 1H, J=7.8 Hz), 3.96 (s, 2H), 3.77 (s, 3H), 2.49 (s, 3H): LCMS: purity: 93%; MS (m/e): 486 (MH$^+$).

I-86: N2-(3-Aminosulfonylphenyl)-N4-[4-(N-cyanoacetyl-N-methyl)aminophneyl]-5-fluoro-2,4-pyrimidinediamine $^1$H NMR (DMSO-d$_6$): δ 8.17 (d, 1H, J=3.6 Hz)), 8.13 (s, 1H), 7.92 (t, 3H, J=8.1 Hz), 7.40 (m, 4H), 3.59 (s, 2H), 3.17 (s, 3H): LCMS: purity: 96%; MS (m/e): 457 (MH$^+$).

I-87: N2-(3-Aminosulfonyl-4-methylphenyl)-N4-[4-(N-cyanoacetyl-N-methyl)aminophneyl]-5-fluoro-2,4-pyrimidinediamine $^1$H NMR (DMSO-d$_6$): δ 8.12 (s, 2H), 7.94 (d, 2H, J=8.7 Hz), 7.86 (d, 1H, J=6.0 Hz), 7.31 (d, 2H, J=9.0 Hz), 7.28 (d, 3H, J=8.4 Hz), 3.60 (s, 2H), 3.17 (s, 3H), 2.49 (s, 3H): LCMS: purity: 93%; MS (m/e): 471 (MH$^+$).

Example 41

Assay for Ramos B-Cell Line Stimulated with IL-4

B-cells stimulated with cytokine Interleukin-4 (IL-4) activate the JAK/Stat pathway through phosphorylation of the JAK family kinases, JAK-1 and JAK-3, which in turn phosphorylate and activate the transcription factor Stat-6. One of the genes upregulated by activated Stat-6 is the low affinity IgE receptor, CD23. To study the effect of inhibitors on the JAK family kinases, human Ramos B cells are stimulated with human IL-4.

The Ramos B-cell line was acquired from ATCC (ATCC Catalog No. CRL-1596). The cells were cultured in RPMI 1640 (Cellgro, MediaTech, Inc., Herndon, VA, Cat No. 10-040-CM) with 10% fetal bovine serum (FBS), heat inactivated (JRH Biosciences, Inc, Lenexa, Kansas, Cat No. 12106-500M) according to ATCC propagation protocol. Cells were maintained at a density of 3.5×10$^5$. The day before the experiment, Ramos B-cells were diluted to 3.5× 10$^5$ cells/mL to ensure that they were in a logarithmic growth phase.

Cells were spun down and suspended in RPMI with 5% serum. 5×10$^4$ cells were used per point in a 96-well tissue culture plate. Cells were pre-incubated with compound or DMSO (Sigma-Aldrich, St. Louis, MO, Cat No. D2650) vehicle control for 1 hour in a 37° C. incubator. Cells were then stimulated with IL-4 (Peprotech Inc., Rocky Hill, NJ, Cat No. 200-04) for a final concentration of 50 units/mL for 20-24 hours. Cells were then spun down and stained with anti-CD23-PE(BD Pharmingen, San Diego, CA, Cat No. 555711) and analyzed by FACS. Detection was performed using a BD LSR I System Flow Cytometer, purchased from Becton Dickinson Biosciences of San Jose, California The IC$_{50}$ calculated based on the results of this assay are provided in TABLE XII.

Example 42

Primary Human T-Cell Proliferation Assay Stimulated with IL-2

Primary human T-cells derived from peripheral blood and pre-activated through stimulation of the T-cell receptor and CD28, proliferate in vitro in response to the cytokine Interleukin-2 (IL-2). This proliferative response is dependent on the activation of JAK-1 and JAK-3 tyrosine kinases, which phosphorylate and activate the transcription factor Stat-5.

Human primary T cells were prepared as follows. Whole blood was obtained from a healthy volunteer, mixed 1:1 with PBS, layered on to Ficoll Hypaque (Amersham Pharmacia Biotech, Piscataway, NJ, Catalog #17-1440-03) in 2:1 blood/PBS:ficoll ratio and centrifuged for 30 min at 4° C. at 1750 rpm. The lymphocytes at the serum: ficoll interface were recovered and washed twice with 5 volumes of PBS. The cells were resuspended in Yssel's medium (Gemini Bio-products, Woodland, CA, Catalog #400-103) containing 40 U/mL recombinant IL2 (R and D Systems, Minneapolis, MN, Catalog #202-IL (20 rig)) and seeded into a flask pre-coated with 1 µg/mL anti-CD3 (BD Pharmingen, San Diego, CA, Catalog #555336) and 5 µg/mL anti-CD28 (Immunotech, Beckman Coulter of Brea CA, Catalog #IM1376). The primary T-cells were stimulated for 3-4 days, then transferred to a fresh flask and maintained in RPMI with 10% FBS and 40 U/mL IL-2.

Primary T-cells were washed twice with PBS to remove the IL-2 and resuspended in Yssel's medium at 2×10$^6$ cells/mL. 50 µL of cell suspension containing 80 U/mL IL-2 was added to each well of a flat bottom 96 well black plate. For the unstimulated control, IL-2 was omitted from the last column on the plate. Compounds were serially diluted in dimethyl sulfoxide (DMSO, 99.7% pure, cell culture tested, Sigma-Aldrich, St. Louis, MO, Catalog No. D2650) from 5 mM in 3-fold dilutions, and then diluted 1:250 in Yssel's medium. 50 µL of 2× compound was added per well in duplicate and the cells were allowed to proliferate for 72 hours at 37° C.

Proliferation was measured using CellTiter-Glo® Luminescent Cell Viability Assay (Promega), which determines the number of viable cells in culture based on quantitation of the ATP present, as an indicator of metabolically active cells. The substrate was thawed and allowed to come to room temperature. After mixing the Cell Titer-Glo reagent and diluent together, 100 µL was added to each well. The plates were mixed on an orbital shaker for two minutes to induce lysis and incubated at room temperature for an additional ten minutes to allow the signal to equilibrate. Detection was performed using a Wallac Victor2 1420 multilabel counter purchased from Perkin Elmer, Shelton, CT The $IC_{50}$ calculated based on the results of this assay are provided in TABLE XII.

Example 43

A549 Epithelial Line Stimulated with IFNγ

A549 lung epithelial cells up-regulate ICAM-1 (CD54) surface expression in response to a variety of different stimuli. Therefore, using ICAM-1 expression as readout, compound effects on different signaling pathways can be assessed in the same cell type. IFNγ up-regulates ICAM-1 through activation of the JAK/Stat pathway. In this example, the up-regulation of ICAM-1 by IFNγ was assessed.

The A549 lung epithelial carcinoma cell line originated from the American Type Culture Collection. Routine culturing was with F12K media (Mediatech Inc., Lenexa, KS, Cat. No. 10-025-CV) with 10% fetal bovine serum, 100 I.U. penicillin and 100 ng/mL streptomycin (complete F12k media). Cells were incubated in a humidified atmosphere of 5% $CO_2$ at 37° C. Prior to use in the assay, A549 cells were washed with PBS and trypsinized (Mediatech Inc., Cat. No. 25-052-CI) to lift the cells. The trypsin cell suspension was neutralized with complete F12K media and centrifuged to pellet the cells. The cell pellet was resuspended in complete F12K media at a concentration of $2.0 \times 10^5$/mL. Cells were seeded at 20,000 per well, 100 µL total volume, in a flat bottom tissue culture plate and allowed to adhere overnight.

On day two, A549 cells were pre-incubated with a 2,4-substituted pyrimidinediamine test compound or DMSO (control) (Sigma-Aldrich, St. Louis, MO, Catalog No. D2650) for 1 hour. The cells were then stimulated with IFNγ (75 ng/mL) (Peprotech Inc., Rocky Hill, NJ, Cat. No. 300-02) and allowed to incubate for 24 hours. The final test compound dose range was 30 µM to 14 nM in 200 µL F12K media containing 5% FBS, 0.3% DMSO.

On day three, the cell media was removed and the cells were washed with 200 µL PBS (phosphate buffered saline). Each well was trypsinized to dissociate the cells, then neutralized by addition of 200 µL complete F12K media. Cells were pelleted and stained with an APC conjugated mouse anti-human ICAM-1 (CD54) (BD Pharmingen, San Diego, CA, Catalog #559771) antibody for 20 minutes at 4° C. Cells were washed with ice cold FACS buffer (PBS+2% FBS) and surface ICAM-1 expression was analyzed by flow cytometry. Detection was performed using a BD LSR I System Flow Cytometer, purchased from BD Biosciences of San Jose, California Events were gated for live scatter and the geometric mean was calculated (Becton-Dickinson Cell-Quest software version 3.3, Franklin Lakes, NJ). Geometric means were plotted against the compound concentration to generate a dose response curve. The $IC_{50}$ calculated based on the results of this assay are provided in TABLE XII.

Example 44

U937 IFNγ ICAM1 FACS Assay

U937 human monocytic cells up-regulate ICAM-1 (CD54) surface expression in response to a variety of different stimuli. Therefore, using ICAM-1 expression as readout, compound effects on different signaling pathways can be assessed in the same cell type. IFNγ up-regulates ICAM-1 through activation of the JAK/Stat pathway. In this example, the up-regulation of ICAM-1 by IFNγ was assessed.

The U937 human monocytic cell line was obtained from ATCC of Rockville Maryland, catalog number CRL-1593.2, and cultured in RPM1-1640 medium containing 10% (v/v) FCS. U937 cells were grown in 10% RPMI. The cells were then plated at a concentration of 100,000 cells per 160 µL in 96 well flat bottom plates. The test compounds were then diluted as follows: 10 mM test compound was diluted 1:5 in DMSO (3 µL 10 mM test compound in 12 µL DMSO), followed by a 1:3 serial dilution of test compound in DMSO (6 µL test compound serially diluted into 12 µL DMSO to give 3-fold dilutions). Then 4 µL of test compound was transferred to 76 µL of 10% RPMI resulting in a 10× solution (100 µM test compound, 5% DMSO). For control wells, 4 µL of DMSO was diluted into 76 µL 10% RPMI.

The assay was performed in duplicate with 8 points (8 3-fold dilution concentrations from 10 µl) and with 4 wells of DMSO only (control wells) under stimulated conditions and 4 wells of DMSO only under unstimulated conditions.

The diluted compound plate was mixed 2× using a multimek (Beckman Coulter of Brea, California) and then 20 µL of the diluted compounds was transferred to the 96 well plate containing 160 µL of cells, which were then mixed again twice at low speeds. The cells and compounds were then pre-incubated for 30 minutes at 37° C. with 5% $CO_2$.

The 10× stimulation mix was made by preparing a 100 ng/mL solution of human IFNγ in 10% RPMI. The cells and compound were then stimulated with 20 µL of IFNγ stimulation mix to give a final concentration of 10 ng/mL IFNγ, 10 µM test compound, and 0.5% DMSO. The cells were kept under conditions for stimulation for 18-24 hours at 37° C. with 5% $CO_2$.

The cells were transferred to a 96 well round bottom plate for staining and then kept on ice for the duration of the staining procedure. Cells were spun down at 1000 rpm for 5 minutes at 4° C., following which the supernatant was removed. Following removal of the supernatant, 1 µL APC conjugated mouse anti-human ICAM-1 antibody was added per 100 µL FACS buffer. The cells were then incubated on ice in the dark for 30 minutes. Following incubation, 1504 of FACS buffer was added and the cells were centrifuged at 1000 rpm for 5 minutes at 4° C., following which the supernatant was removed. After removal of the supernatant, 200 µL of FACS buffer was added and the cells were resuspended. After suspension, the cells were centrifuged at 1000 rpm for 5 min at 4° C. Supernatant was then removed prior to resuspension of the cells in 150 µL FACS buffer.

Detection was performed using a BD LSR I System Flow Cytometer, purchased from BD Biosciences of San Jose, California The live cells were gated for live scatter and the geometric mean of ICAM-APC was measured (Becton-Dickinson CellQuest software version 3.3, Franklin Lakes, NJ). Both % live cells and ICAM-1 expression was analyzed. The assays for the test compounds were carried out in parallel with a control compound of known activity. The $EC_{50}$ for the control compound is typically 40-100 nM. The $IC_{50}$ calculated based on the results of this assay are provided in TABLE XII.

TABLE XII

| Compound | Example 41 | Example 42 | Example 43 | Example 44 |
|---|---|---|---|---|
| I-1 | 0.36551 | 9.89222 | 18.4509 | 35.3335 |
| I-2 | 0.53194 | | | |

TABLE XII-continued

| Compound | Example 41 | Example 42 | Example 43 | Example 44 |
|---|---|---|---|---|
| I-3 | 0.10738 | 0.98708 | 9999 | |
| I-4 | 0.04905 | 0.17843 | 4.85721 | |
| I-5 | 1.64619 | | 29.901 | |
| I-6 | 0.52212 | | 20.9805 | 9999 |
| I-7 | 0.12002 | 0.50172 | | |
| I-8 | 0.0587 | 0.1743 | 9999 | 0.41 |
| I-9 | 0.23306 | 0.48494 | 15.6334 | 0.78723 |
| I-10 | 0.02551 | 0.09568 | 6.54622 | 0.26124 |
| I-11 | 0.02333 | 0.03929 | 17.6237 | 0.3294 |
| I-12 | 0.03694 | 0.05968 | 3.19514 | 0.22195 |
| I-13 | 0.00627 | 0.00505 | 1.34069 | 0.0435 |
| I-14 | 0.01296 | 0.01149 | 0.61167 | 0.04176 |
| I-15 | 0.30896 | 1.18318 | | 4.96519 |
| I-16 | 0.12424 | 0.4356 | 7777 | |
| I-17 | 0.0487 | 0.04318 | 2.34513 | 0.36534 |
| I-18 | 0.28251 | 1.48925 | 8888 | 2505.23 |
| I-19 | 0.50856 | 1.04177 | 24.8675 | 10.0825 |
| I-20 | 0.03672 | 0.06619 | 6.53867 | 0.33882 |
| I-21 | 0.09302 | 0.25767 | 22.7159 | 0.8223 |
| I-22 | 0.23636 | 0.94439 | 14.3679 | 4.43304 |
| I-23 | 0.03013 | 0.08823 | 9999 | 0.45476 |
| I-24 | 0.05422 | 0.29639 | 9999 | 1.04466 |
| I-25 | 0.05582 | 1.6129 | 25.3098 | 8888 |
| I-26 | 0.03781 | 0.40073 | 4.23449 | 0.42446 |
| I-27 | 0.06186 | 0.91443 | 3.48033 | 0.53438 |
| I-28 | 0.06454 | 0.5598 | 7777 | 1.89233 |
| I-29 | 0.1196 | 0.50183 | | |
| I-30 | 5.43333 | 3.57085 | | |
| I-31 | 4.62505 | | | |
| I-32 | 0.16136 | 2.78095 | 5.49713 | 1.96749 |
| I-33 | 0.0965 | 0.1705 | 8888 | 0.89708 |
| I-34 | 0.06229 | 0.80566 | 7777 | 1.05493 |
| I-35 | 0.04696 | 1.1331 | 8.58425 | 1.82151 |
| I-36 | 8.80466 | 9999 | | |
| I-37 | 0.49851 | 3.68499 | | 5.73717 |
| I-38 | 6.44228 | | | |
| I-39 | 0.84081 | | | 9.32297 |
| I-40 | 0.30838 | | 31.0382 | 3345.23 |
| I-41 | 0.03738 | | 10.15 | |
| I-42 | 0.02408 | | 8888 | |
| I-43 | 0.01826 | 0.18317 | 36.6502 | 0.77073 |
| I-44 | 0.05316 | 0.34166 | 9999 | 5.06833 |
| I-45 | 0.1036 | 0.83377 | 17.0422 | 3.63512 |
| I-46 | 0.11322 | 0.40872 | 9999 | 0.75129 |
| I-47 | 0.12011 | 0.55068 | | 0.75908 |
| I-48 | 1.40357 | | | |
| I-49 | 2.31794 | 5.55983 | | |
| I-50 | 0.37337 | | | 25.1264 |
| I-51 | 0.26268 | 2.11715 | | 32.1941 |
| I-52 | 0.15228 | 5.30087 | 9999 | 68.6571 |
| I-53 | 0.23595 | | | 12.2055 |
| I-54 | 0.27682 | | | 7.15982 |
| I-55 | 9999 | | | |
| I-56 | 0.10355 | 0.2618 | 4.97271 | 0.42424 |
| I-57 | 0.02161 | 0.05314 | 9999 | 0.13971 |
| I-58 | 0.00505 | 0.01925 | 0.73026 | 0.06599 |
| I-59 | 0.00655 | 0.02487 | 0.94741 | 0.05766 |
| I-60 | 0.10288 | 2.17439 | 7.89243 | 0.84765 |
| I-61 | 0.04586 | 0.12299 | 8888 | 0.42748 |
| I-62 | 0.10056 | 0.37599 | 3.52859 | 0.73487 |
| I-63 | 0.16924 | 1.31421 | 34.3138 | 0.69103 |
| I-64 | 0.11281 | 1.87772 | 5.16607 | 1.15237 |
| I-65 | 0.09651 | 0.04731 | 8888 | 0.31629 |
| I-66 | 0.10306 | 0.28704 | 9999 | 0.68933 |
| I-67 | 0.03322 | 0.15663 | 4.61611 | 0.23869 |
| I-68 | 0.18704 | 0.48243 | 4.96049 | 0.91274 |
| I-69 | 0.11784 | 1.02837 | 5.64408 | 5000.08 |
| I-70 | 0.06138 | 0.57305 | 3.43038 | 0.384 |
| I-71 | 0.06178 | 0.13591 | 3.26769 | 0.32803 |
| I-72 | 0.05239 | 0.30295 | 3.30881 | 0.57377 |
| I-73 | 0.11976 | 0.7281 | 5.55843 | 1.06264 |
| I-74 | 0.24475 | 1.49815 | 10.7945 | 1.75731 |
| I-75 | 0.19865 | 3.3 | 7777 | 3.1 |
| I-76 | 0.10102 | 0.19585 | 5.13601 | 1.12224 |
| I-77 | 0.14716 | 1.61795 | | |
| I-78 | 0.6349 | 1.2051 | | |
| I-79 | 0.4606 | 1.0611 | | |
| I-80 | 0.3649 | 0.4697 | | |
| I-81 | 0.3597 | 0.9566 | | |
| I-82 | 0.2439 | 1.3819 | | |
| I-83 | 0.158 | 1.7561 | 14.9 | |
| I-84 | 1.4005 | | | |
| I-85 | 0.7913 | | | |
| I-86 | 0.9162 | | | |
| I-87 | 1.0381 | | | |
| I-88 | 1.07518 | | | |
| I-89 | 5.49992 | | 9999 | |
| I-90 | 0.40109 | 2.19063 | | 6.16341 |
| I-91 | 2.03142 | | | |
| I-92 | 0.16624 | 0.54302 | 9999 | 15.59 |
| I-93 | 0.26489 | 1.17393 | 23.774 | 11.0701 |
| I-94 | 0.34492 | 0.56287 | | 5.66845 |
| I-95 | 0.11825 | 0.32508 | 9999 | 6.3 |
| I-96 | 0.13177 | 0.77151 | 40.8692 | 3.30063 |
| I-97 | 0.21244 | 0.86883 | 31.0729 | 27.4081 |
| I-98 | 0.29451 | | 37.2587 | 10.9783 |
| I-99 | 0.06863 | 0.14752 | 9999 | 3.77549 |
| I-100 | 0.38027 | | 9999 | 6670.09 |
| I-101 | 0.32832 | | 51.1576 | 36.6028 |
| I-102 | 0.21893 | 0.21079 | 43.7663 | 15.5943 |
| I-103 | 1.24843 | | 9999 | |
| I-104 | 1.42542 | | 9999 | |
| I-105 | 1.1675 | | 9999 | |
| I-106 | 2.95316 | | | |
| I-107 | 1.51103 | | | |
| I-108 | 0.14545 | 0.14758 | 9999 | 3.97385 |
| I-109 | 0.30527 | 0.20336 | 25.9633 | 9.93933 |
| I-110 | 0.35788 | 0.25307 | 20.584 | 3.92933 |
| I-111 | 0.89035 | | 9999 | |
| I-112 | 2.36464 | | 9999 | |
| I-113 | 0.16466 | 1.6854 | 9999 | 13.5121 |
| I-114 | 0.44754 | 6.70638 | 9999 | 9999 |
| I-115 | 0.79259 | | 7777 | |
| I-116 | 0.27394 | 0.97166 | 9999 | 4455.33 |
| I-117 | 0.35266 | 0.30095 | 36.4268 | 14.5685 |
| I-118 | 0.292 | 0.55723 | | 2.42563 |
| I-119 | 0.21095 | 2.43898 | 9.67128 | 11.8985 |
| I-120 | 0.20071 | 0.27964 | 19.9754 | 4.45634 |
| I-121 | 0.18382 | 0.63384 | 14.5419 | 2.98512 |
| I-122 | 0.29151 | 3.5 | 9999 | 15.6681 |
| I-123 | 0.15927 | 0.22497 | 12.8283 | 2.2221 |
| I-124 | 0.10241 | 0.34199 | 10.373 | 1.33026 |
| I-125 | 0.53802 | | | |
| I-126 | 0.35476 | 0.60989 | | 7.20132 |
| I-127 | 0.2333 | 0.50965 | | 2.5105 |
| I-128 | 0.87135 | | | |
| I-129 | 0.61228 | | | |
| I-130 | 0.60114 | 1.73251 | | |
| I-131 | 0.26226 | 3.78086 | | 2.99277 |
| I-132 | 0.35129 | 0.46431 | | 2.71959 |
| I-133 | 0.23656 | 1.34872 | | 9999 |
| I-134 | 0.17762 | 0.50998 | 9999 | 3.23999 |
| I-135 | 0.11208 | 0.10418 | 3.24251 | 1.82933 |
| I-136 | 0.13205 | 0.19642 | 8.11382 | 1.64002 |
| I-137 | 0.38672 | 1.09918 | 9999 | 29.5795 |
| I-138 | 0.4607 | 0.22286 | 91.4861 | 9.46799 |
| I-139 | 0.37466 | 0.24038 | 11.5578 | 3.26019 |
| I-140 | 0.38751 | | | |
| I-141 | 0.1625 | 0.66903 | 15.6032 | |
| I-142 | 0.15485 | 0.85438 | 9999 | |
| I-143 | 1.19256 | | | |
| I-144 | 1.00541 | | | |
| I-145 | 0.54156 | 0.3493 | | |
| I-146 | 0.36436 | | 7777 | 9999 |
| I-147 | 0.07985 | 0.17442 | 7777 | 9999 |
| I-148 | 0.06117 | 0.24003 | 9999 | 9999 |
| I-149 | 0.1613 | 0.19724 | | 14.7293 |
| I-150 | 0.06569 | 0.06806 | 7777 | 10.5387 |
| I-151 | 0.06185 | 0.07829 | 9999 | 8888 |
| I-152 | 0.30174 | 1.5412 | | |
| I-153 | 0.11405 | 0.33375 | 9999 | |
| I-154 | 0.27631 | 0.9925 | 9999 | |
| I-155 | 0.11775 | 0.09932 | 9999 | 65.0584 |
| I-156 | 0.06549 | 0.14151 | 9999 | 2.62254 |

TABLE XII-continued

| Compound | Example 41 | Example 42 | Example 43 | Example 44 |
|---|---|---|---|---|
| I-157 | 0.24574 | 1.8906 | | 9999 |
| I-158 | 0.2967 | 0.44535 | | 1.38012 |
| I-159 | 0.33805 | 0.53944 | | 1.63449 |
| I-160 | 0.13042 | 0.2484 | | 0.92282 |
| I-161 | 0.31398 | | | 2.41123 |
| I-162 | 0.05105 | 0.13566 | 9999 | 0.59381 |
| I-163 | 0.17656 | 0.4391 | | 1.40511 |
| I-164 | 9999 | | | |
| I-165 | 0.24517 | 0.44644 | | 1.63555 |
| I-166 | 0.61646 | | | |
| I-167 | 0.14175 | | 7777 | |
| I-168 | 0.15437 | 1.17511 | 9999 | |
| I-169 | 0.0546 | 0.1373 | | 8888 |
| I-170 | 0.4507 | | | |
| I-171 | 0.11717 | 0.41497 | | |
| I-172 | 0.04734 | 0.2771 | 38.674 | 1.09663 |
| I-173 | 0.11513 | 0.907 | 9999 | 15.5343 |
| I-174 | 0.11681 | 1.23383 | 8888 | |
| I-175 | 0.14696 | 3.0806 | 9999 | |
| I-176 | 0.25875 | 1.69038 | | |
| I-177 | 8888 | 0.5 | | |
| I-178 | 0.0235 | 0.0293 | | 0.11756 |
| I-179 | 0.02427 | 0.01178 | | 0.11711 |
| I-180 | 0.0624 | 0.02868 | | 0.4558 |
| I-181 | 0.01301 | | | |
| I-182 | 0.18961 | 1.12876 | | 8888 |
| I-183 | 0.24913 | 1.83159 | | 2.27747 |
| I-184 | 0.48571 | 2.57372 | | 6.62465 |
| I-185 | 0.29773 | | | 9999 |
| I-186 | 0.18828 | 1.08437 | | 3.53394 |
| I-187 | 2.91228 | | | |
| I-188 | 0.0427 | 0.0642 | 15.0825 | 0.50022 |
| I-189 | 0.13708 | 0.14331 | 6.74171 | 0.50811 |
| I-190 | 0.14533 | 0.24207 | 9.30992 | 1.5006 |
| I-191 | 0.13487 | 0.29228 | | 0.79644 |
| I-192 | 0.13748 | 0.15499 | | 0.97787 |
| I-193 | 0.03822 | 0.05562 | 9999 | |
| I-194 | 0.02858 | 0.09935 | 5.02722 | |
| I-195 | 0.08263 | 0.12705 | 9999 | 9999 |
| I-196 | 0.12446 | 0.13926 | 9999 | 0.75397 |
| I-197 | 0.13477 | 0.32885 | | 1.2782 |
| I-198 | 0.10154 | 0.46016 | 9999 | 0.80536 |
| I-199 | 0.23967 | 3.02692 | | 2.68752 |
| I-200 | 9999 | | | |
| I-201 | 9999 | | | |
| I-202 | | 3.075 | | |
| I-203 | 0.26472 | 0.68359 | 5.77164 | 3.1332 |
| I-204 | 0.25571 | 1.6463 | | 3.92821 |
| I-205 | 0.31543 | 1.8632 | 9.4856 | 3341.09 |
| I-206 | 0.72572 | | | |
| I-207 | 8888 | | | |
| I-208 | 1.39961 | | | |
| I-209 | 0.58003 | 4.46766 | 2.96679 | 9999 |
| I-210 | 0.86614 | | | |
| I-211 | 1.05253 | | | |
| I-212 | 0.75778 | | | |
| I-213 | 11.4811 | | | |
| I-214 | 0.14442 | 1.32831 | | 1.30455 |
| I-215 | 0.97626 | | | |
| I-216 | 0.20482 | 0.49337 | | 1.56836 |
| I-217 | 0.02498 | 0.21692 | 36.591 | 0.4785 |
| I-218 | 0.07262 | 0.11588 | 3.26785 | 0.43399 |
| I-219 | 0.03162 | 0.12305 | 7.16246 | 0.58776 |
| I-220 | 0.12138 | 1.06662 | 7777 | 8888 |
| I-221 | 0.34372 | 2.68161 | | 4.43571 |
| I-222 | 0.03308 | 0.58244 | 9999 | 0.84 |
| I-223 | 0.08803 | 0.62525 | 9.08836 | 1.20989 |
| I-224 | 0.03615 | 0.19417 | 11.324 | 0.4936 |
| I-225 | 0.69987 | | | |
| I-226 | 0.49797 | | | |
| I-227 | 1.48242 | | | |
| I-228 | 3.80514 | | | |
| I-229 | 3.75639 | | | |
| I-230 | 0.08426 | 0.06925 | 10.477 | 0.46548 |
| I-231 | 0.09468 | 0.29003 | 9999 | 8.40421 |
| I-232 | 1.42979 | | | |
| I-233 | 0.14834 | 0.37693 | 9999 | 1.74874 |
| I-234 | 0.10247 | 1.00762 | 8.15676 | 2.01923 |
| I-235 | 0.17818 | 0.4695 | 9999 | 2.55555 |
| I-236 | 1.98037 | | | |
| I-237 | 0.14699 | 2.04005 | 9999 | 3.57746 |
| I-238 | 0.16427 | 0.45567 | 9999 | 1.12717 |
| I-239 | 0.23965 | | 9999 | 7.05758 |
| I-240 | 0.20499 | 5.25922 | | 8888 |
| I-241 | 0.26564 | 0.44243 | | 2.87423 |
| I-242 | 0.52009 | | | |
| I-243 | 0.91747 | | | |
| I-244 | 0.28501 | 1.40668 | 14.7078 | 3.11959 |
| I-245 | 0.20153 | 1.74332 | 16.6871 | 4.1888 |
| I-246 | 0.10624 | 0.18232 | 8.87569 | 0.87257 |
| I-247 | 0.225 | 0.1187 | 11.115 | 1.0767 |
| I-248 | 0.38838 | 0.13774 | | 2.65851 |
| I-249 | 0.51223 | | | 11.0003 |
| I-250 | 0.67255 | | | |
| I-251 | 0.16719 | 0.15516 | 34.8518 | 1.09204 |
| I-252 | 0.0906 | 0.55777 | 74.2104 | 2.46619 |
| I-253 | 0.12662 | 2.56423 | | |
| I-254 | 0.15452 | 1.91498 | 8.95614 | 1.82459 |
| I-255 | 0.25614 | 2.86397 | 39.3342 | 5.52062 |
| I-256 | 0.28206 | 38.2034 | 9999 | 15.9307 |
| I-257 | 0.14527 | 0.10222 | 3.07682 | 0.95888 |
| I-258 | 0.02798 | 0.05539 | 9999 | 0.3241 |
| I-259 | 0.02793 | 0.06575 | 7.50745 | 0.3147 |
| I-260 | 0.09477 | 0.22271 | 8.44012 | 0.98515 |
| I-261 | 5031.28 | | | |
| I-262 | 0.07832 | 0.16396 | 3.67509 | 1.04486 |
| I-263 | 0.12368 | 0.06443 | | 0.66548 |
| I-264 | 0.59917 | | | 14.9995 |
| I-265 | 0.04232 | 0.0397 | 4.08382 | 0.41479 |
| I-266 | 0.08513 | 0.20071 | 9999 | 0.824 |
| I-267 | 0.32828 | 2.01965 | | 5.06578 |
| I-268 | 0.06074 | 0.13983 | 5.0785 | 0.21895 |
| I-269 | 0.91657 | | | |
| I-270 | 0.77962 | | | |
| I-271 | 9999 | | | |
| I-272 | 0.78775 | | | |
| I-273 | 0.47773 | 0.19296 | 12.8791 | 5.10428 |
| I-274 | 1.17189 | | | |
| I-275 | 0.22313 | 0.57744 | 9999 | 1.9 |
| I-276 | 0.13508 | 0.10582 | 8.0902 | 0.8217 |
| I-277 | 0.15065 | 0.09153 | 6.91127 | 1.47355 |
| I-278 | 0.19343 | 0.41215 | 11.0338 | 2.26901 |
| I-279 | 0.12274 | 0.16744 | 9999 | 0.9178 |
| I-280 | 0.14472 | 0.9783 | | 1.45628 |
| I-281 | 0.09321 | 0.09036 | 9999 | 0.97459 |
| I-282 | 0.33926 | 0.69745 | | 3.10495 |
| I-283 | 0.51821 | 0.3617 | | 2.94063 |
| I-284 | 0.13587 | 0.42105 | | 1.54787 |
| I-285 | 0.13257 | 0.31358 | | 1.485 |
| II-1 | 0.18176 | 1.13989 | | 8.32597 |
| II-2 | 0.24439 | 1.51926 | | 4.59317 |
| II-3 | 0.08404 | 0.91766 | 11.921 | 6.50431 |
| II-4 | 0.31643 | 2.37109 | | 3.51083 |
| II-5 | 2.20619 | | | |
| II-6 | 0.11067 | 1.2178 | | 6.38785 |
| II-7 | 0.14372 | 0.52156 | | 1.62567 |
| II-8 | 0.03878 | 0.56414 | 9999 | |
| II-9 | 0.23159 | 1.31747 | | 2.7171 |
| II-10 | 0.36923 | 0.8756 | | 1.39632 |
| II-11 | 0.10669 | 0.19762 | | 0.91162 |
| II-12 | 0.05626 | 0.40891 | 5.52004 | 1.19102 |
| II-13 | 0.32334 | | | |
| II-14 | 0.04685 | 0.57852 | | |
| II-15 | 0.98189 | 1.10065 | | |
| II-16 | 18.3048 | 3.71528 | | |
| II-17 | 21.2024 | 8.20964 | | |
| II-18 | 2.04279 | 3.30797 | | |
| II-19 | 0.39546 | 8888 | | 9999 |
| II-20 | 0.42846 | 0.96892 | | 11.5294 |
| II-21 | 0.69755 | 1.76163 | | 41.7481 |
| II-22 | 0.85847 | 7.48812 | | |
| III-1 | 0.15102 | 0.54475 | | 1.11685 |
| III-2 | 0.22374 | 3.43534 | | 6.71592 |
| III-3 | 0.53624 | | | |

TABLE XII-continued

| Compound | Example 41 | Example 42 | Example 43 | Example 44 |
|---|---|---|---|---|
| III-4 | 0.01872 | 0.17102 | 8.36734 | 1.71666 |
| III-5 | 4.9773 | | 9999 | |
| III-6 | 0.78109 | | 30.674 | |
| III-7 | 0.0851 | 0.19544 | 12.3228 | 1.08953 |
| III-8 | 0.13823 | 0.92083 | 14.4636 | 2.2522 |
| III-9 | 0.21457 | 1.80396 | 23.6063 | 6.98319 |
| III-10 | 0.22461 | 0.92188 | 9999 | 3.52348 |
| III-11 | 0.0642 | 0.04604 | 2.24405 | 0.16825 |
| III-12 | 0.07001 | 0.10746 | 3.51838 | 0.32092 |
| III-13 | 0.2953 | 0.70092 | | |
| III-14 | 0.13985 | 0.05263 | 3.60147 | 0.58483 |
| III-15 | 0.07596 | 0.10691 | 4.65521 | 0.55294 |
| III-16 | 0.2733 | 0.34222 | 7.23576 | 1.79675 |
| III-17 | 0.05674 | 0.1974 | | 0.78205 |
| III-18 | 0.03659 | 0.13567 | | 0.54387 |
| III-19 | 0.07229 | 0.17392 | 21.8899 | 0.05559 |
| III-20 | 0.04299 | 0.76298 | 6.63588 | 3.33323 |
| III-21 | 0.0303 | 0.11378 | | 0.33867 |
| III-22 | 0.04545 | 0.07611 | 8888 | 0.44428 |
| III-23 | 0.39727 | | | |
| III-24 | 0.25751 | 1.62056 | | |
| III-25 | 0.27162 | 1.25963 | | |
| III-26 | 0.16196 | 0.58276 | | |
| III-27 | 0.05834 | 0.11898 | 7777 | 0.25737 |
| III-28 | 3.74795 | 17.4221 | | |
| III-29 | 3.63333 | 12.3622 | 9999 | |
| III-30 | 0.06455 | 0.31911 | | 9999 |
| III-31 | 0.09536 | 0.32762 | | 1.70465 |
| III-32 | 4.40366 | 3.31651 | 9999 | |
| III-33 | 1.68071 | 0.85213 | | |
| III-34 | 0.47276 | 0.38085 | | |
| III-35 | 1.0814 | | | |
| III-36 | 0.3944 | 0.3819 | | |
| III-37 | 0.2997 | | | 0.834 |
| III-38 | 0.1976 | 1.127 | | |
| III-39 | 0.1171 | 0.1297 | 4.15 | 1.435 |
| III-40 | 0.1341 | 0.2286 | | 1.116 |
| III-41 | 1.0134 | | | |
| III-42 | 0.2936 | 0.6406 | | |
| III-43 | 0.2705 | 0.8975 | | |
| III-44 | 1.43012 | | | |
| III-45 | 0.29277 | 0.38431 | | |
| III-46 | 0.21144 | 1.05234 | | |
| III-47 | 0.21084 | 0.36642 | | 9999 |
| III-48 | 0.20373 | 0.21773 | | 9999 |
| III-49 | 0.17801 | | | |
| III-50 | 0.30572 | 1.96867 | | |
| III-51 | 1.00749 | | | |
| III-52 | 0.18299 | 1.20459 | | |
| III-53 | 0.0977 | 0.28629 | | 1.13155 |
| III-54 | 0.13522 | 0.13989 | 9999 | 1.59326 |
| III-55 | 0.14436 | 0.97312 | | |
| III-56 | 0.19581 | 0.49929 | | |
| III-57 | 0.05356 | 0.16996 | 55.5368 | 0.83776 |
| III-58 | 0.15671 | 1.25684 | | |
| III-59 | 0.14965 | 0.45792 | | |
| III-60 | 0.13462 | 0.17751 | 25.5295 | 1.01469 |
| III-61 | 0.25873 | 1.08295 | | |
| III-62 | 0.1715 | 0.699 | | |
| III-63 | 0.3153 | 1.8768 | | |
| III-64 | 0.4473 | 5.9565 | | |
| III-65 | 0.209 | 0.9359 | | |
| III-66 | 0.14152 | 1.15034 | | 0.96668 |
| III-67 | 0.34745 | | | 3.05467 |
| III-68 | 3.23069 | | | |
| III-69 | 3.31825 | | | |
| III-70 | 0.06446 | 0.16921 | 9999 | 1.64984 |
| III-71 | 0.09785 | 0.36848 | 8.25586 | 1.70255 |
| III-72 | 1.95167 | | | |
| III-73 | 0.13087 | 0.43435 | | |
| III-74 | 0.09524 | 0.17541 | 9999 | 0.93514 |
| III-75 | 0.16969 | 0.22009 | 10.0944 | 1.77125 |
| III-76 | 0.1042 | 0.1348 | | 0.447 |
| III-77 | 0.1774 | 0.2095 | | 0.681 |
| III-78 | 0.2754 | 0.2041 | 7777 | 22.9 |
| III-79 | 0.16853 | 0.96749 | | |
| III-80 | 3.15582 | 0.84435 | | |
| III-81 | 0.18003 | 0.20392 | 48.3461 | 3.42825 |
| III-82 | 0.12695 | 0.15998 | 24.1674 | 2.27381 |
| III-83 | 0.09874 | 0.09622 | 9999 | 1.35976 |
| III-84 | 0.4428 | 1.8956 | | |
| III-85 | 0.07272 | 0.12242 | 9999 | 3.62044 |
| III-86 | 0.0976 | 0.09394 | 9999 | 6.44528 |
| III-87 | 0.14099 | 0.14172 | 76.2393 | 2.94666 |
| III-88 | 0.14065 | 0.16557 | 10.6231 | 2.03999 |
| III-89 | 0.11498 | | | |
| III-90 | 0.35751 | 0.46822 | | 2.6323 |
| III-91 | 0.14274 | 0.46742 | | |
| III-92 | 0.32272 | 1.89757 | | |
| III-93 | 0.17308 | 0.81891 | | |
| III-94 | 0.16161 | 0.71606 | | |
| III-95 | 0.1494 | 0.37003 | | 29.7109 |
| III-96 | 3.32588 | 2.18995 | | |
| III-97 | 0.27887 | 1.02568 | | |
| III-98 | 0.11654 | 0.45747 | | |
| III-99 | 1.03465 | 2.17142 | | |
| III-100 | 0.16233 | 0.19656 | | 1.9107 |
| III-101 | 0.2401 | 0.4464 | | |
| III-102 | 0.30171 | 0.48559 | | |
| III-103 | 0.23001 | 1.05998 | | 2.42638 |
| III-104 | 0.24173 | 1.19132 | | 2.1621 |
| III-105 | 1.27754 | | | |
| III-106 | 0.04277 | 0.07508 | 5.89649 | 0.49188 |
| III-107 | 0.21914 | 0.5404 | | 1.52384 |
| III-108 | 0.18343 | 1.21503 | | 1.50897 |
| III-109 | 0.14312 | 0.25198 | | 0.53111 |
| III-110 | 0.24698 | 0.99788 | | 13.5631 |
| III-111 | 0.32121 | 0.92557 | | 5.34359 |
| III-112 | 2.47605 | | | |
| III-113 | 1.0305 | | | 0.345 |
| III-114 | 2.6833 | | | |
| III-115 | 1.6524 | | | |
| III-116 | 0.19663 | 3.94714 | 7777 | |
| III-117 | 0.39696 | | | |
| III-118 | 0.62434 | 2.29421 | | |
| III-119 | 1.29867 | | | |
| III-120 | 0.65536 | 0.5542 | | |
| III-121 | 0.57495 | 1.0202 | | |
| III-122 | 0.53873 | | | |
| III-123 | 0.17252 | 1.38789 | | |
| III-124 | 0.29523 | | | |
| III-125 | 0.8356 | | | |
| III-126 | 0.1972 | 0.4701 | | |
| III-127 | 0.1982 | 0.6123 | | |
| III-128 | 0.14513 | 0.13942 | 28.0649 | 1.43941 |
| III-129 | 0.17355 | 0.1799 | 31.2977 | 1.187 |
| IV-1 | 0.07356 | 0.28652 | | 0.27169 |
| IV-2 | 0.08002 | 0.36242 | | 0.70488 |
| IV-3 | 0.09325 | | | |
| IV-4 | 0.15095 | 0.3032 | | 2.42396 |
| IV-5 | 0.09767 | 0.11589 | 16.0697 | 0.50367 |
| IV-6 | 0.10292 | 0.13159 | | 0.88048 |
| IV-7 | 0.11241 | 0.20304 | | 1.23784 |
| IV-8 | 0.16592 | 0.62672 | | |
| IV-9 | 0.19023 | 1 | | |
| IV-10 | 0.13472 | 0.71395 | | |
| IV-11 | 0.3672 | | | |
| IV-12 | 0.25666 | 1.21823 | | |
| V-1 | 2.00456 | 9.77279 | | 9999 |
| V-2 | 1.17796 | | | |
| V-3 | 0.66409 | | | 13.7306 |
| V-4 | 0.10843 | 1.53933 | 9.24355 | |
| V-5 | 0.69624 | | | |
| V-6 | 0.02185 | 0.07083 | 7777 | 0.57206 |
| V-7 | 0.05877 | 0.12703 | 5.00173 | 0.82053 |
| V-8 | 0.02908 | 0.22532 | 5.20729 | 0.61971 |
| V-9 | 1.11064 | | | |
| V-10 | 0.26102 | 8.26777 | | 2.69871 |
| V-11 | 0.0698 | 0.79519 | 8888 | 1.41593 |
| V-12 | 0.18817 | 0.95693 | 54.0071 | 3.03787 |
| V-13 | 0.05289 | 0.46847 | 6.86738 | 1.19717 |
| V-14 | 0.19711 | 2.59168 | | 6.84803 |
| V-15 | 0.17289 | 9.30756 | | 8888 |
| V-16 | 8.3722 | | | |

TABLE XII-continued

| Compound | Example 41 | Example 42 | Example 43 | Example 44 |
|---|---|---|---|---|
| VI-1 | 0.20474 | | | |
| VI-2 | 0.08925 | 3.57169 | | 9999 |
| VI-3 | 0.20565 | 8.79279 | 9999 | 9999 |
| VI-4 | 0.02107 | 0.2312 | 9999 | 9999 |
| VI-5 | 0.04047 | 0.71837 | 8888 | 1.3851 |
| VI-6 | 0.03747 | 1.44938 | 14.9708 | 7.70441 |
| VI-7 | 0.76592 | | | |
| VI-8 | 2.28135 | | | |
| VI-9 | 0.05327 | 0.94453 | 9.95895 | 14.5216 |
| VI-10 | 0.22022 | 2.39519 | 24.9026 | 9999 |
| VI-11 | 0.25923 | 4.61735 | 47.0634 | 7.13718 |
| VI-12 | 0.14575 | 1.3099 | 9999 | 8888 |
| VI-13 | 0.09654 | 1.34867 | 8.2263 | 1.3926 |
| VI-14 | 0.41325 | | 7777 | 9.26616 |
| VI-15 | 0.045 | 0.46887 | | 0.76722 |
| VI-16 | 0.25935 | 3.91458 | | 8888 |
| VI-17 | 0.04344 | 0.2436 | 6.42231 | 0.45391 |
| VI-18 | 0.25733 | 4.36513 | | 6.06278 |
| VI-19 | 1.02551 | | | |
| VI-20 | 0.72602 | | | |
| VI-21 | 11.321 | | | |
| VI-22 | 0.66268 | | | |
| VI-23 | 0.59672 | | | |
| VI-24 | 8.61565 | | | |
| VI-25 | 9.91092 | | | |
| VI-26 | 0.04444 | 0.0289 | 1.70264 | 0.257 |
| VI-27 | 0.07613 | | 3.7609 | 0.5446 |
| VI-28 | 0.75443 | | | |
| VI-29 | 0.04982 | 0.36201 | | 8888 |
| VI-30 | 0.01324 | 0.1702 | | 9999 |
| VI-31 | 18.2541 | | | |
| VI-32 | 0.33323 | 1.65819 | | |
| VI-33 | 0.27207 | 0.66049 | | |
| VI-34 | 0.1567 | 0.8386 | | |
| VI-35 | 0.1583 | 1.2589 | | |
| VI-36 | 0.3743 | 4.4975 | | |
| VI-37 | 0.0692 | 1.0785 | 12.4 | |
| VI-38 | 0.4143 | 2.0675 | | |
| VI-39 | 0.401 | 3.139 | | |
| VI-40 | 0.2883 | 1.2369 | | |
| VI-41 | 0.3425 | 6.2401 | | |
| VI-42 | 0.4515 | 6.1678 | | |
| VI-43 | 0.7393 | 6.1404 | | |
| VI-44 | 0.4293 | 7.3093 | | |
| VI-45 | 0.1081 | 1.3279 | 10.53 | |
| VI-46 | 0.1435 | 1.2558 | | |
| VI-47 | 0.0828 | 0.2589 | 9999 | 0.596 |
| VI-48 | 0.3153 | 2.2429 | | |
| VI-49 | 0.26786 | 1.26457 | | 2.09896 |
| VI-50 | 0.21701 | 0.94365 | | 1.87806 |
| VI-51 | 0.15225 | 0.54688 | 9999 | 2.13363 |
| VI-52 | 0.16844 | 0.16223 | 5.91841 | 1.73898 |
| VI-53 | 0.05631 | 0.18115 | 11.3381 | 0.56491 |
| VI-54 | 0.14667 | 0.96651 | 31.0319 | 1.61592 |
| VI-55 | 0.12204 | 0.62467 | | 1.36955 |
| VI-56 | 9.6557 | | | |
| VI-57 | 0.20172 | 1.18287 | | |
| VI-58 | 0.16427 | 0.72381 | 9999 | |
| VI-59 | 0.07598 | 0.33972 | 4.98157 | |
| VI-60 | 0.08692 | 0.18673 | 3.84551 | 0.40964 |
| VI-61 | 0.09897 | 0.18455 | 3.11335 | 0.36684 |
| VI-62 | 3.9717 | | | |
| VI-63 | 0.15987 | 0.36325 | | 1.74329 |
| VI-64 | 5.80304 | | | |
| VI-65 | 0.09062 | 0.20944 | 4.12861 | 0.9643 |
| VI-66 | 6.0949 | | | |
| VI-67 | 0.14725 | 0.7175 | | |
| VI-68 | 0.1016 | 0.74156 | 26.8087 | 1.80963 |
| VI-69 | 0.19376 | 1.34478 | 18.7049 | |
| VI-70 | 0.07056 | 0.31112 | 8888 | 0.65688 |
| VI-71 | 1.07371 | | | |
| VI-72 | 0.45477 | | | |
| VI-73 | 0.25111 | 2.01413 | | |
| VI-74 | 0.09458 | 0.34829 | 9999 | 3.85373 |
| VI-75 | 0.90444 | 0.92854 | | |
| VI-76 | 0.54911 | 0.78345 | | |
| VI-77 | 9999 | 43.2745 | | |
| VI-78 | 0.16137 | | | |
| VI-79 | 0.096 | | | |
| VI-80 | 0.3601 | | | |
| VI-81 | 3.1748 | | | |
| VI-82 | 0.21184 | 1.63499 | 8888 | |
| VI-83 | 0.11255 | 0.29326 | 7.29592 | 0.53506 |
| VI-84 | 0.13247 | 0.51438 | 4.58337 | |
| VI-85 | 0.12862 | 0.76235 | 24.7027 | |
| VI-86 | 0.1531 | 0.17808 | 4.43831 | 0.48745 |
| VI-87 | 0.5411 | 1.24269 | | |
| VI-88 | 0.21559 | 1.18558 | 24.6776 | |
| VI-89 | 0.13188 | 0.17139 | 5.75508 | 2.04395 |
| VI-90 | 1.075 | 3.9664 | | |
| VI-91 | 0.22118 | 1.23424 | 9999 | |
| VI-92 | 0.0835 | 0.10732 | 12.9834 | 1.1583 |
| VI-93 | 0.10988 | 0.5602 | | |
| VI-94 | 0.9442 | | | |
| VI-95 | 1.0032 | | | |
| VI-96 | 0.80335 | | | |
| VI-97 | 3.00715 | | | |
| VI-98 | 0.13555 | 0.9859 | 9999 | 9999 |
| VI-99 | 0.06845 | 0.6166 | 9999 | 9999 |
| VI-100 | 0.32107 | 0.07427 | 9.1817 | 4.89859 |
| VI-101 | 0.91914 | | | |
| VI-102 | 0.18285 | 0.13496 | 14.7259 | 2.7967 |
| VI-103 | 3.07902 | | | |
| VI-104 | 1.98452 | | | |
| VI-105 | 10.2998 | | | |
| VI-106 | 0.06219 | 1.19886 | 9999 | 9999 |
| VI-107 | 0.15912 | 0.07409 | 8888 | 0.85644 |
| VI-108 | 9999 | | | |
| VI-109 | 0.13553 | 2.86926 | 7777 | 9999 |
| VI-110 | 0.08364 | 0.34532 | 9999 | 5.46321 |
| VI-111 | 0.31375 | 1.09272 | | 3.43245 |
| VI-112 | 0.15223 | 0.77009 | | 1.25566 |
| VI-113 | 0.6995 | | | |
| VI-114 | 0.2095 | 2.2419 | 9999 | 33.19 |
| VI-115 | 0.8899 | | | |
| VI-116 | 0.0311 | 0.1742 | 8.101 | 0.673 |
| VII-1 | 6.653 | | | |
| VII-2 | 36.2228 | | | |
| VII-3 | 14.0844 | 16.5455 | | |
| VII-4 | 2.49292 | 9999 | | |
| VII-5 | 4.12527 | | | |
| VII-6 | 0.10208 | 1.99812 | 23.4363 | 3.6535 |
| VII-7 | 0.50186 | 3.91608 | | 9999 |
| VII-8 | 0.39911 | 8.63335 | 7777 | 7777 |
| VII-9 | 0.24627 | 2.71965 | 17.0751 | 5.34695 |
| VII-10 | 0.86258 | | | |
| VII-11 | 0.60232 | | | |
| VII-12 | 0.60208 | 6.68655 | | 31.7728 |
| VII-13 | 0.13967 | 0.38047 | 7777 | 1.28577 |
| VII-14 | 0.10259 | 0.17683 | 9.92695 | 0.87716 |
| VII-15 | 0.06662 | 0.12058 | 13.1417 | 0.56816 |
| VII-16 | 0.27544 | 1.07422 | | 24.3537 |
| VII-17 | 0.35301 | 2.09765 | | 6.96416 |
| VII-18 | 0.22688 | 0.83852 | | 1.29055 |
| VII-19 | 0.08753 | 0.51424 | 12.53 | 1.25627 |
| VII-20 | 0.28603 | 0.69758 | | |
| VII-21 | 0.54792 | | | |
| VII-22 | 0.1114 | 0.1276 | 9999 | 0.84875 |
| VII-23 | 0.12929 | 0.16124 | 61.259 | 0.59644 |
| VII-24 | 0.62303 | | | |
| VII-25 | 0.21695 | | | |
| VII-26 | 0.54544 | 1.20006 | | 9.26107 |
| VII-27 | 0.41342 | 2.05177 | | 6.2489 |
| VII-28 | 0.0367 | 0.70906 | 16.5843 | 8888 |
| VII-29 | 0.0476 | 1.46279 | 30.5071 | 38.4779 |
| VII-30 | 0.0358 | 0.02682 | 8.91572 | 0.70135 |
| VII-31 | 0.12467 | 0.17419 | 9999 | 7.27828 |
| VII-32 | 0.1071 | 0.0321 | 8888 | 2.057 |
| VII-33 | 0.02891 | 0.01839 | | |
| VII-34 | 0.04504 | 0.02248 | | |
| VII-35 | 0.0448 | 0.0461 | 8888 | 0.245 |
| VII-36 | 0.02945 | 0.11909 | 82.8107 | 1.08605 |
| VII-37 | 0.02814 | | | |
| VII-38 | 0.06234 | 0.41674 | | |

TABLE XII-continued

| Compound | Example 41 | Example 42 | Example 43 | Example 44 |
|---|---|---|---|---|
| VII-39 | 0.77157 | 0.91901 | | |
| VII-40 | 0.23602 | 6.48486 | 9999 | |
| VII-41 | 0.04694 | 0.26426 | 9999 | 9999 |
| VII-42 | 0.6688 | 7.28447 | | 45.547 |
| VII-43 | 0.60291 | | | 9999 |
| VII-44 | 0.03299 | 0.54552 | 9.12322 | 1.22643 |
| VII-45 | 0.04385 | 0.28169 | 4.03246 | 0.47741 |
| VII-46 | 0.96115 | | | |
| VII-47 | 2.67352 | | | |
| VII-48 | 0.03083 | 0.3365 | 9999 | 0.66 |
| VII-49 | 0.03778 | 0.05493 | 3.06481 | 0.57652 |
| VII-50 | 0.34963 | 0.85602 | 4.41963 | 5.0643 |
| VII-51 | 0.54109 | 1.79232 | | 9999 |
| VII-52 | 47.0815 | | | |
| VII-53 | 0.16792 | 0.48379 | 5.46124 | |
| VII-54 | 0.29487 | 0.59608 | | 64.6261 |
| VII-55 | 0.18411 | 0.59857 | | 1.66866 |
| VII-56 | 0.18495 | 1.28469 | | 1.92946 |
| VII-57 | 0.10717 | 0.8182 | 10.6982 | 0.73524 |
| VII-58 | 0.13577 | 0.26518 | | 1.09844 |
| VII-59 | 0.83147 | 2.98692 | | |
| VII-60 | 0.06501 | 0.15195 | 2.60397 | 0.56965 |
| VII-61 | 3333.23 | 0.14031 | 2.69156 | 0.35591 |
| VII-62 | 0.10412 | 0.14422 | 9999 | 0.49561 |
| VII-63 | 0.23311 | 0.30064 | | 6.02744 |
| VII-64 | 0.36258 | 3.8097 | | |
| VII-65 | 0.38533 | 3.05525 | | |
| VII-66 | 0.36866 | 2.87032 | | |
| VII-67 | 0.31467 | 0.76791 | | |
| VII-68 | 0.81157 | 1.30092 | | |
| VII-69 | 0.07673 | 0.69583 | 7.50321 | 0.98982 |
| VII-70 | 0.06542 | 0.37513 | 6.47721 | 2.76015 |
| VII-71 | 0.14944 | 0.56875 | 5.47023 | |
| VII-72 | 0.08484 | 0.41516 | 9.93038 | 1.18433 |
| VII-73 | 6.08963 | 4444.5 | | |
| VII-74 | 4.56128 | 8888 | | |
| VII-75 | 0.54401 | | | |
| VII-76 | 0.67316 | | | |
| VII-77 | 0.12407 | 1.78366 | | 3.53562 |
| VII-78 | 0.08583 | 0.6825 | 9999 | 8888 |
| VII-79 | 0.20627 | 3.20167 | | 7777 |
| VII-80 | 2.03294 | | | |
| VII-81 | 3.07323 | | | |
| VII-82 | 0.3126 | 1.07552 | | 8888 |
| VII-83 | 0.0775 | 0.93655 | | 9999 |
| VIII-1 | 1.58839 | | | |
| VIII-2 | 0.1777 | 0.40901 | | 8.54969 |
| VIII-3 | 0.15335 | 1.84224 | | 10.0847 |
| IX-1 | 0.08928 | 0.58079 | 4.88106 | 1.13251 |
| IX-2 | 0.0795 | 0.28213 | 8888 | 1.76728 |
| IX-3 | 0.11457 | | | |
| IX-4 | 0.12037 | | | |
| IX-5 | 0.02962 | 0.07382 | 6.09872 | 1.84617 |
| IX-6 | 0.08403 | 0.53531 | 36.7836 | 8888 |
| IX-7 | 0.10867 | 0.7509 | 9999 | 4.73418 |
| IX-8 | 0.04643 | 0.12398 | 5.24218 | 0.54254 |
| IX-9 | 8.87638 | 5016.37 | | |
| IX-10 | 6.40728 | | | |
| IX-11 | 0.1146 | 0.21538 | 7777 | 2.23698 |
| IX-12 | 0.09731 | 0.11725 | 7777 | 3.47525 |
| IX-13 | 0.13847 | 0.43042 | 30.2755 | 1.84616 |
| IX-14 | 0.05744 | 0.65645 | 3.37992 | 1.08814 |
| IX-15 | 0.21708 | 0.15678 | 7777 | 5.36404 |
| IX-16 | 0.20966 | 0.22281 | 7777 | 2.50539 |
| IX-17 | 0.1084 | 0.8151 | 21.95 | 1.98 |
| IX-18 | 0.1684 | 2.4 | 55.18 | 6.659 |
| IX-19 | 0.1179 | 1.5963 | | 3.368 |
| IX-20 | 0.12232 | 1.79208 | | 2.89558 |
| IX-21 | 0.2709 | 2.7359 | | |
| IX-22 | 0.2953 | 1.59 | | |
| IX-23 | 9.57788 | | | |
| IX-24 | 6.33149 | 38.3916 | | |
| IX-25 | 6.3071 | | | |
| IX-26 | 9999 | | | |
| IX-27 | 1.37969 | 7.62931 | | |
| IX-28 | 1.66076 | 10.0529 | | |
| IX-29 | 3.45769 | | | |
| IX-30 | 1.93529 | 6.79992 | | |
| IX-31 | 1.4025 | | | |
| IX-32 | 9999 | | 9999 | |
| IX-33 | 0.52102 | | | |
| IX-34 | 0.58245 | 0.57557 | | 3.95135 |
| IX-35 | 0.45471 | 0.8665 | 9999 | 2.09598 |
| IX-36 | 1.03601 | | 9999 | |
| IX-37 | 3.70466 | | | |
| IX-38 | 2.31392 | | | |
| IX-39 | 1.39641 | | | |
| IX-40 | 9999 | | 9999 | |
| IX-41 | 0.13318 | 6.25787 | 9999 | |
| IX-42 | 0.29236 | 2.17331 | 9999 | |
| IX-43 | 0.52347 | 2.80149 | | |
| IX-44 | 0.22324 | 0.78907 | 8.16963 | 2.93981 |
| IX-45 | 3.615 | | | |
| IX-46 | 0.07388 | 1.38897 | 7777 | |
| IX-47 | 0.22282 | 2.38854 | | |
| IX-48 | 0.25834 | 2.62415 | 9.56437 | |
| IX-49 | 0.0965 | 61.8954 | 9999 | |
| IX-50 | 0.17891 | 9999 | | |
| IX-51 | 0.23983 | 9999 | | |
| IX-52 | 0.11677 | | | |
| IX-53 | 0.24002 | | | |
| IX-54 | 0.17434 | 2.47371 | 9999 | |
| X-1 | 8.24549 | | | |
| X-2 | 1.84451 | | | |
| X-3 | 0.34839 | 1.09444 | 4.97666 | 1.3837 |

What is claimed is:
1. A compound of formula IV

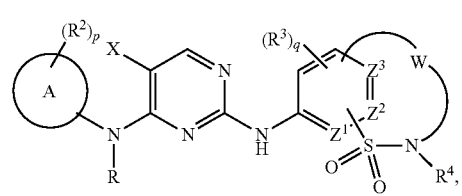

IV or a pharmaceutically acceptable salt thereof, wherein:
ring A is aryl;
p is 0, 1, 2 or 3;
q is 0, 1, 2 or 3;
R and $R^4$ independently are hydrogen, alkyl, substituted alkyl, alkenyl, substituted alkenyl, alkynyl, substituted alkynyl, acyl, cycloalkyl or substituted cycloalkyl;
each $R^2$ independently is alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminoacyl, aminoacyloxy, carboxyl, carboxyl ester, carbonate ester nitro, and halo, or two of $R^2$ on the same carbon form an oxy (=O);
each $R^3$ independently is hydrogen, alkyl, substituted alkyl, alkoxy, substituted alkoxy, cycloalkyl or substituted cycloalkyl, halo, heterocyclic, substituted heterocyclic or sulfonylamine;
X is alkyl, substituted alkyl, alkoxy, substituted alkoxy, amino, substituted amino, carboxyl, carboxyl ester, cyano, halo, nitro, alkenyl, substituted alkenyl, alkynyl or substituted alkynyl;

W is $C_1$-$C_3$ alkylene, substituted $C_1$-$C_3$ alkylene, $C_2$-$C_3$ alkenylene and substituted $C_2$-$C_3$ alkenylene wherein one or more of the carbon atoms have been replaced with a moiety selected from oxygen, sulfur, S(O), S(O)2, C(O), or $NR^8$ where $R^8$ is selected from the group consisting of hydrogen and alkyl or is a bond participating in a —N═C<site of unsaturation; and each $Z^1$, $Z^2$ and $Z^3$ independently is carbon or nitrogen.

2. The compound according to claim 1 wherein ring A is phenyl.

3. The compound according to claim 1 wherein $R^2$ is alkyl, substituted alkyl, alkoxy, halo or heteroaryl.

4. The compound according to claim 1 wherein $R^2$ is —$C_1$, —F, —$CH_3$, pyrazolyl, —$OCH_3$, —$CH_2OH$, or —$CF_3$.

5. The compound according to claim 2 wherein $R^2$ is in the 3 and/or the 4 position.

6. The compound according to claim 1 wherein $R^3$ is alkyl, alkoxy, halo, heterocycle, or sulfonylamine.

7. The compound according to claim 6 wherein $R^3$ is —$CH_3$, —$C_1$, —F, —$OCH_3$piperizinyl.

8. The compound according to claim 1 wherein X is halo or alkyl.

9. The compound according to claim 8 wherein X is chloro, fluoro or methyl.

10. The compound according to claim 1 wherein $Z^1$, $Z^2$, and $Z^3$ are carbon.

11. The compound according to claim 1 wherein $R^4$ is hydrogen, alkyl, substituted alkyl or acyl.

12. The compound according to claim 1 wherein R and $R^4$ are hydrogen or alkyl.

13. The compound according to claim 1 wherein R and $R^4$ are hydrogen or methyl.

14. A pharmaceutical formulation, comprising:
a compound according to claim 1; and
at least one pharmaceutically acceptable excipient, diluent, preservative, stabilizer, or mixtures thereof.

15. A method, comprising contacting a JAK kinase with a compound according to claim 1 in an amount effective to inhibit an activity of the JAK kinase.

16. The method according to claim 15 comprising contacting the JAK kinase in vitro or in vivo.

17. The method according to claim 15 for inhibiting a signal wherein contacting the JAK kinase inhibits a transduction cascade.

18. The method of claim 15 in which the JAK kinase is contacted with the compound according to claim 1 in combination with, or adjunctively to, a second compound that inhibits a JAK kinase.

19. The method according to claim 15 for treating allograft transplant rejection in a transplant recipient, comprising contacting the JAK kinase in the transplant recipient with an amount of a compound according to claim 1 effective to treat the rejection.

* * * * *